United States Patent
Jung et al.

(10) Patent No.: US 8,617,903 B2
(45) Date of Patent: Dec. 31, 2013

(54) METHODS FOR ALLERGEN DETECTION

(75) Inventors: Edward K. Y. Jung, Bellevue, WA (US);
Eric C. Leuthardt, St. Louis, MO (US);
Royce A. Levien, Lexington, MA (US);
Robert W. Lord, Seattle, WA (US);
Mark A. Malamud, Seattle, WA (US);
John D. Rinaldo, Jr., Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1126 days.

(21) Appl. No.: 11/699,770

(22) Filed: Jan. 29, 2007

(65) Prior Publication Data
US 2008/0182339 A1    Jul. 31, 2008

(51) Int. Cl.
*G01N 33/00*    (2006.01)

(52) U.S. Cl.
USPC ........................................... 436/174; 436/181

(58) Field of Classification Search
USPC .......................................... 422/100; 436/181
See application file for complete search history.

(56) References Cited

U.S. PATENT DOCUMENTS

| | | |
|---|---|---|
| 3,971,065 A | 7/1976 | Bayer |
| 4,009,078 A | 2/1977 | Wilkins et al. |
| 4,081,356 A | 3/1978 | Zierdt |
| 4,257,041 A | 3/1981 | Masucci |
| 4,436,378 A | 3/1984 | Kirkman |
| H201 H | 1/1987 | Yager |
| 4,729,636 A | 3/1988 | Te Velde et al. |
| 4,807,967 A | 2/1989 | Veenvliet et al. |
| 5,093,268 A | 3/1992 | Leventis et al. |
| 5,304,487 A | 4/1994 | Wilding et al. |
| 5,705,399 A | 1/1998 | Larue |
| 5,716,852 A | 2/1998 | Yager et al. |
| 5,726,404 A | 3/1998 | Brody |
| 5,747,349 A | 5/1998 | Van den Engh et al. |
| 5,824,494 A | 10/1998 | Feldberg |
| 5,837,196 A | 11/1998 | Pinkel et al. |
| 5,922,210 A | 7/1999 | Brody et al. |
| 5,932,100 A | 8/1999 | Yager et al. |
| 5,948,684 A | 9/1999 | Weigl et al. |
| 5,968,820 A | 10/1999 | Zborowski et al. |
| 5,971,158 A | 10/1999 | Yager et al. |
| 5,972,710 A | 10/1999 | Weigl et al. |
| 5,974,867 A | 11/1999 | Forster et al. |
| 6,007,775 A | 12/1999 | Yager |
| 6,037,167 A | 3/2000 | Adelman et al. |
| 6,090,545 A | 7/2000 | Wohlstadter et al. |
| 6,194,900 B1 | 2/2001 | Freeman et al. |
| 6,221,677 B1 | 4/2001 | Wu et al. |

(Continued)

FOREIGN PATENT DOCUMENTS

| | | |
|---|---|---|
| DE | 10 2004 04078 A1 | 3/2006 |
| JP | 61002060 A | 1/1986 |

(Continued)

OTHER PUBLICATIONS

U.S. Appl. No. 12/011,008, Jung et al.

(Continued)

*Primary Examiner* — Christine T Mui

(57) ABSTRACT

The present disclosure relates to methods that may be used for the detection of allergens.

18 Claims, 62 Drawing Sheets

(56) References Cited

U.S. PATENT DOCUMENTS

| | | |
|---|---|---|
| 6,303,316 B1 | 10/2001 | Kiel et al. |
| 6,303,343 B1 | 10/2001 | Kopf-Sill |
| 6,318,970 B1 | 11/2001 | Backhouse |
| 6,325,904 B1 | 12/2001 | Peeters |
| 6,330,946 B1 | 12/2001 | Allen |
| 6,342,037 B1 | 1/2002 | Roe et al. |
| 6,379,929 B1 | 4/2002 | Burns et al. |
| 6,408,884 B1 | 6/2002 | Kamholz et al. |
| 6,409,832 B2 | 6/2002 | Weigl et al. |
| 6,430,512 B1 | 8/2002 | Gallagher |
| 6,441,142 B1 * | 8/2002 | Burks et al. ............... 530/387.9 |
| 6,454,945 B1 | 9/2002 | Weigl et al. |
| 6,482,306 B1 | 11/2002 | Yager et al. |
| 6,523,392 B2 | 2/2003 | Porter et al. |
| 6,541,213 B1 | 4/2003 | Weigl et al. |
| 6,569,630 B1 | 5/2003 | Vivekananda et al. |
| 6,582,987 B2 | 6/2003 | Jun et al. |
| 6,605,454 B2 | 8/2003 | Barenburg et al. |
| 6,632,400 B1 | 10/2003 | Brennen et al. |
| 6,632,655 B1 | 10/2003 | Mehta et al. |
| 6,664,104 B2 * | 12/2003 | Pourahmadi et al. ...... 435/288.6 |
| 6,709,869 B2 | 3/2004 | Mian et al. |
| 6,716,642 B1 | 4/2004 | Wu et al. |
| 6,729,196 B2 | 5/2004 | Moler et al. |
| 6,730,516 B2 | 5/2004 | Jedrzejewski et al. |
| 6,742,661 B1 | 6/2004 | Schulte et al. |
| 6,763,705 B1 | 7/2004 | Thundat et al. |
| 6,780,582 B1 | 8/2004 | Wagner et al. |
| 6,794,196 B2 | 9/2004 | Fonash et al. |
| 6,812,458 B2 | 11/2004 | Gregori et al. |
| 6,818,435 B2 | 11/2004 | Carvalho et al. |
| 6,821,730 B2 | 11/2004 | Hannah |
| 6,877,892 B2 | 4/2005 | Karp |
| 6,878,255 B1 | 4/2005 | Wang et al. |
| 6,886,557 B2 | 5/2005 | Childers et al. |
| 6,923,907 B2 | 8/2005 | Hobbs et al. |
| 6,926,864 B2 | 8/2005 | Peeters et al. |
| 6,935,165 B2 | 8/2005 | Bashir et al. |
| 6,958,216 B2 | 10/2005 | Kelley et al. |
| 6,960,437 B2 | 11/2005 | Enzelberger et al. |
| 7,030,989 B2 | 4/2006 | Yager et al. |
| 7,070,682 B2 | 7/2006 | Lee et al. |
| 7,081,192 B1 | 7/2006 | Wang et al. |
| 7,110,646 B2 | 9/2006 | Eggleton et al. |
| 7,112,444 B2 | 9/2006 | Beebe et al. |
| 7,118,910 B2 | 10/2006 | Unger et al. |
| 7,141,385 B2 | 11/2006 | Bottomley et al. |
| 7,150,813 B2 | 12/2006 | Lean et al. |
| 7,206,605 B2 | 4/2007 | Hattori |
| 7,215,887 B2 | 5/2007 | Ternullo et al. |
| 7,218,900 B2 | 5/2007 | Suzuki |
| 7,227,956 B1 | 6/2007 | Onishi |
| 7,236,595 B1 | 6/2007 | Bean et al. |
| 7,245,894 B2 | 7/2007 | Sekiguchi et al. |
| RE39,785 E | 8/2007 | Fuse |
| 7,254,160 B2 | 8/2007 | Kawamoto et al. |
| 7,257,327 B2 | 8/2007 | Small |
| 7,260,155 B2 | 8/2007 | Stonick et al. |
| 7,260,402 B1 | 8/2007 | Ahmed |
| 7,260,764 B2 | 8/2007 | Chen |
| 7,260,768 B1 | 8/2007 | Matsumoto et al. |
| 7,605,002 B2 | 10/2009 | Summersgill et al. |
| 2002/0090720 A1 | 7/2002 | Mutz et al. |
| 2002/0177763 A1 | 11/2002 | Burns et al. |
| 2003/0044832 A1 | 3/2003 | Blankenstein |
| 2003/0083685 A1 | 5/2003 | Freeman et al. |
| 2003/0153085 A1 | 8/2003 | Leary et al. |
| 2003/0159999 A1 | 8/2003 | Oakey et al. |
| 2003/0186228 A1 | 10/2003 | McDevitt et al. |
| 2004/0021073 A1 | 2/2004 | Barbic et al. |
| 2004/0053290 A1 | 3/2004 | Terbrueggen et al. |
| 2004/0058454 A1 | 3/2004 | Bolbot et al. |
| 2004/0078219 A1 | 4/2004 | Kaylor et al. |
| 2004/0086872 A1 | 5/2004 | Childers et al. |
| 2004/0118757 A1 | 6/2004 | Terstappen et al. |
| 2004/0121449 A1 | 6/2004 | Pugia et al. |
| 2004/0151629 A1 | 8/2004 | Pease et al. |
| 2004/0166504 A1 | 8/2004 | Rossier et al. |
| 2004/0220498 A1 | 11/2004 | Li et al. |
| 2004/0245102 A1 | 12/2004 | Gilbert et al. |
| 2004/0248167 A1 | 12/2004 | Quake et al. |
| 2005/0014134 A1 | 1/2005 | West et al. |
| 2005/0106713 A1 | 5/2005 | Phan et al. |
| 2005/0130257 A1 | 6/2005 | Mutz et al. |
| 2005/0191620 A1 | 9/2005 | McDevitt et al. |
| 2005/0284763 A1 | 12/2005 | Chen et al. |
| 2006/0073484 A1 | 4/2006 | Mathies et al. |
| 2006/0197723 A1 | 9/2006 | Sikora et al. |
| 2006/0257287 A1 | 11/2006 | Call et al. |
| 2006/0257852 A1 | 11/2006 | Rappuoli et al. |
| 2006/0280307 A1 | 12/2006 | Ikushima et al. |
| 2007/0000838 A1 | 1/2007 | Shih et al. |
| 2007/0003447 A1 | 1/2007 | Gleason et al. |
| 2007/0029257 A1 | 2/2007 | Mueth et al. |
| 2009/0047297 A1 | 2/2009 | Kim et al. |

FOREIGN PATENT DOCUMENTS

| | | | |
|---|---|---|---|
| WO | WO 97/47390 | 12/1997 | |
| WO | WO 98/38293 | 9/1998 | |
| WO | WO 99/17119 | 4/1999 | |
| WO | WO 99/33559 | 7/1999 | |
| WO | WO 99/45354 A2 | 9/1999 | |
| WO | WO 99/45354 A3 | 9/1999 | |
| WO | WO 00/60362 A1 | 10/2000 | |
| WO | WO 01/79529 A1 | 10/2001 | |
| WO | WO 0179529 A1 * | 10/2001 | ............... C12Q 1/04 |
| WO | WO 03/066191 A1 | 8/2003 | |
| WO | WO 2004/061085 A3 | 7/2004 | |
| WO | WO 2004/082838 A1 | 9/2004 | |
| WO | WO 2005/072855 A1 | 8/2005 | |
| WO | WO 2006/021410 A1 | 3/2006 | |
| WO | WO 2006/032044 A3 | 3/2006 | |

OTHER PUBLICATIONS

EPA European Search Report, European App. No. EP 08 25 1104; Sep. 23, 2008; pp. 1-6.

Gehring, Andrew et al.; "Enzyme-linked immunomagnetic chemiluminescent detection of *Escherichia coli* O157:H7"; Journal of Immunological Methods; bearing a date of 2004; pp. 97-106; vol. 293; Elsevier B.V.

International Search Report; International App. No. PCT/US2008/001255; Nov. 18, 2008; pp. 1-3.

Yeung et al.; "A DNA biochip for on-the-spot multiplexed pathogen identification"; Nucleic Acids Research; bearing a date of Sep. 25, 2006; pp. e118, 1-7; vol. 34, No. 18; Oxford Journals; located at http://nar.oxfordjournals.org/cgi/content/full/34/18/e118.

U.S. Appl. No. 11/699,920, Jung et al.

U.S. Appl. No. 11/699,774, Jung et al.

U.S. Appl. No. 11/699,747, Jung et al.

"Allergen Nomenclature: International Union of Immunological Societies Allergen Nomenclature Sub-Committee—List of allergens"; International Union of Immunological Societies Allergen Nomenclature Sub-Committee; Bearing a date of Feb. 20, 2006; pp. 1-40; located at http://www.allergen.org/List.htm; printed on Dec. 6, 2006.

"Allergen Nomenclature: International Union of Immunological Societies Allergen Nomenclature Sub-Committee—List of isoallergens and variants"; International Union of Immunological Societies Allergen Nomenclature Sub-Committee; Bearing a date of Feb. 20, 2006; pp. 1-20; located at http://www.allergen.org/Isoall.htm; printed on Dec. 6, 2006.

Baines, IC.; Colas, P.; "Peptide aptamers as guides for small-molecule drug discovery"; Drug Discovery Today; Apr. 2006; pp. 334-341 (p. 1); vol. 11, Issues 7-8; PubMed; located at: http://www.ncbi.nlm.nih.gov/entrez/query.fcgi?db=pubmed&cmd=Retrieve&dopt=AbstractPlus&list_uids=16580975&query_hl=10&itool=pubmed_docsum; printed on Jan. 10, 2007.

"Basic Microfluidic Concepts"; Bearing a date of Sep. 7, 2001; pp. 1-8; located at: http://faculty.washington.edu/yagerp/microfluiclicstutorial/basicconcepts/basicconcepts.htm; printed on Jan. 17, 2007.

(56) References Cited

OTHER PUBLICATIONS

Belgrader, P.; Okuzumi, M.; Pourahmadi, F.; Borkholder, D.A.; Northrup, M.A.; "A microfluidic cartridge to prepare spores for PCR analysis"; Biosensors and Bioelectronics; Jan. 2000; pp. 849-852 (p. 1); vol. 14, Issues 10-11; PubMed; located at: http://www.ncbi.nlm.nih.gov/entrez/query.fcgi?cmd=Retrieve&db=PubMed&list_uids=10945459&dopt=Abstract; printed on Jan. 9, 2007.

Buchholz, B.A.; Doherty, E.A.; Albarghouthi, M.N.; Bogdan, F.M.; Zahn, J.M.; Barron, A.E.; "Microchannel DNA Sequencing Matrices with a Thermally Controlled 'Viscosity Switch'"; Anal. Chem.; Jan. 15, 2001; pp. 157-164 (p. 1-2); vol. 73, Issue 2; PubMed; located at: http://www.ncbi.nlm.nih.gov/entrez/query.fcgi?cmd=Retrieve&db=PubMed&list_uids=11199960&dopt=Abstract; printed on Jan. 9, 2007.

Cheng, S.B.; Skinner, C.D.; Taylor, J.; Attiya, S.; Lee, W.E.; Picelli, G.; Harrison, D.J.; "Development of a Multichannel Microfluidic Analysis System Employing Affinity Capillary Electrophoresis for Immunoassay"; Anal. Chem.; Apr. 1, 2001; pp. 1472-1479 (p. 1); vol. 73, Issue 7; PubMed; located at: http://www.ncbi.nlm.nih.gov/entrez/query.fcgi?cmd=Retrieve&db=PubMed&list_uids=11321296&dopt=Abstract; printed on Jan. 16, 2007.

Cherif, B.; Roget, A.; Villiers, C.L.; Calemczuk, R.; Leroy, V.; Marche, P.N.; Livache, T.; Villiers, M.B.; "Application 104—Clinically Related Protein—Peptide Interactions Monitored in Real Time on Novel Peptide Chips by Surface Plasmon Resonance Imaging"; Clinical Chemistry; 2006; pp. 255-262 (pp. 1-4); vol. 52; GenOptics; located at: www.genoptics-spr.com; printed on Jan. 10, 2007.

Ching, Shanfun; Lee, Helen; Hook III, Edward W.; Jacobs, Michael R.; Zenilman, Jonathan; "Ligase Chain Reaction for Detection of Neisseria gonorrhoeae in Urogenital Swabs"; Journal of Clinical Microbiology; Dec. 1995; pp. 3111-3114; vol. 33, No. 12; American Society for Microbiology.

Chiu, Daniel T.; Jeon, Noo Li; Huang, Sui; Kane, Ravi S.; Wargo, Christopher J.; Choi, Insung S.; Ingber, Donald E.; Whitesides, George M.; "Patterned deposition of cells and proteins onto surfaces by using three-dimensional microfluidic systems"; PNAS; Mar. 14, 2000; pp. 2408-2413; vol. 97, No. 6; located at: http://www.pnas.org/cgi/content/abstract/97/6/2408; printed on Jan. 10, 2007.

Collett, J.R.; Cho, E.J.; Lee, J.F.; Levy, M.; Hood, A.J.; Wan, C.; Ellington, A.D.; "Functional RNA microarrays for high-throughput screening of antiprotein aptamers"; Anal Biochem.; Mar. 1, 2005; pp. 113-123 (p. 1); vol. 338, Issue 1; PubMed; located at: http://www.ncbi.nlm.nih.gov/entrez/query.fcgi?cmd=Retrieve&db=PubMed&dopt=Citation&list_uids=15707941; printed on Jan. 10, 2007.

Collett, J.R.; Cho, E.J.; Ellington, A.D.; "Production and processing of aptamer microarrays"; Methods; Sep. 2005; pp. 4-15 (p. 1); vol. 37, Issue 1; PubMed; located at: http://www.pubmed.com; printed on Jan. 10, 2007.

Cox, J. Colin; Hayhurst, Andrew; Hesselberth, Jay; Bayer, Travis S.; Georgiou, George; Ellington, Andrew D.; "Automated selection of aptamers against protein targets translated in vitro: from gene to aptamer"; Nucleic Acids Research; 2002; pp. 1-14; vol. 30, No. 20; e108; Oxford University Press; located at: http://nar.oxfordjournals.org/cgi/reprint/30/20/e108.

Davis, M.T.; Stahl, D.C.; Swiderek, K.M.; Lee, T.D.; "Capillary Liquid Chromatography/Mass Spectrometry for Peptide and Protein Characterization"; Methods: A Companion to Methods in Enzymology; Shively J.E., ed.; Sep. 1994; vol. 6, Issue 3; pp. 304-314 (pp. 1-2); ScienceDirect; located at: http://www.sciencedirect.com/science?_ob=ArticleURL&_udi=B6WN5-45NJDKF-V&_coverDate=09%2F30%2F1994&_alid=525661391&_rdoc=1&_fmt=&_orig=search&_qd=1&_cdi=6953&_sort=d&view=c&_acct=C000050221&_version=1&_urlVersion=0&_userid=10&md5=1b757b816dddb9a67e083bb90ce8b592; printed on Jan. 16, 2007.

Dertinger, Stephan K.W.; Chiu, Daniel T.; Jeon, Noo Li; Whitesides, George M.; "Generation of Gradients Having Complex Shapes Using Microfluidic Networks"; Anal. Chem.; Mar. 15, 2001; pp. 1240-1246; vol. 73, No. 6; American Chemical Society; located at: http://nljgroup.eng.uci.edu/Articles/03%20-%20pdf%20-%20ac001132d.pdf.

"Diffusion Immunoassay (DIA)"; Basic Microfluidic Concepts; Bearing a date of Sep. 7, 2001; pp. 1-13; located at: http://faculty.washington.edu/yagerp/microfluidicstutorial/dia/diffusionimmunoassayhome.htm; printed on Jan. 17, 2007.

Eteshola, E.; Leckband, D.; "Development and characterization of an ELISA assay in PDMS microfluidic channels"; Sensors and Actuators B: Chemical; Jan. 25, 2001; vol. 72, Issue 2; pp. 129-133 (pp. 1-2); Elsevier Science B.V.—ScienceDirect; located at: http://www.sciencedirect.com/science?_ob=ArticleURL&_udi=B6THH-423HKF4-5&_user=10&_coverDate=01%2F25%2F2001&_alid=522654785&_rdoc=1&_fmt=summary&_orig=search&_cdi=5283&_sort=d&_docanchor=&view=c&_acct=C000050221&_version=1&_urlVersion=0&_userid=10&md5=41f626b13a6896a2b9bdldca5395ade9; printed on Jan. 10, 2007.

Fan, Chunhai; Plaxco, Kevin W.; Heeger, Alan J.; "Electrochemical interrogation of conformational changes as a reagentless method for the sequence-specific detection of DNA"; PNAS; Aug. 5, 2003; pp. 9134-9137; vol. 100, No. 16; located at: www.pnas.org/cgi/doi/10.1073/pnas.1633515100.

Fan, Z.H.; Mangru, S.; Granzow, R.; Heaney, P.; Ho, W.; Dong, Q.; Kumar, R.; "Dynamic DNA Hybridization on a Chip Using Paramagnetic Beads"; Anal. Chem.; Nov. 1, 1999; pp. 4851-4859 (p. 1); vol. 71, Issue 21; PubMed; located at: http://www.ncbi.nlm.nih.gov/entrez/query.fcgi?cmd=Retrieve&db=PubMed&list_uids=10565276&dopt=Abstract; printed on Jan. 9, 2007.

Folch, A.; Jo, B.H.; Hurtado, O.; Beebe, D.J.; Toner, M.; "Microfabricated elastomeric stencils for micropatterning cell cultures"; J. Biomed Mater Res.; Nov. 2000; pp. 346-353 (p. 1); vol. 52, Issue 2; PubMed; located at: http://www.ncbi.nlm.nih.gov/entrez/query.fcgi?cmd=Retrieve&db=PubMed&list_uids=10951374&dopt=Abstract; printed on Jan. 10, 2007.

Geyer, C.R.; Brent, R.; "Selection of Genetic Agents From Random Peptide Aptamer Expression Libraries"; Methods in Enzymology; 2000; pp. 171-208; vol. 328, Chapter 13 (not provided).

Glasgow, I.K.; Zeringue, H.C.; Beebe, D.J.; Choi, S.J.; Lyman, J.T.; Chan, N.G.; Wheeler, M.B.; "Handling individual mammalian embryos using microtluidics"; IEEE Trans Biomed Eng.; May 2001; pp. 570-578 (p. 1); vol. 48, Issue 5; PubMed; located at: http://www.ncbi.nlm.nih.gov/entrez/query.fcgi?cmd=Retrieve&db=PubMed&list_uids=11341531&dopt=Abstract; printed on Jan. 10, 2007.

Guthrie, J.W.; Hamula, C.L.; Zhang, H.; Le, X.C.; "Assays for cytokines using aptamers"; Methods; Apr. 2006; pp. 324-330 (p. 1); vol. 38, Issue 4; PubMed; located at: http://www.ncbi.nlm.nih.gov/entrez/query.fcgi?cmd=Retrieve&db=PubMed&list_uids=16495077&dopt=Abstract; printed on Jan. 10, 2007.

Harlow, Ed; Lane, David; Antibodies: A Laboratory Manual; Dec. 1, 1988; 726 pages; ISBN: 0879693142; Cold Spring Harbor Laboratory Press (not provided).

Hatch, A.; Kamholz, A.E.; Hawkins, K.R.; Munson, M.S.; Schilling, E.A.; Weigl, B.H.; Yager, P.; "A rapid diffusion immunoassay in a T-sensor"; "Nature biotechnology"; May 2001; pp. 461-465 (p. 1); vol. 19, Issue 5; PubMed; located at: http://www.ncbi.nlm.nih.gov/entrez/query.fcgi?cmd=Retrieve&db=PubMed&list_uids=11329017&dopt=Abstract; printed on Jan. 9, 2007.

Heo, Y.; Saxon, A.; Hankinson, O.; "Effect of diesel exhaust particles and their components on the allergen-specific IgE and IgG1 response in mice"; Toxicology; Feb. 28, 2001; pp. 143-158 (p. 1); vol. 159, Issue 3; PubMed; located at: http://www.ncbi.nlm.nih.gov/entrez/query.fcgi?cmd=Retrieve&db=PubMed&list_uids=11223170&dopt=Abstract; printed on Jan. 9, 2007.

Herr, Amy E.; Molho, Joshua I.; Santiago, Juan G.; Kenny, Thomas W.; Borkholder, David A.; Kintz, Gregory J.; Belgrader, Phillip; Northrup, M. Allen; "Investigation of a Miniaturized Capillary Isoelectric Focusing (cIEF) System Using a Full-Field Detection Approach"; pp. 1-5; Mechanical Engineering Department, Stanford University.

(56) References Cited

OTHER PUBLICATIONS

"The H-Filter"; H-Filter Basics; Bearing a date of Sep. 7, 2001; pp. 1-7; located at: http://faculty.washington.edu/yagerp/microfluidicstutorial/hfilter/hfilterhome.htm; printed on Jan. 17, 2007.
Jarvius, Jonas; DNA Tools and Microfluidic Systems for Molecular Analysis; Digital Comprehensive Summaries of Uppsala Dissertations from the Faculty of Medicine 161; Bearing a date of 2006; pp. 1-66; ISBN 91-554-6616-8; Acta Universitatis Upsaliensis Uppsala.
Jeon, Noo Li; Dertinger, Stephan K.W.; Chiu, Daniel T.; Choi, Insung S.; Stroock, Abraham D.; Whitesides, George M.; "Generation of Solution and Surface Gradients Using Microfluidic Systems"; Langmuir; 2000; pp. 8311-8316; vol. 16, No. 22; American Chemical Society; located at: http://pubs.acs.org/cgi-bin/abstract.cgi/langd5/2000/16/i22/abs/la000600b.html.
Kameoka, Jun; Craighead, Harold G.; Zhang, Hongwei; Henion, Jack; "A Polymeric Microfluidic Chip for CE/MS Determination of Small Molecules"; Anal. Chem.; 2001; pp. 1935-1941 (p. 1); vol. 73, Issue 9; American Chemical Society; located at: http://pubs.acs.org/cgi-bin/abstract.cgi/ancham/2001/73/i09/abs/ac001533t.html; printed on Jan. 10, 2007.
Kamholz, Andrew E.; Schilling, Eric A.; Yager, Paul; "Optical Measurement of Transverse Molecular Diffusion in a Microchannel"; Biophysical Journal; Apr. 2001; pp. 1967-1972; vol. 80, Issue 4; located at: http://www.biophysj.org/cgi/reprint/80/4/1967.pdf; printed on Jan. 10, 2007.
Khandurina, Julia; McKnight, Timothy E.; Jacobson, Stephen C.; Waters, Larry C.; Foote, Robert S.; Ramsey, J. Michael; "Integrated System for Rapid PCR-Based DNA Analysis in Microfluidic Devices"; Anal. Chem.; Jul. 1, 2000; pp. 2995-3000; vol. 72, No. 13, American Chemical Society.
Kilar, F.; Hjerten, S.; "Fast and high resolution analysis of human serum transferrin by high performance isoelectric focusing in capillaries"; Electrophoresis; Jan. 1989; pp. 23-29 (p. 1); vol. 10, Issue 1; PubMed; located at: http://www.ncbi.nlm.nih.gov/entrez/query.fcgi?cmd=Retrieve&db=PubMed&list_uids=2714234&dopt=Abstract; printed on Jan. 10, 2007.
Kirby, Romy; Cho, Eun Jeong; Gehrke, Brian; Bayer, Travis; Park, Yoon Sok; Neikirk, Dean P.; McDevitt, John T.; Ellington, Andrew D.; "Aptamer-Based Sensor Arrays for the Detection and Quantitation of Proteins"; Anal. Chem.; 2004; pp. 4066-4075 (p. 1); vol. 76, Issue 14; located at: http://pubs.acs.org/cgi-bin/abstract.cgi/ancham/2004/76/i14/abs/ac049858n.html; printed on Jan. 10, 2007.
Koutny, L.; Schmalzing, D.; Salas-Solano, O.; El-Difrawy, S.; Adourian, A.; Buonocore, S.; Abbey, K.; McEwan, P.; Matsudaira, P.; Ehrlich, D.; "Eight Hundred-Base Sequencing in a Microfabricated Electrophoretic Device"; Anal. Chem.; Jul. 15, 2000; pp. 3388-3391 (p. 1); vol. 72, Issue 14; PubMed; located at: http://www.ncbi.nlm.nih.gov/entrez/query.fcgi?cmd=Retrieve&db=PubMed&list_uids=10939418&dopt=Abstract; printed on Jan. 10, 2007.
Lagally, E.T.; Medintz, I.; Mathies, R.A.; "Single-Molecule DNA Amplification and Analysis in an Integrated Microfluidic Device"; Anal. Chem.; 2001; pp. 565-570 (p. 1); vol. 73, Issue 3; located at: http://pubs.acs.org/cgi-bin/abstract.cgi/ancham/2001/73/i03/abs/ac001026b.html; printed on Jan. 10, 2007.
Lee, Gwo-Bin; Chen, Shu-Hui; Huang, Guan-Ruey; Sung, Wang-Chou; Lin, Yen-Heng; "Microfabricated plastic chips by hot embossing methods and their applications for DNA separation and detection"; Sensors and Actuators B: Chemical; Apr. 30, 2001; pp. 142-148 (pp. 1-2); vol. 75, Issues 1-2; Elsevier Science B.V.-ScienceDirect; located at: http://www.sciencedirect.com/science?_ob=ArticleURL&_udi=B6THH-42YW4DG-T&_user=10&_coverDate=04%2F30%2F2001&_alid=526564643&_rdoc=1&_fmt=summary&_orig=search&_cdi=5283&_sort=d&_docanchor=&view=c&_acct=C000050221&_version=1&_urlVersion=0&_userid=10&md5=bfa2c2c46253874c8198955434104969; printed on Jan. 10, 2007.
Liou, Ying-Ming; Chen, Ming-Wei; "Calcium-dependent protein-protein interactions induce changes in proximity relationships of Cys48 and Cys64 in chicken skeletal troponin I"; Eur. J. Biochem.; 2003; pp. 3092-3100; vol. 270; FEBS.
Lovik, M.; Hogseth, A.K.; Gaarder, P.I.; Hagemann, R.; Eide, I.; "Diesel exhaust particles and carbon black have adjuvant activity on the local lymph node response and systemic IgE production to ovalbumin"; Toxicology; Aug. 15, 1997; pp. 165-178 (pp. 1-2); vol. 121, Issue 2; located at: http://www.ncbi.nlm.nih.gov/entrez/query.fcgi?cmd=Retrieve&db=PubMed&list_uids=9230448&dopt=Abstract; printed on Jan. 9, 2007.
Macounova, K.; Cabrera, C.R.; Yager, P.; "Concentration and Separation of Proteins in Microfluidic Channels on the Basis of Transverse IEF"; Anal. Chem.; Apr. 1, 2001; pp. 1627-1633 (p. 1); vol. 73, Issue 7; PubMed; located at: http://www.ncbi.nlm.nih.gov/entrez/query.fcgi?cmd=Retrieve&db=PubMed&list_uids=11321320&dopt=Abstract; printed on Jan. 9, 2007.
Macounova, K.; Cabrera, C.R.; Holl, M.R.; Yager, P.; "Generation of Natural pH Gradients in Microfluidic Channels for Use in Isoelectric Focusing"; Anal. Chem.; Aug. 15, 2000; pp. 3745-3751 (p. 1); vol. 72, Issue 16; PubMed; located at: http://www.ncbi.nlm.nih.gov/entrez/query.fcgi?db=pubmed&cmd=Retrieve&dopt=AbstractPlus&list_uids=10959958&query_hl=5&itool=pubmed_docsum; printed on Jan. 9, 2007.
"Magnetic Fluid"; pp. 1-3; Sigma Hi-Chemical Inc.; located at: http://www.sigma-hc.co.jp/english/magnetic_fluid.html; printed on Jan. 17, 2007.
"Microfluidic Materials: Polymeric Laminate Technology"; Polymeric Laminates; Bearing a date of Sep. 7, 2001; pp. 1-6; located at: http://faculty.washington.edu/yagerp/microfluidicstutorial/polymericlaminates/polymericlaminates.htm; printed on Jan. 17, 2007.
Mondal, K.; Gupta, M.N.; "The affinity concept in bioseparation: evolving paradigms and expanding range of applications"; Biomol Eng.; Jun. 2006; pp. 59-76 (p. 1); vol. 23, Issues 2-3; located at: http://www.ncbi.nlm.nih.gov/entrez/query.fcgi?cmd=Retrieve&db=PubMed&list_uids=16527537&dopt=Abstract; printed on Jan. 10, 2007.
Moritz, R.L.; Simpson, R.J.; "Application of capillary reversed-phase high-performance liquid chromatography to high-sensitivity protein sequence analysis"; J. Chromatogr; May 22, 1992; pp. 119-130 (p. 1); vol. 599, Issues 1-2; located at: http://www.ncbi.nlm.nih.gov/entrez/query.fcgi?cmd=Retrieve&db=PubMed&list_uids=1618985&dopt=Abstract; printed on Jan. 10, 2007.
Nelson, Thomas J.; Backlund, Jr., Peter S.; Yergey, Alfred L.; Alkon, Daniel L.; "Technology: Isolation of Protein Subpopulations Undergoing Protein-Protein Interactions"; Molecular & Cellular Proteomics; Feb. 14, 2002; pp. 253-259; vol. 1, Issue 3; The American Society for Biochemistry and Molecular Biology, Inc.; located at: http://www.mcponline.org/cgi/content/abstract/1/3/253.
O'Connor, T.M.; Sheehan, S.; Cryan, B.; Brennan, N.; Bredin, C.P.; "The ligase chain reaction as a primary screening tool for the detection of culture positive tuberculosis"; Thorax; 2000; pp. 955-957; vol. 55; located at: www.thoraxjnl.com; printed on Jan. 9, 2007.
Salomon, Jesper; Flower, Darren R.; "Research article—Predicting Class II MHC-Peptide binding: a kernel based approach using similarity scores"; BMC Bioinformatics; Nov. 14, 2006; vol. 7, Article No. 501; pp. 1-11; BioMed Central Ltd.; located at: http://www.biomedcentral.com/1471-2105/7/501.
Singh-Zocchi, Mukta; Dixit, Sanhita; Ivanov, Vassili; Zocchi, Giovanni; "Single-Molecule Detection of DNA Hybridization"; PNAS; Jun. 24, 2003; pp. 7605-7610; vol. 100, No. 13; located at: www.pnas.org/cgi/doi/10.1073/pnas.1337215100.
Sohn, L.L.; Saleh, O.A.; Facer, G.R.; Beavis, A.J.; Allan, R.S.; Notterman, D.A.; "Capacitance cytometry: Measuring biological cells one by one"; PNAS; Sep. 26, 2000; pp. 10687-10690; vol. 97, No. 20.
Steffora Mutschler, Ann; "ST Prototypes Medical Diagnostic Chip"; Electronic News: EDN Network; Nov. 30, 2006; pp. 1-6; Reed Business Information—Reed Elsevier Inc.; located at: http://www.edn.com/article/CA6396045.html?ref=nbra; printed on Jan. 24, 2007.
Swiderek, K.M.; Lee, T.D.; Shively, J.E.; Trace Structural Analysis of Proteins; Methods of Enzymology; 1996; pp. 68-86; vol. 271, Spectrum, Publisher Services (not provided).

(56) References Cited

OTHER PUBLICATIONS

Taylor, Richard; Protein Immobilization: Fundamentals and Applications; 1991; 377 pages; ISBN 0824782712; Marcel Dekker, Inc.; New York (not provided).
"The T-Sensor"; Bearing a date of Sep. 7, 2001; pp. 1-5; located at: http://faculty.washington.edu/vagerp/microfluidicstutorial/tsensor/tsensor.htm; printed on Jan. 17, 2007.
Tooley, P.W.; Hatziloukas, E.; Scott, D.L.; Carras, M.M.; "Epidemiology: Use of ligase chain reaction for enhanced detection of *Phytophthora infestans*"; Can. J. Plant Pathol.; 2002; pp. 294-301; vol. 24.
Ulrich, H.; "RNA aptamers: from basic science towards therapy"; Handb. Exp. Pharmacol.; 2006; pp. 305-326 (pp. 1-2); vol. 173; PubMed; located at: http://www.ncbi.nlm.nih.gov/entrez/query.fcgi?cmd=Retrieve&db=PubMed&list_uids=16594622&dopt=Abstract; printed on Jan. 10, 2007.
Walter, G.; Bussow, K.; Lueking, A.; Glokler, J.; "High-throughput protein arrays: prospects for molecular diagnostics"; Trends Mol. Med.; Jun. 2002; pp. 250-253 (p. 1); vol. 8, Issue 6; PubMed; located at: http://www.ncbi.nlm.nih.gov/entrez/query.fcgi?cmd=Retrieve&db=PubMed&list_uids =12067604&dopt=Abstract; printed on Jan. 10, 2007.
Wang, J.; Li, J.; Baca, A.J.; Hu, J.; Zhou, F.; Yan, W.; Pang, D.W.; "Amplified Voltammetric Detection of DNA Hybridization via Oxidation of Ferrocene Caps on Gold Nanoparticle/Streptavidin Conjugates"; Anal. Chem.; Aug. 1, 2003; pp. 3941-3945 (p. 1); vol. 75, No. 15; PubMed; located at: http://www.ncbi.nlm.nih.gov/entrez/query.fcgi?cmd=Retrieve&db=PubMed&list_uids =14572067&dopt—Abstract; printed on Nov. 29, 2006.
Warren, Erin N.; Elms, Phillip J.; Parker, Carol E.; Borchers, Christoph H.; "Development of a Protein Chip: A MS-Based Method for Quantitation of Protein Expression and Modification Levels Using an Immunoaffinity Approach"; Anal. Chem.; 2004; pp. 4082-4092 (p. 1); vol. 76, Issue 14; located at: http://pubs.acs.org/cgi-bin/abstract.cgi/ancham/2004/76/i14/abs/ac049880g.html; printed on Jan. 10, 2007.
Wu, Jiaqi; Pawliszyn, Janusz; "Isoelectric focusing of proteins in a microcapillary with universal concentration gradient detection"; Journal of Microcolumn Separations; 1992; pp. 419-422 (pp. 1-2); vol. 4, Issue 5; located at: http://www3.interscience.wiley.com/cgi-bin/abstract/110429293/ABSTRACT?CRETRY=1&SRETRY=0, printed on Jan. 10, 2007.
Xu, J.; Lee, C.S.; Locascio, L.E.; "Isoelectric focusing of green fluorescent proteins in plastic microfluidic channels"; Abstracts of Papers of the American Chemical Society; 2000; vol. 219, 9-ANYL (not provided).
Yang, Tinglu; Jung, Seung-Yong; Mao, Hanbin; Cremer, Paul S.; "Fabrication of Phospholipid Bilayer-Coated Microchannels for On-Chip Immunoassays"; Anal. Chem.; 2001; pp. 165-169 (p. 1); vol. 73, Issue 2; American Chemical Society; located at: http://pubs.acs.org/cgi-bin/abstract.cgi/ancham/2001/73/i02/abs/ac000997o.html; printed on Jan. 10, 2007.
Yang, Jun; Huang, Ying; Wang, Xiao-Bo; Becker, Frederick F.; Gascoyne, Peter R.C.; "Cell Separation on Microfabricated Electrodes Using Dielectrophoretic/Gravitational Field-Flow Fractionation"; Anal. Chem.; 1999; pp. 911-918 (p. 1); vol. 71, Issue 5; American Chemical Society; located at: http://pubs.acs.org/cgi-bin/abstract.cgi/ancham/1999/71/i05/abs/ac981250p.html; printed on Jan. 10, 2007.
Yang, Peilin; Whelan, Rebecca J.; Mao, Yingwei; Lee, Angel W.M.; Carter-Su, Christin; Kennedy, Robert T.; "Multiplexed Detection of Protein-Peptide Interaction and Inhibition Using Capillary Electrophoresis"; Anal. Chem.; ASAP Article; Bearing a date of Dec. 8, 2006; p. 1; DOI 10.1021/ac061936e S0003-2700(06)01936-6; American Chemical Society; located at: http://pubs.acs.org/cgi-bin/abstract.cgi/ancham/asap/abs/ac061936e.html; printed on Jan. 10, 2007.
"Reasonably priced and battery-driven: a pocket PCR device"; Physorg.com; Bearing a date of Apr. 24, 2007; p. 1; located at: http://www.physorg.com/news96638279.html; printed on Apr. 24, 2007.
U.S. Appl. No. 11/906,170, Jung et al.
U.S. Appl. No. 11/906,124, Jung et al.
U.S. Appl. No. 11/906,171, Jung et al.
U.S. Appl. No. 11/906,168, Jung et al.
U.S. Appl. No. 11/906,143, Jung et al.
U.S. Appl. No. 11/900,660, Jung et al.
U.S. Appl. No. 11/900,649, Jung et al.
U.S. Appl. No. 11/900,637, Jung et al.
U.S. Appl. No. 11/799,462, Jung et al.
U.S. Appl. No. 11/799,465, Jung et al.
U.S. Appl. No. 11/729,301, Jung et al.
U.S. Appl. No. 11/729,276, Jung et al.
U.S. Appl. No. 11/729,275, Jung et al.
U.S. Appl. No. 11/729,274, Jung et al.
Brüssow, Harald; "Phage Therapy: the *Escherichia coli* experience"; Microbiology; 2005; pp. 2133-2140; vol. 151.
Merril, Carl R.; Biswas, Biswajit; Carlton, Richard; Jensen, Nicole C.; Creed, G. Joseph; Zullo, Steve; Adhya, Sankar; "Long-circulating bacteriophage as antibacterial agents"; Proc. Natl. Acad. Sci.; Apr. 1996; pp. 3188-3192; vol. 93.
PCT International Search Report; International App. No. PCT/US2005/033347; Aug. 23, 2006; 4 pages.
PCT International Search Report; International App. No. PCT/US03/41466; Aug. 26, 2004; 2 pages.
PCT International Search Report; International App. No. PCT/US01/09745; Aug. 2, 2001; 1 page.
PCT International Search Report; International App. No. PCT/IL99/00122; Aug. 30, 1999; 2 pages.
"Smart Pillbox Goes Direct to Consumer"; Health Data Management; Bearing dates of Aug. 28, 2007 and Aug. 29, 2007; pp. 1-2; Health Data Management and SourceMedia, Inc.; located at: http://healthdatamanagement.com/html/news/NewsStory.cfm?articleId=15652; printed on Aug. 29, 2007.
Woolley, AT et al.; "Functional integration of PCR amplification and capillary electrophoresis in a microfabricated DNA analysis device"; Anal Chem; Bearing a date of Dec. 1, 1996; pp. 4081-4086 (p. 1); vol. 68, No. 23; PubMed; located at: http://www.ncbi.nlm.nih.gov; printed on Aug. 2, 2007.
Evans et al., "A Computer-Assisted Management Program for Antibiotics and Other Antiinfective Agents"; The New England Journal of Medicine; bearing a date of Jan. 22, 1998; pp. 232-238; vol. 338, No. 4; The Departments of Clinical Epidemiology (R.S.E., S.L.P., D.C. C., J.F.L., J.P.B.), Critical Care (T.P.C., L.K.W., J.F.O..), and Medical Informatics (R.S.E.), LDS Hospital, Salt Lake City, UT.
Lagally et al.; "Integrated Portable Genetic Analysis Microsystem for Pathogen/Infectious Disease Detection"; Analytical Chemistry; bearing a date of Jun. 1, 2004; pp. 3162-3170; vol. 76, No. 11; © 2004 American Chemical Society.
Leibovici et al.; "A Causal Probabilistic Network for Optimal Treatment of Bacterial Infections"; IEEE Transactions on Knowledge and Data Engineering; bearing a date of Jul./Aug. 2000; pp. 517-528; vol. 12, No. 4; © 2000 IEEE.
Datta et al.; "Development of an Integrated Polymer Microfluidic Stack"; International MEMS Conference 2006; Journal of Physics: Conference Series 34; pp. 853-858; Institute of Physics Publishing.
Gelfand, Alexander; "Device Offers a Roadside Dope Test"; Technology Review; Aug. 4, 2009; pp. 1-4; Published by MIT; located at http://wwx.technologyreview.com/biomedicine/23111/; printed on Aug. 10, 2009.
PCT International Search Report; International App. No. PCT/US 08/01256; pp. 1-5; Aug. 12, 2009.
UK Intellectual Property Office Examination Report Under Section 18(3); App. No. GB0915116.8; Sep. 23, 2010; pp. 1-5.
UK Intellectual Property Office Examination Report Under Section 18(3); App. No. GB0915119.2; Oct. 20, 2010; pp. 1-5.

* cited by examiner

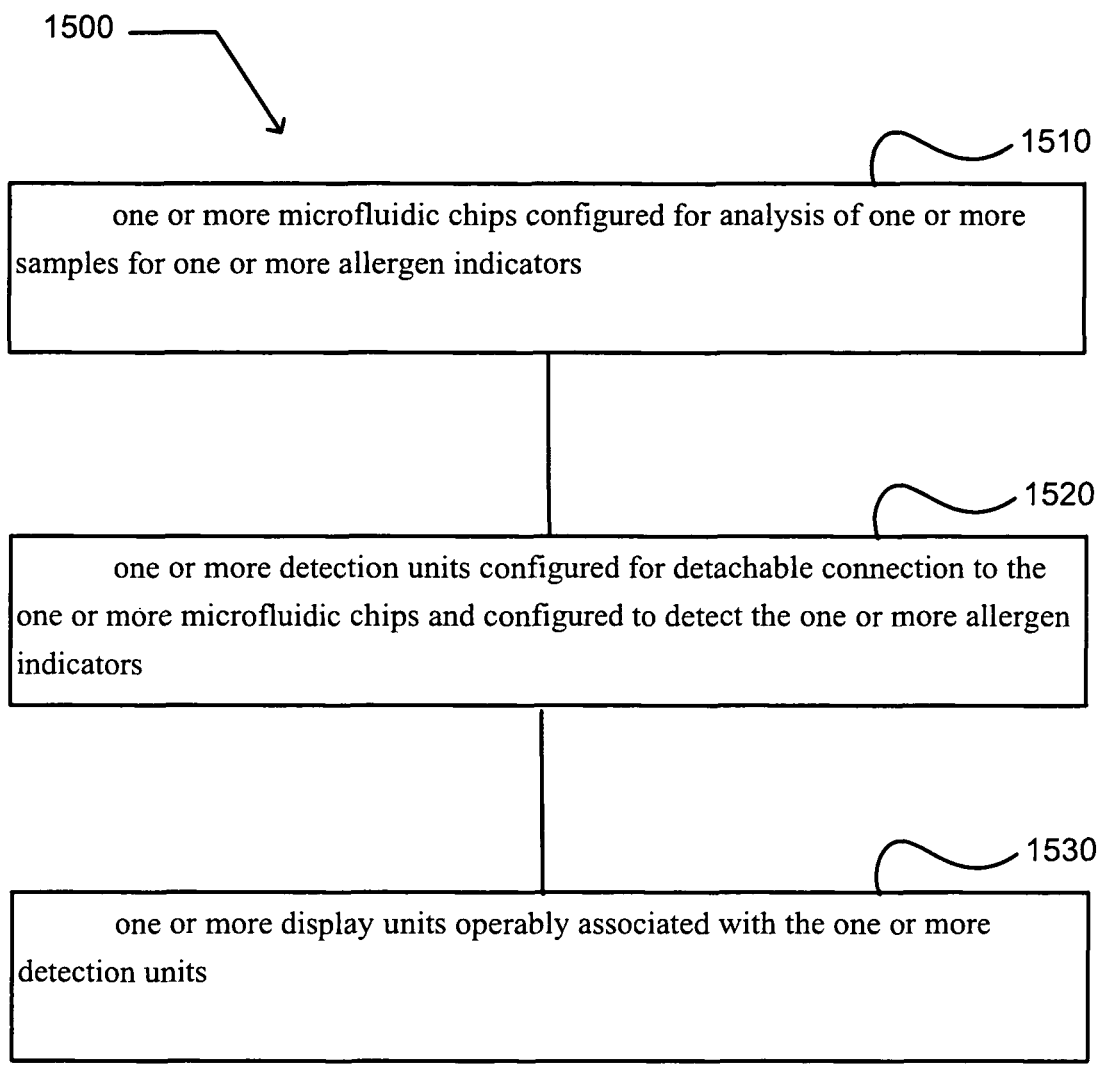

1510 — one or more microfluidic chips configured for analysis of one or more samples for one or more allergen indicators

| 1602 one or more microfluidic chips configured for analysis of the one or more allergen indicators associated with one or more liquids | 1604 one or more microfluidic chips configured for analysis of the one or more allergen indicators associated with one or more solids | 1606 one or more microfluidic chips configured for analysis of the one or more allergen indicators associated with one or more gases | 1608 one or more microfluidic chips configured for analysis of the one or more allergen indicators associated with one or more airborne allergens | 1610 one or more microfluidic chips configured for analysis of the one or more allergen indicators associated with one or more food products |

1520 — one or more detection units configured for detachable connection to the one or more microfluidic chips and configured to detect the one or more allergen indicators 1530 — one or more display units operably associated with the one or more detection units

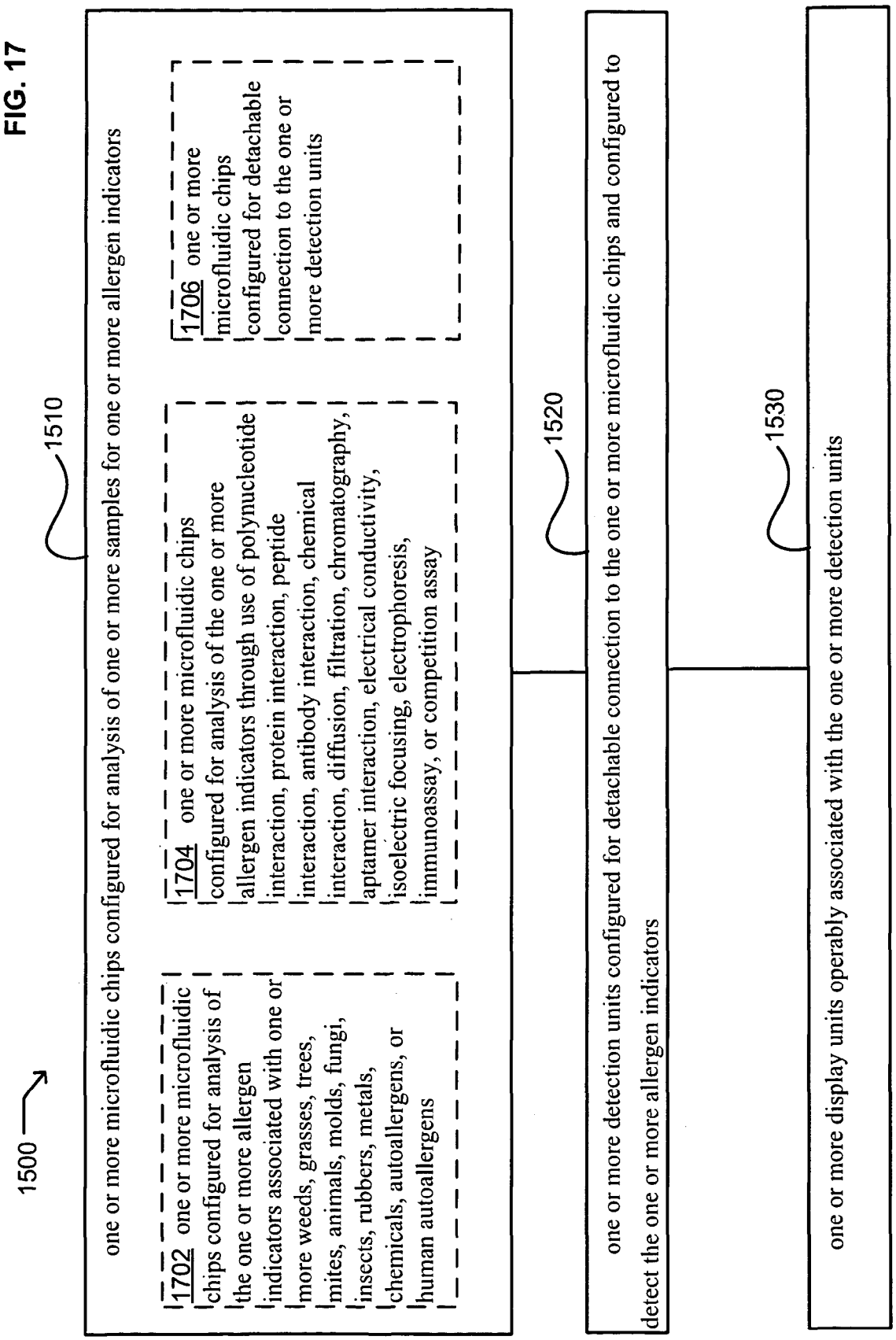

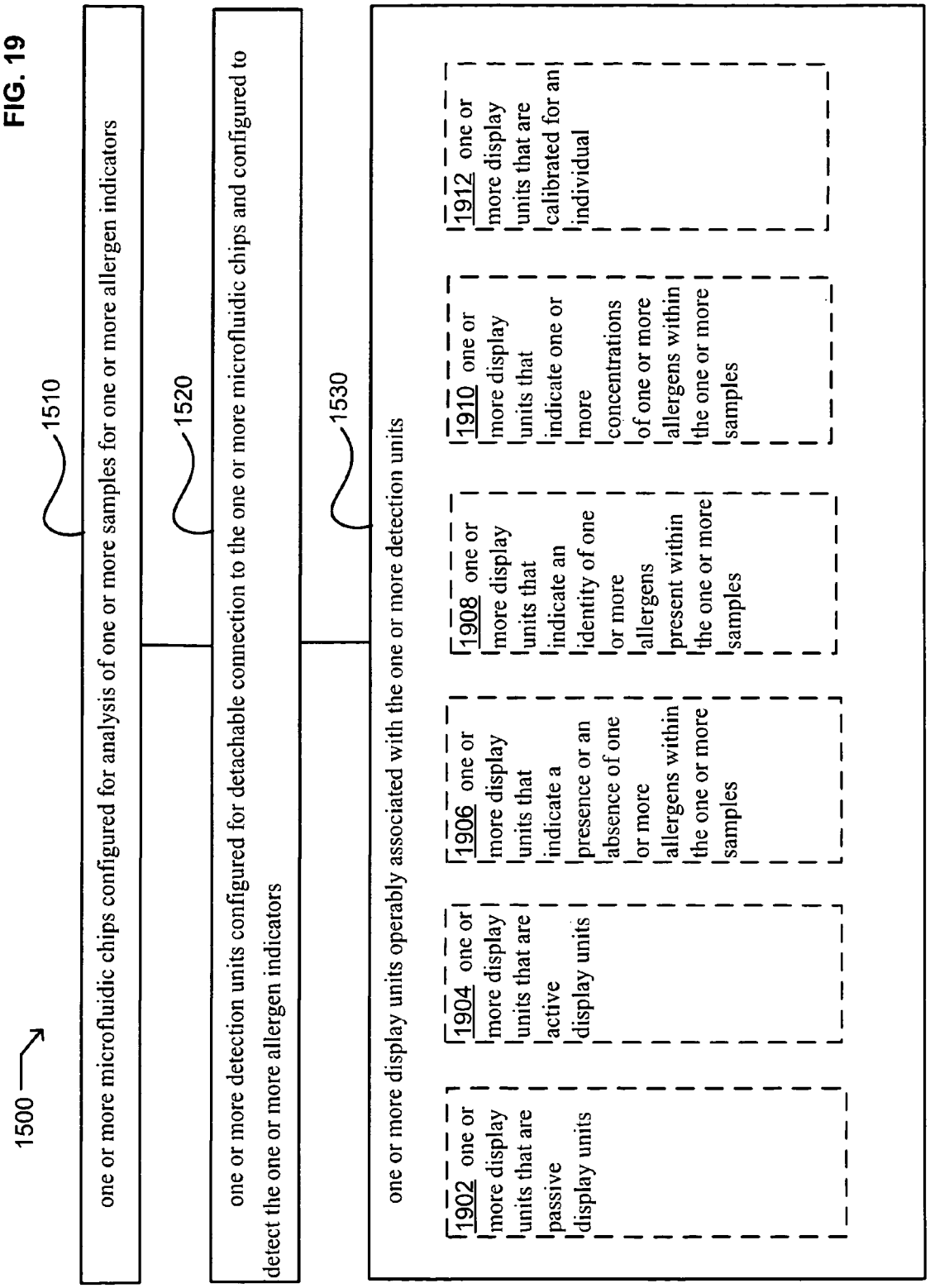

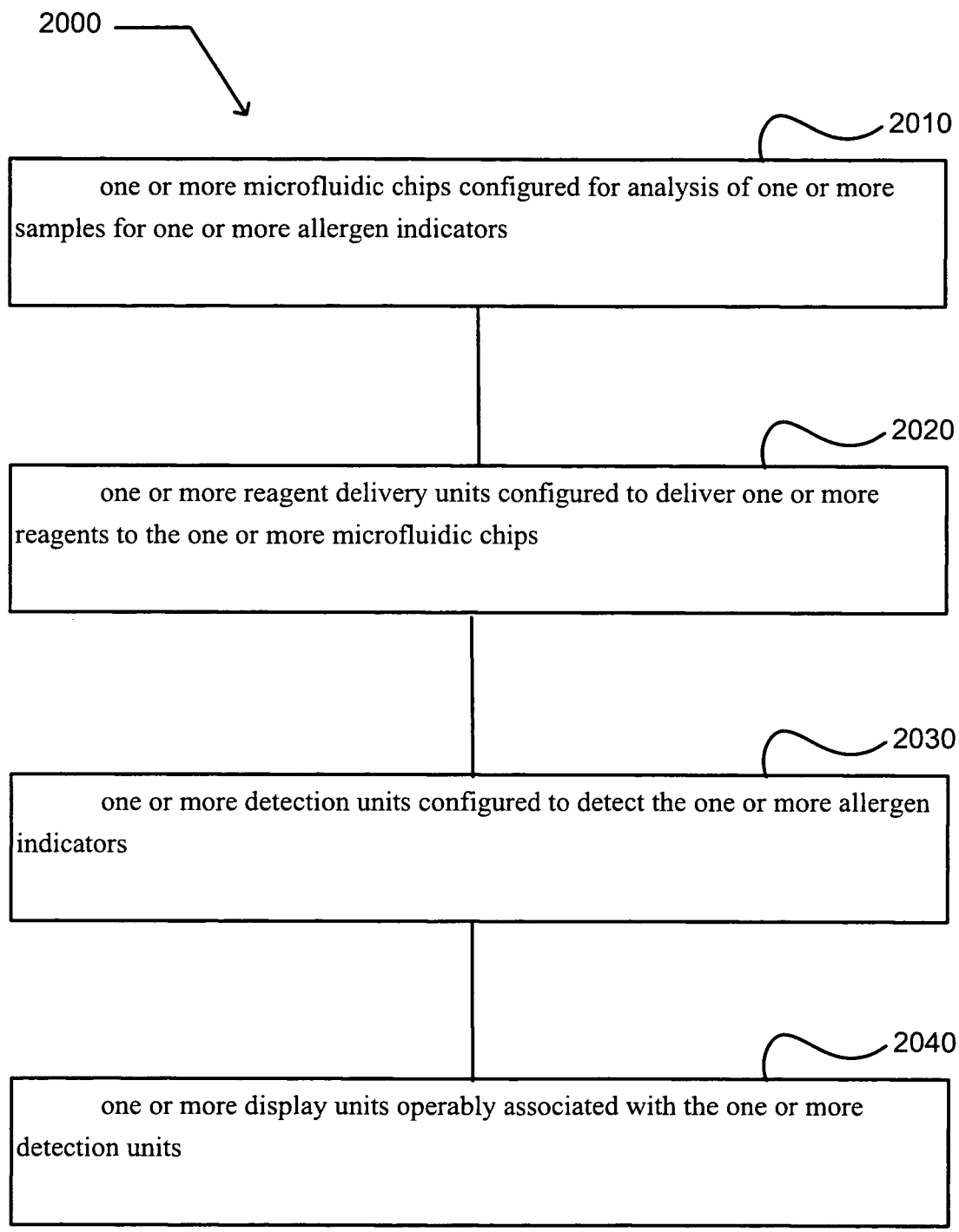

2010 — one or more microfluidic chips configured for analysis of one or more samples for one or more allergen indicators

| 2102 one or more microfluidic chips configured for detachable connection to the one or more detection units | 2104 one or more microfluidic chips configured for detachable connection to the one or more reagent delivery units | 2106 one or more microfluidic chips configured for detachable connection to the one or more detection units and configured for detachable connection to the one or more reagent delivery units | 2108 one or more microfluidic chips configured for analysis of the one or more samples that include one or more liquids | 2110 one or more microfluidic chips configured for analysis of the one or more samples that include one or more solids |

2020 — one or more reagent delivery units configured to deliver one or more reagents to the one or more microfluidic chips 2030 — one or more detection units configured to detect the one or more allergen indicators 2040 — one or more display units operably associated with the one or more detection units

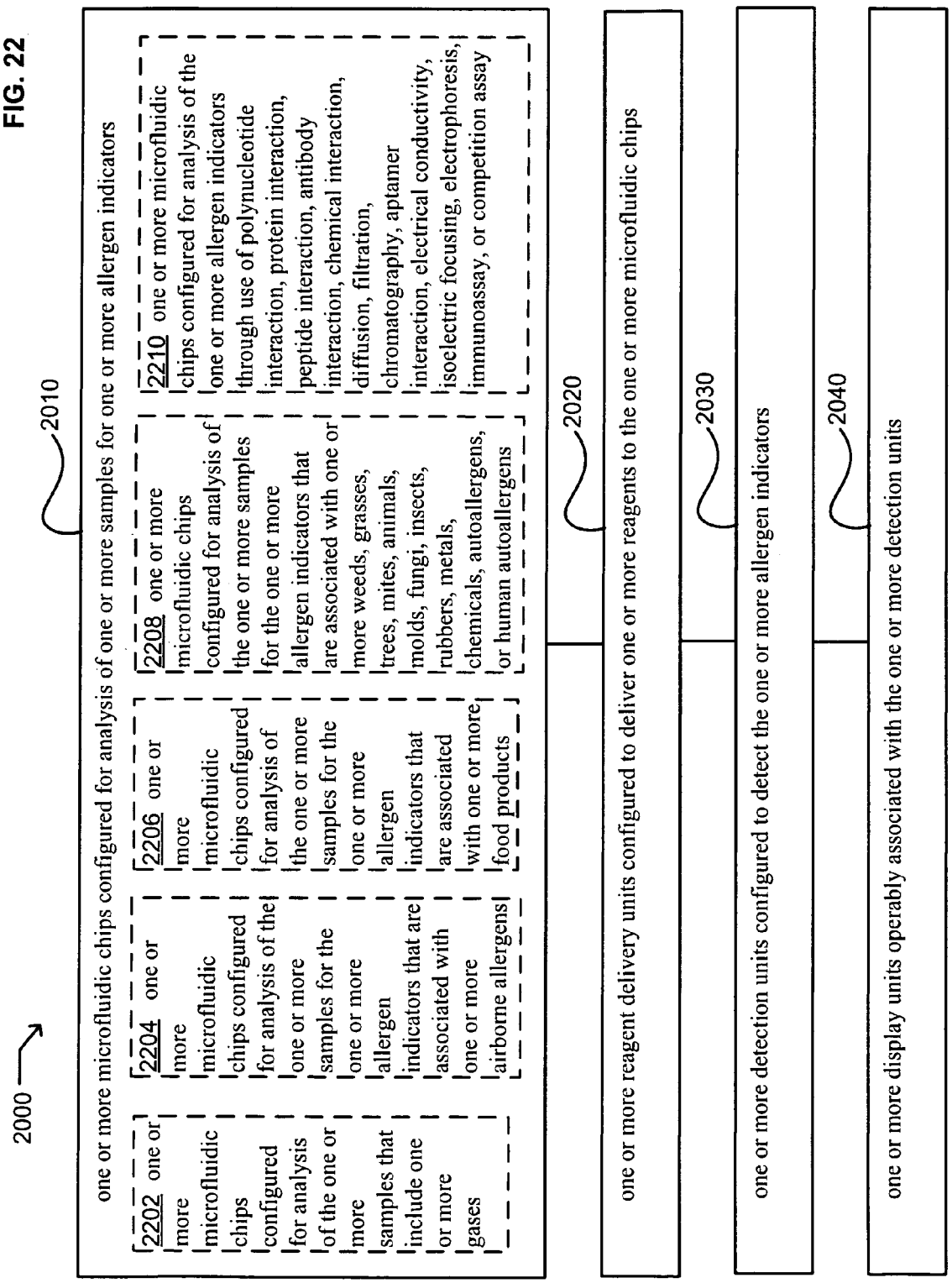

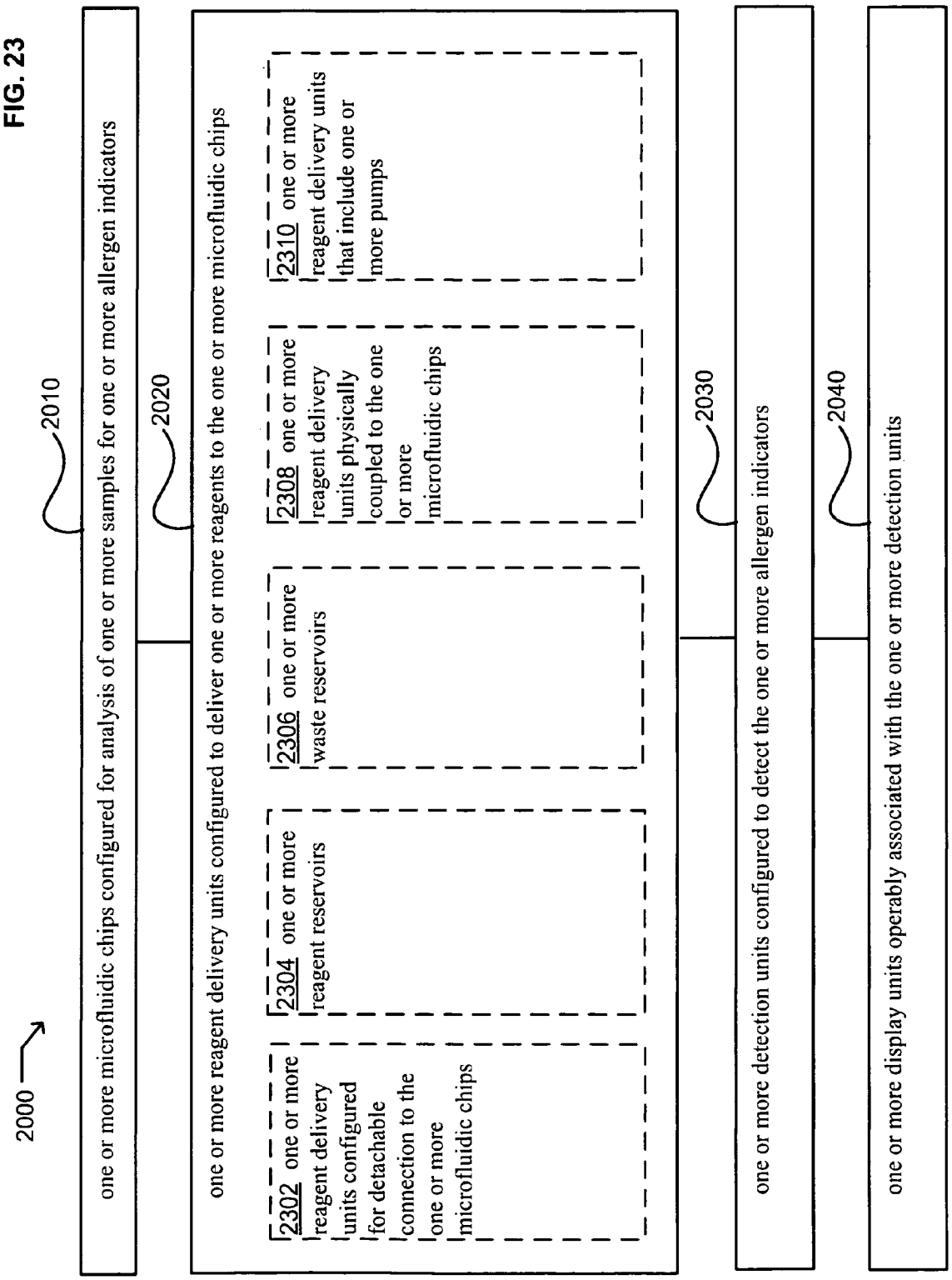

3910 — one or more accepting units that are configured to accept one or more samples associated with one or more food products 4002 one or more accepting units that are configured to accept the one or more samples associated with cod, Atlantic salmon, domestic cattle milk, chicken, shrimp, squid, snail, abalone, frog, oriental mustard, rapeseed, cabbage, turnip, barley, rye, wheat, corn, rice, celery, carrot, hazelnut, strawberry, apple, pear, avocado, apricot, sweet cherry, European plum, almond, peach, asparagus, saffron crocus, lettuce, grape, banana, pineapple, lemon, sweet orange, litchi, yellow mustard, soybean, mung bean, peanut, lentil, pea, kiwi, bell pepper, tomato, potato, Brazil nut, black walnut, English walnut, cashew, castor bean, sesame, muskmelon, Chinese-date, anacardium occidentale, apium graveolens, daucus carota, citrus sinensis, glycine max, lens culinaris, pisum sativum, lycopersicon esculentum, fragaria ananassa, malus domestica, prunus avium, or prunus persica 3920 — one or more analysis units that are configured for analysis of one or more allergen indicators associated with the one or more food products 3930 — one or more display units that are operably associated with the one or more analysis units

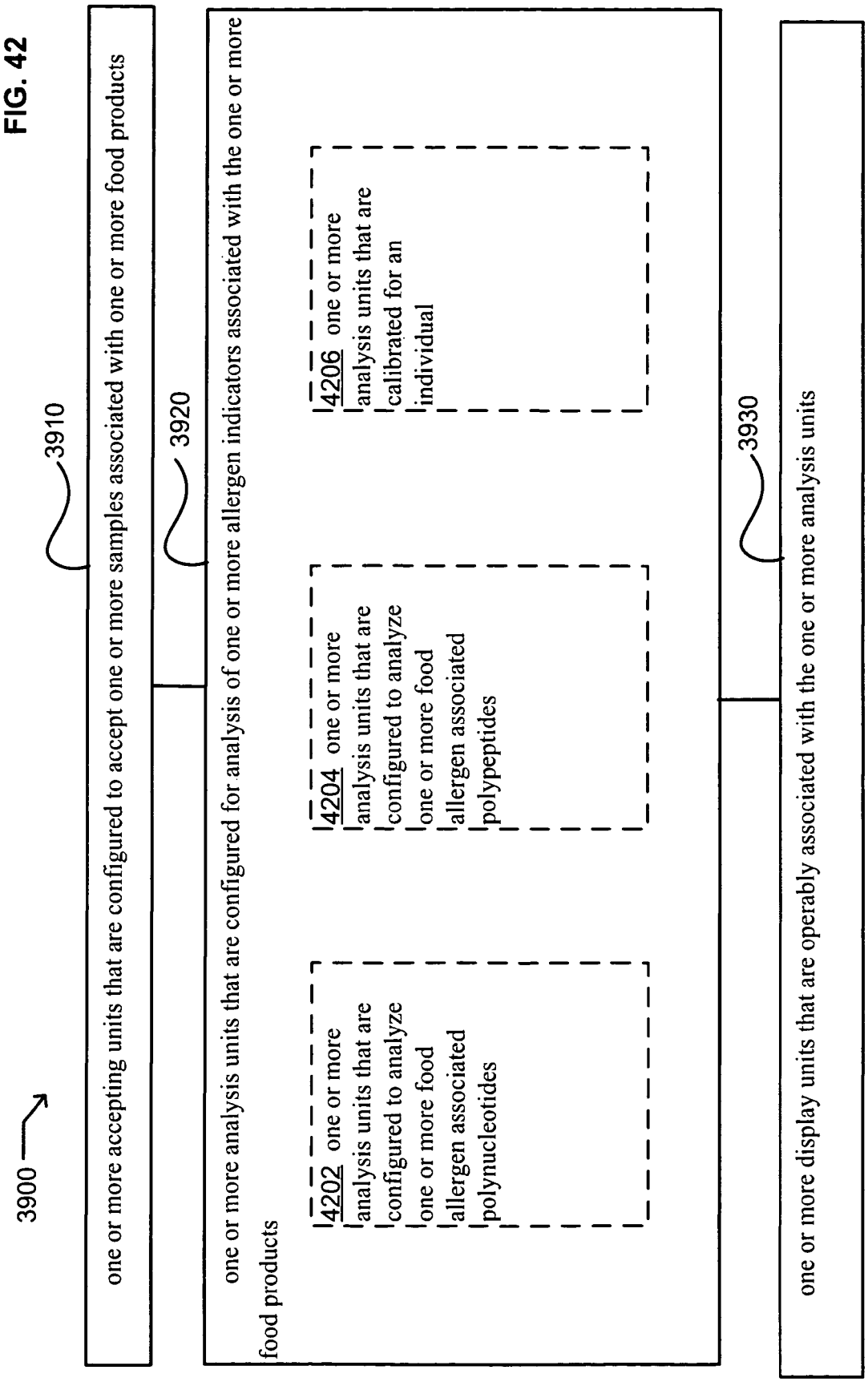

3910 — one or more accepting units that are configured to accept one or more samples associated with one or more food products 3920 — one or more analysis units that are configured for analysis of one or more allergen indicators associated with the one or more food products 3930 — one or more display units that are operably associated with the one or more analysis units

- 4302 one or more display units that include one or more active display units
- 4304 one or more display units that include one or more passive display units
- 4306 one or more display units that indicate a presence or an absence of one or more allergens within the one or more samples
- 4308 one or more display units that indicate an identity of one or more allergens within the one or more samples
- 4310 one or more display units that indicate one or more concentrations of one or more allergens within the one or more samples
- 4312 one or more display units that are calibrated for an individual

FIG. 45

4400 one or more accepting units configured to accept one or more samples — 4410

| 4502 one or more accepting units configured to accept the one or more samples that include one or more liquids | 4504 one or more accepting units configured to accept the one or more samples that include one or more solids | 4506 one or more accepting units configured to accept the one or more samples that include one or more gases | 4508 one or more accepting units configured to accept the one or more samples that include one or more food products | 4510 one or more accepting units configured to accept the one or more samples that are associated with one or more weeds, grasses, trees, mites, animals, molds, fungi, insects, rubbers, metals, chemicals, autoallergens, or human autoallergens | one or more reagent inputs configured to accept one or more reagents — 4420 one or more analysis units configured for analysis of the one or more samples for one or more allergen indicators — 4430 one or more display units that are operably associated with the one or more analysis units — 4440

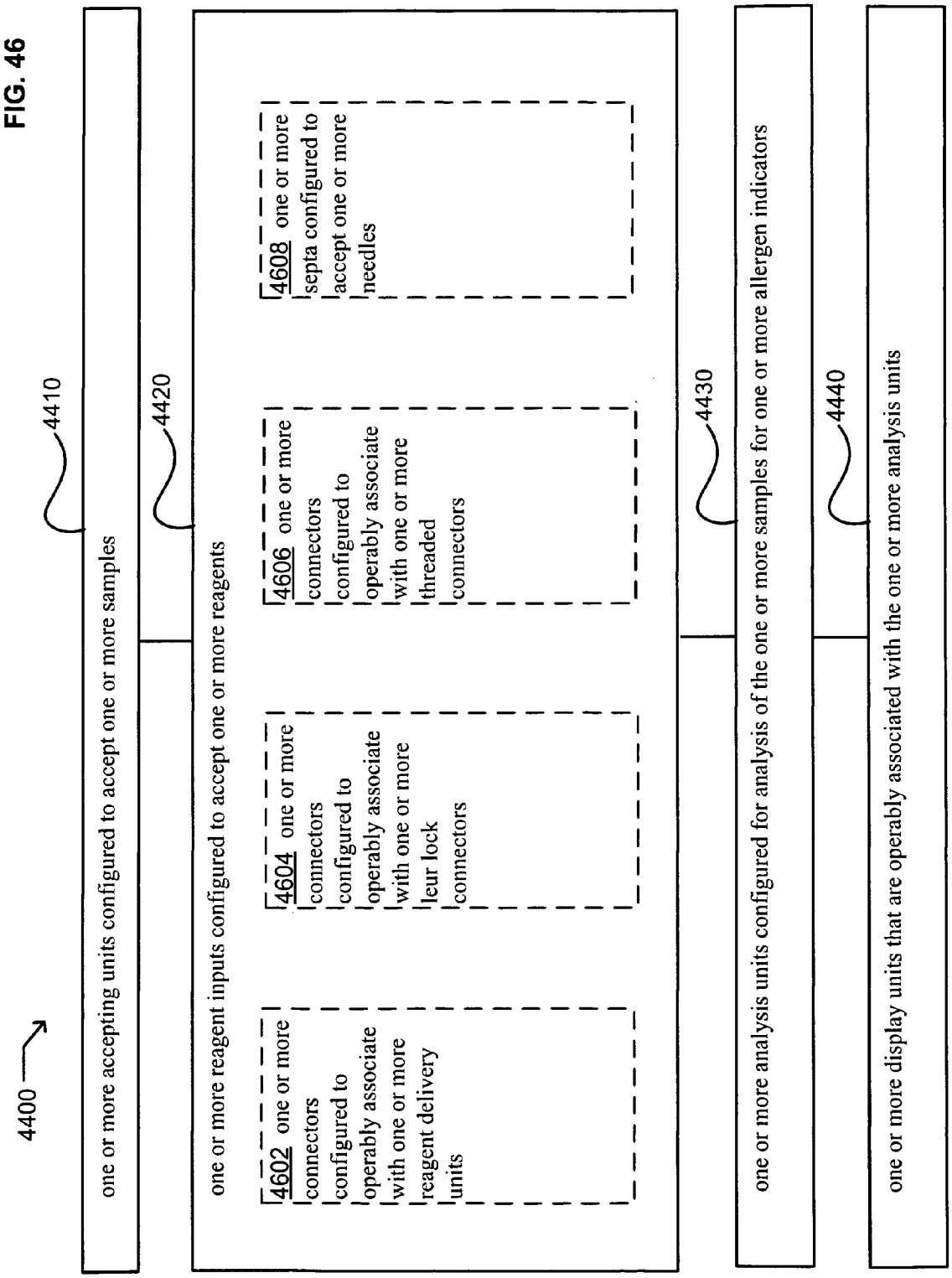

5110 — one or more detection units configured to detachably connect to one or more microfluidic chips and configured to detect one or more allergen indicators that are associated with one or more allergens

| 5202 one or more detection units configured to detect the one or more allergen indicators that are associated with one or more allergens that are airborne | 5204 one or more detection units configured to detect the one or more allergen indicators that are associated with one or more food products | 5206 one or more detection units configured to detect the one or more allergen indicators that are associated with one or more weeds, grasses, trees, mites, animals, molds, fungi, insects, rubbers, metals, chemicals, autoallergens, or human autoallergens | 5208 one or more detection units that are calibrated for an individual |

5120 — one or more display units operably associated with the one or more detection units

5110 — one or more detection units configured to detachably connect to one or more microfluidic chips and configured to detect one or more allergen indicators that are associated with one or more allergens 5120 — one or more display units operably associated with the one or more detection units

| 5302 one or more display units that are passive display units | 5304 one or more display units that are active display units | 5306 one or more display units that indicate a presence or an absence of the one or more allergens within one or more samples | 5308 one or more display units that indicate an identity of the one or more allergens present within one or more samples | 5310 one or more display units that indicate one or more concentrations of the one or more allergens within one or more samples | 5312 one or more display units that are calibrated for an individual |

5410 — one or more reagent delivery units that are configured to operably associate with one or more microfluidic chips and provide one or more reagents to the one or more microfluidic chips 5502 one or more reagent delivery units configured for detachable connection to the one or more microfluidic chips 5504 one or more reagent reservoirs 5506 one or more waste reservoirs 5508 one or more reagent delivery units physically coupled to the one or more detection units 5510 one or more reagent delivery units that include one or more pumps 5420 — one or more detection units configured to detachably associate with the one or more microfluidic chips and configured to detect one or more allergen indicators 5430 — one or more display units that are operably associated with the one or more detection units

5410 — one or more reagent delivery units that are configured to operably associate with one or more microfluidic chips and provide one or more reagents to the one or more microfluidic chips 5420 — one or more detection units configured to detachably associate with the one or more microfluidic chips and configured to detect one or more allergen indicators

| 5602 one or more detection units configured to detect the one or more allergen indicators that are associated with one or more allergens that are airborne | 5604 one or more detection units configured to detect the one or more allergen indicators that are associated with one or more food products | 5606 one or more detection units configured to detect the one or more allergen indicators that are associated with one or more weeds, grasses, trees, mites, animals, molds, fungi, insects, rubbers, metals, chemicals, autoallergens, or human autoallergens | 5608 one or more detection units configured to detect the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay | 5610 one or more detection units that are calibrated for an individual |

5430 — one or more display units that are operably associated with the one or more detection units

5410 — one or more reagent delivery units that are configured to operably associate with one or more microfluidic chips and provide one or more reagents to the one or more microfluidic chips 5420 — one or more detection units configured to detachably associate with the one or more microfluidic chips and configured to detect one or more allergen indicators 5430 — one or more display units that are operably associated with the one or more detection units

| 5702 one or more display units that are passive display units | 5704 one or more display units that are active display units | 5706 one or more display units that indicate a presence or an absence of one or more allergens within one or more samples | 5708 one or more display units that indicate an identity of one or more allergens present within one or more samples | 5710 one or more display units that indicate one or more concentrations of one or more allergens within one or more samples | 5712 one or more display units that are calibrated for an individual |

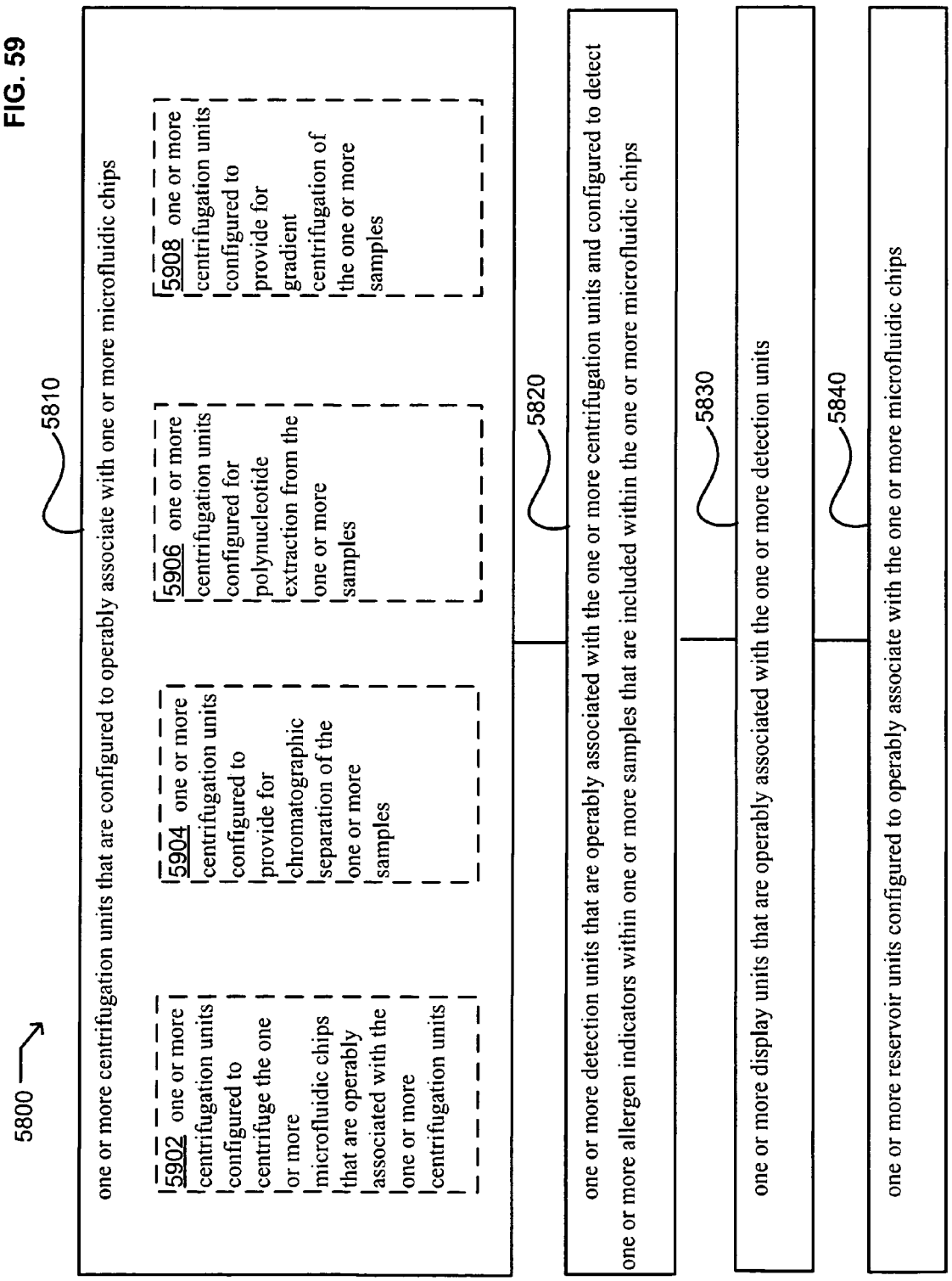

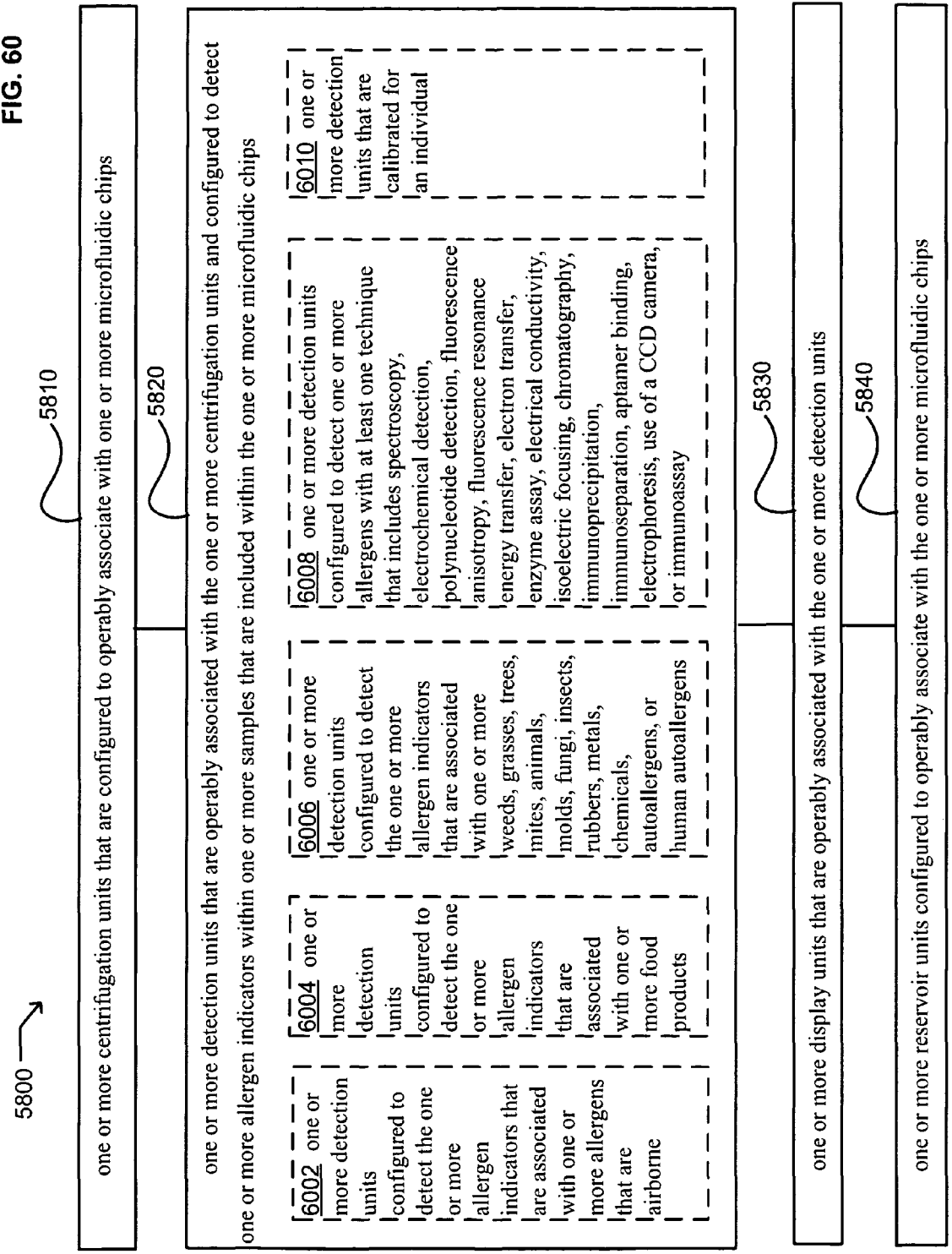

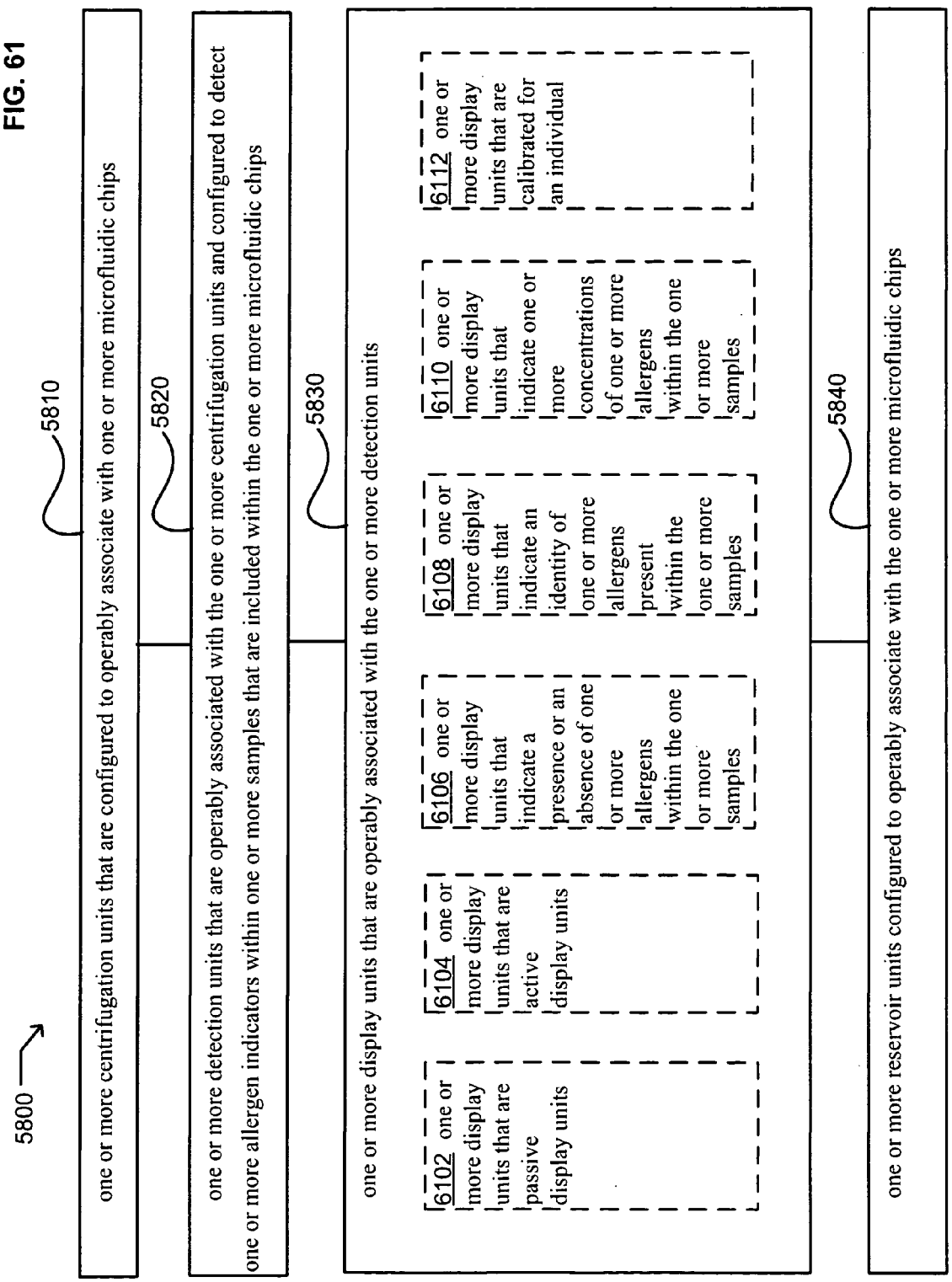

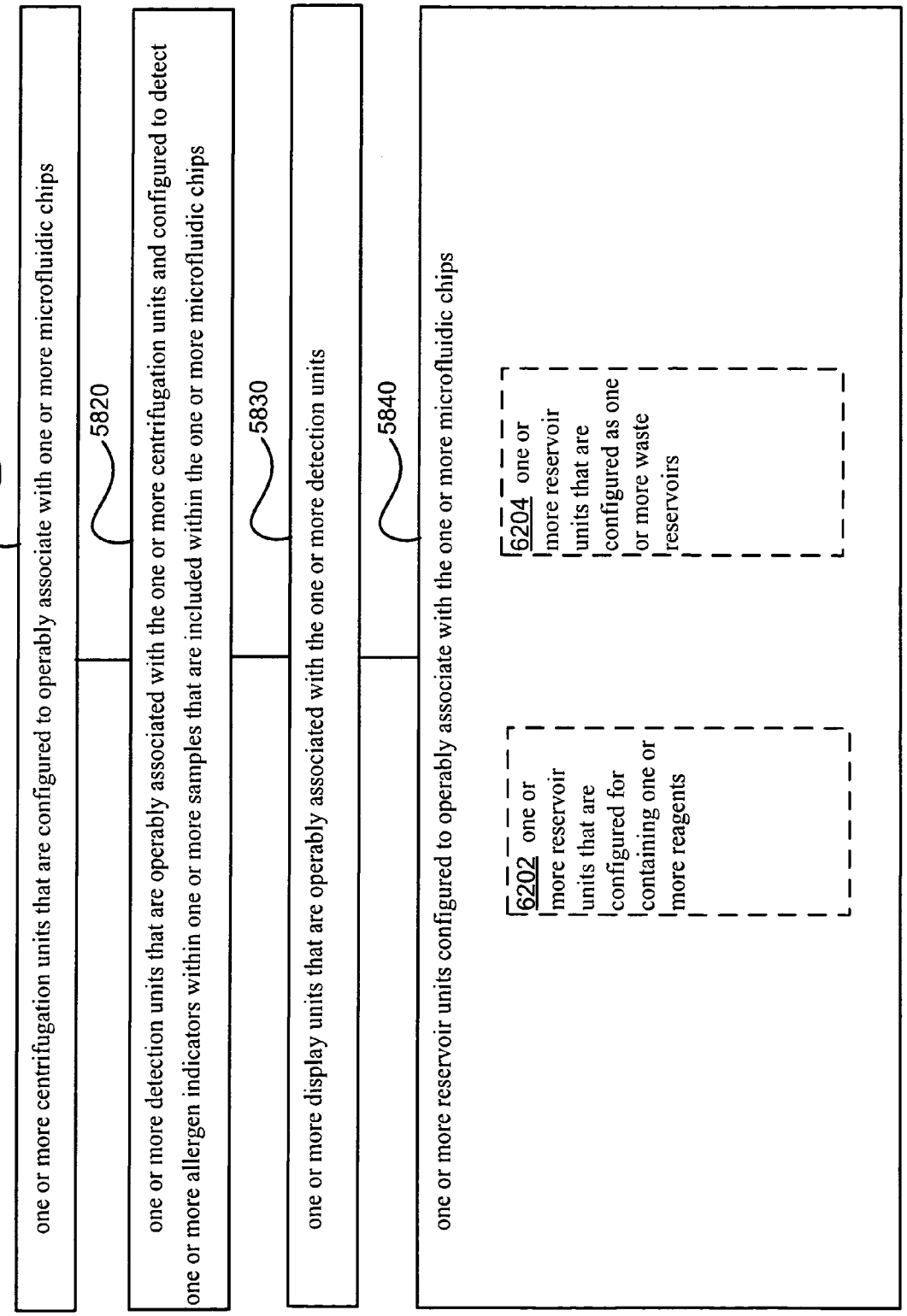

METHODS FOR ALLERGEN DETECTION

TECHNICAL FIELD

The present disclosure relates to methods that may be used for detection of one or more allergens.

SUMMARY

In some embodiments one or more methods are provided that include processing one or more samples with one or more microfluidic chips configured for analysis of one or more allergen indicators and detecting the one or more allergen indicators with one or more detection units that are operably associated with the one or more microfluidic chips. The method may optionally include displaying results of the detecting with one or more display units that are operably associated with the one or more detection units. In addition to the foregoing, other aspects are described in the claims, drawings, and text forming a part of the present disclosure.

In some embodiments one or more methods are provided that include detecting one or more allergen indicators with one or more detection units that are configured to detachably connect to one or more microfluidic chips that are configured for analysis of the one or more allergen indicators and displaying results of the detecting with one or more display units that are operably associated with the one or more detection units. The method may optionally include processing one or more samples with the one or more microfluidic chips that are configured for analysis of the one or more allergen indicators. In addition to the foregoing, other aspects are described in the claims, drawings, and text forming a part of the present disclosure.

In some embodiments one or more methods are provided that include processing one or more samples with one or more microfluidic chips that are configured for analysis of one or more allergen indicators, detecting the one or more allergen indicators with one or more detection units that are operably associated with the one or more microfluidic chips, and displaying results of the detecting with one or more display units that are operably associated with the one or more detection units. In addition to the foregoing, other aspects are described in the claims, drawings, and text forming a part of the present disclosure.

In some embodiments one or more methods are provided that include processing one or more samples with one or more microfluidic chips that are configured for analysis of one or more allergen indicators and extracting the one or more allergen indicators from the one or more samples with the one or more microfluidic chips. The method may optionally include detecting the one or more allergen indicators with one or more detection units. The method may optionally include displaying results of the detecting with one or more display units. In addition to the foregoing, other aspects are described in the claims, drawings, and text forming a part of the present disclosure.

In some embodiments one or more systems are provided that include one or more microfluidic chips configured for analysis of one or more samples for one or more allergen indicators and one or more detection units configured for detachable connection to the one or more microfluidic chips and configured to detect the one or more allergen indicators. The system may optionally include one or more display units operably associated with the one or more detection units. In addition to the foregoing, other aspects are described in the claims, drawings, and text forming a part of the present disclosure.

In some embodiments one or more systems are provided that include one or more microfluidic chips configured for analysis of one or more samples for one or more allergen indicators and one or more reagent delivery units configured to deliver one or more reagents to the one or more microfluidic chips. The system may optionally include one or more detection units configured to detect the one or more allergen indicators. The system may optionally include one or more display units operably associated with the one or more detection units. In addition to the foregoing, other aspects are described in the claims, drawings, and text forming a part of the present disclosure.

In some embodiments one or more systems are provided that include one or more microfluidic chips configured for analysis of one or more samples for one or more allergen indicators, one or more centrifugation units configured to operably associate with the one or more microfluidic chips, and one or more detection units operably associated with the one or more microfluidic chips. The system may optionally include one or more display units operably associated with the one or more detection units. The system may optionally include one or more reservoir units that are operably associated with the one or more microfluidic chips. In addition to the foregoing, other aspects are described in the claims, drawings, and text forming a part of the present disclosure.

In some embodiments one or more microfluidic chips are provided that include one or more accepting units configured to accept one or more samples and one or more analysis units configured for analysis of one or more allergen indicators associated with the one or more samples. The microfluidic chips may optionally include one or more display units that are operably associated with the one or more analysis units. In addition to the foregoing, other aspects are described in the claims; drawings, and text forming a part of the present disclosure.

In some embodiments one or more microfluidic chips are provided that include one or more accepting units that are configured to accept one or more samples associated with one or more food products and one or more analysis units that are configured for analysis of one or more allergen indicators associated with the one or more food products. The microfluidic chips may optionally include one or more display units that are operably associated with the one or more analysis units. In addition to the foregoing, other aspects are described in the claims, drawings, and text forming a part of the present disclosure.

In some embodiments one or more microfluidic chips are provided that include one or more accepting units configured to accept one or more samples, one or more reagent inputs configured to accept one or more reagents, and one or more analysis units configured for analysis of the one or more samples for one or more allergen indicators. The microfluidic chips may optionally include one or more display units that are operably associated with the one or more analysis units. In addition to the foregoing, other aspects are described in the claims, drawings, and text forming a part of the present disclosure.

In some embodiments one or more devices are provided that include one or more detection units configured to detachably connect to one or more microfluidic chips and configured to detect one or more allergen indicators that are associated with one or more allergens. The device may optionally include one or more display units operably associated with the one or more detection units. In addition to the foregoing, other aspects are described in the claims, drawings, and text forming a part of the present disclosure.

In some embodiments one or more devices are provided that include one or more reagent delivery units that are configured to operably associate with one or more microfluidic chips and provide one or more reagents to the one or more microfluidic chips and one or more detection units configured to detachably associate with the one or more microfluidic chips and configured to detect one or more allergen indicators. The device may optionally include one or more display units that are operably associated with the one or more detection units. In addition to the foregoing, other aspects are described in the claims, drawings, and text forming a part of the present disclosure.

In some embodiments one or more devices are provided that include one or more centrifugation units that are configured to operably associate with one or more microfluidic chips and one or more detection units that are operably associated with the one or more centrifugation units and configured to detect one or more allergen indicators within one or more samples that are included within the one or more microfluidic chips. The device may optionally include one or more display units that are operably associated with the one or more detection units. The device may optionally include one or more reservoir units configured to operably associate with the one or more microfluidic chips. In addition to the foregoing, other aspects are described in the claims, drawings, and text forming a part of the present disclosure.

In some embodiments, means include but are not limited to circuitry and/or programming for effecting the herein-referenced functional aspects; the circuitry and/or programming can be virtually any combination of hardware, software, and/or firmware configured to effect the herein-referenced functional aspects depending upon the design choices of the system designer. In addition to the foregoing, other system aspects means are described in the claims, drawings, and/or text forming a part of the present disclosure.

In some embodiments, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects, embodiments, and features will become apparent by reference to the drawings, claims, and the following detailed description.

BRIEF DESCRIPTION OF THE FIGURES

FIG. 15 illustrates an example system 1500 in which embodiments may be implemented.

FIG. 16 illustrates alternate embodiments of the system of FIG. 15.

FIG. 17 illustrates alternate embodiments of the system of FIG. 15.

FIG. 19 illustrates alternate embodiments of the system of FIG. 15.

FIG. 20 illustrates an example system 2000 in which embodiments may be implemented.

FIG. 21 illustrates alternate embodiments of the system of FIG. 20.

FIG. 22 illustrates alternate embodiments of the system of FIG. 20.

FIG. 23 illustrates alternate embodiments of the system of FIG. 20.

FIG. 40 illustrates alternate embodiments of the microfluidic chip of FIG. 39.

FIG. 42 illustrates alternate embodiments of the microfluidic chip of FIG. 39.

FIG. 43 illustrates alternate embodiments of the microfluidic chip of FIG. 39.

FIG. 45 illustrates alternate embodiments of the microfluidic chip of FIG. 44.

FIG. 46 illustrates alternate embodiments of the microfluidic chip of FIG. 44.

FIG. 52 illustrates alternate embodiments of the device of FIG. 51.

FIG. 53 illustrates alternate embodiments of the device of FIG. 51.

FIG. 55 illustrates alternate embodiments of the device of FIG. 54.

FIG. 56 illustrates alternate embodiments of the device of FIG. 54.

FIG. 57 illustrates alternate embodiments of the device of FIG. 54.

FIG. 59 illustrates alternate embodiments of the device of FIG. 58.

FIG. 60 illustrates alternate embodiments of the device of FIG. 58.

FIG. 61 illustrates alternate embodiments of the device of FIG. 58.

FIG. 62 illustrates alternate embodiments of the device of FIG. 58.

DETAILED DESCRIPTION

Figure 1:
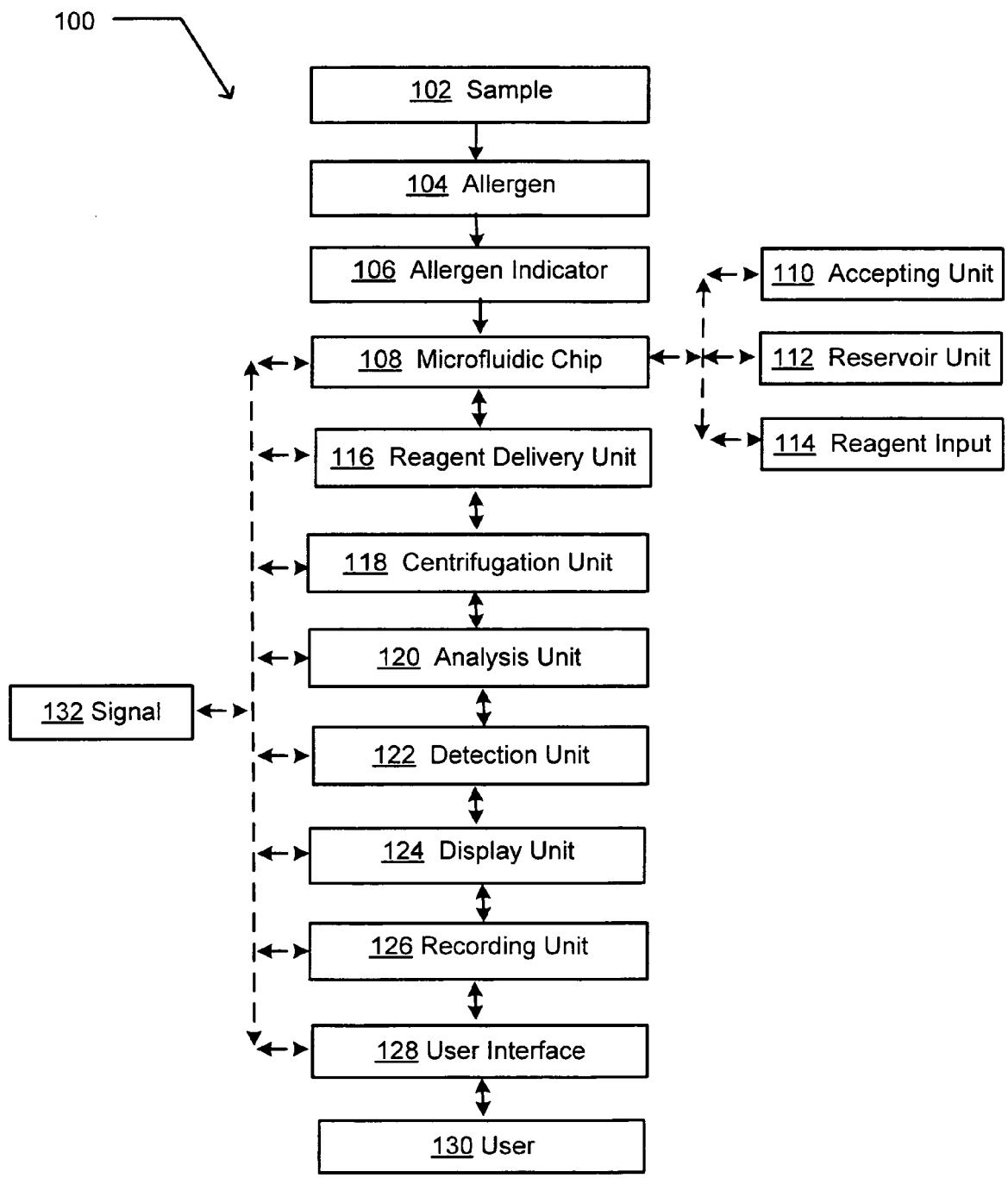
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates an example system 100 in which embodiments may be implemented. In some embodiments, the system 100 is operable to provide a method that may be used to analyze one or more allergens 104. In some embodiments, one or more samples 102 may be processed with one or more microfluidic chips 108 that are configured to process one or more allergens 104. In some embodiments, one or more samples 102 associated with an individual may be processed. In some embodiments, one sample 102 associated with an individual may be processed. In some embodiments, one or more microfluidic chips 108 may be used to process one or more samples 102. In some embodiments, one microfluidic chip 108 may be used to process one or more samples 102. In some embodiments, one or more microfluidic chips 108 may be used to process one or more allergens 104. In some embodiments, one or more microfluidic chips 108 may be used to process one allergen 104. In some embodiments, one or more microfluidic chips 108 may include one or more accepting units 110. In some embodiments, one or more microfluidic chips 108 may include one or more reservoir units 112. In some embodiments, one or more microfluidic chips 108 may include one or more reagent inputs 114. In some embodiments, one or more microfluidic chips 108 may be configured to operably associate with one or more reagent delivery units 116. In some embodiments, one or more microfluidic chips 108 may be configured to operably associate with one or more centrifugation units 118. In some embodiments, one or more microfluidic chips 108 may be configured to operably associate with one or more analysis units 120. In some embodiments, one or more microfluidic chips 108 may be configured to operably associate with one or more detection units 122. In some embodiments, one or more microfluidic chips 108 may be configured to operably associate with one or more display units 124. In some embodiments, one or more microfluidic chips 108 may be configured to operably associate with one or more recording units 126. In some embodiments, one or more microfluidic chips 108 may receive one or more signals 132. In some embodiments, one or more microfluidic chips 108 may transmit one or more signals 132. In some embodiments, one or more detection units 122 may be used to detect one or more allergens 104. In some embodiments, one detection unit 122 may be used to detect one or more allergens 104. In some embodiments, one or more detection units 122 may be used to detect one or more allergen indicators 106. In some embodiments, one or more detection units 122 may be portable detection units 122. In some embodiments, one or more detection units 122 may be non-portable detection units 122. In some embodiments, one or more detection units 122 may be hand-held detection units 122. In some embodiments, one or more detection units 122 may include one or more user interfaces 128. In some embodiments, one or more detection units 122 may include one user interface 128. In some embodiments, one or more detection units 122 may include one or more user interfaces 128 that are directly coupled with the one or more detection units 122. In some embodiments, one or more detection units 122 may include one or more user interfaces 128 that are remotely coupled with the one or more detection units 122. For example, in some embodiments, a user 130 may interact with the one or more detection units 122 through direct physical interaction with the one or more detection units 122. In other embodiments, a user 130 may interact with one or more detection units 122 through remote interaction. In some embodiments, one or more detection units 122 may transmit one or more signals 132. In some embodiments, one or more detection units 122 may receive one or more signals 132. In some embodiments, one or more detection units 122 may include one or more display units 124. In some embodiments, one or more detection units 122 may be directly coupled to one or more display units 124. In some embodiments, one or more detection units 122 may be remotely coupled to one or more display units 124. In some embodiments, one or more detection units 122 may transmit one or more signals 132 that are received by one or more display units 124. In some embodiments, one or more display units 124 may include one or more user interfaces 128. In some embodiments, one or more display units 124 may include one user interface 128. In some embodiments, one or more display units 124 may transmit one or more signals 132. In some embodiments, one or more display units 124 may receive one or more signals 132. In some embodiments, system 100 may include one or more recording units 126. In some embodiments, one or more recording units 126 may be directly coupled to one or more detection units 122. In some embodiments, one or more recording units 126 may be directly coupled to one or more display units 124. In some embodiments, one or more recording units 126 may be directly coupled to one or more detection units 122 and one or more display units 124. In some embodiments, one or more recording units 126 may include one or more user interfaces 128. In some embodiments, one or more recording units 126 may include one or more directly coupled user interfaces 128. In some embodiments, one or more recording units 126 may include one or more remotely coupled user interfaces 128. In some embodiments, one or more recording units 126 may receive one or more signals 132. In some embodiments, one or more recording units 126 may transmit one or more signals 132.

Sample

Numerous types of samples 102 may be analyzed through use of system 100. In some embodiments, one or more samples 102 may be associated with an individual. In some embodiments, one or more samples 102 may include a liquid. In some embodiments, one or more samples 102 may include a solid. In some embodiments, one or more samples 102 may include a vapor. In some embodiments, one or more samples 102 may include a semi-solid. In some embodiments, one or more samples 102 may include a gas. Examples of such samples 102 include, but are not limited to, air, water, food, food products, solids, samples 102 obtained from animals, samples 102 that are associated with, but not limited to, one or more weeds, grasses, trees, mites, animals, molds, fungi, insects, rubbers, metals, chemicals, autoallergens, human autoallergens, or substantially any combination thereof.

Allergen Indicator

Numerous allergen indicators 106 may be processed, analyzed and/or detected through use of system 100. In some embodiments, allergen indicators 106 include allergens 104 and components of allergens 104. For example, in some embodiments, allergen indicators 106 may include polynucleotides and/or polypeptides that are associated with an allergen 104. In some embodiments, allergen indicators 106 may include one or more products of an allergen 104. For example, in some embodiments, allergen indicators 106 may include byproducts of cooking a food allergen 104. In some embodiments, allergen indicators 106 may include products and/or substrates that are associated with the activity of one or more allergen 104 associated enzymes. In some embodiments, allergen indicators 106 may include compounds and/or particles that exhibit an adjuvant effect with regard to one or more allergens 104. For example, diesel exhaust particles are known to increase allergic responses to allergens 104 (e.g., Heo et al., Toxicology, 159:143-158 (2001); Lovik et al., Toxicology, 121:165-178 (1997)). Examples of allergen indicators 106 that may be processed, analyzed and/or detected through use of system 100 include, but are not limited to, allergen indicators 106 that are associated with one or more weeds, grasses, trees, mites, animals, molds, fungi, insects, rubbers, metals, autoallergens, human autoallergens, metals, chemicals (e.g., drugs) or substantially any combination thereof (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants).

Examples of weed associated allergen indicators 106 include, but are not limited to, short ragweed (Amba1, Amba2, Amba3, Amba5, Amba6, Amba7, Amba8, Amba9, Amba10); giant ragweed (Ambt5); mugwort (Artv1, Artv2, Artv3, Artv4, Artv5, Artv6); sunflower (Hela1, Hela2, Hela3); *Mercurialis annua* (Mera1); lamb's-quarters, pigweed (Chea1); white goosefoot (Chea2, Chea3); Russian-thistle (Salk1); Rosy periwinkle (Catr1); English plantain (Plal1); Japanese hop (Humj1); *Parietaria judaica* (Parj1, Parj2, Parj3); *Parietaria officinalis* (Paro1); *Ambrosia artemisiifolia* (Amba8.0101, Amba8.0102, Amba9.0101, Amba9.0102); *Plantago lanceolata* (Plal1.0101, Plal1.0102, Plal1.0103); and *Parietaria judaica* (Parj1.0101, Parj1.0102, Parj1.0201, Parj2.0101, Parj2.0102, Parj3.0101, Parj3.0102).

Examples of grass associated allergen indicators 106 include, but are not limited to, Bermuda grass (Cynd1, Cynd7, Cynd12, Cynd15, Cynd22w, Cynd23, Cynd24); orchard grass (Dacg1, Dacg2, Dacg3, Dacg5); meadow fescue (Fesp4w); velvet grass (Holl1); rye grass (Lolp1, Lolp2, Lolp3, Lolp5, Lolp11); canary grass (Phaa1); Timothy (Phlp1, Phlp2, Phlp4, Phlp5, Phlp6, Phlp11, Phlp12, Phlp13); Kentucky blue grass (Poap1, Poap5); Johnson grass (Sorh1); *Cynodon dactylon* (Cynd1.0101, Cynd1.0102, Cynd1.0103, Cynd1.0104, Cynd1.0105, Cynd1.0106, Cynd1.0107, Cynd1.0201, Cynd1.0202, Cynd1.0203, Cynd1.0204); *Holcus lanatus* (Holl1.0101, Holl1.0102); *Lolium perenne* (Lolp1.0101, Lolp1.0102, Lolp1.0103, Lolp5.0101, Lolp5.0102); *Phleum pretense* (Phlp1.0101, Phlp1.0102, Phlp4.0101, Phlp4.0201, Phlp5.0101, Phlp5.0102, Phlp5.0103, Phlp5.0104, Phlp5.0105, Phlp5.0106, Phlp5.0107, Phlp5.0108, Phlp5.0201, Phlp5.0202); and *Secale cereale* (Secc20.0101, Secc20.0201).

Examples of tree associated allergen indicators 106 include, but are not limited to, Alder (Alng1); Birch (Betv1, Betv2, Betv3, Betv4, Betv6, Betv7); hornbeam (Carb1); chestnut (Cass1, Cass5, Cass8); hazel (Cora1, Cora2, Cora8, Cora9, Cora10, Cora11); White oak (Quea1); Ash (Frae1); privet (Ligv1); olive (Olee1, Olee2, Olee3, Olee4, Olee5, Olee6, Olee7, Olee8, Olee9, Olee10); Lilac (Syrv1); Sugi (Cryj1, Cryj2); cypress (Cupa1); common cypress (Cups1, Cups3w); mountain cedar (Juna1, Juna2, Juna3); prickly juniper (Juno4); mountain cedar (Juns1); eastern red cedar (Junv1); London plane tree (Plaa1, Plaa2, Plaa3); date palm (Phod2); *Betula verrucosa* (Betv1.0101, Betv1.0102, Betv1.0103, Betv1.0201, Betv1.0301, Betv1.0401, Betv1.0402, Betv1.0501, Betv1.0601, Betv1.0602, Betv1.0701, Betv1.0801, Betv1.0901, Betv1.1001, Betv1.1101, Betv1.1201, Betv1.1301, Betv1.1401, Betv1.1402, Betv1.1501, Betv1.1502, Betv1.1601, Betv1.1701, Betv1.1801, Betv1.1901, Betv1.2001, Betv1.2101, Betv1.2201, Betv1.2301, Betv1.2401, Betv1.2501, Betv1.2601, Betv1.2701, Betv1.2801, Betv1.2901, Betv1.3001, Betv1.3101, Betv6.0101, Betv6.0102); *Carpinus betulus* (Carb1.0101, Carb1.0102, Carb1.0103, Carb1.0104, Carb1.0105, Carb1.0106, Carb1.0106, Carb1.0106, Carb1.0106, Carb1.0107, Carb1.0107, Carb1.0108, Carb1.0201, Carb1.0301, Carb1.0302); *Corylus avellana* (Cora1.0101, Cora1.0102, Cora1.0103, Cora1.0104, Cora1.0201, Cora1.0301, Cora1.0401, Cora1.0402, Cora1.0403, Cora1.0404); *Ligustrum vulgare* (Ligv1.0101, Ligv1.0102); *Olea europea* (Olee1.0101, Olee1.0102, Olee1.0103, Olee1.0104, Olee1.0105, Olee1.0106, Olee1.0107); *Syringa vulgaris* (Syrv1.0101, Syrv1.0102, Syrv1.0103); *Cryptomeria japonica* (Cryj2.0101, Cryj2.0102); and *Cupressus sempervirens* (Cups1.0101, Cups1.0102, Cups1.0103, Cups1.0104, Cups1.0105).

Examples of mite associated allergen indicators 106 include, but are not limited to, mite (Acas13, Blot1, Blot3, Blot4, Blot5, Blot6, Blot10, Blot11, Blot12, Blot13, Blot19); American house dust mite (Derf1, Derf2, Derf3, Derf7, Derf10, Derf11, Derf14, Derf15, Derf16, Derf17, Derf18w); house dust mite (Derm1); European house dust mite (Derp1, Derp2, Derp3, Derp4, Derp5, Derp6, Derp7, Derp8, Derp9, Derp10, Derp11, Derp14, Derp20, Derp21); mite (Eurm2; Eurm14); storage mite (Glyd2, Lepd2, Lepd5, Lepd7, Lepd10, Lepd13, Tyrp2, Tyrp13); *Dermatophagoides farinae* (Derf1.0101, Derf1.0102, Derf1.0103, Derf1.0104, Derf1.0105, Derf2.0101, Derf2.0102, Derf2.0103, Derf2.0104, Derf2.0105, Derf2.0106, Derf2.0107, Derf2.0108, Derf2.0109, Derf2.0110, Derf2.0111, Derf2.0112, Derf2.0113, Derf2.0114, Derf2.0115, Derf2.0116, Derf2.0117); *Dermatophagoides pteronyssinus* (Derp1.0101, Derp1.0102, Derp1.0103, Derp1.0104, Derp1.0105, Derp1.0106, Derp1.0107, Derp1.0108, Derp1.0109, Derp1.0110, Derp1.0111, Derp1.0112, Derp1.0113, Derp1.0114, Derp1.0115, Derp1.0116, Derp1.0117, Derp1.0118, Derp1.0119, Derp1.0120, Derp1.0121, Derp1.0122, Derp1.0123, Derp2.0101, Derp2.0102, Derp2.0103, Derp2.0104, Derp2.0105, Derp2.0106, Derp2.0107, Derp2.0108, Derp2.0109, Derp2.0110, Derp2.0111, Derp2.0112, Derp2.0113); *Euroglyphus maynei* (Eurm2.0101, Eurm2.0102); *Glycyphagus domesticus* (Glyd2.0101, Glyd2.0201); and *Lepidoglyphus destructor* (Lepd2.0101, Lepd2.0101, Lepd2.0101, Lepd2.0102, Lepd2.0201, Lepd2.0202).

Examples of animal associated allergen indicators 106 include, but are not limited to, domestic cattle (Bosd2, Bosd3, Bosd4, Bosd5, Bosd6, Bosd7, Bosd8); dog (Canf1, Canf2, Can3, Canf4); domestic horse (Equc1, Equc 2, Equc 3, Equc 4, Equc 5); cat (saliva)(Feld1, Feld2, Feld3, Feld4, Feld5w, Feld6w, Feld7w); guinea pig (Cavp1, Cavp2); mouse (urine) (Musm1); rat (urine)(Ratn1); *Bos domesticus* (Bosd2.0101, Bosd2.0102, Bosd2.0103); and *Equus caballus* (Equc2.0101, Equc 2.0102).

Examples of fungus (mold) associated allergen indicators 106 include, but are not limited to, *Alternaria alternate* (Alta1, Alta3, Alta4, Alta5, Alta6, Alta7, Alta8, Alta10, Alta12, Alta13); *Cladosporium herbarum* (Clah2, Clah5, Clah6, Clah7, Clah8, Clah9, Clah10, Clah12); *Aspergillus flavus* (Aspf13); *Aspergillus fumigatus* (Aspf1, Aspf2, Aspf3, Aspf4, Aspf5, Aspf6, Aspf7, Aspf8, Aspf9, Aspf10, Aspf11, Aspf12, Aspf13, Aspf15, Aspf16, Aspf17, Aspf18, Aspf22w, Aspf23, Aspf27, Aspf28, Aspf29); *Aspergillus niger* (Aspn14, Aspn18, Aspn25); *Aspergillus oryzae* (Aspo13, Aspo21); *Penicillium brevicompactum* (Penb13, Penb26); *Penicillium chrysogenum* (Pench13, Pench18, Pench20); *Penicillium citrinum* (Penc3, Penc13, Penc19, Penc22w, Penc24); *Penicillium oxalicum* (Peno18); *Fusarium culmorum* (Fusc1, Fusc2); *Trichophyton rubrum* (Trir2, Trir4); *Trichophyton tonsurans* (Trit1, Trit4); *Candida albicans* (Canda1, Canda3); *Candida boidinii* (Candb2); *Psilocybe cubensis* (Psic1, Psic2); shaggy cap (Copc1, Copc2, Copc3, Copc5, Copc7); *Rhodotorula mucilaginosa* (Rhom1, Rhom2); *Malassezia furfur* (Malaf2, Malaf3, Malaf4); *Malassezia sympodialis* (Malas1, Malas5, Malas6, Malas7, Malas8, Malas9, Malas10, Malas11, Malas12, Malas13); *Epicoccum purpurascens* (Epip1); and *Alternaria alternate* (Alta1.0101, Alta1.0102).

Examples of insect associated allergen indicators 106 include, but are not limited to, Mosquito (Aeda1, Aeda2); honey bee (Apim1, Apim2, Apim4, Apim6, Apim7); bumble bee (Bomp1, Bomp4); German cockroach (Blag1, Blag2, Blag4, Blag5, Blag6, Blag7, Blag8); American cockroach (Pera1, Pera3, Pera6, Pera7); midge (Chit1-9, Chit1.01, Chit1.02, Chit2.0101, Chit2.0102, Chit3, Chit4, Chit5, Chit6.01, Chit6.02, Chit7, Chit8, Chit9); cat flea (Ctef1, Ctef2, Ctef3); pine processionary moth (Thap1); silverfish (Leps1); white face hornet (Dolm1, Dolm2, Dolm5); yellow hornet (Dola5); wasp (Pola1, Pola2, Pola5, Pole1, Pole5, Polf5, Polg5, Polm5, Vesvi5); Mediterranean paper wasp (Pold1, Pold4, Pold5); European hornet (Vespc1, Vespc5); giant asian hornet (Vespm1, Vespm5); yellowjacket (Vesf5, Vesg5, Vesm1, Vesm2, Vesm5, Vesp5, Vess5, Vesv1, Vesv2, Vesv5); Australian jumper ant (Myrp1, Myrp2); tropical fire ant (Solg2, Solg4); fire ant (Soli2, Soli3, Soli4); Brazilian fire ant (Sols2); California kissing bug (Triap1); *Blattella germanica* (Blag1.0101, Blag1.0102, Blag1.0103, Blag1.02, Blag6.0101, Blag6.0201, Blag6.0301); *Periplaneta Americana* (Pera1.0101, Pera1.0102, Pera1.0103, Pera1.0104, Pera1.02, Pera3.01, Pera3.0201, Pera3.0202, Pera3.0203, Pera7.0101, Pera7.0102); *Vespa crabo* (Vespc5.0101, Vespc5.0101); and *Vespa mandarina* (Vesp m 1.01, Vesp m 1.02).

Examples of food associated allergen indicators 106 include, but are not limited to, Cod (Gadc1); Atlantic salmon (Sals1); domestic cattle milk (Bosd4, Bosd5, Bosd6, Bosd7, Bosd8); chicken (Gald1, Gald2, Gald3, Gald4, Gald5); shrimp (Mete1); shrimp (Pena1, Peni1); black tiger shrimp (Penm1, Penm2); squid (Todp1), brown garden snail (Helas1); abalone (Halm1); edible frog (Rane1, Rane2); oriental mustard (Braj1); rapeseed (Bran1); cabbage (Brao3); turnip (Brar1, Brar2); barley (Horv15, Horv16, Horv17, Horv21); rye (Secc20); wheat (Tria18, Tria19, Tria25, Tria26); corn (Zeam14, Zeam25); rice (Orys1), celery (Apig1, Apig4, Apig5); carrot (Dauc1, Dauc4); hazelnut (Cora1.04, Cora2, Cora8); strawberry (Fraa1, Fraa3, Fraa4); apple (Mald1, Mald2, Mald3, Mald4); pear (Pyrc1, Pyrc4, Pyrc5); avocado (Persa1); apricot (Pruar1, Pruar3); sweet cherry (Pruav1, Pruav2, Pruav3, Pruav4); European plum (Prud3); almond (Prudu4); peach (Prup3, Prup4); asparagus (Aspao1); saffron crocus (Cros1, Cros2); lettuce (Lacs1); grape (Vitv1); banana (Musxp1); pineapple (Anac1, Anac2); lemon (Cit13); sweet orange (Cits1, Cits2, Cits3); litchi (Litc1); yellow mustard (Sina1); soybean (Glym1, Glym2, Glym3, Glym4); mung bean (Vigr1); peanut (Arah1, Arah2, Arah3, Arah4, Arah5, Arah6, Arah7, Arah8); lentil (Lenc1, Lenc2); pea (Piss1, Piss2); kiwi (Actc1, Actc2); bell pepper (Capa1w, Capa2); tomato (Lyce1, Lyce2, Lyce3); potato (Solat1, Solat2, Solat3, Solat4); Brazil nut (Bere1, Bere2); black walnut (Jugn1, Jugn2); English walnut (Jugr1, Jugr2, Jugr3); Cashew (Anao1, Anao2, Anao3); Castor bean (Ricc1); sesame (Sesi1, Sesi2, Sesi3, Sesi4, Sesi5, Sesi6); muskmelon (Cucm1, Cucm2, Cucm3); Chinese-date (Zizm1); *Anacardium occidentale* (Anao1.0101, Anao1.0102); *Apium graveolens* (Apig1.0101, Apig1.0201); *Daucus carota*

(Dauc1.0101, Dauc1.0102, Dauc1.0103, Dauc1.0104, Dauc1.0105, Dauc1.0201); *Citrus sinensis* (Cits3.0101, Cits3.0102); *Glycine max* (Glym1.0101, Glym1.0102, Glym3.0101, Glym3.0102); *Lens culinaris* (Lenc1.0101, Lenc1.0102, Lenc1.0103); *Pisum sativum* (Piss1.0101, Piss1.0102); *Lycopersicon sativum* (Lyce2.0101, Lyce2.0102); *Fragaria ananassa* (Fraa3.0101, Fraa3.0102, Fraa3.0201, Fraa3.0202, Fraa3.0203, Fraa3.0204, Fraa3.0301); *Malus domestica* (Mald1.0101, Mald1.0102, Mald1.0103, Mald1.0104, Mald1.0105, Mald1.0106, Mald1.0107, Mald1.0108, Mald1.0109, Mald1.0201, Mald1.0202, Mald1.0203, Mald1.0204, Mald1.0205, Mald1.0206, Mald1.0207, Mald1.0208, Mald1.0301, Mald1.0302, Mald1.0303, Mald1.0304, Mald1.0401, Mald1.0402, Mald1.0403, Mald3.0101w, Mald3.0102w, Mald3.0201w, Mald3.0202w, Mald3.0203w, Mald4.0101, Mald4.0102, Mald4.0201, Mald4.0202, Mald4.0301, Mald4.0302); *Prunus avium* (Pruav1.0101, Pruav1.0201, Pruav1.0202, Pruav1.0203); and *Prunus persica* (Prup4.0101, Prup4.0201).

Examples of additional allergen indicators 106 include, but are not limited to, Nematode (Anis1, Anis2, Anis3, Anis4); pigeon tick (Argr1); worm (Ascs1); papaya (Carp1); soft coral (Denn1); rubber (latex)(Hevb1, Hevb2, Hevb3, Hevb4, Hevb5, Hevb6.01, Hevb6.02, Hevb6.03, Hevb7.01, Hevb7.02, Hevb8, Hevb9, Hevb10, Hevb11, Hevb12, Hevb13); human autoallergens (Homs1, Homs2, Homs3, Homs4, Homs5); *obeche* (Trips1); and *Heveabrasiliensis* (Hevb6.01, Hevb6.0201, Hevb6.0202, Hevb6.03, Hevb8.0101, Hevb8.0102, Hevb8.0201, Hevb8.0202, Hevb8.0203, Hevb8.0204, Hevb10.0101, Hevb10.0102, Hevb10.0103, Hevb11.0101, Hevb11.0102).

Microfluidic Chip

Numerous types of microfluidic chips 108 may be utilized within system 100. Methods to construct microfluidic chips 108 have been described (e.g., U.S. Statutory Invention Registration No. H201; U.S. Pat. Nos. 6,454,945; 6,818,435; 6,812,458; 6,794,196; 6,709,869; 6,582,987; 6,482,306; 5,726,404; 7,118,910; herein incorporated by reference).

In some embodiments, a microfluidic chip 108 may be configured to utilize microfluidic principles. Accordingly, in some embodiments, a microfluidic chip 108 may be configured to include one or more channels with at least one dimension that is less than 1 millimeter. However, in some embodiments, microfluidic chips 108 may be configured such that they do not utilize microfluidic principles. Accordingly, in some embodiments, microfluidic chips 108 may be configured such that there are not any components that have a dimension that is less than 1 millimeter. Accordingly, in some embodiments, microfluidic chips 108 may be configured that include components having a dimension that is less than 1 millimeter, while in other embodiments, microfluidic chips 108 may be configured with components having dimensions that are greater than 1 millimeter. In some embodiments, a microfluidic chip 108 may include at least one component that has at least one dimension that is less than 1 millimeter and at least one component having at least one dimension that is greater than 1 millimeter.

In some embodiments, one or more microfluidic chips 108 may include a lancet. Methods to construct lancets are known and have been described (e.g., U.S. Patent Application No. 20020177763 and 20030083685; herein incorporated by reference). Numerous additional methods may be used to construct microfluidic chips 108 that may be used for analysis of one or more allergens 104.

For example, microfluidic chips 108 may be configured to utilize a variety of methods to process one or more allergens 104. Examples of such methods include, but are not limited to, nucleic acid (polynucleotide) hybridization based methods, immunological based methods, chromatographic based methods, affinity based methods, extraction based methods, separation based methods, isolation based methods, filtration based methods, enzyme based methods, isoelectric focusing methods, or substantially any combination thereof.

Microfluidic chips 108 may utilize numerous methods for analysis of one or more allergen indicators 106. For example, in some embodiments, one or more microfluidic chips 108 may be configured to utilize: chemiluminescent methods (e.g., U.S. Pat. Nos. 6,090,545 and 5,093,268; herein incorporated by reference), plasmon resonance sensors (e.g., U.S. Pat. No. 7,030,989; herein incorporated by reference), nuclear magnetic resonance detectors (e.g., U.S. Pat. No. 6,194,900; herein incorporated by reference), gradient-based assays (e.g., U.S. Pat. No. 7,112,444; herein incorporated by reference), reporter beads (e.g., U.S. Pat. No. 5,747,349; herein incorporated by reference), transverse electrophoresis (e.g., Macounova et al., Analytical Chemistry, 73:1627-1633 (2001)); isoelectric focusing (e.g., Macounova et al., Analytical Chemistry, 72:3745-3751 (2000); Xu et al., Isoelectric focusing of green fluorescent proteins in plastic microfluidic channels. Abstracts of Papers of the American Chemical Society, 219:9-ANYL (2000); Macounova et al., Analytical Chemistry, 73:1627-1633 (2001)), diffusion based systems (e.g., Kamholz et al., Biophysical Journal, 80:1967-1972 (2001); Hatch et al., Nature Biotechnology, 19:461-465 (2001); U.S. Pat. Nos. 6,221,677 and 5,972,710; herein incorporated by reference), high performance liquid chromatography (e.g., U.S. Pat. No. 6,923,907; herein incorporated by reference), polynucleotide analysis (e.g., Belgrader et al., Biosensors & Bioelectronics, 14:849-852 (2000); Buchholz et al., Analytical Chemistry, 73:157-164 (2001); Fan et al., Analytical Chemistry, 71:4851-4859 (1999); Koutny et al., Analytical Chemistry, 72:3388-3391 (2000); Lee et al., Microfabricated plastic chips by hot embossing methods and their applications for DNA separation and detection. Sensors and Actuators B-Chemical, 75:142-148 (2001); U.S. Pat. No. 6,958,216; herein incorporated by reference), capillary electrophoresis (e.g., Kameoka et al., Analytical Chemistry, 73:1935-1941 (2001)), immunoassays (e.g., Hatch et al., Nature Biotechnology, 19:461-465 (2001); Eteshola and Leckband, Development and characterization of an ELISA assay in PDMS microfluidic channels. Sensors and Actuators B-Chemical 72:129-133 (2001); Cheng et al., Analytical Chemistry, 73:1472-1479 (2001); Yang et al., Analytical Chemistry, 73:165-169 (2001)), flow cytometry (e.g., Sohn et al., Proc. Natl. Acad. Sci., 97:10687-10690 (2000)), PCR amplification (e.g., Belgrader et al., Biosensors & Bioelectronics, 14:849-852 (2000); Khandurina et al., Analytical Chemistry, 72:2995-3000 (2000); Lagally et al., Analytical Chemistry, 73:565-570 (2001)), cell manipulation (e.g., Glasgow et al., IEEE Transactions On Biomedical Engineering, 48:570-578 (2001)), cell separation (e.g., Yang et al., Analytical Chemistry, 71:911-918 (1999)), cell patterning (e.g., Chiu et al., Proc. Natl. Acad. Sci., 97:2408-2413 (2000); Folch et al., Journal of Biomedical Materials Research, 52:346-353 (2000)), chemical gradient formation (e.g., Dertinger et al., Analytical Chemistry, 73:1240-1246 (2001); Jeon et al., Langmuir, 16:8311-8316 (2000)), microcantilevers (e.g., U.S. Pat. Nos. 7,141,385; 6,935,165; 6,926,864; 6,763,705; 6,523,392; 6,325,904; herein incorporated by reference), or substantially any combination thereof.

In some embodiments, one or more microfluidic chips 108 may be configured to utilize one or more magnets that may be used during processing and/or analysis of one or more samples 102. For example, in some embodiments, ferrous metallic particles may be associated with one or more allergen indicators 106 that are associated with one or more samples 102 (e.g., use of antibodies, aptamers, peptides, polynucleotides, and the like that bind to one or more allergen indicators 106 and that are coupled to a ferrous metallic particle). The one or more allergen indicators 106 may be separated from the remainder of the one or more samples 102 through use of one or more magnets. In some embodiments, one or more magnets may be used to create eddy currents that may be used to process and/or analyze one or more samples 102. For example, in some embodiments, non-ferrous metallic particles may be associated with one or more allergen indicators 106 that are associated with one or more samples 102 (e.g., use of antibodies, aptamers, peptides, polynucleotides, and the like that bind to one or more allergen indicators 106 and that are coupled to a non-ferrous metallic particle). One or more microfluidic chips 108 may be configured such that passage of a non-ferrous metallic particle through a magnetic field will cause an eddy current to impart kinetic energy to the non-ferrous metallic particle and provide for separation of the associated allergen indicators 106 from the remainder of the one or more samples 102. In some embodiments, such methods may be combined with additional methods to provide for separation of one or more allergen indicators 106 from one or more samples 102. For example, magnetic separation may be used in combination with one or more methods that may include, but are not limited to, diffusion (e.g., use of an H-filter), filtration, precipitation, immunoassay, immunodiffusion, and the like.

In some embodiments, one or more microfluidic chips 108 may be configured to utilize ferrofluids to separate one or more allergen indicators 106 from one or more samples 102. For example, in some embodiments, a microfluidic chip 108 may include an H-filter where a sample fluid and a ferrofluid flow in parallel (e.g., the sample fluid and the ferrofluid flow side-by-side through the H-filter). In some embodiments, one or more microfluidic chips 108 may include a ferrofluid having magnetic particles such that ferrous materials contained within the sample fluid are attracted to the ferrofluid and thereby separated from the sample fluid. Accordingly, such microfluidic chips 108 may be configured to separate one or more allergen indicators 106 from one or more samples 102. In some embodiments, one or more microfluidic chips 108 may include a ferrofluid having ferrous particles such that magnetic materials contained within the sample fluid are attracted to the ferrofluid and thereby separated from the sample fluid. Accordingly, in such embodiments, one or more microfluidic chips 108 may be configured to utilize ferrofluids to separate one or more allergen indicators 106 from one or more samples 102.

Microfluidic chips 108 may be configured to process numerous types of samples 102. For example, in some embodiments, a microfluidic chip 108 may be configured to sonicate one or more samples 102. In some embodiments, a microfluidic chip 108 may include one or more ultrasonic electronic generators that produce a signal (e.g., 20 kilohertz) that can be used to drive a piezoelectric convertor/transducer. This electrical signal may be converted by the transducer to a mechanical vibration due to the characteristics of the internal piezoelectric crystals. This vibration can be amplified and transmitted to one or more probes having tips that expand and contract to provide for sonication of one or more samples 102. In some embodiments, a microfluidic chip 108 may include one or more sonication probes. Such probes may be configured such that are able to operably associate with one or more vibration sources in a detachable manner. Accordingly, in some embodiments, one or more microfluidic chips 108 that include one or more probes may be configured to detachably connect with one or more vibration sources that produce a vibration that can be coupled to the one or more probes. In some embodiments, one or more detection units 122 may include one or more vibration sources.

In some embodiments, a microfluidic chip 108 may be configured to mix one or more samples 102. For example, in some embodiments, a microfluidic chip 108 may include a mixing chamber which includes one or more ferrous mixing members and electromagnetics which are configured such that motion may be imparted to the one or more ferrous mixing members. In some embodiments, a microfluidic chip 108 may include one or more mixing chambers that include two or more electromagnets positioned around the one or more mixing chambers and one or more ferrous members positioned within the one or more mixing chambers and between the electromagnetics. Accordingly, mixing of one or more materials within the one or more mixing chambers may be facilitated by alternating current between the electromagnets positioned around the mixing chamber. In some embodiments, a mixing chamber may include an elastomeric material that includes a ferrous material (e.g., an elastomeric-ferrous material) such that movement of the elastomeric-ferrous material may be facilitated through use of one or more magnets, such as electromagnets.

In some embodiments, elastomeric-ferrous materials may be utilized to fabricate pumps that are associated with microfluidic chips 108. For example, in some embodiments, a tube may include an elastomeric material that includes ferrous material such that movement of the elastomeric material may be facilitated through use of one or more magnets. Accordingly, valves and ferrous materials may be associated with the elastomeric tube such that expansion of a portion of the elastomeric tube through the action of a magnet, such as an electromagnetic, will act like a vacuum pump to draw fluids into the expanded portion of the elastomeric tube. In some embodiments, release of the elastomeric material from the magnetic field will cause the expanded portion of the tube to contract and will act to push the fluid from the formerly expanded portion of the elastomeric tubing. In some embodiments, valves may be positioned within the tube to provide for directional flow of fluid through the elastomeric tube. Accordingly, such pumps may be configured as vacuum pumps, propulsion type pumps, and/or both vacuum and propulsion type pumps.

In some embodiments, microfluidic chips 108 may be configured to utilize magnetically actuated fluid handling. In some embodiments, a microfluidic chip 108 may utilize magnetic fluid (e.g., ferrofluid, ferrogel, and the like) to move one or more gases and/or liquids through flow channels. For example, magnetically actuated slugs of magnetic fluid may be moved within channels of a microfluidic chip 108 to facilitate valving and/or pumping of one or more gases and/or liquids. In some embodiments, the magnets used to control gas and/or liquid movement may be individual magnets that are moved along the flow channels and/or one or more arrays of magnets that may be individually controlled to hold or move one or more magnetic slugs. In some embodiments, an array of electromagnets may be positioned along a flow channel which may be turned on and off in a predetermined pattern to move magnetic fluid slugs in desired paths in one or more flow channels. Methods to construct magnetically actuated fluid handling devices have been described (e.g., U.S. Pat. Nos. 6,408,884 and 7,110,646; herein incorporated by reference).

Accordingly, microfluidic chips 108 may be configured for analysis of numerous types of allergen indicators 106.

Reagent Delivery Unit

System 100 may include one or more reagent delivery units 116. In some embodiments, one or more reagent delivery units 116 may be configured to operably associate with one or more microfluidic chips 108. Accordingly, in some embodiments, one or more reagent delivery units 116 may be configured to contain one or more reagents that may be used within one or more microfluidic chips 108 to extract, analyze, and/or detect one or more allergens 104 and/or one or more allergen indicators 106. In some embodiments, one or more reagent delivery units 116 may include one or more pumps to facilitate delivery of one or more reagents. Numerous types of pumps may be used within a reagent delivery unit 116. In some embodiments, one or more reagent delivery units 116 may be configured to operably associate with one or more centrifugation units 118. Accordingly, reagents may be delivered through use of centrifugal force. Reagent delivery units 116 may be configured in numerous ways. For example, in some embodiments, reagent delivery units 116 may include one or more reagent reservoirs, one or more waste reservoirs, or substantially any combination thereof. Reagent delivery units 116 may be configured to contain and/or deliver numerous types of reagents. Examples of such reagents include, but are not limited to, phenol, chloroform, alcohol, salt solutions, detergent solutions, solvents, reagents used for polynucleotide precipitation, reagents used for polypeptide precipitation, reagents used for polynucleotide extraction, reagents used for polypeptide extraction, reagents used for chemical extractions, and the like. Accordingly, reagent delivery units 116 may be configured to contain and/or deliver virtually any reagent that may be used for the analysis of one or more allergens 104 and/or allergen indicators 106.

Centrifugation Unit

System 100 may include one or more centrifugation units 118. In some embodiments, one or more centrifugation units 118 may be configured to operably associate with one or more microfluidic chips 108. Accordingly, in some embodiments, one or more centrifugation units 118 may be used to facilitate the extraction, analysis, and/or detection of one or more allergens 104 and/or one or more allergen indicators 106. Methods to fabricate devices that may be used to drive fluid movement through centripetal acceleration in a microfluidics system have been described (e.g., U.S. Pat. No. 6,709,869; herein incorporated by reference).

For example, in some embodiments, one or more centrifugation units 118 may be used to facilitate the extraction of one or more polynucleotides from one or more samples 102 that are applied to one or more microfluidic chips 108. Briefly, one or more samples 102 may be applied to a microfluidic chip 108 where the sample 102 is mixed with a solubilizing agent, such as a detergent, that solubilizes the sample 102 to facilitate extraction of polynucleotides from the sample 102. A second reagent may be added to the solubilized sample 102 to facilitate precipitation of the non-polynucleotide portion of the sample 102. The microfluidic chip 108 may then be centrifuged to pellet the non-polynucleotide portion of the sample 102. The portion of the sample 102 that contains the polynucleotides can then be transferred to another portion of the microfluidic chip 108 where the polynucleotides may be further extracted. The further extracted portion of the sample 102 may then be transferred to another portion of the microfluidic chip 108 where it may be mixed with a reagent that facilitates precipitation of the polynucleotides. The microfluidic chip 108 may be centrifuged to pellet the polynucleotides. The pelleted polynucleotides may then be resuspended for analysis. Such methods may be used with polynucleotides, polypeptides, and numerous other components that may be included within one or more samples 102.

In some embodiments, one or more centrifugation units 118 may be configured to centrifuge one or more microfluidic chips 108 to facilitate movement of one or more samples 102, one or more reagents, one or more fluids, and the like through the one or more microfluidic chips 108.

In some embodiments, one or more centrifugation units 118 may be configured to centrifuge one or more microfluidic chips 108 to create a gradient. In some embodiments, velocity gradients may be created to facilitate analysis of one or more samples 102. For example, glycerol gradients may be used to separate polypeptides from one or more samples 102. In other embodiments, density gradients may be created to facilitate analysis of one or more samples 102. For example, cesium chloride may be used to create a density gradient to facilitate the analysis of one or more polynucleotides.

In some embodiments, one or more centrifugation units 118 may be configured to centrifuge one or more microfluidic chips 108 to facilitate chromatographic separations of components within one or more samples 102. For example, chromatographic media may be packed within a microfluidic chip 108 that facilitates the separation of components, such as allergens 104 and/or allergen indicators 106, from one or more samples 102. Such chromatographic media is commercially available (e.g., Qiagen Sciences, Germantown, Md. and Pfizer, New York, N.Y.).

Analysis Unit

System 100 may include one or more analysis units 120. Analysis units 120 may be configured for analysis of numerous types of allergens 104 and/or allergen indicators 106. In some embodiments, one or more analysis units 120 may be configured for analysis of one or more polynucleotides, polypeptides, spores, dander samples 102, food products, small molecules, and the like.

For example, in some embodiments, one or more analysis units 120 may be configured for analysis of one or more polypeptides. Briefly, an analysis unit 120 may include a portion that is configured to separate the one or more polypeptides from a sample 102. The one or more polypeptides may then be applied to another portion of the analysis unit 120 that includes antibodies or aptamers that are immobilized on an array such that the one or more polypeptides are bound by the antibodies or aptamers. Such binding will provide for detection of the one or more bound polypeptides through use of numerous techniques. Examples of such techniques include, but are not limited to, competition assays, immunological methods (e.g., sandwich assays), and the like.

In other embodiments, one or more analysis units 120 may be configured for analysis of one or more polynucleotides. Briefly, an analysis unit 120 may include a portion that is configured to separate the one or more polynucleotides from a sample 102. The one or more polynucleotides may then be applied to another portion of the analysis unit 120 that includes complementary polynucleotides that are immobilized on an array such that the one or more polynucleotides hybridize with the immobilized polynucleotides. Such binding will provide for detection of the one or more bound polynucleotides through use of numerous techniques. Examples of such techniques include, but are not limited to, competition assays, electron transfer assays, electrical conductivity assays, and the like.

Detection Unit

Numerous types of detection units 122 may be used within system 100. Accordingly, numerous types of detection methods may be used within system 100. Examples of such detection methods include, but are not limited to, colorimetric methods, spectroscopic methods, resonance based methods, electron transfer based methods (redox), conductivity based methods, gravimetric based assays, turbidity based methods, ion-specific based methods, refractive index based methods, radiological based methods, or substantially any combination thereof. For example, in some embodiments, one or more detection units 122 may be configured to utilize one or more ion-specific electrodes to detect one or more allergen indicators 106. Examples of such allergen indicators 106 that may be detected with an ion specific electrode include, but are not limited to, metals (e.g., tin, silver, nickel, cobalt, chromate), nitrates, nitrites, sulfites, and the like. Such allergen indicators 106 are often associated with food, beverages, clothing, jewelry, and the like. In some embodiments, a detection unit 122 may be stationary. For example, in some embodiments, a detection unit 122 may be a laboratory instrument. In some embodiments, a detection unit 122 may be portable. For example, in some embodiments, a detection unit 122 may be a hand-held device.

Display Unit

The system 100 may include one or more display units 124. Numerous types of display units 124 may be used in association with system 100. Examples of such display units 124 include, but are not limited to, liquid crystal displays, printers, audible displays, cathode ray displays, plasma display panels, Braille displays, passive displays, chemical displays, active displays, and the like. In some embodiments, display units 124 may display information in numerous languages. Examples of such languages include, but are not limited to, English, Spanish, German, Japanese, Chinese, Italian, and the like. In some embodiments, display units 124 may display information pictographically, colorometrically, and/or physically, such as displaying information in Braille.

In some embodiments, one or more display units 124 may be physically coupled to one or more microfluidic chips 108. In some embodiments, one or more display units 124 may be remotely coupled to one or more microfluidic chips 108. For example, in some embodiments, one or more display units 124 may receive one or more signals 132 from one or more microfluidic chips 108 that are remotely positioned relative to the detection units 122. In some embodiments, one or more display units 124 may be physically coupled to one or more analysis units 120. In some embodiments, one or more display units 124 may be remotely coupled to one or more analysis units 120. For example, in some embodiments, one or more display units 124 may receive one or more signals 132 from one or more analysis units 120 that are remotely positioned relative to the display units 124. In some embodiments, one or more display units 124 may be physically coupled to one or more detection units 122. In some embodiments, one or more display units 124 may be remotely coupled to one or more detection units 122. For example, in some embodiments, one or more display units 124 may receive one or more signals 132 from one or more detection units 122 that are remotely positioned relative to the display units 124. Accordingly, one or more display units 124 may be positioned in one or more locations that are remote from the position where analysis of one or more allergens 104 takes place. Examples of such remote locations include, but are not limited to, the offices of physicians, nurses, dietitians, pharmacists, coaches, personal trainers, clerks at food supplement stores, clerks at grocery stores, and the like.

Recording Unit

The system 100 may include one or more recording units 126. In some embodiments, one or more recording units 126 can communicate with one or more microfluidic chips 108, one or more reagent delivery units 116, one or more centrifugation units 118, one or more analysis units 120, one or more detection units 122, one or more display units 124, one or more user interfaces 128, and/or substantially any combination thereof. Many types of recording units 126 may be used within system 100. Examples of such recording devices include those that utilize a recordable medium that includes, but is not limited to, many types of memory, optical disks, magnetic disks, magnetic tape, and the like.

In some embodiments, one or more recording units 126 may be physically coupled to one or more detection units 122. In some embodiments, one or more recording units 126 may be physically coupled to one or more display units 124. In some embodiments, one or more recording units 126 may be remotely coupled to one or more detection units 122 and/or one or more display units 124. For example, in some embodiments, one or more recording units 126 may receive one or more signals 132 from one or more detection units 122 and/or one or more display units 124 that are remotely positioned relative to the one or more recording units 126. Accordingly, one or more recording units 126 may be positioned in one or more locations that are remote from the position where analysis of one or more allergens 104 takes place. Examples of such remote locations include, but are not limited to, the offices of physicians, nurses, dietitians, pharmacists, coaches, personal trainers, clerks at food supplement stores, clerks at grocery stores, and the like.

User Interface/User

Numerous types of users 130 may interact with system 100. In some embodiments, a user 130 may be human. In some embodiments, a user 130 may be non-human. In some embodiments, a user 130 may interact with one or more microfluidic chips 108, one or more reagent delivery units 116, one or more centrifugation units 118, one or more analysis units 120, one or more detection units 122, one or more display units 124, one or more user interfaces 128, one or more recording units 126, or substantially any combination thereof. The user 130 can interact through use of numerous types of user interfaces 128. For example, one or more users 130 may interact through use of numerous user interfaces 128 that utilize hardwired methods, such as through use of a keyboard, use of wireless methods, use of the internet, and the like. In some embodiments, a user 130 may be a health-care worker. Examples of such health-care workers include, but are not limited to, physicians, nurses, dietitians, pharmacists, and the like. In some embodiments, users 130 may include those persons who work in health-related fields, such as coaches, personal trainers, clerks at food supplement stores, clerks at grocery stores, and the like.

Signal

The system 100 may include one or more signals 132. Numerous types of signals 132 may be transmitted. Examples of such signals 132 include, but are not limited to, hardwired signals 132, wireless signals 132, infrared signals 132, optical signals 132, radiofrequency (RF) signals 132, audible signals 132, digital signals 132, analog signals 132, or substantially any combination thereof.

I. Method for Analysis of One or More Allergens

Figure 2:
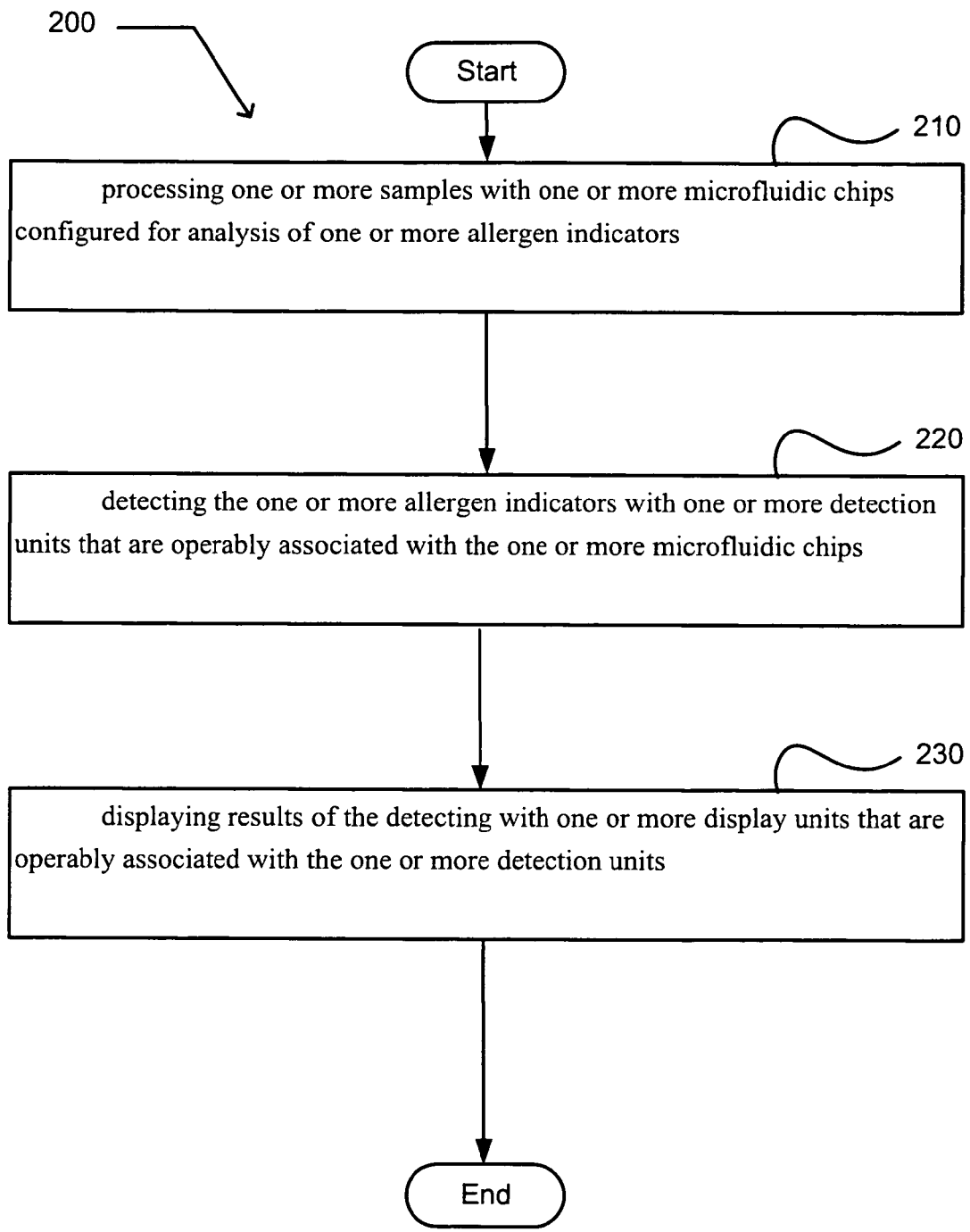
FIG. 2 illustrates an operational flow representing example operations related to methods and systems for analysis of allergens.

FIG. 2 illustrates an operational flow 200 representing examples of operations that are related to the performance of a method for analysis of one or more allergens 104. In FIG. 2 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 200 includes a processing operation 210 involving processing one or more samples with one or more microfluidic chips configured for analysis of one or more allergen indicators. In some embodiments, processing operation 210 may include processing the one or more samples that include one or more liquids. In some embodiments, processing operation 210 may include processing the one or more samples that include one or more solids. In some embodiments, processing operation 210 may include processing the one or more samples that include one or more gases. In some embodiments, processing operation 210 may include processing the one or more samples for the one or more allergen indicators that are associated with one or more airborne allergens. In some embodiments, processing operation 210 may include processing the one or more samples for the one or more allergen indicators that are associated with one or more food products. In some embodiments, processing operation 210 may include processing the one or more samples for the one or more allergen indicators that are associated with one or more weeds, grasses, trees, mites, animals, molds, fungi, insects, rubbers, autoallergens, metals, chemicals, or human autoallergens. In some embodiments, processing operation 210 may include processing the one or more samples with the one or more microfluidic chips that are configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay.

The operational flow 200 includes a detecting operation 220 involving detecting the one or more allergen indicators with one or more detection units that are operably associated with the one or more microfluidic chips. In some embodiments, detecting operation 220 may include detecting the one or more allergen indicators that are associated with one or more airborne allergens. In some embodiments, detecting operation 220 may include detecting the one or more allergen indicators that are associated with one or more food products. In some embodiments, detecting operation 220 may include detecting the one or more allergen indicators that are associated with one or more weeds, grasses, trees, mites, animals, molds, fungi, insects, rubbers, metals, chemicals, autoallergens, or human autoallergens. In some embodiments, detecting operation 220 may include detecting the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, detecting operation 220 may include detecting the one or more allergen indicators with one or more detection units that are calibrated for use with an individual.

The operational flow 200 may optionally include a displaying operation 230 involving displaying results of the detecting with one or more display units that are operably associated with the one or more detection units. In some embodiments, displaying operation 230 may include displaying results of the detecting with one or more display units that are passive display units. In some embodiments, displaying operation 230 may include displaying results of the detecting with one or more display units that are active display units. In some embodiments, displaying operation 230 may include indicating a presence or an absence of the one or more allergen indicators within the one or more samples. In some embodiments, displaying operation 230 may include indicating an identity of one or more allergens that correspond to the one or more allergen indicators present within the one or more samples. In some embodiments, displaying operation 230 may include indicating one or more concentrations of one or more allergens that correspond to the one or more allergen indicators present within the one or more samples. In some embodiments, displaying operation 230 may include displaying results of the detecting with one or more display units that are calibrated for an individual. In some embodiments, displaying operation 230 may include transmitting one or more signals to one or more recording units.

Figure 3:
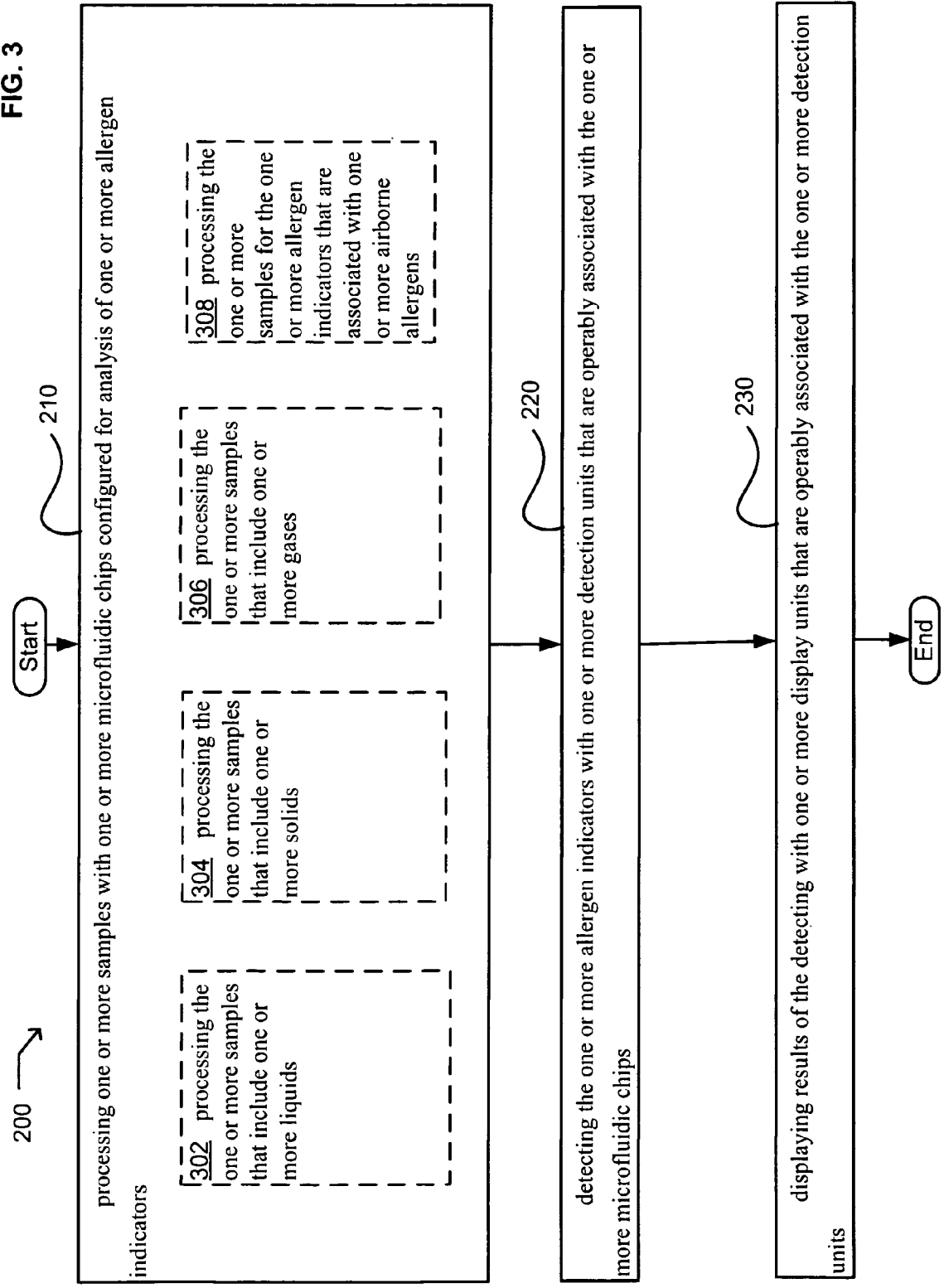
FIG. 3 illustrates alternate embodiments of the example operational flow of FIG. 2.

FIG. 3 illustrates alternative embodiments of the example operational flow 200 of FIG. 2. FIG. 3 illustrates example embodiments where the processing operation 210 may include at least one additional operation. Additional operations may include an operation 302, an operation 304, an operation 306, and/or an operation 308.

At operation 302, the processing operation 210 may include processing the one or more samples that include one or more liquids. In some embodiments, one or more samples 102 that include a liquid may be processed with one or more microfluidic chips 108 that are configured for analysis of one or more allergen indicators 106. Numerous types of liquids may be processed by one or more microfluidic chips 108. Examples of such liquids include, but are not limited to, beverages (e.g., water, soda, milk, milk substitutes, juice, wine, beer, and the like), environmental samples 102 (e.g., water samples 102, plant sap, plant nectar, suspended soil samples 102, suspended air filtrate samples 102, and the like), animal samples 102 (e.g., suspended dander samples 102, saliva, urine, excrement, suspended fur samples 102, and the like), food samples 102 (e.g., suspended food samples 102, extracted food samples 102, and the like), or substantially any combination thereof. In some embodiments, one or more liquids may include a solvent. In some embodiments, a liquid may include one or more solvents that may be used to extract one or more allergen indicators 106. For example, in some embodiments, one or more solvents may be used to extract one or more allergen indicators 106 from one or more samples 102.

At operation 304, the processing operation 210 may include processing the one or more samples that include one or more solids. In some embodiments, one or more samples 102 that include a solid may be processed with one or more microfluidic chips 108 that are configured for analysis of one or more allergen indicators 106. In some embodiments, processing one or more samples 102 that include a solid may include suspending the samples 102 in a liquid. In some embodiments, processing one or more samples 102 that include a solid may include extracting the samples 102 with a solvent. In some embodiments, processing one or more samples 102 that include a solid may include accepting the one or more samples 102 into one or more microfluidic chips 108 where the samples 102 are resuspended in a liquid and/or extracted in a solvent.

At operation 306, the processing operation 210 may include processing the one or more samples that include one or more gases. In some embodiments, one or more samples 102 that include a gas may be processed with one or more microfluidic chips 108 that are configured for analysis of one or more allergen indicators 106. For example, in some embodiments, one or more gases that are being analyzed may be passed through one or more microfluidic chips 108. In some embodiments, gas may be pumped through a microfluidic chip 108. In some embodiments, gas may be drawn through a microfluidic chip 108 through use of a vacuum. In some embodiments, gas may be passed through a filter on which suspected allergen indicators 106 are collected for analysis. Accordingly, large volumes of gas may be analyzed. In some embodiments, one or more gases may be analyzed for one or more allergen indicators 106 that include one or more metals. For example, gases may be analyzed for metals that are associated with tanks in which the gases are stored, such as iron, steel, aluminum, and the like.

At operation 308, the processing operation 210 may include processing the one or more samples for the one or more allergen indicators that are associated with one or more airborne allergens. In some embodiments, one or more samples 102 may be processed with one or more microfluidic chips 108 that are configured for processing the one or more samples 102 for one or more allergen indicators 106 that are associated with one or more airborne allergens 104. Examples of such airborne allergens 104 include, but are not limited to, pollen, dander, seeds, and the like. In some embodiments, the allergen indicators 106 may be collected within one or more microfluidic chips 108 through filtering air that is passed through the one or more microfluidic chips 108. Such filtering may occur through numerous mechanisms that may include, but are not limited to, use of physical filters, passing air through a fluid bubble chamber, passing the air through an electrostatic filter, and the like. In some embodiments, one or more microfluidic chips 108 may be configured to process the allergen 104 directly. In some embodiments, one or more microfluidic chips 108 may be configured to process the allergen 104 to obtain allergen indicators 106 that are associated with the allergen 104.

Figure 4:
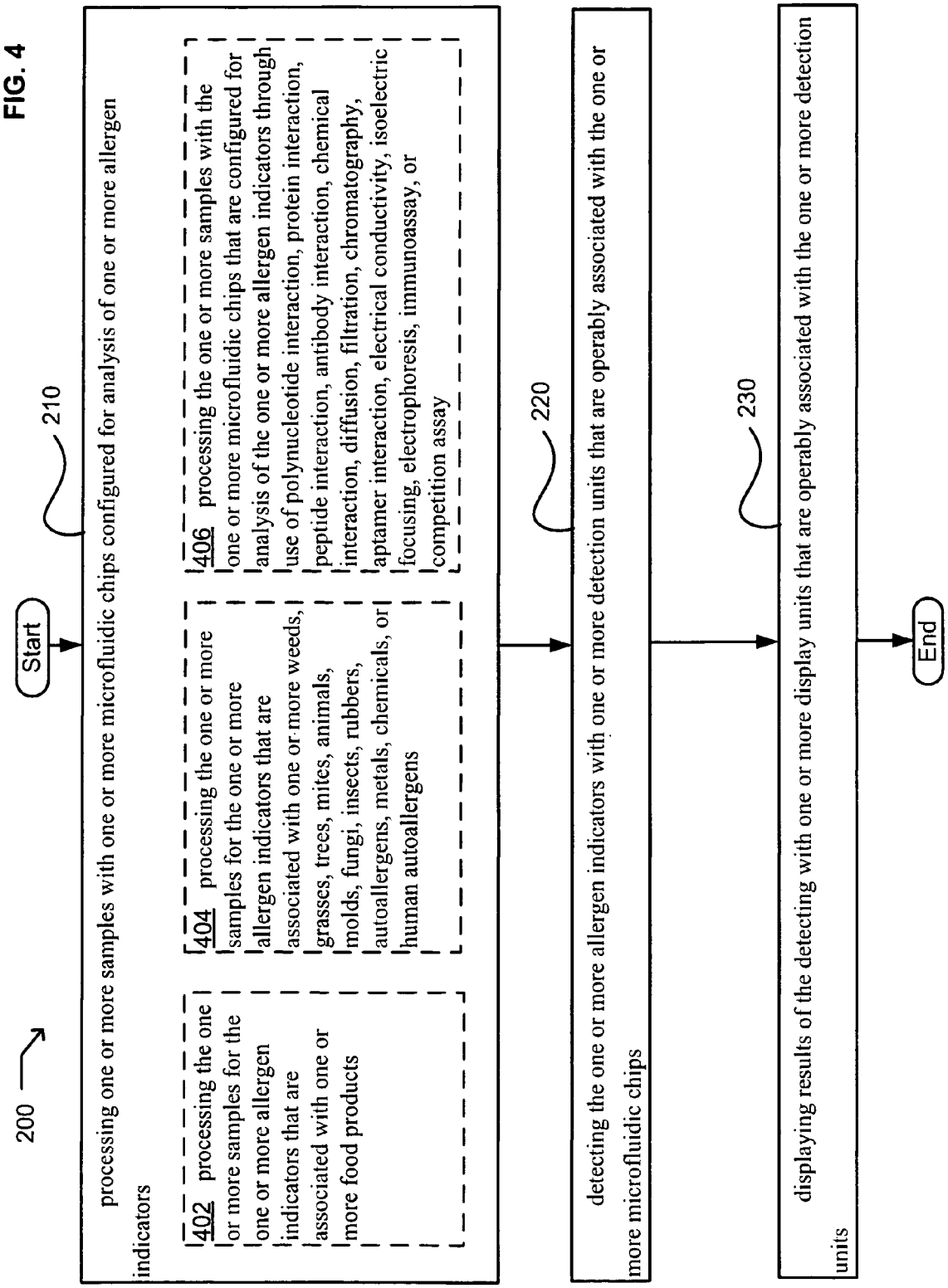
FIG. 4 illustrates alternate embodiments of the example operational flow of FIG. 2.

FIG. 4 illustrates alternative embodiments of the example operational flow 200 of FIG. 2. FIG. 4 illustrates example embodiments where the processing operation 210 may include at least one additional operation. Additional operations may include an operation 402, an operation 404, and/or an operation 406.

At operation 402, the processing operation 210 may include processing the one or more samples for the one or more allergen indicators that are associated with one or more food products. In some embodiments, one or more samples 102 may be processed with one or more microfluidic chips 108 that are configured for processing the one or more samples 102 for the one or more allergen indicators 106 that are associated with one or more food products (e.g., the foods themselves or processed products that include one or more foods). Such allergen indicators 106 are described herein and are known. For example, in some embodiments, one or more microfluidic chips 108 may be configured to process one or more food products at a restaurant to facilitate detection of a presence or an absence of an allergen indicator 106 within the food product, such as a presence of one or more allergen indicators 106 associated with nuts, dairy products, crustaceans, eggs, gluten, soy, and the like. In some embodiments, one or more microfluidic chips 108 may be configured to process one or more polynucleotides, one or more polypeptides, one or more portions of one or more polynucleotides, and/or one or more portions of one or more polypeptides that have a nucleic acid sequence and/or an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, or AY839230. Accordingly, one or more microfluidic chips 108 may be configured to process numerous types of food products to facilitate detection of numerous types of allergen indicators 106.

At operation 404, the processing operation 210 may include processing the one or more samples for the one or more allergen indicators that are associated with one or more weeds, grasses, trees, mites, animals, molds, fungi, insects, rubbers, autoallergens, metals, chemicals, or human autoallergens. In some embodiments, one or more samples 102 may be processed with one or more microfluidic chips 108 that are configured for processing the one or more samples 102 for the one or more allergen indicators 106 that are associated with one or more weeds, grasses, trees, mites, animals, molds, fungi, insects, rubbers, metals, chemicals, autoallergens, or human autoallergens. Such allergen indicators 106 are described herein and are known. For example, in some embodiments, one or more microfluidic chips 108 may be configured to process one or more material samples 102 to determine if the material contains latex.

At operation 406, the processing operation 210 may include processing the one or more samples with the one or more microfluidic chips that are configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay. In some embodiments, one or more samples 102 may be processed with one or more microfluidic chips 108 that are configured for processing the one or more allergen indicators 106 through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay. In some embodiments, allergen indicators 106 may be separated from other materials included within one or more samples 102 through processing. In some embodiments, allergen indicators 106 may be immobilized through processing to facilitate detection and/or identification of the one or more allergen indicators 106.

In some embodiments, one or more microfluidic chips 108 may be configured to process one or more samples 102 through use of polynucleotide interaction. Numerous methods based on polynucleotide interaction may be used. Examples of such methods include, but are not limited to, those based on polynucleotide hybridization, polynucleotide ligation, polynucleotide amplification, polynucleotide degradation, and the like. Methods that utilize intercalation dyes, FRET analysis, capacitive DNA detection, and nucleic acid amplification have been described (e.g., U.S. Pat. Nos. 7,118, 910 and 6,960,437; herein incorporated by reference). In some embodiments, fluorescence resonance energy transfer, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube are combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or an ultraviolet laser) and the emission spectra of the excited nanotubes may be correlated with hybridization of the one or more polynucleotides that include at least one carbon nanotube with one or more polynucleotides that are included within the one or more samples 102. Methods to utilize carbon nanotubes as probes for nucleic acid interaction have been described (e.g., U.S. Pat. No. 6,821,730; herein incorporated by reference).

In some embodiments, one or more microfluidic chips 108 may be configured to process one or more samples 102 through use of protein interaction. Numerous methods based on protein interaction may be used. In some embodiments, protein interaction may be used to immobilize one or more allergen indicators 106. In some embodiments, protein interaction may be used to separate one or more allergen indicators 106 from one or more samples 102. Examples of such methods include, but are not limited to, those based on ligand binding, protein-protein binding, protein cross-linking, use of green fluorescent protein, phage display, the two-hybrid system, protein arrays, fiber optic evanescent wave sensors, chromatographic techniques, fluorescence resonance energy transfer, regulation of pH to control protein assembly and/or oligomerization, and the like. For example, tropomyosin is a major muscle protein in crustaceans that is thought to be a major shrimp allergen 104. Tropomyosin is associated with the well known actin-troponin-myosin complex. Calcium ion binding to troponin enables troponin to bind tropomyosin and shift it from the binding sites of myosin on the actin proteins. Without the presence of Calcium ion, troponin is no longer able to bind to tropomyosin, and tropomyosin again blocks the binding sites of myosin on the actin proteins. Tropomyosin also binds to the calcium-binding protein calcyclin (Nelson et al., Molecular & Cellular Proteomics 1:253-259 (2002) and Liou and Chen, European Journal of Biochemistry, 270: 3092-3100 (2003)). Accordingly, protein interactions may be used to separate tropomyosin (allergen indicator 106) from one or more samples 102. Similar methods may be used with numerous proteins. Methods that may be used to construct protein arrays have been described (e.g., Warren et al., Anal. Chem., 76:4082-4092 (2004) and Walter et al., Trends Mol. Med., 8:250-253 (2002), U.S. Pat. No. 6,780,582; herein incorporated by reference).

In some embodiments, one or more microfluidic chips 108 may be configured to process one or more samples 102 through use of peptide interaction. Peptides are generally described as being polypeptides that include less than one hundred amino acids. For example, peptides include dipeptides, tripeptides, and the like. In some embodiments, peptides may include from two to one hundred amino acids. In some embodiments, peptides may include from two to fifty amino acids. In some embodiments, peptides may include from two to one twenty amino acids. In some embodiments, peptides may include from ten to one hundred amino acids. In some embodiments, peptides may include from ten to fifty amino acids. Accordingly, peptides can include numerous numbers of amino acids. Numerous methods based on peptide interaction may be used. In some embodiments, peptide interaction may be used to immobilize one or more allergen indicators 106. In some embodiments, peptide interaction may be used to separate one or more allergen indicators 106 from one or more samples 102. Examples of such methods include, but are not limited to, those based on ligand binding, peptide-protein binding, peptide-peptide binding, peptide-polynucleotide binding, peptide cross-linking, use of green fluorescent protein, phage display, the two-hybrid system, protein arrays, peptide arrays, fiber optic evanescent wave sensors, chromatographic techniques, fluorescence resonance energy transfer, regulation of pH to control peptide and/or protein assembly and/or oligomerization, and the like. Accordingly, virtually any technique that may be used to analyze proteins may be utilized for the analysis of peptides. In some embodiments, high-speed capillary electrophoresis may be used to detect binding through use of fluorescently labeled phosphopeptides as affinity probes (Yang et al., Anal. Chem., 10.1021/ac061936e (2006)). Methods to immobilize proteins and peptides have been reported (Taylor, Protein Immobilization: Fundamentals and Applications, Marcel Dekker, Inc., New York (1991)).

In some embodiments, one or more microfluidic chips 108 may be configured to process one or more samples 102 through use of antibody interaction. Antibodies may be raised that will bind to numerous allergen indicators 106 through use of known methods (e.g., Harlow and Lane, Antibodies: A Laboratory Manual, Cold Spring Harbor Laboratory Press, Cold Spring Harbor, N.Y. (1988)). Antibodies may be configured in numerous ways within one or more microfluidic chips 108 to process one or more allergen indicators 106. For example, in some embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. A labeled detector antibody that binds to the allergen indicator 106 (or the antibody-allergen indicator 106 complex) may then be passed over the one or more antibody-allergen indicator 106 complexes such that the labeled detector antibody will label the allergen indicator 106 (or the antibody-allergen indicator 106 complex). Numerous labels may be used that include, but are not limited to, enzymes, fluorescent molecules (e.g., quantum dots), radioactive labels, spin labels, redox labels, and the like. In other embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. Such binding provides for detection of the antibody-allergen indicator 106 complex through use of methods that include, but are not limited to, surface plasmon resonance, conductivity, and the like (e.g., U.S. Pat. No. 7,030,989; herein incorporated by reference). In some embodiments, antibodies may be coupled to a substrate within a microfluidic chip 108 to provide for a competition assay. One or more samples 102 may be mixed with one or more reagent mixtures that include one or more labeled allergen indicators 106. The mixture may then be passed over the antibodies to facilitate binding of allergen indicators 106 in the sample 102 and labeled allergen indicators 106 in the reagent mixture to the antibodies. The unlabeled allergen indicators 106 in the sample 102 will compete with the labeled allergen indicators 106 in the reagent mixture for binding to the antibodies. Accordingly, the amount of label bound to the antibodies will vary in accordance with the concentration of unlabeled allergen indicators 106 in the sample 102. In some embodiments, antibody interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more antibodies may be used in conjunction with one or more aptamers to process one or more samples 102. Accordingly, in some embodiments, aptamers and antibodies may be used interchangeably to process one or more samples 102.

In some embodiments, one or more microfluidic chips 108 may be configured to process one or more samples 102 through use of chemical interaction. In some embodiments, one or more microfluidic chips 108 may be configured to utilize chemical extraction to process one or more samples 102. For example, in some embodiments, one or more samples 102 may be mixed with a reagent mixture that includes one or more solvents in which the one or more allergen indicators 106 are soluble. Accordingly, the solvent phase containing the one or more allergen indicators 106 may be separated from the sample phase to provide for detection of the one or more allergen indicators 106. In some embodiments, one or more samples 102 may be mixed with a reagent mixture that includes one or more chemicals that cause precipitation of one or more allergen indicators 106. Accordingly, the sample phase may be washed away from the one or more precipitated allergen indicators 106 to provide for detection of the one or more allergen indicators 106. Accordingly, reagent mixtures that include numerous types of chemicals that interact with one or more allergen indicators 106 may be used.

In some embodiments, one or more microfluidic chips 108 may be configured to process one or more samples 102 through use of diffusion. In some embodiments, one or more microfluidic chips 108 may be configured to process one or more fluid samples 102 through use of an H-filter. For example, a microfluidic chip 108 may be configured to include a channel through which a fluid sample 102 and a second fluid flow such that the fluid sample 102 and the second fluid undergo parallel flow through the channel without significant mixing of the sample fluid and the second fluid. As the fluid sample 102 and the second fluid flow through the channel, one or more allergen indicators 106 in the fluid sample 102 may diffuse through the fluid sample 102 into the second fluid. Accordingly, such diffusion provides for the separation of the one or more allergen indicators 106 from the sample 102. Methods to construct H-filters have been described (e.g., U.S. Pat. Nos. 6,742,661; 6,409,832; 6,007,775; 5,974,867; 5,971,158; 5,948,684; 5,932,100; 5,716,852; herein incorporated by reference). In some embodiments, diffusion based methods may be combined with immunoassay based methods to process and detect one or more allergen indicators 106. Methods to conduct microscale diffusion immunoassays have been described (e.g., U.S. Pat. No. 6,541,213; herein incorporated by reference). Accordingly, microfluidic chips 108 may be configured in numerous ways to process one or more allergen indicators 106 through use of diffusion.

In some embodiments, one or more microfluidic chips 108 may be configured to process one or more samples 102 through use of filtration. In some embodiments, one or more microfluidic chips 108 may be configured to include one or more filters that have a molecular weight cut-off. For example, a filter may allow molecules of low molecular weight to pass through the filter while disallowing molecules of high molecular weight to pass through the filter. Accordingly, one or more allergen indicators 106 that are contained within a sample 102 may be allowed to pass through a filter while larger molecules contained within the sample 102 are disallowed from passing through the filter. Accordingly, in some embodiments, a microfluidic chip 108 may include two or more filters that selectively retain, or allow passage, of one or more allergen indicators 106 through the filters. Such configurations provide for selective separation of one or more allergen indicators 106 from one or more samples 102. Membranes and filters having numerous molecular weight cut-offs are commercially available (e.g., Millipore, Billerica, Mass.). In some embodiments, one or more microfluidic chips 108 may be configured to provide for dialysis of one or more samples 102. For example, in some embodiments, a microfluidic chip 108 may be configured to contain one or more samples 102 in one or more sample chambers that are separated from one or more dialysis chambers by a semi-permeable membrane. Accordingly, in some embodiments, one or more allergen indicators 106 that are able to pass through the semi-permeable membrane may be collected in the dialysis chamber. In other embodiments, one or more allergen indicators 106 may be retained in the one or more sample chambers while other sample 102 components may be separated from the one or more allergen indicators 106 by their passage through the semi-permeable membrane into the dialysis chamber. Accordingly, one or more microfluidic chips 108 may be configured to include two or more dialysis chambers for selective separation of one or more allergen indicators 106 from one or more samples 102. Semi-permeable membranes and dialysis tubing is available from numerous commercial sources (e.g., Millipore, Billerica, Mass.; Pierce, Rockford, Ill.; Sigma-Aldrich, St. Louis, Mo.). Methods that may be used for microfiltration have been described (e.g., U.S. Pat. No. 5,922,210; herein incorporated by reference).

In some embodiments, one or more microfluidic chips 108 may be configured to process one or more samples 102 through use of chromatography. Numerous chromatographic methods may be used to process one or more samples 102. Examples of such chromatographic methods include, but are not limited to, ion-exchange chromatography, affinity chromatography, gel filtration chromatography, hydroxyapatite chromatography, gas chromatography, reverse phase chromatography, thin layer chromatography, capillary chromatography, size exclusion chromatography, hydrophobic interaction media, and the like. In some embodiments, a microfluidic chip 108 may be configured to process one or more samples 102 through use of one or more chromatographic methods. In some embodiments, chromatographic methods may be used to process one or more samples 102 for one or more allergen indicators 106 that include one or more polynucleotides. For example, in some embodiments, one or more samples 102 may be applied to a chromatographic media to which the one or more polynucleotides bind. The remaining components of the sample 102 may be washed from the chromatographic media. The one or more polynucleotides may then be eluted from chromatographic media in a more purified state. Similar methods may be used to process one or more samples 102 for one or more allergen indicators 106 that include one or more proteins or polypeptides (e.g., Mondal and Gupta, Biomol. Eng., 23:59-76 (2006)). Chromatography media able to separate numerous types of molecules is commercially available (e.g., Bio-Rad, Hercules, Calif.; Qiagen, Valencia, Calif.; Pfizer, New York, N.Y.; Millipore, Billerica, Mass.; GE Healthcare Bio-Sciences Corp., Piscataway, N.J.).

In some embodiments, one or more microfluidic chips 108 may be configured to process one or more samples 102 through use of aptamer interaction. In some embodiments, one or more aptamers may include polynucleotides (e.g., deoxyribonucleic acid; ribonucleic acid; and derivatives of polynucleotides that may include polynucleotides that include modified bases, polynucleotides in which the phosphodiester bond is replaced by a different type of bond, or many other types of modified polynucleotides). In some embodiments, one or more aptamers may include peptide aptamers. Methods to prepare and use aptamers have been described (e.g., Collett et al., Methods, 37:4-15 (2005); Collet et al., Anal. Biochem., 338:113-123 (2005); Cox et al., Nucleic Acids Res., 30:20 e108 (2002); Kirby et al., Anal. Chem., 76:4066-4075 (2004); Ulrich, Handb. Exp. Pharmacol., 173:305-326 (2006); Baines and Colas, Drug Discovery Today, 11:334-341 (2006); Guthrie et al., Methods, 38:324-330 (2006); Geyer et al., Chapter 13: Selection of Genetic Agents from Random Peptide Aptamer Expression Libraries, Methods in Enzymology, Academic Press, pg. 171-208 (2000); U.S. Pat. No. 6,569,630; herein incorporated by reference). Aptamers may be configured in numerous ways within one or more microfluidic chips 108 to process one or more allergen indicators 106. For example, in some embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Labeled detector antibodies and/or aptamers that bind to the allergen indicator 106 (or the aptamer-allergen indicator 106 complex) may then be passed over the one or more aptamer-allergen indicator 106 complexes such that the labeled detector antibodies and/or aptamers will label the allergen indicator 106 (or the aptamer-allergen indicator 106 complex). Numerous labels may be used that include, but are not limited to, enzymes, fluorescent molecules, radioactive labels, spin labels, redox labels, and the like. In other embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Such binding provides for detection of the aptamer-allergen indicator 106 complex through use of methods that include, but are not limited to, surface plasmon resonance, conductivity, and the like (e.g., U.S. Pat. No. 7,030,989; herein incorporated by reference). In some embodiments, aptamers may be coupled to a substrate within a microfluidic chip 108 to provide for a competition assay. One or more samples 102 may be mixed with one or more reagent mixtures that include one or more labeled allergen indicators 106. The mixture may then be passed over the aptamers to facilitate binding of allergen indicators 106 in the sample 102 and labeled allergen indicators 106 in the reagent mixture to the aptamers. The unlabeled allergen indicators 106 in the sample 102 will compete with the labeled allergen indicators 106 in the reagent mixture for binding to the aptamers. Accordingly, the amount of label bound to the aptamers will vary in accordance with the concentration of unlabeled allergen indicators 106 in the sample 102. In some embodiments, aptamer interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more aptamers may be used in conjunction with one or more antibodies to process one or more samples 102. In some embodiments, aptamers and antibodies may be used interchangeably to process one or more samples 102. Accordingly, in some embodiments, methods and/or systems for processing and/or detecting allergen indicators 106 may utilize antibodies and aptamers interchangeably and/or in combination.

In some embodiments, one or more microfluidic chips 108 may be configured to process one or more samples 102 through use of electrical conductivity. In some embodiments, one or more samples 102 may be processed though use of magnetism. For example, in some embodiments, one or more samples 102 may be combined with one or more tagged polynucleotides that are tagged with a ferrous material, such as a ferrous bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed over an electromagnet to immobilize the hybridized complexes. Other components in the sample 102 may then be washed away from the hybridized complexes. In some embodiments, a chamber containing the magnetically immobilized hybridized complexes may be heated to release the sample polynucleotides from the magnetically immobilized tagged polynucleotides. The sample polynucleotides may then be collected in a more purified state. In other embodiments, similar methods may be used in conjunction with antibodies, aptamers, peptides, ligands, and the like. Accordingly, one or more microfluidic chips 108 may be configured in numerous ways to utilize magnetism to process one or more samples 102. In some embodiments, one or more samples 102 may be processed though use of eddy currents. Eddy current separation uses the principles of electromagnetic induction in conducting materials to separate non-ferrous metals by their different electric conductivities. An electrical charge is induced into a conductor by changes in magnetic flux cutting through it. Moving permanent magnets passing a conductor generates the change in magnetic flux. Accordingly, in some embodiments, one or more microfluidic chips 108 may be configured to include a magnetic rotor such that when conducting particles move through the changing flux of the magnetic rotor, a spiraling current and resulting magnetic field are induced. The magnetic field of the conducting particles may interact with the magnetic field of the magnetic rotor to impart kinetic energy to the conducting particles. The kinetic energy imparted to the conducting particles may then be used to direct movement of the conducting particles. Accordingly, non-ferrous particles, such as metallic beads, may be utilized to process one or more samples 102. For example, in some embodiments, one or more samples 102 may be combined with one or more tagged polynucleotides that are tagged with a non-ferrous material, such as an aluminum bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed through a magnetic field to impart kinetic energy to the non-ferrous bead. This kinetic energy may then be used to separate the hybridized complex. In other embodiments, similar methods may be used in conjunction with antibodies, aptamers, peptides, ligands, and the like. Accordingly, one or more microfluidic chips 108 may be configured in numerous ways to utilize eddy currents to process one or more samples 102. One or more microfluidic chips 108 may be configured in numerous ways to utilize electrical conductivity to process one or more samples 102.

In some embodiments, one or more microfluidic chips 108 may be configured to process one or more samples 102 through use of isoelectric focusing. Methods have been described that may be used to construct capillary isoelectric focusing systems (e.g., Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). Such systems may be modified to provide for the processing of one or more samples 102.

In some embodiments, one or more microfluidic chips 108 may be configured to process one or more samples 102 through use of electrophoresis. In some embodiments, one or more microfluidic chips 108 may be configured to process one or more samples 102 through use of one-dimensional electrophoresis. In some embodiments, one or more microfluidic chips 108 may be configured to process one or more samples 102 through use of two-dimensional electrophoresis. In some embodiments, one or more microfluidic chips 108 may be configured to process one or more samples 102 through use of gradient gel electrophoresis. In some embodiments, one or more microfluidic chips 108 may be configured to process one or more samples 102 through use of electrophoresis under denaturing conditions. In some embodiments, one or more microfluidic chips 108 may be configured to process one or more samples 102 through use of electrophoresis under native conditions. One or more microfluidic chips 108 may be configured to utilize numerous electrophoretic methods.

In some embodiments, one or more microfluidic chips 108 may be configured to process one or more samples 102 through use of immunoassay. In some embodiments, one or more microfluidic chips 108 may be configured to process one or more samples 102 through use of enzyme linked immunosorbant assay (ELISA). In some embodiments, one or more microfluidic chips 108 may be configured to process one or more samples 102 through use of radioimmuno assay (RIA). In some embodiments, one or more microfluidic chips 108 may be configured to process one or more samples 102 through use of enzyme immunoassay (EIA). In some embodiments, such methods may utilize antibodies (e.g., monoclonal antibodies, polyclonal antibodies, antibody fragments, single-chain antibodies, and the like), aptamers, or substantially any combination thereof. In some embodiments, a labeled antibody and/or aptamer may be used within an immunoassay. In some embodiments, a labeled ligand to which the antibody and/or aptamer binds may be used within an immunoassay. Numerous types of labels may be utilized. Examples of such labels include, but are not limited to, radioactive labels, fluorescent labels, enzyme labels, spin labels, magnetic labels, gold labels, colorimetric labels, redox labels, and the like. Numerous immunoassays are known and may be configured for processing one or more samples 102.

In some embodiments, one or more microfluidic chips 108 may be configured to process one or more samples 102 through use of one or more competition assays. In some embodiments, one or more microfluidic chips 108 may be configured to process one or more samples 102 through use of one or more polynucleotide based competition assays. One or more microfluidic chips 108 may be configured to include one or more polynucleotides coupled to a substrate, such as a polynucleotide array. The one or more microfluidic chips 108 may be further configured so that a sample 102 and/or substantially purified polynucleotides obtained from one or more samples 102, may be mixed with one or more reagent mixtures that include one or more labeled polynucleotides to form an analysis mixture. This analysis mixture is then passed over the substrate such that the labeled polynucleotides and the sample polynucleotides are allowed to hybridize to the polynucleotides that are immobilized on the substrate. The sample polynucleotides and the labeled polynucleotides will compete for binding to the polynucleotides that are coupled on the substrate. Accordingly, the presence and/or concentration of the polynucleotides in the sample 102 can be determined through detection of the label (e.g., the concentration of the polynucleotides in the sample 102 will be inversely related to the amount of label that is bound to the substrate). Numerous labels may be used that include, but are not limited to, enzymes, fluorescent molecules, radioactive labels, spin labels, redox labels, and the like. In some embodiments, one or more microfluidic chips 108 may be configured to include one or more antibodies, proteins, peptides, and/or aptamers that are coupled to a substrate. The one or more microfluidic chips 108 may be further configured so that a sample 102 and/or substantially purified sample polynucleotides and/or sample peptides obtained from one or more samples 102, may be mixed with one or more reagent mixtures that include one or more labeled polypeptides and/or labeled peptides to form an analysis mixture. This analysis mixture can then be passed over the substrate such that the labeled polypeptides and/or labeled peptides and the sample polynucleotides and/or sample peptides are allowed to bind to the antibodies, proteins, peptides, and/or aptamers that are immobilized on the substrate. The sample polypeptides and/or sample peptides and the labeled polypeptides and/or sample peptides will compete for binding to the antibodies, proteins, peptides, and/or aptamers that are coupled on the substrate. Accordingly, the presence and/or concentration of the sample polypeptides and/or sample peptides in the sample 102 can be determined through detection of the label (e.g., the concentration of the sample polypeptides and/or sample peptides in the sample 102 will be inversely related to the amount of label that is bound to the substrate). Numerous labels may be used that include, but are not limited to, enzymes, fluorescent molecules, radioactive labels, spin labels, redox labels, and the like. Microfluidic chips 108 may be configured to utilize numerous types of competition assays.

In some embodiments, one or more microfluidic chips 108 may be configured to utilize numerous processing methods. For example, in some embodiments, one or more allergen indicators 106 may be precipitated with salt, dialyzed, and then applied to a chromatographic column.

Figure 5:
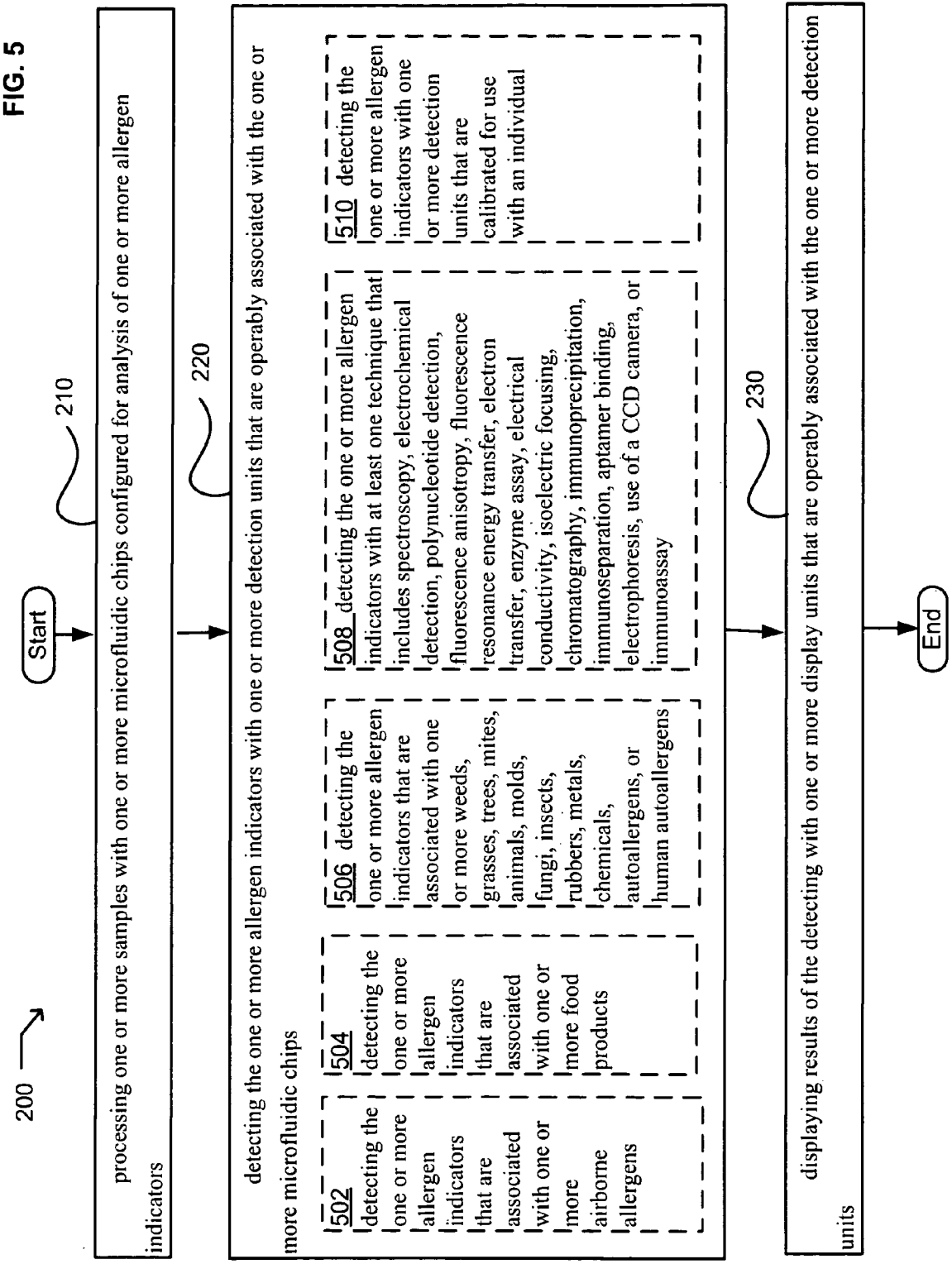
FIG. 5 illustrates alternate embodiments of the example operational flow of FIG. 2.

FIG. 5 illustrates alternative embodiments of the example operational flow 200 of FIG. 2. FIG. 5 illustrates example embodiments where the detecting operation 220 may include at least one additional operation. Additional operations may include an operation 502, an operation 504, an operation 506, an operation 508, and/or an operation 510

At operation 502, the detecting operation 220 may include detecting the one or more allergen indicators that are associated with one or more airborne allergens. In some embodiments, one or more detection units 122 may be used to detect one or more allergen indicators 106 that are associated with one or more airborne allergens 104. In some embodiments, one or more microfluidic chips 108 may be configured to provide for detection of one or more allergens 104 that are airborne. Accordingly, in some embodiments, one or more detection units 122 may be configured to operably associate with the one or more microfluidic chips 108 and to detect one or more airborne allergens 104. For example, in some embodiments, one or more microfluidic chips 108 may be configured to allow one or more air samples 102 to contact the one or more microfluidic chips 108 such that one or more allergen indicators 106 included within the one or more air samples 102 are retained by the one or more microfluidic chips 108. In some embodiments, the one or more air samples 102 may be passed through a filter on which one or more airborne allergen indicators 106 are collected. The collected airborne allergen indicators 106 may then be washed from the filter and caused to pass over an antibody array to which the one or more airborne allergen indicators 106 become immobilized. The immobilized airborne allergen indicators 106 may then be detected through numerous methods that include, but are not limited to, electrical conductivity, immunoassay based methods, and the like. Accordingly, one or more detection units 122 may be configured to detect the one or more airborne allergen indicators 106. In some embodiments, one or more detection units 122 may be configured to operably associate with one or more microfluidic chips 108 such that the one or more detection units 122 facilitate air flow through the one or more microfluidic chips 108 to provide for air sampling. For example, in some embodiments, one or more detection units 122 may include one or more fans to push and/or pull air through one or more operably associated microfluidic chips 108. In some embodiments, one or more detection units 122 may include one or more bellows to push and/or pull air through one or more operably associated microfluidic chips 108. Detection units 122 may be configured in numerous ways to provide for detection of one or more airborne allergen indicators 106.

At operation 504, the detecting operation 220 may include detecting the one or more allergen indicators that are associated with one or more food products. In some embodiments, one or more detection units 122 may be used to detect the one or more allergen indicators 106 that are associated with one or more food products. In some embodiments, one or more microfluidic chips 108 may be configured to provide for detection of one or more allergens 104 that are associated with one or more food products. Accordingly, in some embodiments, one or more detection units 122 may be configured to operably associate with the one or more microfluidic chips 108 and to detect one or more allergen indicators 106 that are associated with one or more food products. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Numerous methods may be used to detect one or more allergen indicators 106 that are associated with one or more food products. Such methods have been described herein. In addition, other detection methods that have been described may be modified to provide for detection of one or more allergen indicators 106 that are associated with one or more food products. In some embodiments, one or more detection units 122 may be configured to detect one or more polynucleotides, one or more polypeptides, one or more portions of one or more polynucleotides, and/or one or more portions of one or more polypeptides that have a nucleic acid sequence and/or an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, or AY839230.

At operation 506, the detecting operation 220 may include detecting the one or more allergen indicators that are associated with one or more weeds, grasses, trees, mites, animals, molds, fungi, insects, rubbers, metals, chemicals, autoallergens, or human autoallergens. In some embodiments, one or more detection units 122 may be used to detect one or more allergen indicators 106 that are associated with one or more weeds, grasses, trees, mites, animals, molds, fungi, insects, rubbers, metals, chemicals, autoallergens, human autoallergens, or substantially any combination thereof. Numerous allergen indicators 106 are known to be associated with weeds, grasses, trees, mites, animals, molds, fungi, insects, rubbers, metals, chemicals, autoallergens, human autoallergens, or substantially any combination thereof. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Accordingly, in some embodiments, one or more microfluidic chips 108 may be configured to process one or more samples 102 and provide for detection of one or more allergen indicators 106. In some embodiments, an allergen indicator 106 may be an allergenic particle. For example, in some embodiments, an allergen indicator 106 may include a complete pollen particle, such as a pollen particle, a spore, a flake of dander, and the like. In some embodiments, an allergen indicator 106 may be a portion of an allergenic particle. For example, in some embodiments, an allergen indicator 106 may include a portion of a pollen particle (e.g., polynucleotides, sporoderm, and the like). In some embodiments, allergen indicators 106 may include polynucleotides that are associated with one or more allergens 104. In some embodiments, allergen indicators 106 may include fragments of polynucleotides that are associated with one or more allergens 104. In some embodiments, allergen indicators 106 may include polypeptides, peptides, and/or proteins that are associated with one or more allergens 104. In some embodiments, allergen indicators 106 may include polysaccharides that are associated with one or more allergens 104. Accordingly, in some embodiments, one or more microfluidic chips 108 may be configured to provide for detection of one or more allergen indicators 106. In some embodiments, one or more detection units 122 may be configured to operably associate with one or more such microfluidic chips 108 and configured to detect one or more allergen indicators 106. Numerous detection methods may be used to detect one or more allergen indicators 106. Such methods have been described herein. In addition, detection methods that have been described may be modified to provide for detection of one or more allergen indicators 106. In some embodiments, one or more detection units 122 may be configured to detect and determine a concentration of one or more allergen indicators 106 that are included within a sample 102. For example, in some embodiments, one or more microfluidic chips 108 may be configured to provide for detection of one or more polynucleotides that are allergen indicators 106 through detection of electrical current produced upon hybridization of the one or more polynucleotides. Accordingly, in such embodiments, the one or more microfluidic chips 108 may be configured to produce an electrical current that is relative to polynucleotide concentration to provide for determination of polynucleotide concentration within one or more samples 102. Numerous configurations may be used in association with one or more allergen indicators 106 to provide for determination of allergen 104 concentration. In some embodiments, one or more microfluidic chips 108 may be configured to provide for identification of one or more allergens 104. For example, in some embodiments, one or more microfluidic chips 108 may include immobilized polynucleotides that selectively hybridize to one or more polynucleotides that are associated with a known allergen indicator 106. Accordingly, hybridization of one or more polynucleotides with the one or more immobilized polynucleotides indicates that a sample 102 includes one or more allergen indicators 106 that correspond to one or more known allergens 104. Accordingly, one or more detection units 122 may be configured to operably associate with such microfluidic chips 108 to provide for specific detection of one or more allergens 104. In some embodiments, microfluidic chips 108 and/or detection units 122 may be configured to determine the identity and concentration of one or more allergen indicators 106 that are included within one or more samples 102.

At operation 508, the detecting operation 220 may include detecting the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, one or more detection units 122 may be used to detect one or more allergen indicators 106 with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, filtration, electrophoresis, use of a CCD camera, immunoassay, or substantially any combination thereof. In some embodiments, one or more detection units 122 may be configured to detect one or more allergen indicators 106 that have been processed by one or more microfluidic chips 108. For example, in some embodiments, one or more microfluidic chips 108 may include a window (e.g., a quartz window, a cuvette analog, and/or the like) through which one or more detection units 122 may determine if one or more allergen indicators 106 are present or determine the concentration of one or more allergen indicators 106. In such embodiments, numerous techniques may be used to detect the one or more allergen indicators 106, such as visible light spectroscopy, ultraviolet light spectroscopy, infrared spectroscopy, fluorescence spectroscopy, and the like. Accordingly, in some embodiments, one or more detection units 122 may include circuitry and/or electro-mechanical mechanisms to detect one or more allergen indicators 106 present within one or more microfluidic chips 108 through a window in the one or more microfluidic chips 108. In some embodiments, one or more microfluidic chips 108 may be configured to process one or more samples 102 through use of surface plasmon resonance. In some embodiments, the one or more microfluidic chips 108 may include one or more antibodies, aptamers, proteins, peptides, polynucleotides, and the like, that are bound to a substrate (e.g., a metal film) within the one or more microfluidic chips 108. In some embodiments, such microfluidic chips 108 may include a prism through which one or more detection units 122 may shine light to detect one or more allergen indicators 106 that interact with the one or more antibodies, aptamers, proteins, peptides, polynucleotides, and the like, that are bound to a substrate. In some embodiments, one or more microfluidic chips 108 may include an exposed substrate surface that is configured to operably associate with one or more prisms that are included within one or more detection units 122. In some embodiments, one or more microfluidic chips 108 may include a nuclear magnetic resonance (NMR) probe. In such embodiments, the microfluidic chips 108 may be configured to associate with one or more detection units 122 that accept the NMR probe and are configured to detect one or more allergen indicators 106 through use of NMR spectroscopy. Accordingly, microfluidic chips 108 and detection units 122 may be configured in numerous ways to associate with each other to provide for detection of one or more allergen indicators 106.

In some embodiments, one or more allergen indicators 106 may be detected through use of spectroscopy. Numerous types of spectroscopic methods may be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., Clinical Chemistry, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, one or more allergen indicators 106 may be detected through use of electrochemical detection. In some embodiments, one or more polynucleotides may be detected through electrochemical detection. For example, in some embodiments, a polynucleotide that includes a redox label, such as ferrocene is coupled to a gold electrode. The labeled polynucleotide forms a stem-loop structure that can self-assemble onto a gold electrode by means of facile gold-thiol chemistry. Hybridization of a sample 102 polynucleotide induces a large conformational change in the surface-confined polynucleotide structure, which in turn alters the electron-transfer tunneling distance between the electrode and the redoxable label. The resulting change in electron transfer efficiency may be measured by cyclic voltammetry (Fan et al., Proc. Natl. Acad. Sci., 100:9134-9137 (2003); Wang et al., Anal. Chem., 75:3941-3945 (2003); Singh-Zocchi et al., Proc. Natl. Acad. Sci., 100:7605-7610 (2003)). Such methods may be used to detect messenger ribonucleic acid, genomic deoxyribonucleic acid, and fragments thereof.

In some embodiments, one or more allergen indicators 106 may be detected through use of polynucleotide detection. In some embodiments, one or more detection units 122 may be configured to detect one or more allergen indicators 106 through use of polynucleotide detection. Numerous methods may be used to detect one or more polynucleotides. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described (e.g., U.S. Pat. Nos. 7,118,910 and 6,960,437; herein incorporated by reference). Such methods may be adapted to provide for detection of one or more allergen indicators 106. In some embodiments, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube may be combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Accordingly, polynucleotides that hybridize to one or more allergen indicators 106 may include one or more carbon nanotubes. Methods to utilize carbon nanotubes as probes for nucleic acid interaction have been described (e.g., U.S. Pat. No. 6,821,730; herein incorporated by reference). Numerous other methods based on polynucleotide detection may be used to detect one or more allergen indicators 106.

In some embodiments, one or more allergen indicators 106 may be detected through use of fluorescence anisotropy. Fluorescence anisotropy is based on measuring the steady state polarization of sample 102 fluorescence imaged in a confocal arrangement. A linearly polarized laser excitation source preferentially excites fluorescent target molecules with transition moments aligned parallel to the incident polarization vector. The resultant fluorescence is collected and directed into two channels that measure the intensity of the fluorescence polarized both parallel and perpendicular to that of the excitation beam. With these two measurements, the fluorescence anisotropy, r, can be determined from the equation: r=(Intensity parallel−Intensity perpendicular)/(Intensity parallel+2(Intensity perpendicular)) where the I terms indicate intensity measurements parallel and perpendicular to the incident polarization. Fluorescence anisotropy detection of fluorescent molecules has been described. Accordingly, fluorescence anisotropy may be coupled to numerous fluorescent labels as have been described herein and as have been described.

In some embodiments, one or more allergen indicators 106 may be detected through use of fluorescence resonance energy transfer (FRET). Fluorescence resonance energy transfer refers to an energy transfer mechanism between two fluorescent molecules. A fluorescent donor is excited at its fluorescence excitation wavelength. This excited state is then nonradiatively transferred to a second molecule, the fluorescent acceptor. Fluorescence resonance energy transfer may be used within numerous configurations to detect one or more allergen indicators 106. For example, in some embodiments, an antibody may be labeled with a fluorescent donor and one or more allergen indicators 106 may be labeled with a fluorescent acceptor. Accordingly, such labeled antibodies and allergen indicators 106 may be used within competition assays to detect the presence and/or concentration of one or more allergen indicators 106 in one or more samples 102. Numerous combinations of fluorescent donors and fluorescent acceptors may be used to detect one or more allergen indicators 106. Accordingly, one or more detection units 122 may be configured to emit one or more wavelength of light to excite a fluorescent donor and may be configured to detect one or more wavelength of light emitted by the fluorescent acceptor. Accordingly, in some embodiments, one or more detection units 122 may be configured to accept one or more microfluidic chips 108 that include a quartz window through which fluorescent light may pass to provide for detection of one or more allergen indicators 106 through use of fluorescence resonance energy transfer. Accordingly, fluorescence resonance energy transfer may be used in conjunction with competition assays and/or numerous other types of assays to detect one or more allergen indicators 106.

In some embodiments, one or more allergen indicators 106 may be detected through use of electron transfer. Electron transfer is the process by which an electron moves from an electron donor to an electron acceptor causing the oxidation states of the electron donor and the electron acceptor to change. In some embodiments, electron transfer may occur when an electron is transferred from one or more electron donors to an electrode. In some embodiments, electron transfer may be utilized within competition assays to detect one or more allergen indicators 106. For example, in some embodiments, one or more microfluidic chips 108 may include one or more polynucleotides that may be immobilized on one or more electrodes. The immobilized polynucleotides may be incubated with a reagent mixture that includes sample polynucleotides and polynucleotides that are tagged with an electron donor. Hybridization of the tagged polynucleotides to the immobilized polynucleotides allows the electron donor to transfer an electron to the electrode to produce a detectable signal 132. Accordingly, a decrease in signal 132 due to the presence of one or more polynucleotides that are allergen indicators 106 in the reagent mixture indicates the presence of an allergen indicator 106 in the sample 102. Such methods may be used in conjunction with polynucleotides, polypeptides, peptides, antibodies, aptamers, and the like. One or more microfluidic chips 108 may be configured to utilize numerous electron transfer based assays to provide for detection of one or more allergen indicators 106 by a detection unit 122.

In some embodiments, one or more allergen indicators 106 may be detected through use of one or more enzyme assays. Numerous enzyme assays may be used to provide for detection of one or more allergen indicators 106. Examples of such enzyme assays include, but are not limited to, beta-galactosidase assays, peroxidase assays, catalase assays, alkaline phosphatase assays, and the like. In some embodiments, enzyme assays may be configured such that an enzyme will catalyze a reaction involving an enzyme substrate that produces a fluorescent product. Accordingly, one or more detection units 122 may be configured to detect fluorescence resulting from the fluorescent product. Enzymes and fluorescent enzyme substrates are known and are commercially available (e.g., Sigma-Aldrich, St. Louis, Mo.). In some embodiments, enzyme assays may be configured as binding assays that provide for detection of one or more allergen indicators 106. For example, in some embodiments, one or more microfluidic chips 108 may be configured to include a substrate to which is coupled to one or more antibodies, aptamers, peptides, proteins, polynucleotides, ligands, and the like, that will interact with one or more allergen indicators 106. One or more samples 102 may be passed across the substrate such that one or more allergen indicators 106 present within the one or more samples 102 will interact with the one or more antibodies, aptamers, peptides, proteins, polynucleotides, ligands, and the like, and be immobilized on the substrate. One or more antibodies, aptamers, peptides, proteins, polynucleotides, ligands, and the like, that are labeled with an enzyme may then be passed across the substrate such that the one or more labeled antibodies, aptamers, peptides, proteins, polynucleotides, ligands, and the like, will bind to the one or more immobilized allergen indicators 106. An enzyme substrate may then be introduced to the one or more immobilized enzymes such that the enzymes are able to catalyze a reaction involving the enzyme substrate to produce a fluorescent product. Such assays are often referred to as sandwich assays. Accordingly, one or more detection units 122 may be configured to detect one or more products of enzyme catalysis to provide for detection of one or more allergen indicators 106.

In some embodiments, one or more allergen indicators 106 may be detected through use of electrical conductivity. In some embodiments, one or more microfluidic chips 108 may be configured to process one or more samples 102 and provide for detection of one or more allergen indicators 106 through use of electrical conductivity. In some embodiments, such microfluidic chips 108 may be configured to operably associate with one or more detection units 122 such that the one or more detection units 122 can detect one or more allergen indicators 106 through use of electrical conductivity. In some embodiments, one or more microfluidic chips 108 may be configured to include two or more electrodes that are each coupled to one or more detector polynucleotides. Interaction of an allergen 104 associated polynucleotide, such as hybridization, with two detector polynucleotides that are coupled to two different electrodes will complete an electrical circuit. This completed circuit will provide for the flow of a detectable electrical current between the two electrodes and thereby provide for detection of one or more allergen 104 associated polynucleotides that are allergen indicators 106. In some embodiments, the electrodes may be carbon nanotubes (e.g., U.S. Pat. No. 6,958,216; herein incorporated by reference). In some embodiments, electrodes may include, but are not limited to, one or more conductive metals, such as gold, copper, iron, silver, platinum, and the like; one or more conductive alloys; one or more conductive ceramics; and the like. In some embodiments, electrodes may be selected and configured according to protocols typically used in the computer industry that include, but are not limited to, photolithography, masking, printing, stamping, and the like. In some embodiments, other molecules and complexes that interact with one or more allergen indicators 106 may be used to detect the one or more allergen indicators 106 through use of electrical conductivity. Examples of such molecules and complexes include, but are not limited to, proteins, peptides, antibodies, aptamers, and the like. For example, in some embodiments, two or more antibodies may be immobilized on one or more electrodes such that contact of the two or more antibodies with an allergen indicator 106, such as a spore, a pollen particle, a dander particle, and the like, will complete an electrical circuit and facilitate the production of a detectable electrical current. Accordingly, in some embodiments, one or more microfluidic chips 108 may be configured to include electrical connectors that are able to operably associate with one or more detection units 122 such that the detection units 122 may detect an electrical current that is due to interaction of one or more allergen indicators 106 with two or more electrodes. In some embodiments, one or more detection units 122 may include electrical connectors that provide for operable association of one or more microfluidic chips 108 with the one or more detection units 122. In some embodiments, the one or more detectors are configured for detachable connection to one or more microfluidic chips 108. Microfluidic chips 108 and detection units 122 may be configured in numerous ways to process one or more samples 102 and detect one or more allergen indicators 106.

In some embodiments, one or more allergen indicators 106 may be detected through use of isoelectric focusing. In some embodiments, one or more microfluidic chips 108 may be configured to process one or more samples 102 and provide for detection of one or more allergen indicators 106 through use of isoelectric focusing. In some embodiments, native isoelectric focusing may be utilized to process and/or detect one or more allergen indicators 106. In some embodiments, denaturing isoelectric focusing may be utilized to process and/or detect one or more allergen indicators 106. Methods to construct microfluidic channels that may be used for isoelectric focusing have been reported (e.g., Macounova et al., Anal Chem., 73:1627-1633 (2001); Macounova et al., Anal Chem., 72:3745-3751 (2000); Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). In some embodiments, one or more microfluidic chips 108 may be configured to process one or more samples 102 through use of methods that include isoelectric focusing. In some embodiments, one or more detection units 122 may be configured to operably associate with one or more such microfluidic chips 108 such that the one or more detection units 122 can be used to detect one or more allergen indicators 106 that have been focused within one or more microfluidic channels of the one or more microfluidic chips 108. In some embodiments, one or more detection units 122 may be configured to include one or more CCD cameras that can be used to detect one or more allergen indicators 106. In some embodiments, one or more detection units 122 may be configured to include one or more spectrometers that can be used to detect one or more allergen indicators 106. Numerous types of spectrometers may be utilized to detect one or more allergen indicators 106 following isoelectric focusing. In some embodiments, one or more detection units 122 may be configured to utilize refractive index to detect one or more allergen indicators 106. In some embodiments, one or more microfluidic chips 108 may be configured to combine one or more samples 102 with one or more reagent mixtures that include one or more binding molecules and/or binding complexes that bind to one or more allergen indicators 106 that may be present within the one or more samples 102 to form an allergen indicator-binding molecule/binding complex. Examples of such binding molecules and/or binding complexes that bind to one or more allergen indicators 106 include, but are not limited to, antibodies, aptamers, peptides, proteins, polynucleotides, and the like. In some embodiments, an allergen indicator-binding molecule/binding complex may be processed through use of isoelectric focusing and then detected with one or more detection units 122. In some embodiments, one or more binding molecules and/or one or more binding complexes may include a label. Numerous labels may be used and include, but are not limited to, radioactive labels, fluorescent labels, colorimetric labels, spin labels, fluorescent labels, and the like. Accordingly, in some embodiments, an allergen indicator-binding molecule (labeled)/binding complex (labeled) may be processed through use of isoelectric focusing and then detected with one or more detection units 122 that are configured to detect the one or more labels. Microfluidic chips 108 and detection units 122 may be configured in numerous ways to process one or more samples 102 and detect one or more allergen indicators 106 though use of isoelectric focusing.

In some embodiments, one or more allergen indicators 106 may be detected through use of chromatographic methodology alone or in combination with additional processing and/or detection methods. In some embodiments, one or more microfluidic chips 108 may be configured to process one or more samples 102 and provide for detection of one or more allergen indicators 106 through use of chromatographic methods. Accordingly, in some embodiments, one or more detection units 122 may be configured to operably associate with the one or more microfluidic chips 108 and detect one or more allergen indicators 106 that were processed through use of chromatographic methods. In some embodiments, the one or more detection units 122 may be configured to operably associate with one or more microfluidic chips 108 and supply solvents and other reagents to the one or more microfluidic chips 108. For example, in some embodiments, one or more detection units 122 may include pumps and solvent/buffer reservoirs that are configured to supply solvent/buffer flow through chromatographic media (e.g., a chromatographic column) that is operably associated with one or more microfluidic chips 108. In some embodiments, one or more detection units 122 may be configured to operably associate with one or more microfluidic chips 108 and be configured to utilize one or more methods to detect one or more allergen indicators 106. Numerous types of chromatographic methods and media may be used to process one or more samples 102 and provide for detection of one or more allergen indicators 106. Chromatographic methods include, but are not limited to, low pressure liquid chromatography, high pressure liquid chromatography (HPLC), microcapillary low pressure liquid chromatography, microcapillary high pressure liquid chromatography, ion exchange chromatography, affinity chromatography, gel filtration chromatography, size exclusion chromatography, thin layer chromatography, paper chromatography, gas chromatography, and the like. In some embodiments, one or more microfluidic chips 108 may be configured to include one or more high pressure microcapillary columns. Methods that may be used to prepare microcapillary HPLC columns (e.g., columns with a 100 micrometer-500 micrometer inside diameter) have been described (e.g., Davis et al., Methods, A Companion to Methods in Enzymology, 6: Micromethods for Protein Structure Analysis, ed. by John E. Shively, Academic Press, Inc., San Diego, 304-314 (1994); Swiderek et al., Trace Structural Analysis of Proteins. Methods of Enzymology, ed. by Barry L. Karger & William S. Hancock, Spectrum, Publisher Services, 271, Chap. 3, 68-86 (1996); Moritz and Simpson, J. Chromatogr., 599:119-130 (1992)). In some embodiments, one or more microfluidic chips 108 may be configured to include one or more affinity columns. Methods to prepare affinity columns have been described. Briefly, a biotinylated site may be engineered into a polypeptide, peptide, aptamer, antibody, or the like. The biotinylated protein may then be incubated with avidin coated polystyrene beads and slurried in Tris buffer. The slurry may then be packed into a capillary affinity column through use of high pressure packing. Affinity columns may be prepared that may include one or more molecules and/or complexes that interact with one or more allergen indicators 106. For example, in some embodiments, one or more aptamers that bind to one or more allergen indicators 106 may be used to construct an affinity column. Accordingly, numerous chromatographic methods may be used alone, or in combination with additional methods, to process and detect one or more allergen indicators 106. Numerous detection methods may be used in combination with numerous types of chromatographic methods. Accordingly, one or more detection units 122 may be configured to utilize numerous detection methods to detect one or more allergen indicators 106 that are processed through use of one or more chromatographic methods. Examples of such detection methods include, but are not limited to, conductivity detection, use of ion-specific electrodes, refractive index detection, colorimetric detection, radiological detection, detection by retention time, detection through use of elution conditions, spectroscopy, and the like. For example, in some embodiments, one or more chromatographic markers may be added to one or more samples 102 prior to the samples 102 being applied to a chromatographic column. One or more detection units 122 that are operably associated with the chromatographic column may be configured to detect the one or more chromatographic markers and use the elution time and/or position of the chromatographic markers as a calibration tool for use in detecting one or more allergen indicators 106 if those allergen indicators 106 are eluted from the chromatographic column. In some embodiments, one or more detection units 122 may be configured to utilize one or more ion-specific electrodes to detect one or more allergen indicators 106. For example, such electrodes may be used to detect allergen indicators 106 that include, but are not limited to, metals (e.g., tin, silver, nickel, cobalt, chromate), nitrates, nitrites, sulfites, and the like. Such allergen indicators 106 are often associated with food, beverages, clothing, jewelry, and the like. Accordingly, chromatographic methods may be used in combination with additional methods and in combination with numerous types of detection methods.

In some embodiments, one or more allergen indicators 106 may be detected through use of immunoprecipitation. In some embodiments, one or more detection units 122 may be configured to detect one or more allergen indicators 106 through use of immunoprecipitation. In some embodiments, immunoprecipitation may be utilized in combination with additional processing and/or detection methods to detect one or more allergen indicators 106. In some embodiments, one or more microfluidic chips 108 may be configured to process one or more samples 102 through use of immunoprecipitation. For example, in some embodiments, one or more samples 102 may be combined with one or more antibodies that bind to one or more allergen indicators 106 to form one or more antibody-allergen indicator 106 complexes. An insoluble form of an antibody binding constituent, such as protein A (e.g., protein A-sepharose bead, protein A-magnetic bead, protein A-ferrous bead, protein A-non-ferrous bead, and the like), Protein G, a second antibody, an aptamer, and the like, may then be mixed with the antibody-allergen indicator 106 complex such that the insoluble antibody binding constituent binds to the antibody-allergen indicator 106 complex and provides for precipitation of the antibody-allergen indicator 106 complex. Such complexes may be separated from other sample 102 components to provide for detection of one or more allergen indicators 106. For example, in some embodiments, sample 102 components may be washed away from the precipitated antibody-allergen indicator 106 complexes. In some embodiments, one or more microfluidic chips 108 that are configured for immunoprecipitation may be operably associated with one or more centrifugation units 118 to assist in precipitating one or more antibody-allergen indicator 106 complexes. In some embodiments, aptamers (polypeptide and/or polynucleotide) may be used in combination with antibodies or in place of antibodies. Accordingly, one or more detection units 122 may be configured to detect one or more allergen indicators 106 through use of numerous detection methods in combination with immunoprecipitation based methods.

In some embodiments, one or more allergen indicators 106 may be detected through use of immunoseparation. In some embodiments, one or more detection units 122 may be configured to detect one or more allergen indicators 106 through use of immunoseparation. In some embodiments, immunoseparation may be utilized in combination with additional processing and/or detection methods to detect one or more allergen indicators 106. In some embodiments, one or more microfluidic chips 108 may be configured to process one or more samples 102 through use of immunoseparation. For example, in some embodiments, one or more samples 102 may be combined with one or more antibodies that bind to one or more allergen indicators 106 to form one or more antibody-allergen indicator 106 complexes. An antibody binding constituent may be added that binds to the antibody-allergen complex.

Examples of such antibody binding constituents that may be used alone or in combination include, but are not limited to, protein A (e.g., protein A-sepharose bead, protein A-magnetic bead, protein A-ferrous bead, protein A-non-ferrous bead, and the like), Protein G, a second antibody, an aptamer, and the like. Such antibody binding constituents may be mixed with an antibody-allergen indicator 106 complex such that the antibody binding constituent binds to the antibody-allergen indicator 106 complex and provides for separation of the antibody-allergen indicator 106 complex. In some embodiments, the antibody binding constituent may include a tag that allows the antibody binding constituent and complexes that include the antibody binding constituent to be separated from other components in one or more samples 102. In some embodiments, the antibody binding constituent may include a ferrous material. Accordingly, antibody-allergen indicator 106 complexes may be separated from other sample 102 components through use of a magnet, such as an electromagnet. In some embodiments, an antibody binding constituent may include a non-ferrous metal. Accordingly, antibody-allergen indicator 106 complexes may be separated from other sample 102 components through use of an eddy current to direct movement of one or more antibody-allergen indicator 106 complexes. In some embodiments, two or more forms of an antibody binding constituents may be used to detect one or more allergen indicators 106. For example, in some embodiments, a first antibody binding constituent may be coupled to a ferrous material and a second antibody binding constituent may be coupled to a non-ferrous material. Accordingly, the first antibody binding constituent and the second antibody binding constituent may be mixed with antibody-allergen indicator 106 complexes such that the first antibody binding constituent and the second antibody binding constituent bind to antibody-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more antibodies that bind to one or more allergen indicators 106 to form one or more antibody-allergen indicator 106 complexes. In some embodiments, the one or more antibodies may include one or more tags that provide for separation of the antibody-allergen indicator 106 complexes. For example, in some embodiments, an antibody may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with immunoseparation based methods. In some embodiments, aptamers (polypeptide and/or polynucleotide) may be used in combination with antibodies or in place of antibodies.

In some embodiments, one or more allergen indicators 106 may be detected through use of aptamer binding. In some embodiments, one or more detection units 122 may be configured to detect one or more allergen indicators 106 through use of aptamer binding. In some embodiments, aptamer binding may be utilized in combination with additional processing and/or detection methods to detect one or more allergen indicators 106. In some embodiments, one or more microfluidic chips 108 may be configured to process one or more samples 102 through use of aptamer binding. For example, in some embodiments, one or more samples 102 may be combined with one or more aptamers that bind to one or more allergen indicators 106 to form one or more aptamer-allergen indicator 106 complexes. In some embodiments, aptamer binding constituents may be added that bind to the aptamer-allergen 104 complex. Numerous aptamer binding constituents may be utilized. For example, in some embodiments, one or more aptamers may include one or more tags to which one or more aptamer binding constituents may bind. Examples of such tags include, but are not limited to, biotin, avidin, streptavidin, histidine tags, nickel tags, ferrous tags, non-ferrous tags, and the like. In some embodiments, one or more tags may be conjugated with a label to provide for detection of one or more complexes. Examples of such tag-label conjugates include, but are not limited to, Texas red conjugated avidin, alkaline phosphatase conjugated avidin, CY2 conjugated avidin, CY3 conjugated avidin, CY3.5 conjugated avidin, CY5 conjugated avidin, CY5.5 conjugated avidin, fluorescein conjugated avidin, glucose oxidase conjugated avidin, peroxidase conjugated avidin, rhodamine conjugated avidin, agarose conjugated anti-protein A, alkaline phosphatase conjugated protein A, anti-protein A, fluorescein conjugated protein A, IRDye® 800 conjugated protein A, peroxidase conjugated protein A, sepharose protein A, alkaline phosphatase conjugated streptavidin, AMCA conjugated streptavidin, anti-streptavidin (*Streptomyces avidinii*) (rabbit) IgG Fraction, beta-galactosidase conjugated streptavidin, CY2 conjugated streptavidin, CY3 conjugated streptavidin, CY3.5 conjugated streptavidin, CY5 conjugated streptavidin, CY5.5 conjugated streptavidin, fluorescein conjugated streptavidin, IRDye® 700DX conjugated streptavidin, IRDye® 800 conjugated streptavidin, IRDye® 800CW conjugated streptavidin, peroxidase conjugated streptavidin, phycoerythrin conjugated streptavidin, rhodamine conjugated streptavidin, Texas red conjugated streptavidin, alkaline phosphatase conjugated biotin, anti-biotin (rabbit) IgG fraction, beta-galactosidase conjugated biotin, glucose oxidase conjugated biotin, peroxidase conjugated biotin, alkaline phosphatase conjugated protein G, anti-protein G (rabbit) Agarose conjugated, anti-protein G (Rabbit) IgG fraction, fluorescein conjugated protein G, IRDye® 800 conjugated protein G, peroxidase conjugated protein G, and the like. Many such labeled tags are commercially available (e.g., Rockland Immunochemicals, Inc., Gilbertsville, Pa.). Such labels may also be used in association with other methods to process and detect one or more allergen indicators 106. Aptamer binding constituents may be mixed with an aptamer-allergen indicator 106 complex such that the aptamer binding constituent binds to the aptamer-allergen indicator 106 complex and provides for separation of the aptamer-allergen indicator 106 complex. In some embodiments, the aptamer binding constituent may include a tag that allows the aptamer binding constituent and complexes that include the aptamer binding constituent to be separated from other components in one or more samples 102. In some embodiments, the aptamer binding constituent may include a ferrous material. Accordingly, aptamer-allergen indicator 106 complexes may be separated from other sample 102 components through use of a magnet, such as an electromagnet. In some embodiments, an aptamer binding constituent may include a non-ferrous metal. Accordingly, aptamer-allergen indicator 106 complexes may be separated from other sample 102 components through use of an eddy current to direct movement of one or more aptamer-allergen indicator 106 complexes. In some embodiments, two or more forms of aptamer binding constituents may be used to detect one or more allergen indicators 106. For example, in some embodiments, a first aptamer binding constituent may be coupled to a ferrous material and a second aptamer binding constituent may be coupled to a non-ferrous material. Accordingly, the first aptamer binding constituent and the second aptamer binding constituent may be mixed with aptamer-allergen indicator 106 complexes such that the first aptamer binding constituent and the second aptamer binding constituent bind to aptamer-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more aptamers that bind to one or more allergen indicators 106 to form one or more aptamer-allergen indicator 106 complexes. In some embodiments, the one or more aptamer may include one or more tags that provide for separation of the aptamer-allergen indicator 106 complexes. For example, in some embodiments, an aptamer may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with aptamer binding based methods. In some embodiments, antibodies may be used in combination with aptamers or in place of aptamers.

In some embodiments, one or more allergen indicators 106 may be detected through use of electrophoresis. In some embodiments, one or more microfluidic chips 108 may be configured to process one or more samples 102 through use of electrophoresis. In some embodiments, such microfluidic chips 108 may be configured to operably associate with one or more detection units 122. Accordingly, in some embodiments, one or more detection units 122 may be configured to operably associate with one or more microfluidic chips 108 and detect one or more allergen indicators 106 that were processed through use of electrophoresis. Numerous electrophoretic methods may be utilized to provide for detection of one or more allergen indicators 106. Examples of such electrophoretic methods include, but are not limited to, capillary electrophoresis, one-dimensional electrophoresis, two-dimensional electrophoresis, native electrophoresis, denaturing electrophoresis, polyacrylamide gel electrophoresis, agarose gel electrophoresis, and the like. Numerous detection methods may be used in combination with one or more electrophoretic methods to detect one or more allergen indicators 106. In some embodiments, one or more allergen indicators 106 may be detected according to the position to which the one or more allergen indicators 106 migrate within an electrophoretic field (e.g., a capillary and/or a gel). In some embodiments, the position of one or more allergen indicators 106 may be compared to one or more standards. For example, in some embodiments, one or more samples 102 may be mixed with one or more molecular weight markers prior to gel electrophoresis. The one or more samples 102, that include the one or more molecular weight markers, may be subjected to electrophoresis and then the gel may be stained. In such embodiments, the molecular weight markers may be used as a reference to detect one or more allergen indicators 106 present within the one or more samples 102. In some embodiments, one or more components that are known to be present within one or more samples 102 may be used as a reference to detect one or more allergen indicators 106 present within the one or more samples 102. In some embodiments, gel shift assays may be used to detect one or more allergen indicators 106. For example, in some embodiments, a sample 102 (e.g., a single sample 102 or combination of multiple samples 102) may be split into a first sample 102 and a second sample 102. The first sample 102 may be mixed with an antibody, aptamer, ligand, or other molecule and/or complex that binds to the one or more allergen indicators 106. The first and second samples 102 may then be subjected to electrophoresis. The gels corresponding to the first sample 102 and the second sample 102 may then be analyzed to determine if one or more allergen indicators 106 are present within the one or more samples 102. Microfluidic chips 108 and detection units 122 may be configured in numerous ways to process and detect one or more allergen indicators 106 through use of electrophoresis.

In some embodiments, one or more allergen indicators 106 may be detected through use of one or more charge-coupled device (CCD) cameras. In some embodiments, one or more detection units 122 that include one or more CCD cameras may be configured to operably associate with one or more microfluidic chips 108. Such detection units 122 may be utilized in combination with numerous processing methods. Examples of such methods include, but are not limited to, electrophoresis; competition assays; methods based on polynucleotide interaction, protein interaction, peptide interaction, antibody interaction, aptamer interaction, immunoprecipitation, immunoseparation, and the like. For example, in some embodiments, one or more microfluidic chips 108 may be configured to process one or more samples 102 through use of immunoprecipitation. In some embodiments, one or more antibodies may be conjugated to a fluorescent label such that binding of one or more labeled antibodies to one or more allergen indicators 106 included within one or more samples 102 will form a fluorescently labeled antibody-allergen indicator 106 complex. One or more insoluble allergen indicator 106 binding constituents, such as a sepharose bead that includes an antibody or aptamer that binds to the one or more allergen indicators 106, may be bound to the fluorescently labeled antibody-allergen indicator 106 complex and used to precipitate the complex. One or more detection units 122 that include a CCD camera that is configured to detect fluorescent emission from the one or more fluorescent labels may be used to detect the one or more allergen indicators 106. In some embodiments, one or more CCD cameras may be configured to utilize dark frame subtraction to cancel background and increase sensitivity of the camera. In some embodiments, one or more detection units 122 may include one or more filters to select and/or filter wavelengths of energy that can be detected by one or more CCD cameras (e.g., U.S. Pat. No. 3,971,065; herein incorporated by reference). In some embodiments, one or more detection units 122 may include polarized lenses. One or more detection units 122 may be configured in numerous ways to utilize one or more CCD cameras to detect one or more allergen indicators 106.

In some embodiments, one or more allergen indicators 106 may be detected through use of immunoassay. In some embodiments, one or more microfluidic chips 108 may be configured to process one or more samples 102 through use of immunoassay. In some embodiments, one or more detection units 122 may be configured to operably associate with one or more such microfluidic chips 108 and to detect one or more allergen indicators 106 associated with the use of immunoassay. Numerous types of detection methods may be used in combination with immunoassay based methods. In some embodiments, a label may be used within one or more immunoassays that may be detected by one or more detection units 122. Examples of such labels include, but are not limited to, fluorescent labels, spin labels, fluorescence resonance energy transfer labels, radiolabels, electrochemiluminescent labels (e.g., U.S. Pat. Nos. 5,093,268; 6,090,545; herein incorporated by reference), and the like. In some embodiments, electrical conductivity may be used in combination with immunoassay based methods.

At operation 510, the detecting operation 220 may include detecting the one or more allergen indicators with one or more detection units that are calibrated for use with an individual. In some embodiments, one or more detection units 122 that are calibrated for use with an individual may be used to detect the one or more allergen indicators 106. In some embodiments, one or more detection units 122 may be calibrated to detect one or more specific allergens 104 and/or allergen indicators 106 that produce an allergic response by an individual. For example, in some embodiments, one or more detection units 122 may be calibrated to detect peanuts and/or peanut associated products for an individual who is allergic to peanuts. In some embodiments, one or more detection units 122 may be calibrated to detect different concentrations of allergen indicators 106. For example, in some embodiments, an individual may produce an allergic response if exposed to an allergen 104 at a concentration that is above a certain level. Accordingly, in some embodiments, a detection unit 122 may be calibrated to detect one or more concentrations of one or more allergen indicators 106 that produce an allergic response within an individual.

Figure 6:
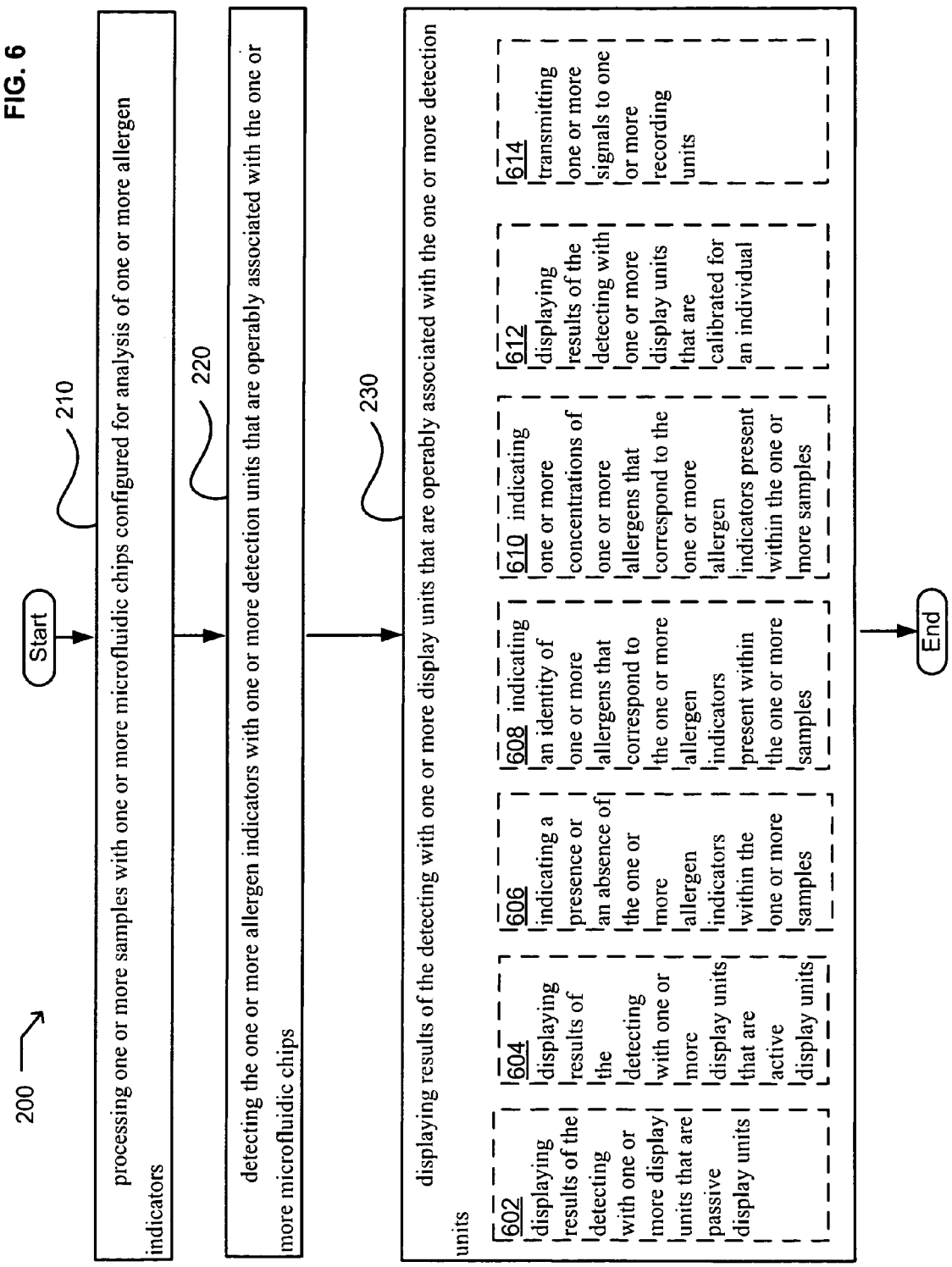
FIG. 6 illustrates alternate embodiments of the example operational flow of FIG. 2.

FIG. 6 illustrates alternative embodiments of the example operational flow 200 of FIG. 2. FIG. 6 illustrates example embodiments where the optional displaying operation 230 may include at least one additional operation. Additional operations may include an operation 602, an operation 604, an operation 606, an operation 608, an operation 610, an operation 612, and/or an operation 614.

At operation 602, the displaying operation 230 may include displaying results of the detecting with one or more display units that are passive display units. In some embodiments, one or more display units 124 may display results of the detecting with one or more display units 124 that are passive display units 124. In some embodiments, one or more display units 124 may include one or more liquid crystal displays (LCD). Methods to construct passive displays have been described (e.g., U.S. Pat. Nos. 4,807,967; 4,729,636; 4,436,378; 4,257,041; herein incorporated by reference).

At operation 604, the displaying operation 230 may include displaying results of the detecting with one or more display units that are active display units. In some embodiments, one or more display units 124 may display results of the detecting with one or more display units 124 that are active display units 124. Numerous active display units 124 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), wide ultra extended graphics array (WUXGA).

At operation 606, the displaying operation 230 may include indicating a presence or an absence of the one or more allergen indicators within the one or more samples. In some embodiments, one or more display units 124 may indicate a presence or an absence of the one or more allergen indicators 106 within the one or more samples 102. In some embodiments, one or more display units 124 may use a colorimetric message to indicate a presence or an absence of one or more allergen indicators 106 within one or more samples 102. For example, in some embodiments, one or more display units 124 may display a green light if one or more allergen indicators 106 are not found within one or more samples 102 and a red light if one or more allergen indicators 106 are found within one or more samples 102. In some embodiments, one or more display units 124 may use a pictographic message to indicate a presence or an absence of one or more allergen indicators 106 within one or more samples 102. For example, in some embodiments, one or more display units 124 may display a smiley face if one or more allergen indicators 106 are not found within one or more samples 102 and a frowny face if one or more allergen indicators 106 are found within one or more samples 102. In some embodiments, one or more display units 124 may use a typographical message to indicate a presence or an absence of one or more allergen indicators 106 within one or more samples 102. For example, in some embodiments, one or more display units 124 may display an "Allergen Not Present" message if one or more allergen indicators 106 are not found within one or more samples 102 and an "Allergen Present" message if one or more allergen indicators 106 are found within one or more samples 102. Such messages may be displayed in numerous languages. In some embodiments, one or more display units 124 may display one or more messages in multiple formats. For example, in some embodiments, one or more messages may be displayed in colored text.

At operation 608, the displaying operation 230 may include indicating an identity of one or more allergens that correspond to the one or more allergen indicators present within the one or more samples. In some embodiments, one or more display units 124 may indicate an identity of one or more allergens 104 that correspond to the one or more allergen indicators 106 present within the one or more samples 102. In some embodiments, one or more display units 124 may be operably associated with one or more microfluidic chips 108 that are configured to identify one or more allergen indicators 106. Accordingly, in some embodiments, one or more display units 124 may be configured to display the identity of one or more allergens 104 that are present and/or absent from one or more samples 102. For example, in some embodiments, a display unit 124 may be configured to indicate a presence or an absence of beta-lactoglobulin in a food product.

At operation 610, the displaying operation 230 may include indicating one or more concentrations of one or more allergens that correspond to the one or more allergen indicators present within the one or more samples. In some embodiments, one or more display units 124 may indicate one or more concentrations of one or more allergens 104 that correspond to the one or more allergen indicators 106 present within the one or more samples 102. Concentration may be displayed in numerous formats. For example, in some embodiments, concentration may be expressed numerically (e.g., mass allergen indicator 106 per volume sample 102 (e.g., milligrams per milliliter), mass allergen indicator 106 per mass sample 102 (e.g., milligrams per milligram of sample), parts per million, and the like). In some embodiments, concentration may be expressed graphically. For example, in some embodiments, one or more display units 124 may include a display having a gray scale on which the concentration of one or more allergen indicators 106 that are present within one or more samples 102 may be indicated (e.g., higher concentrations of one or more allergens 104 may be displayed as dark gray while lower concentrations of one or more allergens 104 may be displayed as light gray). In some embodiments, one or more display units 124 may include a display having a color scale on which the concentration of one or more allergen indicators 106 that are present within one or more samples 102 may be indicated (e.g., low concentrations of one or more allergen indicators 106 may be indicated by a green light, intermediate concentrations of one or more allergen indicators 106 may be indicated by a yellow light, high concentrations of one or more allergen indicators 106 may be indicated by a red light). In some embodiments, one or more display units 124 may be calibrated to an individual. For example, in such embodiments, an individual may use the display to obtain an immediate reading that will indicate if a food product contains a dangerous level of one or more allergens 104.

At operation 612, the displaying operation 230 may include displaying results of the detecting with one or more display units that are calibrated for an individual. In some embodiments, one or more display units 124 that are calibrated for an individual may display the results of the detecting. In some embodiments, one or more display units 124 may be calibrated to display whether one or more allergens 104, and/or allergen indicators 106, that are specific to an individual are present or absent within one or more samples 102. For example, in some embodiments, one or more display units 124 may be configured to display whether one or more samples 102 contain shellfish associated allergens 104 for an individual known to be allergic to shellfish. In some embodiments, one or more display units 124 may be calibrated to indicate safe and/or unsafe concentrations of one or more allergens 104 within one or more samples 102 for an individual.

At operation 614, the displaying operation 230 may include transmitting one or more signals to one or more recording units. In some embodiments, one or more display units 124 may transmit one or more signals 132 to one or more recording units 126. In some embodiments, one or more signals 132 may be transmitted from one or more microfluidic chips 108, one or more reagent delivery units 116, one or more centrifugation units 118, one or more analysis units 120, one or more detection units 122, one or more display units 124, one or more user interfaces 128, and/or substantially any combination thereof. Numerous types of signals 132 may be transmitted. Examples of such signals 132 include, but are not limited to, hardwired signals 132, wireless signals 132, infrared signals 132, optical signals 132, radiofrequency (RF) signals 132, audible signals 132, digital signals 132, analog signals 132, and/or substantially any combination thereof. One or more signals 132 may include numerous types of information. For example, one or more signals 132 may include information with regard to the presence of an absence of one or more allergen indicators 106 within one or more samples 102, a type of reagent used to process one or more samples 102, conditions used to process one or more samples 102, an identity of a user 130, and the like. Such information may be recorded by one or more recording units 126.

Figure 7:
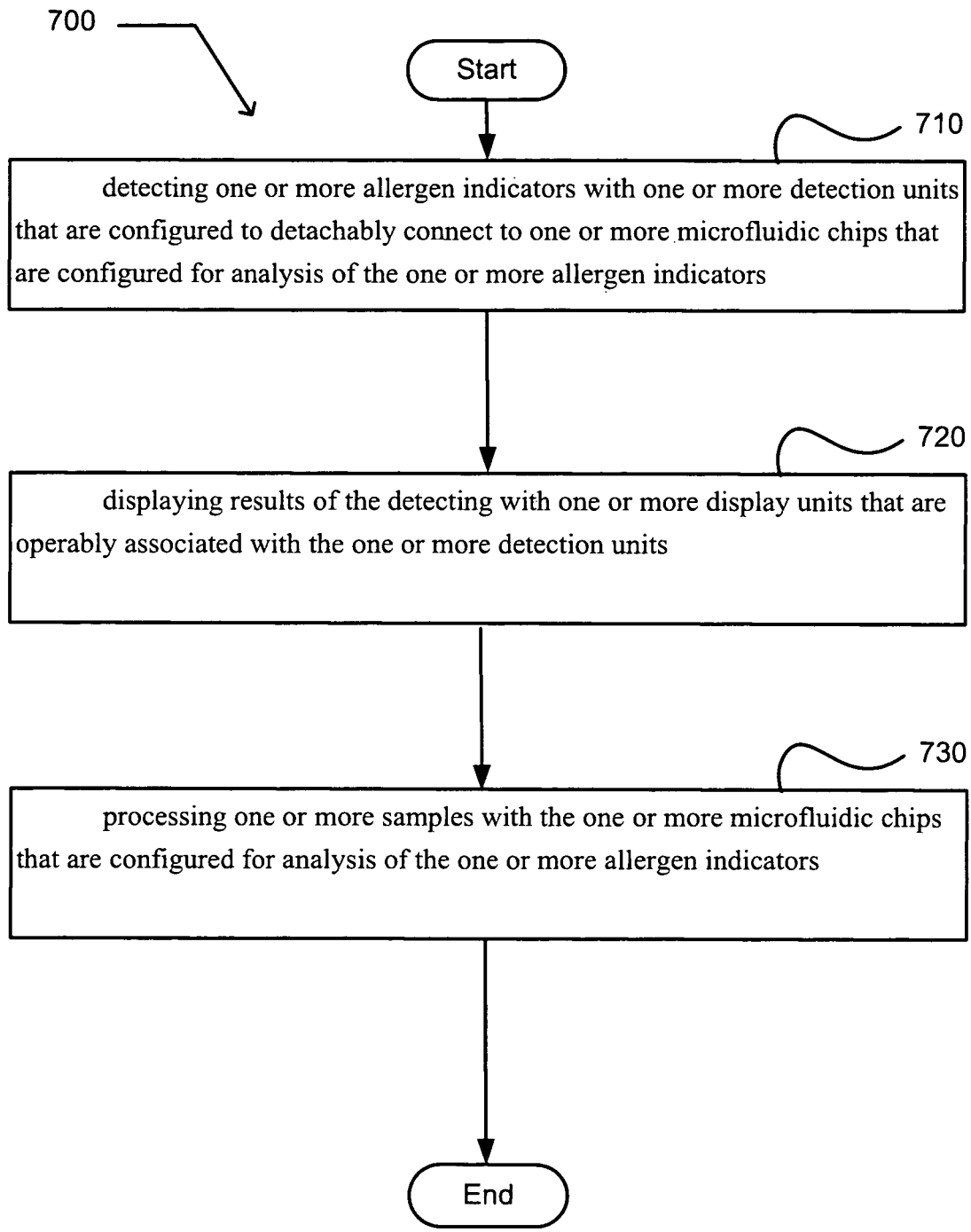
FIG. 7 illustrates an operational flow representing example operations related to methods and systems for analysis of allergens.

FIG. 7 illustrates an operational flow 700 representing examples of operations that are related to the performance of a method for analysis of one or more allergens 104. In FIG. 7 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 700 includes a detecting operation 710 involving detecting one or more allergen indicators with one or more detection units that are configured to detachably connect to one or more microfluidic chips that are configured for analysis of the one or more allergen indicators. In some embodiments, detecting operation 710 may include detecting the one or more allergen indicators that are associated with one or more airborne allergens. In some embodiments, detecting operation 710 may include detecting the one or more allergen indicators that are associated with one or more food products. In some embodiments, detecting operation 710 may include detecting the one or more allergen indicators that are associated with one or more weeds, grasses, trees, mites, animals, molds, fungi, insects, rubbers, metals, chemicals, autoallergens, or human autoallergens. In some embodiments, detecting operation 710 may include detecting the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, detecting operation 710 may include detecting the one or more allergen indicators with one or more detection units that are calibrated for use with an individual.

After a start operation, the operational flow 700 includes a displaying operation 720 involving displaying results of the detecting with one or more display units that are operably associated with the one or more detection units. In some embodiments, displaying operation 720 may include displaying results of the detecting with one or more display units that are passive display units. In some embodiments, displaying operation 720 may include displaying results of the detecting with one or more display units that are active display units. In some embodiments, displaying operation 720 may include indicating a presence or an absence of the one or more allergen indicators within the one or more samples. In some embodiments, displaying operation 720 may include indicating an identity of one or more allergens that correspond to the one or more allergen indicators present within the one or more samples. In some embodiments, displaying operation 720 may include indicating one or more concentrations of one or more allergens that correspond to the one or more allergen indicators present within the one or more samples. In some embodiments, displaying operation 720 may include displaying results of the detecting with one or more display units that are calibrated for an individual. In some embodiments, displaying operation 720 may include transmitting one or more signals to one or more recording units.

After a start operation, the operational flow 700 may optionally include a processing operation 730 involving processing one or more samples with the one or more microfluidic chips that are configured for analysis of the one or more allergen indicators. In some embodiments, processing operation 730 may include processing the one or more samples that include one or more liquids. In some embodiments, processing operation 730 may include processing the one or more samples that include one or more solids. In some embodiments, processing operation 730 may include processing the one or more samples that include one or more gases. In some embodiments, processing operation 730 may include processing the one or more samples for the one or more allergen indicators that are associated with one or more airborne allergens. In some embodiments, processing operation 730 may include processing the one or more samples for the one or more allergen indicators that are associated with one or more food products. In some embodiments, processing operation 730 may include processing the one or more samples for the one or more allergen indicators that are associated with one or more weeds, grasses, trees, mites, animals, molds, fungi, insects, rubbers, autoallergens, metals, chemicals, or human autoallergens. In some embodiments, processing operation 730 may include processing the one or more samples with the one or more microfluidic chips that are configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay.

Figure 8:
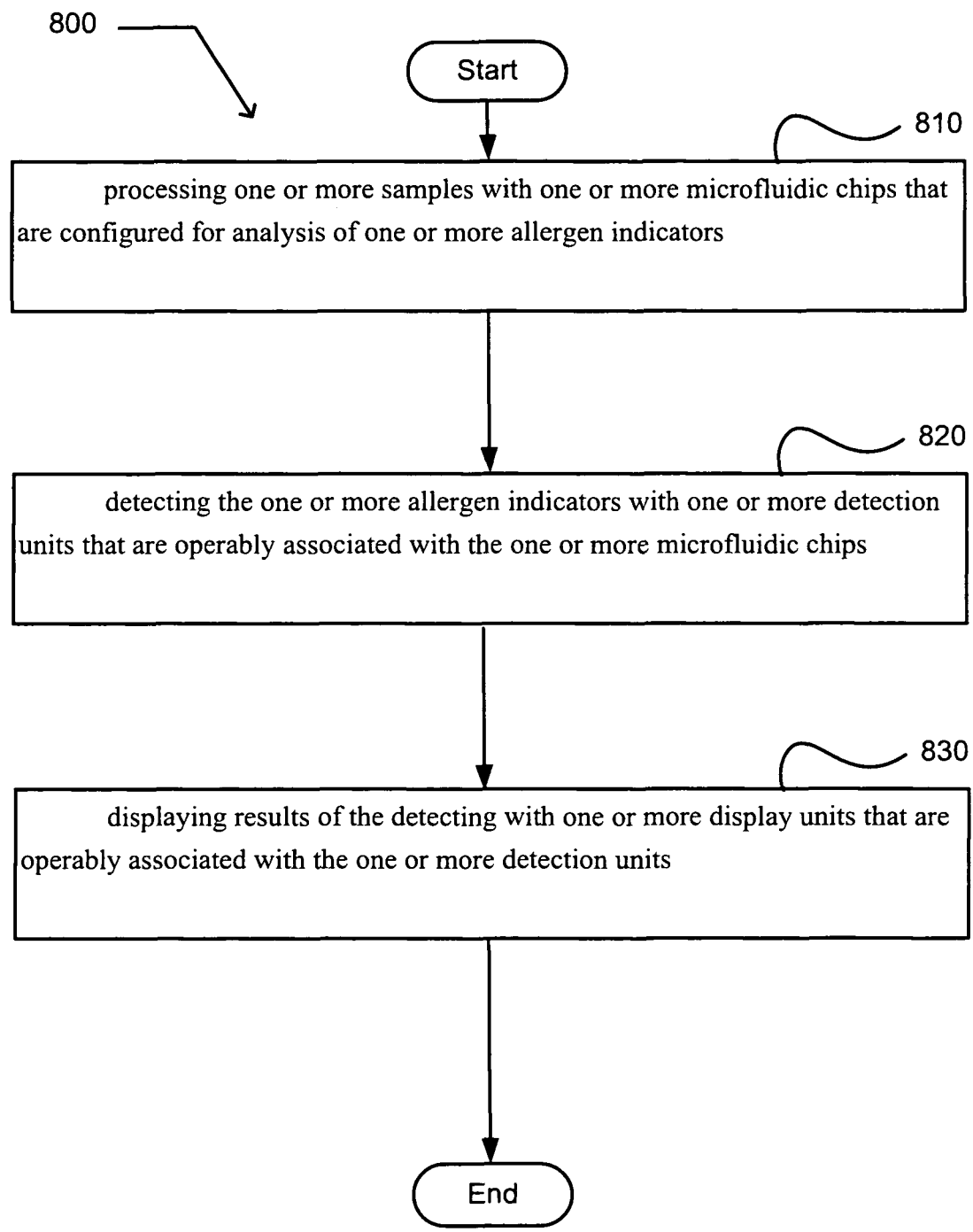
FIG. 8 illustrates an operational flow representing example operations related to methods and systems for analysis of allergens.

FIG. 8 illustrates an operational flow 800 representing examples of operations that are related to the performance of a method for analysis of one or more allergens 104. In FIG. 8 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 800 includes a processing operation 810 involving processing one or more samples with one or more microfluidic chips that are configured for analysis of one or more allergen indicators. In some embodiments, processing operation 810 may include processing the one or more samples that include one or more liquids. In some embodiments, processing operation 810 may include processing the one or more samples that include one or more solids. In some embodiments, processing operation 810 may include processing the one or more samples that include one or more gases. In some embodiments, processing operation 810 may include processing the one or more samples for the one or more allergen indicators that are associated with one or more airborne allergens. In some embodiments, processing operation 810 may include processing the one or more samples for the one or more allergen indicators that are associated with one or more food products. In some embodiments, processing operation 810 may include processing the one or more samples for the one or more allergen indicators that are associated with one or more weeds, grasses, trees, mites, animals, molds, fungi, insects, rubbers, autoallergens, metals, chemicals, or human autoallergens. In some embodiments, processing operation 810 may include processing the one or more samples with the one or more microfluidic chips that are configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay.

The operational flow 800 includes a detecting operation 820 involving detecting the one or more allergen indicators with one or more detection units that are operably associated with the one or more microfluidic chips. In some embodiments, detecting operation 820 may include detecting the one or more allergen indicators that are associated with one or more airborne allergens. In some embodiments, detecting operation 820 may include detecting the one or more allergen indicators that are associated with one or more food products. In some embodiments, detecting operation 820 may include detecting the one or more allergen indicators that are associated with one or more weeds, grasses, trees, mites, animals, molds, fungi, insects, rubbers, metals, chemicals, autoallergens, or human autoallergens. In some embodiments, detecting operation 820 may include detecting the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, detecting operation 820 may include detecting the one or more allergen indicators with one or more detection units that are calibrated for use with an individual.

The operational flow 800 includes a displaying operation 830 involving displaying results of the detecting with one or more display units that are operably associated with the one or more detection units. In some embodiments, displaying operation 830 may include displaying results of the detecting with one or more display units that are passive display units. In some embodiments, displaying operation 830 may include displaying results of the detecting with one or more display units that are active display units. In some embodiments, displaying operation 830 may include indicating a presence or an absence of the one or more allergen indicators within the one or more samples. In some embodiments, displaying operation 830 may include indicating an identity of one or more allergens that correspond to the one or more allergen indicators present within the one or more samples. In some embodiments, displaying operation 830 may include indicating one or more concentrations of one or more allergens that correspond to the one or more allergen indicators present within the one or more samples. In some embodiments, displaying operation 830 may include displaying results of the detecting with one or more display units that are calibrated for an individual. In some embodiments, displaying operation 830 may include transmitting one or more signals to one or more recording units.

Figure 9:
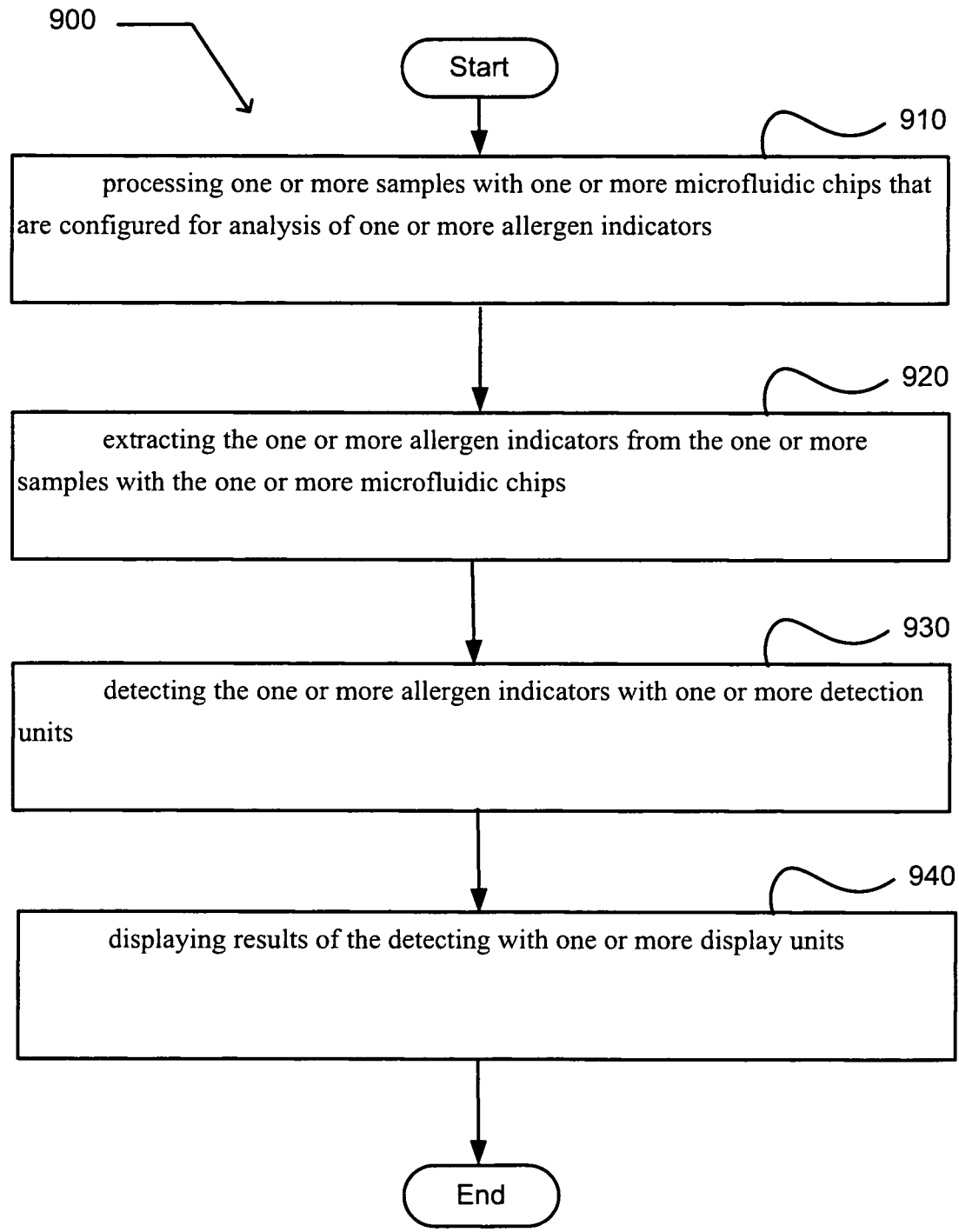
FIG. 9 illustrates an operational flow representing example operations related to methods and systems for analysis of allergens.

FIG. 9 illustrates an operational flow 900 representing examples of operations that are related to the performance of a method for analysis of one or more allergens 104. In FIG. 9 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 900 includes a processing operation 910 involving processing one or more samples with one or more microfluidic chips that are configured for analysis of one or more allergen indicators. In some embodiments, processing operation 910 may include processing the one or more samples that include one or more liquids. In some embodiments, processing operation 910 may include processing the one or more samples that include one or more solids. In some embodiments, processing operation 910 may include processing the one or more samples that include one or more gases. In some embodiments, processing operation 910 may include processing the one or more samples that include one or more air samples. In some embodiments, processing operation 910 may include processing the one or more samples that are associated with one or more food products. In some embodiments, processing operation 910 may include processing the one or more samples that are associated with one or more weeds, grasses, trees, mites, animals, molds, fungi, insects, rubbers, metals, chemicals, autoallergens, or human autoallergens. In some embodiments, processing operation 910 may include processing the one or more samples through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay.

After a start operation, the operational flow 900 includes an extracting operation 920 involving extracting the one or more allergen indicators from the one or more samples with the one or more microfluidic chips. In some embodiments, extracting operation 920 may include extracting the one or more allergen indicators from the one or more samples through use of one or more techniques that include polynucleotide interaction, protein interaction, peptide interaction, antibody interaction, chemical interaction, diffusion, precipitation, filtration, chromatography, aptamer interaction, isoelectric focusing, electrophoresis, immunoassay, solvent extraction, polynucleotide extraction, polypeptide extraction, or centrifugation.

After a start operation, the operational flow 900 may optionally include a detecting operation 930 involving detecting the one or more allergen indicators with one or more detection units. In some embodiments, detecting operation 930 may include detecting the one or more allergen indicators that are associated with one or more airborne allergens. In some embodiments, detecting operation 930 may include detecting the one or more allergen indicators that are associated with one or more food products. In some embodiments, detecting operation 930 may include detecting the one or more allergen indicators that are associated with one or more weeds, grasses, trees, mites, animals, molds, fungi, insects, rubbers, metals, chemicals, autoallergens, or human autoallergens. In some embodiments, detecting operation 930 may include detecting the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, detecting operation 930 may include detecting the one or more allergen indicators that include one or more allergen associated polynucleotides. In some embodiments, detecting operation 930 may include detecting the one or more allergen indicators that include one or more allergen associated polypeptides. In some embodiments, detecting operation 930 may include detecting the one or more allergen indicators with one or more detection units that are calibrated for use with an individual.

After a start operation, the operational flow 900 may optionally include a displaying operation 940 involving displaying results of the detecting with one or more display units. In some embodiments, displaying operation 940 may include displaying results of the detecting with one or more display units that are passive display units. In some embodiments, displaying operation 940 may include displaying results of the detecting with one or more display units that are active display units. In some embodiments, displaying operation 940 may include indicating a presence or an absence of the one or more allergen indicators within the one or more samples. In some embodiments, displaying operation 940 may include indicating an identity of one or more allergens that correspond to the one or more allergen indicators present within the one or more samples. In some embodiments, displaying operation 940 may include indicating one or more concentrations of one or more allergens that correspond to the one or more allergen indicators present within the one or more samples. In some embodiments, displaying operation 940 may include transmitting one or more signals to one or more recording units.

Figure 10:
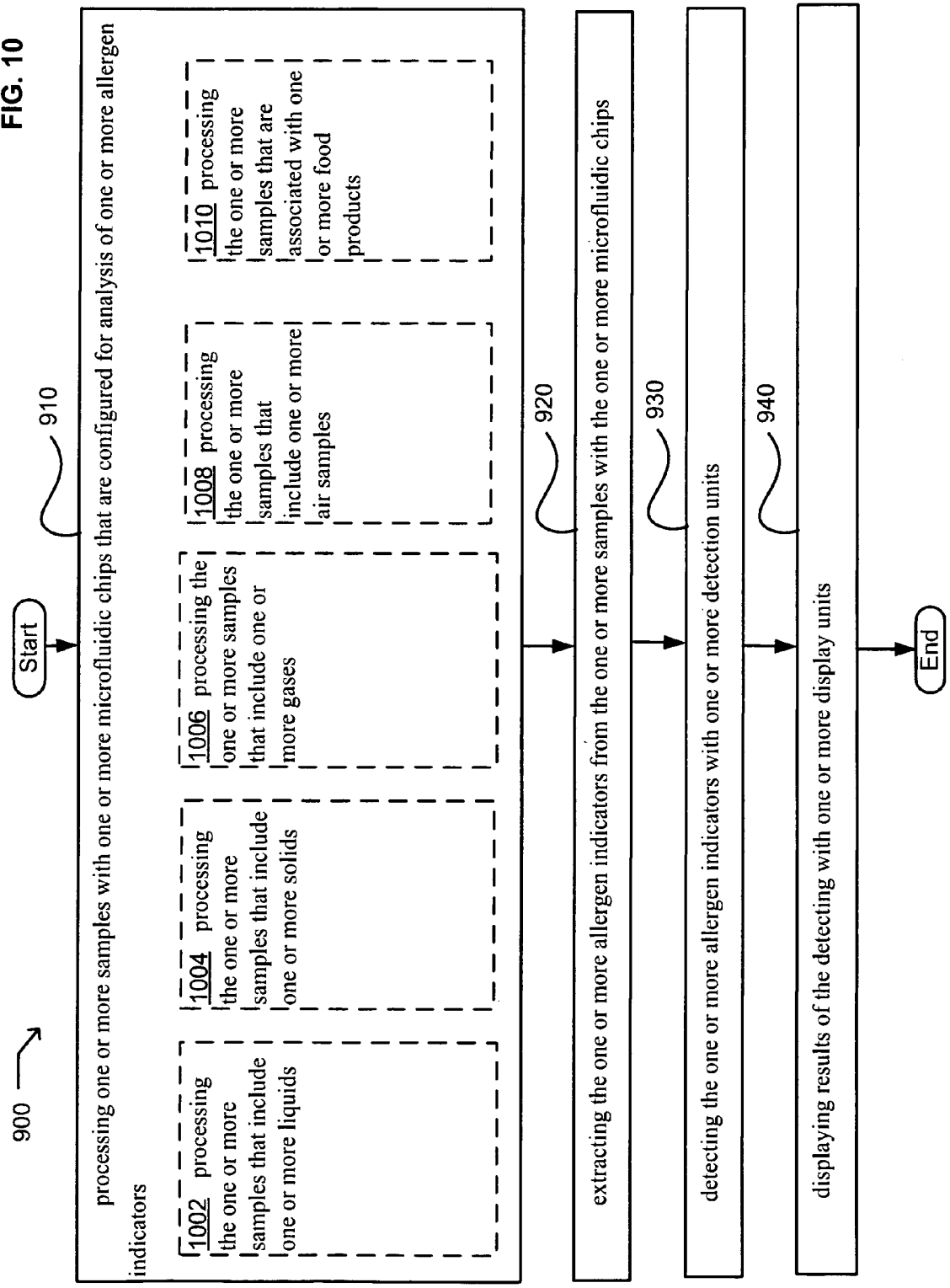
FIG. 10 illustrates alternate embodiments of the example operational flow of FIG. 9.

FIG. 10 illustrates alternative embodiments of the example operational flow 900 of FIG. 9. FIG. 10 illustrates example embodiments where the processing operation 910 may include at least one additional operation. Additional operations may include an operation 1002, an operation 1004, an operation 1006, an operation 1008, and/or an operation 1010.

At operation 1002, the processing operation 910 may include processing the one or more samples that include one or more liquids. In some embodiments, one or more samples 102 that include a liquid may be processed with one or more microfluidic chips 108 that are configured for analysis of one or more allergen indicators 106. Numerous types of liquids may be processed by one or more microfluidic chips 108. Examples of such liquids include, but are not limited to, beverages (e.g., water, soda, milk, milk substitutes, juice, wine, beer, and the like), environmental samples 102 (e.g., water samples 102, plant sap, plant nectar, suspended soil samples 102, suspended air filtrate samples 102, and the like), animal samples 102 (e.g., suspended dander samples 102, saliva, urine, excrement, suspended fur samples 102, and the like), food samples 102 (e.g., suspended food samples 102, extracted food samples 102, and the like), or substantially any combination thereof. In some embodiments, one or more liquids may include a solvent. In some embodiments, a liquid may include one or more solvents that may be used to extract one or more allergen indicators 106. For example, in some embodiments, one or more solvents may be used to extract one or more allergen indicators 106 from one or more samples 102.

At operation 1004, the processing operation 910 may include processing the one or more samples that include one or more solids. In some embodiments, one or more samples 102 that include a solid may be processed with one or more microfluidic chips 108 that are configured for analysis of one or more allergen indicators 106. In some embodiments, processing one or more samples 102 that include a solid may include suspending the samples 102 in a liquid. In some embodiments, processing one or more samples 102 that include a solid may include extracting the samples 102 with a solvent. In some embodiments, processing one or more samples 102 that include a solid may include accepting the one or more samples 102 into one or more microfluidic chips 108 where the samples 102 are resuspended in a liquid and/or extracted in a solvent.

At operation 1006, the processing operation 910 may include processing the one or more samples that include one or more gases. In some embodiments, one or more samples 102 that include a gas may be processed with one or more microfluidic chips 108 that are configured for analysis of one or more allergen indicators 106. For example, in some embodiments, one or more gases that are being analyzed may be passed through one or more microfluidic chips 108. In some embodiments, gas may be pumped through a microfluidic chip 108. In some embodiments, gas may be drawn through a microfluidic chip 108 through use of a vacuum. In some embodiments, gas may be passed through a filter on which suspected allergen indicators 106 are collected for analysis. Accordingly, large volumes of gas may be analyzed. In some embodiments, one or more gases may be analyzed for one or more allergen indicators 106 that include one or more metals. For example, gases may be analyzed for metals that are associated with tanks in which the gases are stored, such as iron, steel, aluminum, and the like.

At operation 1008, the processing operation 910 may include processing the one or more samples that include one or more air samples. In some embodiments, one or more samples 102 may be processed with one or more microfluidic chips 108 that are configured for processing the one or more air samples 102 for one or more allergen indicators 106. Examples of allergen indicators 106 that may be included within one or more air samples 102 include, but are not limited to, pollen, dander, seeds, diesel exhaust, and the like. In some embodiments, the allergen indicators 106 may be collected within one or more microfluidic chips 108 through filtering air that is passed through the one or more microfluidic chips 108. Such filtering may occur through numerous mechanisms that may include, but are not limited to, use of physical filters, passing air through a fluid bubble chamber, passing the air through an electrostatic filter, and the like.

At operation 1010, the processing operation 910 may include processing the one or more samples that are associated with one or more food products. In some embodiments, one or more samples 102 may be processed with one or more microfluidic chips 108 that are configured for processing the one or more samples 102 for the one or more allergen indicators 106 that are associated with one or more food products (e.g., the foods themselves or processed products that include one or more foods). Such allergen indicators 106 are described herein and are known. For example, in some embodiments, one or more microfluidic chips 108 may be configured to process one or more food products at a restaurant to facilitate detection of a presence or an absence of an allergen indicator 106 within the food product, such as a presence of one or more allergen indicators 106 associated with nuts, dairy products, crustaceans, eggs, gluten, soy, and the like. In some embodiments, one or more microfluidic chips 108 may be configured to process one or more polynucleotides, one or more polypeptides, one or more portions of one or more polynucleotides, and/or one or more portions of one or more polypeptides that have a nucleic acid sequence and/or an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, or AY839230. Accordingly, one or more microfluidic chips 108 may be configured to process numerous types of food products to facilitate detection of numerous types of allergen indicators 106.

Figure 11:
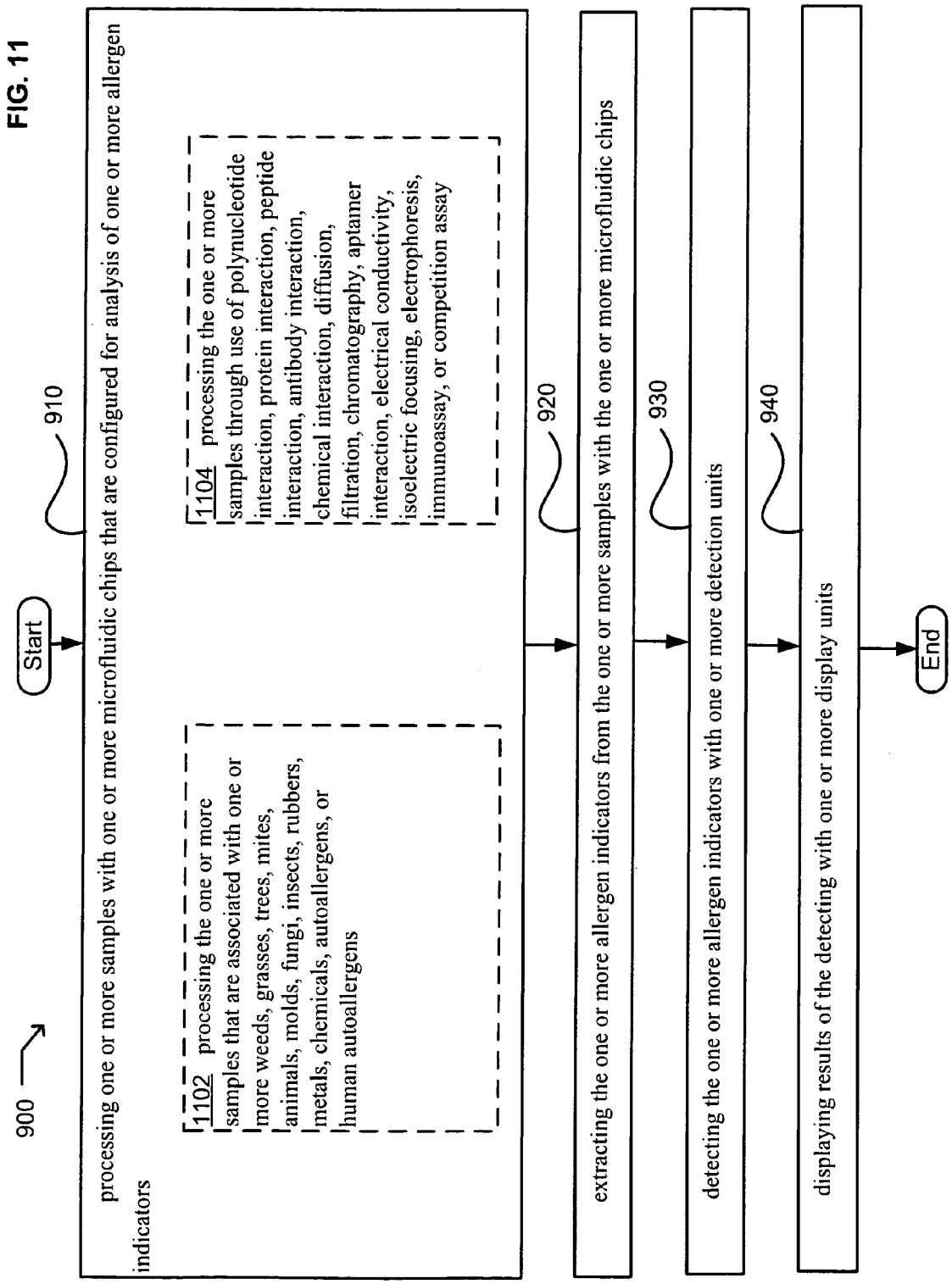
FIG. 11 illustrates alternate embodiments of the example operational flow of FIG. 9.

FIG. 11 illustrates alternative embodiments of the example operational flow 900 of FIG. 9. FIG. 11 illustrates example embodiments where the processing operation 910 may include at least one additional operation. Additional operations may include an operation 1102 and/or an operation 1104.

At operation 1102, the processing operation 910 may include processing the one or more samples that are associated with one or more weeds, grasses, trees, mites, animals, molds, fungi, insects, rubbers, metals, chemicals, autoallergens, or human autoallergens. In some embodiments, one or more samples 102 may be processed with one or more microfluidic chips 108 that are configured for processing the one or more samples 102 for the one or more allergen indicators 106 that are associated with one or more weeds, grasses, trees, mites, animals, molds, fungi, insects, rubbers, metals, chemicals, autoallergens, human autoallergens, or substantially any combination thereof. Such allergen indicators 106 are described herein and are known. For example, in some embodiments, one or more microfluidic chips 108 may be configured to process one or more material samples 102 to determine if the material contains latex.

At operation 1104, the processing operation 910 may include processing the one or more samples through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay. In some embodiments, one or more samples 102 may be processed with one or more microfluidic chips 108 that are configured for processing the one or more allergen indicators 106 through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof. In some embodiments, allergen indicators 106 may be separated from other materials included within one or more samples 102 through processing. In some embodiments, allergen indicators 106 may be immobilized through processing to facilitate detection and/or identification of the one or more allergen indicators 106.

In some embodiments, one or more microfluidic chips 108 may be configured to process one or more samples 102 through use of polynucleotide interaction. Numerous methods based on polynucleotide interaction may be used. Examples of such methods include, but are not limited to, those based on polynucleotide hybridization, polynucleotide ligation, polynucleotide amplification, polynucleotide degradation, and the like. Methods that utilize intercalation dyes, FRET analysis, capacitive DNA detection, and nucleic acid amplification have been described (e.g., U.S. Pat. Nos. 7,118,910 and 6,960,437; herein incorporated by reference). In some embodiments, fluorescence resonance energy transfer, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube are combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Methods to utilize carbon nanotubes as probes for nucleic acid interaction have been described (e.g., U.S. Pat. No. 6,821,730; herein incorporated by reference).

In some embodiments, one or more microfluidic chips 108 may be configured to process one or more samples 102 through use of protein interaction. Numerous methods based on protein interaction may be used. In some embodiments, protein interaction may be used to immobilize one or more allergen indicators 106. In some embodiments, protein interaction may be used to separate one or more allergen indicators 106 from one or more samples 102. Examples of such methods include, but are not limited to, those based on ligand binding, protein-protein binding, protein cross-linking, use of green fluorescent protein, phage display, the two-hybrid system, protein arrays, fiber optic evanescent wave sensors, chromatographic techniques, fluorescence resonance energy transfer, regulation of pH to control protein assembly and/or oligomerization, and the like. For example, tropomyosin is a major muscle protein in crustaceans that is thought to be a major shrimp allergen 104. Tropomyosin is associated with the well known actin-troponin-myosin complex. Calcium ion binding to troponin enables troponin to bind tropomyosin and shift it from the binding sites of myosin on the actin proteins. Without the presence of Calcium ion, troponin is no longer able to bind to tropomyosin, and tropomyosin again blocks the binding sites of myosin on the actin proteins. Tropomyosin also binds to the calcium-binding protein calcyclin (Nelson et al., Molecular & Cellular Proteomics 1:253-259 (2002) and Liou and Chen, European Journal of Biochemistry, 270: 3092-3100 (2003)). Accordingly, protein interactions may be used to separate tropomyosin (allergen indicator 106) from one or more samples 102. Similar methods may be used with numerous proteins. Methods that may be used to construct protein arrays have been described (e.g., Warren et al., Anal. Chem., 76:4082-4092 (2004) and Walter et al., Trends Mol. Med., 8:250-253 (2002), U.S. Pat. No. 6,780,582; herein incorporated by reference).

In some embodiments, one or more microfluidic chips 108 may be configured to process one or more samples 102 through use of peptide interaction. Peptides are generally described as being polypeptides that include less than one hundred amino acids. For example, peptides include dipeptides, tripeptides, and the like. In some embodiments, peptides may include from two to one hundred amino acids. In some embodiments, peptides may include from two to fifty amino acids. In some embodiments, peptides may include from two to one twenty amino acids. In some embodiments, peptides may include from ten to one hundred amino acids. In some embodiments, peptides may include from ten to fifty amino acids. Accordingly, peptides can include numerous numbers of amino acids. Numerous methods based on peptide interaction may be used. In some embodiments, peptide interaction may be used to immobilize one or more allergen indicators 106. In some embodiments, peptide interaction may be used to separate one or more allergen indicators 106 from one or more samples 102. Examples of such methods include, but are not limited to, those based on ligand binding, peptide-protein binding, peptide-peptide binding, peptide-polynucleotide binding, peptide cross-linking, use of green fluorescent protein, phage display, the two-hybrid system, protein arrays, peptide arrays, fiber optic evanescent wave sensors, chromatographic techniques, fluorescence resonance energy transfer, regulation of pH to control peptide and/or protein assembly and/or oligomerization, and the like. Accordingly, virtually any technique that may be used to analyze proteins may be utilized for the analysis of peptides. In some embodiments, high-speed capillary electrophoresis may be used to detect binding through use of fluorescently labeled phosphopeptides as affinity probes (Yang et al., Anal. Chem., 10.1021/ac061936e (2006)). Methods to immobilize proteins and peptides have been reported (Taylor, Protein Immobilization: Fundamentals and Applications, Marcel Dekker, Inc., New York (1991)).

In some embodiments, one or more microfluidic chips 108 may be configured to process one or more samples 102 through use of antibody interaction. Antibodies may be raised that will bind to numerous allergen indicators 106 through use of known methods (e.g., Harlow and Lane, Antibodies: A Laboratory Manual, Cold Spring Harbor Laboratory Press, Cold Spring Harbor, N.Y. (1988)). Antibodies may be configured in numerous ways within one or more microfluidic chips 108 to process one or more allergen indicators 106. For example, in some embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. A labeled detector antibody that binds to the allergen indicator 106 (or the antibody-allergen indicator 106 complex) may then be passed over the one or more antibody-allergen indicator 106 complexes such that the labeled detector antibody will label the allergen indicator 106 (or the antibody-allergen indicator 106 complex). Numerous labels may be used that include, but are not limited to, enzymes, fluorescent molecules, radioactive labels, spin labels, redox labels, and the like. In other embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. Such binding provides for detection of the antibody-allergen indicator 106 complex through use of methods that include, but are not limited to, surface plasmon resonance, conductivity, and the like (e.g., U.S. Pat. No. 7,030,989; herein incorporated by reference). In some embodiments, antibodies may be coupled to a substrate within a microfluidic chip 108 to provide for a competition assay. One or more samples 102 may be mixed with one or more reagent mixtures that include one or more labeled allergen indicators 106. The mixture may then be passed over the antibodies to facilitate binding of allergen indicators 106 in the sample 102 and labeled allergen indicators 106 in the reagent mixture to the antibodies. The unlabeled allergen indicators 106 in the sample 102 will compete with the labeled allergen indicators 106 in the reagent mixture for binding to the antibodies. Accordingly, the amount of label bound to the antibodies will vary in accordance with the concentration of unlabeled allergen indicators 106 in the sample 102. In some embodiments, antibody interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more antibodies may be used in conjunction with one or more aptamers to process one or more samples 102. Accordingly, in some embodiments, aptamers and antibodies may be used interchangeably to process one or more samples 102.

In some embodiments, one or more microfluidic chips 108 may be configured to process one or more samples 102 through use of chemical interaction. In some embodiments, one or more microfluidic chips 108 may be configured to utilize chemical extraction to process one or more samples 102. For example, in some embodiments, one or more samples 102 may be mixed with a reagent mixture that includes one or more solvents in which the one or more allergen indicators 106 are soluble. Accordingly, the solvent phase containing the one or more allergen indicators 106 may be separated from the sample phase to provide for detection of the one or more allergen indicators 106. In some embodiments, one or more samples 102 may be mixed with a reagent mixture that includes one or more chemicals that cause precipitation of one or more allergen indicators 106. Accordingly, the sample phase may be washed away from the one or more precipitated allergen indicators 106 to provide for detection of the one or more allergen indicators 106. Accordingly, reagent mixtures that include numerous types of chemicals that interact with one or more allergen indicators 106 may be used.

In some embodiments, one or more microfluidic chips 108 may be configured to process one or more samples 102 through use of diffusion. In some embodiments, one or more microfluidic chips 108 may be configured to process one or more fluid samples 102 through use of an H-filter. For example, a microfluidic chip 108 may be configured to include a channel through which a fluid sample 102 and a second fluid flow such that the fluid sample 102 and the second fluid undergo parallel flow through the channel without significant mixing of the sample fluid and the second fluid. As the fluid sample 102 and the second fluid flow through the channel, one or more allergen indicators 106 in the fluid sample 102 may diffuse through the fluid sample 102 into the second fluid. Accordingly, such diffusion provides for the separation of the one or more allergen indicators 106 from the sample 102. Methods to construct H-filters have been described (e.g., U.S. Pat. Nos. 6,742,661; 6,409,832; 6,007,775; 5,974,867; 5,971,158; 5,948,684; 5,932,100; 5,716,852; herein incorporated by reference). In some embodiments, diffusion based methods may be combined with immunoassay based methods to process and detect one or more allergen indicators 106. Methods to conduct microscale diffusion immunoassays have been described (e.g., U.S. Pat. No. 6,541,213; herein incorporated by reference). Accordingly, microfluidic chips 108 may be configured in numerous ways to process one or more allergen indicators 106 through use of diffusion.

In some embodiments, one or more microfluidic chips 108 may be configured to process one or more samples 102 through use of filtration. In some embodiments, one or more microfluidic chips 108 may be configured to include one or more filters that have a molecular weight cut-off. For example, a filter may allow molecules of low molecular weight to pass through the filter while disallowing molecules of high molecular weight to pass through the filter. Accordingly, one or more allergen indicators 106 that are contained within a sample 102 may be allowed to pass through a filter while larger molecules contained within the sample 102 are disallowed from passing through the filter. Accordingly, in some embodiments, a microfluidic chip 108 may include two or more filters that selectively retain, or allow passage, of one or more allergen indicators 106 through the filters. Such configurations provide for selective separation of one or more allergen indicators 106 from one or more samples 102. Membranes and filters having numerous molecular weight cut-offs are commercially available (e.g., Millipore, Billerica, Mass.). In some embodiments, one or more microfluidic chips 108 may be configured to provide for dialysis of one or more samples 102. For example, in some embodiments, a microfluidic chip 108 may be configured to contain one or more samples 102 in one or more sample chambers that are separated from one or more dialysis chambers by a semi-permeable membrane. Accordingly, in some embodiments, one or more allergen indicators 106 that are able to pass through the semi-permeable membrane may be collected in the dialysis chamber. In other embodiments, one or more allergen indicators 106 may be retained in the one or more sample chambers while other sample 102 components may be separated from the one or more allergen indicators 106 by their passage through the semi-permeable membrane into the dialysis chamber. Accordingly, one or more microfluidic chips 108 may be configured to include two or more dialysis chambers for selective separation of one or more allergen indicators 106 from one or more samples 102. Semi-permeable membranes and dialysis tubing is available from numerous commercial sources (e.g., Millipore, Billerica, Mass.; Pierce, Rockford, Ill.; Sigma-Aldrich, St. Louis, Mo.). Methods that may be used for microfiltration have been described (e.g., U.S. Pat. No. 5,922,210; herein incorporated by reference).

In some embodiments, one or more microfluidic chips 108 may be configured to process one or more samples 102 through use of chromatography. Numerous chromatographic methods may be used to process one or more samples 102. Examples of such chromatographic methods include, but are not limited to, ion-exchange chromatography, affinity chromatography, gel filtration chromatography, hydroxyapatite chromatography, gas chromatography, reverse phase chromatography, thin layer chromatography, capillary chromatography, size exclusion chromatography, hydrophobic interaction media, and the like. In some embodiments, a microfluidic chip 108 may be configured to process one or more samples 102 through use of one or more chromatographic methods. In some embodiments, chromatographic methods may be used to process one or more samples 102 for one or more allergen indicators 106 that include one or more polynucleotides. For example, in some embodiments, one or more samples 102 may be applied to a chromatographic media to which the one or more polynucleotides bind. The remaining components of the sample 102 may be washed from the chromatographic media. The one or more polynucleotides may then be eluted from chromatographic media in a more purified state. Similar methods may be used to process one or more samples 102 for one or more allergen indicators 106 that include one or more proteins or polypeptides (e.g., Mondal and Gupta, Biomol. Eng., 23:59-76 (2006)). Chromatography media able to separate numerous types of molecules is commercially available (e.g., Bio-Rad, Hercules, Calif.; Qiagen, Valencia, Calif.; Pfizer, New York, N.Y.; Millipore, Billerica, Mass.; GE Healthcare Bio-Sciences Corp., Piscataway, N.J.).

In some embodiments, one or more microfluidic chips 108 may be configured to process one or more samples 102 through use of aptamer interaction. In some embodiments, one or more aptamers may include polynucleotides (e.g., deoxyribonucleic acid; ribonucleic acid; and derivatives of polynucleotides that may include polynucleotides that include modified bases, polynucleotides in which the phosphodiester bond is replaced by a different type of bond, or many other types of modified polynucleotides). In some embodiments, one or more aptamers may include peptide aptamers. Methods to prepare and use aptamers have been described (e.g., Collett et al., Methods, 37:4-15 (2005); Collet et al., Anal. Biochem., 338:113-123 (2005); Cox et al., Nucleic Acids Res., 30:20 e108 (2002); Kirby et al., Anal. Chem., 76:4066-4075 (2004); Ulrich, Handb. Exp. Pharmacol., 173:305-326 (2006); Baines and Colas, Drug Discovery Today, 11:334-341 (2006); Guthrie et al., Methods, 38:324-330 (2006); Geyer et al., Chapter 13: Selection of Genetic Agents from Random Peptide Aptamer Expression Libraries, Methods in Enzymology, Academic Press, pg. 171-208 (2000); U.S. Pat. No. 6,569,630; herein incorporated by reference). Aptamers may be configured in numerous ways within one or more microfluidic chips 108 to process one or more allergen indicators 106. For example, in some embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Labeled detector antibodies and/or aptamers that bind to the allergen indicator 106 (or the aptamer-allergen indicator 106 complex) may then be passed over the one or more aptamer-allergen indicator 106 complexes such that the labeled detector antibodies and/or aptamers will label the allergen indicator 106 (or the aptamer-allergen indicator 106 complex). Numerous labels may be used that include, but are not limited to, enzymes, fluorescent molecules, radioactive labels, spin labels, redox labels, and the like. In other embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Such binding provides for detection of the aptamer-allergen indicator 106 complex through use of methods that include, but are not limited to, surface plasmon resonance, conductivity, and the like (e.g., U.S. Pat. No. 7,030,989; herein incorporated by reference). In some embodiments, aptamers may be coupled to a substrate within a microfluidic chip 108 to provide for a competition assay. One or more samples 102 may be mixed with one or more reagent mixtures that include one or more labeled allergen indicators 106. The mixture may then be passed over the aptamers to facilitate binding of allergen indicators 106 in the sample 102 and labeled allergen indicators 106 in the reagent mixture to the aptamers. The unlabeled allergen indicators 106 in the sample 102 will compete with the labeled allergen indicators 106 in the reagent mixture for binding to the aptamers. Accordingly, the amount of label bound to the aptamers will vary in accordance with the concentration of unlabeled allergen indicators 106 in the sample 102. In some embodiments, aptamer interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more aptamers may be used in conjunction with one or more antibodies to process one or more samples 102. In some embodiments, aptamers and antibodies may be used interchangeably to process one or more samples 102. Accordingly, in some embodiments, methods and/or systems for processing and/or detecting allergen indicators 106 may utilize antibodies and aptamers interchangeably and/or in combination.

In some embodiments, one or more microfluidic chips 108 may be configured to process one or more samples 102 through use of electrical conductivity. In some embodiments, one or more samples 102 may be processed though use of magnetism. For example, in some embodiments, one or more samples 102 may be combined with one or more tagged polynucleotides that are tagged with a ferrous material, such as a ferrous bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed over an electromagnet to immobilize the hybridized complexes. Other components in the sample 102 may then be washed away from the hybridized complexes. In some embodiments, a chamber containing the magnetically immobilized hybridized complexes may be heated to release the sample polynucleotides from the magnetically immobilized tagged polynucleotides. The sample polynucleotides may then be collected in a more purified state. In other embodiments, similar methods may be used in conjunction with antibodies, aptamers, peptides, ligands, and the like. Accordingly, one or more microfluidic chips 108 may be configured in numerous ways to utilize magnetism to process one or more samples 102. In some embodiments, one or more samples 102 may be processed though use of eddy currents. Eddy current separation uses the principles of electromagnetic induction in conducting materials to separate non-ferrous metals by their different electric conductivities. An electrical charge is induced into a conductor by changes in magnetic flux cutting through it. Moving permanent magnets passing a conductor generates the change in magnetic flux. Accordingly, in some embodiments, one or more microfluidic chips 108 may be configured to include a magnetic rotor such that when conducting particles move through the changing flux of the magnetic rotor, a spiraling current and resulting magnetic field are induced. The magnetic field of the conducting particles may interact with the magnetic field of the magnetic rotor to impart kinetic energy to the conducting particles. The kinetic energy imparted to the conducting particles may then be used to direct movement of the conducting particles. Accordingly, non-ferrous particles, such as metallic beads, may be utilized to process one or more samples 102. For example, in some embodiments, one or more samples 102 may be combined with one or more tagged polynucleotides that are tagged with a non-ferrous material, such as an aluminum bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed through a magnetic field to impart kinetic energy to the non-ferrous bead. This kinetic energy may then be used to separate the hybridized complex. In other embodiments, similar methods may be used in conjunction with antibodies, aptamers, peptides, ligands, and the like. Accordingly, one or more microfluidic chips 108 may be configured in numerous ways to utilize eddy currents to process one or more samples 102. One or more microfluidic chips 108 may be configured in numerous ways to utilize electrical conductivity to process one or more samples 102.

In some embodiments, one or more microfluidic chips 108 may be configured to process one or more samples 102 through use of isoelectric focusing. Methods have been described that may be used to construct capillary isoelectric focusing systems (e.g., Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). Such systems may be modified to provide for the processing of one or more samples 102.

In some embodiments, one or more microfluidic chips 108 may be configured to process one or more samples 102 through use of electrophoresis. In some embodiments, one or more microfluidic chips 108 may be configured to process one or more samples 102 through use of one-dimensional electrophoresis. In some embodiments, one or more microfluidic chips 108 may be configured to process one or more samples 102 through use of two-dimensional electrophoresis. In some embodiments, one or more microfluidic chips 108 may be configured to process one or more samples 102 through use of gradient gel electrophoresis. In some embodiments, one or more microfluidic chips 108 may be configured to process one or more samples 102 through use electrophoresis under denaturing conditions. In some embodiments, one or more microfluidic chips 108 may be configured to process one or more samples 102 through use electrophoresis under native conditions. One or more microfluidic chips 108 may be configured to utilize numerous electrophoretic methods.

In some embodiments, one or more microfluidic chips 108 may be configured to process one or more samples 102 through use of immunoassay. In some embodiments, one or more microfluidic chips 108 may be configured to process one or more samples 102 through use of enzyme linked immunosorbant assay (ELISA). In some embodiments, one or more microfluidic chips 108 may be configured to process one or more samples 102 through use of radioimmuno assay (RIA). In some embodiments, one or more microfluidic chips 108 may be configured to process one or more samples 102 through use of enzyme immunoassay (EIA). In some embodiments, such methods may utilize antibodies (e.g., monoclonal antibodies, polyclonal antibodies, antibody fragments, single-chain antibodies, and the like), aptamers, or substantially any combination thereof. In some embodiments, a labeled antibody and/or aptamer may be used within an immunoassay. In some embodiments, a labeled ligand to which the antibody and/or aptamer binds may be used within an immunoassay. Numerous types of labels may be utilized. Examples of such labels include, but are not limited to, radioactive labels, fluorescent labels, enzyme labels, spin labels, magnetic labels, gold labels, colorimetric labels, redox labels, and the like. Numerous immunoassays are known and may be configured for processing one or more samples 102.

In some embodiments, one or more microfluidic chips 108 may be configured to process one or more samples 102 through use of one or more competition assays. In some embodiments, one or more microfluidic chips 108 may be configured to process one or more samples 102 through use of one or more polynucleotide based competition assays. One or more microfluidic chips 108 may be configured to include one or more polynucleotides coupled to a substrate, such as a polynucleotide array. The one or more microfluidic chips 108 may be further configured so that a sample 102 and/or substantially purified polynucleotides obtained from one or more samples 102, may be mixed with one or more reagent mixtures that include one or more labeled polynucleotides to form an analysis mixture. This analysis mixture is then passed over the substrate such that the labeled polynucleotides and the sample polynucleotides are allowed to hybridize to the polynucleotides that are immobilized on the substrate. The sample polynucleotides and the labeled polynucleotides will compete for binding to the polynucleotides that are coupled on the substrate. Accordingly, the presence and/or concentration of the polynucleotides in the sample 102 can be determined through detection of the label (e.g., the concentration of the polynucleotides in the sample 102 will be inversely related to the amount of label that is bound to the substrate). Numerous labels may be used that include, but are not limited to, enzymes, fluorescent molecules, radioactive labels, spin labels, redox labels, and the like. In some embodiments, one or more microfluidic chips 108 may be configured to include one or more antibodies, proteins, peptides, and/or aptamers that are coupled to a substrate. The one or more microfluidic chips 108 may be further configured so that a sample 102 and/or substantially purified sample polypeptides and/or sample peptides obtained from one or more samples 102, may be mixed with one or more reagent mixtures that include one or more labeled polypeptides and/or labeled peptides to form an analysis mixture. This analysis mixture can then be passed over the substrate such that the labeled polypeptides and/or labeled peptides and the sample polypeptides and/or sample peptides are allowed to bind to the antibodies, proteins, peptides, and/or aptamers that are immobilized on the substrate. The sample polypeptides and/or sample peptides and the labeled polypeptides and/or sample peptides will compete for binding to the antibodies, proteins, peptides, and/or aptamers that are coupled on the substrate. Accordingly, the presence and/or concentration of the sample polypeptides and/or sample peptides in the sample 102 can be determined through detection of the label (e.g., the concentration of the sample polypeptides and/or sample peptides in the sample 102 will be inversely related to the amount of label that is bound to the substrate). Numerous labels may be used that include, but are not limited to, enzymes, fluorescent molecules, radioactive labels, spin labels, redox labels, and the like. Microfluidic chips 108 may be configured to utilize numerous types of competition assays.

In some embodiments, one or more microfluidic chips 108 may be configured to utilize numerous processing methods. For example, in some embodiments, one or more allergen indicators 106 may be precipitated with salt, dialyzed, and then applied to a chromatographic column.

Figure 12:
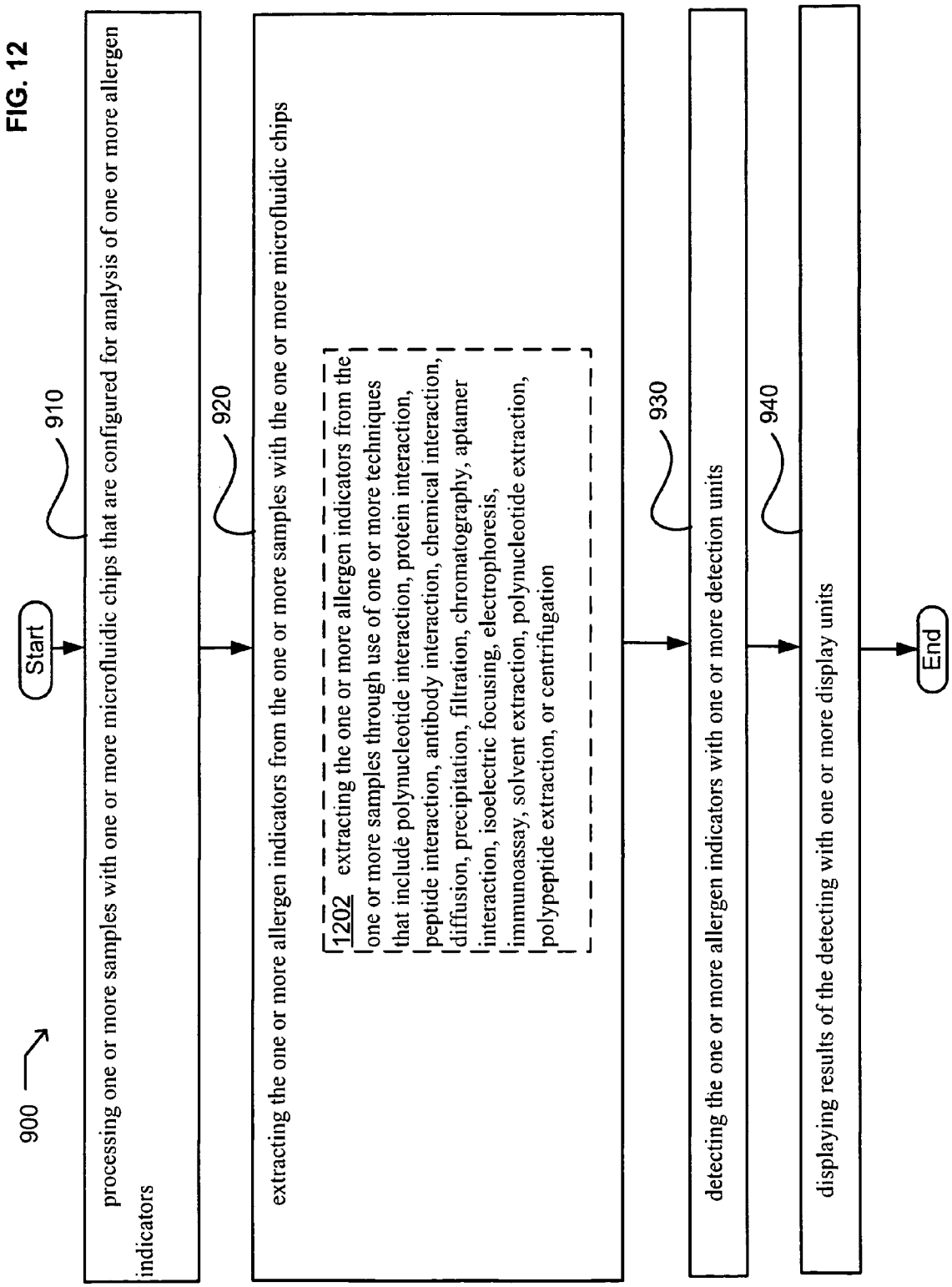
FIG. 12 illustrates alternate embodiments of the example operational flow of FIG. 9.

FIG. 12 illustrates alternative embodiments of the example operational flow 900 of FIG. 9. FIG. 12 illustrates example embodiments where the extracting operation 920 may include at least one additional operation. Additional operations may include an operation 1202.

At operation 1202, the extracting operation 920 may include extracting the one or more allergen indicators from the one or more samples through use of one or more techniques that include polynucleotide interaction, protein interaction, peptide interaction, antibody interaction, chemical interaction, diffusion, precipitation, filtration, chromatography, aptamer interaction, isoelectric focusing, electrophoresis, immunoassay, solvent extraction, polynucleotide extraction, polypeptide extraction, or centrifugation. In some embodiments, one or more microfluidic chips 108 may be configured to extract the one or more allergen indicators 106 from the one or more samples 102 through use of one or more techniques that include polynucleotide interaction, protein interaction, peptide interaction, antibody interaction, chemical interaction, diffusion, precipitation, filtration, chromatography, aptamer interaction, isoelectric focusing, electrophoresis, immunoassay, solvent extraction, polynucleotide extraction, polypeptide extraction, centrifugation, or substantially any combination thereof.

In some embodiments, one or more microfluidic chips 108 may be configured to utilize polynucleotide extraction to extract one or more allergen indicators 106 from one or more samples 102. In some embodiments, extraction polynucleotides may be coupled to a support and then used to prepare an extraction column. One or more samples 102 may then be applied to the extraction column under conditions that allow hybridization and/or binding of one or more allergen indicators 106 to the extraction polynucleotides that are coupled to the support. The column may then be washed to separate the one or more hybridized allergen indicators 106 from other components in the sample 102. The allergen indicators 106 may then be eluted from the extraction column. In some embodiments, one or more extraction polynucleotides may be coupled to a ferromagnetic bead. An extraction mixture may then be prepared by adding the extraction polynucleotides to one or more samples 102 under conditions that allow hybridization and/or binding of one or more allergen indicators 106 to the extraction polynucleotides that are coupled to the ferromagnetic bead. The extraction mixture may then be subjected to a magnetic field to facilitate separation of allergen indicators 106 from other components in the one or more samples 102. In some embodiments, one or more polynucleotide arrays may be used to extract one or more allergen indicators 106 from one or more samples 102.

In some embodiments, one or more microfluidic chips 108 may be configured to utilize polypeptide interaction (e.g., proteins, peptides, antibodies, aptamers, and the like) to extract one or more allergen indicators 106 from one or more samples 102. In some embodiments, extraction polypeptides may be coupled to a support and then used to prepare an extraction column. One or more samples 102 may then be applied to the extraction column under conditions that allow interaction of one or more allergen indicators 106 to the extraction polypeptides that are coupled to the support. The column may then be washed to separate the one or more allergen indicators 106 from other components in the sample 102. The allergen indicators 106 may then be eluted from the extraction column. In some embodiments, one or more extraction polypeptides may be coupled to a ferromagnetic bead. An extraction mixture may then be prepared by adding the extraction polypeptides to one or more samples 102 under conditions that allow binding of one or more allergen indicators 106 to the extraction polypeptides that are coupled to the ferromagnetic bead. The extraction mixture may then be subjected to a magnetic field to facilitate separation of allergen indicators 106 from other components in the one or more samples 102. In some embodiments, one or more polypeptide arrays may be used to extract one or more allergen indicators 106 from one or more samples 102.

In some embodiments, one or more microfluidic chips 108 may be configured to utilize chemical extraction to extract one or more allergen indicators 106 from one or more samples 102. In some embodiments, one or more allergen indicators 106 may be extracted from one or more samples 102 through precipitation with one or more chemical agents. In some embodiments, one or more allergen indicators 106 may be extracted from one or more samples 102 through use of one or more solvents.

In some embodiments, one or more microfluidic chips 108 may be configured to utilize diffusion to extract one or more allergen indicators 106 from one or more samples 102. In some embodiments, one or more H-filters may be used to extract one or more allergen indicators 106 from one or more samples 102. In some embodiments, dialysis may be used to extract one or more allergen indicators 106 from one or more samples 102.

In some embodiments, one or more microfluidic chips 108 may be configured to utilize filtration to extract one or more allergen indicators 106 from one or more samples 102. In some embodiments, one or more filters may be used to extract one or more allergen indicators 106 from one or more samples 102. For example, in some embodiments one or more samples 102 may be passed through one or more filters that selectively retain or allow allergen indicators 106 to pass through the one or more filters. Accordingly, in some embodiments, one or more samples 102 may be passed through one or more filters to extract one or more allergen indicators 106 from the one or more samples 102. Examples of types of filters that may be used include, but are not limited to, paper, ceramic, polyvinylidene fluoride sheets, and the like.

In some embodiments, one or more microfluidic chips 108 may be configured to utilize chromatography to extract one or more allergen indicators 106 from one or more samples 102. Numerous chromatographic methods may be used to extract one or more allergen indicators 106 from one or more samples 102. Examples of such chromatographic methods include, but are not limited to, thin layer chromatography, liquid chromatography, high pressure liquid chromatography, fast protein liquid chromatography, paper chromatography, capillary chromatography, gas chromatography, affinity chromatography, and the like.

In some embodiments, one or more microfluidic chips 108 may be configured to utilize aptamer (e.g., peptide aptamer and/or polynucleotide aptamer) interaction to extract one or more allergen indicators 106 from one or more samples 102. In some embodiments, one or more microfluidic chips 108 may be configured to utilize one or more aptamers to extract one or more allergen indicators 106 from one or more samples 102. In some embodiments, one or more aptamers may be coupled to a support and then used to prepare an extraction column. One or more samples 102 may then be applied to the extraction column under conditions that allow binding of one or more allergen indicators 106 to the one or more aptamers that are coupled to the support. The column may then be washed to separate the one or more hybridized allergen indicators 106 from other components in the sample 102. The allergen indicators 106 may then be eluted from the extraction column. In some embodiments, one or more aptamers may be coupled to a ferromagnetic bead. An extraction mixture may then be prepared by adding the one or more aptamers to one or more samples 102 under conditions that allow binding of one or more allergen indicators 106 to the aptamers that are coupled to the ferromagnetic bead. The extraction mixture may then be subjected to a magnetic field to facilitate separation of allergen indicators 106 from other components in the one or more samples 102. In some embodiments, one or more aptamer arrays may be used to extract one or more allergen indicators 106 from one or more samples 102.

In some embodiments, one or more microfluidic chips 108 may be configured to utilize isoelectric focusing to extract one or more allergen indicators 106 from one or more samples 102. For example, in some embodiments, one or more samples 102 may be applied to an isoelectric focusing column (e.g., microcapillary column) where one or more allergen indicators 106 may be separated according to their isoelectric points. In some embodiments, the one or more allergen indicators 106 may then be extracted from the isoelectric focusing column.

In some embodiments, one or more microfluidic chips 108 may be configured to utilize electrophoresis to extract one or more allergen indicators 106 from one or more samples 102. Numerous electrophoretic methods may be used to extract one or more allergen indicators 106 from one or more samples 102. Examples of such electrophoretic methods include, but are not limited to, gel electrophoresis (e.g., polyacrylamide, agarose, and the like), native electrophoresis, denaturing electrophoresis, two-dimensional electrophoresis, paper electrophoresis, and the like.

In some embodiments, one or more microfluidic chips 108 may be configured to utilize centrifugation to extract one or more allergen indicators 106 from one or more samples 102. For example, in some embodiments, one or more samples 102 may be centrifuged to extract one or more allergen indicators 106 through use of a density gradient. In some embodiments, one or more allergen indicators 106 may be extracted from one or more samples 102 through use of a velocity gradient.

Figure 13:
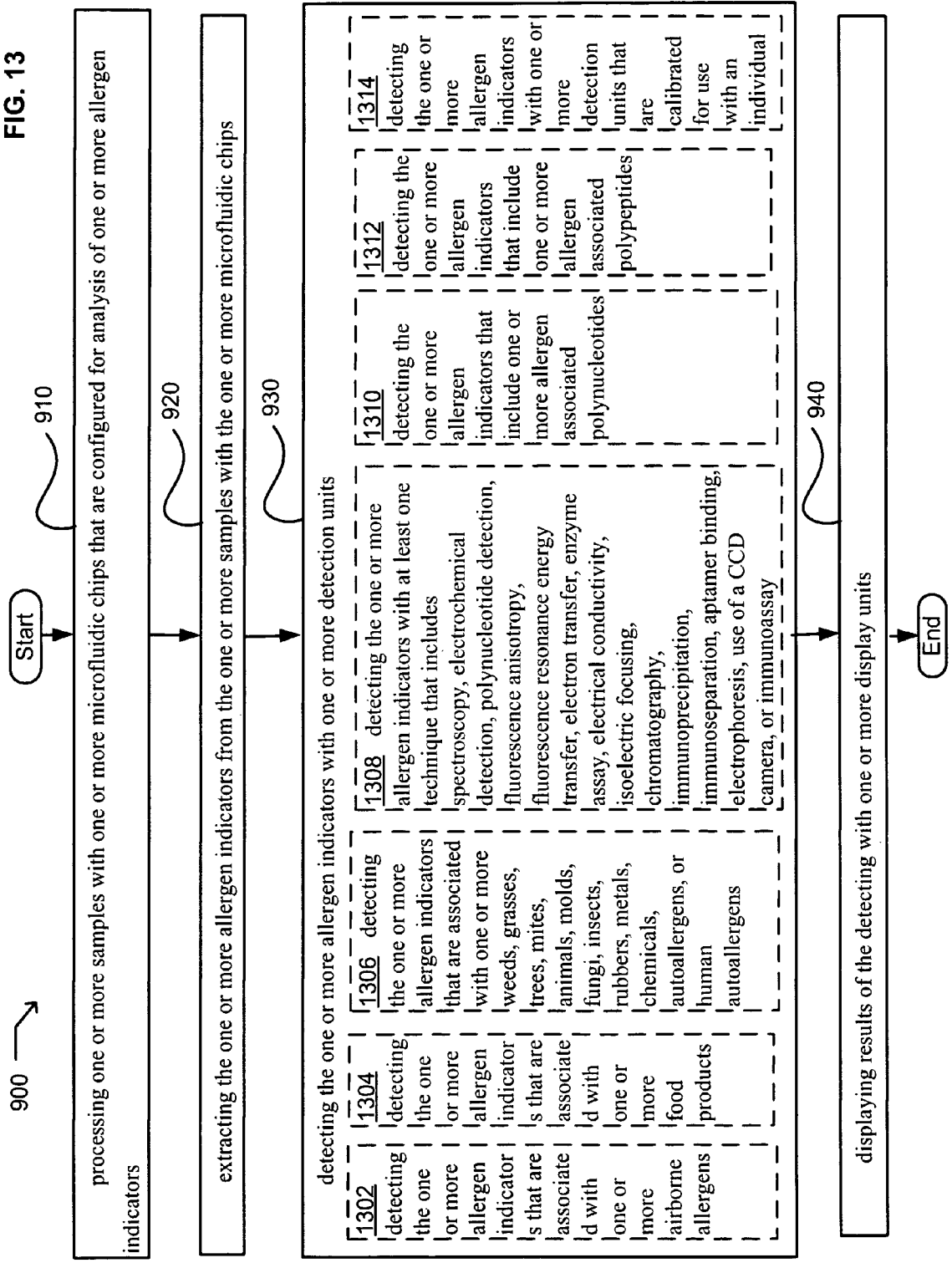
FIG. 13 illustrates alternate embodiments of the example operational flow of FIG. 9.

FIG. 13 illustrates alternative embodiments of the example operational flow 900 of FIG. 9. FIG. 13 illustrates example embodiments where the detecting operation 930 may include at least one additional operation. Additional operations may include an operation 1302, an operation 1304, an operation 1306, an operation 1308, an operation 1310, an operation 1312, and/or an operation 1314.

At operation 1302, the detecting operation 930 may include detecting the one or more allergen indicators that are associated with one or more airborne allergens. In some embodiments, one or more detection units 122 may be used to detect one or more allergens 104 that are airborne. In some embodiments, one or more microfluidic chips 108 may be configured to provide for detection of one or more allergens 104 that are airborne. Accordingly, in some embodiments, one or more detection units 122 may be configured to operably associate with the one or more microfluidic chips 108 and to detect one or more airborne allergens 104. For example, in some embodiments, one or more microfluidic chips 108 may be configured to allow one or more air samples 102 to contact the one or more microfluidic chips 108 such that one or more allergen indicators 106 included within the one or more air samples 102 are retained by the one or more microfluidic chips 108. In some embodiments, the one or more air samples 102 may be passed through a filter on which one or more airborne allergen indicators 106 are collected. The collected airborne allergen indicators 106 may then be washed from the filter and caused to pass over an antibody array to which the one or more airborne allergen indicators 106 become immobilized. The immobilized airborne allergen indicators 106 may then be detected through numerous methods that include, but are not limited to, electrical conductivity, immunoassay based methods, and the like. Accordingly, one or more detection units 122 may be configured to detect the one or more airborne allergen indicators 106. In some embodiments, one or more detection units 122 may be configured to operably associate with one or more microfluidic chips 108 such that the one or more detection units 122 facilitate air flow through the one or more microfluidic chips 108 to provide for air sampling. For example, in some embodiments, one or more detection units 122 may include one or more fans to push and/or pull air through one or more operably associated microfluidic chips 108. In some embodiments, one or more detection units 122 may include one or more bellows to push and/or pull air through one or more operably associated microfluidic chips 108. Detection units 122 may be configured in numerous ways to provide for detection of one or more airborne allergen indicators 106.

At operation 1304, the detecting operation 930 may include detecting the one or more allergen indicators that are associated with one or more food products. In some embodiments, one or more detection units 122 may be used to detect the one or more allergen indicators 106 that are associated with one or more food products. In some embodiments, one or more microfluidic chips 108 may be configured to provide for detection of one or more allergens 104 that are associated with one or more food products. Accordingly, in some embodiments, one or more detection units 122 may be configured to operably associate with the one or more microfluidic chips 108 and to detect one or more allergen indicators 106 that are associated with one or more food products. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Numerous methods may be used to detect one or more allergen indicators 106 that are associated with one or more food products. Such methods have been described herein. In addition, other detection methods that have been described may be modified to provide for detection of one or more allergen indicators 106 that are associated with one or more food products. In some embodiments, one or more detection units 122 may be configured to detect one or more polynucleotides, one or more polypeptides, one or more portions of one or more polynucleotides, and/or one or more portions of one or more polypeptides that have a nucleic acid sequence and/or an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, or AY839230.

At operation 1306, the detecting operation 930 may include detecting the one or more allergen indicators that are associated with one or more weeds, grasses, trees, mites, animals, molds, fungi, insects, rubbers, metals, chemicals, autoallergens, or human autoallergens. In some embodiments, one or more detection units 122 may be used to detect one or more allergen indicators 106 that are associated with one or more weeds, grasses, trees, mites, animals, molds, fungi, insects, rubbers, metals, chemicals, autoallergens, human autoallergens, or substantially any combination thereof. Numerous allergen indicators 106 are known to be associated with weeds, grasses, trees, mites, animals, molds, fungi, insects, rubbers, metals, chemicals, autoallergens, human autoallergens, or substantially any combination thereof. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Accordingly, in some embodiments, one or more microfluidic chips 108 may be configured to process one or more samples 102 and provide for detection of one or more allergen indicators 106. In some embodiments, an allergen indicator 106 may be an allergenic particle. For example, in some embodiments, an allergen indicator 106 may include a complete pollen particle, such as a pollen particle, a spore, a flake of dander, and the like. In some embodiments, an allergen indicator 106 may be a portion of an allergenic particle. For example, in some embodiments, an allergen indicator 106 may include a portion of a pollen particle (e.g., polynucleotides, sporoderm, and the like). In some embodiments, allergen indicators 106 may include polynucleotides that are associated with one or more allergens 104. In some embodiments, allergen indicators 106 may include fragments of polynucleotides that are associated with one or more allergens 104. In some embodiments, allergen indicators 106 may include polypeptides, peptides, and/or proteins that are associated with one or more allergens 104. In some embodiments, allergen indicators 106 may include polysaccharides that are associated with one or more allergens 104. Accordingly, in some embodiments, one or more microfluidic chips 108 may be configured to provide for detection of one or more allergen indicators 106. In some embodiments, one or more detection units 122 may be configured to operably associate with one or more such microfluidic chips 108 and configured to detect one or more allergen indicators 106. Numerous detection methods may be used to detect one or more allergen indicators 106. Such methods have been described herein. In addition, detection methods that have been described may be modified to provide for detection of one or more allergen indicators 106. In some embodiments, one or more detection units 122 may be configured to detect and determine a concentration of one or more allergen indicators 106 that are included within a sample 102. For example, in some embodiments, one or more microfluidic chips 108 may be configured to provide for detection of one or more polynucleotides that are allergen indicators 106 through detection of electrical current produced upon hybridization of the one or more polynucleotides. Accordingly, in such embodiments, the one or more microfluidic chips 108 may be configured to produce an electrical current that is relative to polynucleotide concentration to provide for determination of polynucleotide concentration within one or more samples 102. Numerous configurations may be used in association with one or more allergen indicators 106 to provide for determination of allergen 104 concentration. In some embodiments, one or more microfluidic chips 108 may be configured to provide for identification of one or more allergens 104. For example, in some embodiments, one or more microfluidic chips 108 may include immobilized polynucleotides that selectively hybridize to one or more polynucleotides that are associated with a known allergen indicator 106. Accordingly, hybridization of one or more polynucleotides with the one or more immobilized polynucleotides indicates that a sample 102 includes one or more allergen indicators 106 that correspond to one or more known allergens 104. Accordingly, one or more detection units 122 may be configured to operably associate with such microfluidic chips 108 to provide for specific detection of one or more allergens 104. In some embodiments, microfluidic chips 108 and/or detection units 122 may be configured to determine the identity and concentration of one or more allergen indicators 106 that are included within one or more samples 102.

At operation 1308, the detecting operation 930 may include detecting the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, one or more detection units 122 may be used to detect one or more allergens 104 with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, filtration, electrophoresis, use of a CCD camera, immunoassay, or substantially any combination thereof. In some embodiments, one or more detection units 122 may be configured to detect one or more allergen indicators 106 that have been processed by one or more microfluidic chips 108. For example, in some embodiments, one or more microfluidic chips 108 may include a window (e.g., a quartz window, a cuvette analog, and/or the like) through which one or more detection units 122 may determine if one or more allergen indicators 106 are present or determine the concentration of one or more allergen indicators 106. In such embodiments, numerous techniques may be used to detect the one or more allergen indicators 106, such as visible light spectroscopy, ultraviolet light spectroscopy, infrared spectroscopy, fluorescence spectroscopy, and the like. Accordingly, in some embodiments, one or more detection units 122 may include circuitry and/or electro-mechanical mechanisms to detect one or more allergen indicators 106 present within one or more microfluidic chips 108 through a window in the one or more microfluidic chips 108. In some embodiments, one or more microfluidic chips 108 may be configured to process one or more samples 102 through use of surface plasmon resonance. In some embodiments, the one or more microfluidic chips 108 may include one or more antibodies, aptamers, proteins, peptides, polynucleotides, and the like, that are bound to a substrate (e.g., a metal film) within the one or more microfluidic chips 108. In some embodiments, such microfluidic chips 108 may include a prism through which one or more detection units 122 may shine light to detect one or more allergen indicators 106 that interact with the one or more antibodies, aptamers, proteins, peptides, polynucleotides, and the like, that are bound to a substrate. In some embodiments, one or more microfluidic chips 108 may include an exposed substrate surface that is configured to operably associate with one or more prisms that are included within one or more detection units 122. In some embodiments, one or more microfluidic chips 108 may include a nuclear magnetic resonance (NMR) probe. In such embodiments, the microfluidic chips 108 may be configured to associate with one or more detection units 122 that accept the NMR probe and are configured to detect one or more allergen indicators 106 through use of NMR spectroscopy. Accordingly, microfluidic chips 108 and detection units 122 may be configured in numerous ways to associate with each other to provide for detection of one or more allergen indicators 106.

In some embodiments, one or more allergen indicators 106 may be detected through use of spectroscopy. Numerous types of spectroscopic methods may be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., Clinical Chemistry, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, one or more allergen indicators 106 may be detected through use of electrochemical detection. In some embodiments, one or more polynucleotides may be detected through electrochemical detection. For example, in some embodiments, a polynucleotide that includes a redox label, such as ferrocene is coupled to a gold electrode. The labeled polynucleotide forms a stem-loop structure that can self-assemble onto a gold electrode by means of facile gold-thiol chemistry. Hybridization of a sample 102 polynucleotide induces a large conformational change in the surface-confined polynucleotide structure, which in turn alters the electron-transfer tunneling distance between the electrode and the redoxable label. The resulting change in electron transfer efficiency may be measured by cyclic voltammetry (Fan et al., Proc. Natl. Acad. Sci., 100:9134-9137 (2003); Wang et al., Anal. Chem., 75:3941-3945 (2003); Singh-Zocchi et al., Proc. Natl. Acad. Sci., 100:7605-7610 (2003)). Such methods may be used to detect messenger ribonucleic acid, genomic deoxyribonucleic acid, and fragments thereof.

In some embodiments, one or more allergen indicators 106 may be detected through use of polynucleotide detection. In some embodiments, one or more detection units 122 may be configured to detect one or more allergen indicators 106 through use of polynucleotide detection. Numerous methods may be used to detect one or more polynucleotides. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described (e.g., U.S. Pat. Nos. 7,118,910 and 6,960,437; herein incorporated by reference). Such methods may be adapted to provide for detection of one or more allergen indicators 106. In some embodiments, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube may be combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Accordingly, polynucleotides that hybridize to one or more allergen indicators 106 may include one or more carbon nanotubes. Methods to utilize carbon nanotubes as probes for nucleic acid interaction have been described (e.g., U.S. Pat. No. 6,821,730; herein incorporated by reference). Numerous other methods based on polynucleotide detection may be used to detect one or more allergen indicators 106.

In some embodiments, one or more allergen indicators 106 may be detected through use of fluorescence anisotropy. Fluorescence anisotropy is based on measuring the steady state polarization of sample 102 fluorescence imaged in a confocal arrangement. A linearly polarized laser excitation source preferentially excites fluorescent target molecules with transition moments aligned parallel to the incident polarization vector. The resultant fluorescence is collected and directed into two channels that measure the intensity of the fluorescence polarized both parallel and perpendicular to that of the excitation beam. With these two measurements, the fluorescence anisotropy, r, can be determined from the equation: r=(Intensity parallel−Intensity perpendicular)/(Intensity parallel+2(Intensity perpendicular)) where the I terms indicate intensity measurements parallel and perpendicular to the incident polarization. Fluorescence anisotropy detection of fluorescent molecules has been described. Accordingly, fluorescence anisotropy may be coupled to numerous fluorescent labels as have been described herein and as have been described.

In some embodiments, one or more allergen indicators 106 may be detected through use of fluorescence resonance energy transfer (FRET). Fluorescence resonance energy transfer refers to an energy transfer mechanism between two fluorescent molecules. A fluorescent donor is excited at its fluorescence excitation wavelength. This excited state is then nonradiatively transferred to a second molecule, the fluorescent acceptor. Fluorescence resonance energy transfer may be used within numerous configurations to detect one or more allergen indicators 106. For example, in some embodiments, an antibody may be labeled with a fluorescent donor and one or more allergen indicators 106 may be labeled with a fluorescent acceptor. Accordingly, such labeled antibodies and allergen indicators 106 may be used within competition assays to detect the presence and/or concentration of one or more allergen indicators 106 in one or more samples 102. Numerous combinations of fluorescent donors and fluorescent acceptors may be used to detect one or more allergen indicators 106. Accordingly, one or more detection units 122 may be configured to emit one or more wavelength of light to excite a fluorescent donor and may be configured to detect one or more wavelength of light emitted by the fluorescent acceptor. Accordingly, in some embodiments, one or more detection units 122 may be configured to accept one or more microfluidic chips 108 that include a quartz window through which fluorescent light may pass to provide for detection of one or more allergen indicators 106 through use of fluorescence resonance energy transfer. Accordingly, fluorescence resonance energy transfer may be used in conjunction with competition assays and/or numerous other types of assays to detect one or more allergen indicators 106.

In some embodiments, one or more allergen indicators 106 may be detected through use of electron transfer. Electron transfer is the process by which an electron moves from an electron donor to an electron acceptor causing the oxidation states of the electron donor and the electron acceptor to change. In some embodiments, electron transfer may occur when an electron is transferred from one or more electron donors to an electrode. In some embodiments, electron transfer may be utilized within competition assays to detect one or more allergen indicators 106. For example, in some embodiments, one or more microfluidic chips 108 may include one or more polynucleotides that may be immobilized on one or more electrodes. The immobilized polynucleotides may be incubated with a reagent mixture that includes sample polynucleotides and polynucleotides that are tagged with an electron donor. Hybridization of the tagged polynucleotides to the immobilized polynucleotides allows the electron donor to transfer an electron to the electrode to produce a detectable signal. Accordingly, a decrease in signal due to the presence of one or more polynucleotides that are allergen indicators 106 in the reagent mixture indicates the presence of an allergen indicator 106 in the sample 102. Such methods may be used in conjunction with polynucleotides, polypeptides, peptides, antibodies, aptamers, and the like. One or more microfluidic chips 108 may be configured to utilize numerous electron transfer based assays to provide for detection of one or more allergen indicators 106 by a detection unit 122.

In some embodiments, one or more allergen indicators 106 may be detected through use of one or more enzyme assays. Numerous enzyme assays may be used to provide for detection of one or more allergen indicators 106. Examples of such enzyme assays include, but are not limited to, beta-galactosidase assays, peroxidase assays, catalase assays, alkaline phosphatase assays, and the like. In some embodiments, enzyme assays may be configured such that an enzyme will catalyze a reaction involving an enzyme substrate that produces a fluorescent product. Accordingly, one or more detection units 122 may be configured to detect fluorescence resulting from the fluorescent product. Enzymes and fluorescent enzyme substrates are known and are commercially available (e.g., Sigma-Aldrich, St. Louis, Mo.). In some embodiments, enzyme assays may be configured as binding assays that provide for detection of one or more allergen indicators 106. For example, in some embodiments, one or more microfluidic chips 108 may be configured to include a substrate to which is coupled to one or more antibodies, aptamers, peptides, proteins, polynucleotides, ligands, and the like, that will interact with one or more allergen indicators 106. One or more samples 102 may be passed across the substrate such that one or more allergen indicators 106 present within the one or more samples 102 will interact with the one or more antibodies, aptamers, peptides, proteins, polynucleotides, ligands, and the like, and be immobilized on the substrate. One or more antibodies, aptamers, peptides, proteins, polynucleotides, ligands, and the like, that are labeled with an enzyme may then be passed across the substrate such that the one or more labeled antibodies, aptamers, peptides, proteins, polynucleotides, ligands, and the like, will bind to the one or more immobilized allergen indicators 106. An enzyme substrate may then be introduced to the one or more immobilized enzymes such that the enzymes are able to catalyze a reaction involving the enzyme substrate to produce a fluorescent product. Such assays are often referred to as sandwich assays. Accordingly, one or more detection units 122 may be configured to detect one or more products of enzyme catalysis to provide for detection of one or more allergen indicators 106.

In some embodiments, one or more allergen indicators 106 may be detected through use of electrical conductivity. In some embodiments, one or more microfluidic chips 108 may be configured to process one or more samples 102 and provide for detection of one or more allergen indicators 106 through use of electrical conductivity. In some embodiments, such microfluidic chips 108 may be configured to operably associate with one or more detection units 122 such that the one or more detection units 122 can detect one or more allergen indicators 106 through use of electrical conductivity. In some embodiments, one or more microfluidic chips 108 may be configured to include two or more electrodes that are each coupled to one or more detector polynucleotides. Interaction of an allergen 104 associated polynucleotide, such as hybridization, with two detector polynucleotides that are coupled to two different electrodes will complete an electrical circuit. This completed circuit will provide for the flow of a detectable electrical current between the two electrodes and thereby provide for detection of one or more allergen 104 associated polynucleotides that are allergen indicators 106. In some embodiments, the electrodes may be carbon nanotubes (e.g., U.S. Pat. No. 6,958,216; herein incorporated by reference). In some embodiments, electrodes may include, but are not limited to, one or more conductive metals, such as gold, copper, iron, silver, platinum, and the like; one or more conductive alloys; one or more conductive ceramics; and the like. In some embodiments, electrodes may be selected and configured according to protocols typically used in the computer industry that include, but are not limited to, photolithography, masking, printing, stamping, and the like. In some embodiments, other molecules and complexes that interact with one or more allergen indicators 106 may be used to detect the one or more allergen indicators 106 through use of electrical conductivity. Examples of such molecules and complexes include, but are not limited to, proteins, peptides, antibodies, aptamers, and the like. For example, in some embodiments, two or more antibodies may be immobilized on one or more electrodes such that contact of the two or more antibodies with an allergen indicator 106, such as a spore, a pollen particle, a dander particle, and the like, will complete an electrical circuit and facilitate the production of a detectable electrical current. Accordingly, in some embodiments, one or more microfluidic chips 108 may be configured to include electrical connectors that are able to operably associate with one or more detection units 122 such that the detection units 122 may detect an electrical current that is due to interaction of one or more allergen indicators 106 with two or more electrodes. In some embodiments, one or more detection units 122 may include electrical connectors that provide for operable association of one or more microfluidic chips 108 with the one or more detection units 122. In some embodiments, the one or more detectors are configured for detachable connection to one or more microfluidic chips 108. Microfluidic chips 108 and detection units 122 may be configured in numerous ways to process one or more samples 102 and detect one or more allergen indicators 106.

In some embodiments, one or more allergen indicators 106 may be detected through use of isoelectric focusing. In some embodiments, one or more microfluidic chips 108 may be configured to process one or more samples 102 and provide for detection of one or more allergen indicators 106 through use of isoelectric focusing. In some embodiments, native isoelectric focusing may be utilized to process and/or detect one or more allergen indicators 106. In some embodiments, denaturing isoelectric focusing may be utilized to process and/or detect one or more allergen indicators 106. Methods to construct microfluidic channels that may be used for isoelectric focusing have been reported (e.g., Macounova et al., Anal Chem., 73:1627-1633 (2001); Macounova et al., Anal Chem., 72:3745-3751 (2000); Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). In some embodiments, one or more microfluidic chips 108 may be configured to process one or more samples 102 through use of methods that include isoelectric focusing. In some embodiments, one or more detection units 122 may be configured to operably associate with one or more such microfluidic chips 108 such that the one or more detection units 122 can be used to detect one or more allergen indicators 106 that have been focused within one or more microfluidic channels of the one or more microfluidic chips 108. In some embodiments, one or more detection units 122 may be configured to include one or more CCD cameras that can be used to detect one or more allergen indicators 106. In some embodiments, one or more detection units 122 may be configured to include one or more spectrometers that can be used to detect one or more allergen indicators 106. Numerous types of spectrometers may be utilized to detect one or more allergen indicators 106 following isoelectric focusing. In some embodiments, one or more detection units 122 may be configured to utilize refractive index to detect one or more allergen indicators 106. In some embodiments, one or more microfluidic chips 108 may be configured to combine one or more samples 102 with one or more reagent mixtures that include one or more binding molecules and/or binding complexes that bind to one or more allergen indicators 106 that may be present within the one or more samples 102 to form an allergen indicator-binding molecule/binding complex. Examples of such binding molecules and/or binding complexes that bind to one or more allergen indicators 106 include, but are not limited to, antibodies, aptamers, peptides, proteins, polynucleotides, and the like. In some embodiments, an allergen indicator-binding molecule/binding complex may be processed through use of isoelectric focusing and then detected with one or more detection units 122. In some embodiments, one or more binding molecules and/or one or more binding complexes may include a label. Numerous labels may be used and include, but are not limited to, radioactive labels, fluorescent labels, colorimetric labels, spin labels, fluorescent labels, and the like. Accordingly, in some embodiments, an allergen indicator-binding molecule (labeled)/binding complex (labeled) may be processed through use of isoelectric focusing and then detected with one or more detection units 122 that are configured to detect the one or more labels. Microfluidic chips 108 and detection units 122 may be configured in numerous ways to process one or more samples 102 and detect one or more allergen indicators 106 though use of isoelectric focusing.

In some embodiments, one or more allergen indicators 106 may be detected through use of chromatographic methodology alone or in combination with additional processing and/or detection methods. In some embodiments, one or more microfluidic chips 108 may be configured to process one or more samples 102 and provide for detection of one or more allergen indicators 106 through use of chromatographic methods. Accordingly, in some embodiments, one or more detection units 122 may be configured to operably associate with the one or more microfluidic chips 108 and detect one or more allergen indicators 106 that were processed through use of chromatographic methods. In some embodiments, the one or more detection units 122 may be configured to operably associate with one or more microfluidic chips 108 and supply solvents and other reagents to the one or more microfluidic chips 108. For example, in some embodiments, one or more detection units 122 may include pumps and solvent/buffer reservoirs that are configured to supply solvent/buffer flow through chromatographic media (e.g., a chromatographic column) that is operably associated with one or more microfluidic chips 108. In some embodiments, one or more detection units 122 may be configured to operably associate with one or more microfluidic chips 108 and be configured to utilize one or more methods to detect one or more allergen indicators 106. Numerous types of chromatographic methods and media may be used to process one or more samples 102 and provide for detection of one or more allergen indicators 106. Chromatographic methods include, but are not limited to, low pressure liquid chromatography, high pressure liquid chromatography (HPLC), microcapillary low pressure liquid chromatography, microcapillary high pressure liquid chromatography, ion exchange chromatography, affinity chromatography, gel filtration chromatography, size exclusion chromatography, thin layer chromatography, paper chromatography, gas chromatography, and the like. In some embodiments, one or more microfluidic chips 108 may be configured to include one or more high pressure microcapillary columns. Methods that may be used to prepare microcapillary HPLC columns (e.g., columns with a 100 micrometer-500 micrometer inside diameter) have been described (e.g., Davis et al., Methods, A Companion to Methods in Enzymology, 6: Micromethods for Protein Structure Analysis, ed. by John E. Shively, Academic Press, Inc., San Diego, 304-314 (1994); Swiderek et al., Trace Structural Analysis of Proteins. Methods of Enzymology, ed. by Barry L. Karger & William S. Hancock, Spectrum, Publisher Services, 271, Chap. 3, 68-86 (1996); Moritz and Simpson, J. Chromatogr., 599:119-130 (1992)). In some embodiments, one or more microfluidic chips 108 may be configured to include one or more affinity columns. Methods to prepare affinity columns have been described. Briefly, a biotinylated site may be engineered into a polypeptide, peptide, aptamer, antibody, or the like. The biotinylated protein may then be incubated with avidin coated polystyrene beads and slurried in Tris buffer. The slurry may then be packed into a capillary affinity column through use of high pressure packing. Affinity columns may be prepared that may include one or more molecules and/or complexes that interact with one or more allergen indicators 106. For example, in some embodiments, one or more aptamers that bind to one or more allergen indicators 106 may be used to construct an affinity column. Accordingly, numerous chromatographic methods may be used alone, or in combination with additional methods, to process and detect one or more allergen indicators 106. Numerous detection methods may be used in combination with numerous types of chromatographic methods. Accordingly, one or more detection units 122 may be configured to utilize numerous detection methods to detect one or more allergen indicators 106 that are processed through use of one or more chromatographic methods. Examples of such detection methods include, but are not limited to, conductivity detection, use of ion-specific electrodes, refractive index detection, colorimetric detection, radiological detection, detection by retention time, detection through use of elution conditions, spectroscopy, and the like. For example, in some embodiments, one or more chromatographic markers may be added to one or more samples 102 prior to the samples 102 being applied to a chromatographic column. One or more detection units 122 that are operably associated with the chromatographic column may be configured to detect the one or more chromatographic markers and use the elution time and/or position of the chromatographic markers as a calibration tool for use in detecting one or more allergen indicators 106 if those allergen indicators 106 are eluted from the chromatographic column. In some embodiments, one or more detection units 122 may be configured to utilize one or more ion-specific electrodes to detect one or more allergen indicators 106. For example, such electrodes may be used to detect allergen indicators 106 that include, but are not limited to, metals (e.g., tin, silver, nickel, cobalt, chromate), nitrates, nitrites, sulfites, and the like. Such allergen indicators 106 are often associated with food, beverages, clothing, jewelry, and the like. Accordingly, chromatographic methods may be used in combination with additional methods and in combination with numerous types of detection methods.

In some embodiments, one or more allergen indicators 106 may be detected through use of immunoprecipitation. In some embodiments, one or more detection units 122 may be configured to detect one or more allergen indicators 106 through use of immunoprecipitation. In some embodiments, immunoprecipitation may be utilized in combination with additional processing and/or detection methods to detect one or more allergen indicators 106. In some embodiments, one or more microfluidic chips 108 may be configured to process one or more samples 102 through use of immunoprecipitation. For example, in some embodiments, one or more samples 102 may be combined with one or more antibodies that bind to one or more allergen indicators 106 to form one or more antibody-allergen indicator 106 complexes. An insoluble form of an antibody binding constituent, such as protein A (e.g., protein A-sepharose bead, protein A-magnetic bead, protein A-ferrous bead, protein A-non-ferrous bead, and the like), Protein G, a second antibody, an aptamer, and the like, may then be mixed with the antibody-allergen indicator 106 complex such that the insoluble antibody binding constituent binds to the antibody-allergen indicator 106 complex and provides for precipitation of the antibody-allergen indicator 106 complex. Such complexes may be separated from other sample 102 components to provide for detection of one or more allergen indicators 106. For example, in some embodiments, sample 102 components may be washed away from the precipitated antibody-allergen indicator 106 complexes. In some embodiments, one or more microfluidic chips 108 that are configured for immunoprecipitation may be operably associated with one or more centrifugation units 118 to assist in precipitating one or more antibody-allergen indicator 106 complexes. In some embodiments, aptamers (polypeptide and/or polynucleotide) may be used in combination with antibodies or in place of antibodies. Accordingly, one or more detection units 122 may be configured to detect one or more allergen indicators 106 through use of numerous detection methods in combination with immunoprecipitation based methods.

In some embodiments, one or more allergen indicators 106 may be detected through use of immunoseparation. In some embodiments, one or more detection units 122 may be configured to detect one or more allergen indicators 106 through use of immunoseparation. In some embodiments, immunoseparation may be utilized in combination with additional processing and/or detection methods to detect one or more allergen indicators 106. In some embodiments, one or more microfluidic chips 108 may be configured to process one or more samples 102 through use of immunoseparation. For example, in some embodiments, one or more samples 102 may be combined with one or more antibodies that bind to one or more allergen indicators 106 to form one or more antibody-allergen indicator 106 complexes. An antibody binding constituent may be added that binds to the antibody-allergen complex.

Examples of such antibody binding constituents that may be used alone or in combination include, but are not limited to, protein A (e.g., protein A-sepharose bead, protein A-magnetic bead, protein A-ferrous bead, protein A-non-ferrous bead, and the like), Protein G, a second antibody, an aptamer, and the like. Such antibody binding constituents may be mixed with an antibody-allergen indicator 106 complex such that the antibody binding constituent binds to the antibody-allergen indicator 106 complex and provides for separation of the antibody-allergen indicator 106 complex. In some embodiments, the antibody binding constituent may include a tag that allows the antibody binding constituent and complexes that include the antibody binding constituent to be separated from other components in one or more samples 102. In some embodiments, the antibody binding constituent may include a ferrous material. Accordingly, antibody-allergen indicator 106 complexes may be separated from other sample 102 components through use of a magnet, such as an electromagnet. In some embodiments, an antibody binding constituent may include a non-ferrous metal. Accordingly, antibody-allergen indicator 106 complexes may be separated from other sample 102 components through use of an eddy current to direct movement of one or more antibody-allergen indicator 106 complexes. In some embodiments, two or more forms of an antibody binding constituents may be used to detect one or more allergen indicators 106. For example, in some embodiments, a first antibody binding constituent may be coupled to a ferrous material and a second antibody binding constituent may be coupled to a non-ferrous material. Accordingly, the first antibody binding constituent and the second antibody binding constituent may be mixed with antibody-allergen indicator 106 complexes such that the first antibody binding constituent and the second antibody binding constituent bind to antibody-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more antibodies that bind to one or more allergen indicators 106 to form one or more antibody-allergen indicator 106 complexes. In some embodiments, the one or more antibodies may include one or more tags that provide for separation of the antibody-allergen indicator 106 complexes. For example, in some embodiments, an antibody may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with immunoseparation based methods. In some embodiments, aptamers (polypeptide and/or polynucleotide) may be used in combination with antibodies or in place of antibodies.

In some embodiments, one or more allergen indicators 106 may be detected through use of aptamer binding. In some embodiments, one or more detection units 122 may be configured to detect one or more allergen indicators 106 through use of aptamer binding. In some embodiments, aptamer binding may be utilized in combination with additional processing and/or detection methods to detect one or more allergen indicators 106. In some embodiments, one or more microfluidic chips 108 may be configured to process one or more samples 102 through use of aptamer binding. For example, in some embodiments, one or more samples 102 may be combined with one or more aptamers that bind to one or more allergen indicators 106 to form one or more aptamer-allergen indicator 106 complexes. In some embodiments, aptamer binding constituents may be added that bind to the aptamer-allergen complex. Numerous aptamer binding constituents may be utilized. For example, in some embodiments, one or more aptamers may include one or more tags to which one or more aptamer binding constituents may bind. Examples of such tags include, but are not limited to, biotin, avidin, streptavidin, histidine tags, nickel tags, ferrous tags, non-ferrous tags, and the like. In some embodiments, one or more tags may be conjugated with a label to provide for detection of one or more complexes. Examples of such tag-label conjugates include, but are not limited to, Texas red conjugated avidin, alkaline phosphatase conjugated avidin, CY2 conjugated avidin, CY3 conjugated avidin, CY3.5 conjugated avidin, CY5 conjugated avidin, CY5.5 conjugated avidin, fluorescein conjugated avidin, glucose oxidase conjugated avidin, peroxidase conjugated avidin, rhodamine conjugated avidin, agarose conjugated anti-protein A, alkaline phosphatase conjugated protein A, anti-protein A, fluorescein conjugated protein A, IRDye® 800 conjugated protein A, peroxidase conjugated protein A, sepharose protein A, alkaline phosphatase conjugated streptavidin, AMCA conjugated streptavidin, anti-streptavidin (*Streptomyces avidinii*) (rabbit) IgG Fraction, beta-galactosidase conjugated streptavidin, CY2 conjugated streptavidin, CY3 conjugated streptavidin, CY3.5 conjugated streptavidin, CY5 conjugated streptavidin, CY5.5 conjugated streptavidin, fluorescein conjugated streptavidin, IRDye® 700DX conjugated streptavidin, IRDye® 800 conjugated streptavidin, IRDye® 800CW conjugated streptavidin, peroxidase conjugated streptavidin, phycoerythrin conjugated streptavidin, rhodamine conjugated streptavidin, Texas red conjugated streptavidin, alkaline phosphatase conjugated biotin, anti-biotin (rabbit) IgG fraction, beta-galactosidase conjugated biotin, glucose oxidase conjugated biotin, peroxidase conjugated biotin, alkaline phosphatase conjugated protein G, anti-protein G (rabbit) Agarose conjugated, anti-protein G (Rabbit) IgG fraction, fluorescein conjugated protein G, IRDye® 800 conjugated protein G, peroxidase conjugated protein G, and the like. Many such labeled tags are commercially available (e.g., Rockland Immunochemicals, Inc., Gilbertsville, Pa.). Such labels may also be used in association with other methods to process and detect one or more allergen indicators 106. Aptamer binding constituents may be mixed with an aptamer-allergen indicator 106 complex such that the aptamer binding constituent binds to the aptamer-allergen indicator 106 complex and provides for separation of the aptamer-allergen indicator 106 complex. In some embodiments, the aptamer binding constituent may include a tag that allows the aptamer binding constituent and complexes that include the aptamer binding constituent to be separated from other components in one or more samples 102. In some embodiments, the aptamer binding constituent may include a ferrous material. Accordingly, aptamer-allergen indicator 106 complexes may be separated from other sample 102 components through use of a magnet, such as an electromagnet. In some embodiments, an aptamer binding constituent may include a non-ferrous metal. Accordingly, aptamer-allergen indicator 106 complexes may be separated from other sample 102 components through use of an eddy current to direct movement of one or more aptamer-allergen indicator 106 complexes. In some embodiments, two or more forms of aptamer binding constituents may be used to detect one or more allergen indicators 106. For example, in some embodiments, a first aptamer binding constituent may be coupled to a ferrous material and a second aptamer binding constituent may be coupled to a non-ferrous material. Accordingly, the first aptamer binding constituent and the second aptamer binding constituent may be mixed with aptamer-allergen indicator 106 complexes such that the first aptamer binding constituent and the second aptamer binding constituent bind to aptamer-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more aptamers that bind to one or more allergen indicators 106 to form one or more aptamer-allergen indicator 106 complexes. In some embodiments, the one or more aptamer may include one or more tags that provide for separation of the aptamer-allergen indicator 106 complexes. For example, in some embodiments, an aptamer may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with aptamer binding based methods. In some embodiments, antibodies may be used in combination with aptamers or in place of aptamers.

In some embodiments, one or more allergen indicators 106 may be detected through use of electrophoresis. In some embodiments, one or more microfluidic chips 108 may be configured to process one or more samples 102 through use of electrophoresis. In some embodiments, such microfluidic chips 108 may be configured to operably associate with one or more detection units 122. Accordingly, in some embodiments, one or more detection units 122 may be configured to operably associate with one or more microfluidic chips 108 and detect one or more allergen indicators 106 that were processed through use of electrophoresis. Numerous electrophoretic methods may be utilized to provide for detection of one or more allergen indicators 106. Examples of such electrophoretic methods include, but are not limited to, capillary electrophoresis, one-dimensional electrophoresis, two-dimensional electrophoresis, native electrophoresis, denaturing electrophoresis, polyacrylamide gel electrophoresis, agarose gel electrophoresis, and the like. Numerous detection methods may be used in combination with one or more electrophoretic methods to detect one or more allergen indicators 106. In some embodiments, one or more allergen indicators 106 may be detected according to the position to which the one or more allergen indicators 106 migrate within an electrophoretic field (e.g., a capillary and/or a gel). In some embodiments, the position of one or more allergen indicators 106 may be compared to one or more standards. For example, in some embodiments, one or more samples 102 may be mixed with one or more molecular weight markers prior to gel electrophoresis. The one or more samples 102, that include the one or more molecular weight markers, may be subjected to electrophoresis and then the gel may be stained. In such embodiments, the molecular weight markers may be used as a reference to detect one or more allergen indicators 106 present within the one or more samples 102. In some embodiments, one or more components that are known to be present within one or more samples 102 may be used as a reference to detect one or more allergen indicators 106 present within the one or more samples 102. In some embodiments, gel shift assays may be used to detect one or more allergen indicators 106. For example, in some embodiments, a sample 102 (e.g., a single sample 102 or combination of multiple samples 102) may be split into a first sample 102 and a second sample 102. The first sample 102 may be mixed with an antibody, aptamer, ligand, or other molecule and/or complex that binds to the one or more allergen indicators 106. The first and second samples 102 may then be subjected to electrophoresis. The gels corresponding to the first sample 102 and the second sample 102 may then be analyzed to determine if one or more allergen indicators 106 are present within the one or more samples 102. Microfluidic chips 108 and detection units 122 may be configured in numerous ways to process and detect one or more allergen indicators 106 through use of electrophoresis.

In some embodiments, one or more allergen indicators 106 may be detected through use of one or more charge-coupled device (CCD) cameras. In some embodiments, one or more detection units 122 that include one or more CCD cameras may be configured to operably associate with one or more microfluidic chips 108. Such detection units 122 may be utilized in combination with numerous processing methods. Examples of such methods include, but are not limited to, electrophoresis; competition assays; methods based on polynucleotide interaction, protein interaction, peptide interaction, antibody interaction, aptamer interaction, immunoprecipitation, immunoseparation, and the like. For example, in some embodiments, one or more microfluidic chips 108 may be configured to process one or more samples 102 through use of immunoprecipitation. In some embodiments, one or more antibodies may be conjugated to a fluorescent label such that binding of one or more labeled antibodies to one or more allergen indicators 106 included within one or more samples 102 will form a fluorescently labeled antibody-allergen indicator 106 complex. One or more insoluble allergen indicator 106 binding constituents, such as a sepharose bead that includes an antibody or aptamer that binds to the one or more allergen indicators 106, may be bound to the fluorescently labeled antibody-allergen indicator 106 complex and used to precipitate the complex. One or more detection units 122 that include a CCD camera that is configured to detect fluorescent emission from the one or more fluorescent labels may be used to detect the one or more allergen indicators 106. In some embodiments, one or more CCD cameras may be configured to utilize dark frame subtraction to cancel background and increase sensitivity of the camera. In some embodiments, one or more detection units 122 may include one or more filters to select and/or filter wavelengths of energy that can be detected by one or more CCD cameras (e.g., U.S. Pat. No. 3,971,065; herein incorporated by reference). In some embodiments, one or more detection units 122 may include polarized lenses. One or more detection units 122 may be configured in numerous ways to utilize one or more CCD cameras to detect one or more allergen indicators 106.

In some embodiments, one or more allergen indicators 106 may be detected through use of immunoassay. In some embodiments, one or more microfluidic chips 108 may be configured to process one or more samples 102 through use of immunoassay. In some embodiments, one or more detection units 122 may be configured to operably associate with one or more such microfluidic chips 108 and to detect one or more allergen indicators 106 associated with the use of immunoassay. Numerous types of detection methods may be used in combination with immunoassay based methods. In some embodiments, a label may be used within one or more immunoassays that may be detected by one or more detection units 122. Examples of such labels include, but are not limited to, fluorescent labels, spin labels, fluorescence resonance energy transfer labels, radiolabels, electrochemiluminescent labels (e.g., U.S. Pat. Nos. 5,093,268; 6,090,545; herein incorporated by reference), and the like. In some embodiments, electrical conductivity may be used in combination with immunoassay based methods.

At operation 1310, the detecting operation 930 may include detecting the one or more allergen indicators that include one or more allergen associated polynucleotides. In some embodiments, one or more detection units 122 may be used to detect one or more allergen indicators 106 that include one or more allergen associated polynucleotides. Examples of such allergen indicator 106 associated polynucleotides include, but are not limited to, polynucleotides and/or portions of one or more polynucleotides that have a nucleic acid sequence and/or that encode an amino acid sequence that corresponds to, but is not limited to, one or more of the following accession numbers: AY894659, AY904434, AY904433, Y15210, AF529201, Y13271, AY049012, AY082337, AY082338, X85185, P82242, AY335187, S83343, X91256, Y08390, AF517686, AF517685, S45354, U25343, Z27084, X73363, S80654, X78813, X75925, Z27082, AF521563, X77583, AJ238848, S50892, M65179, X79267, X87153, S54819, P81531, AJ295617, AF441864, AF526295, P80741, P80740, U86342, P81430, AF078679, AF249675, AY082335, D29772, A1243570, P81294, AJ404653, P81295, P81825, P82817, P82967, AJ006774, AF277840, U59102, AF525465, U27479, U58106, SW:Q26456, D17686, AF178772, Y14906, AY189697, DQ354124, AF149827, AJ250278, AJ271058, AJ250096, AJ250279, Y12690, AY710432, L39834, M18780, X14712, M73993, S72946, A59491, U70823, X74045, X84842, AF238996, AY497902, SW:P83507, SW:P83508, U82633, U87807, U87808, X84217, X78222, U87806, U82437, X78225, AY191815, X78227, P2041, X84216, AY514673, X78223, X78226, X78224, AY191816, AY787775, X78228, X85180, M83781, S39330, U56938, U20722, AJ001732, Z30424, U53561, AJ223315, AJ224333, AJ223327, X85092, AJ002026, g3643813, AJ224865, AF284645, AF464911, AF108944, P34754, Z84377, X17561, D00434, M33218, AY786077, U64207, AF254643, AY363911, AY077706, AY077707, AY136739, J04984, J04985, AJ132235, AJ242791, AJ242792, AJ242793, AJ242794, AY547285, AB011804, AB011805, AF084828, X96486, AJ011955, AJ011956, AJ011957, AJ011958, AJ011959, AJ428052, AJ548421, AJ871960, SW:P83340, L12389, M33157, AY127579, AF260897, AY792950, Y14854, AJ012184, P02229, P02230, P02221, P02222, P02231, P02224, P02226, P02223, P02225, P02227, P02228, AF231352, PIR: A59396, AJ309202, P81656, P83377, P81657, X70256, S81785, AF179004, X97824, M18780, X14712, M73993, X60688, U08008, AF479772, Y14855, AJ315959, AJ414730, P80208, CAA46782, P81729, SW:P80198, PIR: A59156, AJ404845, X12928, P19656, AJ890020, U31771, Z48967, AF129423, P81943, AF456482, AF327622, AF329829, Q5ULZ4, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, X60043, AY792956, L34402, L77197, AF093541, AF086821, AF059616, AF092846, AF091737, AY328088, P00785, SW:P81370, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, AY839230, A59069, AF173004, Y19221, P83885, AJ697694, M15203, U42640, M36986, p02877, p02877, p02877, U80598, AJ223038, AJ132580, AY057860, P83269, Y14314, X80909, X89985, Y17711, P02538, AY894660, AY894661, AY894657, AY894658, AJ313166, AJ313167, AJ313168, X77414, X95867, X85012, X95865, X95866, Y15208, Y15209, S83343, AF177030, AF177378, AF177380, AF159703, Z27084, Z68893, M57474, M57476, X57678, L13083, M59163, Z27090, X78813, AJ512487, AJ512488, X74735, X70942, Z82986, AF061066, AF061067, AF061068, AF061069, Z27083, Z82985, PIR:S70327, PIR: S70328, X15877, Z80098, Z80099, X77200, X77265, X77266, X77270, X77267, X77268, X77274, X77269, X77271, X77272, X77273, X77599, X77600, X77601, X81972, X82028, Z72429, Z72432, Z72437, Z72430, Z72431, Z72433, Z72434, Z72435, Z72438, Z72436, Z80100, Z80101, Z80102, Z80103, Z80104, Z80105, Z80106, AF135127, AF282850, X66932, X66918, Z80159, Z80160, Z80161, Z80162, Z80163, Z80164, Z80165, Z80166, Z80167, Z80168, X66933, Z80169, Z80170, X70999, X71000, X70997, X70998, Z72439, Z72440, AF136945, AF323973, AF323974, AF323975, X77787, X77788, S75766, X76395, X76396, X76397, Y12428, Y12427, Y12426, X76541, X76539, X76540, D29772, D37765, AF257491, AF257492, AF257493, AF257494, AF257495, X65196, DQ185509, DQ185509, DQ185509, DQ185509, BAA01239, BAA01240, BAA01241, A61501, AAL47677, CAF33200, CAF33201, CAF33202, DQ185511, U11695, DQ185508, AF276239, DQ185510, AF047613, AF047614, AJ249864, AJ272216, X81399, X83876, X89014, AJ487972, X83875, AJ487973, L42867, A59225, B59225, P81216, P81217, U82633, U86752, AF072219, L47595, AF072221, AF072220, AF072222, U78970, U69957, U69261, U69260, L40818, L40820, L40819, L40821, Y14854, AF106961, AF395894, AF395893, Z48967, Z75662, U47087, D88388, Z81361, Z81362, Z84376, AF456481, AJ783335, swQ9S8F3, swQ9S8F2, AJ223982, AJ223981, AJ551424, AJ551425, AJ626897, AJ626898, AF465612, AF465613, AJ315844, DQ066728, DQ066727, DQ066731, DQ066729, DQ066730, DQ066732, CAA58646, JC4276, AAD26546, AAD26552, AAD26553, AAD26554, AAD26555, AAD29671, AAK13029, AAB01362, AAD26545, AAD26547, AAD26548, AAD26558, AAD13683, AAK13030, CAD32318, CAA96534, AAK13027, AAK13028, AAO25113, CAA96535, CAA96536, CAA96537, AF129428, AJ507459, AF129427, AJ507458, AF129426, AJ507457, U66076, AY540507, AY540508, AY540509, AJ491881, AJ491882, M36986, Y15042, AJ132397, AF 119365, AF119366, AF119367, AJ243325, L11707, AJ249148, AJ289158, AJ238579, AJ431363, or substantially any combination thereof.

At operation 1312, the detecting operation 930 may include detecting the one or more allergen indicators that include one or more allergen associated polypeptides. In some embodiments, one or more detection units 122 may be used to detect one or more allergen indicators 106 that include one or more allergen associated polypeptides. Examples of such allergen indicator 106 associated polypeptides include, but are not limited to, polypeptides and/or portions of one or more polypeptides that have an amino acid sequence that corresponds to, but is not limited to, and/or a polypeptide that is encoded by a nucleic acid sequence corresponding to one or more of the following accession numbers: AY894659, AY904434, AY904433, Y15210, AF529201, Y13271, AY049012, AY082337, AY082338, X85185, P82242, AY335187, S83343, X91256, Y08390, AF517686, AF517685, S45354, U25343, Z27084, X73363, S80654, X78813, X75925, Z27082, AF521563, X77583, AJ238848, S50892, M65179, X79267, X87153, S54819, P81531, AJ295617, AF441864, AF526295, P80741, P80740, U86342, P81430, AF078679, AF249675, AY082335, D29772, A1243570, P81294, AJ404653, P81295, P81825, P82817, P82967, AJ006774, AF277840, U59102, AF525465, U27479, U58106, SW:Q26456, D17686, AF178772, Y14906, AY189697, DQ354124, AF149827, AJ250278, AJ271058, AJ250096, AJ250279, Y12690, AY710432, L39834, M18780, X14712, M73993, S72946, A59491, U70823, X74045, X84842, AF238996, AY497902, SW:P83507, SW:P83508, U82633, U87807, U87808, X84217, X78222, U87806, U82437, X78225, AY191815, X78227, P2041, X84216, AY514673, X78223, X78226, X78224, AY191816, AY787775, X78228, X85180, M83781, S39330, U56938, U20722, AJ001732, Z30424, U53561, AJ223315, AJ224333, AJ223327, X85092, AJ002026, g3643813, AJ224865, AF284645, AF464911, AF108944, P34754, Z84377, X17561, D00434, M33218, AY786077, U64207, AF254643, AY363911, AY077706, AY077707, AY136739, J04984, J04985, AJ132235, AJ242791, AJ242792, AJ242793, AJ242794, AY547285, AB011804, AB011805, AF084828, X96486, AJ011955, AJ011956, AJ011957, AJ011958, AJ011959, AJ428052, AJ548421, AJ871960, SW:P83340, L12389, M33157, AY127579, AF260897, AY792950, Y14854, AJ012184, P02229, P02230, P02221, P02222, P02231, P02224, P02226, P02223, P02225, P02227, P02228, AF231352, PIR:A59396, AJ309202, P81656, P83377, P81657, X70256, S81785, AF179004, X97824, M18780, X14712, M73993, X60688, U08008, AF479772, Y14855, AJ315959, AJ414730, P80208, CAA46782, P81729, SW:P80198, PIR:A59156, AJ404845, X12928, P19656, AJ890020, U31771, Z48967, AF129423, P81943, AF456482, AF327622, AF329829, Q5ULZ4, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, X60043, AY792956, L34402, L77197, AF093541, AF086821, AF059616, AF092846, AF091737, AY328088, P00785, SW:P81370, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, AY839230, A59069, AF173004, Y19221, P83885, AJ697694, M15203, U42640, M36986, p02877, p02877, p02877, U80598, AJ223038, AJ132580, AY057860, P83269, Y14314, X80909, X89985, Y17711, P02538, AY894660, AY894661, AY894657, AY894658, AJ313166, AJ313167, AJ313168, X77414, X95867, X85012, X95865, X95866, Y15208, Y15209, S83343, AF177030, AF177378, AF177380, AF159703, Z27084, Z68893, M57474, M57476, X57678, L13083, M59163, Z27090, X78813, AJ512487, AJ512488, X74735, X70942, Z82986, AF061066, AF061067, AF061068, AF061069, Z27083, Z82985, PIR:S70327, PIR:S70328, X15877, Z80098, Z80099, X77200, X77265, X77266, X77270, X77267, X77268, X77274, X77269, X77271, X77272, X77273, X77599, X77600, X77601, X81972, X82028, Z72429, Z72432, Z72437, Z72430, Z72431, Z72433, Z72434, Z72435, Z72438, Z72436, Z80100, Z80101, Z80102, Z80103, Z80104, Z80105, Z80106, AF135127, AF282850, X66932, X66918, Z80159, Z80160, Z80161, Z80162, Z80163, Z80164, Z80165, Z80166, Z80167, Z80168, X66933, Z80169, Z80170, X70999, X71000, X70997, X70998, Z72439, Z72440, AF136945, AF323973, AF323974, AF323975, X77787, X77788, S75766, X76395, X76396, X76397, Y12428, Y12427, Y12426, X76541, X76539, X76540, D29772, D37765, AF257491, AF257492, AF257493, AF257494, AF257495, X65196, DQ185509, DQ185509, DQ185509, DQ185509, BAA01239, BAA01240, BAA01241, A61501, AAL47677, CAF33200, CAF33201, CAF33202, DQ185511, U11695, DQ185508, AF276239, DQ185510, AF047613, AF047614, AJ249864, AJ272216, X81399, X83876, X89014, AJ487972, X83875, AJ487973, L42867, A59225, B59225, P81216, P81217, U82633, U86752, AF072219, L47595, AF072221, AF072220, AF072222, U78970, U69957, U69261, U69260, L40818, L40820, L40819, L40821, Y14854, AF106961, AF395894, AF395893, Z48967, Z75662, U47087, D88388, Z81361, Z81362, Z84376, AF456481, AJ783335, swQ9S8F3, swQ9S8F2, AJ223982, AJ223981, AJ551424, AJ551425, AJ626897, AJ626898, AF465612, AF465613, AJ315844, DQ066728, DQ066727, DQ066731, DQ066729, DQ066730, DQ066732, CAA58646, JC4276, AAD26546, AAD26552, AAD26553, AAD26554, AAD26555, AAD29671, AAK13029, AAB01362, AAD26545, AAD26547, AAD26548, AAD26558, AAD13683, AAK13030, CAD32318, CAA96534, AAK13027, AAK13028, AA025113, CAA96535, CAA96536, CAA96537, AF129428, AJ507459, AF129427, AJ507458, AF129426, AJ507457, U66076, AY540507, AY540508, AY540509, AJ491881, AJ491882, M36986, Y15042, AJ132397, AF119365, AF119366, AF119367, AJ243325, L11707, AJ249148, AJ289158, AJ238579, AJ431363, or substantially any combination thereof.

At operation 1314, the detecting operation 930 may include detecting the one or more allergen indicators with one or more detection units that are calibrated for use with an individual. In some embodiments, one or more detection units 122 that are calibrated for use with an individual may be used to detect the one or more allergen indicators 106. In some embodiments, one or more detection units 122 may be calibrated to detect one or more specific allergens 104 and/or allergen indicators 106 that produce an allergic response by an individual. For example, in some embodiments, one or more detection units 122 may be calibrated to detect peanuts and/or peanut associated products for an individual who is allergic to peanuts. In some embodiments, one or more detection units 122 may be calibrated to detect different concentrations of allergen indicators 106. For example, in some embodiments, an individual may produce an allergic response if exposed to an allergen 104 at a concentration that is above a certain level. Accordingly, in some embodiments, a detection unit 122 may be calibrated to detect one or more concentrations of one or more allergen indicators 106 that produce an allergic response within an individual.

Figure 14:
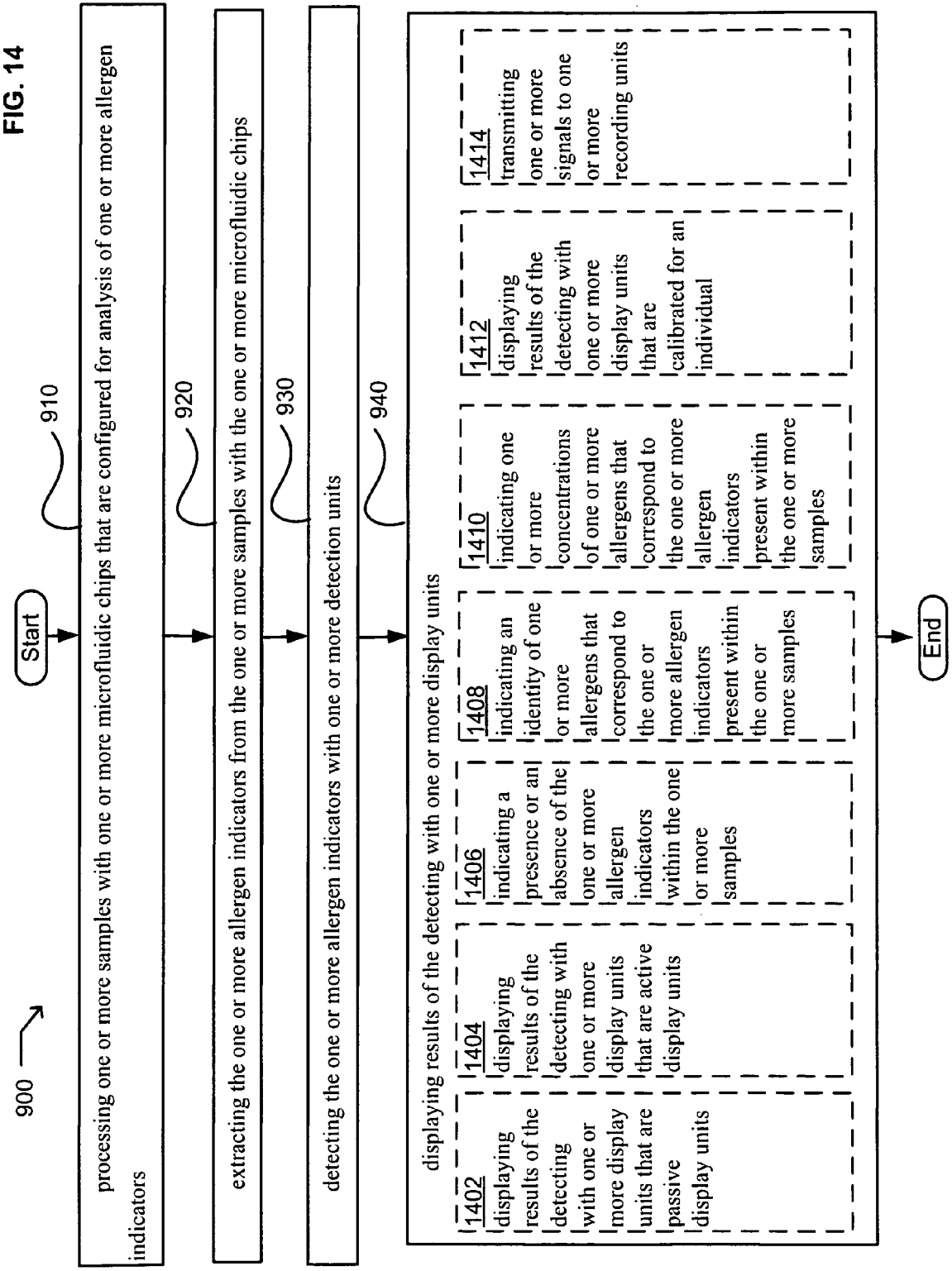
FIG. 14 illustrates alternate embodiments of the example operational flow of FIG. 9.

FIG. 14 illustrates alternative embodiments of the example operational flow 900 of FIG. 9. FIG. 14 illustrates example embodiments where the displaying operation 940 may include at least one additional operation. Additional operations may include an operation 1402, an operation 1404, an operation 1406, an operation 1408, an operation 1410, an operation 1412, and/or an operation 1414.

At operation 1402, the displaying operation 940 may include displaying results of the detecting with one or more display units that are passive display units. In some embodiments, one or more display units 124 may display results of the detecting with one or more display units 124 that are passive display units 124. In some embodiments, one or more display units 124 may include one or more liquid crystal displays (LCD). Methods to construct passive displays have been described (e.g., U.S. Pat. Nos. 4,807,967; 4,729,636: 4,436,378; 4,257,041; herein incorporated by reference).

At operation 1404, the displaying operation 940 may include displaying results of the detecting with one or more display units that are active display units. In some embodiments, one or more display units 124 may display results of the detecting with one or more display units 124 that are active display units 124. Numerous active display units 124 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), wide ultra extended graphics array (WUXGA).

At operation 1406, the displaying operation 940 may include indicating a presence or an absence of the one or more allergen indicators within the one or more samples. In some embodiments, one or more display units 124 may indicate a presence or an absence of the one or more allergen indicators 106 within the one or more samples 102. In some embodiments, one or more display units 124 may use a colorimetric message to indicate a presence or an absence of one or more allergen indicators 106 within one or more samples 102. For example, in some embodiments, one or more display units 124 may display a green light if one or more allergen indicators 106 are not found within one or more samples 102 and a red light if one or more allergen indicators 106 are found within one or more samples 102. In some embodiments, one or more display units 124 may use a pictographic message to indicate a presence or an absence of one or more allergen indicators 106 within one or more samples 102. For example, in some embodiments, one or more display units 124 may display a smiley face if one or more allergen indicators 106 are not found within one or more samples 102 and a frowny face if one or more allergen indicators 106 are found within one or more samples 102. In some embodiments, one or more display units 124 may use a typographical message to indicate a presence or an absence of one or more allergen indicators 106 within one or more samples 102. For example, in some embodiments, one or more display units 124 may display an "Allergen Not Present" message if one or more allergen indicators 106 are not found within one or more samples 102 and an "Allergen Present" message if one or more allergen indicators 106 are found within one or more samples 102. Such messages may be displayed in numerous languages. In some embodiments, one or more display units 124 may display one or more messages in multiple formats. For example, in some embodiments, one or more messages may be displayed in colored text.

At operation 1408, the displaying operation 940 may include indicating an identity of one or more allergens that correspond to the one or more allergen indicators present within the one or more samples. In some embodiments, one or more display units 124 may indicate an identity of one or more allergens 104 that correspond to the one or more allergen indicators 106 present within the one or more samples 102. In some embodiments, one or more display units 124 may be operably associated with one or more microfluidic chips 108 that are configured to identify one or more allergen indicators 106. Accordingly, in some embodiments, one or more display units 124 may be configured to display the identity of one or more allergens 104 that are present and/or absent from one or more samples 102. For example, in some embodiments, a display unit 124 may be configured to indicate a presence or an absence of beta-lactoglobulin in a food product.

At operation 1410, the displaying operation 940 may include indicating one or more concentrations of one or more allergens that correspond to the one or more allergen indicators present within the one or more samples. In some embodiments, one or more display units 124 may indicate one or more concentrations of one or more allergens 104 that correspond to the one or more allergen indicators 106 present within the one or more samples 102. Concentration may be displayed in numerous formats. For example, in some embodiments, concentration may be expressed numerically (e.g., mass allergen indicator 106 per volume sample 102 (e.g., milligrams per milliliter), mass allergen indicator 106 per mass sample 102 (e.g., milligrams per milligram of sample), parts per million, and the like). In some embodiments, concentration may be expressed graphically. For example, in some embodiments, one or more display units 124 may include a display having a gray scale on which the concentration of one or more allergen indicators 106 that are present within one or more samples 102 may be indicated (e.g., higher concentrations of one or more allergens 104 may be displayed as dark gray while lower concentrations of one or more allergens 104 may be displayed as light gray). In some embodiments, one or more display units 124 may include a display having a color scale on which the concentration of one or more allergen indicators 106 that are present within one or more samples 102 may be indicated (e.g., low concentrations of one or more allergen indicators 106 may be indicated by a green light, intermediate concentrations of one or more allergen indicators 106 may be indicated by a yellow light, high concentrations of one or more allergen indicators 106 may be indicated by a red light). In some embodiments, one or more display units 124 may be calibrated to an individual. For example, in such embodiments, an individual may use the display to obtain an immediate reading that will indicate if a food product contains a dangerous level of one or more allergens 104.

At operation 1412, the displaying operation 940 may include displaying results of the detecting with one or more display units that are calibrated for an individual. In some embodiments, one or more display units 124 that are calibrated for an individual may display the results of the detecting. In some embodiments, one or more display units 124 may be calibrated to display whether one or more allergens 104, and/or allergen indicators 106, that are specific to an individual are present or absent within one or more samples 102. For example, in some embodiments, one or more display units 124 may be configured to display whether one or more samples 102 contain shellfish associated allergens 104 for an individual known to be allergic to shellfish. In some embodiments, one or more display units 124 may be calibrated to indicate safe and/or unsafe concentrations of one or more allergens 104 within one or more samples 102 for an individual.

At operation 1414, the displaying operation 940 may include transmitting one or more signals to one or more recording units. In some embodiments, one or more display units 124 may transmit one or more signals 132 to one or more recording units 126. In some embodiments, one or more signals 132 may be transmitted from one or more microfluidic chips 108, one or more reagent delivery units 116, one or more centrifugation units 118, one or more analysis units 120, one or more detection units 122, one or more display units 124, one or more user interfaces 128, and/or substantially any combination thereof. Numerous types of signals 132 may be transmitted. Examples of such signals 132 include, but are not limited to, hardwired signals 132, wireless signals 132, infrared signals 132, optical signals 132, radiofrequency (RF) signals 132, audible signals 132, digital signals 132, analog signals 132, and/or substantially any combination thereof. One or more signals 132 may include numerous types of information. For example, one or more signals 132 may include information with regard to the presence or an absence of one or more allergen indicators 106 within one or more samples 102, a type of reagent used to process one or more samples 102, conditions used to process one or more samples 102, an identity of a user 130, and the like. Such information may be recorded by one or more recording units 126.

II. Systems for Analysis of One of More Allergens

FIG. 15 illustrates a system 1500 representing examples of modules that may be used to perform a method for analysis of one or more allergens 104. In FIG. 15, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various modules are presented in the sequence(s) illustrated, it should be understood that the various modules may be configured in numerous orientations.

The system 1500 includes module 1510 that includes one or more microfluidic chips configured for analysis of one or more samples for one or more allergen indicators. In some embodiments, module 1510 may include one or more microfluidic chips configured for analysis of the one or more allergen indicators associated with one or more liquids. In some embodiments, module 1510 may include one or more microfluidic chips configured for analysis of the one or more allergen indicators associated with one or more solids. In some embodiments, module 1510 may include one or more microfluidic chips configured for analysis of the one or more allergen indicators associated with one or more gases. In some embodiments, module 1510 may include one or more microfluidic chips configured for analysis of the one or more allergen indicators associated with one or more airborne allergens. In some embodiments, module 1510 may include one or more microfluidic chips configured for analysis of the one or more allergen indicators associated with one or more food products. In some embodiments, module 1510 may include one or more microfluidic chips configured for analysis of the one or more allergen indicators associated with one or more weeds, grasses, trees, mites, animals, molds, fungi, insects, rubbers, metals, chemicals, autoallergens, or human autoallergens. In some embodiments, module 1510 may include one or more microfluidic chips configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay. In some embodiments, module 1510 may include one or more microfluidic chips configured for detachable connection to the one or more detection units.

The system 1500 also includes module 1520 that includes one or more detection units configured for detachable connection to the one or more microfluidic chips and configured to detect the one or more allergen indicators. In some embodiments, module 1520 may include one or more detection units configured to detect the one or more allergen indicators that are associated with one or more allergens that are airborne. In some embodiments, module 1520 may include one or more detection units configured to detect the one or more allergen indicators that are associated with one or more food products. In some embodiments, module 1520 may include one or more detection units configured to detect the one or more allergen indicators that are associated with one or more weeds, grasses, trees, mites, animals, molds, fungi, insects, rubbers, metals, chemicals, autoallergens, or human autoallergens. In some embodiments, module 1520 may include one or more detection units configured to detect the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, module 1520 may include one or more detection units that are calibrated for an individual.

The system 1500 may optionally include module 1530 that includes one or more display units operably associated with the one or more detection units. In some embodiments, module 1530 may include one or more display units that are passive display units. In some embodiments, module 1530 may include one or more display units that are active display units. In some embodiments, module 1530 may include one or more display units that indicate a presence or an absence of one or more allergens within the one or more samples. In some embodiments, module 1530 may include one or more display units that indicate an identity of one or more allergens present within the one or more samples. In some embodiments, module 1530 may include one or more display units that indicate one or more concentrations of one or more allergens within the one or more samples. In some embodiments, module 1530 may include one or more display units that are calibrated for an individual.

FIG. 16 illustrates alternative embodiments of system 1500 of FIG. 15. FIG. 16 illustrates example embodiments of module 1510. Additional embodiments may include an embodiment 1602, an embodiment 1604, an embodiment 1606, an embodiment 1608, and/or an embodiment 1610.

At embodiment 1602, module 1510 may include one or more microfluidic chips configured for analysis of the one or more allergen indicators associated with one or more liquids. In some embodiments, one or more microfluidic chips 108 may be configured for analysis of the one or more allergen indicators 106 associated with one or more liquids. Numerous types of liquids may be processed by one or more microfluidic chips 108. Examples of such liquids include, but are not limited to, beverages (e.g., water, soda, milk, milk substitutes, juice, wine, beer, and the like), environmental samples 102 (e.g., water samples 102, plant sap, plant nectar, suspended soil samples 102, suspended air filtrate samples 102, and the like), animal samples 102 (e.g., suspended dander samples 102, saliva, urine, excrement, suspended fur samples 102, and the like), food samples 102 (e.g., suspended food samples 102, extracted food samples 102, and the like), or substantially any combination thereof. In some embodiments, one or more liquids may include a solvent. In some embodiments, a liquid may include one or more solvents that may be used to extract one or more allergen indicators 106. For example, in some embodiments, one or more solvents may be used to extract one or more allergen indicators 106 from one or more samples 102.

At embodiment 1604, module 1510 may include one or more microfluidic chips configured for analysis of the one or more allergen indicators associated with one or more solids. In some embodiments, one or more microfluidic chips 108 may be configured for analysis of the one or more allergen indicators 106 associated with one or more solids. In some embodiments, one or more microfluidic chips 108 may be configured to provide for suspension of solids in a liquid. In some embodiments, one or more microfluidic chips 108 may be configured to provide for extraction of one or more samples 102 that include a solid with a solvent. In some embodiments, one or more microfluidic chips 108 may be configured to accept the one or more samples 102 into one or more microfluidic chips 108 where the samples 102 are resuspended in a liquid and/or extracted in a solvent. In some embodiments, one or more microfluidic chips 108 may include one or more sonicators, one or more mixers, one or more grinders, or substantially any combination thereof, to facilitate analysis of one or more allergen indicators 106 associated with one or more solids.

At embodiment 1606, module 1510 may include one or more microfluidic chips configured for analysis of the one or more allergen indicators associated with one or more gases. In some embodiments, one or more microfluidic chips 108 may be configured for analysis of the one or more allergen indicators 106 associated with one or more gases. For example, in some embodiments, one or more gases that are being analyzed may be passed through one or more microfluidic chips 108. In some embodiments, gas may be pumped through a microfluidic chip 108. In some embodiments, gas may be drawn through a microfluidic chip 108 through use of a vacuum. In some embodiments, gas may be passed through a filter on which suspected allergen indicators 106 are collected for analysis. Accordingly, large volumes of gas may be analyzed. In some embodiments, one or more gases may be analyzed for one or more allergen indicators 106 that include one or more metals. For example, gases may be analyzed for metals that are associated with tanks in which the gases are stored, such as iron, steel, aluminum, and the like.

At embodiment 1608, module 1510 may include one or more microfluidic chips configured for analysis of the one or more allergen indicators associated with one or more airborne allergens. In some embodiments, one or more microfluidic chips 108 may be configured for analysis of the one or more allergen indicators 106 associated with one or more airborne allergens 104. Examples of such airborne allergens 104 include, but are not limited to, pollen, dander, seeds, and the like. In some embodiments, the allergen indicators 106 may be collected within one or more microfluidic chips 108 through filtering air that is passed through the one or more microfluidic chips 108. Such filtering may occur through numerous mechanisms that may include, but are not limited to, use of physical filters, passing air through a fluid bubble chamber, passing the air through an electrostatic filter, and the like.

At embodiment 1610, module 1510 may include one or more microfluidic chips configured for analysis of the one or more allergen indicators associated with one or more food products. In some embodiments, one or more microfluidic chips 108 may be configured for analysis of the one or more allergen indicators 106 associated with one or more food products. Such allergen indicators 106 are described herein and are known. For example, in some embodiments, one or more microfluidic chips 108 may be configured to analyze one or more food products at a restaurant to facilitate detection of a presence or an absence of an allergen indicator 106 within the food product, such as a presence of one or more allergen indicators 106 associated with nuts, dairy products, crustaceans, eggs, gluten, soy, and the like. In some embodiments, one or more microfluidic chips 108 may be configured to analyze one or more polynucleotides, one or more polypeptides, one or more portions of one or more polynucleotides, and/or one or more portions of one or more polypeptides that have a nucleic acid sequence and/or an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, or AY839230. Accordingly, one or more microfluidic chips 108 may be configured to process numerous types of food products to facilitate detection of numerous types of allergen indicators 106.

FIG. 17 illustrates alternative embodiments of system 1500 of FIG. 15. FIG. 17 illustrates example embodiments of module 1510. Additional embodiments may include an embodiment 1702, an embodiment 1704, and/or an embodiment 1706.

At embodiment 1702, module 1510 may include one or more microfluidic chips configured for analysis of the one or more allergen indicators associated with one or more weeds, grasses, trees, mites, animals, molds, fungi, insects, rubbers, metals, chemicals, autoallergens, or human autoallergens. In some embodiments, one or more microfluidic chips 108 may be configured for analysis of the one or more allergen indicators 106 associated with one or more weeds, grasses, trees, mites, animals, molds, fungi, insects, rubbers, metals, chemicals, autoallergens, human autoallergens, or substantially any combination thereof. Such allergen indicators 106 are described herein and are known. For example, in some embodiments, one or more microfluidic chips 108 may be configured to process one or more material samples 102 to determine if the material contains latex.

At embodiment 1704, module 1510 may include one or more microfluidic chips configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay.

In some embodiments, one or more microfluidic chips 108 may be configured for analysis of the one or more allergen indicators 106 through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof. In some embodiments, allergen indicators 106 may be separated from other materials included within one or more samples 102 through processing.

In some embodiments, one or more microfluidic chips 108 may be configured to analyze one or more allergen indicators 106 through use of polynucleotide interaction. Numerous methods based on polynucleotide interaction may be used. Examples of such methods include, but are not limited to, those based on polynucleotide hybridization, polynucleotide ligation, polynucleotide amplification, polynucleotide degradation, and the like. Methods that utilize intercalation dyes, FRET analysis, capacitive DNA detection, and nucleic acid amplification have been described (e.g., U.S. Pat. Nos. 7,118, 910 and 6,960,437; herein incorporated by reference). In some embodiments, fluorescence resonance energy transfer, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube are combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Methods to utilize carbon nanotubes as probes for nucleic acid interaction have been described (e.g., U.S. Pat. No. 6,821,730; herein incorporated by reference).

In some embodiments, one or more microfluidic chips 108 may be configured to analyze one or more allergen indicators 106 through use of protein interaction. Numerous methods based on protein interaction may be used. In some embodiments, protein interaction may be used to immobilize one or more allergen indicators 106. In some embodiments, protein interaction may be used to separate one or more allergen indicators 106 from one or more samples 102. Examples of such methods include, but are not limited to, those based on ligand binding, protein-protein binding, protein cross-linking, use of green fluorescent protein, phage display, the two-hybrid system, protein arrays, fiber optic evanescent wave sensors, chromatographic techniques, fluorescence resonance energy transfer, regulation of pH to control protein assembly and/or oligomerization, and the like. For example, tropomyosin is a major muscle protein in crustaceans that is thought to be a major shrimp allergen 104. Tropomyosin is associated with the well known actin-troponin-myosin complex. Calcium ion binding to troponin enables troponin to bind tropomyosin and shift it from the binding sites of myosin on the actin proteins. Without the presence of Calcium ion, troponin is no longer able to bind to tropomyosin, and tropomyosin again blocks the binding sites of myosin on the actin proteins. Tropomyosin also binds to the calcium-binding protein calcyclin (Nelson et al., Molecular & Cellular Proteomics 1:253-259 (2002) and Liou and Chen, European Journal of Biochemistry, 270:3692-3100 (2003)). Accordingly, protein interactions may be used to separate tropomyosin (allergen indicator 106) from one or more samples 102. Similar methods may be used with numerous proteins. Methods that may be used to construct protein arrays have been described (e.g., Warren et al., Anal. Chem., 76:4082-4092 (2004) and Walter et al., Trends Mol. Med., 8:250-253 (2002), U.S. Pat. No. 6,780,582; herein incorporated by reference).

In some embodiments, one or more microfluidic chips 108 may be configured to analyze one or more samples 102 through use of peptide interaction. Peptides are generally described as being polypeptides that include less than one hundred amino acids. For example, peptides include dipeptides, tripeptides, and the like. In some embodiments, peptides may include from two to one hundred amino acids. In some embodiments, peptides may include from two to fifty amino acids. In some embodiments, peptides may include from two to one twenty amino acids. In some embodiments, peptides may include from ten to one hundred amino acids. In some embodiments, peptides may include from ten to fifty amino acids. Accordingly, peptides can include numerous numbers of amino acids. Numerous methods based on peptide interaction may be used. In some embodiments, peptide interaction may be used to immobilize one or more allergen indicators 106. In some embodiments, peptide interaction may be used to separate one or more allergen indicators 106 from one or more samples 102. Examples of such methods include, but are not limited to, those based on ligand binding, peptide-protein binding, peptide-peptide binding, peptide-polynucleotide binding, peptide cross-linking, use of green fluorescent protein, phage display, the two-hybrid system, protein arrays, peptide arrays, fiber optic evanescent wave sensors, chromatographic techniques, fluorescence resonance energy transfer, regulation of pH to control peptide and/or protein assembly and/or oligomerization, and the like. Accordingly, virtually any technique that may be used to analyze proteins may be utilized for the analysis of peptides. In some embodiments, high-speed capillary electrophoresis may be used to detect binding through use of fluorescently labeled phosphopeptides as affinity probes (Yang et al., Anal. Chem., 10.1021/ac061936e (2006)). Methods to immobilize proteins and peptides have been reported (Taylor, Protein Immobilization: Fundamentals and Applications, Marcel Dekker, Inc., New York (1991)).

In some embodiments, one or more microfluidic chips 108 may be configured to analyze one or more samples 102 through use of antibody interaction. Antibodies may be raised that will bind to numerous allergen indicators 106 through use of known methods (e.g., Harlow and Lane, Antibodies: A Laboratory Manual, Cold Spring Harbor Laboratory Press, Cold Spring Harbor, N.Y. (1988)). Antibodies may be configured in numerous ways within one or more microfluidic chips 108 to process one or more allergen indicators 106. For example, in some embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. A labeled detector antibody that binds to the allergen indicator 106 (or the antibody-allergen indicator 106 complex) may then be passed over the one or more antibody-allergen indicator 106 complexes such that the labeled detector antibody will label the allergen indicator 106 (or the antibody-allergen indicator 106 complex). Numerous labels may be used that include, but are not limited to, enzymes, fluorescent molecules, radioactive labels, spin labels, redox labels, and the like. In other embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. Such binding provides for detection of the antibody-allergen indicator 106 complex through use of methods that include, but are not limited to, surface plasmon resonance, conductivity, and the like (e.g., U.S. Pat. No. 7,030,989; herein incorporated by reference). In some embodiments, antibodies may be coupled to a substrate within a microfluidic chip 108 to provide for a competition assay. One or more samples 102 may be mixed with one or more reagent mixtures that include one or more labeled allergen indicators 106. The mixture may then be passed over the antibodies to facilitate binding of allergen indicators 106 in the sample 102 and labeled allergen indicators 106 in the reagent mixture to the antibodies. The unlabeled allergen indicators 106 in the sample 102 will compete with the labeled allergen indicators 106 in the reagent mixture for binding to the antibodies. Accordingly, the amount of label bound to the antibodies will vary in accordance with the concentration of unlabeled allergen indicators 106 in the sample 102. In some embodiments, antibody interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more antibodies may be used in conjunction with one or more aptamers to process one or more samples 102. Accordingly, in some embodiments, aptamers and antibodies may be used interchangeably to process one or more samples 102.

In some embodiments, one or more microfluidic chips 108 may be configured to analyze one or more samples 102 through use of chemical interaction. In some embodiments, one or more microfluidic chips 108 may be configured to utilize chemical extraction to process one or more samples 102. For example, in some embodiments, one or more samples 102 may be mixed with a reagent mixture that includes one or more solvents in which the one or more allergen indicators 106 are soluble. Accordingly, the solvent phase containing the one or more allergen indicators 106 may be separated from the sample phase to provide for detection of the one or more allergen indicators 106. In some embodiments, one or more samples 102 may be mixed with a reagent mixture that includes one or more chemicals that cause precipitation of one or more allergen indicators 106. Accordingly, the sample phase may be washed away from the one or more precipitated allergen indicators 106 to provide for detection of the one or more allergen indicators 106. Accordingly, reagent mixtures that include numerous types of chemicals that interact with one or more allergen indicators 106 may be used.

In some embodiments, one or more microfluidic chips 108 may be configured to analyze one or more samples 102 through use of diffusion. In some embodiments, one or more microfluidic chips 108 may be configured to process one or more fluid samples 102 through use of an H-filter. For example, a microfluidic chip 108 may be configured to include a channel through which a fluid sample 102 and a second fluid flow such that the fluid sample 102 and the second fluid undergo parallel flow through the channel without significant mixing of the sample fluid and the second fluid. As the fluid sample 102 and the second fluid flow through the channel, one or more allergen indicators 106 in the fluid sample 102 may diffuse through the fluid sample 102 into the second fluid. Accordingly, such diffusion provides for the separation of the one or more allergen indicators 106 from the sample 102. Methods to construct H-filters have been described (e.g., U.S. Pat. Nos. 6,742,661; 6,409,832; 6,007,775; 5,974,867; 5,971,158; 5,948,684; 5,932,100; 5,716,852; herein incorporated by reference). In some embodiments, diffusion based methods may be combined with immunoassay based methods to process and detect one or more allergen indicators 106. Methods to conduct microscale diffusion immunoassays have been described (e.g., U.S. Pat. No. 6,541,213; herein incorporated by reference). Accordingly, microfluidic chips 108 may be configured in numerous ways to process one or more allergen indicators 106 through use of diffusion.

In some embodiments, one or more microfluidic chips 108 may be configured to analyze one or more samples 102 through use of filtration. In some embodiments, one or more microfluidic chips 108 may be configured to include one or more filters that have a molecular weight cut-off. For example, a filter may allow molecules of low molecular weight to pass through the filter while disallowing molecules of high molecular weight to pass through the filter. Accordingly, one or more allergen indicators 106 that are contained within a sample 102 may be allowed to pass through a filter while larger molecules contained within the sample 102 are disallowed from passing through the filter. Accordingly, in some embodiments, a microfluidic chip 108 may include two or more filters that selectively retain, or allow passage, of one or more allergen indicators 106 through the filters. Such configurations provide for selective separation of one or more allergen indicators 106 from one or more samples 102. Membranes and filters having numerous molecular weight cut-offs are commercially available (e.g., Millipore, Billerica, Mass.). In some embodiments, one or more microfluidic chips 108 may be configured to provide for dialysis of one or more samples 102. For example, in some embodiments, a microfluidic chip 108 may be configured to contain one or more samples 102 in one or more sample chambers that are separated from one or more dialysis chambers by a semi-permeable membrane. Accordingly, in some embodiments, one or more allergen indicators 106 that are able to pass through the semi-permeable membrane may be collected in the dialysis chamber. In other embodiments, one or more allergen indicators 106 may be retained in the one or more sample chambers while other sample 102 components may be separated from the one or more allergen indicators 106 by their passage through the semi-permeable membrane into the dialysis chamber. Accordingly, one or more microfluidic chips 108 may be configured to include two or more dialysis chambers for selective separation of one or more allergen indicators 106 from one or more samples 102. Semi-permeable membranes and dialysis tubing is available from numerous commercial sources (e.g., Millipore, Billerica, Mass.; Pierce, Rockford, Ill.; Sigma-Aldrich, St. Louis, Mo.). Methods that may be used for microfiltration have been described (e.g., U.S. Pat. No. 5,922,210; herein incorporated by reference).

In some embodiments, one or more microfluidic chips 108 may be configured to analyze one or more samples 102 through use of chromatography. Numerous chromatographic methods may be used to process one or more samples 102. Examples of such chromatographic methods include, but are not limited to, ion-exchange chromatography, affinity chromatography, gel filtration chromatography, hydroxyapatite chromatography, gas chromatography, reverse phase chromatography, thin layer chromatography, capillary chromatography, size exclusion chromatography, hydrophobic interaction media, and the like. In some embodiments, a microfluidic chip 108 may be configured to process one or more samples 102 through use of one or more chromatographic methods. In some embodiments, chromatographic methods may be used to process one or more samples 102 for one or more allergen indicators 106 that include one or more polynucleotides. For example, in some embodiments, one or more samples 102 may be applied to a chromatographic media to which the one or more polynucleotides bind. The remaining components of the sample 102 may be washed from the chromatographic media. The one or more polynucleotides may then be eluted from chromatographic media in a more purified state. Similar methods may be used to process one or more samples 102 for one or more allergen indicators 106 that include one or more proteins or polypeptides (e.g., Mondal and Gupta, Biomol. Eng., 23:59-76 (2006)). Chromatography media able to separate numerous types of molecules is commercially available (e.g., Bio-Rad, Hercules, Calif.; Qiagen, Valencia, Calif.; Pfizer, New York, N.Y.; Millipore, Billerica, Mass.; GE Healthcare Bio-Sciences Corp., Piscataway, N.J.).

In some embodiments, one or more microfluidic chips 108 may be configured to analyze one or more samples 102 through use of aptamer interaction. In some embodiments, one or more aptamers may include polynucleotides (e.g., deoxyribonucleic acid; ribonucleic acid; and derivatives of polynucleotides that may include polynucleotides that include modified bases, polynucleotides in which the phosphodiester bond is replaced by a different type of bond, or many other types of modified polynucleotides). In some embodiments, one or more aptamers may include peptide aptamers. Methods to prepare and use aptamers have been described (e.g., Collett et al., Methods, 37:4-15 (2005); Collet et al., Anal. Biochem., 338:113-123 (2005); Cox et al., Nucleic Acids Res., 30:20 e108 (2002); Kirby et al., Anal. Chem., 76:4066-4075 (2004); Ulrich, Handb. Exp. Pharmacol., 173:305-326 (2006); Baines and Colas, Drug Discovery Today, 11:334-341 (2006); Guthrie et al., Methods, 38:324-330 (2006); Geyer et al., Chapter 13: Selection of Genetic Agents from Random Peptide Aptamer Expression Libraries, Methods in Enzymology, Academic Press, pg. 171-208 (2000); U.S. Pat. No. 6,569,630; herein incorporated by reference). Aptamers may be configured in numerous ways within one or more microfluidic chips 108 to process one or more allergen indicators 106. For example, in some embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Labeled detector antibodies and/or aptamers that bind to the allergen indicator 106 (or the aptamer-allergen indicator 106 complex) may then be passed over the one or more aptamer-allergen indicator 106 complexes such that the labeled detector antibodies and/or aptamers will label the allergen indicator 106 (or the aptamer-allergen indicator 106 complex). Numerous labels may be used that include, but are not limited to, enzymes, fluorescent molecules, radioactive labels, spin labels, redox labels, and the like. In other embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Such binding provides for detection of the aptamer-allergen indicator 106 complex through use of methods that include, but are not limited to, surface plasmon resonance, conductivity, and the like (e.g., U.S. Pat. No. 7,030,989; herein incorporated by reference). In some embodiments, aptamers may be coupled to a substrate within a microfluidic chip 108 to provide for a competition assay. One or more samples 102 may be mixed with one or more reagent mixtures that include one or more labeled allergen indicators 106. The mixture may then be passed over the aptamers to facilitate binding of allergen indicators 106 in the sample 102 and labeled allergen indicators 106 in the reagent mixture to the aptamers. The unlabeled allergen indicators 106 in the sample 102 will compete with the labeled allergen indicators 106 in the reagent mixture for binding to the aptamers. Accordingly, the amount of label bound to the aptamers will vary in accordance with the concentration of unlabeled allergen indicators 106 in the sample 102. In some embodiments, aptamer interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more aptamers may be used in conjunction with one or more antibodies to process one or more samples 102. In some embodiments, aptamers and antibodies may be used interchangeably to process one or more samples 102. Accordingly, in some embodiments, methods and/or systems for processing and/or detecting allergen indicators 106 may utilize antibodies and aptamers interchangeably and/or in combination.

In some embodiments, one or more microfluidic chips 108 may be configured to analyze one or more samples 102 through use of electrical conductivity. In some embodiments, one or more samples 102 may be processed though use of magnetism. For example, in some embodiments, one or more samples 102 may be combined with one or more tagged polynucleotides that are tagged with a ferrous material, such as a ferrous bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed over an electromagnet to immobilize the hybridized complexes. Other components in the sample 102 may then be washed away from the hybridized complexes. In some embodiments, a chamber containing the magnetically immobilized hybridized complexes may be heated to release the sample polynucleotides from the magnetically immobilized tagged polynucleotides. The sample polynucleotides may then be collected in a more purified state. In other embodiments, similar methods may be used in conjunction with antibodies, aptamers, peptides, ligands, and the like. Accordingly, one or more microfluidic chips 108 may be configured in numerous ways to utilize magnetism to process one or more samples 102. In some embodiments, one or more samples 102 may be processed though use of eddy currents. Eddy current separation uses the principles of electromagnetic induction in conducting materials to separate non-ferrous metals by their different electric conductivities. An electrical charge is induced into a conductor by changes in magnetic flux cutting through it. Moving permanent magnets passing a conductor generates the change in magnetic flux. Accordingly, in some embodiments, one or more microfluidic chips 108 may be configured to include a magnetic rotor such that when conducting particles move through the changing flux of the magnetic rotor, a spiraling current and resulting magnetic field are induced. The magnetic field of the conducting particles may interact with the magnetic field of the magnetic rotor to impart kinetic energy to the conducting particles. The kinetic energy imparted to the conducting particles may then be used to direct movement of the conducting particles. Accordingly, non-ferrous particles, such as metallic beads, may be utilized to process one or more samples 102. For example, in some embodiments, one or more samples 102 may be combined with one or more tagged polynucleotides that are tagged with a non-ferrous material, such as an aluminum bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed through a magnetic field to impart kinetic energy to the non-ferrous bead. This kinetic energy may then be used to separate the hybridized complex. In other embodiments, similar methods may be used in conjunction with antibodies, aptamers, peptides, ligands, and the like. Accordingly, one or more microfluidic chips 108 may be configured in numerous ways to utilize eddy currents to process one or more samples 102. One or more microfluidic chips 108 may be configured in numerous ways to utilize electrical conductivity to process one or more samples 102.

In some embodiments, one or more microfluidic chips 108 may be configured to analyze one or more samples 102 through use of isoelectric focusing. Methods have been described that may be used to construct capillary isoelectric focusing systems (e.g., Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). Such systems may be modified to provide for the processing of one or more samples 102.

In some embodiments, one or more microfluidic chips 108 may be configured to analyze one or more samples 102 through use of electrophoresis. In some embodiments, one or more microfluidic chips 108 may be configured to process one or more samples 102 through use of one-dimensional electrophoresis. In some embodiments, one or more microfluidic chips 108 may be configured to process one or more samples 102 through use of two-dimensional electrophoresis. In some embodiments, one or more microfluidic chips 108 may be configured to process one or more samples 102 through use of gradient gel electrophoresis. In some embodiments, one or more microfluidic chips 108 may be configured to process one or more samples 102 through use electrophoresis under denaturing conditions. In some embodiments, one or more microfluidic chips 108 may be configured to process one or more samples 102 through use electrophoresis under native conditions. One or more microfluidic chips 108 may be configured to utilize numerous electrophoretic methods.

In some embodiments, one or more microfluidic chips 108 may be configured to analyze one or more samples 102 through use of immunoassay. In some embodiments, one or more microfluidic chips 108 may be configured to process one or more samples 102 through use of enzyme linked immunosorbant assay (ELISA). In some embodiments, one or more microfluidic chips 108 may be configured to process one or more samples 102 through use of radioimmuno assay (RIA). In some embodiments, one or more microfluidic chips 108 may be configured to process one or more samples 102 through use of enzyme immunoassay (EIA). In some embodiments, such methods may utilize antibodies (e.g., monoclonal antibodies, polyclonal antibodies, antibody fragments, single-chain antibodies, and the like), aptamers, or substantially any combination thereof. In some embodiments, a labeled antibody and/or aptamer may be used within an immunoassay. In some embodiments, a labeled ligand to which the antibody and/or aptamer binds may be used within an immunoassay. Numerous types of labels may be utilized. Examples of such labels include, but are not limited to, radioactive labels, fluorescent labels, enzyme labels, spin labels, magnetic labels, gold labels, colorimetric labels, redox labels, and the like. Numerous immunoassays are known and may be configured for processing one or more samples 102.

In some embodiments, one or more microfluidic chips 108 may be configured to analyze one or more samples 102 through use of one or more competition assays. In some embodiments, one or more microfluidic chips 108 may be configured to process one or more samples 102 through use of one or more polynucleotide based competition assays. One or more microfluidic chips 108 may be configured to include one or more polynucleotides coupled to a substrate, such as a polynucleotide array. The one or more microfluidic chips 108 may be further configured so that a sample 102 and/or substantially purified polynucleotides obtained from one or more samples 102, may be mixed with one or more reagent mixtures that include one or more labeled polynucleotides to form an analysis mixture. This analysis mixture is then passed over the substrate such that the labeled polynucleotides and the sample polynucleotides are allowed to hybridize to the polynucleotides that are immobilized on the substrate. The sample polynucleotides and the labeled polynucleotides will compete for binding to the polynucleotides that are coupled on the substrate. Accordingly, the presence and/or concentration of the polynucleotides in the sample 102 can be determined through detection of the label (e.g., the concentration of the polynucleotides in the sample 102 will be inversely related to the amount of label that is bound to the substrate). Numerous labels may be used that include, but are not limited to, enzymes, fluorescent molecules, radioactive labels, spin labels, redox labels, and the like. In some embodiments, one or more microfluidic chips 108 may be configured to include one or more antibodies, proteins, peptides, and/or aptamers that are coupled to a substrate. The one or more microfluidic chips 108 may be further configured so that a sample 102 and/or substantially purified sample polypeptides and/or sample peptides obtained from one or more samples 102, may be mixed with one or more reagent mixtures that include one or more labeled polypeptides and/or labeled peptides to form an analysis mixture. This analysis mixture can then be passed over the substrate such that the labeled polypeptides and/or labeled peptides and the sample polypeptides and/or sample peptides are allowed to bind to the antibodies, proteins, peptides, and/or aptamers that are immobilized on the substrate. The sample polypeptides and/or sample peptides and the labeled polypeptides and/or sample peptides will compete for binding to the antibodies, proteins, peptides, and/or aptamers that are coupled on the substrate. Accordingly, the presence and/or concentration of the sample polypeptides and/or sample peptides in the sample 102 can be determined through detection of the label (e.g., the concentration of the sample polypeptides and/or sample peptides in the sample 102 will be inversely related to the amount of label that is bound to the substrate). Numerous labels may be used that include, but are not limited to, enzymes, fluorescent molecules, radioactive labels, spin labels, redox labels, and the like. Microfluidic chips 108 may be configured to utilize numerous types of competition assays.

In some embodiments, one or more microfluidic chips 108 may be configured to utilize numerous analysis methods.

At embodiment 1706, module 1510 may include one or more microfluidic chips configured for detachable connection to the one or more detection units. In some embodiments, one or more microfluidic chips 108 may be configured to detachably connect to the one or more detection units 122. Accordingly, in some embodiments, one or more detection units 122 may be configured to detachably connect to microfluidic chips 108 having different configurations. For example, in some embodiments, a detection unit 122 may detachably connect to a first microfluidic chip 108 that is configured to process and/or analyze one or more food associated allergen indicators 106 and to a second microfluidic chip 108 that is configured to process and/or analyze one or more airborne allergen indicators 106. Accordingly, in some embodiments, the same detection unit 122 may be utilized with microfluidic chips 108 that are configured to process and/or analyze numerous types of samples 102 and allergen indicators 106.

Figure 18:
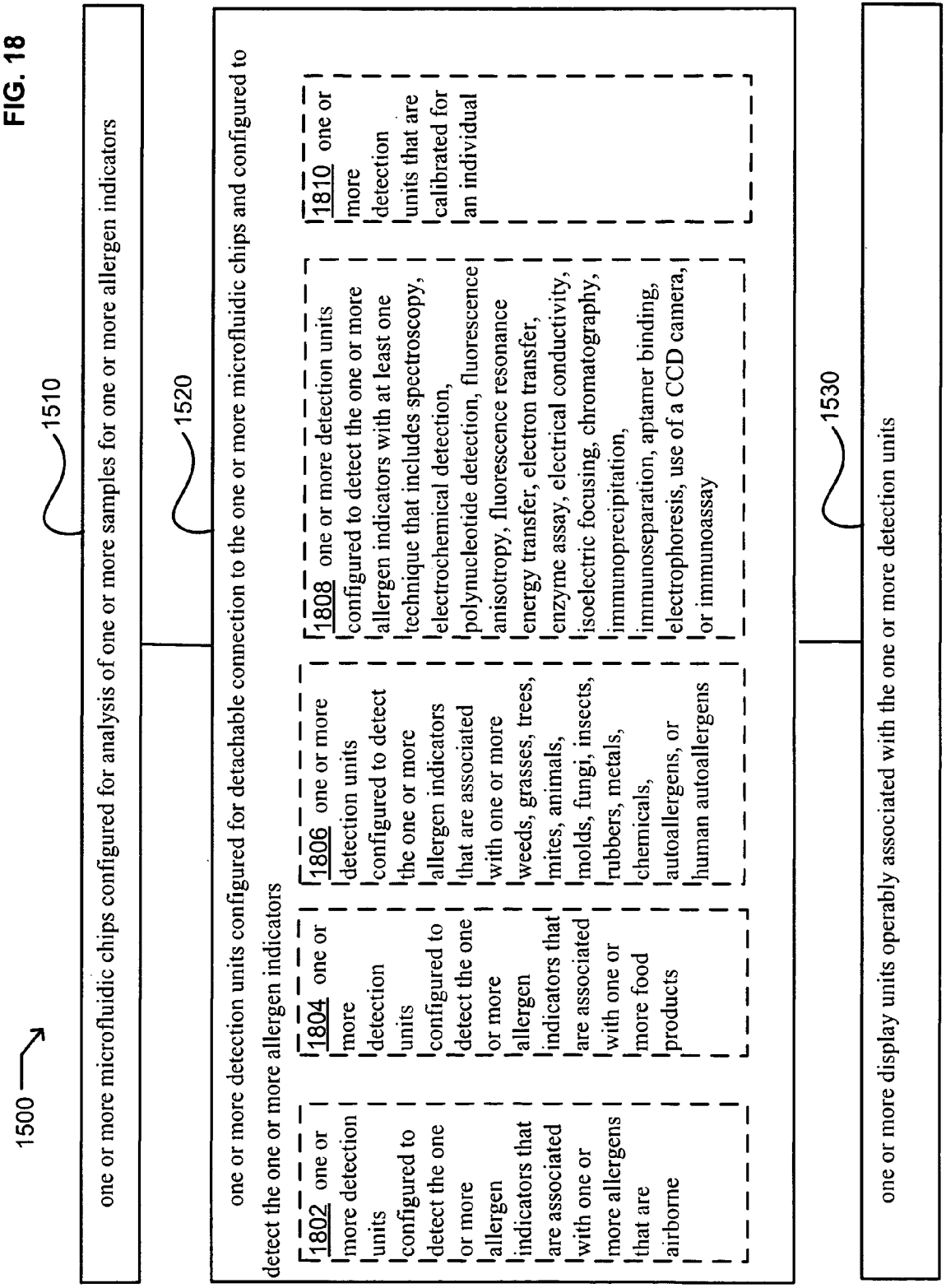
FIG. 18 illustrates alternate embodiments of the system of FIG. 15.

FIG. 18 illustrates alternative embodiments of system 1500 of FIG. 15. FIG. 18 illustrates example embodiments of module 1520. Additional embodiments may include an embodiment 1802, an embodiment 1804, an embodiment 1806, an embodiment 1808, and/or an embodiment 1810.

At embodiment 1802, module 1520 may include one or more detection units configured to detect the one or more allergen indicators that are associated with one or more allergens that are airborne. In some embodiments, one or more detection units 122 may be configured to detect the one or more allergen indicators 106 that are associated with one or more allergens 104 that are airborne. Accordingly, in some embodiments, one or more detection units 122 may be configured to operably associate with the one or more microfluidic chips 108 and to detect one or more airborne allergens 104. For example, in some embodiments, one or more microfluidic chips 108 may be configured to allow one or more air samples 102 to contact the one or more microfluidic chips 108 such that one or more allergen indicators 106 included within the one or more air samples 102 are retained by the one or more microfluidic chips 108. In some embodiments, the one or more air samples 102 may be passed through a filter on which one or more airborne allergen indicators 106 are collected. The collected airborne allergen indicators 106 may then be washed from the filter and caused to pass over an antibody array to which the one or more airborne allergen indicators 106 become immobilized. The immobilized airborne allergen indicators 106 may then be detected through numerous methods that include, but are not limited to, electrical conductivity, immunoassay based methods, and the like. Accordingly, one or more detection units 122 may be configured to detect the one or more airborne allergen indicators 106. In some embodiments, one or more detection units 122 may be configured to operably associate with one or more microfluidic chips 108 such that the one or more detection units 122 facilitate air flow through the one or more microfluidic chips 108 to provide for air sampling. For example, in some embodiments, one or more detection units 122 may include one or more fans to push and/or pull air through one or more operably associated microfluidic chips 108. In some embodiments, one or more detection units 122 may include one or more bellows to push and/or pull air through one or more operably associated microfluidic chips 108. Detection units 122 may be configured in numerous ways to provide for detection of one or more airborne allergen indicators 106.

At embodiment 1804, module 1520 may include one or more detection units configured to detect the one or more allergen indicators that are associated with one or more food products. In some embodiments, one or more detection units 122 may be configured to detect the one or more allergen indicators 106 that are associated with one or more food products. In some embodiments, one or more microfluidic chips 108 may be configured to provide for detection of one or more allergens 104 that are associated with one or more food products. Accordingly, in some embodiments, one or more detection units 122 may be configured to operably associate with the one or more microfluidic chips 108 and to detect one or more allergen indicators 106 that are associated with one or more food products. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Numerous methods may be used to detect one or more allergen indicators 106 that are associated with one or more food products. Such methods have been described herein. In addition, other detection methods that have been described may be modified to provide for detection of one or more allergen indicators 106 that are associated with one or more food products. In some embodiments, one or more detection units 122 may be configured to detect one or more polynucleotides, one or more polypeptides, one or more portions of one or more polynucleotides, and/or one or more portions of one or more polypeptides that have a nucleic acid sequence and/or an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, or AY839230.

At embodiment 1806, module 1520 may include one or more detection units configured to detect the one or more allergen indicators that are associated with one or more weeds, grasses, trees, mites, animals, molds, fungi, insects, rubbers, metals, chemicals, autoallergens, or human autoallergens. In some embodiments, one or more detection units 122 may be configured to detect the one or more allergen indicators 106 that are associated with one or more weeds, grasses, trees, mites, animals, molds, fungi, insects, rubbers, metals, chemicals, autoallergens, human autoallergens, or substantially any combination thereof Numerous allergen indicators 106 are known to be associated with weeds, grasses, trees, mites, animals, molds, fungi, insects, rubbers, metals, chemicals, autoallergens, or human autoallergens. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Accordingly, in some embodiments, one or more microfluidic chips 108 may be configured to process one or more samples 102 and provide for detection of one or more allergen indicators 106. In some embodiments, an allergen indicator 106 may be an allergenic particle. For example, in some embodiments, an allergen indicator 106 may include a complete pollen particle, such as a pollen particle, a spore, a flake of dander, and the like. In some embodiments, an allergen indicator 106 may be a portion of an allergenic particle. For example, in some embodiments, an allergen indicator 106 may include a portion of a pollen particle (e.g., polynucleotides, sporoderm, and the like). In some embodiments, allergen indicators 106 may include polynucleotides that are associated with one or more allergens 104. In some embodiments, allergen indicators 106 may include fragments of polynucleotides that are associated with one or more allergens 104. In some embodiments, allergen indicators 106 may include polypeptides, peptides, and/or proteins that are associated with one or more allergens 104. In some embodiments, allergen indicators 106 may include polysaccharides that are associated with one or more allergens 104. Accordingly, in some embodiments, one or more microfluidic chips 108 may be configured to provide for detection of one or more allergen indicators 106. In some embodiments, one or more detection units 122 may be configured to operably associate with one or more such microfluidic chips 108 and configured to detect one or more allergen indicators 106. Numerous detection methods may be used to detect one or more allergen indicators 106. Such methods have been described herein. In addition, detection methods that have been described may be modified to provide for detection of one or more allergen indicators 106. In some embodiments, one or more detection units 122 may be configured to detect and determine a concentration of one or more allergen indicators 106 that are included within a sample 102. For example, in some embodiments, one or more microfluidic chips 108 may be configured to provide for detection of one or more polynucleotides that are allergen indicators 106 through detection of electrical current produced upon hybridization of the one or more polynucleotides. Accordingly, in such embodiments, the one or more microfluidic chips 108 may be configured to produce an electrical current that is relative to polynucleotide concentration to provide for determination of polynucleotide concentration within one or more samples 102. Numerous configurations may be used in association with one or more allergen indicators 106 to provide for determination of allergen 104 concentration. In some embodiments, one or more microfluidic chips 108 may be configured to provide for identification of one or more allergens 104. For example, in some embodiments, one or more microfluidic chips 108 may include immobilized polynucleotides that selectively hybridize to one or more polynucleotides that are associated with a known allergen indicator 106. Accordingly, hybridization of one or more polynucleotides with the one or more immobilized polynucleotides indicates that a sample 102 includes one or more allergen indicators 106 that correspond to one or more known allergens 104. Accordingly, one or more detection units 122 may be configured to operably associate with such microfluidic chips 108 to provide for specific detection of one or more allergen indicators 106. In some embodiments, microfluidic chips 108 and/or detection units 122 may be configured to determine the identity and concentration of one or more allergen indicators 106 that are included within one or more samples 102.

At embodiment 1808, module 1520 may include one or more detection units configured to detect the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay.

In some embodiments, one or more detection units 122 may be configured to detect the one or more allergens 104 with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, filtration, electrophoresis, use of a CCD camera, immunoassay, or substantially any combination thereof. In some embodiments, one or more detection units 122 may be configured to detect one or more allergen indicators 106 that have been processed by one or more microfluidic chips 108. For example, in some embodiments, one or more microfluidic chips 108 may include a window (e.g., a quartz window, a cuvette analog, and/or the like) through which one or more detection units 122 may determine if one or more allergen indicators 106 are present or determine the concentration of one or more allergen indicators 106. In such embodiments, numerous techniques may be used to detect the one or more allergen indicators 106, such as visible light spectroscopy, ultraviolet light spectroscopy, infrared spectroscopy, fluorescence spectroscopy, and the like. Accordingly, in some embodiments, one or more detection units 122 may include circuitry and/or electro-mechanical mechanisms to detect one or more allergen indicators 106 present within one or more microfluidic chips 108 through a window in the one or more microfluidic chips 108. In some embodiments, one or more microfluidic chips 108 may be configured to process one or more samples 102 through use of surface plasmon resonance. In some embodiments, the one or more microfluidic chips 108 may include one or more antibodies, aptamers, proteins, peptides, polynucleotides, and the like, that are bound to a substrate (e.g., a metal film) within the one or more microfluidic chips 108. In some embodiments, such microfluidic chips 108 may include a prism through which one or more detection units 122 may shine light to detect one or more allergen indicators 106 that interact with the one or more antibodies, aptamers, proteins, peptides, polynucleotides, and the like, that are bound to a substrate. In some embodiments, one or more microfluidic chips 108 may include an exposed substrate surface that is configured to operably associate with one or more prisms that are included within one or more detection units 122. In some embodiments, one or more microfluidic chips 108 may include a nuclear magnetic resonance (NMR) probe. In such embodiments, the microfluidic chips 108 may be configured to associate with one or more detection units 122 that accept the NMR probe and are configured to detect one or more allergen indicators 106 through use of NMR spectroscopy. Accordingly, microfluidic chips 108 and detection units 122 may be configured in numerous ways to associate with each other to provide for detection of one or more allergen indicators 106.

In some embodiments, one or more allergen indicators 106 may be detected through use of spectroscopy. Numerous types of spectroscopic methods may be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., Clinical Chemistry, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, one or more allergen indicators 106 may be detected through use of electrochemical detection. In some embodiments, one or more polynucleotides may be detected through electrochemical detection. For example, in some embodiments, a polynucleotide that includes a redox label, such as ferrocene is coupled to a gold electrode. The labeled polynucleotide forms a stem-loop structure that can self-assemble onto a gold electrode by means of facile gold-thiol chemistry. Hybridization of a sample 102 polynucleotide induces a large conformational change in the surface-confined polynucleotide structure, which in turn alters the electron-transfer tunneling distance between the electrode and the redoxable label. The resulting change in electron transfer efficiency may be measured by cyclic voltammetry (Fan et al., Proc. Natl. Acad. Sci., 100:9134-9137 (2003); Wang et al., Anal. Chem., 75:3941-3945 (2003); Singh-Zocchi et al., Proc. Natl. Acad. Sci., 100:7605-7610 (2003)). Such methods may be used to detect messenger ribonucleic acid, genomic deoxyribonucleic acid, and fragments thereof.

In some embodiments, one or more allergen indicators 106 may be detected through use of polynucleotide detection. In some embodiments, one or more detection units 122 may be configured to detect one or more allergen indicators 106 through use of polynucleotide detection. Numerous methods may be used to detect one or more polynucleotides. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described (e.g., U.S. Pat. Nos. 7,118,910 and 6,960,437; herein incorporated by reference). Such methods may be adapted to provide for detection of one or more allergen indicators 106. In some embodiments, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube may be combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Accordingly, polynucleotides that hybridize to one or more allergen indicators 106 may include one or more carbon nanotubes. Methods to utilize carbon nanotubes as probes for nucleic acid interaction have been described (e.g., U.S. Pat. No. 6,821,730; herein incorporated by reference). Numerous other methods based on polynucleotide detection may be used to detect one or more allergen indicators 106.

In some embodiments, one or more allergen indicators 106 may be detected through use of fluorescence anisotropy. Fluorescence anisotropy is based on measuring the steady state polarization of sample 102 fluorescence imaged in a confocal arrangement. A linearly polarized laser excitation source preferentially excites fluorescent target molecules with transition moments aligned parallel to the incident polarization vector. The resultant fluorescence is collected and directed into two channels that measure the intensity of the fluorescence polarized both parallel and perpendicular to that of the excitation beam. With these two measurements, the fluorescence anisotropy, r, can be determined from the equation: r=(Intensity parallel−Intensity perpendicular)/(Intensity parallel+2(Intensity perpendicular)) where the I terms indicate intensity measurements parallel and perpendicular to the incident polarization. Fluorescence anisotropy detection of fluorescent molecules has been described. Accordingly, fluorescence anisotropy may be coupled to numerous fluorescent labels as have been described herein and as have been described.

In some embodiments, one or more allergen indicators 106 may be detected through use of fluorescence resonance energy transfer (FRET). Fluorescence resonance energy transfer refers to an energy transfer mechanism between two fluorescent molecules. A fluorescent donor is excited at its fluorescence excitation wavelength. This excited state is then nonradiatively transferred to a second molecule, the fluorescent acceptor. Fluorescence resonance energy transfer may be used within numerous configurations to detect one or more allergen indicators 106. For example, in some embodiments, an antibody may be labeled with a fluorescent donor and one or more allergen indicators 106 may be labeled with a fluorescent acceptor. Accordingly, such labeled antibodies and allergen indicators 106 may be used within competition assays to detect the presence and/or concentration of one or more allergen indicators 106 in one or more samples 102. Numerous combinations of fluorescent donors and fluorescent acceptors may be used to detect one or more allergen indicators 106. Accordingly, one or more detection units 122 may be configured to emit one or more wavelength of light to excite a fluorescent donor and may be configured to detect one or more wavelength of light emitted by the fluorescent acceptor. Accordingly, in some embodiments, one or more detection units 122 may be configured to accept one or more microfluidic chips 108 that include a quartz window through which fluorescent light may pass to provide for detection of one or more allergen indicators 106 through use of fluorescence resonance energy transfer. Accordingly, fluorescence resonance energy transfer may be used in conjunction with competition assays and/or numerous other types of assays to detect one or more allergen indicators 106.

In some embodiments, one or more allergen indicators 106 may be detected through use of electron transfer. Electron transfer is the process by which an electron moves from an electron donor to an electron acceptor causing the oxidation states of the electron donor and the electron acceptor to change. In some embodiments, electron transfer may occur when an electron is transferred from one or more electron donors to an electrode. In some embodiments, electron transfer may be utilized within competition assays to detect one or more allergen indicators 106. For example, in some embodiments, one or more microfluidic chips 108 may include one or more polynucleotides that may be immobilized on one or more electrodes. The immobilized polynucleotides may be incubated with a reagent mixture that includes sample polynucleotides and polynucleotides that are tagged with an electron donor. Hybridization of the tagged polynucleotides to the immobilized polynucleotides allows the electron donor to transfer an electron to the electrode to produce a detectable signal. Accordingly, a decrease in signal due to the presence of one or more polynucleotides that are allergen indicators 106 in the reagent mixture indicates the presence of an allergen indicator 106 in the sample 102. Such methods may be used in conjunction with polynucleotides, polypeptides, peptides, antibodies, aptamers, and the like. One or more microfluidic chips 108 may be configured to utilize numerous electron transfer based assays to provide for detection of one or more allergen indicators 106 by a detection unit 122.

In some embodiments, one or more allergen indicators 106 may be detected through use of one or more enzyme assays. Numerous enzyme assays may be used to provide for detection of one or more allergen indicators 106. Examples of such enzyme assays include, but are not limited to, beta-galactosidase assays, peroxidase assays, catalase assays, alkaline phosphatase assays, and the like. In some embodiments, enzyme assays may be configured such that an enzyme will catalyze a reaction involving an enzyme substrate that produces a fluorescent product. Accordingly, one or more detection units 122 may be configured to detect fluorescence resulting from the fluorescent product. Enzymes and fluorescent enzyme substrates are known and are commercially available (e.g., Sigma-Aldrich, St. Louis, Mo.). In some embodiments, enzyme assays may be configured as binding assays that provide for detection of one or more allergen indicators 106. For example, in some embodiments, one or more microfluidic chips 108 may be configured to include a substrate to which is coupled to one or more antibodies, aptamers, peptides, proteins, polynucleotides, ligands, and the like, that will interact with one or more allergen indicators 106. One or more samples 102 may be passed across the substrate such that one or more allergen indicators 106 present within the one or more samples 102 will interact with the one or more antibodies, aptamers, peptides, proteins, polynucleotides, ligands, and the like, and be immobilized on the substrate. One or more antibodies, aptamers, peptides, proteins, polynucleotides, ligands, and the like, that are labeled with an enzyme may then be passed across the substrate such that the one or more labeled antibodies, aptamers, peptides, proteins, polynucleotides, ligands, and the like, will bind to the one or more immobilized allergen indicators 106. An enzyme substrate may then be introduced to the one or more immobilized enzymes such that the enzymes are able to catalyze a reaction involving the enzyme substrate to produce a fluorescent product. Such assays are often referred to as sandwich assays. Accordingly, one or more detection units 122 may be configured to detect one or more products of enzyme catalysis to provide for detection of one or more allergen indicators 106.

In some embodiments, one or more allergen indicators 106 may be detected through use of electrical conductivity. In some embodiments, one or more microfluidic chips 108 may be configured to process one or more samples 102 and provide for detection of one or more allergen indicators 106 through use of electrical conductivity. In some embodiments, such microfluidic chips 108 may be configured to operably associate with one or more detection units 122 such that the one or more detection units 122 can detect one or more allergen indicators 106 through use of electrical conductivity. In some embodiments, one or more microfluidic chips 108 may be configured to include two or more electrodes that are each coupled to one or more detector polynucleotides. Interaction of an allergen associated polynucleotide, such as hybridization, with two detector polynucleotides that are coupled to two different electrodes will complete an electrical circuit. This completed circuit will provide for the flow of a detectable electrical current between the two electrodes and thereby provide for detection of one or more allergen associated polynucleotides that are allergen indicators 106. In some embodiments, the electrodes may be carbon nanotubes (e.g., U.S. Pat. No. 6,958,216; herein incorporated by reference). In some embodiments, electrodes may include, but are not limited to, one or more conductive metals, such as gold, copper, iron, silver, platinum, and the like; one or more conductive alloys; one or more conductive ceramics; and the like. In some embodiments, electrodes may be selected and configured according to protocols typically used in the computer industry that include, but are not limited to, photolithography, masking, printing, stamping, and the like. In some embodiments, other molecules and complexes that interact with one or more allergen indicators 106 may be used to detect the one or more allergen indicators 106 through use of electrical conductivity. Examples of such molecules and complexes include, but are not limited to, proteins, peptides, antibodies, aptamers, and the like. For example, in some embodiments, two or more antibodies may be immobilized on one or more electrodes such that contact of the two or more antibodies with an allergen indicator 106, such as a spore, a pollen particle, a dander particle, and the like, will complete an electrical circuit and facilitate the production of a detectable electrical current. Accordingly, in some embodiments, one or more microfluidic chips 108 may be configured to include electrical connectors that are able to operably associate with one or more detection units 122 such that the detection units 122 may detect an electrical current that is due to interaction of one or more allergen indicators 106 with two or more electrodes. In some embodiments, one or more detection units 122 may include electrical connectors that provide for operable association of one or more microfluidic chips 108 with the one or more detection units 122. In some embodiments, the one or more detectors are configured for detachable connection to one or more microfluidic chips 108. Microfluidic chips 108 and detection units 122 may be configured in numerous ways to process one or more samples 102 and detect one or more allergen indicators 106.

In some embodiments, one or more allergen indicators 106 may be detected through use of isoelectric focusing. In some embodiments, one or more microfluidic chips 108 may be configured to process one or more samples 102 and provide for detection of one or more allergen indicators 106 through use of isoelectric focusing. In some embodiments, native isoelectric focusing may be utilized to process and/or detect one or more allergen indicators 106. In some embodiments, denaturing isoelectric focusing may be utilized to process and/or detect one or more allergen indicators 106. Methods to construct microfluidic channels that may be used for isoelectric focusing have been reported (e.g., Macounova et al., Anal Chem., 73:1627-1633 (2001); Macounova et al., Anal Chem., 72:3745-3751 (2000); Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). In some embodiments, one or more microfluidic chips 108 may be configured to process one or more samples 102 through use of methods that include isoelectric focusing. In some embodiments, one or more detection units 122 may be configured to operably associate with one or more such microfluidic chips 108 such that the one or more detection units 122 can be used to detect one or more allergen indicators 106 that have been focused within one or more microfluidic channels of the one or more microfluidic chips 108. In some embodiments, one or more detection units 122 may be configured to include one or more CCD cameras that can be used to detect one or more allergen indicators 106. In some embodiments, one or more detection units 122 may be configured to include one or more spectrometers that can be used to detect one or more allergen indicators 106. Numerous types of spectrometers may be utilized to detect one or more allergen indicators 106 following isoelectric focusing. In some embodiments, one or more detection units 122 may be configured to utilize refractive index to detect one or more allergen indicators 106. In some embodiments, one or more microfluidic chips 108 may be configured to combine one or more samples 102 with one or more reagent mixtures that include one or more binding molecules and/or binding complexes that bind to one or more allergen indicators 106 that may be present within the one or more samples 102 to form an allergen indicator-binding molecule/binding complex. Examples of such binding molecules and/or binding complexes that bind to one or more allergen indicators 106 include, but are not limited to, antibodies, aptamers, peptides, proteins, polynucleotides, and the like. In some embodiments, an allergen indicator-binding molecule/binding complex may be processed through use of isoelectric focusing and then detected with one or more detection units 122. In some embodiments, one or more binding molecules and/or one or more binding complexes may include a label. Numerous labels may be used and include, but are not limited to, radioactive labels, fluorescent labels, colorimetric labels, spin labels, fluorescent labels, and the like. Accordingly, in some embodiments, an allergen indicator-binding molecule (labeled)/binding complex (labeled) may be processed through use of isoelectric focusing and then detected with one or more detection units 122 that are configured to detect the one or more labels. Microfluidic chips 108 and detection units 122 may be configured in numerous ways to process one or more samples 102 and detect one or more allergen indicators 106 though use of isoelectric focusing.

In some embodiments, one or more allergen indicators 106 may be detected through use of chromatographic methodology alone or in combination with additional processing and/or detection methods. In some embodiments, one or more microfluidic chips 108 may be configured to process one or more samples 102 and provide for detection of one or more allergen indicators 106 through use of chromatographic methods. Accordingly, in some embodiments, one or more detection units 122 may be configured to operably associate with the one or more microfluidic chips 108 and detect one or more allergen indicators 106 that were processed through use of chromatographic methods. In some embodiments, the one or more detection units 122 may be configured to operably associate with one or more microfluidic chips 108 and supply solvents and other reagents to the one or more microfluidic chips 108. For example, in some embodiments, one or more detection units 122 may include pumps and solvent/buffer reservoirs that are configured to supply solvent/buffer flow through chromatographic media (e.g., a chromatographic column) that is operably associated with one or more microfluidic chips 108. In some embodiments, one or more detection units 122 may be configured to operably associate with one or more microfluidic chips 108 and be configured to utilize one or more methods to detect one or more allergen indicators 106. Numerous types of chromatographic methods and media may be used to process one or more samples 102 and provide for detection of one or more allergen indicators 106. Chromatographic methods include, but are not limited to, low pressure liquid chromatography, high pressure liquid chromatography (HPLC), microcapillary low pressure liquid chromatography, microcapillary high pressure liquid chromatography, ion exchange chromatography, affinity chromatography, gel filtration chromatography, size exclusion chromatography, thin layer chromatography, paper chromatography, gas chromatography, and the like. In some embodiments, one or more microfluidic chips 108 may be configured to include one or more high pressure microcapillary columns. Methods that may be used to prepare microcapillary HPLC columns (e.g., columns with a 100 micrometer-500 micrometer inside diameter) have been described (e.g., Davis et al., Methods, A Companion to Methods in Enzymology, 6: Micromethods for Protein Structure Analysis, ed. by John E. Shively, Academic Press, Inc., San Diego, 304-314 (1994); Swiderek et al., Trace Structural Analysis of Proteins. Methods of Enzymology, ed. by Barry L. Karger & William S. Hancock, Spectrum, Publisher Services, 271, Chap. 3, 68-86 (1996); Moritz and Simpson, J. Chromatogr., 599:119-130 (1992)). In some embodiments, one or more microfluidic chips 108 may be configured to include one or more affinity columns. Methods to prepare affinity columns have been described. Briefly, a biotinylated site may be engineered into a polypeptide, peptide, aptamer, antibody, or the like. The biotinylated protein may then be incubated with avidin coated polystyrene beads and slurried in Tris buffer. The slurry may then be packed into a capillary affinity column through use of high pressure packing. Affinity columns may be prepared that may include one or more molecules and/or complexes that interact with one or more allergen indicators 106. For example, in some embodiments, one or more aptamers that bind to one or more allergen indicators 106 may be used to construct an affinity column. Accordingly, numerous chromatographic methods may be used alone, or in combination with additional methods, to process and detect one or more allergen indicators 106. Numerous detection methods may be used in combination with numerous types of chromatographic methods. Accordingly, one or more detection units 122 may be configured to utilize numerous detection methods to detect one or more allergen indicators 106 that are processed through use of one or more chromatographic methods. Examples of such detection methods include, but are not limited to, conductivity detection, use of ion-specific electrodes, refractive index detection, colorimetric detection, radiological detection, detection by retention time, detection through use of elution conditions, spectroscopy, and the like. For example, in some embodiments, one or more chromatographic markers may be added to one or more samples 102 prior to the samples 102 being applied to a chromatographic column. One or more detection units 122 that are operably associated with the chromatographic column may be configured to detect the one or more chromatographic markers and use the elution time and/or position of the chromatographic markers as a calibration tool for use in detecting one or more allergen indicators 106 if those allergen indicators 106 are eluted from the chromatographic column. In some embodiments, one or more detection units 122 may be configured to utilize one or more ion-specific electrodes to detect one or more allergen indicators 106. For example, such electrodes may be used to detect allergen indicators 106 that include, but are not limited to, metals (e.g., tin, silver, nickel, cobalt, chromate), nitrates, nitrites, sulfites, and the like. Such allergen indicators 106 are often associated with food, beverages, clothing, jewelry, and the like. Accordingly, chromatographic methods may be used in combination with additional methods and in combination with numerous types of detection methods.

In some embodiments, one or more allergen indicators 106 may be detected through use of immunoprecipitation. In some embodiments, one or more detection units 122 may be configured to detect one or more allergen indicators 106 through use of immunoprecipitation. In some embodiments, immunoprecipitation may be utilized in combination with additional processing and/or detection methods to detect one or more allergen indicators 106. In some embodiments, one or more microfluidic chips 108 may be configured to process one or more samples 102 through use of immunoprecipitation. For example, in some embodiments, one or more samples 102 may be combined with one or more antibodies that bind to one or more allergen indicators 106 to form one or more antibody-allergen indicator 106 complexes. An insoluble form of an antibody binding constituent, such as protein A (e.g., protein A-sepharose bead, protein A-magnetic bead, protein A-ferrous bead, protein A-non-ferrous bead, and the like), Protein G, a second antibody, an aptamer, and the like, may then be mixed with the antibody-allergen indicator 106 complex such that the insoluble antibody binding constituent binds to the antibody-allergen indicator 106 complex and provides for precipitation of the antibody-allergen indicator 106 complex. Such complexes may be separated from other sample 102 components to provide for detection of one or more allergen indicators 106. For example, in some embodiments, sample 102 components may be washed away from the precipitated antibody-allergen indicator 106 complexes. In some embodiments, one or more microfluidic chips 108 that are configured for immunoprecipitation may be operably associated with one or more centrifugation units 118 to assist in precipitating one or more antibody-allergen indicator 106 complexes. In some embodiments, aptamers (polypeptide and/or polynucleotide) may be used in combination with antibodies or in place of antibodies. Accordingly, one or more detection units 122 may be configured to detect one or more allergen indicators 106 through use of numerous detection methods in combination with immunoprecipitation based methods.

In some embodiments, one or more allergen indicators 106 may be detected through use of immunoseparation. In some embodiments, one or more detection units 122 may be configured to detect one or more allergen indicators 106 through use of immunoseparation. In some embodiments, immunoseparation may be utilized in combination with additional processing and/or detection methods to detect one or more allergen indicators 106. In some embodiments, one or more microfluidic chips 108 may be configured to process one or more samples 102 through use of immunoseparation. For example, in some embodiments, one or more samples 102 may be combined with one or more antibodies that bind to one or more allergen indicators 106 to form one or more antibody-allergen indicator 106 complexes. An antibody binding constituent may be added that binds to the antibody-allergen complex.

Examples of such antibody binding constituents that may be used alone or in combination include, but are not limited to, protein A (e.g., protein A-sepharose bead, protein A-magnetic bead, protein A-ferrous bead, protein A-non-ferrous bead, and the like), Protein G, a second antibody, an aptamer, and the like. Such antibody binding constituents may be mixed with an antibody-allergen indicator 106 complex such that the antibody binding constituent binds to the antibody-allergen indicator 106 complex and provides for separation of the antibody-allergen indicator 106 complex. In some embodiments, the antibody binding constituent may include a tag that allows the antibody binding constituent and complexes that include the antibody binding constituent to be separated from other components in one or more samples 102. In some embodiments, the antibody binding constituent may include a ferrous material. Accordingly, antibody-allergen indicator 106 complexes may be separated from other sample 102 components through use of a magnet, such as an electromagnet. In some embodiments, an antibody binding constituent may include a non-ferrous metal. Accordingly, antibody-allergen indicator 106 complexes may be separated from other sample 102 components through use of an eddy current to direct movement of one or more antibody-allergen indicator 106 complexes. In some embodiments, two or more forms of an antibody binding constituents may be used to detect one or more allergen indicators 106. For example, in some embodiments, a first antibody binding constituent may be coupled to a ferrous material and a second antibody binding constituent may be coupled to a non-ferrous material. Accordingly, the first antibody binding constituent and the second antibody binding constituent may be mixed with antibody-allergen indicator 106 complexes such that the first antibody binding constituent and the second antibody binding constituent bind to antibody-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more antibodies that bind to one or more allergen indicators 106 to form one or more antibody-allergen indicator 106 complexes. In some embodiments, the one or more antibodies may include one or more tags that provide for separation of the antibody-allergen indicator 106 complexes. For example, in some embodiments, an antibody may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with immunoseparation based methods. In some embodiments, aptamers (polypeptide and/or polynucleotide) may be used in combination with antibodies or in place of antibodies.

In some embodiments, one or more allergen indicators 106 may be detected through use of aptamer binding. In some embodiments, one or more detection units 122 may be configured to detect one or more allergen indicators 106 through use of aptamer binding. In some embodiments, aptamer binding may be utilized in combination with additional processing and/or detection methods to detect one or more allergen indicators 106. In some embodiments, one or more microfluidic chips 108 may be configured to process one or more samples 102 through use of aptamer binding. For example, in some embodiments, one or more samples 102 may be combined with one or more aptamers that bind to one or more allergen indicators 106 to form one or more aptamer-allergen indicator 106 complexes. In some embodiments, aptamer binding constituents may be added that bind to the aptamer-allergen complex. Numerous aptamer binding constituents may be utilized. For example, in some embodiments, one or more aptamers may include one or more tags to which one or more aptamer binding constituents may bind. Examples of such tags include, but are not limited to, biotin, avidin, streptavidin, histidine tags, nickel tags, ferrous tags, non-ferrous tags, and the like. In some embodiments, one or more tags may be conjugated with a label to provide for detection of one or more complexes. Examples of such tag-label conjugates include, but are not limited to, Texas red conjugated avidin, alkaline phosphatase conjugated avidin, CY2 conjugated avidin, CY3 conjugated avidin, CY3.5 conjugated avidin, CY5 conjugated avidin, CY5.5 conjugated avidin, fluorescein conjugated avidin, glucose oxidase conjugated avidin, peroxidase conjugated avidin, rhodamine conjugated avidin, agarose conjugated anti-protein A, alkaline phosphatase conjugated protein A, anti-protein A, fluorescein conjugated protein A, IRDye® 800 conjugated protein A, peroxidase conjugated protein A, sepharose protein A, alkaline phosphatase conjugated streptavidin, AMCA conjugated streptavidin, anti-streptavidin (*Streptomyces avidinii*) (rabbit) IgG Fraction, beta-galactosidase conjugated streptavidin, CY2 conjugated streptavidin, CY3 conjugated streptavidin, CY3.5 conjugated streptavidin, CY5 conjugated streptavidin, CY5.5 conjugated streptavidin, fluorescein conjugated streptavidin, IRDye® 700DX conjugated streptavidin, IRDye® 800 conjugated streptavidin, IRDye® 800CW conjugated streptavidin, peroxidase conjugated streptavidin, phycoerythrin conjugated streptavidin, rhodamine conjugated streptavidin, Texas red conjugated streptavidin, alkaline phosphatase conjugated biotin, anti-biotin (rabbit) IgG fraction, beta-galactosidase conjugated biotin, glucose oxidase conjugated biotin, peroxidase conjugated biotin, alkaline phosphatase conjugated protein G, anti-protein G (rabbit) Agarose conjugated, anti-protein G (Rabbit) IgG fraction, fluorescein conjugated protein G, IRDye® 800 conjugated protein G, peroxidase conjugated protein G, and the like. Many such labeled tags are commercially available (e.g., Rockland Immunochemicals, Inc., Gilbertsville, Pa.). Such labels may also be used in association with other methods to process and detect one or more allergen indicators 106. Aptamer binding constituents may be mixed with an aptamer-allergen indicator 106 complex such that the aptamer binding constituent binds to the aptamer-allergen indicator 106 complex and provides for separation of the aptamer-allergen indicator 106 complex. In some embodiments, the aptamer binding constituent may include a tag that allows the aptamer binding constituent and complexes that include the aptamer binding constituent to be separated from other components in one or more samples 102. In some embodiments, the aptamer binding constituent may include a ferrous material. Accordingly, aptamer-allergen indicator 106 complexes may be separated from other sample 102 components through use of a magnet, such as an electromagnet. In some embodiments, an aptamer binding constituent may include a non-ferrous metal. Accordingly, aptamer-allergen indicator 106 complexes may be separated from other sample 102 components through use of an eddy current to direct movement of one or more aptamer-allergen indicator 106 complexes. In some embodiments, two or more forms of aptamer binding constituents may be used to detect one or more allergen indicators 106. For example, in some embodiments, a first aptamer binding constituent may be coupled to a ferrous material and a second aptamer binding constituent may be coupled to a non-ferrous material. Accordingly, the first aptamer binding constituent and the second aptamer binding constituent may be mixed with aptamer-allergen indicator 106 complexes such that the first aptamer binding constituent and the second aptamer binding constituent bind to aptamer-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more aptamers that bind to one or more allergen indicators 106 to form one or more aptamer-allergen indicator 106 complexes. In some embodiments, the one or more aptamer may include one or more tags that provide for separation of the aptamer-allergen indicator 106 complexes. For example, in some embodiments, an aptamer may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with aptamer binding based methods. In some embodiments, antibodies may be used in combination with aptamers or in place of aptamers.

In some embodiments, one or more allergen indicators 106 may be detected through use of electrophoresis. In some embodiments, one or more microfluidic chips 108 may be configured to process one or more samples 102 through use of electrophoresis. In some embodiments, such microfluidic chips 108 may be configured to operably associate with one or more detection units 122. Accordingly, in some embodiments, one or more detection units 122 may be configured to operably associate with one or more microfluidic chips 108 and detect one or more allergen indicators 106 that were processed through use of electrophoresis. Numerous electrophoretic methods may be utilized to provide for detection of one or more allergen indicators 106. Examples of such electrophoretic methods include, but are not limited to, capillary electrophoresis, one-dimensional electrophoresis, two-dimensional electrophoresis, native electrophoresis, denaturing electrophoresis, polyacrylamide gel electrophoresis, agarose gel electrophoresis, and the like. Numerous detection methods may be used in combination with one or more electrophoretic methods to detect one or more allergen indicators 106. In some embodiments, one or more allergen indicators 106 may be detected according to the position to which the one or more allergen indicators 106 migrate within an electrophoretic field (e.g., a capillary and/or a gel). In some embodiments, the position of one or more allergen indicators 106 may be compared to one or more standards. For example, in some embodiments, one or more samples 102 may be mixed with one or more molecular weight markers prior to gel electrophoresis. The one or more samples 102, that include the one or more molecular weight markers, may be subjected to electrophoresis and then the gel may be stained. In such embodiments, the molecular weight markers may be used as a reference to detect one or more allergen indicators 106 present within the one or more samples 102. In some embodiments, one or more components that are known to be present within one or more samples 102 may be used as a reference to detect one or more allergen indicators 106 present within the one or more samples 102. In some embodiments, gel shift assays may be used to detect one or more allergen indicators 106. For example, in some embodiments, a sample 102 (e.g., a single sample 102 or combination of multiple samples 102) may be split into a first sample 102 and a second sample 102. The first sample 102 may be mixed with an antibody, aptamer, ligand, or other molecule and/or complex that binds to the one or more allergen indicators 106. The first and second samples 102 may then be subjected to electrophoresis. The gels corresponding to the first sample 102 and the second sample 102 may then be analyzed to determine if one or more allergen indicators 106 are present within the one or more samples 102. Microfluidic chips 108 and detection units 122 may be configured in numerous ways to process and detect one or more allergen indicators 106 through use of electrophoresis.

In some embodiments, one or more allergen indicators 106 may be detected through use of one or more charge-coupled device (CCD) cameras. In some embodiments, one or more detection units 122 that include one or more CCD cameras may be configured to operably associate with one or more microfluidic chips 108. Such detection units 122 may be utilized in combination with numerous processing methods. Examples of such methods include, but are not limited to, electrophoresis; competition assays; methods based on polynucleotide interaction, protein interaction, peptide interaction, antibody interaction, aptamer interaction, immunoprecipitation, immunoseparation, and the like. For example, in some embodiments, one or more microfluidic chips 108 may be configured to process one or more samples 102 through use of immunoprecipitation. In some embodiments, one or more antibodies may be conjugated to a fluorescent label such that binding of one or more labeled antibodies to one or more allergen indicators 106 included within one or more samples 102 will form a fluorescently labeled antibody-allergen indicator 106 complex. One or more insoluble allergen indicator 106 binding constituents, such as a sepharose bead that includes an antibody or aptamer that binds to the one or more allergen indicators 106, may be bound to the fluorescently labeled antibody-allergen indicator 106 complex and used to precipitate the complex. One or more detection units 122 that include a CCD camera that is configured to detect fluorescent emission from the one or more fluorescent labels may be used to detect the one or more allergen indicators 106. In some embodiments, one or more CCD cameras may be configured to utilize dark frame subtraction to cancel background and increase sensitivity of the camera. In some embodiments, one or more detection units 122 may include one or more filters to select and/or filter wavelengths of energy that can be detected by one or more CCD cameras (e.g., U.S. Pat. No. 3,971,065; herein incorporated by reference). In some embodiments, one or more detection units 122 may include polarized lenses. One or more detection units 122 may be configured in numerous ways to utilize one or more CCD cameras to detect one or more allergen indicators 106.

In some embodiments, one or more allergen indicators 106 may be detected through use of immunoassay. In some embodiments, one or more microfluidic chips 108 may be configured to process one or more samples 102 through use of immunoassay. In some embodiments, one or more detection units 122 may be configured to operably associate with one or more such microfluidic chips 108 and to detect one or more allergen indicators 106 associated with the use of immunoassay. Numerous types of detection methods may be used in combination with immunoassay based methods. In some embodiments, a label may be used within one or more immunoassays that may be detected by one or more detection units 122. Examples of such labels include, but are not limited to, fluorescent labels, spin labels, fluorescence resonance energy transfer labels, radiolabels, electrochemiluminescent labels (e.g., U.S. Pat. Nos. 5,093,268; 6,090,545; herein incorporated by reference), and the like. In some embodiments, electrical conductivity may be used in combination with immunoassay based methods.

At embodiment 1810, module 1520 may include one or more detection units that are calibrated for an individual. In some embodiments, one or more detection units 122 may be calibrated for an individual. In some embodiments, one or more detection units 122 may be calibrated to detect one or more specific allergens 104 and/or allergen indicators 106 that produce an allergic response by an individual. For example, in some embodiments, one or more detection units 122 may be calibrated to detect peanuts and/or peanut associated products for an individual who is allergic to peanuts. In some embodiments, one or more detection units 122 may be calibrated to detect different concentrations of allergen indicators 106. For example, in some embodiments, an individual may produce an allergic response if exposed to an allergen 104 at a concentration that is above a certain level. Accordingly, in some embodiments, a detection unit 122 may be calibrated to detect one or more concentrations of one or more allergen indicators 106 that produce an allergic response within an individual.

FIG. 19 illustrates alternative embodiments of system 1500 of FIG. 15. FIG. 19 illustrates example embodiments of module 1530. Additional embodiments may include an embodiment 1902, an embodiment 1904, an embodiment 1906, an embodiment 1908, an embodiment 1910, and/or an embodiment 1912.

At embodiment 1902, module 1530 may include one or more display units that are passive display units. In some embodiments, one or more display units 124 may display results of the detecting with one or more display units 124 that are passive display units 124. In some embodiments, one or more display units 124 may include one or more liquid crystal displays (LCD). Methods to construct passive displays have been described (e.g., U.S. Pat. Nos. 4,807,967; 4,729,636: 4,436,378; 4,257,041; herein incorporated by reference).

At embodiment 1904, module 1530 may include one or more display units that are active display units. In some embodiments, one or more display units 124 may display results of the detecting with one or more display units 124 that are active display units 124. Numerous active display units 124 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), wide ultra extended graphics array (WUXGA).

At embodiment 1906, module 1530 may include one or more display units that indicate a presence or an absence of one or more allergens within the one or more samples. In some embodiments, one or more display units 124 may indicate a presence or an absence of one or more allergen indicators 106 within the one or more samples 102. In some embodiments, one or more display units 124 may use a colorimetric message to indicate a presence or an absence of one or more allergen indicators 106 within one or more samples 102. For example, in some embodiments, one or more display units 124 may display a green light if one or more allergen indicators 106 are not found within one or more samples 102 and a red light if one or more allergen indicators 106 are found within one or more samples 102. In some embodiments, one or more display units 124 may use a pictographic message to indicate a presence or an absence of one or more allergen indicators 106 within one or more samples 102. For example, in some embodiments, one or more display units 124 may display a smiley face if one or more allergen indicators 106 are not found within one or more samples 102 and a frowny face if one or more allergen indicators 106 are found within one or more samples 102. In some embodiments, one or more display units 124 may use a typographical message to indicate a presence or an absence of one or more allergen indicators 106 within one or more samples 102. For example, in some embodiments, one or more display units 124 may display an "Allergen Not Present" message if one or more allergen indicators 106 are not found within one or more samples 102 and an "Allergen Present" message if one or more allergen indicators 106 are found within one or more samples 102. Such messages may be displayed in numerous languages. In some embodiments, one or more display units 124 may display one or more messages in multiple formats. For example, in some embodiments, one or more messages may be displayed in colored text.

At embodiment 1908, module 1530 may include one or more display units that indicate an identity of one or more allergens present within the one or more samples. In some embodiments, one or more display units 124 may indicate an identity of one or more allergens 104 present within the one or more samples 102. In some embodiments, one or more display units 124 may be operably associated with one or more microfluidic chips 108 that are configured to identify one or more allergen indicators 106. Accordingly, in some embodiments, one or more display units 124 may be configured to display the identity of one or more allergens 104 that are present and/or absent from one or more samples 102. For example, in some embodiments, a display unit 124 may be configured to indicate a presence or an absence of beta-lactoglobulin in a food product.

At embodiment 1910, module 1530 may include one or more display units that indicate one or more concentrations of one or more allergens within the one or more samples. In some embodiments, one or more display units 124 may indicate one or more concentrations of one or more allergens 104 within the one or more samples 102. Concentration may be displayed in numerous formats. For example, in some embodiments, concentration may be expressed numerically (e.g., mass allergen indicator 106 per volume sample 102 (e.g., milligrams per milliliter), mass allergen indicator 106 per mass sample 102 (e.g., milligrams per milligram of sample), parts per million, and the like). In some embodiments, concentration may be expressed graphically. For example, in some embodiments, one or more display units 124 may include a display having a gray scale on which the concentration of one or more allergen indicators 106 that are present within one or more samples 102 may be indicated (e.g., higher concentrations of one or more allergens 104 may be displayed as dark gray while lower concentrations of one or more allergens 104 may be displayed as light gray). In some embodiments, one or more display units 124 may include a display having a color scale on which the concentration of one or more allergen indicators 106 that are present within one or more samples 102 may be indicated (e.g., low concentrations of one or more allergen indicators 106 may be indicated by a green light, intermediate concentrations of one or more allergen indicators 106 may be indicated by a yellow light, high concentrations of one or more allergen indicators 106 may be indicated by a red light). In some embodiments, one or more display units 124 may be calibrated to an individual. For example, in such embodiments, an individual may use the display to obtain an immediate reading that will indicate if a food product contains a dangerous level of one or more allergens 104.

At embodiment 1912, module 1530 may include one or more display units that are calibrated for an individual. In some embodiments, one or more display units 124 may be calibrated for an individual. In some embodiments, one or more display units 124 may be calibrated to display whether one or more allergens 104, and/or allergen indicators 106, that are specific to an individual are present or absent within one or more samples 102. For example, in some embodiments, one or more display units 124 may be configured to display whether one or more samples 102 contain shellfish associated allergens 104 for an individual known to be allergic to shellfish. In some embodiments, one or more display units 124 may be calibrated to indicate safe and/or unsafe concentrations of one or more allergens 104 within one or more samples 102 for an individual.

FIG. 20 illustrates a system 2000 representing examples of modules that may be used to perform a method for analysis of one or more allergens 104. In FIG. 20, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various modules are presented in the sequence(s) illustrated, it should be understood that the various modules may be configured in numerous orientations.

The system 2000 includes module 2010 that includes one or more microfluidic chips configured for analysis of one or more samples for one or more allergen indicators. In some embodiments, module 2010 may include one or more microfluidic chips configured for detachable connection to the one or more detection units. In some embodiments, module 2010 may include one or more microfluidic chips configured for detachable connection to the one or more reagent delivery units. In some embodiments, module 2010 may include one or more microfluidic chips configured for detachable connection to the one or more detection units and configured for detachable connection to the one or more reagent delivery units. In some embodiments, module 2010 may include one or more microfluidic chips configured for analysis of the one or more samples that include one or more liquids. In some embodiments, module 2010 may include one or more microfluidic chips configured for analysis of the one or more samples that include one or more solids. In some embodiments, module 2010 may include one or more microfluidic chips configured for analysis of the one or more samples that include one or more gases. In some embodiments, module 2010 may include one or more microfluidic chips configured for analysis of the one or more samples for the one or more allergen indicators that are associated with one or more airborne allergens. In some embodiments, module 2010 may include one or more microfluidic chips configured for analysis of the one or more samples for the one or more allergen indicators that are associated with one or more food products. In some embodiments, module 2010 may include one or more microfluidic chips configured for analysis of the one or more samples for the one or more allergen indicators that are associated with one or more weeds, grasses, trees, mites, animals, molds, fungi, insects, rubbers, metals, chemicals, autoallergens, or human autoallergens. In some embodiments, module 2010 may include one or more microfluidic chips configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay.

The system 2000 includes module 2020 that includes one or more reagent delivery units configured to deliver one or more reagents to the one or more microfluidic chips. In some embodiments, module 2020 may include one or more reagent delivery units configured for detachable connection to the one or more microfluidic chips. In some embodiments, module 2020 may include one or more reagent reservoirs. In some embodiments, module 2020 may include one or more waste reservoirs. In some embodiments, module 2020 may include one or more reagent delivery units physically coupled to the one or more microfluidic chips. In some embodiments, module 2020 may include one or more reagent delivery units that include one or more pumps.

The system 2000 includes module 2030 that includes one or more detection units configured to detect the one or more allergen indicators. In some embodiments, module 2030 may include one or more detection units configured to detect the one or more allergen indicators that are associated with one or more allergens that are airborne. In some embodiments, module 2030 may include one or more detection units configured to detect the one or more allergen indicators that are associated with one or more food products. In some embodiments, module 2030 may include one or more detection units configured to detect the one or more allergen indicators that are associated with one or more weeds, grasses, trees, mites, animals, molds, fungi, insects, rubbers, metals, chemicals, autoallergens, or human autoallergens. In some embodiments, module 2030 may include one or more detection units configured to detect the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, module 2030 may include one or more detection units that are calibrated for an individual.

The system 2000 may optionally include module 2040 that includes one or more display units operably associated with the one or more detection units. In some embodiments, module 2040 may include one or more display units that are passive display units. In some embodiments, module 2040 may include one or more display units that are active display units. In some embodiments, module 2040 may include one or more display units that indicate a presence or an absence of one or more allergens within the one or more samples. In some embodiments, module 2040 may include one or more display units that indicate an identity of one or more allergens present within the one or more samples. In some embodiments, module 2040 may include one or more display units that indicate one or more concentrations of one or more allergens within the one or more samples. In some embodiments, module 2040 may include one or more display units that are calibrated for an individual.

FIG. 21 illustrates alternative embodiments of system 2000 of FIG. 20. FIG. 21 illustrates example embodiments of module 2010. Additional embodiments may include an embodiment 2102, an embodiment 2104, an embodiment 2106, an embodiment 2108, and/or an embodiment 2110.

At embodiment 2102, module 2010 may include one or more microfluidic chips configured for detachable connection to the one or more detection units. In some embodiments, a system may include one or more microfluidic chips 108 configured for detachable connection to the one or more detection units 122. Accordingly, in some embodiments, one or more detection units 122 may be configured to detachably connect to microfluidic chips 108 having different configurations. For example, in some embodiments, a detection unit 122 may detachably connect to a first microfluidic chip 108 that is configured to process and/or analyze one or more food associated allergen indicators 106 and to a second microfluidic chip 108 that is configured to process and/or analyze one or more airborne allergen indicators 106. Accordingly, in some embodiments, the same detection unit 122 may be utilized with microfluidic chips 108 that are configured to process and/or analyze numerous types of samples 102 and allergen indicators 106.

At embodiment 2104, module 2010 may include one or more microfluidic chips configured for detachable connection to the one or more reagent delivery units. In some embodiments, a system may include one or more microfluidic chips 108 configured for detachable connection to the one or more reagent delivery units 116. Numerous types of connectors may be utilized to detachably connect one or more microfluidic chips 108 to one or more reagent delivery units 116. Examples of such connectors include, but are not limited to, leur lock connectors, friction connectors, threaded connectors, septa, quick connect/disconnect type connectors, and the like. In some embodiments, two or more different microfluidic chips 108 may be configured to detachably connect to one or more reagent delivery units 116 but may be configured to process, analyze, and/or detect different types of allergen indicators 106. Accordingly, one or more reagent delivery units 116 may be configured to detachably connect to microfluidic chips 108 that are configured to process, analyze, and/or detect different types of allergen indicators 106. In some embodiments, such configurations provide for the use of reagent delivery units 116 that may include numerous types of reagents that may provide for processing, analysis, and/or detection of numerous types of allergen indicators 106. Accordingly, systems that include such configurations may be configured to be portable such that they may be used in field situations. In some embodiments, such systems may be self-contained such that one or more reagent delivery units 116 may include one or more reagent reservoirs and one or more waste reservoirs. In some embodiments, such systems provide for repeated connection of single use microfluidic chips 108 for the analysis of one or more allergen indicators 106.

At embodiment 2106, module 2010 may include one or more microfluidic chips configured for detachable connection to the one or more detection units and configured for detachable connection to the one or more reagent delivery units. In some embodiments, a system may include one or more microfluidic chips 108 configured for detachable connection to the one or more detection units 122 and configured for detachable connection to the one or more reagent delivery units 116.

In some embodiments, one or more detection units 122 may be configured to detachably connect to microfluidic chips 108 having different configurations. For example, in some embodiments, a detection unit 122 may detachably connect to a first microfluidic chip 108 that is configured to process and/or analyze one or more food associated allergen indicators 106 and to a second microfluidic chip 108 that is configured to process and/or analyze one or more airborne allergen indicators 106. Accordingly, in some embodiments, the same detection unit 122 may be utilized with microfluidic chips 108 that are configured to process and/or analyze numerous types of samples 102 and allergen indicators 106.

Numerous types of connectors may be utilized to detachably connect one or more microfluidic chips 108 to one or more reagent delivery units 116. Examples of such connectors include, but are not limited to, leur lock connectors, friction connectors, threaded connectors, septa, quick connect/disconnect type connectors, and the like. In some embodiments, two or more different microfluidic chips 108 may be configured to detachably connect to one or more reagent delivery units 116 but may be configured to process, analyze, and/or detect different types of allergen indicators 106. Accordingly, one or more reagent delivery units 116 may be configured to detachably connect to microfluidic chips 108 that are configured to process, analyze, and/or detect different types of allergen indicators 106. In some embodiments, such configurations provide for the use of reagent delivery units 116 that may include numerous types of reagents that may provide for processing, analysis, and/or detection of numerous types of allergen indicators 106. Accordingly, systems that include such configurations may be configured to be portable such that they may be used in field situations. In some embodiments, such systems may be self-contained such that one or more reagent delivery units 116 may include one or more reagent reservoirs and one or more waste reservoirs. In some embodiments, such systems provide for repeated connection of single use microfluidic chips 108 for the analysis of one or more allergen indicators 106.

At embodiment 2108, module 2010 may include one or more microfluidic chips configured for analysis of the one or more samples that include one or more liquids. In some embodiments, a system may include one or more microfluidic chips 108 configured for analysis of the one or more samples 102 that include one or more liquids. Microfluidic chips 108 may be configured for analysis of numerous types of liquids. Examples of such liquids include, but are not limited to, beverages, water, food products, solvents, and the like. In some embodiments, a microfluidic chip 108 may be configured to analyze one or more solvents that include one or more dissolved metal samples 102. For example, metal may be contacted with a solvent to obtain a sample 102 of the metal. The solvent may then be delivered to a microfluidic chip 108 for analysis. Accordingly, microfluidic chips 108 may be configured in numerous ways such that they may analyze one or more samples 102 that include a liquid.

At embodiment 2110, module 2010 may include one or more microfluidic chips configured for analysis of the one or more samples that include one or more solids. In some embodiments, a system may include one or more microfluidic chips 108 configured for analysis of the one or more samples 102 that include one or more solids. In some embodiments, such microfluidic chips 108 may be configured to suspend a solid sample 102 in a fluid. In some embodiments, such microfluidic chips 108 may be configured to crush a sample 102 into smaller particles. For example, in some embodiments, a microfluidic chip 108 may crush a solid sample 102. In some embodiments, a microfluidic chip 108 may include one or more sonicators that break a sample 102 into smaller particles to facilitate detection of one or more allergen indicators 106 that may be present within the sample 102. For example, in some embodiments, solid spores may be broken into smaller particles to provide for detection of one or more polynucleotides that are associated with the spores. In some embodiments, a microfluidic chip 108 may be configured to analyze one or more samples 102 that include metal. For example, in some embodiments, a microfluidic chip 108 may be configured to accept a metal sample 102 (e.g., from a piece of jewelry). In such embodiments, a microfluidic chip 108 may be configured to dissolve the metal sample 102 in a suitable solvent. For example, the metal sample 102 may be dissolved in hydrochloric acid media and then tin may be extracted from the hydrochloric acid with 2-ethylhexyl phosphonic acid mono-2-ethylhexyl ester in toluene. The extracted tin may then be detected through use of an ion-specific electrode. Accordingly, microfluidic chips 108 may be configured in numerous ways such that they may analyze one or more samples 102 that include a solid.

FIG. 22 illustrates alternative embodiments of system 2000 of FIG. 20. FIG. 22 illustrates example embodiments of module 2010. Additional embodiments may include an embodiment 2202, an embodiment 2204, an embodiment 2206, an embodiment 2208, and/or an embodiment 2210.

At embodiment 2202, module 2010 may include one or more microfluidic chips configured for analysis of the one or more samples that include one or more gases. In some embodiments, a system may include one or more microfluidic chips 108 that are configured for analysis of the one or more samples 102 that include one or more gases. For example, in some embodiments, one or more gases that are being analyzed may be passed through one or more microfluidic chips 108. In some embodiments, gas may be pumped through a microfluidic chip 108. In some embodiments, gas may be drawn through a microfluidic chip 108 through use of a vacuum. In some embodiments, gas may be passed through a filter on which suspected allergen indicators 106 are collected for analysis. Accordingly, large volumes of gas may be analyzed. In some embodiments, one or more gases may be analyzed for one or more allergen indicators 106 that include one or more metals. For example, gases may be analyzed for metals that are associated with tanks in which the gases are stored, such as iron, steel, aluminum, and the like.

At embodiment 2204, module 2010 may include one or more microfluidic chips configured for analysis of the one or more samples for the one or more allergen indicators that are associated with one or more airborne allergens. In some embodiments, a system may include one or more microfluidic chips 108 that are configured for analysis of the one or more samples 102 for the one or more allergen indicators 106 that are associated with one or more airborne allergens 104. Examples of such airborne allergens 104 include, but are not limited to, pollen, dander, seeds, exhaust particles (e.g., diesel exhaust) and the like. In some embodiments, the allergen indicators 106 may be collected within one or more microfluidic chips 108 through filtering air that is passed through the one or more microfluidic chips 108. Such filtering may occur through numerous mechanisms that may include, but are not limited to, use of physical filters, passing air through a fluid bubble chamber, passing the air through an electrostatic filter, and the like.

At embodiment 2206, module 2010 may include one or more microfluidic chips configured for analysis of the one or more samples for the one or more allergen indicators that are associated with one or more food products. In some embodiments, a system may include one or more microfluidic chips 108 that are configured for analysis of the one or more samples 102 for the one or more allergen indicators 106 that are associated with one or more food products. Such allergen indicators 106 are described herein and are known. For example, in some embodiments, one or more microfluidic chips 108 may be configured to analyze one or more food products at a restaurant to facilitate detection of a presence or an absence of an allergen indicator 106 within the food product, such as a presence of one or more allergen indicators 106 associated with nuts, dairy products, crustaceans, eggs, gluten, soy, and the like. In some embodiments, one or more microfluidic chips 108 may be configured to analyze one or more polynucleotides, one or more polypeptides, one or more portions of one or more polynucleotides, and/or one or more portions of one or more polypeptides that have a nucleic acid sequence and/or an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, AY839230, or substantially any combination thereof. Accordingly, one or more microfluidic chips 108 may be configured to process numerous types of food products to facilitate detection of numerous types of allergen indicators 106.

At embodiment 2208, module 2010 may include one or more microfluidic chips configured for analysis of the one or more samples for the one or more allergen indicators that are associated with one or more weeds, grasses, trees, mites, animals, molds, fungi, insects, rubbers, metals, chemicals, autoallergens, or human autoallergens. In some embodiments, a system may include one or more microfluidic chips 108 that are configured for analysis of the one or more samples 102 for the one or more allergen indicators 106 associated with one or more weeds, grasses, trees, mites, animals, molds, fungi, insects, rubbers, metals, chemicals, autoallergens, human autoallergens, or substantially any combination thereof. Such allergen indicators 106 are described herein and are known. For example, in some embodiments, one or more microfluidic chips 108 may be configured to process one or more material samples 102 to determine if the material contains latex.

At embodiment 2210, module 2010 may include one or more microfluidic chips configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay.

In some embodiments, a system may include one or more microfluidic chips 108 that are configured for analysis of one or more allergen indicators 106 through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof. In some embodiments, allergen indicators 106 may be separated from other materials included within one or more samples 102 through processing.

In some embodiments, one or more microfluidic chips 108 may be configured to analyze one or more allergen indicators 106 through use of polynucleotide interaction. Numerous methods based on polynucleotide interaction may be used. Examples of such methods include, but are not limited to, those based on polynucleotide hybridization, polynucleotide ligation, polynucleotide amplification, polynucleotide degradation, and the like. Methods that utilize intercalation dyes, FRET analysis, capacitive DNA detection, and nucleic acid amplification have been described (e.g., U.S. Pat. Nos. 7,118, 910 and 6,960,437; herein incorporated by reference). In some embodiments, fluorescence resonance energy transfer, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube are combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Methods to utilize carbon nanotubes as probes for nucleic acid interaction have been described (e.g., U.S. Pat. No. 6,821,730; herein incorporated by reference).

In some embodiments, one or more microfluidic chips 108 may be configured to analyze one or more allergen indicators 106 through use of protein interaction. Numerous methods based on protein interaction may be used. In some embodiments, protein interaction may be used to immobilize one or more allergen indicators 106. In some embodiments, protein interaction may be used to separate one or more allergen indicators 106 from one or more samples 102. Examples of such methods include, but are not limited to, those based on ligand binding, protein-protein binding, protein cross-linking, use of green fluorescent protein, phage display, the two-hybrid system, protein arrays, fiber optic evanescent wave sensors, chromatographic techniques, fluorescence resonance energy transfer, regulation of pH to control protein assembly and/or oligomerization, and the like. For example, tropomyosin is a major muscle protein in crustaceans that is thought to be a major shrimp allergen 104. Tropomyosin is associated with the well known actin-troponin-myosin complex. Calcium ion binding to troponin enables troponin to bind tropomyosin and shift it from the binding sites of myosin on the actin proteins. Without the presence of Calcium ion, troponin is no longer able to bind to tropomyosin, and tropomyosin again blocks the binding sites of myosin on the actin proteins. Tropomyosin also binds to the calcium-binding protein calcyclin (Nelson et al., Molecular & Cellular Proteomics 1:253-259 (2002) and Liou and Chen, European Journal of Biochemistry, 270:3092-3100 (2003)). Accordingly, protein interactions may be used to separate tropomyosin (allergen indicator 106) from one or more samples 102. Similar methods may be used with numerous proteins. Methods that may be used to construct protein arrays have been described (e.g., Warren et al., Anal. Chem., 76:4082-4092 (2004) and Walter et al., Trends Mol. Med., 8:250-253 (2002), U.S. Pat. No. 6,780,582; herein incorporated by reference).

In some embodiments, one or more microfluidic chips 108 may be configured to analyze one or more samples 102 through use of peptide interaction. Peptides are generally described as being polypeptides that include less than one hundred amino acids. For example, peptides include dipeptides, tripeptides, and the like. In some embodiments, peptides may include from two to one hundred amino acids. In some embodiments, peptides may include from two to fifty amino acids. In some embodiments, peptides may include from two to one twenty amino acids. In some embodiments, peptides may include from ten to one hundred amino acids. In some embodiments, peptides may include from ten to fifty amino acids. Accordingly, peptides can include numerous numbers of amino acids. Numerous methods based on peptide interaction may be used. In some embodiments, peptide interaction may be used to immobilize one or more allergen indicators 106. In some embodiments, peptide interaction may be used to separate one or more allergen indicators 106 from one or more samples 102. Examples of such methods include, but are not limited to, those based on ligand binding, peptide-protein binding, peptide-peptide binding, peptide-polynucleotide binding, peptide cross-linking, use of green fluorescent protein, phage display, the two-hybrid system, protein arrays, peptide arrays, fiber optic evanescent wave sensors, chromatographic techniques, fluorescence resonance energy transfer, regulation of pH to control peptide and/or protein assembly and/or oligomerization, and the like. Accordingly, virtually any technique that may be used to analyze proteins may be utilized for the analysis of peptides. In some embodiments, high-speed capillary electrophoresis may be used to detect binding through use of fluorescently labeled phosphopeptides as affinity probes (Yang et al., Anal. Chem., 10.1021/ac061936e (2006)). Methods to immobilize proteins and peptides have been reported (Taylor, Protein Immobilization: Fundamentals and Applications, Marcel Dekker, Inc., New York (1991)).

In some embodiments, one or more microfluidic chips 108 may be configured to analyze one or more samples 102 through use of antibody interaction. Antibodies may be raised that will bind to numerous allergen indicators 106 through use of known methods (e.g., Harlow and Lane, Antibodies: A Laboratory Manual, Cold Spring Harbor Laboratory Press, Cold Spring Harbor, N.Y. (1988)). Antibodies may be configured in numerous ways within one or more microfluidic chips 108 to process one or more allergen indicators 106. For example, in some embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. A labeled detector antibody that binds to the allergen indicator 106 (or the antibody-allergen indicator 106 complex) may then be passed over the one or more antibody-allergen indicator 106 complexes such that the labeled detector antibody will label the allergen indicator 106 (or the antibody-allergen indicator 106 complex). Numerous labels may be used that include, but are not limited to, enzymes, fluorescent molecules, radioactive labels, spin labels, redox labels, and the like. In other embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. Such binding provides for detection of the antibody-allergen indicator 106 complex through use of methods that include, but are not limited to, surface plasmon resonance, conductivity, and the like (e.g., U.S. Pat. No. 7,030,989; herein incorporated by reference). In some embodiments, antibodies may be coupled to a substrate within a microfluidic chip 108 to provide for a competition assay. One or more samples 102 may be mixed with one or more reagent mixtures that include one or more labeled allergen indicators 106. The mixture may then be passed over the antibodies to facilitate binding of allergen indicators 106 in the sample 102 and labeled allergen indicators 106 in the reagent mixture to the antibodies. The unlabeled allergen indicators 106 in the sample 102 will compete with the labeled allergen indicators 106 in the reagent mixture for binding to the antibodies. Accordingly, the amount of label bound to the antibodies will vary in accordance with the concentration of unlabeled allergen indicators 106 in the sample 102. In some embodiments, antibody interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more antibodies may be used in conjunction with one or more aptamers to process one or more samples 102. Accordingly, in some embodiments, aptamers and antibodies may be used interchangeably to process one or more samples 102.

In some embodiments, one or more microfluidic chips 108 may be configured to analyze one or more samples 102 through use of chemical interaction. In some embodiments, one or more microfluidic chips 108 may be configured to utilize chemical extraction to process one or more samples 102. For example, in some embodiments, one or more samples 102 may be mixed with a reagent mixture that includes one or more solvents in which the one or more allergen indicators 106 are soluble. Accordingly, the solvent phase containing the one or more allergen indicators 106 may be separated from the sample phase to provide for detection of the one or more allergen indicators 106. In some embodiments, one or more samples 102 may be mixed with a reagent mixture that includes one or more chemicals that cause precipitation of one or more allergen indicators 106. Accordingly, the sample phase may be washed away from the one or more precipitated allergen indicators 106 to provide for detection of the one or more allergen indicators 106. Accordingly, reagent mixtures that include numerous types of chemicals that interact with one or more allergen indicators 106 may be used.

In some embodiments, one or more microfluidic chips 108 may be configured to analyze one or more samples 102 through use of diffusion. In some embodiments, one or more microfluidic chips 108 may be configured to process one or more fluid samples 102 through use of an H-filter. For example, a microfluidic chip 108 may be configured to include a channel through which a fluid sample 102 and a second fluid flow such that the fluid sample 102 and the second fluid undergo parallel flow through the channel without significant mixing of the sample fluid and the second fluid. As the fluid sample 102 and the second fluid flow through the channel, one or more allergen indicators 106 in the fluid sample 102 may diffuse through the fluid sample 102 into the second fluid. Accordingly, such diffusion provides for the separation of the one or more allergen indicators 106 from the sample 102. Methods to construct H-filters have been described (e.g., U.S. Pat. Nos. 6,742,661; 6,409,832; 6,007,775; 5,974,867; 5,971,158; 5,948,684; 5,932,100; 5,716,852; herein incorporated by reference). In some embodiments, diffusion based methods may be combined with immunoassay based methods to process and detect one or more allergen indicators 106. Methods to conduct microscale diffusion immunoassays have been described (e.g., U.S. Pat. No. 6,541,213; herein incorporated by reference). Accordingly, microfluidic chips 108 may be configured in numerous ways to process one or more allergen indicators 106 through use of diffusion.

In some embodiments, one or more microfluidic chips 108 may be configured to analyze one or more samples 102 through use of filtration. In some embodiments, one or more microfluidic chips 108 may be configured to include one or more filters that have a molecular weight cut-off. For example, a filter may allow molecules of low molecular weight to pass through the filter while disallowing molecules of high molecular weight to pass through the filter. Accordingly, one or more allergen indicators 106 that are contained within a sample 102 may be allowed to pass through a filter while larger molecules contained within the sample 102 are disallowed from passing through the filter. Accordingly, in some embodiments, a microfluidic chip 108 may include two or more filters that selectively retain, or allow passage, of one or more allergen indicators 106 through the filters. Such configurations provide for selective separation of one or more allergen indicators 106 from one or more samples 102. Membranes and filters having numerous molecular weight cut-offs are commercially available (e.g., Millipore, Billerica, Mass.). In some embodiments, one or more microfluidic chips 108 may be configured to provide for dialysis of one or more samples 102. For example, in some embodiments, a microfluidic chip 108 may be configured to contain one or more samples 102 in one or more sample chambers that are separated from one or more dialysis chambers by a semi-permeable membrane. Accordingly, in some embodiments, one or more allergen indicators 106 that are able to pass through the semi-permeable membrane may be collected in the dialysis chamber. In other embodiments, one or more allergen indicators 106 may be retained in the one or more sample chambers while other sample 102 components may be separated from the one or more allergen indicators 106 by their passage through the semi-permeable membrane into the dialysis chamber. Accordingly, one or more microfluidic chips 108 may be configured to include two or more dialysis chambers for selective separation of one or more allergen indicators 106 from one or more samples 102. Semi-permeable membranes and dialysis tubing is available from numerous commercial sources (e.g., Millipore, Billerica, Mass.; Pierce, Rockford, Ill.; Sigma-Aldrich, St. Louis, Mo.). Methods that may be used for microfiltration have been described (e.g., U.S. Pat. No. 5,922,210; herein incorporated by reference).

In some embodiments, one or more microfluidic chips 108 may be configured to analyze one or more samples 102 through use of chromatography. Numerous chromatographic methods may be used to process one or more samples 102. Examples of such chromatographic methods include, but are not limited to, ion-exchange chromatography, affinity chromatography, gel filtration chromatography, hydroxyapatite chromatography, gas chromatography, reverse phase chromatography, thin layer chromatography, capillary chromatography, size exclusion chromatography, hydrophobic interaction media, and the like. In some embodiments, a microfluidic chip 108 may be configured to process one or more samples 102 through use of one or more chromatographic methods. In some embodiments, chromatographic methods may be used to process one or more samples 102 for one or more allergen indicators 106 that include one or more polynucleotides. For example, in some embodiments, one or more samples 102 may be applied to a chromatographic media to which the one or more polynucleotides bind. The remaining components of the sample 102 may be washed from the chromatographic media. The one or more polynucleotides may then be eluted from chromatographic media in a more purified state. Similar methods may be used to process one or more samples 102 for one or more allergen indicators 106 that include one or more proteins or polypeptides (e.g., Mondal and Gupta, Biomol. Eng., 23:59-76 (2006)). Chromatography media able to separate numerous types of molecules is commercially available (e.g., Bio-Rad, Hercules, Calif.; Qiagen, Valencia, Calif.; Pfizer, New York, N.Y.; Millipore, Billerica, Mass.; GE Healthcare Bio-Sciences Corp., Piscataway, N.J.).

In some embodiments, one or more microfluidic chips 108 may be configured to analyze one or more samples 102 through use of aptamer interaction. In some embodiments, one or more aptamers may include polynucleotides (e.g., deoxyribonucleic acid; ribonucleic acid; and derivatives of polynucleotides that may include polynucleotides that include modified bases, polynucleotides in which the phosphodiester bond is replaced by a different type of bond, or many other types of modified polynucleotides). In some embodiments, one or more aptamers may include peptide aptamers. Methods to prepare and use aptamers have been described (e.g., Collett et al., Methods, 37:4-15 (2005); Collet et al., Anal. Biochem., 338:113-123 (2005); Cox et al., Nucleic Acids Res., 30:20 e108 (2002); Kirby et al., Anal. Chem., 76:4066-4075 (2004); Ulrich, Handb. Exp. Pharmacol., 173:305-326 (2006); Baines and Colas, Drug Discovery Today, 11:334-341 (2006); Guthrie et al., Methods, 38:324-330 (2006); Geyer et al., Chapter 13: Selection of Genetic Agents from Random Peptide Aptamer Expression Libraries, Methods in Enzymology, Academic Press, pg. 171-208 (2000); U.S. Pat. No. 6,569,630; herein incorporated by reference). Aptamers may be configured in numerous ways within one or more microfluidic chips 108 to process one or more allergen indicators 106. For example, in some embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Labeled detector antibodies and/or aptamers that bind to the allergen indicator 106 (or the aptamer-allergen indicator 106 complex) may then be passed over the one or more aptamer-allergen indicator 106 complexes such that the labeled detector antibodies and/or aptamers will label the allergen indicator 106 (or the aptamer-allergen indicator 106 complex). Numerous labels may be used that include, but are not limited to, enzymes, fluorescent molecules, radioactive labels, spin labels, redox labels, and the like. In other embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Such binding provides for detection of the aptamer-allergen indicator 106 complex through use of methods that include, but are not limited to, surface plasmon resonance, conductivity, and the like (e.g., U.S. Pat. No. 7,030,989; herein incorporated by reference). In some embodiments, aptamers may be coupled to a substrate within a microfluidic chip 108 to provide for a competition assay. One or more samples 102 may be mixed with one or more reagent mixtures that include one or more labeled allergen indicators 106. The mixture may then be passed over the aptamers to facilitate binding of allergen indicators 106 in the sample 102 and labeled allergen indicators 106 in the reagent mixture to the aptamers. The unlabeled allergen indicators 106 in the sample 102 will compete with the labeled allergen indicators 106 in the reagent mixture for binding to the aptamers. Accordingly, the amount of label bound to the aptamers will vary in accordance with the concentration of unlabeled allergen indicators 106 in the sample 102. In some embodiments, aptamer interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more aptamers may be used in conjunction with one or more antibodies to process one or more samples 102. In some embodiments, aptamers and antibodies may be used interchangeably to process one or more samples 102. Accordingly, in some embodiments, methods and/or systems for processing and/or detecting allergen indicators 106 may utilize antibodies and aptamers interchangeably and/or in combination.

In some embodiments, one or more microfluidic chips 108 may be configured to analyze one or more samples 102 through use of electrical conductivity. In some embodiments, one or more samples 102 may be processed though use of magnetism. For example, in some embodiments, one or more samples 102 may be combined with one or more tagged polynucleotides that are tagged with a ferrous material, such as a ferrous bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed over an electromagnet to immobilize the hybridized complexes. Other components in the sample 102 may then be washed away from the hybridized complexes. In some embodiments, a chamber containing the magnetically immobilized hybridized complexes may be heated to release the sample polynucleotides from the magnetically immobilized tagged polynucleotides. The sample polynucleotides may then be collected in a more purified state. In other embodiments, similar methods may be used in conjunction with antibodies, aptamers, peptides, ligands, and the like. Accordingly, one or more microfluidic chips 108 may be configured in numerous ways to utilize magnetism to process one or more samples 102. In some embodiments, one or more samples 102 may be processed though use of eddy currents. Eddy current separation uses the principles of electromagnetic induction in conducting materials to separate non-ferrous metals by their different electric conductivities. An electrical charge is induced into a conductor by changes in magnetic flux cutting through it. Moving permanent magnets passing a conductor generates the change in magnetic flux. Accordingly, in some embodiments, one or more microfluidic chips 108 may be configured to include a magnetic rotor such that when conducting particles move through the changing flux of the magnetic rotor, a spiraling current and resulting magnetic field are induced. The magnetic field of the conducting particles may interact with the magnetic field of the magnetic rotor to impart kinetic energy to the conducting particles. The kinetic energy imparted to the conducting particles may then be used to direct movement of the conducting particles. Accordingly, non-ferrous particles, such as metallic beads, may be utilized to process one or more samples 102. For example, in some embodiments, one or more samples 102 may be combined with one or more tagged polynucleotides that are tagged with a non-ferrous material, such as an aluminum bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed through a magnetic field to impart kinetic energy to the non-ferrous bead. This kinetic energy may then be used to separate the hybridized complex. In other embodiments, similar methods may be used in conjunction with antibodies, aptamers, peptides, ligands, and the like. Accordingly, one or more microfluidic chips 108 may be configured in numerous ways to utilize eddy currents to process one or more samples 102. One or more microfluidic chips 108 may be configured in numerous ways to utilize electrical conductivity to process one or more samples 102.

In some embodiments, one or more microfluidic chips 108 may be configured to analyze one or more samples 102 through use of isoelectric focusing. Methods have been described that may be used to construct capillary isoelectric focusing systems (e.g., Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). Such systems may be modified to provide for the processing of one or more samples 102.

In some embodiments, one or more microfluidic chips 108 may be configured to analyze one or more samples 102 through use of electrophoresis. In some embodiments, one or more microfluidic chips 108 may be configured to process one or more samples 102 through use of one-dimensional electrophoresis. In some embodiments, one or more microfluidic chips 108 may be configured to process one or more samples 102 through use of two-dimensional electrophoresis. In some embodiments, one or more microfluidic chips 108 may be configured to process one or more samples 102 through use of gradient gel electrophoresis. In some embodiments, one or more microfluidic chips 108 may be configured to process one or more samples 102 through use electrophoresis under denaturing conditions. In some embodiments, one or more microfluidic chips 108 may be configured to process one or more samples 102 through use electrophoresis under native conditions. One or more microfluidic chips 108 may be configured to utilize numerous electrophoretic methods.

In some embodiments, one or more microfluidic chips 108 may be configured to analyze one or more samples 102 through use of immunoassay. In some embodiments, one or more microfluidic chips 108 may be configured to process one or more samples 102 through use of enzyme linked immunosorbant assay (ELISA). In some embodiments, one or more microfluidic chips 108 may be configured to process one or more samples 102 through use of radioimmuno assay (RIA). In some embodiments, one or more microfluidic chips 108 may be configured to process one or more samples 102 through use of enzyme immunoassay (EIA). In some embodiments, such methods may utilize antibodies (e.g., monoclonal antibodies, polyclonal antibodies, antibody fragments, single-chain antibodies, and the like), aptamers, or substantially any combination thereof. In some embodiments, a labeled antibody and/or aptamer may be used within an immunoassay. In some embodiments, a labeled ligand to which the antibody and/or aptamer binds may be used within an immunoassay. Numerous types of labels may be utilized. Examples of such labels include, but are not limited to, radioactive labels, fluorescent labels, enzyme labels, spin labels, magnetic labels, gold labels, colorimetric labels, redox labels, and the like. Numerous immunoassays are known and may be configured for processing one or more samples 102.

In some embodiments, one or more microfluidic chips 108 may be configured to analyze one or more samples 102 through use of one or more competition assays. In some embodiments, one or more microfluidic chips 108 may be configured to process one or more samples 102 through use of one or more polynucleotide based competition assays. One or more microfluidic chips 108 may be configured to include one or more polynucleotides coupled to a substrate, such as a polynucleotide array. The one or more microfluidic chips 108 may be further configured so that a sample 102 and/or substantially purified polynucleotides obtained from one or more samples 102, may be mixed with one or more reagent mixtures that include one or more labeled polynucleotides to form an analysis mixture. This analysis mixture is then passed over the substrate such that the labeled polynucleotides and the sample polynucleotides are allowed to hybridize to the polynucleotides that are immobilized on the substrate. The sample polynucleotides and the labeled polynucleotides will compete for binding to the polynucleotides that are coupled on the substrate. Accordingly, the presence and/or concentration of the polynucleotides in the sample 102 can be determined through detection of the label (e.g., the concentration of the polynucleotides in the sample 102 will be inversely related to the amount of label that is bound to the substrate). Numerous labels may be used that include, but are not limited to, enzymes, fluorescent molecules, radioactive labels, spin labels, redox labels, and the like. In some embodiments, one or more microfluidic chips 108 may be configured to include one or more antibodies, proteins, peptides, and/or aptamers that are coupled to a substrate. The one or more microfluidic chips 108 may be further configured so that a sample 102 and/or substantially purified sample polypeptides and/or sample peptides obtained from one or more samples 102, may be mixed with one or more reagent mixtures that include one or more labeled polypeptides and/or labeled peptides to form an analysis mixture. This analysis mixture can then be passed over the substrate such that the labeled polypeptides and/or labeled peptides and the sample polypeptides and/or sample peptides are allowed to bind to the antibodies, proteins, peptides, and/or aptamers that are immobilized on the substrate. The sample polypeptides and/or sample peptides and the labeled polypeptides and/or sample peptides will compete for binding to the antibodies, proteins, peptides, and/or aptamers that are coupled on the substrate. Accordingly, the presence and/or concentration of the sample polypeptides and/or sample peptides in the sample 102 can be determined through detection of the label (e.g., the concentration of the sample polypeptides and/or sample peptides in the sample 102 will be inversely related to the amount of label that is bound to the substrate). Numerous labels may be used that include, but are not limited to, enzymes, fluorescent molecules, radioactive labels, spin labels, redox labels, and the like. Microfluidic chips 108 may be configured to utilize numerous types of competition assays.

In some embodiments, one or more microfluidic chips 108 may be configured to utilize numerous analysis methods.

FIG. 23 illustrates alternative embodiments of system 2000 of FIG. 20. FIG. 23 illustrates example embodiments of module 2020. Additional embodiments may include an embodiment 2302, an embodiment 2304, an embodiment 2306, an embodiment 2308, and/or an embodiment 2310.

At embodiment 2302, module 2020 may include one or more reagent delivery units configured for detachable connection to the one or more microfluidic chips. In some embodiments, a system may include one or more reagent delivery units 116 configured for detachable connection to the one or more microfluidic chips 108. Reagent delivery units 116 may be configured to deliver one or more types of reagents to one or more microfluidic chips 108. In some embodiments, such reagents may be utilized to process one or more samples 102. In some embodiments, such reagents may be utilized to detect one or more allergen indicators 106. Examples of such reagents include, but are not limited to, solvents, water, tags, labels, antibodies, aptamers, polynucleotides, and the like. In some embodiments, one or more reagent delivery units 116 may include connectors that may be coupled to one or more microfluidic chips 108 to provide for delivery of one or more reagents to the one or more microfluidic chips 108. Examples of such connectors include, but are not limited to, leur lock fittings, needles, fluid connectors, and the like. In some embodiments, a reagent delivery unit 116 may include one or more pumps. In some embodiments, a reagent delivery unit 116 may include numerous reservoirs that may include numerous types of reagents. Accordingly, in some embodiments, a reagent delivery unit 116 may be configured to detachably connect with numerous types of microfluidic chips 108 that are configured to process and/or provide for detection of numerous types of allergen indicators 106.

At embodiment 2304, module 2020 may include one or more reagent reservoirs. In some embodiments, a system may include one or more reagent reservoirs. In some embodiments, the one or more reagent reservoirs may be configured to contain reagents that may be used to process and/or detect a single type of allergen indicator 106. In some embodiments, the one or more reagent reservoirs may be configured to contain reagents that may be used to process and/or detect numerous types of allergen indicators 106.

At embodiment 2306, module 2020 may include one or more waste reservoirs. In some embodiments, a system may include one or more waste reservoirs. Such waste reservoirs may be configured in numerous ways. For example such waste reservoirs may be configured for containing reagents, samples 102, and the like. In some embodiments, waste reservoirs may be configured to contain liquids, solids, gels, and substantially any combination thereof.

At embodiment 2308, module 2020 may include one or more reagent delivery units physically coupled to the one or more microfluidic chips. In some embodiments, a system may include one or more reagent delivery units 116 physically coupled to the one or more microfluidic chips 108. For example, in some embodiments, one or more reagent delivery units 116 may be included within a microfluidic chip 108 (e.g., as opposed to being separate from a microfluidic chip). In some embodiments, such microfluidic chips 108 may be configured for single use to process and/or analyze one or more allergen indicators 106 that may be present within one or more samples 102. The reagent delivery units 1.16 may contain numerous types of reagents that may provide for processing and/or analysis of one or more samples 102.

For example, in some embodiments, a microfluidic chip 108 may be configured for extraction and/or analysis of polynucleotides that may be included within one or more samples 102. In some embodiments, such a microfluidic chip 108 may include: a first reagent delivery unit 116 that includes an alkaline lysis buffer (e.g., sodium hydroxide/sodium dodecyl sulfate), a second reagent delivery unit 116 that includes an agent that precipitates the sodium dodecyl sulfate (e.g., potassium acetate), a third reagent delivery unit 116 that includes an extraction agent (e.g., phenol/chloroform), and a fourth reagent delivery unit 116 that includes a precipitation agent for precipitating any polynucleotides that may be present within the one or more samples 102. Accordingly, in some embodiments, a system may include one or more microfluidic chips 108 that are configured to include all of the reagents necessary to process and/or analyze one or more samples 102 for one or more allergen indicators 106. In some embodiments, such microfluidic chips 108 may be configured for single use. In some embodiments, such microfluidic chips 108 may be configured to detachably connect to one or more detection units 122 such that the same detection unit 122 may be used repeatedly through association with a new microfluidic chip 108.

At embodiment 2310, module 2020 may include one or more reagent delivery units that include one or more pumps. In some embodiments, a system may include one or more reagent delivery units 116 that include one or more pumps. Numerous types of pumps may be associated with one or more reagent delivery units 116.

Figure 24:
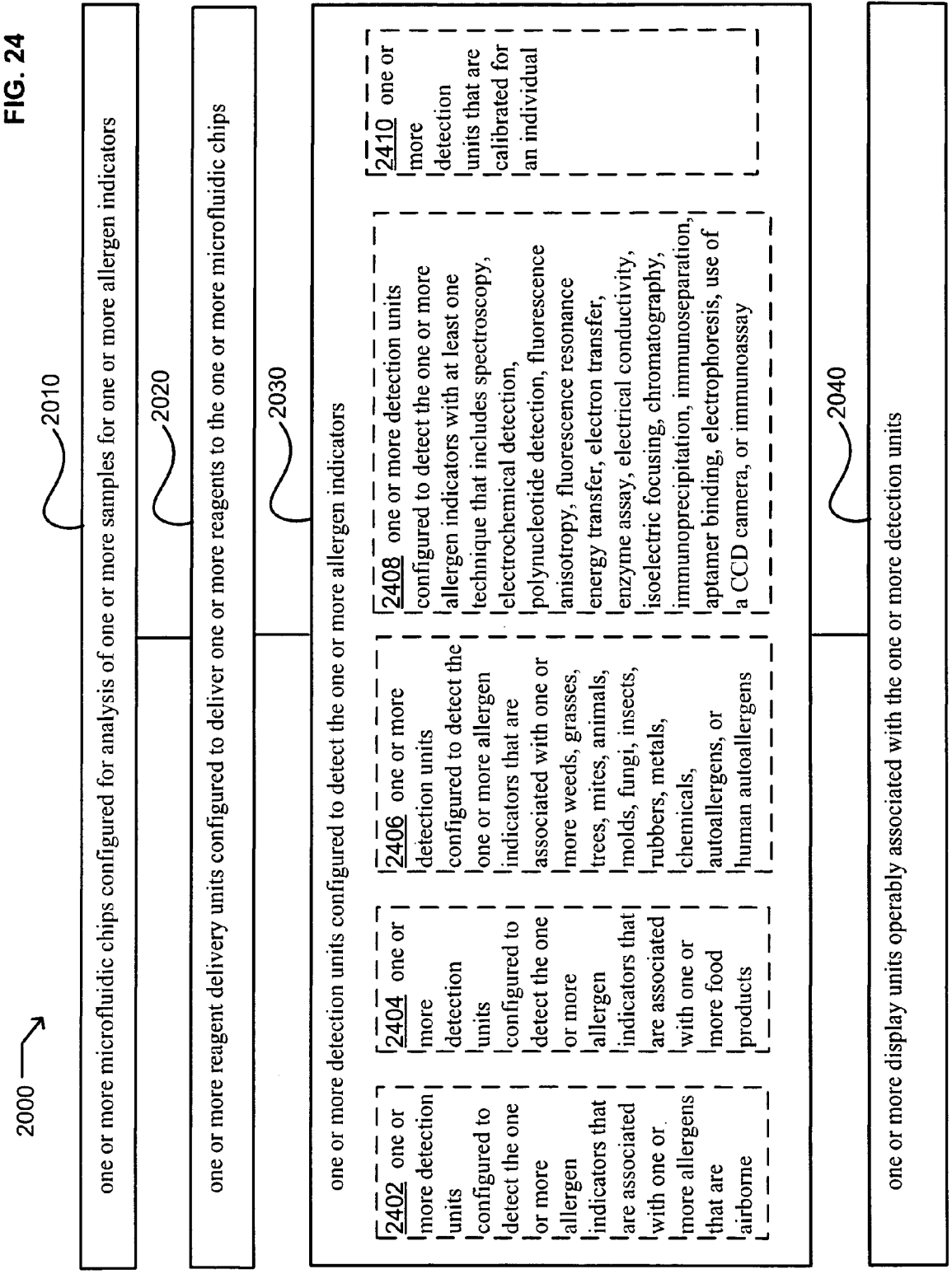
FIG. 24 illustrates alternate embodiments of the system of FIG. 20.

FIG. 24 illustrates alternative embodiments of system 2000 of FIG. 20. FIG. 24 illustrates example embodiments of module 2030. Additional embodiments may include an embodiment 2402, an embodiment 2404, an embodiment 2406, an embodiment 2408, and/or an embodiment 2410.

At embodiment 2402, module 2030 may include one or more detection units configured to detect the one or more allergen indicators that are associated with one or more allergens that are airborne. In some embodiments, a system may include one or more detection units 122 configured to detect one or more allergen indicators 106 that are associated with one or more allergens 104 that are airborne. Accordingly, in some embodiments, one or more detection units 122 may be configured to operably associate with the one or more microfluidic chips 108 and to detect one or more airborne allergens 104. For example, in some embodiments, one or more microfluidic chips 108 may be configured to allow one or more air samples 102 to contact the one or more microfluidic chips 108 such that one or more allergen indicators 106 included within the one or more air samples 102 are retained by the one or more microfluidic chips 108. In some embodiments, the one or more air samples 102 may be passed through a filter on which one or more airborne allergen indicators 106 are collected. The collected airborne allergen indicators 106 may then be washed from the filter and caused to pass over an antibody array to which the one or more airborne allergen indicators 106 become immobilized. The immobilized airborne allergen indicators 106 may then be detected through numerous methods that include, but are not limited to, electrical conductivity, immunoassay based methods, and the like. Accordingly, one or more detection units 122 may be configured to detect the one or more airborne allergen indicators 106. In some embodiments, one or more detection units 122 may be configured to operably associate with one or more microfluidic chips 108 such that the one or more detection units 122 facilitate air flow through the one or more microfluidic chips 108 to provide for air sampling. For example, in some embodiments, one or more detection units 122 may include one or more fans to push and/or pull air through one or more operably associated microfluidic chips 108. In some embodiments, one or more detection units 122 may include one or more bellows to push and/or pull air through one or more operably associated microfluidic chips 108. Detection units 122 may be configured in numerous ways to provide for detection of one or more airborne allergen indicators 106.

At embodiment 2404, module 2030 may include one or more detection units configured to detect the one or more allergen indicators that are associated with one or more food products. In some embodiments, a system may include one or more detection units 122 configured to detect one or more allergen indicators 106 that are associated with one or more food products. In some embodiments, one or more microfluidic chips 108 may be configured to provide for detection of one or more allergens 104 that are associated with one or more food products. Accordingly, in some embodiments, one or more detection units 122 may be configured to operably associate with the one or more microfluidic chips 108 and to detect one or more allergen indicators 106 that are associated with one or more food products. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Numerous methods may be used to detect one or more allergen indicators 106 that are associated with one or more food products. Such methods have been described herein. In addition, other detection methods that have been described may be modified to provide for detection of one or more allergen indicators 106 that are associated with one or more food products. In some embodiments, one or more detection units 122 may be configured to detect one or more polynucleotides, one or more polypeptides, one or more portions of one or more polynucleotides, and/or one or more portions of one or more polypeptides that have a nucleic acid sequence and/or an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, AY839230, or substantially any combination thereof.

At embodiment 2406, module 2030 may include one or more detection units configured to detect the one or more allergen indicators that are associated with one or more weeds, grasses, trees, mites, animals, molds, fungi, insects, rubbers, metals, chemicals, autoallergens, or human autoallergens. In some embodiments, a system may include one or more detection units 122 configured to detect one or more allergen indicators 106 that are associated with one or more weeds, grasses, trees, mites, animals, molds, fungi, insects, rubbers, metals, chemicals, autoallergens, human autoallergens, or substantially any combination thereof. Numerous allergen indicators 106 are known to be associated with weeds, grasses, trees, mites, animals, molds, fungi, insects, rubbers, metals, chemicals, autoallergens, or human autoallergens. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Accordingly, in some embodiments, one or more microfluidic chips 108 may be configured to process one or more samples 102 and provide for detection of one or more allergen indicators 106. In some embodiments, an allergen indicator 106 may be an allergenic particle. For example, in some embodiments, an allergen indicator 106 may include a complete pollen particle, such as a pollen particle, a spore, a flake of dander, and the like. In some embodiments, an allergen indicator 106 may be a portion of an allergenic particle. For example, in some embodiments, an allergen indicator 106 may include a portion of a pollen particle (e.g., polynucleotides, sporoderm, and the like). In some embodiments, allergen indicators 106 may include polynucleotides that are associated with one or more allergens 104. In some embodiments, allergen indicators 106 may include fragments of polynucleotides that are associated with one or more allergens 104. In some embodiments, allergen indicators 106 may include polypeptides, peptides, and/or proteins that are associated with one or more allergens 104. In some embodiments, allergen indicators 106 may include polysaccharides that are associated with one or more allergens 104. Accordingly, in some embodiments, one or more microfluidic chips 108 may be configured to provide for detection of one or more allergen indicators 106. In some embodiments, one or more detection units 122 may be configured to operably associate with one or more such microfluidic chips 108 and configured to detect one or more allergen indicators 106. Numerous detection methods may be used to detect one or more allergen indicators 106. Such methods have been described herein. In addition, detection methods that have been described may be modified to provide for detection of one or more allergen indicators 106. In some embodiments, one or more detection units 122 may be configured to detect and determine a concentration of one or more allergen indicators 106 that are included within a sample 102. For example, in some embodiments, one or more microfluidic chips 108 may be configured to provide for detection of one or more polynucleotides that are allergen indicators 106 through detection of electrical current produced upon hybridization of the one or more polynucleotides. Accordingly, in such embodiments, the one or more microfluidic chips 108 may be configured to produce an electrical current that is relative to polynucleotide concentration to provide for determination of polynucleotide concentration within one or more samples 102. Numerous configurations may be used in association with one or more allergen indicators 106 to provide for determination of allergen 104 concentration. In some embodiments, one or more microfluidic chips 108 may be configured to provide for identification of one or more allergens 104. For example, in some embodiments, one or more microfluidic chips 108 may include immobilized polynucleotides that selectively hybridize to one or more polynucleotides that are associated with a known allergen indicator 106. Accordingly, hybridization of one or more polynucleotides with the one or more immobilized polynucleotides indicates that a sample 102 includes one or more allergen indicators 106 that correspond to one or more known allergens 104. Accordingly, one or more detection units 122 may be configured to operably associate with such microfluidic chips 108 to provide for specific detection of one or more allergen indicators 106. In some embodiments, microfluidic chips 108 and/or detection units 122 may be configured to determine the identity and concentration of one or more allergen indicators 106 that are included within one or more samples 102.

At embodiment 2408, module 2030 may include one or more detection units configured to detect the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, a system may include one or more detection units 122 configured to detect one or more allergens 104 with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, filtration, electrophoresis, use of a CCD camera, immunoassay, or substantially any combination thereof. In some embodiments, one or more detection units 122 may be configured to detect one or more allergen indicators 106 that have been processed by one or more microfluidic chips 108. For example, in some embodiments, one or more microfluidic chips 108 may include a window (e.g., a quartz window, a cuvette analog, and/or the like) through which one or more detection units 122 may determine if one or more allergen indicators 106 are present or determine the concentration of one or more allergen indicators 106. In such embodiments, numerous techniques may be used to detect the one or more allergen indicators 106, such as visible light spectroscopy, ultraviolet light spectroscopy, infrared spectroscopy, fluorescence spectroscopy, and the like. Accordingly, in some embodiments, one or more detection units 122 may include circuitry and/or electro-mechanical mechanisms to detect one or more allergen indicators 106 present within one or more microfluidic chips 108 through a window in the one or more microfluidic chips 108. In some embodiments, one or more microfluidic chips 108 may be configured to process one or more samples 102 through use of surface plasmon resonance. In some embodiments, the one or more microfluidic chips 108 may include one or more antibodies, aptamers, proteins, peptides, polynucleotides, and the like, that are bound to a substrate (e.g., a metal film) within the one or more microfluidic chips 108. In some embodiments, such microfluidic chips 108 may include a prism through which one or more detection units 122 may shine light to detect one or more allergen indicators 106 that interact with the one or more antibodies, aptamers, proteins, peptides, polynucleotides, and the like, that are bound to a substrate. In some embodiments, one or more microfluidic chips 108 may include an exposed substrate surface that is configured to operably associate with one or more prisms that are included within one or more detection units 122. In some embodiments, one or more microfluidic chips 108 may include a nuclear magnetic resonance (NMR) probe. In such embodiments, the microfluidic chips 108 may be configured to associate with one or more detection units 122 that accept the NMR probe and are configured to detect one or more allergen indicators 106 through use of NMR spectroscopy. Accordingly, microfluidic chips 108 and detection units 122 may be configured in numerous ways to associate with each other to provide for detection of one or more allergen indicators 106.

In some embodiments, one or more allergen indicators 106 may be detected through use of spectroscopy. Numerous types of spectroscopic methods may be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., Clinical Chemistry, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, one or more allergen indicators 106 may be detected through use of electrochemical detection. In some embodiments, one or more polynucleotides may be detected through electrochemical detection. For example, in some embodiments, a polynucleotide that includes a redox label, such as ferrocene is coupled to a gold electrode. The labeled polynucleotide forms a stem-loop structure that can self-assemble onto a gold electrode by means of facile gold-thiol chemistry. Hybridization of a sample 102 polynucleotide induces a large conformational change in the surface-confined polynucleotide structure, which in turn alters the electron-transfer tunneling distance between the electrode and the redoxable label. The resulting change in electron transfer efficiency may be measured by cyclic voltammetry (Fan et al., Proc. Natl. Acad. Sci., 100:9134-9137 (2003); Wang et al., Anal. Chem., 75:3941-3945 (2003); Singh-Zocchi et al., Proc. Natl. Acad. Sci., 100:7605-7610 (2003)).

Such methods may be used to detect messenger ribonucleic acid, genomic deoxyribonucleic acid, and fragments thereof.

In some embodiments, one or more allergen indicators 106 may be detected through use of polynucleotide detection. In some embodiments, one or more detection units 122 may be configured to detect one or more allergen indicators 106 through use of polynucleotide detection. Numerous methods may be used to detect one or more polynucleotides. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described (e.g., U.S. Pat. Nos. 7,118,910 and 6,960,437; herein incorporated by reference). Such methods may be adapted to provide for detection of one or more allergen indicators 106. In some embodiments, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube may be combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Accordingly, polynucleotides that hybridize to one or more allergen indicators 106 may include one or more carbon nanotubes. Methods to utilize carbon nanotubes as probes for nucleic acid interaction have been described (e.g., U.S. Pat. No. 6,821,730; herein incorporated by reference). Numerous other methods based on polynucleotide detection may be used to detect one or more allergen indicators 106.

In some embodiments, one or more allergen indicators 106 may be detected through use of fluorescence anisotropy. Fluorescence anisotropy is based on measuring the steady state polarization of sample 102 fluorescence imaged in a confocal arrangement. A linearly polarized laser excitation source preferentially excites fluorescent target molecules with transition moments aligned parallel to the incident polarization vector. The resultant fluorescence is collected and directed into two channels that measure the intensity of the fluorescence polarized both parallel and perpendicular to that of the excitation beam. With these two measurements, the fluorescence anisotropy, r, can be determined from the equation: r=(Intensity parallel−Intensity perpendicular)/(Intensity parallel+2(Intensity perpendicular)) where the I terms indicate intensity measurements parallel and perpendicular to the incident polarization. Fluorescence anisotropy detection of fluorescent molecules has been described. Accordingly, fluorescence anisotropy may be coupled to numerous fluorescent labels as have been described herein and as have been described.

In some embodiments, one or more allergen indicators 106 may be detected through use of fluorescence resonance energy transfer (FRET). Fluorescence resonance energy transfer refers to an energy transfer mechanism between two fluorescent molecules. A fluorescent donor is excited at its fluorescence excitation wavelength. This excited state is then nonradiatively transferred to a second molecule, the fluorescent acceptor. Fluorescence resonance energy transfer may be used within numerous configurations to detect one or more allergen indicators 106. For example, in some embodiments, an antibody may be labeled with a fluorescent donor and one or more allergen indicators 106 may be labeled with a fluorescent acceptor. Accordingly, such labeled antibodies and allergen indicators 106 may be used within competition assays to detect the presence and/or concentration of one or more allergen indicators 106 in one or more samples 102. Numerous combinations of fluorescent donors and fluorescent acceptors may be used to detect one or more allergen indicators 106. Accordingly, one or more detection units 122 may be configured to emit one or more wavelength of light to excite a fluorescent donor and may be configured to detect one or more wavelength of light emitted by the fluorescent acceptor. Accordingly, in some embodiments, one or more detection units 122 may be configured to accept one or more microfluidic chips 108 that include a quartz window through which fluorescent light may pass to provide for detection of one or more allergen indicators 106 through use of fluorescence resonance energy transfer. Accordingly, fluorescence resonance energy transfer may be used in conjunction with competition assays and/or numerous other types of assays to detect one or more allergen indicators 106.

In some embodiments, one or more allergen indicators 106 may be detected through use of electron transfer. Electron transfer is the process by which an electron moves from an electron donor to an electron acceptor causing the oxidation states of the electron donor and the electron acceptor to change. In some embodiments, electron transfer may occur when an electron is transferred from one or more electron donors to an electrode. In some embodiments, electron transfer may be utilized within competition assays to detect one or more allergen indicators 106. For example, in some embodiments, one or more microfluidic chips 108 may include one or more polynucleotides that may be immobilized on one or more electrodes. The immobilized polynucleotides may be incubated with a reagent mixture that includes sample polynucleotides and polynucleotides that are tagged with an electron donor. Hybridization of the tagged polynucleotides to the immobilized polynucleotides allows the electron donor to transfer an electron to the electrode to produce a detectable signal. Accordingly, a decrease in signal due to the presence of one or more polynucleotides that are allergen indicators 106 in the reagent mixture indicates the presence of an allergen indicator 106 in the sample 102. Such methods may be used in conjunction with polynucleotides, polypeptides, peptides, antibodies, aptamers, and the like. One or more microfluidic chips 108 may be configured to utilize numerous electron transfer based assays to provide for detection of one or more allergen indicators 106 by a detection unit 122.

In some embodiments, one or more allergen indicators 106 may be detected through use of one or more enzyme assays. Numerous enzyme assays may be used to provide for detection of one or more allergen indicators 106. Examples of such enzyme assays include, but are not limited to, beta-galactosidase assays, peroxidase assays, catalase assays, alkaline phosphatase assays, and the like. In some embodiments, enzyme assays may be configured such that an enzyme will catalyze a reaction involving an enzyme substrate that produces a fluorescent product. Accordingly, one or more detection units 122 may be configured to detect fluorescence resulting from the fluorescent product. Enzymes and fluorescent enzyme substrates are known and are commercially available (e.g., Sigma-Aldrich, St. Louis, Mo.). In some embodiments, enzyme assays may be configured as binding assays that provide for detection of one or more allergen indicators 106. For example, in some embodiments, one or more microfluidic chips 108 may be configured to include a substrate to which is coupled to one or more antibodies, aptamers, peptides, proteins, polynucleotides, ligands, and the like, that will interact with one or more allergen indicators 106. One or more samples 102 may be passed across the substrate such that one or more allergen indicators 106 present within the one or more samples 102 will interact with the one or more antibodies, aptamers, peptides, proteins, polynucleotides, ligands, and the like, and be immobilized on the substrate. One or more antibodies, aptamers, peptides, proteins, polynucleotides, ligands, and the like, that are labeled with an enzyme may then be passed across the substrate such that the one or more labeled antibodies, aptamers, peptides, proteins, polynucleotides, ligands, and the like, will bind to the one or more immobilized allergen indicators 106. An enzyme substrate may then be introduced to the one or more immobilized enzymes such that the enzymes are able to catalyze a reaction involving the enzyme substrate to produce a fluorescent product. Such assays are often referred to as sandwich assays. Accordingly, one or more detection units 122 may be configured to detect one or more products of enzyme catalysis to provide for detection of one or more allergen indicators 106.

In some embodiments, one or more allergen indicators 106 may be detected through use of electrical conductivity. In some embodiments, one or more microfluidic chips 108 may be configured to process one or more samples 102 and provide for detection of one or more allergen indicators 106 through use of electrical conductivity. In some embodiments, such microfluidic chips 108 may be configured to operably associate with one or more detection units 122 such that the one or more detection units 122 can detect one or more allergen indicators 106 through use of electrical conductivity. In some embodiments, one or more microfluidic chips 108 may be configured to include two or more electrodes that are each coupled to one or more detector polynucleotides. Interaction of an allergen associated polynucleotide, such as hybridization, with two detector polynucleotides that are coupled to two different electrodes will complete an electrical circuit. This completed circuit will provide for the flow of a detectable electrical current between the two electrodes and thereby provide for detection of one or more allergen associated polynucleotides that are allergen indicators 106. In some embodiments, the electrodes may be carbon nanotubes (e.g., U.S. Pat. No. 6,958,216; herein incorporated by reference). In some embodiments, electrodes may include, but are not limited to, one or more conductive metals, such as gold, copper, iron, silver, platinum, and the like; one or more conductive alloys; one or more conductive ceramics; and the like. In some embodiments, electrodes may be selected and configured according to protocols typically used in the computer industry that include, but are not limited to, photolithography, masking, printing, stamping, and the like. In some embodiments, other molecules and complexes that interact with one or more allergen indicators 106 may be used to detect the one or more allergen indicators 106 through use of electrical conductivity. Examples of such molecules and complexes include, but are not limited to, proteins, peptides, antibodies, aptamers, and the like. For example, in some embodiments, two or more antibodies may be immobilized on one or more electrodes such that contact of the two or more antibodies with an allergen indicator 106, such as a spore, a pollen particle, a dander particle, and the like, will complete an electrical circuit and facilitate the production of a detectable electrical current. Accordingly, in some embodiments, one or more microfluidic chips 108 may be configured to include electrical connectors that are able to operably associate with one or more detection units 122 such that the detection units 122 may detect an electrical current that is due to interaction of one or more allergen indicators 106 with two or more electrodes. In some embodiments, one or more detection units 122 may include electrical connectors that provide for operable association of one or more microfluidic chips 108 with the one or more detection units 122. In some embodiments, the one or more detectors are configured for detachable connection to one or more microfluidic chips 108. Microfluidic chips 108 and detection units 122 may be configured in numerous ways to process one or more samples 102 and detect one or more allergen indicators 106.

In some embodiments, one or more allergen indicators 106 may be detected through use of isoelectric focusing. In some embodiments, one or more microfluidic chips 108 may be configured to process one or more samples 102 and provide for detection of one or more allergen indicators 106 through use of isoelectric focusing. In some embodiments, native isoelectric focusing may be utilized to process and/or detect one or more allergen indicators 106. In some embodiments, denaturing isoelectric focusing may be utilized to process and/or detect one or more allergen indicators 106. Methods to construct microfluidic channels that may be used for isoelectric focusing have been reported (e.g., Macounova et al., Anal Chem., 73:1627-1633 (2001); Macounova et al., Anal Chem., 72:3745-3751 (2000); Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). In some embodiments, one or more microfluidic chips 108 may be configured to process one or more samples 102 through use of methods that include isoelectric focusing. In some embodiments, one or more detection units 122 may be configured to operably associate with one or more such microfluidic chips 108 such that the one or more detection units 122 can be used to detect one or more allergen indicators 106 that have been focused within one or more microfluidic channels of the one or more microfluidic chips 108. In some embodiments, one or more detection units 122 may be configured to include one or more CCD cameras that can be used to detect one or more allergen indicators 106. In some embodiments, one or more detection units 122 may be configured to include one or more spectrometers that can be used to detect one or more allergen indicators 106. Numerous types of spectrometers may be utilized to detect one or more allergen indicators 106 following isoelectric focusing. In some embodiments, one or more detection units 122 may be configured to utilize refractive index to detect one or more allergen indicators 106. In some embodiments, one or more microfluidic chips 108 may be configured to combine one or more samples 102 with one or more reagent mixtures that include one or more binding molecules and/or binding complexes that bind to one or more allergen indicators 106 that may be present within the one or more samples 102 to form an allergen indicator-binding molecule/binding complex. Examples of such binding molecules and/or binding complexes that bind to one or more allergen indicators 106 include, but are not limited to, antibodies, aptamers, peptides, proteins, polynucleotides, and the like. In some embodiments, an allergen indicator-binding molecule/binding complex may be processed through use of isoelectric focusing and then detected with one or more detection units 122. In some embodiments, one or more binding molecules and/or one or more binding complexes may include a label. Numerous labels may be used and include, but are not limited to, radioactive labels, fluorescent labels, colorimetric labels, spin labels, fluorescent labels, and the like. Accordingly, in some embodiments, an allergen indicator-binding molecule (labeled)/binding complex (labeled) may be processed through use of isoelectric focusing and then detected with one or more detection units 122 that are configured to detect the one or more labels. Microfluidic chips 108 and detection units 122 may be configured in numerous ways to process one or more samples 102 and detect one or more allergen indicators 106 though use of isoelectric focusing.

In some embodiments, one or more allergen indicators 106 may be detected through use of chromatographic methodology alone or in combination with additional processing and/or detection methods. In some embodiments, one or more microfluidic chips 108 may be configured to process one or more samples 102 and provide for detection of one or more allergen indicators 106 through use of chromatographic methods. Accordingly, in some embodiments, one or more detection units 122 may be configured to operably associate with the one or more microfluidic chips 108 and detect one or more allergen indicators 106 that were processed through use of chromatographic methods. In some embodiments, the one or more detection units 122 may be configured to operably associate with one or more microfluidic chips 108 and supply solvents and other reagents to the one or more microfluidic chips 108. For example, in some embodiments, one or more detection units 122 may include pumps and solvent/buffer reservoirs that are configured to supply solvent/buffer flow through chromatographic media (e.g., a chromatographic column) that is operably associated with one or more microfluidic chips 108. In some embodiments, one or more detection units 122 may be configured to operably associate with one or more microfluidic chips 108 and be configured to utilize one or more methods to detect one or more allergen indicators 106. Numerous types of chromatographic methods and media may be used to process one or more samples 102 and provide for detection of one or more allergen indicators 106. Chromatographic methods include, but are not limited to, low pressure liquid chromatography, high pressure liquid chromatography (HPLC), microcapillary low pressure liquid chromatography, microcapillary high pressure liquid chromatography, ion exchange chromatography, affinity chromatography, gel filtration chromatography, size exclusion chromatography, thin layer chromatography, paper chromatography, gas chromatography, and the like. In some embodiments, one or more microfluidic chips 108 may be configured to include one or more high pressure microcapillary columns. Methods that may be used to prepare microcapillary HPLC columns (e.g., columns with a 100 micrometer-500 micrometer inside diameter) have been described (e.g., Davis et al., Methods, A Companion to Methods in Enzymology, 6: Micromethods for Protein Structure Analysis, ed. by John E. Shively, Academic Press, Inc., San Diego, 304-314 (1994); Swiderek et al., Trace Structural Analysis of Proteins. Methods of Enzymology, ed. by Barry L. Karger & William S. Hancock, Spectrum, Publisher Services, 271, Chap. 3, 68-86 (1996); Moritz and Simpson, J. Chromatogr., 599:119-130 (1992)). In some embodiments, one or more microfluidic chips 108 may be configured to include one or more affinity columns. Methods to prepare affinity columns have been described. Briefly, a biotinylated site may be engineered into a polypeptide, peptide, aptamer, antibody, or the like. The biotinylated protein may then be incubated with avidin coated polystyrene beads and slurried in Tris buffer. The slurry may then be packed into a capillary affinity column through use of high pressure packing. Affinity columns may be prepared that may include one or more molecules and/or complexes that interact with one or more allergen indicators 106. For example, in some embodiments, one or more aptamers that bind to one or more allergen indicators 106 may be used to construct an affinity column. Accordingly, numerous chromatographic methods may be used alone, or in combination with additional methods, to process and detect one or more allergen indicators 106. Numerous detection methods may be used in combination with numerous types of chromatographic methods. Accordingly, one or more detection units 122 may be configured to utilize numerous detection methods to detect one or more allergen indicators 106 that are processed through use of one or more chromatographic methods. Examples of such detection methods include, but are not limited to, conductivity detection, use of ion-specific electrodes, refractive index detection, colorimetric detection, radiological detection, detection by retention time, detection through use of elution conditions, spectroscopy, and the like. For example, in some embodiments, one or more chromatographic markers may be added to one or more samples 102 prior to the samples 102 being applied to a chromatographic column. One or more detection units 122 that are operably associated with the chromatographic column may be configured to detect the one or more chromatographic markers and use the elution time and/or position of the chromatographic markers as a calibration tool for use in detecting one or more allergen indicators 106 if those allergen indicators 106 are eluted from the chromatographic column. In some embodiments, one or more detection units 122 may be configured to utilize one or more ion-specific electrodes to detect one or more allergen indicators 106. For example, such electrodes may be used to detect allergen indicators 106 that include, but are not limited to, metals (e.g., tin, silver, nickel, cobalt, chromate), nitrates, nitrites, sulfites, and the like. Such allergen indicators 106 are often associated with food, beverages, clothing, jewelry, and the like. Accordingly, chromatographic methods may be used in combination with additional methods and in combination with numerous types of detection methods.

In some embodiments, one or more allergen indicators 106 may be detected through use of immunoprecipitation. In some embodiments, one or more detection units 122 may be configured to detect one or more allergen indicators 106 through use of immunoprecipitation. In some embodiments, immunoprecipitation may be utilized in combination with additional processing and/or detection methods to detect one or more allergen indicators 106. In some embodiments, one or more microfluidic chips 108 may be configured to process one or more samples 102 through use of immunoprecipitation. For example, in some embodiments, one or more samples 102 may be combined with one or more antibodies that bind to one or more allergen indicators 106 to form one or more antibody-allergen indicator 106 complexes. An insoluble form of an antibody binding constituent, such as protein A (e.g., protein A-sepharose bead, protein A-magnetic bead, protein A-ferrous bead, protein A-non-ferrous bead, and the like), Protein G, a second antibody, an aptamer, and the like, may then be mixed with the antibody-allergen indicator 106 complex such that the insoluble antibody binding constituent binds to the antibody-allergen indicator 106 complex and provides for precipitation of the antibody-allergen indicator 106 complex. Such complexes may be separated from other sample 102 components to provide for detection of one or more allergen indicators 106. For example, in some embodiments, sample 102 components may be washed away from the precipitated antibody-allergen indicator 106 complexes. In some embodiments, one or more microfluidic chips 108 that are configured for immunoprecipitation may be operably associated with one or more centrifugation units 118 to assist in precipitating one or more antibody-allergen indicator 106 complexes. In some embodiments, aptamers (polypeptide and/or polynucleotide) may be used in combination with antibodies or in place of antibodies. Accordingly, one or more detection units 122 may be configured to detect one or more allergen indicators 106 through use of numerous detection methods in combination with immunoprecipitation based methods.

In some embodiments, one or more allergen indicators 106 may be detected through use of immunoseparation. In some embodiments, one or more detection units 122 may be configured to detect one or more allergen indicators 106 through use of immunoseparation. In some embodiments, immunoseparation may be utilized in combination with additional processing and/or detection methods to detect one or more allergen indicators 106. In some embodiments, one or more microfluidic chips 108 may be configured to process one or more samples 102 through use of immunoseparation. For example, in some embodiments, one or more samples 102 may be combined with one or more antibodies that bind to one or more allergen indicators 106 to form one or more antibody-allergen indicator 106 complexes. An antibody binding constituent may be added that binds to the antibody-allergen complex.

Examples of such antibody binding constituents that may be used alone or in combination include, but are not limited to, protein A (e.g., protein A-sepharose bead, protein A-magnetic bead, protein A-ferrous bead, protein A-non-ferrous bead, and the like), Protein G, a second antibody, an aptamer, and the like. Such antibody binding constituents may be mixed with an antibody-allergen indicator 106 complex such that the antibody binding constituent binds to the antibody-allergen indicator 106 complex and provides for separation of the antibody-allergen indicator 106 complex. In some embodiments, the antibody binding constituent may include a tag that allows the antibody binding constituent and complexes that include the antibody binding constituent to be separated from other components in one or more samples 102. In some embodiments, the antibody binding constituent may include a ferrous material. Accordingly, antibody-allergen indicator 106 complexes may be separated from other sample 102 components through use of a magnet, such as an electromagnet. In some embodiments, an antibody binding constituent may include a non-ferrous metal. Accordingly, antibody-allergen indicator 106 complexes may be separated from other sample 102 components through use of an eddy current to direct movement of one or more antibody-allergen indicator 106 complexes. In some embodiments, two or more forms of an antibody binding constituents may be used to detect one or more allergen indicators 106. For example, in some embodiments, a first antibody binding constituent may be coupled to a ferrous material and a second antibody binding constituent may be coupled to a non-ferrous material. Accordingly, the first antibody binding constituent and the second antibody binding constituent may be mixed with antibody-allergen indicator 106 complexes such that the first antibody binding constituent and the second antibody binding constituent bind to antibody-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more antibodies that bind to one or more allergen indicators 106 to form one or more antibody-allergen indicator 106 complexes. In some embodiments, the one or more antibodies may include one or more tags that provide for separation of the antibody-allergen indicator 106 complexes. For example, in some embodiments, an antibody may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with immunoseparation based methods. In some embodiments, aptamers (polypeptide and/or polynucleotide) may be used in combination with antibodies or in place of antibodies.

In some embodiments, one or more allergen indicators 106 may be detected through use of aptamer binding. In some embodiments, one or more detection units 122 may be configured to detect one or more allergen indicators 106 through use of aptamer binding. In some embodiments, aptamer binding may be utilized in combination with additional processing and/or detection methods to detect one or more allergen indicators 106. In some embodiments, one or more microfluidic chips 108 may be configured to process one or more samples 102 through use of aptamer binding. For example, in some embodiments, one or more samples 102 may be combined with one or more aptamers that bind to one or more allergen indicators 106 to form one or more aptamer-allergen indicator 106 complexes. In some embodiments, aptamer binding constituents may be added that bind to the aptamer-allergen complex. Numerous aptamer binding constituents may be utilized. For example, in some embodiments, one or more aptamers may include one or more tags to which one or more aptamer binding constituents may bind. Examples of such tags include, but are not limited to, biotin, avidin, streptavidin, histidine tags, nickel tags, ferrous tags, non-ferrous tags, and the like. In some embodiments, one or more tags may be conjugated with a label to provide for detection of one or more complexes. Examples of such tag-label conjugates include, but are not limited to, Texas red conjugated avidin, alkaline phosphatase conjugated avidin, CY2 conjugated avidin, CY3 conjugated avidin, CY3.5 conjugated avidin, CY5 conjugated avidin, CY5.5 conjugated avidin, fluorescein conjugated avidin, glucose oxidase conjugated avidin, peroxidase conjugated avidin, rhodamine conjugated avidin, agarose conjugated anti-protein A, alkaline phosphatase conjugated protein A, anti-protein A, fluorescein conjugated protein A, IRDye® 800 conjugated protein A, peroxidase conjugated protein A, sepharose protein A, alkaline phosphatase conjugated streptavidin, AMCA conjugated streptavidin, anti-streptavidin (*Streptomyces avidinii*) (rabbit) IgG Fraction, beta-galactosidase conjugated streptavidin, CY2 conjugated streptavidin, CY3 conjugated streptavidin, CY3.5 conjugated streptavidin, CY5 conjugated streptavidin, CY5.5 conjugated streptavidin, fluorescein conjugated streptavidin, IRDye® 700DX conjugated streptavidin, IRDye® 800 conjugated streptavidin, IRDye® 800CW conjugated streptavidin, peroxidase conjugated streptavidin, phycoerythrin conjugated streptavidin, rhodamine conjugated streptavidin, Texas red conjugated streptavidin, alkaline phosphatase conjugated biotin, anti-biotin (rabbit) IgG fraction, beta-galactosidase conjugated biotin, glucose oxidase conjugated biotin, peroxidase conjugated biotin, alkaline phosphatase conjugated protein G, anti-protein G (rabbit) Agarose conjugated, anti-protein G (Rabbit) IgG fraction, fluorescein conjugated protein G, IRDye® 800 conjugated protein G, peroxidase conjugated protein G, and the like. Many such labeled tags are commercially available (e.g., Rockland Immunochemicals, Inc., Gilbertsville, Pa.). Such labels may also be used in association with other methods to process and detect one or more allergen indicators 106. Aptamer binding constituents may be mixed with an aptamer-allergen indicator 106 complex such that the aptamer binding constituent binds to the aptamer-allergen indicator 106 complex and provides for separation of the aptamer-allergen indicator 106 complex. In some embodiments, the aptamer binding constituent may include a tag that allows the aptamer binding constituent and complexes that include the aptamer binding constituent to be separated from other components in one or more samples 102. In some embodiments, the aptamer binding constituent may include a ferrous material. Accordingly, aptamer-allergen indicator 106 complexes may be separated from other sample 102 components through use of a magnet, such as an electromagnet. In some embodiments, an aptamer binding constituent may include a non-ferrous metal. Accordingly, aptamer-allergen indicator 106 complexes may be separated from other sample 102 components through use of an eddy current to direct movement of one or more aptamer-allergen indicator 106 complexes. In some embodiments, two or more forms of aptamer binding constituents may be used to detect one or more allergen indicators 106. For example, in some embodiments, a first aptamer binding constituent may be coupled to a ferrous material and a second aptamer binding constituent may be coupled to a non-ferrous material. Accordingly, the first aptamer binding constituent and the second aptamer binding constituent may be mixed with aptamer-allergen indicator 106 complexes such that the first aptamer binding constituent and the second aptamer binding constituent bind to aptamer-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more aptamers that bind to one or more allergen indicators 106 to form one or more aptamer-allergen indicator 106 complexes. In some embodiments, the one or more aptamer may include one or more tags that provide for separation of the aptamer-allergen indicator 106 complexes. For example, in some embodiments, an aptamer may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with aptamer binding based methods. In some embodiments, antibodies may be used in combination with aptamers or in place of aptamers.

In some embodiments, one or more allergen indicators 106 may be detected through use of electrophoresis. In some embodiments, one or more microfluidic chips 108 may be configured to process one or more samples 102 through use of electrophoresis. In some embodiments, such microfluidic chips 108 may be configured to operably associate with one or more detection units 122. Accordingly, in some embodiments, one or more detection units 122 may be configured to operably associate with one or more microfluidic chips 108 and detect one or more allergen indicators 106 that were processed through use of electrophoresis. Numerous electrophoretic methods may be utilized to provide for detection of one or more allergen indicators 106. Examples of such electrophoretic methods include, but are not limited to, capillary electrophoresis, one-dimensional electrophoresis, two-dimensional electrophoresis, native electrophoresis, denaturing electrophoresis, polyacrylamide gel electrophoresis, agarose gel electrophoresis, and the like. Numerous detection methods may be used in combination with one or more electrophoretic methods to detect one or more allergen indicators 106. In some embodiments, one or more allergen indicators 106 may be detected according to the position to which the one or more allergen indicators 106 migrate within an electrophoretic field (e.g., a capillary and/or a gel). In some embodiments, the position of one or more allergen indicators 106 may be compared to one or more standards. For example, in some embodiments, one or more samples 102 may be mixed with one or more molecular weight markers prior to gel electrophoresis. The one or more samples 102, that include the one or more molecular weight markers, may be subjected to electrophoresis and then the gel may be stained. In such embodiments, the molecular weight markers may be used as a reference to detect one or more allergen indicators 106 present within the one or more samples 102. In some embodiments, one or more components that are known to be present within one or more samples 102 may be used as a reference to detect one or more allergen indicators 106 present within the one or more samples 102. In some embodiments, gel shift assays may be used to detect one or more allergen indicators 106. For example, in some embodiments, a sample 102 (e.g., a single sample 102 or combination of multiple samples 102) may be split into a first sample 102 and a second sample 102. The first sample 102 may be mixed with an antibody, aptamer, ligand, or other molecule and/or complex that binds to the one or more allergen indicators 106. The first and second samples 102 may then be subjected to electrophoresis. The gels corresponding to the first sample 102 and the second sample 102 may then be analyzed to determine if one or more allergen indicators 106 are present within the one or more samples 102. Microfluidic chips 108 and detection units 122 may be configured in numerous ways to process and detect one or more allergen indicators 106 through use of electrophoresis.

In some embodiments, one or more allergen indicators 106 may be detected through use of one or more charge-coupled device (CCD) cameras. In some embodiments, one or more detection units 122 that include one or more CCD cameras may be configured to operably associate with one or more microfluidic chips 108. Such detection units 122 may be utilized in combination with numerous processing methods. Examples of such methods include, but are not limited to, electrophoresis; competition assays; methods based on polynucleotide interaction, protein interaction, peptide interaction, antibody interaction, aptamer interaction, immunoprecipitation, immunoseparation, and the like. For example, in some embodiments, one or more microfluidic chips 108 may be configured to process one or more samples 102 through use of immunoprecipitation. In some embodiments, one or more antibodies may be conjugated to a fluorescent label such that binding of one or more labeled antibodies to one or more allergen indicators 106 included within one or more samples 102 will form a fluorescently labeled antibody-allergen indicator 106 complex. One or more insoluble allergen indicator 106 binding constituents, such as a sepharose bead that includes an antibody or aptamer that binds to the one or more allergen indicators 106, may be bound to the fluorescently labeled antibody-allergen indicator 106 complex and used to precipitate the complex. One or more detection units 122 that include a CCD camera that is configured to detect fluorescent emission from the one or more fluorescent labels may be used to detect the one or more allergen indicators 106. In some embodiments, one or more CCD cameras may be configured to utilize dark frame subtraction to cancel background and increase sensitivity of the camera. In some embodiments, one or more detection units 122 may include one or more filters to select and/or filter wavelengths of energy that can be detected by one or more CCD cameras (e.g., U.S. Pat. No. 3,971,065; herein incorporated by reference). In some embodiments, one or more detection units 122 may include polarized lenses. One or more detection units 122 may be configured in numerous ways to utilize one or more CCD cameras to detect one or more allergen indicators 106.

In some embodiments, one or more allergen indicators 106 may be detected through use of immunoassay. In some embodiments, one or more microfluidic chips 108 may be configured to process one or more samples 102 through use of immunoassay. In some embodiments, one or more detection units 122 may be configured to operably associate with one or more such microfluidic chips 108 and to detect one or more allergen indicators 106 associated with the use of immunoassay. Numerous types of detection methods may be used in combination with immunoassay based methods. In some embodiments, a label may be used within one or more immunoassays that may be detected by one or more detection units 122. Examples of such labels include, but are not limited to, fluorescent labels, spin labels, fluorescence resonance energy transfer labels, radiolabels, electrochemiluminescent labels (e.g., U.S. Pat. Nos. 5,093,268; 6,090,545; herein incorporated by reference), and the like. In some embodiments, electrical conductivity may be used in combination with immunoassay based methods.

At embodiment 2410, module 2030 may include one or more detection units that are calibrated for an individual. In some embodiments, a system may include one or more detection units 122 that are calibrated for an individual. In some embodiments, one or more detection units 122 may be calibrated to detect one or more specific allergens 104 and/or allergen indicators 106 that produce an allergic response by an individual. For example, in some embodiments, one or more detection units 122 may be calibrated to detect peanuts and/or peanut associated products for an individual who is allergic to peanuts. In some embodiments, one or more detection units 122 may be calibrated to detect different concentrations of allergen indicators 106. For example, in some embodiments, an individual may produce an allergic response if exposed to an allergen 104 at a concentration that is above a certain level. Accordingly, in some embodiments, a detection unit 122 may be calibrated to detect one or more concentrations of one or more allergen indicators 106 that produce an allergic response within an individual.

Figure 25:
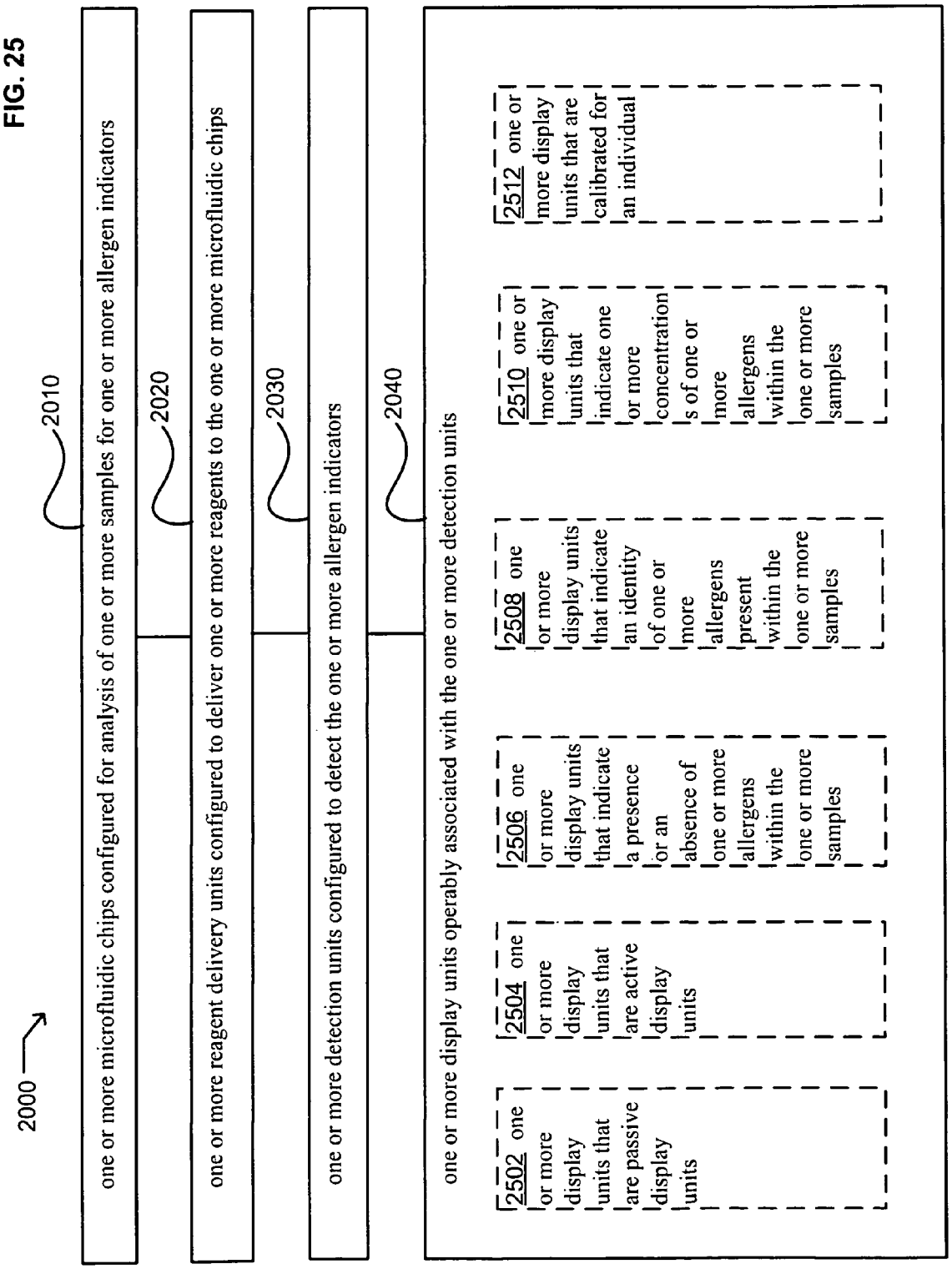
FIG. 25 illustrates alternate embodiments of the system of FIG. 20.

FIG. 25 illustrates alternative embodiments of system 2000 of FIG. 20. FIG. 25 illustrates example embodiments of module 2040. Additional embodiments may include an embodiment 2502, an embodiment 2504, an embodiment 2506, an embodiment 2508, an embodiment 2510, and/or an embodiment 2512.

At embodiment 2502, module 2040 may include one or more display units that are passive display units. In some embodiments, a system may include one or more display units 124 that are passive display units 124. In some embodiments, one or more display units 124 may include one or more liquid crystal displays (LCD). Methods to construct passive displays have been described (e.g., U.S. Pat. Nos. 4,807,967; 4,729,636: 4,436,378; 4,257,041; herein incorporated by reference).

At embodiment 2504, module 2040 may include one or more display units that are active display units. In some embodiments, a system may include one or more display units 124 that are active display units 124. Numerous active display units 124 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), wide ultra extended graphics array (WUXGA).

At embodiment 2506, module 2040 may include one or more display units that indicate a presence or an absence of one or more allergens within the one or more samples. In some embodiments, a system may include one or more display units 124 that indicate a presence or an absence of one or more allergens 104 within the one or more samples 102. In some embodiments, one or more display units 124 may use a colorimetric message to indicate a presence or an absence of one or more allergen indicators 106 within one or more samples 102. For example, in some embodiments, one or more display units 124 may display a green light if one or more allergen indicators 106 are not found within one or more samples 102 and a red light if one or more allergen indicators 106 are found within one or more samples 102. In some embodiments, one or more display units 124 may use a pictographic message to indicate a presence or an absence of one or more allergen indicators 106 within one or more samples 102. For example, in some embodiments, one or more display units 124 may display a smiley face if one or more allergen indicators 106 are not found within one or more samples 102 and a frowny face if one or more allergen indicators 106 are found within one or more samples 102. In some embodiments, one or more display units 124 may use a typographical message to indicate a presence or an absence of one or more allergen indicators 106 within one or more samples 102. For example, in some embodiments, one or more display units 124 may display an "Allergen Not Present" message if one or more allergen indicators 106 are not found within one or more samples 102 and an "Allergen Present" message if one or more allergen indicators 106 are found within one or more samples 102. Such messages may be displayed in numerous languages. In some embodiments, one or more display units 124 may display one or more messages in multiple formats. For example, in some embodiments, one or more messages may be displayed in colored text.

At embodiment 2508, module 2040 may include one or more display units that indicate an identity of one or more allergens present within the one or more samples. In some embodiments, a system may include one or more display units 124 that indicate an identity of one or more allergens 104 present within the one or more samples 102. In some embodiments, one or more display units 124 may indicate an identity of one or more allergens 104 that correspond to the one or more allergen indicators 106 present within the one or more samples 102. In some embodiments, one or more display units 124 may be operably associated with one or more microfluidic chips 108 that are configured to identify one or more allergen indicators 106. Accordingly, in some embodiments, one or more display units 124 may be configured to display the identity of one or more allergens 104 that are present and/or absent from one or more samples 102. For example, in some embodiments, a display unit 124 may be configured to indicate a presence or an absence of beta-lactoglobulin in a food product.

At embodiment 2510, module 2040 may include one or more display units that indicate one or more concentrations of one or more allergens within the one or more samples. In some embodiments, a system may include one or more display units 124 that indicate one or more concentrations of one or more allergens 104 within the one or more samples 102. In some embodiments, one or more display units 124 may indicate one or more concentrations of one or more allergens 104 that correspond to the one or more allergen indicators 106 present within the one or more samples 102. Concentration may be displayed in numerous formats. For example, in some embodiments, concentration may be expressed numerically (e.g., mass allergen indicator 106 per volume sample 102 (e.g., milligrams per milliliter), mass allergen indicator 106 per mass sample 102 (e.g., milligrams per milligram of sample), parts per million, and the like). In some embodiments, concentration may be expressed graphically. For example, in some embodiments, one or more display units 124 may include a display having a gray scale on which the concentration of one or more allergen indicators 106 that are present within one or more samples 102 may be indicated (e.g., higher concentrations of one or more allergens 104 may be displayed as dark gray while lower concentrations of one or more allergens 104 may be displayed as light gray). In some embodiments, one or more display units 124 may include a display having a color scale on which the concentration of one or more allergen indicators 106 that are present within one or more samples 102 may be indicated (e.g., low concentrations of one or more allergen indicators 106 may be indicated by a green light, intermediate concentrations of one or more allergen indicators 106 may be indicated by a yellow light, high concentrations of one or more allergen indicators 106 may be indicated by a red light). In some embodiments, one or more display units 124 may be calibrated to an individual. For example, in such embodiments, an individual may use the display to obtain an immediate reading that will indicate if a food product contains a dangerous level of one or more allergens 104.

At embodiment 2512, module 2040 may include one or more display units that are calibrated for an individual. In some embodiments, a system may include one or more display units 124 that are calibrated for an individual. In some embodiments, one or more display units 124 may be calibrated to display whether one or more allergens 104, and/or allergen indicators 106, that are specific to an individual are present or absent within one or more samples 102. For example, in some embodiments, one or more display units 124 may be configured to display whether one or more samples 102 contain shellfish associated allergens 104 for an individual known to be allergic to shellfish. In some embodiments, one or more display units 124 may be calibrated to indicate safe and/or unsafe concentrations of one or more allergens 104 within one or more samples 102 for an individual.

Figure 26:
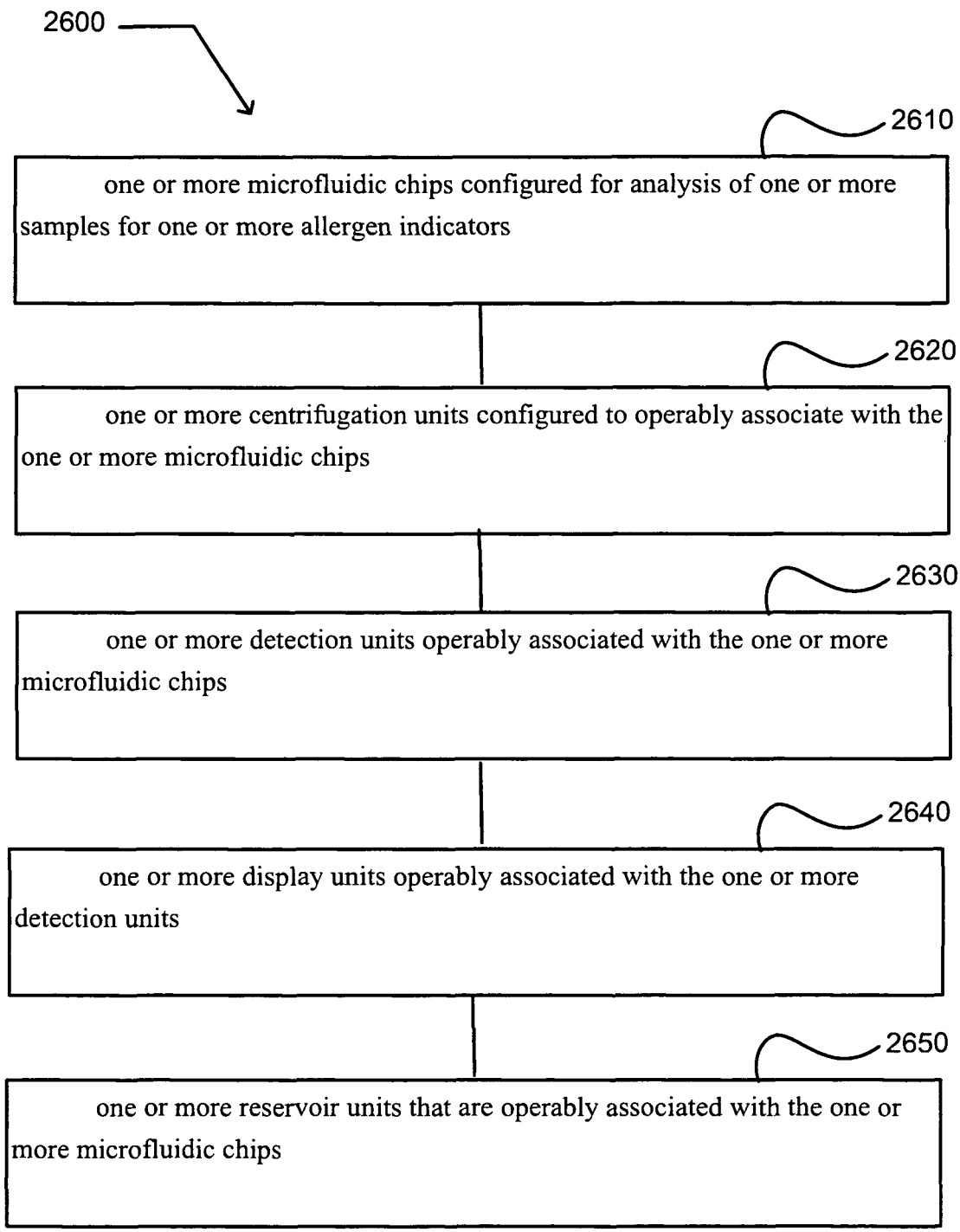
FIG. 26 illustrates an example system 2600 in which embodiments may be implemented.

FIG. 26 illustrates a system 2600 representing examples of modules that may be used to perform a method for analysis of one or more allergens 104. In FIG. 26, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various modules are presented in the sequence(s) illustrated, it should be understood that the various modules may be configured in numerous orientations.

The system 2600 includes module 2610 that includes one or more microfluidic chips configured for analysis of one or more samples for one or more allergen indicators. In some embodiments, module 2610 may include one or more microfluidic chips configured for detachable connection to the one or more detection units. In some embodiments, module 2610 may include one or more microfluidic chips configured for analysis of the one or more samples that include one or more liquids. In some embodiments, module 2610 may include one or more microfluidic chips configured for analysis of the one or more samples that include one or more solids. In some embodiments, module 2610 may include one or more microfluidic chips configured for analysis of the one or more samples that include one or more gases. In some embodiments, module 2610 may include one or more microfluidic chips configured for analysis of the one or more samples for the one or more allergen indicators that are associated with one or more airborne allergens. In some embodiments, module 2610 may include one or more microfluidic chips configured for analysis of the one or more samples for the one or more allergen indicators that are associated with one or more food products. In some embodiments, module 2610 may include one or more microfluidic chips configured for analysis of the one or more samples for the one or more allergen indicators that are associated with one or more weeds, grasses, trees, mites, animals, molds, fungi, insects, rubbers, autoallergens, or human autoallergens. In some embodiments, module 2610 may include one or more microfluidic chips configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay.

The system 2600 includes module 2620 that includes one or more centrifugation units configured to operably associate with the one or more microfluidic chips. In some embodiments, module 2620 may include one or more centrifugation units configured to centrifuge the one or more microfluidic chips that are operably associated with the one or more centrifugation units. In some embodiments, module 2620 may include one or more centrifugation units configured to provide for chromatographic separation. In some embodiments, module 2620 may include one or more centrifugation units configured for polynucleotide extraction from the one or more samples. In some embodiments, module 2620 may include one or more centrifugation units configured to provide for gradient centrifugation.

The system 2600 includes module 2630 that includes one or more detection units operably associated with the one or more microfluidic chips. In some embodiments, module 2630 may include one or more detection units configured to detect the one or more allergen indicators that are associated with one or more allergens that are airborne. In some embodiments, module 2630 may include one or more detection units configured to detect the one or more allergen indicators that are associated with one or more food products. In some embodiments, module 2630 may include one or more detection units configured to detect the one or more allergen indicators that are associated with one or more weeds, grasses, trees, mites, animals, molds, fungi, insects, rubbers, metals, chemicals, autoallergens, or human autoallergens. In some embodiments, module 2630 may include one or more detection units configured to detect the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, module 2630 may include one or more detection units that are calibrated for an individual.

The system 2600 may optionally include module 2640 that includes one or more display units operably associated with the one or more detection units. In some embodiments, module 2640 may include one or more display units that are passive display units. In some embodiments, module 2640 may include one or more display units that are active display units. In some embodiments, module 2640 may include one or more display units that indicate a presence or an absence of one or more allergens within the one or more samples. In some embodiments, module 2640 may include one or more display units that indicate an identity of one or more allergens present within the one or more samples. In some embodiments, module 2640 may include one or more display units that indicate one or more concentrations of one or more allergens within the one or more samples. In some embodiments, module 2640 may include one or more display units that are calibrated for an individual.

The system 2600 may optionally include module 2650 that includes one or more reservoir units that are operably associated with the one or more microfluidic chips. In some embodiments, module 2650 may include one or more reservoirs that are configured for containing one or more reagents. In some embodiments, module 2650 may include one or more reservoirs that are configured as one or more waste reservoirs.

Figure 27:
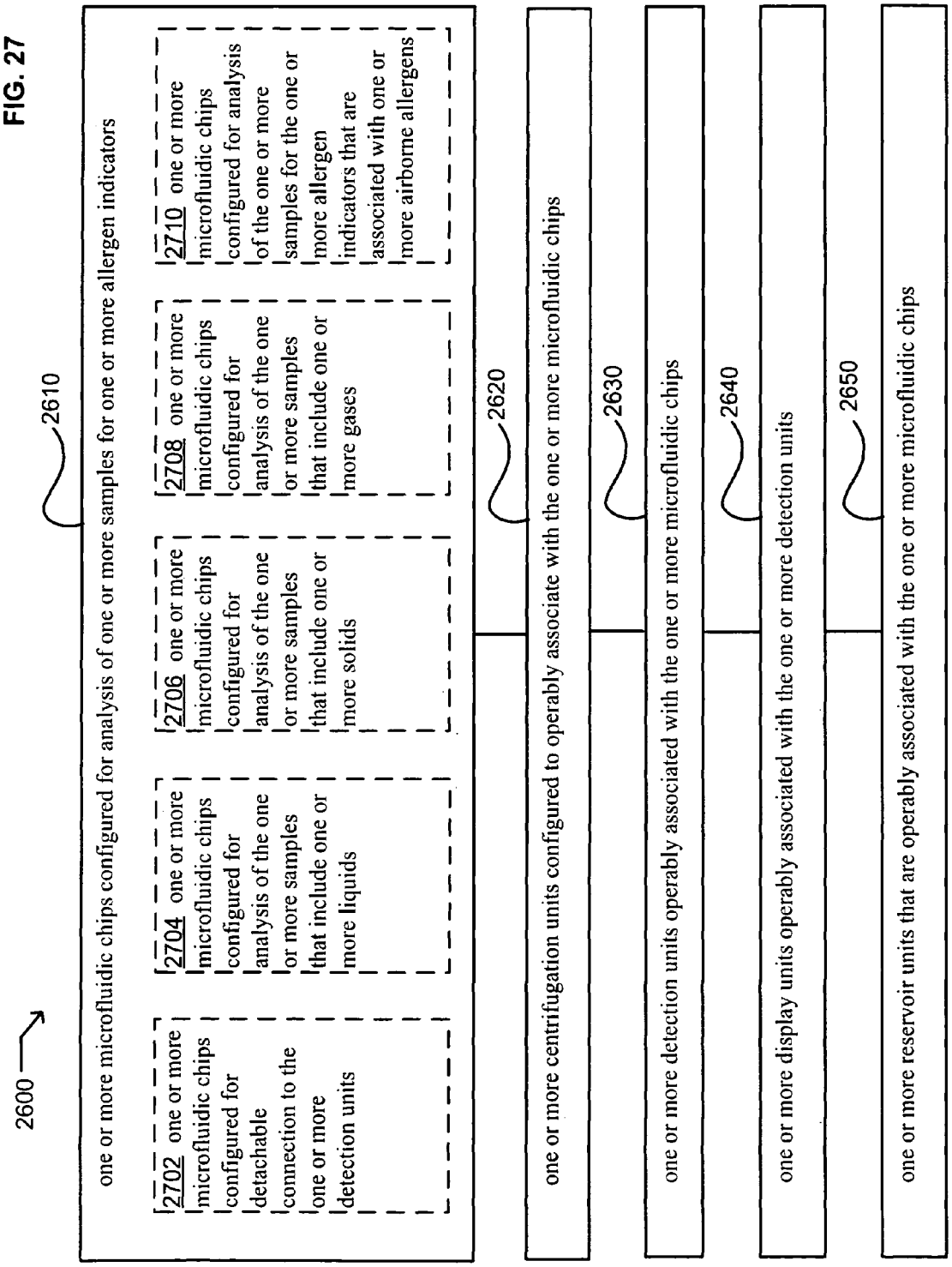
FIG. 27 illustrates alternate embodiments of the system of FIG. 26.

FIG. 27 illustrates alternative embodiments of system 2600 of FIG. 26. FIG. 27 illustrates example embodiments of module 2610. Additional embodiments may include an embodiment 2702, an embodiment 2704, an embodiment 2706, an embodiment 2708, and/or an embodiment 2710.

At embodiment 2702, module 2610 may include one or more microfluidic chips configured for detachable connection to the one or more detection units. In some embodiments, a system may include one or more microfluidic chips 108 configured for detachable connection to the one or more detection units 122. In some embodiments, a system may include one or more detection units 122 that are configured to detachably connect with microfluidic chips 108 that are configured to process and/or analyze different types of allergen indicators 106. For example, a system may include a detection unit 122 that may detachably connect to a first microfluidic chip 108 that is configured to analyze airborne allergen indicators 106 and detachably connect to a second microfluidic chip 108 that is configured to analyze food associated allergen indicators 106. Accordingly, in some embodiments, a system may include a single detection unit 122 that may be utilized to detect numerous types of allergen indicators 106 through use of microfluidic chips 108 that are configured to process and/or analyze numerous types of allergen indicators 106. Such configurations may be configured for field use. For example, in some embodiments, a system may include one or more detection units 122 that are configured to associate with microfluidic chips 108 that are designed for single use. In some embodiments, such systems provide for the detection of specific allergen indicators 106 through use of a common detection unit 122 that is configured to detachably connect with microfluidic chips 108 that are configured to process and/or analyze the specific allergen indicators 106. The one or more detection units 122 may be configured to utilize numerous methods to detect one or more allergen indicators 106. Examples of such methods include, but are not limited to, surface plasmon resonance, spectroscopy, radioassay, electrical conductivity, and the like.

At embodiment 2704, module 2610 may include one or more microfluidic chips configured for analysis of the one or more samples that include one or more liquids. In some embodiments, a system may include one or more microfluidic chips 108 configured for analysis of the one or more samples 102 that include one or more liquids. Microfluidic chips 108 may be configured for analysis of numerous types of liquids. Examples of such liquids include, but are not limited to, beverages, water, food products, solvents, and the like. In some embodiments, a microfluidic chip 108 may be configured to analyze one or more solvents that include one or more dissolved metal samples 102. For example, metal may be contacted with a solvent to obtain a sample 102 of the metal. The solvent may then be delivered to a microfluidic chip 108 for analysis. Accordingly, microfluidic chips 108 may be configured in numerous ways such that they may analyze one or more samples 102 that include a liquid.

At embodiment 2706, module 2610 may include one or more microfluidic chips configured for analysis of the one or more samples that include one or more solids. In some embodiments, a system may include one or more microfluidic chips 108 configured for analysis of the one or more samples 102 that include one or more solids. In some embodiments, such microfluidic chips 108 may be configured to suspend a solid sample 102 in a fluid. In some embodiments, such microfluidic chips 108 may be configured to crush a sample 102 into smaller particles. For example, in some embodiments, a microfluidic chip 108 may crush a solid sample 102. In some embodiments, a microfluidic chip 108 may include one or more sonicators that break a sample 102 into smaller particles to facilitate detection of one or more allergen indicators 106 that may be present within the sample 102. For example, in some embodiments, solid spores may be broken into smaller particles to provide for detection of one or more polynucleotides that are associated with the spores. In some embodiments, a microfluidic chip 108 may be configured to analyze one or more samples 102 that include metal. For example, in some embodiments, a microfluidic chip 108 may be configured to accept a metal sample 102 (e.g., from a piece of jewelry). In such embodiments, a microfluidic chip 108 may be configured to dissolve the metal sample 102 in a suitable solvent. For example, the metal sample 102 may be dissolved in hydrochloric acid media and then tin may be extracted from the hydrochloric acid with 2-ethylhexyl phosphonic acid mono-2-ethylhexyl ester in toluene. The extracted tin may then be detected through use of an ion-specific electrode. Accordingly, microfluidic chips 108 may be configured in numerous ways such that they may analyze one or more samples 102 that include a solid.

At embodiment 2708, module 2610 may include one or more microfluidic chips configured for analysis of the one or more samples that include one or more gases. In some embodiments, a system may include one or more microfluidic chips 108 configured for analysis of the one or more samples 102 that include one or more gases. For example, in some embodiments, one or more gases that are being analyzed may be passed through one or more microfluidic chips 108. In some embodiments, gas may be pumped through a microfluidic chip 108. In some embodiments, gas may be drawn through a microfluidic chip 108 through use of a vacuum. In some embodiments, gas may be passed through a filter on which suspected allergen indicators 106 are collected for analysis. Accordingly, large volumes of gas may be analyzed. In some embodiments, one or more gases may be analyzed for one or more allergen indicators 106 that include one or more metals. For example, gases may be analyzed for metals that are associated with tanks in which the gases are stored, such as iron, steel, aluminum, and the like.

At embodiment 2710, module 2610 may include one or more microfluidic chips configured for analysis of the one or more samples for the one or more allergen indicators that are associated with one or more airborne allergens. In some embodiments, a system may include one or more microfluidic chips 108 configured for analysis of the one or more samples 102 for the one or more allergen indicators 106 that are associated with one or more airborne allergens 104. Examples of such airborne allergens 104 include, but are not limited to, pollen, dander, seeds, exhaust particles (e.g., diesel exhaust) and the like. In some embodiments, the allergen indicators 106 may be collected within one or more microfluidic chips 108 through filtering air that is passed through the one or more microfluidic chips 108. Such filtering may occur through numerous mechanisms that may include, but are not limited to, use of physical filters, passing air through a fluid bubble chamber, passing the air through an electrostatic filter, and the like.

Figure 28:
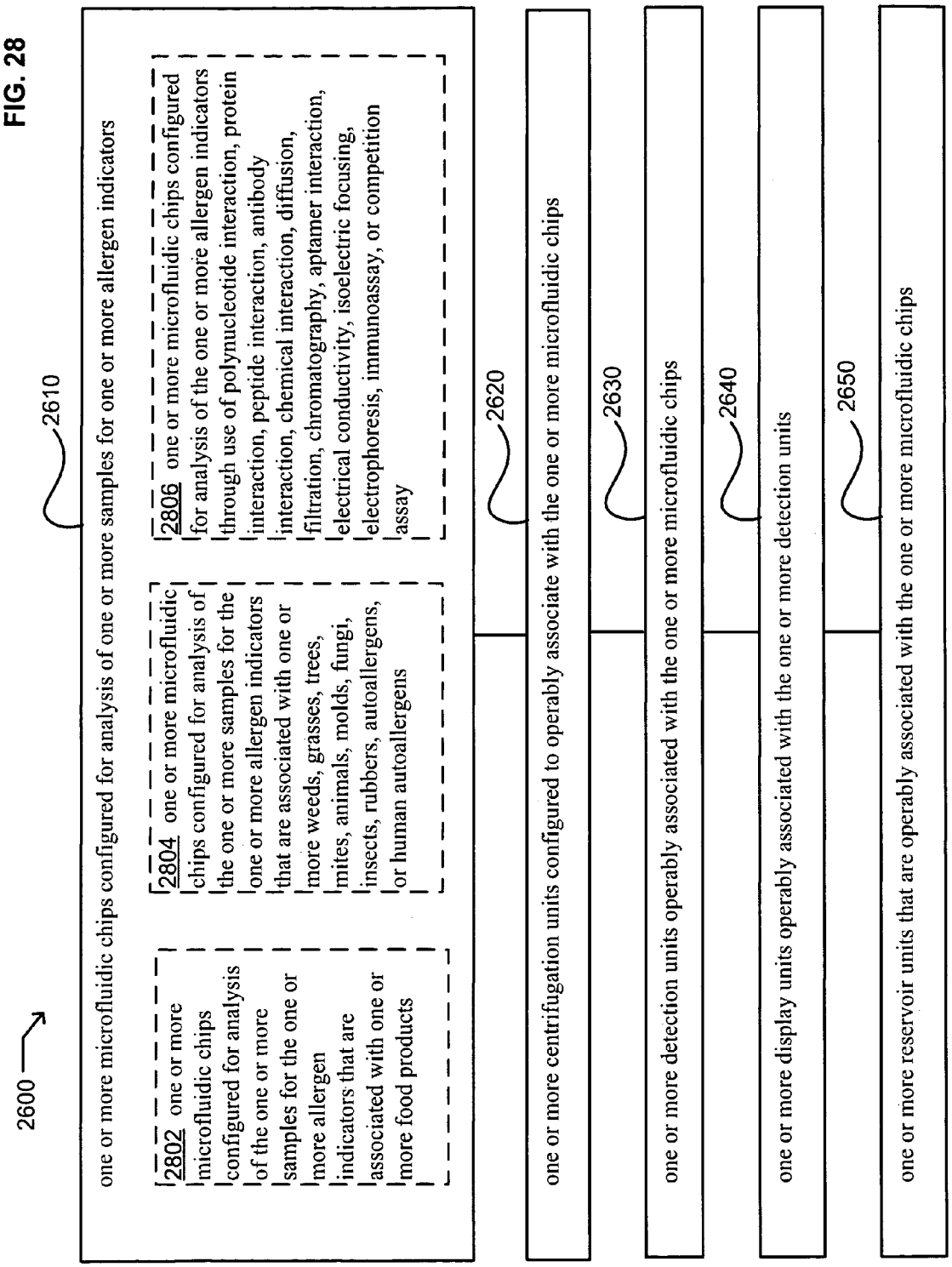
FIG. 28 illustrates alternate embodiments of the system of FIG. 26.

FIG. 28 illustrates alternative embodiments of system 2600 of FIG. 26. FIG. 28 illustrates example embodiments of module 2610. Additional embodiments may include an embodiment 2802, an embodiment 2804, and/or an embodiment 2806.

At embodiment 2802, module 2610 may include one or more microfluidic chips configured for analysis of the one or more samples for the one or more allergen indicators that are associated with one or more food products. In some embodiments, a system may include one or more microfluidic chips 108 configured for analysis of the one or more samples 102 for the one or more allergen indicators 106 that are associated with one or more food products. Such allergen indicators 106 are described herein and are known. For example, in some embodiments, one or more microfluidic chips 108 may be configured to analyze one or more food products at a restaurant to facilitate detection of a presence or an absence of an allergen indicator 106 within the food product, such as a presence of one or more allergen indicators 106 associated with nuts, dairy products, crustaceans, eggs, gluten, soy, and the like. In some embodiments, one or more microfluidic chips 108 may be configured to analyze one or more polynucleotides, one or more polypeptides, one or more portions of one or more polynucleotides, and/or one or more portions of one or more polypeptides that have a nucleic acid sequence and/or an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, AY839230, or substantially any combination thereof. Accordingly, one or more microfluidic chips 108 may be configured to process numerous types of food products to facilitate detection of numerous types of allergen indicators 106.

At embodiment 2804, module 2610 may include one or more microfluidic chips configured for analysis of the one or more samples for the one or more allergen indicators that are associated with one or more weeds, grasses, trees, mites, animals, molds, fungi, insects, rubbers, autoallergens, or human autoallergens. In some embodiments, a system may include one or more microfluidic chips 108 configured for analysis of the one or more samples 102 for the one or more allergen indicators 106 that are associated with one or more weeds, grasses, trees, mites, animals, molds, fungi, insects, rubbers, autoallergens, human autoallergens, or substantially any combination thereof. In some embodiments, one or more microfluidic chips 108 may be configured for analysis of the one or more samples 102 for the one or more allergen indicators 106 associated with one or more weeds, grasses, trees, mites, animals, molds, fungi, insects, rubbers, metals, chemicals, autoallergens, or human autoallergens. Such allergen indicators 106 are described herein and are known. For example, in some embodiments, one or more microfluidic chips 108 may be configured to process one or more material samples 102 to determine if the material contains latex.

At embodiment 2806, module 2610 may include one or more microfluidic chips configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay. In some embodiments, a system may include one or more microfluidic chips 108 configured for analysis of the one or more allergen indicators 106 through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof. In some embodiments, allergen indicators 106 may be separated from other materials included within one or more samples 102 through processing.

In some embodiments, one or more microfluidic chips 108 may be configured to analyze one or more allergen indicators 106 through use of polynucleotide interaction. Numerous methods based on polynucleotide interaction may be used. Examples of such methods include, but are not limited to, those based on polynucleotide hybridization, polynucleotide ligation, polynucleotide amplification, polynucleotide degradation, and the like. Methods that utilize intercalation dyes, FRET analysis, capacitive DNA detection, and nucleic acid amplification have been described (e.g., U.S. Pat. Nos. 7,118, 910 and 6,960,437; herein incorporated by reference). In some embodiments, fluorescence resonance energy transfer, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube are combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Methods to utilize carbon nanotubes as probes for nucleic acid interaction have been described (e.g., U.S. Pat. No. 6,821,730; herein incorporated by reference).

In some embodiments, one or more microfluidic chips 108 may be configured to analyze one or more allergen indicators 106 through use of protein interaction. Numerous methods based on protein interaction may be used. In some embodiments, protein interaction may be used to immobilize one or more allergen indicators 106. In some embodiments, protein interaction may be used to separate one or more allergen indicators 106 from one or more samples 102. Examples of such methods include, but are not limited to, those based on ligand binding, protein-protein binding, protein cross-linking, use of green fluorescent protein, phage display, the two-hybrid system, protein arrays, fiber optic evanescent wave sensors, chromatographic techniques, fluorescence resonance energy transfer, regulation of pH to control protein assembly and/or oligomerization, and the like. For example, tropomyosin is a major muscle protein in crustaceans that is thought to be a major shrimp allergen 104. Tropomyosin is associated with the well known actin-troponin-myosin complex. Calcium ion binding to troponin enables troponin to bind tropomyosin and shift it from the binding sites of myosin on the actin proteins. Without the presence of Calcium ion, troponin is no longer able to bind to tropomyosin, and tropomyosin again blocks the binding sites of myosin on the actin proteins. Tropomyosin also binds to the calcium-binding protein calcyclin (Nelson et al., Molecular & Cellular Proteomics 1:253-259 (2002) and Liou and Chen, European Journal of Biochemistry, 270:3092-3100 (2003)). Accordingly, protein interactions may be used to separate tropomyosin (allergen indicator 106) from one or more samples 102. Similar methods may be used with numerous proteins. Methods that may be used to construct protein arrays have been described (e.g., Warren et al., Anal. Chem., 76:4082-4092 (2004) and Walter et al., Trends Mol. Med., 8:250-253 (2002), U.S. Pat. No. 6,780,582; herein incorporated by reference).

In some embodiments, one or more microfluidic chips 108 may be configured to analyze one or more samples 102 through use of peptide interaction. Peptides are generally described as being polypeptides that include less than one hundred amino acids. For example, peptides include dipeptides, tripeptides., and the like. In some embodiments, peptides may include from two to one hundred amino acids. In some embodiments, peptides may include from two to fifty amino acids. In some embodiments, peptides may include from two to one twenty amino acids. In some embodiments, peptides may include from ten to one hundred amino acids. In some embodiments, peptides may include from ten to fifty amino acids. Accordingly, peptides can include numerous numbers of amino acids. Numerous methods based on peptide interaction may be used. In some embodiments, peptide interaction may be used to immobilize one or more allergen indicators 106. In some embodiments, peptide interaction may be used to separate one or more allergen indicators 106 from one or more samples 102. Examples of such methods include, but are not limited to, those based on ligand binding, peptide-protein binding, peptide-peptide binding, peptide-polynucleotide binding, peptide cross-linking, use of green fluorescent protein, phage display, the two-hybrid system, protein arrays, peptide arrays, fiber optic evanescent wave sensors, chromatographic techniques, fluorescence resonance energy transfer, regulation of pH to control peptide and/or protein assembly and/or oligomerization, and the like. Accordingly, virtually any technique that may be used to analyze proteins may be utilized for the analysis of peptides. In some embodiments, high-speed capillary electrophoresis may be used to detect binding through use of fluorescently labeled phosphopeptides as affinity probes (Yang et al., Anal. Chem., 10.1021/ac061936e (2006)). Methods to immobilize proteins and peptides have been reported (Taylor, Protein Immobilization: Fundamentals and Applications, Marcel Dekker, Inc., New York (1991)).

In some embodiments, one or more microfluidic chips 108 may be configured to analyze one or more samples 102 through use of antibody interaction. Antibodies may be raised that will bind to numerous allergen indicators 106 through use of known methods (e.g., Harlow and Lane, Antibodies: A Laboratory Manual, Cold Spring Harbor Laboratory Press, Cold Spring Harbor, N.Y. (1988)). Antibodies may be configured in numerous ways within one or more microfluidic chips 108 to process one or more allergen indicators 106. For example, in some embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. A labeled detector antibody that binds to the allergen indicator 106 (or the antibody-allergen indicator 106 complex) may then be passed over the one or more antibody-allergen indicator 106 complexes such that the labeled detector antibody will label the allergen indicator 106 (or the antibody-allergen indicator 106 complex). Numerous labels may be used that include, but are not limited to, enzymes, fluorescent molecules, radioactive labels, spin labels, redox labels, and the like. In other embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. Such binding provides for detection of the antibody-allergen indicator 106 complex through use of methods that include, but are not limited to, surface plasmon resonance, conductivity, and the like (e.g., U.S. Pat. No. 7,030,989; herein incorporated by reference). In some embodiments, antibodies may be coupled to a substrate within a microfluidic chip 108 to provide for a competition assay. One or more samples 102 may be mixed with one or more reagent mixtures that include one or more labeled allergen indicators 106. The mixture may then be passed over the antibodies to facilitate binding of allergen indicators 106 in the sample 102 and labeled allergen indicators 106 in the reagent mixture to the antibodies. The unlabeled allergen indicators 106 in the sample 102 will compete with the labeled allergen indicators 106 in the reagent mixture for binding to the antibodies. Accordingly, the amount of label bound to the antibodies will vary in accordance with the concentration of unlabeled allergen indicators 106 in the sample 102. In some embodiments, antibody interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more antibodies may be used in conjunction with one or more aptamers to process one or more samples 102. Accordingly, in some embodiments, aptamers and antibodies may be used interchangeably to process one or more samples 102.

In some embodiments, one or more microfluidic chips 108 may be configured to analyze one or more samples 102 through use of chemical interaction. In some embodiments, one or more microfluidic chips 108 may be configured to utilize chemical extraction to process one or more samples 102. For example, in some embodiments, one or more samples 102 may be mixed with a reagent mixture that includes one or more solvents in which the one or more allergen indicators 106 are soluble. Accordingly, the solvent phase containing the one or more allergen indicators 106 may be separated from the sample phase to provide for detection of the one or more allergen indicators 106. In some embodiments, one or more samples 102 may be mixed with a reagent mixture that includes one or more chemicals that cause precipitation of one or more allergen indicators 106. Accordingly, the sample phase may be washed away from the one or more precipitated allergen indicators 106 to provide for detection of the one or more allergen indicators 106. Accordingly, reagent mixtures that include numerous types of chemicals that interact with one or more allergen indicators 106 may be used.

In some embodiments, one or more microfluidic chips 108 may be configured to analyze one or more samples 102 through use of diffusion. In some embodiments, one or more microfluidic chips 108 may be configured to process one or more fluid samples 102 through use of an H-filter. For example, a microfluidic chip 108 may be configured to include a channel through which a fluid sample 102 and a second fluid flow such that the fluid sample 102 and the second fluid undergo parallel flow through the channel without significant mixing of the sample fluid and the second fluid. As the fluid sample 102 and the second fluid flow through the channel, one or more allergen indicators 106 in the fluid sample 102 may diffuse through the fluid sample 102 into the second fluid. Accordingly, such diffusion provides for the separation of the one or more allergen indicators 106 from the sample 102. Methods to construct H-filters have been described (e.g., U.S. Pat. Nos. 6,742,661; 6,409,832; 6,007,775; 5,974,867; 5,971,158; 5,948,684; 5,932,100; 5,716,852; herein incorporated by reference). In some embodiments, diffusion based methods may be combined with immunoassay based methods to process and detect one or more allergen indicators 106. Methods to conduct microscale diffusion immunoassays have been described (e.g., U.S. Pat. No. 6,541,213; herein incorporated by reference). Accordingly, microfluidic chips 108 may be configured in numerous ways to process one or more allergen indicators 106 through use of diffusion.

In some embodiments, one or more microfluidic chips 108 may be configured to analyze one or more samples 102 through use of filtration. In some embodiments, one or more microfluidic chips 108 may be configured to include one or more filters that have a molecular weight cut-off. For example, a filter may allow molecules of low molecular weight to pass through the filter while disallowing molecules of high molecular weight to pass through the filter. Accordingly, one or more allergen indicators 106 that are contained within a sample 102 may be allowed to pass through a filter while larger molecules contained within the sample 102 are disallowed from passing through the filter. Accordingly, in some embodiments, a microfluidic chip 108 may include two or more filters that selectively retain, or allow passage, of one or more allergen indicators 106 through the filters. Such configurations provide for selective separation of one or more allergen indicators 106 from one or more samples 102. Membranes and filters having numerous molecular weight cut-offs are commercially available (e.g., Millipore, Billerica, Mass.). In some embodiments, one or more microfluidic chips 108 may be configured to provide for dialysis of one or more samples 102. For example, in some embodiments, a microfluidic chip 108 may be configured to contain one or more samples 102 in one or more sample chambers that are separated from one or more dialysis chambers by a semi-permeable membrane. Accordingly, in some embodiments, one or more allergen indicators 106 that are able to pass through the semi-permeable membrane may be collected in the dialysis chamber. In other embodiments, one or more allergen indicators 106 may be retained in the one or more sample chambers while other sample 102 components may be separated from the one or more allergen indicators 106 by their passage through the semi-permeable membrane into the dialysis chamber. Accordingly, one or more microfluidic chips 108 may be configured to include two or more dialysis chambers for selective separation of one or more allergen indicators 106 from one or more samples 102. Semi-permeable membranes and dialysis tubing is available from numerous commercial sources (e.g., Millipore, Billerica, Mass.; Pierce, Rockford, Ill.; Sigma-Aldrich, St. Louis, Mo.). Methods that may be used for microfiltration have been described (e.g., U.S. Pat. No. 5,922,210; herein incorporated by reference).

In some embodiments, one or more microfluidic chips 108 may be configured to analyze one or more samples 102 through use of chromatography. Numerous chromatographic methods may be used to process one or more samples 102. Examples of such chromatographic methods include, but are not limited to, ion-exchange chromatography, affinity chromatography, gel filtration chromatography, hydroxyapatite chromatography, gas chromatography, reverse phase chromatography, thin layer chromatography, capillary chromatography, size exclusion chromatography, hydrophobic interaction media, and the like. In some embodiments, a microfluidic chip 108 may be configured to process one or more samples 102 through use of one or more chromatographic methods. In some embodiments, chromatographic methods may be used to process one or more samples 102 for one or more allergen indicators 106 that include one or more polynucleotides. For example, in some embodiments, one or more samples 102 may be applied to a chromatographic media to which the one or more polynucleotides bind. The remaining components of the sample 102 may be washed from the chromatographic media. The one or more polynucleotides may then be eluted from chromatographic media in a more purified state. Similar methods may be used to process one or more samples 102 for one or more allergen indicators 106 that include one or more proteins or polypeptides (e.g., Mondal and Gupta, Biomol. Eng., 23:59-76 (2006)). Chromatography media able to separate numerous types of molecules is commercially available (e.g., Bio-Rad, Hercules, Calif.; Qiagen, Valencia, Calif.;

Pfizer, New York, N.Y.; Millipore, Billerica, Mass.; GE Healthcare Bio-Sciences Corp., Piscataway, N.J.).

In some embodiments, one or more microfluidic chips 108 may be configured to analyze one or more samples 102 through use of aptamer interaction. In some embodiments, one or more aptamers may include polynucleotides (e.g., deoxyribonucleic acid; ribonucleic acid; and derivatives of polynucleotides that may include polynucleotides that include modified bases, polynucleotides in which the phosphodiester bond is replaced by a different type of bond, or many other types of modified polynucleotides). In some embodiments, one or more aptamers may include peptide aptamers. Methods to prepare and use aptamers have been described (e.g., Collett et al., Methods, 37:4-15 (2005); Collet et al., Anal. Biochem., 338:113-123 (2005); Cox et al., Nucleic Acids Res., 30:20 e108 (2002); Kirby et al., Anal. Chem., 76:4066-4075 (2004); Ulrich, Handb. Exp. Pharmacol., 173:305-326 (2006); Baines and Colas, Drug Discovery Today, 11:334-341 (2006); Guthrie et al., Methods, 38:324-330 (2006); Geyer et al., Chapter 13: Selection of Genetic Agents from Random Peptide Aptamer Expression Libraries, Methods in Enzymology, Academic Press, pg. 171-208 (2000); U.S. Pat. No. 6,569,630; herein incorporated by reference). Aptamers may be configured in numerous ways within one or more microfluidic chips 108 to process one or more allergen indicators 106. For example, in some embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Labeled detector antibodies and/or aptamers that bind to the allergen indicator 106 (or the aptamer-allergen indicator 106 complex) may then be passed over the one or more aptamer-allergen indicator 106 complexes such that the labeled detector antibodies and/or aptamers will label the allergen indicator 106 (or the aptamer-allergen indicator 106 complex). Numerous labels may be used that include, but are not limited to, enzymes, fluorescent molecules, radioactive labels, spin labels, redox labels, and the like. In other embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Such binding provides for detection of the aptamer-allergen indicator 106 complex through use of methods that include, but are not limited to, surface plasmon resonance, conductivity, and the like (e.g., U.S. Pat. No. 7,030,989; herein incorporated by reference). In some embodiments, aptamers may be coupled to a substrate within a microfluidic chip 108 to provide for a competition assay. One or more samples 102 may be mixed with one or more reagent mixtures that include one or more labeled allergen indicators 106. The mixture may then be passed over the aptamers to facilitate binding of allergen indicators 106 in the sample 102 and labeled allergen indicators 106 in the reagent mixture to the aptamers. The unlabeled allergen indicators 106 in the sample 102 will compete with the labeled allergen indicators 106 in the reagent mixture for binding to the aptamers. Accordingly, the amount of label bound to the aptamers will vary in accordance with the concentration of unlabeled allergen indicators 106 in the sample 102. In some embodiments, aptamer interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more aptamers may be used in conjunction with one or more antibodies to process one or more samples 102. In some embodiments, aptamers and antibodies may be used interchangeably to process one or more samples 102. Accordingly, in some embodiments, methods and/or systems for processing and/or detecting allergen indicators 106 may utilize antibodies and aptamers interchangeably and/or in combination.

In some embodiments, one or more microfluidic chips 108 may be configured to analyze one or more samples 102 through use of electrical conductivity. In some embodiments, one or more samples 102 may be processed though use of magnetism. For example, in some embodiments, one or more samples 102 may be combined with one or more tagged polynucleotides that are tagged with a ferrous material, such as a ferrous bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed over an electromagnet to immobilize the hybridized complexes. Other components in the sample 102 may then be washed away from the hybridized complexes. In some embodiments, a chamber containing the magnetically immobilized hybridized complexes may be heated to release the sample polynucleotides from the magnetically immobilized tagged polynucleotides. The sample polynucleotides may then be collected in a more purified state. In other embodiments, similar methods may be used in conjunction with antibodies, aptamers, peptides, ligands, and the like. Accordingly, one or more microfluidic chips 108 may be configured in numerous ways to utilize magnetism to process one or more samples 102. In some embodiments, one or more samples 102 may be processed though use of eddy currents. Eddy current separation uses the principles of electromagnetic induction in conducting materials to separate non-ferrous metals by their different electric conductivities. An electrical charge is induced into a conductor by changes in magnetic flux cutting through it. Moving permanent magnets passing a conductor generates the change in magnetic flux. Accordingly, in some embodiments, one or more microfluidic chips 108 may be configured to include a magnetic rotor such that when conducting particles move through the changing flux of the magnetic rotor, a spiraling current and resulting magnetic field are induced. The magnetic field of the conducting particles may interact with the magnetic field of the magnetic rotor to impart kinetic energy to the conducting particles. The kinetic energy imparted to the conducting particles may then be used to direct movement of the conducting particles. Accordingly, non-ferrous particles, such as metallic beads, may be utilized to process one or more samples 102. For example, in some embodiments, one or more samples 102 may be combined with one or more tagged polynucleotides that are tagged with a non-ferrous material, such as an aluminum bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed through a magnetic field to impart kinetic energy to the non-ferrous bead. This kinetic energy may then be used to separate the hybridized complex. In other embodiments, similar methods may be used in conjunction with antibodies, aptamers, peptides, ligands, and the like.

Accordingly, one or more microfluidic chips 108 may be configured in numerous ways to utilize eddy currents to process one or more samples 102. One or more microfluidic chips 108 may be configured in numerous ways to utilize electrical conductivity to process one or more samples 102.

In some embodiments, one or more microfluidic chips 108 may be configured to analyze one or more samples 102 through use of isoelectric focusing. Methods have been described that may be used to construct capillary isoelectric focusing systems (e.g., Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). Such systems may be modified to provide for the processing of one or more samples 102.

In some embodiments, one or more microfluidic chips 108 may be configured to analyze one or more samples 102 through use of electrophoresis. In some embodiments, one or more microfluidic chips 108 may be configured to process one or more samples 102 through use of one-dimensional electrophoresis. In some embodiments, one or more microfluidic chips 108 may be configured to process one or more samples 102 through use of two-dimensional electrophoresis. In some embodiments, one or more microfluidic chips 108 may be configured to process one or more samples 102 through use of gradient gel electrophoresis. In some embodiments, one or more microfluidic chips 108 may be configured to process one or more samples 102 through use electrophoresis under denaturing conditions. In some embodiments, one or more microfluidic chips 108 may be configured to process one or more samples 102 through use electrophoresis under native conditions. One or more microfluidic chips 108 may be configured to utilize numerous electrophoretic methods.

In some embodiments, one or more microfluidic chips 108 may be configured to analyze one or more samples 102 through use of immunoassay. In some embodiments, one or more microfluidic chips 108 may be configured to process one or more samples 102 through use of enzyme linked immunosorbant assay (ELISA). In some embodiments, one or more microfluidic chips 108 may be configured to process one or more samples 102 through use of radioimmuno assay (RIA). In some embodiments, one or more microfluidic chips 108 may be configured to process one or more samples 102 through use of enzyme immunoassay (EIA). In some embodiments, such methods may utilize antibodies (e.g., monoclonal antibodies, polyclonal antibodies, antibody fragments, single-chain antibodies, and the like), aptamers, or substantially any combination thereof. In some embodiments, a labeled antibody and/or aptamer may be used within an immunoassay. In some embodiments, a labeled ligand to which the antibody and/or aptamer binds may be used within an immunoassay. Numerous types of labels may be utilized. Examples of such labels include, but are not limited to, radioactive labels, fluorescent labels, enzyme labels, spin labels, magnetic labels, gold labels, colorimetric labels, redox labels, and the like. Numerous immunoassays are known and may be configured for processing one or more samples 102.

In some embodiments, one or more microfluidic chips 108 may be configured to analyze one or more samples 102 through use of one or more competition assays. In some embodiments, one or more microfluidic chips 108 may be configured to process one or more samples 102 through use of one or more polynucleotide based competition assays. One or more microfluidic chips 108 may be configured to include one or more polynucleotides coupled to a substrate, such as a polynucleotide array. The one or more microfluidic chips 108 may be further configured so that a sample 102 and/or substantially purified polynucleotides obtained from one or more samples 102, may be mixed with one or more reagent mixtures that include one or more labeled polynucleotides to form an analysis mixture. This analysis mixture is then passed over the substrate such that the labeled polynucleotides and the sample polynucleotides are allowed to hybridize to the polynucleotides that are immobilized on the substrate. The sample polynucleotides and the labeled polynucleotides will compete for binding to the polynucleotides that are coupled on the substrate. Accordingly, the presence and/or concentration of the polynucleotides in the sample 102 can be determined through detection of the label (e.g., the concentration of the polynucleotides in the sample 102 will be inversely related to the amount of label that is bound to the substrate). Numerous labels may be used that include, but are not limited to, enzymes, fluorescent molecules, radioactive labels, spin labels, redox labels, and the like. In some embodiments, one or more microfluidic chips 108 may be configured to include one or more antibodies, proteins, peptides, and/or aptamers that are coupled to a substrate. The one or more microfluidic chips 108 may be further configured so that a sample 102 and/or substantially purified sample polypeptides and/or sample peptides obtained from one or more samples 102, may be mixed with one or more reagent mixtures that include one or more labeled polypeptides and/or labeled peptides to form an analysis mixture. This analysis mixture can then be passed over the substrate such that the labeled polypeptides and/or labeled peptides and the sample polypeptides and/or sample peptides are allowed to bind to the antibodies, proteins, peptides, and/or aptamers that are immobilized on the substrate. The sample polypeptides and/or sample peptides and the labeled polypeptides and/or sample peptides will compete for binding to the antibodies, proteins, peptides, and/or aptamers that are coupled on the substrate. Accordingly, the presence and/or concentration of the sample polypeptides and/or sample peptides in the sample 102 can be determined through detection of the label (e.g., the concentration of the sample polypeptides and/or sample peptides in the sample 102 will be inversely related to the amount of label that is bound to the substrate). Numerous labels may be used that include, but are not limited to, enzymes, fluorescent molecules, radioactive labels, spin labels, redox labels, and the like. Microfluidic chips 108 may be configured to utilize numerous types of competition assays.

In some embodiments, one or more microfluidic chips 108 may be configured to utilize numerous analysis methods.

Figure 29:
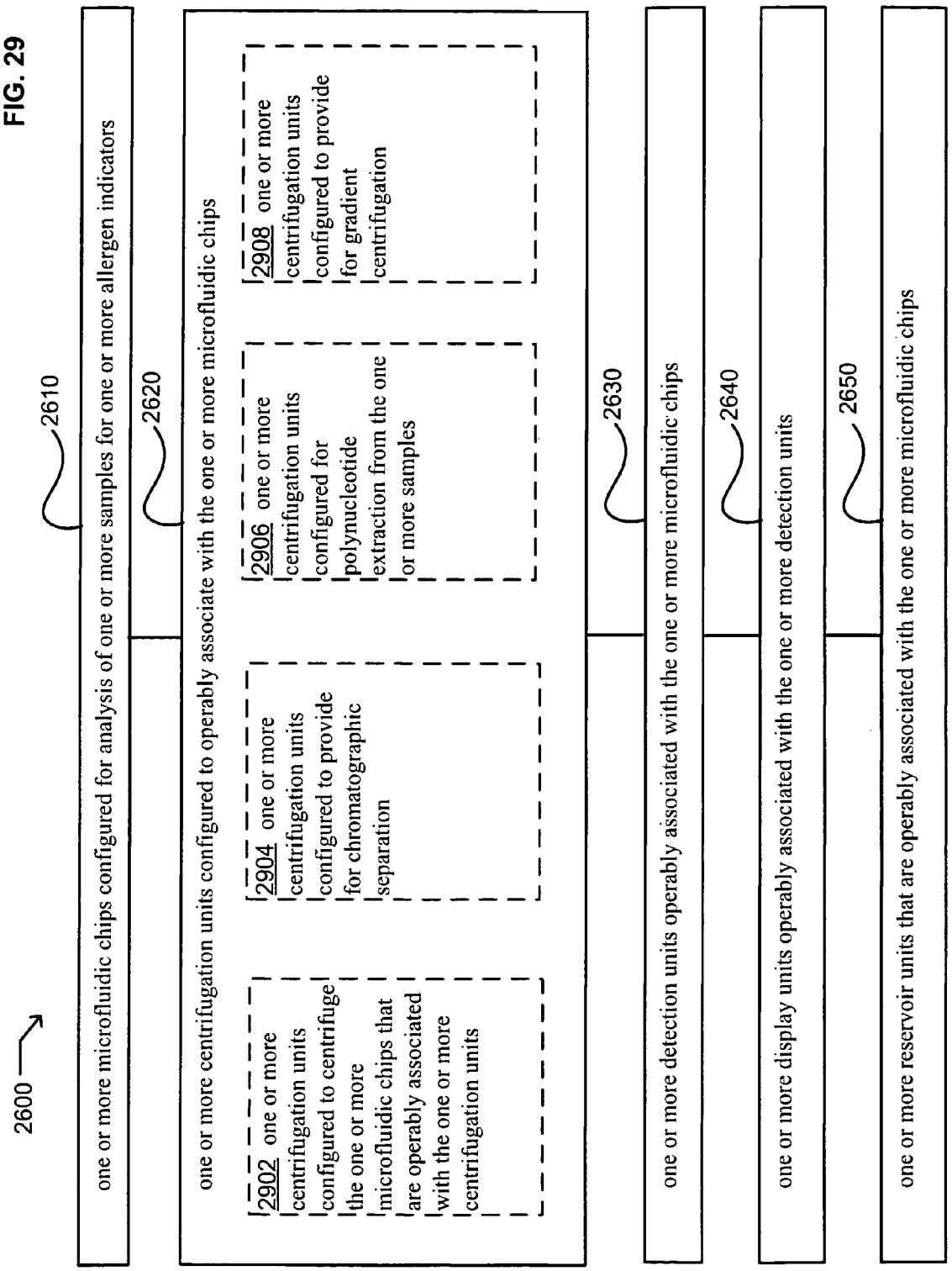
FIG. 29 illustrates alternate embodiments of the system of FIG. 26.

FIG. 29 illustrates alternative embodiments of system 2600 of FIG. 26. FIG. 29 illustrates example embodiments of module 2620. Additional embodiments may include an embodiment 2902, an embodiment 2904, an embodiment 2906, and/or an embodiment 2908.

At embodiment 2902, module 2620 may include one or more centrifugation units configured to centrifuge the one or more microfluidic chips that are operably associated with the one or more centrifugation units. In some embodiments, a system may include one or more centrifugation units 118 configured to centrifuge the one or more microfluidic chips 108 that are operably associated with the one or more centrifugation units 118. In some embodiments, one or more centrifugation units 118 may be configured to detachably associate with one or more microfluidic chips 108. For example, in some embodiments, a centrifugation unit 118 may include one or more centrifuge drives that are configured to detachably associate with one or more centrifuge rotors that are included within one or more microfluidic chips 108. In some embodiments, such centrifuge drives may magnetically couple with the one or more centrifuge rotors. In some embodiments, such centrifuge drives may physically couple with the one or more centrifuge rotors. In some embodiments, one or more centrifugation units 118 may be configured to centrifuge an entire microfluidic chip 108. For example, in some embodiments, a microfluidic chip 108 may be configured to associate with one or more centrifugation units 118 such that the microfluidic chip 108 is subjected to centrifugal force. In some embodiments, such a microfluidic chip 108 may be configured in a manner that resembles a compact disc. Accordingly, in some embodiments, a centrifugation unit 118 may be configured in a manner that resembles a compact disc player.

At embodiment 2904, module 2620 may include one or more centrifugation units configured to provide for chromatographic separation. In some embodiments, a system may include one or more centrifugation units 118 configured to provide for chromatographic separation. For example, in some embodiments, one or more centrifugation units 118 may be configured to centrifuge one or more samples 102 through one or more chromatographic columns that are associated with one or more microfluidic chips 108. In some embodiments, such microfluidic chips 108 may be coupled to one or more reagent reservoirs such that one or more fluids may be passed through one or more chromatographic columns through use of centrifugation. For example, in some embodiments, chromatographic separation may be used to separate one or more polynucleotides from one or more samples 102 through use of chromatographic media that is configured as a spin column.

At embodiment 2906, module 2620 may include one or more centrifugation units configured for polynucleotide extraction from the one or more samples. In some embodiments, a system may include one or more centrifugation units 118 configured for polynucleotide extraction from the one or more samples 102. For example, a microfluidic chip 108 may be configured to utilize alkaline lysis (e.g., miniprep procedure) to extract polynucleotides from one or more samples 102. In such examples, a microfluidic chip 108 may include a chamber where one or more samples 102 may be combined with a lysis buffer (e.g., sodium hydroxide/sodium dodecyl sulfate) to solubilize the one or more samples 102. The solubilized samples 102 may then be combined with an agent that precipitates the sodium dodecyl sulfate (e.g., potassium acetate) and the microfluidic chip 108 may be centrifuged through use of a centrifugation unit 118. The supernatant may then be transferred to another chamber where it may be chemically extracted (e.g., phenol/chloroform). The supernatant may then be transferred to another chamber and combined with an agent to precipitate polynucleotides present within the supernatant (e.g., alcohol). The microfluidic chip 108 may then be centrifuged to pellet any polynucleotides and then the supernatant may be drawn off and the pellet resuspended to facilitate analysis of the polynucleotides. In some embodiments, one or more samples 102 may be combined with a lysis buffer (e.g., sodium hydroxide/sodium dodecyl sulfate) to solubilize the one or more samples 102. The solubilized samples 102 may then be combined with an agent that precipitates the sodium dodecyl sulfate (e.g., potassium acetate) and the microfluidic chip 108 may be centrifuged through use of a centrifugation unit 118. The supernatant may then be applied to a chromatographic column. One or more wash buffers may then be centrifuged through the column to further separate the one or more polynucleotides. An elution buffer may then be centrifuged through the column to elute the one or more polynucleotides from the column. The elution buffer that includes the one or more polynucleotides may be combined with an agent (e.g., alcohol) to precipitate any polynucleotides present within the elution buffer. The microfluidic chip 108 may then be centrifuged to pellet any polynucleotides.

At embodiment 2908, module 2620 may include one or more centrifugation units configured to provide for gradient centrifugation. In some embodiments, a system may include one or more centrifugation units 118 configured to provide for gradient centrifugation. In some embodiments, one or more centrifugation units 118 may be configured to provide for density gradient centrifugation. In some embodiments, one or more centrifugation units 118 may be configured to provide for velocity gradient centrifugation.

Figure 30:
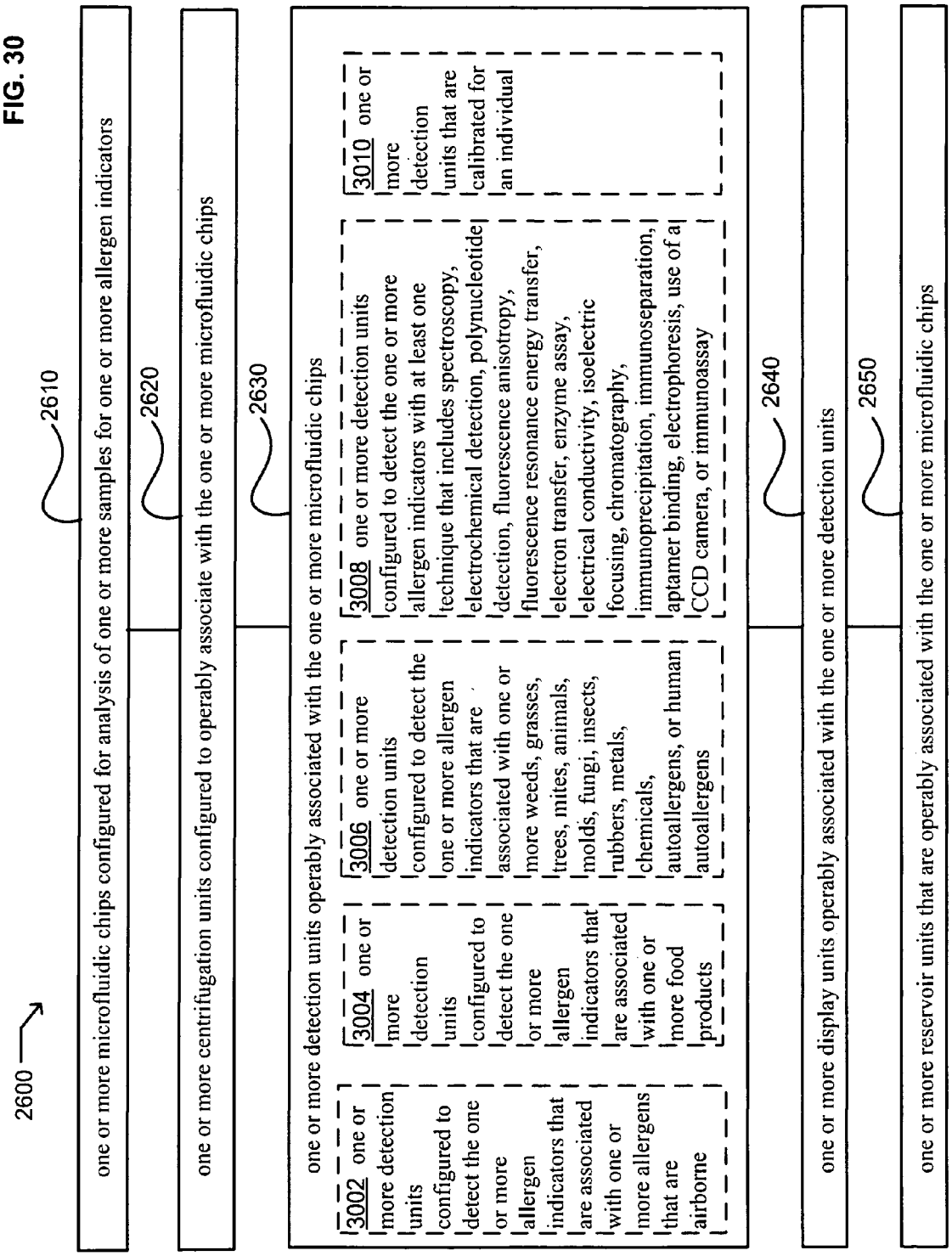
FIG. 30 illustrates alternate embodiments of the system of FIG. 26.

FIG. 30 illustrates alternative embodiments of system 2600 of FIG. 26. FIG. 30 illustrates example embodiments of module 2630. Additional embodiments may include an embodiment 3002, an embodiment 3004, an embodiment 3006, an embodiment 3008, and/or an embodiment 3010.

At embodiment 3002, module 2630 may include one or more detection units configured to detect the one or more allergen indicators that are associated with one or more allergens that are airborne. In some embodiments, a system may include one or more detection units 122 configured to detect the one or more allergen indicators 106 that are associated with one or more allergens 104 that are airborne. Accordingly, in some embodiments, one or more detection units 122 may be configured to operably associate with the one or more microfluidic chips 108 and to detect one or more airborne allergens 104. For example, in some embodiments, one or more microfluidic chips 108 may be configured to allow one or more air samples 102 to contact the one or more microfluidic chips 108 such that one or more allergen indicators 106 included within the one or more air samples 102 are retained by the one or more microfluidic chips 108. In some embodiments, the one or more air samples 102 may be passed through a filter on which one or more airborne allergen indicators 106 are collected. The collected airborne allergen indicators 106 may then be washed from the filter and caused to pass over an antibody array to which the one or more airborne allergen indicators 106 become immobilized. The immobilized airborne allergen indicators 106 may then be detected through numerous methods that include, but are not limited to, electrical conductivity, immunoassay based methods, and the like. Accordingly, one or more detection units 122 may be configured to detect the one or more airborne allergen indicators 106. In some embodiments, one or more detection units 122 may be configured to operably associate with one or more microfluidic chips 108 such that the one or more detection units 122 facilitate air flow through the one or more microfluidic chips 108 to provide for air sampling. For example, in some embodiments, one or more detection units 122 may include one or more fans to push and/or pull air through one or more operably associated microfluidic chips 108. In some embodiments, one or more detection units 122 may include one or more bellows to push and/or pull air through one or more operably associated microfluidic chips 108. Detection units 122 may be configured in numerous ways to provide for detection of one or more airborne allergen indicators 106.

At embodiment 3004, module 2630 may include one or more detection units configured to detect the one or more allergen indicators that are associated with one or more food products. In some embodiments, a system may include one or more detection units 122 configured to detect the one or more allergen indicators 106 that are associated with one or more food products. Accordingly, in some embodiments, one or more detection units 122 may be configured to operably associate with the one or more microfluidic chips 108 and to detect one or more allergen indicators 106 that are associated with one or more food products. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Numerous methods may be used to detect one or more allergen indicators 106 that are associated with one or more food products. Such methods have been described herein. In addition, other detection methods that have been described may be modified to provide for detection of one or more allergen indicators 106 that are associated with one or more food products. In some embodiments, one or more detection units 122 may be configured to detect one or more polynucleotides, one or more polypeptides, one or more portions of one or more polynucleotides, and/or one or more portions of one or more polypeptides that have a nucleic acid sequence and/or an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, AY839230, or substantially any combination thereof.

At embodiment 3006, module 2630 may include one or more detection units configured to detect the one or more allergen indicators that are associated with one or more weeds, grasses, trees, mites, animals, molds, fungi, insects, rubbers, metals, chemicals, autoallergens, or human autoallergens. In some embodiments, a system may include one or more detection units 122 configured to detect the one or more allergen indicators 106 that are associated with one or more weeds, grasses, trees, mites, animals, molds, fungi, insects, rubbers, metals, chemicals, autoallergens, human autoallergens, or substantially any combination thereof. Numerous allergen indicators 106 are known to be associated with weeds, grasses, trees, mites, animals, molds, fungi, insects, rubbers, metals, chemicals, autoallergens, or human autoallergens. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Accordingly, in some embodiments, one or more microfluidic chips 108 may be configured to process one or more samples 102 and provide for detection of one or more allergen indicators 106. In some embodiments, an allergen indicator 106 may be an allergenic particle. For example, in some embodiments, an allergen indicator 106 may include a complete pollen particle, such as a pollen particle, a spore, a flake of dander, and the like. In some embodiments, an allergen indicator 106 may be a portion of an allergenic particle. For example, in some embodiments, an allergen indicator 106 may include a portion of a pollen particle (e.g., polynucleotides, sporoderm, and the like). In some embodiments, allergen indicators 106 may include polynucleotides that are associated with one or more allergens 104. In some embodiments, allergen indicators 106 may include fragments of polynucleotides that are associated with one or more allergens 104. In some embodiments, allergen indicators 106 may include polypeptides, peptides, and/or proteins that are associated with one or more allergens 104. In some embodiments, allergen indicators 106 may include polysaccharides that are associated with one or more allergens 104. Accordingly, in some embodiments, one or more microfluidic chips 108 may be configured to provide for detection of one or more allergen indicators 106. In some embodiments, one or more detection units 122 may be configured to operably associate with one or more such microfluidic chips 108 and configured to detect one or more allergen indicators 106. Numerous detection methods may be used to detect one or more allergen indicators 106. Such methods have been described herein. In addition, detection methods that have been described may be modified to provide for detection of one or more allergen indicators 106. In some embodiments, one or more detection units 122 may be configured to detect and determine a concentration of one or more allergen indicators 106 that are included within a sample 102. For example, in some embodiments, one or more microfluidic chips 108 may be configured to provide for detection of one or more polynucleotides that are allergen indicators 106 through detection of electrical current produced upon hybridization of the one or more polynucleotides. Accordingly, in such embodiments, the one or more microfluidic chips 108 may be configured to produce an electrical current that is relative to polynucleotide concentration to provide for determination of polynucleotide concentration within one or more samples 102. Numerous configurations may be used in association with one or more allergen indicators 106 to provide for determination of allergen 104 concentration. In some embodiments, one or more microfluidic chips 108 may be configured to provide for identification of one or more allergens 104. For example, in some embodiments, one or more microfluidic chips 108 may include immobilized polynucleotides that selectively hybridize to one or more polynucleotides that are associated with a known allergen indicator 106. Accordingly, hybridization of one or more polynucleotides with the one or more immobilized polynucleotides indicates that a sample 102 includes one or more allergen indicators 106 that correspond to one or more known allergens 104. Accordingly, one or more detection units 122 may be configured to operably associate with such microfluidic chips 108 to provide for specific detection of one or more allergen indicators 106. In some embodiments, microfluidic chips 108 and/or detection units 122 may be configured to determine the identity and concentration of one or more allergen indicators 106 that are included within one or more samples 102.

At embodiment 3008, module 2630 may include one or more detection units configured to detect the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, a system may include one or more detection units 122 configured to detect the one or more allergen indicators 106 with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, immunoassay, or substantially any combination thereof. In some embodiments, one or more detection units 122 may be configured to detect one or more allergen indicators 106 that have been processed by one or more microfluidic chips 108. For example, in some embodiments, one or more microfluidic chips 108 may include a window (e.g., a quartz window, a cuvette analog, and/or the like) through which one or more detection units 122 may determine if one or more allergen indicators 106 are present or determine the concentration of one or more allergen indicators 106. In such embodiments, numerous techniques may be used to detect the one or more allergen indicators 106, such as visible light spectroscopy, ultraviolet light spectroscopy, infrared spectroscopy, fluorescence spectroscopy, and the like. Accordingly, in some embodiments, one or more detection units 122 may include circuitry and/or electro-mechanical mechanisms to detect one or more allergen indicators 106 present within one or more microfluidic chips 108 through a window in the one or more microfluidic chips 108. In some embodiments, one or more microfluidic chips 108 may be configured to process one or more samples 102 through use of surface plasmon resonance. In some embodiments, the one or more microfluidic chips 108 may include one or more antibodies, aptamers, proteins, peptides, polynucleotides, and the like, that are bound to a substrate (e.g., a metal film) within the one or more microfluidic chips 108. In some embodiments, such microfluidic chips 108 may include a prism through which one or more detection units 122 may shine light to detect one or more allergen indicators 106 that interact with the one or more antibodies, aptamers, proteins, peptides, polynucleotides, and the like, that are bound to a substrate. In some embodiments, one or more microfluidic chips 108 may include an exposed substrate surface that is configured to operably associate with one or more prisms that are included within one or more detection units 122. In some embodiments, one or more microfluidic chips 108 may include a nuclear magnetic resonance (NMR) probe. In such embodiments, the microfluidic chips 108 may be configured to associate with one or more detection units 122 that accept the NMR probe and are configured to detect one or more allergen indicators 106 through use of NMR spectroscopy. Accordingly, microfluidic chips 108 and detection units 122 may be configured in numerous ways to associate with each other to provide for detection of one or more allergen indicators 106.

In some embodiments, one or more allergen indicators 106 may be detected through use of spectroscopy. Numerous types of spectroscopic methods may be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., Clinical Chemistry, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, one or more allergen indicators 106 may be detected through use of electrochemical detection. In some embodiments, one or more polynucleotides may be detected through electrochemical detection. For example, in some embodiments, a polynucleotide that includes a redox label, such as ferrocene is coupled to a gold electrode. The labeled polynucleotide forms a stem-loop structure that can self-assemble onto a gold electrode by means of facile gold-thiol chemistry. Hybridization of a sample 102 polynucleotide induces a large conformational change in the surface-confined polynucleotide structure, which in turn alters the electron-transfer tunneling distance between the electrode and the redoxable label. The resulting change in electron transfer efficiency may be measured by cyclic voltammetry (Fan et al., Proc. Natl. Acad. Sci., 100:9134-9137 (2003); Wang et al., Anal. Chem., 75:3941-3945 (2003); Singh-Zocchi et al., Proc. Natl. Acad. Sci., 100:7605-7610 (2003)). Such methods may be used to detect messenger ribonucleic acid, genomic deoxyribonucleic acid, and fragments thereof.

In some embodiments, one or more allergen indicators 106 may be detected through use of polynucleotide detection. In some embodiments, one or more detection units 122 may be configured to detect one or more allergen indicators 106 through use of polynucleotide detection. Numerous methods may be used to detect one or more polynucleotides. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described (e.g., U.S. Pat. Nos. 7,118,910 and 6,960,437; herein incorporated by reference). Such methods may be adapted to provide for detection of one or more allergen indicators 106. In some embodiments, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube may be combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Accordingly, polynucleotides that hybridize to one or more allergen indicators 106 may include one or more carbon nanotubes. Methods to utilize carbon nanotubes as probes for nucleic acid interaction have been described (e.g., U.S. Pat. No. 6,821,730; herein incorporated by reference). Numerous other methods based on polynucleotide detection may be used to detect one or more allergen indicators 106.

In some embodiments, one or more allergen indicators 106 may be detected through use of fluorescence anisotropy. Fluorescence anisotropy is based on measuring the steady state polarization of sample 102 fluorescence imaged in a confocal arrangement. A linearly polarized laser excitation source preferentially excites fluorescent target molecules with transition moments aligned parallel to the incident polarization vector. The resultant fluorescence is collected and directed into two channels that measure the intensity of the fluorescence polarized both parallel and perpendicular to that of the excitation beam. With these two measurements, the fluorescence anisotropy, r, can be determined from the equation: r=(Intensity parallel−Intensity perpendicular)/(Intensity parallel+2(Intensity perpendicular)) where the I terms indicate intensity measurements parallel and perpendicular to the incident polarization. Fluorescence anisotropy detection of fluorescent molecules has been described. Accordingly, fluorescence anisotropy may be coupled to numerous fluorescent labels as have been described herein and as have been described.

In some embodiments, one or more allergen indicators 106 may be detected through use of fluorescence resonance energy transfer (FRET). Fluorescence resonance energy transfer refers to an energy transfer mechanism between two fluorescent molecules. A fluorescent donor is excited at its fluorescence excitation wavelength. This excited state is then nonradiatively transferred to a second molecule, the fluorescent acceptor. Fluorescence resonance energy transfer may be used within numerous configurations to detect one or more allergen indicators 106. For example, in some embodiments, an antibody may be labeled with a fluorescent donor and one or more allergen indicators 106 may be labeled with a fluorescent acceptor. Accordingly, such labeled antibodies and allergen indicators 106 may be used within competition assays to detect the presence and/or concentration of one or more allergen indicators 106 in one or more samples 102. Numerous combinations of fluorescent donors and fluorescent acceptors may be used to detect one or more allergen indicators 106. Accordingly, one or more detection units 122 may be configured to emit one or more wavelength of light to excite a fluorescent donor and may be configured to detect one or more wavelength of light emitted by the fluorescent acceptor. Accordingly, in some embodiments, one or more detection units 122 may be configured to accept one or more microfluidic chips 108 that include a quartz window through which fluorescent light may pass to provide for detection of one or more allergen indicators 106 through use of fluorescence resonance energy transfer. Accordingly, fluorescence resonance energy transfer may be used in conjunction with competition assays and/or numerous other types of assays to detect one or more allergen indicators 106.

In some embodiments, one or more allergen indicators 106 may be detected through use of electron transfer. Electron transfer is the process by which an electron moves from an electron donor to an electron acceptor causing the oxidation states of the electron donor and the electron acceptor to change. In some embodiments, electron transfer may occur when an electron is transferred from one or more electron donors to an electrode. In some embodiments, electron transfer may be utilized within competition assays to detect one or more allergen indicators 106. For example, in some embodiments, one or more microfluidic chips 108 may include one or more polynucleotides that may be immobilized on one or more electrodes. The immobilized polynucleotides may be incubated with a reagent mixture that includes sample polynucleotides and polynucleotides that are tagged with an electron donor. Hybridization of the tagged polynucleotides to the immobilized polynucleotides allows the electron donor to transfer an electron to the electrode to produce a detectable signal. Accordingly, a decrease in signal due to the presence of one or more polynucleotides that are allergen indicators 106 in the reagent mixture indicates the presence of an allergen indicator 106 in the sample 102. Such methods may be used in conjunction with polynucleotides, polypeptides, peptides, antibodies, aptamers, and the like. One or more microfluidic chips 108 may be configured to utilize numerous electron transfer based assays to provide for detection of one or more allergen indicators 106 by a detection unit 122.

In some embodiments, one or more allergen indicators 106 may be detected through use of one or more enzyme assays. Numerous enzyme assays may be used to provide for detection of one or more allergen indicators 106. Examples of such enzyme assays include, but are not limited to, beta-galactosidase assays, peroxidase assays, catalase assays, alkaline phosphatase assays, and the like. In some embodiments, enzyme assays may be configured such that an enzyme will catalyze a reaction involving an enzyme substrate that produces a fluorescent product. Accordingly, one or more detection units 122 may be configured to detect fluorescence resulting from the fluorescent product. Enzymes and florescent enzyme substrates are known and are commercially available (e.g., Sigma-Aldrich, St. Louis, Mo.). In some embodiments, enzyme assays may be configured as binding assays that provide for detection of one or more allergen indicators 106. For example, in some embodiments, one or more microfluidic chips 108 may be configured to include a substrate to which is coupled to one or more antibodies, aptamers, peptides, proteins, polynucleotides, ligands, and the like, that will interact with one or more allergen indicators 106. One or more samples 102 may be passed across the substrate such that one or more allergen indicators 106 present within the one or more samples 102 will interact with the one or more antibodies, aptamers, peptides, proteins, polynucleotides, ligands, and the like, and be immobilized on the substrate. One or more antibodies, aptamers, peptides, proteins, polynucleotides, ligands, and the like, that are labeled with an enzyme may then be passed across the substrate such that the one or more labeled antibodies, aptamers, peptides, proteins, polynucleotides, ligands, and the like, will bind to the one or more immobilized allergen indicators 106. An enzyme substrate may then be introduced to the one or more immobilized enzymes such that the enzymes are able to catalyze a reaction involving the enzyme substrate to produce a fluorescent product. Such assays are often referred to as sandwich assays. Accordingly, one or more detection units 122 may be configured to detect one or more products of enzyme catalysis to provide for detection of one or more allergen indicators 106.

In some embodiments, one or more allergen indicators 106 may be detected through use of electrical conductivity. In some embodiments, one or more microfluidic chips 108 may be configured to process one or more samples 102 and provide for detection of one or more allergen indicators 106 through use of electrical conductivity. In some embodiments, such microfluidic chips 108 may be configured to operably associate with one or more detection units 122 such that the one or more detection units 122 can detect one or more allergen indicators 106 through use of electrical conductivity. In some embodiments, one or more microfluidic chips 108 may be configured to include two or more electrodes that are each coupled to one or more detector polynucleotides. Interaction of an allergen associated polynucleotide, such as hybridization, with two detector polynucleotides that are coupled to two different electrodes will complete an electrical circuit. This completed circuit will provide for the flow of a detectable electrical current between the two electrodes and thereby provide for detection of one or more allergen associated polynucleotides that are allergen indicators 106. In some embodiments, the electrodes may be carbon nanotubes (e.g., U.S. Pat. No. 6,958,216; herein incorporated by reference). In some embodiments, electrodes may include, but are not limited to, one or more conductive metals, such as gold, copper, iron, silver, platinum, and the like; one or more conductive alloys; one or more conductive ceramics; and the like. In some embodiments, electrodes may be selected and configured according to protocols typically used in the computer industry that include, but are not limited to, photolithography, masking, printing, stamping, and the like. In some embodiments, other molecules and complexes that interact with one or more allergen indicators 106 may be used to detect the one or more allergen indicators 106 through use of electrical conductivity. Examples of such molecules and complexes include, but are not limited to, proteins, peptides, antibodies, aptamers, and the like. For example, in some embodiments, two or more antibodies may be immobilized on one or more electrodes such that contact of the two or more antibodies with an allergen indicator 106, such as a spore, a pollen particle, a dander particle, and the like, will complete an electrical circuit and facilitate the production of a detectable electrical current. Accordingly, in some embodiments, one or more microfluidic chips 108 may be configured to include electrical connectors that are able to operably associate with one or more detection units 122 such that the detection units 122 may detect an electrical current that is due to interaction of one or more allergen indicators 106 with two or more electrodes. In some embodiments, one or more detection units 122 may include electrical connectors that provide for operable association of one or more microfluidic chips 108 with the one or more detection units 122. In some embodiments, the one or more detectors are configured for detachable connection to one or more microfluidic chips 108. Microfluidic chips 108 and detection units 122 may be configured in numerous ways to process one or more samples 102 and detect one or more allergen indicators 106.

In some embodiments, one or more allergen indicators 106 may be detected through use of isoelectric focusing. In some embodiments, one or more microfluidic chips 108 may be configured to process one or more samples 102 and provide for detection of one or more allergen indicators 106 through use of isoelectric focusing. In some embodiments, native isoelectric focusing may be utilized to process and/or detect one or more allergen indicators 106. In some embodiments, denaturing isoelectric focusing may be utilized to process and/or detect one or more allergen indicators 106. Methods to construct microfluidic channels that may be used for isoelectric focusing have been reported (e.g., Macounova et al., Anal Chem., 73:1627-1633 (2001); Macounova et al., Anal Chem., 72:3745-3751 (2000); Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). In some embodiments, one or more microfluidic chips 108 may be configured to process one or more samples 102 through use of methods that include isoelectric focusing. In some embodiments, one or more detection units 122 may be configured to operably associate with one or more such microfluidic chips 108 such that the one or more detection units 122 can be used to detect one or more allergen indicators 106 that have been focused within one or more microfluidic channels of the one or more microfluidic chips 108. In some embodiments, one or more detection units 122 may be configured to include one or more CCD cameras that can be used to detect one or more allergen indicators 106. In some embodiments, one or more detection units 122 may be configured to include one or more spectrometers that can be used to detect one or more allergen indicators 106. Numerous types of spectrometers may be utilized to detect one or more allergen indicators 106 following isoelectric focusing. In some embodiments, one or more detection units 122 may be configured to utilize refractive index to detect one or more allergen indicators 106. In some embodiments, one or more microfluidic chips 108 may be configured to combine one or more samples 102 with one or more reagent mixtures that include one or more binding molecules and/or binding complexes that bind to one or more allergen indicators 106 that may be present within the one or more samples 102 to form an allergen indicator-binding molecule/binding complex. Examples of such binding molecules and/or binding complexes that bind to one or more allergen indicators 106 include, but are not limited to, antibodies, aptamers, peptides, proteins, polynucleotides, and the like. In some embodiments, an allergen indicator-binding molecule/binding complex may be processed through use of isoelectric focusing and then detected with one or more detection units 122. In some embodiments, one or more binding molecules and/or one or more binding complexes may include a label. Numerous labels may be used and include, but are not limited to, radioactive labels, fluorescent labels, colorimetric labels, spin labels, fluorescent labels, and the like. Accordingly, in some embodiments, an allergen indicator-binding molecule (labeled)/binding complex (labeled) may be processed through use of isoelectric focusing and then detected with one or more detection units 122 that are configured to detect the one or more labels. Microfluidic chips 108 and detection units 122 may be configured in numerous ways to process one or more samples 102 and detect one or more allergen indicators 106 though use of isoelectric focusing.

In some embodiments, one or more allergen indicators 106 may be detected through use of chromatographic methodology alone or in combination with additional processing and/or detection methods. In some embodiments, one or more microfluidic chips 108 may be configured to process one or more samples 102 and provide for detection of one or more allergen indicators 106 through use of chromatographic methods. Accordingly, in some embodiments, one or more detection units 122 may be configured to operably associate with the one or more microfluidic chips 108 and detect one or more allergen indicators 106 that were processed through use of chromatographic methods. In some embodiments, the one or more detection units 122 may be configured to operably associate with one or more microfluidic chips 108 and supply solvents and other reagents to the one or more microfluidic chips 108. For example, in some embodiments, one or more detection units 122 may include pumps and solvent/buffer reservoirs that are configured to supply solvent/buffer flow through chromatographic media (e.g., a chromatographic column) that is operably associated with one or more microfluidic chips 108. In some embodiments, one or more detection units 122 may be configured to operably associate with one or more microfluidic chips 108 and be configured to utilize one or more methods to detect one or more allergen indicators 106. Numerous types of chromatographic methods and media may be used to process one or more samples 102 and provide for detection of one or more allergen indicators 106. Chromatographic methods include, but are not limited to, low pressure liquid chromatography, high pressure liquid chromatography (HPLC), microcapillary low pressure liquid chromatography, microcapillary high pressure liquid chromatography, ion exchange chromatography, affinity chromatography, gel filtration chromatography, size exclusion chromatography, thin layer chromatography, paper chromatography, gas chromatography, and the like. In some embodiments, one or more microfluidic chips 108 may be configured to include one or more high pressure microcapillary columns. Methods that may be used to prepare microcapillary HPLC columns (e.g., columns with a 100 micrometer-500 micrometer inside diameter) have been described (e.g., Davis et al., Methods, A Companion to Methods in Enzymology, 6: Micromethods for Protein Structure Analysis, ed. by John E. Shively, Academic Press, Inc., San Diego, 304-314 (1994); Swiderek et al., Trace Structural Analysis of Proteins. Methods of Enzymology, ed. by Barry L. Karger & William S. Hancock, Spectrum, Publisher Services, 271, Chap. 3, 68-86 (1996); Moritz and Simpson, J. Chromatogr., 599:119-130 (1992)). In some embodiments, one or more microfluidic chips 108 may be configured to include one or more affinity columns. Methods to prepare affinity columns have been described. Briefly, a biotinylated site may be engineered into a polypeptide, peptide, aptamer, antibody, or the like. The biotinylated protein may then be incubated with avidin coated polystyrene beads and slurried in Tris buffer. The slurry may then be packed into a capillary affinity column through use of high pressure packing. Affinity columns may be prepared that may include one or more molecules and/or complexes that interact with one or more allergen indicators 106. For example, in some embodiments, one or more aptamers that bind to one or more allergen indicators. 106 may be used to construct an affinity column. Accordingly, numerous chromatographic methods may be used alone, or in combination with additional methods, to process and detect one or more allergen indicators 106. Numerous detection methods may be used in combination with numerous types of chromatographic methods. Accordingly, one or more detection units 122 may be configured to utilize numerous detection methods to detect one or more allergen indicators 106 that are processed through use of one or more chromatographic methods. Examples of such detection methods include, but are not limited to, conductivity detection, use of ion-specific electrodes, refractive index detection, colorimetric detection, radiological detection, detection by retention time, detection through use of elution conditions, spectroscopy, and the like. For example, in some embodiments, one or more chromatographic markers may be added to one or more samples 102 prior to the samples 102 being applied to a chromatographic column. One or more detection units 122 that are operably associated with the chromatographic column may be configured to detect the one or more chromatographic markers and use the elution time and/or position of the chromatographic markers as a calibration tool for use in detecting one or more allergen indicators 106 if those allergen indicators 106 are eluted from the chromatographic column. In some embodiments, one or more detection units 122 may be configured to utilize one or more ion-specific electrodes to detect one or more allergen indicators 106. For example, such electrodes may be used to detect allergen indicators 106 that include, but are not limited to, metals (e.g., tin, silver, nickel, cobalt, chromate), nitrates, nitrites, sulfites, and the like. Such allergen indicators 106 are often associated with food, beverages, clothing, jewelry, and the like. Accordingly, chromatographic methods may be used in combination with additional methods and in combination with numerous types of detection methods.

In some embodiments, one or more allergen indicators 106 may be detected through use of immunoprecipitation. In some embodiments, one or more detection units 122 may be configured to detect one or more allergen indicators 106 through use of immunoprecipitation. In some embodiments, immunoprecipitation may be utilized in combination with additional processing and/or detection methods to detect one or more allergen indicators 106. In some embodiments, one or more microfluidic chips 108 may be configured to process one or more samples 102 through use of immunoprecipitation. For example, in some embodiments, one or more samples 102 may be combined with one or more antibodies that bind to one or more allergen indicators 106 to form one or more antibody-allergen indicator 106 complexes. An insoluble form of an antibody binding constituent, such as protein A (e.g., protein A-sepharose bead, protein A-magnetic bead, protein A-ferrous bead, protein A-non-ferrous bead, and the like), Protein G, a second antibody, an aptamer, and the like, may then be mixed with the antibody-allergen indicator 106 complex such that the insoluble antibody binding constituent binds to the antibody-allergen indicator 106 complex and provides for precipitation of the antibody-allergen indicator 106 complex. Such complexes may be separated from other sample 102 components to provide for detection of one or more allergen indicators 106. For example, in some embodiments, sample 102 components may be washed away from the precipitated antibody-allergen indicator 106 complexes. In some embodiments, one or more microfluidic chips 108 that are configured for immunoprecipitation may be operably associated with one or more centrifugation units 118 to assist in precipitating one or more antibody-allergen indicator 106 complexes. In some embodiments, aptamers (polypeptide and/or polynucleotide) may be used in combination with antibodies or in place of antibodies. Accordingly, one or more detection units 122 may be configured to detect one or more allergen indicators 106 through use of numerous detection methods in combination with immunoprecipitation based methods.

In some embodiments, one or more allergen indicators 106 may be detected through use of immunoseparation. In some embodiments, one or more detection units 122 may be configured to detect one or more allergen indicators 106 through use of nimunoseparation. In some embodiments, immunoseparation may be utilized in combination with additional processing and/or detection methods to detect one or more allergen indicators 106. In some embodiments, one or more microfluidic chips 108 may be configured to process one or more samples 102 through use of immunoseparation. For example, in some embodiments, one or more samples 102 may be combined with one or more antibodies that bind to one or more allergen indicators 106 to form one or more antibody-allergen indicator 106 complexes. An antibody binding constituent may be added that binds to the antibody-allergen complex.

Examples of such antibody binding constituents that may be used alone or in combination include, but are not limited to, protein A (e.g., protein A-sepharose bead, protein A-magnetic bead, protein A-ferrous bead, protein A-non-ferrous bead, and the like), Protein G, a second antibody, an aptamer, and the like. Such antibody binding constituents may be mixed with an antibody-allergen indicator 106 complex such that the antibody binding constituent binds to the antibody-allergen indicator 106 complex and provides for separation of the antibody-allergen indicator 106 complex. In some embodiments, the antibody binding constituent may include a tag that allows the antibody binding constituent and complexes that include the antibody binding constituent to be separated from other components in one or more samples 102. In some embodiments, the antibody binding constituent may include a ferrous material. Accordingly, antibody-allergen indicator 106 complexes may be separated from other sample 102 components through use of a magnet, such as an electromagnet. In some embodiments, an antibody binding constituent may include a non-ferrous metal. Accordingly, antibody-allergen indicator 106 complexes may be separated from other sample 102 components through use of an eddy current to direct movement of one or more antibody-allergen indicator 106 complexes. In some embodiments, two or more forms of an antibody binding constituents may be used to detect one or more allergen indicators 106. For example, in some embodiments, a first antibody binding constituent may be coupled to a ferrous material and a second antibody binding constituent may be coupled to a non-ferrous material. Accordingly, the first antibody binding constituent and the second antibody binding constituent may be mixed with antibody-allergen indicator 106 complexes such that the first antibody binding constituent and the second antibody binding constituent bind to antibody-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more antibodies that bind to one or more allergen indicators 106 to form one or more antibody-allergen indicator 106 complexes. In some embodiments, the one or more antibodies may include one or more tags that provide for separation of the antibody-allergen indicator 106 complexes. For example, in some embodiments, an antibody may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with immunoseparation based methods. In some embodiments, aptamers (polypeptide and/or polynucleotide) may be used in combination with antibodies or in place of antibodies.

In some embodiments, one or more allergen indicators 106 may be detected through use of aptamer binding. In some embodiments, one or more detection units 122 may be configured to detect one or more allergen indicators 106 through use of aptamer binding. In some embodiments, aptamer binding may be utilized in combination with additional processing and/or detection methods to detect one or more allergen indicators 106. In some embodiments, one or more microfluidic chips 108 may be configured to process one or more samples 102 through use of aptamer binding. For example, in some embodiments, one or more samples 102 may be combined with one or more aptamers that bind to one or more allergen indicators 106 to form one or more aptamer-allergen indicator 106 complexes. In some embodiments, aptamer binding constituents may be added that bind to the aptamer-allergen complex. Numerous aptamer binding constituents may be utilized. For example, in some embodiments, one or more aptamers may include one or more tags to which one or more aptamer binding constituents may bind. Examples of such tags include, but are not limited to, biotin, avidin, streptavidin, histidine tags, nickel tags, ferrous tags, non-ferrous tags, and the like. In some embodiments, one or more tags may be conjugated with a label to provide for detection of one or more complexes. Examples of such tag-label conjugates include, but are not limited to, Texas red conjugated avidin, alkaline phosphatase conjugated avidin, CY2 conjugated avidin, CY3 conjugated avidin, CY3.5 conjugated avidin, CY5 conjugated avidin, CY5.5 conjugated avidin, fluorescein conjugated avidin, glucose oxidase conjugated avidin, peroxidase conjugated avidin, rhodamine conjugated avidin, agarose conjugated anti-protein A, alkaline phosphatase conjugated protein A, anti-protein A, fluorescein conjugated protein A, IRDye® 800 conjugated protein A, peroxidase conjugated protein A, sepharose protein A, alkaline phosphatase conjugated streptavidin, AMCA conjugated streptavidin, anti-streptavidin (*Streptomyces avidinii*) (rabbit) IgG Fraction, beta-galactosidase conjugated streptavidin, CY2 conjugated streptavidin, CY3 conjugated streptavidin, CY3.5 conjugated streptavidin, CY5 conjugated streptavidin, CY5.5 conjugated streptavidin, fluorescein conjugated streptavidin, IRDye® 700DX conjugated streptavidin, IRDye® 800 conjugated streptavidin, IRDye® 800CW conjugated streptavidin, peroxidase conjugated streptavidin, phycoerythrin conjugated streptavidin, rhodamine conjugated streptavidin, Texas red conjugated streptavidin, alkaline phosphatase conjugated biotin, anti-biotin (rabbit) IgG fraction, beta-galactosidase conjugated biotin, glucose oxidase conjugated biotin, peroxidase conjugated biotin, alkaline phosphatase conjugated protein G, anti-protein G (rabbit) Agarose conjugated, anti-protein G (Rabbit) IgG fraction, fluorescein conjugated protein G, IRDye® 800 conjugated protein G, peroxidase conjugated protein G, and the like. Many such labeled tags are commercially available (e.g., Rockland Immunochemicals, Inc., Gilbertsville, Pa.). Such labels may also be used in association with other methods to process and detect one or more allergen indicators 106. Aptamer binding constituents may be mixed with an aptamer-allergen indicator 106 complex such that the aptamer binding constituent binds to the aptamer-allergen indicator 106 complex and provides for separation of the aptamer-allergen indicator 106 complex. In some embodiments, the aptamer binding constituent may include a tag that allows the aptamer binding constituent and complexes that include the aptamer binding constituent to be separated from other components in one or more samples 102. In some embodiments, the aptamer binding constituent may include a ferrous material. Accordingly, aptamer-allergen indicator 106 complexes may be separated from other sample 102 components through use of a magnet, such as an electromagnet. In some embodiments, an aptamer binding constituent may include a non-ferrous metal. Accordingly, aptamer-allergen indicator 106 complexes may be separated from other sample 102 components through use of an eddy current to direct movement of one or more aptamer-allergen indicator 106 complexes. In some embodiments, two or more forms of aptamer binding constituents may be used to detect one or more allergen indicators 106. For example, in some embodiments, a first aptamer binding constituent may be coupled to a ferrous material and a second aptamer binding constituent may be coupled to a non-ferrous material. Accordingly, the first aptamer binding constituent and the second aptamer binding constituent may be mixed with aptamer-allergen indicator 106 complexes such that the first aptamer binding constituent and the second aptamer binding constituent bind to aptamer-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more aptamers that bind to one or more allergen indicators 106 to form one or more aptamer-allergen indicator 106 complexes. In some embodiments, the one or more aptamer may include one or more tags that provide for separation of the aptamer-allergen indicator 106 complexes. For example, in some embodiments, an aptamer may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with aptamer binding based methods. In some embodiments, antibodies may be used in combination with aptamers or in place of aptamers.

In some embodiments, one or more allergen indicators 106 may be detected through use of electrophoresis. In some embodiments, one or more microfluidic chips 108 may be configured to process one or more samples 102 through use of electrophoresis. In some embodiments, such microfluidic chips 108 may be configured to operably associate with one or more detection units 122. Accordingly, in some embodiments, one or more detection units 122 may be configured to operably associate with one or more microfluidic chips 108 and detect one or more allergen indicators 106 that were processed through use of electrophoresis. Numerous electrophoretic methods may be utilized to provide for detection of one or more allergen indicators 106. Examples of such electrophoretic methods include, but are not limited to, capillary electrophoresis, one-dimensional electrophoresis, two-dimensional electrophoresis, native electrophoresis, denaturing electrophoresis, polyacrylamide gel electrophoresis, agarose gel electrophoresis, and the like. Numerous detection-methods may be used in combination with one or more electrophoretic methods to detect one or more allergen indicators 106. In some embodiments, one or more allergen indicators 106 may be detected according to the position to which the one or more allergen indicators 106 migrate within an electrophoretic field (e.g., a capillary and/or a gel). In some embodiments, the position of one or more allergen indicators 106 may be compared to one or more standards. For example, in some embodiments, one or more samples 102 may be mixed with one or more molecular weight markers prior to gel electrophoresis. The one or more samples 102, that include the one or more molecular weight markers, may be subjected to electrophoresis and then the gel may be stained. In such embodiments, the molecular weight markers may be used as a reference to detect one or more allergen indicators 106 present within the one or more samples 102. In some embodiments, one or more components that are known to be present within one or more samples 102 may be used as a reference to detect one or more allergen indicators 106 present within the one or more samples 102. In some embodiments, gel shift assays may be used to detect one or more allergen indicators 106. For example, in some embodiments, a sample 102 (e.g., a single sample 102 or combination of multiple samples 102) may be split into a first sample 102 and a second sample 102. The first sample 102 may be mixed with an antibody, aptamer, ligand, or other molecule and/or complex that binds to the one or more allergen indicators 106. The first and second samples 102 may then be subjected to electrophoresis. The gels corresponding to the first sample 102 and the second sample 102 may then be analyzed to determine if one or more allergen indicators 106 are present within the one or more samples 102. Microfluidic chips 108 and detection units 122 may be configured in numerous ways to process and detect one or more allergen indicators 106 through use of electrophoresis.

In some embodiments, one or more allergen indicators 106 may be detected through use of one or more charge-coupled device (CCD) cameras. In some embodiments, one or more detection units 122 that include one or more CCD cameras may be configured to operably associate with one or more microfluidic chips 108. Such detection units 122 may be utilized in combination with numerous processing methods. Examples of such methods include, but are not limited to, electrophoresis; competition assays; methods based on polynucleotide interaction, protein interaction, peptide interaction, antibody interaction, aptamer interaction, immunoprecipitation, immunoseparation, and the like. For example, in some embodiments, one or more microfluidic chips 108 may be configured to process one or more samples 102 through use of immunoprecipitation. In some embodiments, one or more antibodies may be conjugated to a fluorescent label such that binding of one or more labeled antibodies to one or more allergen indicators 106 included within one or more samples 102 will form a fluorescently labeled antibody-allergen indicator 106 complex. One or more insoluble allergen indicator 106 binding constituents, such as a sepharose bead that includes an antibody or aptamer that binds to the one or more allergen indicators 106, may be bound to the fluorescently labeled antibody-allergen indicator 106 complex and used to precipitate the complex. One or more detection units 122 that include a CCD camera that is configured to detect fluorescent emission from the one or more fluorescent labels may be used to detect the one or more allergen indicators 106. In some embodiments, one or more CCD cameras may be configured to utilize dark frame subtraction to cancel background and increase sensitivity of the camera. In some embodiments, one or more detection units 122 may include one or more filters to select and/or filter wavelengths of energy that can be detected by one or more CCD cameras (e.g., U.S. Pat. No. 3,971,065; herein incorporated by reference). In some embodiments, one or more detection units 122 may include polarized lenses. One or more detection units 122 may be configured in numerous ways to utilize one or more CCD cameras to detect one or more allergen indicators 106.

In some embodiments, one or more allergen indicators 106 may be detected through use of immunoassay. In some embodiments, one or more microfluidic chips 108 may be configured to process one or more samples 102 through use of immunoassay. In some embodiments, one or more detection units 122 may be configured to operably associate with one or more such microfluidic chips 108 and to detect one or more allergen indicators 106 associated with the use of immunoassay. Numerous types of detection methods may be used in combination with immunoassay based methods. In some embodiments, a label may be used within one or more immunoassays that may be detected by one or more detection units 122. Examples of such labels include, but are not limited to, fluorescent labels, spin labels, fluorescence resonance energy transfer labels, radiolabels, electrochemiluminescent labels (e.g., U.S. Pat. Nos. 5,093,268; 6,090,545; herein incorporated by reference), and the like. In some embodiments, electrical conductivity may be used in combination with immunoassay based methods.

At embodiment 3010, module 2630 may include one or more detection units that are calibrated for an individual. In some embodiments, a system may include one or more detection units 122 that are calibrated for an individual. In some embodiments, one or more detection units 122 may be calibrated to detect one or more specific allergens 104 and/or allergen indicators 106 that produce an allergic response by an individual. For example, in some embodiments, one or more detection units 122 may be calibrated to detect peanuts and/or peanut associated products for an individual who is allergic to peanuts. In some embodiments, one or more detection units 122 may be calibrated to detect different concentrations of allergen indicators 106. For example, in some embodiments, an individual may produce an allergic response if exposed to an allergen 104 at a concentration that is above a certain level. Accordingly, in some embodiments, a detection unit 122 may be calibrated to detect one or more concentrations of one or more allergen indicators 106 that produce an allergic response within an individual.

Figure 31:
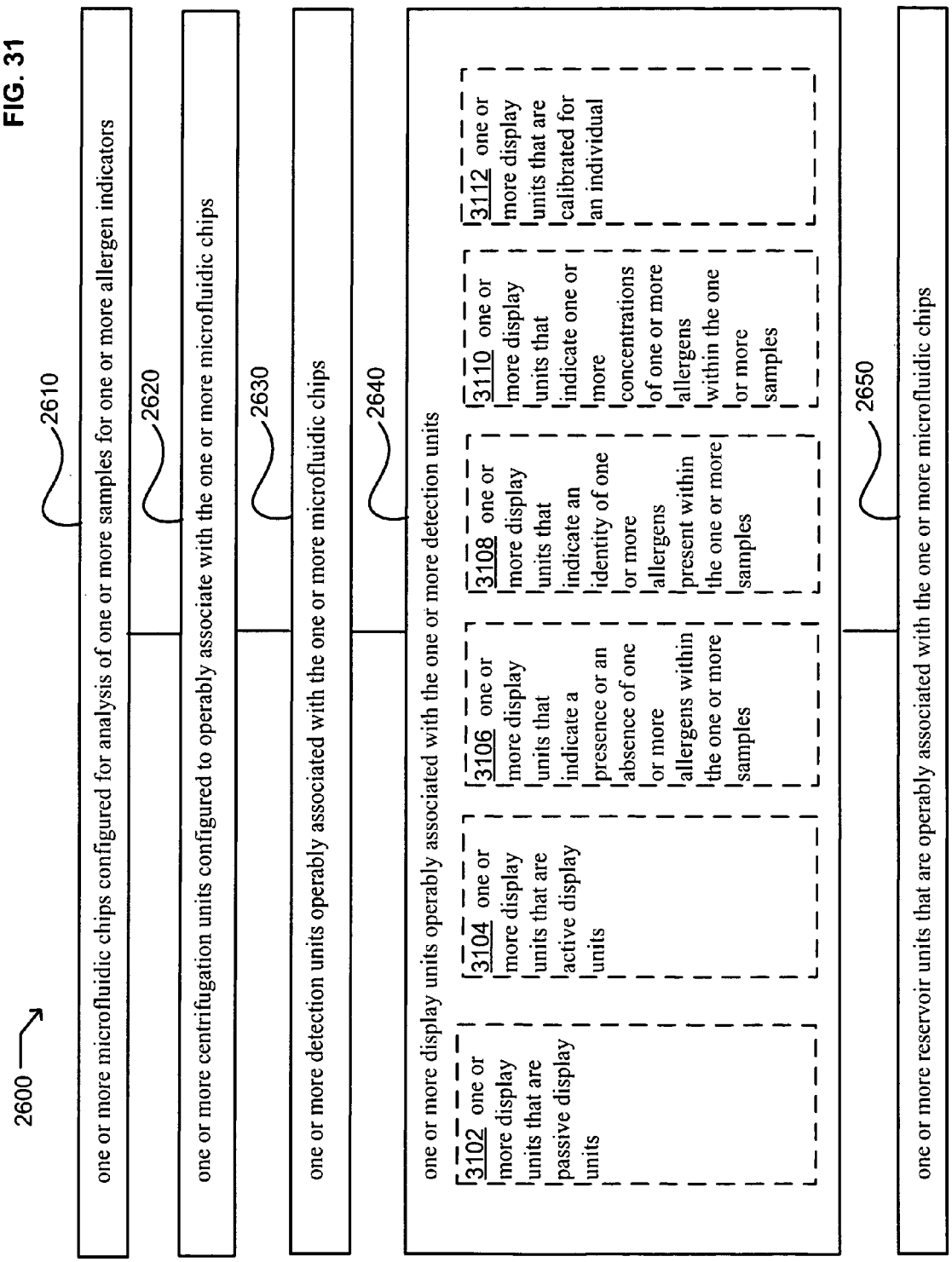
FIG. 31 illustrates alternate embodiments of the system of FIG. 26.

FIG. 31 illustrates alternative embodiments of system 2600 of FIG. 26. FIG. 31 illustrates example embodiments of module 2640. Additional embodiments may include an embodiment 3102, an embodiment 3104, an embodiment 3106, an embodiment 3108, an embodiment 3110, and/or an embodiment 3112.

At embodiment 3102, module 2640 may include one or more display units that are passive display units. In some embodiments, a system may include one or more display units 124 that may display results of the detecting with one or more display units 124 that are passive display units 124. In some embodiments, one or more display units 124 may include one or more liquid crystal displays (LCD). Methods to construct passive displays have been described (e.g., U.S. Pat. Nos. 4,807,967; 4,729,636: 4,436,378; 4,257,041; herein incorporated by reference).

At embodiment 3104, module 2640 may include one or more display units that are active display units. In some embodiments, a system may include one or more display units 124 that may display results of the detecting with one or more display units 124 that are active display units 124. Numerous active display units 124 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), wide ultra extended graphics array (WUXGA).

At embodiment 3106, module 2640 may include one or more display units that indicate a presence or an absence of one or more allergens within the one or more samples. In some embodiments, a system may include one or more display units 124 that may indicate a presence or an absence of the one or more allergen indicators 106 within the one or more samples 102. In some embodiments, one or more display units 124 may use a colorimetric message to indicate a presence or an absence of one or more allergen indicators 106 within one or more samples 102. For example, in some embodiments, one or more display units 124 may display a green light if one or more allergen indicators 106 are not found within one or more samples 102 and a red light if one or more allergen indicators 106 are found within one or more samples 102. In some embodiments, one or more display units 124 may use a pictographic message to indicate a presence or an absence of one or more allergen indicators 106 within one or more samples 102. For example, in some embodiments, one or more display units 124 may display a smiley face if one or more allergen indicators 106 are not found within one or more samples 102 and a frowny face if one or more allergen indicators 106 are found within one or more samples 102. In some embodiments, one or more display units 124 may use a typographical message to indicate a presence or an absence of one or more allergen indicators 106 within one or more samples 102. For example, in some embodiments, one or more display units 124 may display an "Allergen Not Present" message if one or more allergen indicators 106 are not found within one or more samples 102 and an "Allergen Present" message if one or more allergen indicators 106 are found within one or more samples 102. Such messages may be displayed in numerous languages. In some embodiments, one or more display units 124 may display one or more messages in multiple formats. For example, in some embodiments, one or more messages may be displayed in colored text.

At embodiment 3108, module 2640 may include one or more display units that indicate an identity of one or more allergens present within the one or more samples. In some embodiments, a system may include one or more display units 124 that may indicate an identity of one or more allergens 104 that correspond to the one or more allergen indicators 106 present within the one or more samples 102. In some embodiments, one or more display units 124 may be operably associated with one or more microfluidic chips 108 that are configured to identify one or more allergen indicators 106. Accordingly, in some embodiments, one or more display units 124 may be configured to display the identity of one or more allergens 104 that are present and/or absent from one or more samples 102. For example, in some embodiments, a display unit 124 may be configured to indicate a presence or an absence of beta-lactoglobulin in a food product.

At embodiment 3110, module 2640 may include one or more display units that indicate one or more concentrations of one or more allergens within the one or more samples. In some embodiments, a system may include one or more display units 124 that may indicate one or more concentrations of one or more allergens 104 that correspond to the one or more allergen indicators 106 present within the one or more samples 102. Concentration may be displayed in numerous formats. For example, in some embodiments, concentration may be expressed numerically (e.g., mass allergen indicator 106 per volume sample 102 (e.g., milligrams per milliliter), mass allergen indicator 106 per mass sample 102 (e.g., milligrams per milligram of sample), parts per million, and the like). In some embodiments, concentration may be expressed graphically. For example, in some embodiments, one or more display units 124 may include a display having a gray scale on which the concentration of one or more allergen indicators 106 that are present within one or more samples 102 may be indicated (e.g., higher concentrations of one or more allergens 104 may be displayed as dark gray while lower concentrations of one or more allergens 104 may be displayed as light gray). In some embodiments, one or more display units 124 may include a display having a color scale on which the concentration of one or more allergen indicators 106 that are present within one or more samples 102 may be indicated (e.g., low concentrations of one or more allergen indicators 106 may be indicated by a green light, intermediate concentrations of one or more allergen indicators 106 may be indicated by a yellow light, high concentrations of one or more allergen indicators 106 may be indicated by a red light). In some embodiments, one or more display units 124 may be calibrated to an individual. For example, in such embodiments, an individual may use the display to obtain an immediate reading that will indicate if a food product contains a dangerous level of one or more allergens 104.

At embodiment 3112, module 2640 may include one or more display units that are calibrated for an individual. In some embodiments, a system may include one or more display units 124 that are calibrated for an individual. In some embodiments, one or more display units 124 may be calibrated to display whether one or more allergens 104, and/or allergen indicators 106, that are specific to an individual are present or absent within one or more samples 102. For example, in some embodiments, one or more display units 124 may be configured to display whether one or more samples 102 contain shellfish associated allergens 104 for an individual known to be allergic to shellfish. In some embodiments, one or more display units 124 may be calibrated to indicate safe and/or unsafe concentrations of one or more allergens 104 within one or more samples 102 for an individual.

Figure 32:
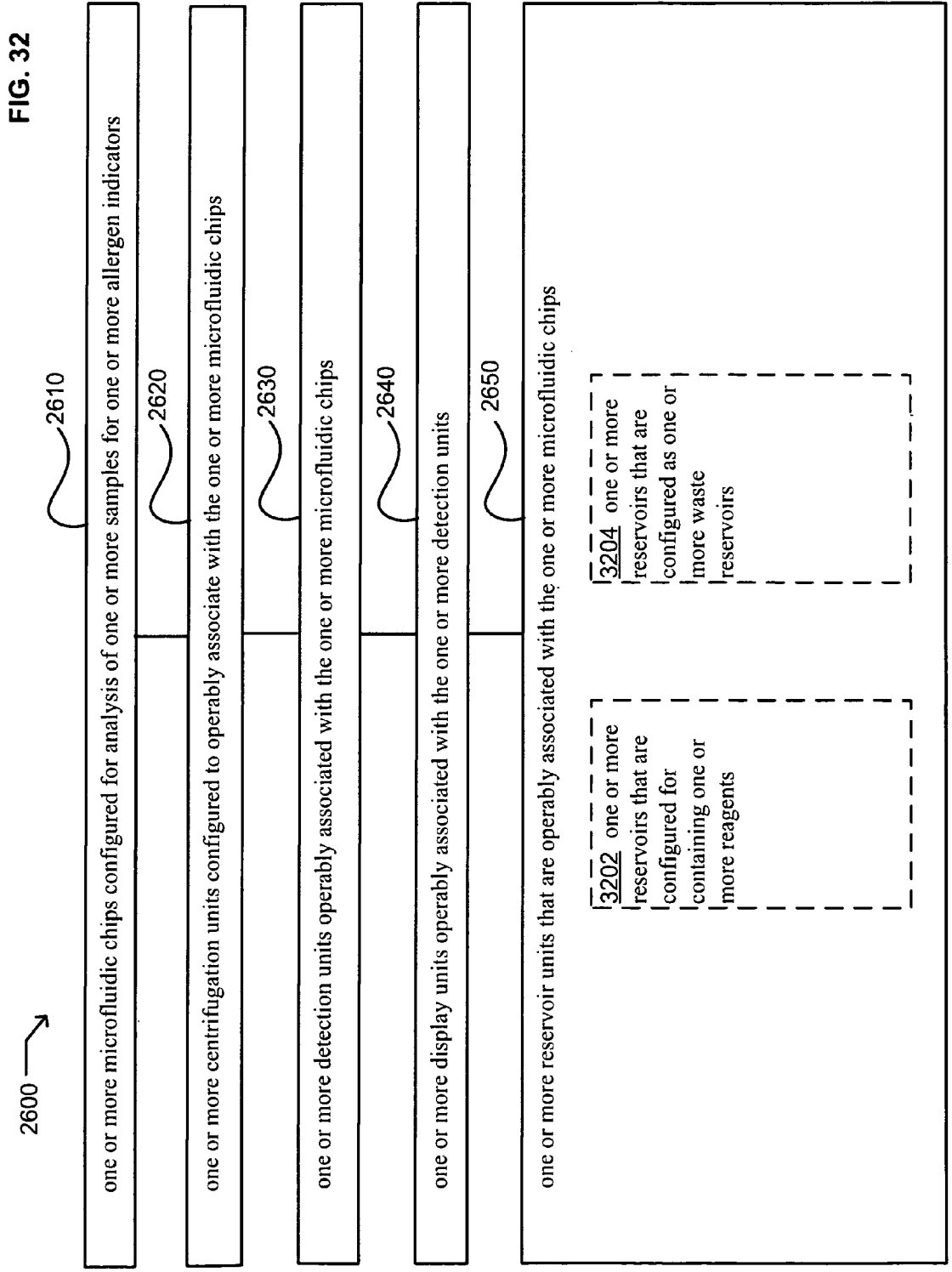
FIG. 32 illustrates alternate embodiments of the system of FIG. 26.

FIG. 32 illustrates alternative embodiments of system 2600 of FIG. 26. FIG. 32 illustrates example embodiments of module 2650. Additional embodiments may include an embodiment 3202 and/or an embodiment 3204.

At embodiment 3202, module 2650 may include one or more reservoirs that are configured for containing one or more reagents. In some embodiments, a system may include one or more reservoirs that are configured for containing one or more reagents. Reservoirs may be configured to contain and/or deliver numerous types of reagents. Examples of such reagents include, but are not limited to, phenol, chloroform, alcohol, salt solutions, detergent solutions, solvents, reagents used for polynucleotide precipitation, reagents used for polypeptide precipitation, reagents used for polynucleotide extraction, reagents used for polypeptide extraction, reagents used for chemical extractions, and the like. Accordingly, reservoirs may be configured to contain and/or analyze any reagent that may be used for the analysis of one or more allergens 104 and/or allergen indicators 106.

At embodiment 3204, module 2650 may include one or more reservoirs that are configured as one or more waste reservoirs. In some embodiments, a system may include one or more reservoirs that are configured as waste reservoirs. Such waste reservoirs may be configured in numerous ways. For example such waste reservoirs may be configured for containing reagents, samples 102, and the like. In some embodiments, waste reservoirs may be configured to contain liquids, solids, gels, and substantially any combination thereof.

III. Microfluidic Chips for Analysis of One or More Allergens

Figure 33:
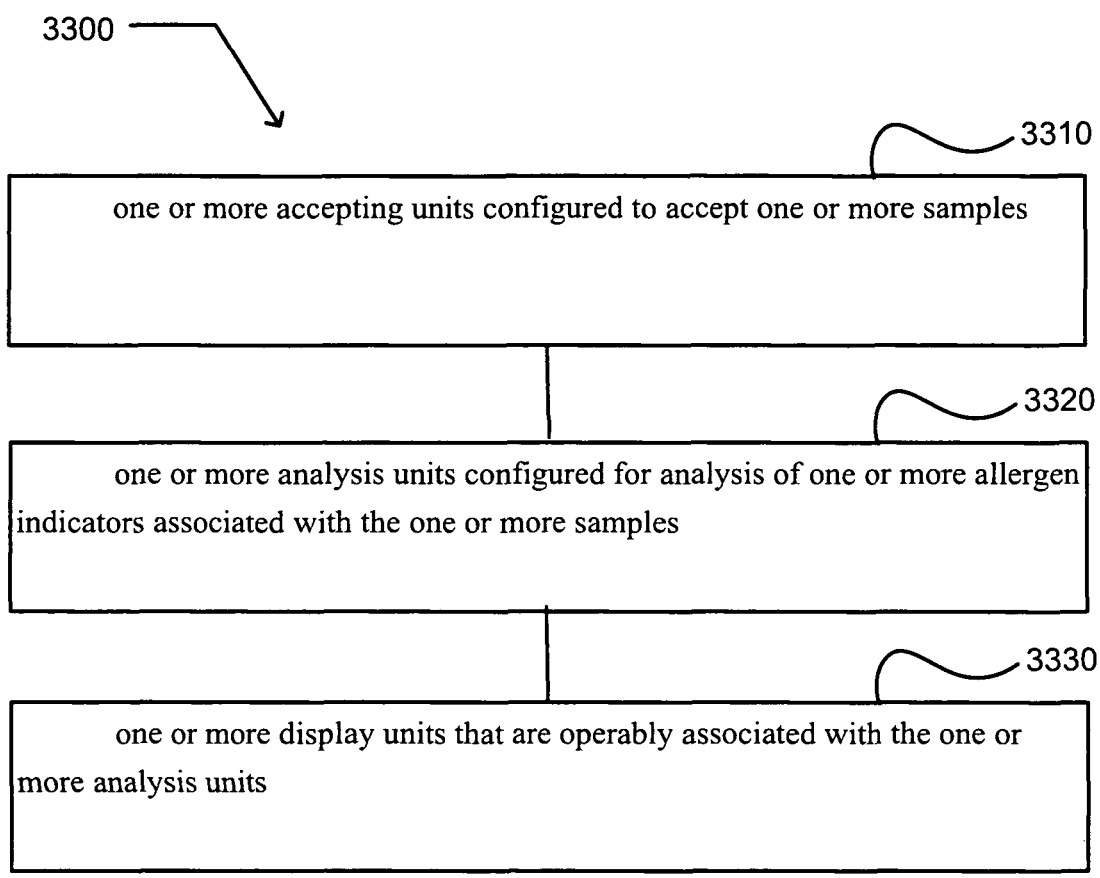
FIG. 33 illustrates an example microfluidic chip 3300 in which embodiments may be implemented.

FIG. 33 illustrates embodiments of microfluidic chips 3300 that may be configured for analysis of one or more allergens 104. In FIG. 33, discussion and explanation may be provided with respect to use of one or more microfluidic chips 108 within the above-described example of FIG. 1, and/or with respect to other examples and contexts. However, it should be understood that the microfluidic chips 108 may be configured in a number of other environments and contexts, and/or utilized within modified versions of FIG. 1. Also, although the microfluidic chips 108 are presented in the configuration(s) illustrated, it should be understood that the microfluidic chips 108 may be configured in numerous orientations.

The microfluidic chip 3300 includes module 3310 that includes one or more accepting units configured to accept one or more samples. In some embodiments, module 3310 may include one or more accepting units configured to accept the one or more samples that include one or more liquids. In some embodiments, module 3310 may include one or more accepting units configured to accept the one or more samples that include one or more solids. In some embodiments, module 3310 may include one or more accepting units configured to accept the one or more samples that include one or more gases. In some embodiments, module 3310 may include one or more accepting units configured to accept the one or more samples that include one or more food products. In some embodiments, module 3310 may include one or more accepting units configured to accept the one or more samples that are associated with one or more weeds, grasses, trees, mites, animals, molds, fungi, insects, rubbers, metals, chemicals, autoallergens, or human autoallergens.

The microfluidic chip 3300 includes module 3320 that includes one or more analysis units configured for analysis of one or more allergen indicators associated with the one or more samples. In some embodiments, module 3320 may include one or more analysis units configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay. In some embodiments, module 3320 may include one or more analysis units configured for analysis of the one or more allergen indicators that are associated with one or more food products. In some embodiments, module 3320 may include one or more analysis units configured for analysis of the one or more allergen indicators that are associated with one or more weeds, grasses, trees, mites, animals, molds, fungi, insects, rubbers, metals, chemicals, autoallergens, or human autoallergens. In some embodiments, module 3320 may include one or more analysis units configured for polynucleotide extraction. In some embodiments, module 3320 may include one or more analysis units configured for polypeptide extraction. In some embodiments, module 3320 may include one or more analysis units configured for chemical extraction. In some embodiments, module 3320 may include one or more analysis units that include one or more H-filters. In some embodiments, module 3320 may include one or more analysis units that are configured to provide for polynucleotide analysis. In some embodiments, module 3320 may include one or more analysis units that are configured to provide for one or more analysis methods that include polynucleotide amplification, polynucleotide ligation, polynucleotide interaction, or polynucleotide degradation. In some embodiments, module 3320 may include one or more analysis units that are configured to provide for polypeptide analysis. In some embodiments, module 3320 may include one or more analysis units that are configured to provide for enzymatic analysis. In some embodiments, module 3320 may include one or more analysis units that are configured to provide for reagent mixing. In some embodiments, module 3320 may include one or more analysis units that are configured to provide for centrifugal separation. In some embodiments, module 3320 may include one or more analysis units that are calibrated for an individual.

The microfluidic chip 3300 may optionally include module 3330 that includes one or more display units that are operably associated with the one or more analysis units. In some embodiments, module 3330 may include one or more display units that include one or more active display units. In some embodiments, module 3330 may include one or more display units that include one or more passive display units. In some embodiments, module 3330 may include one or more display units that indicate a presence or an absence of one or more allergens within the one or more samples. In some embodiments, module 3330 may include one or more display units that indicate an identity of one or more allergens within the one or more samples. In some embodiments, module 3330 may include one or more display units that indicate one or more concentrations of one or more allergens within the one or more samples. In some embodiments, module 3330 may include one or more display units that are calibrated for an individual.

Figure 34:
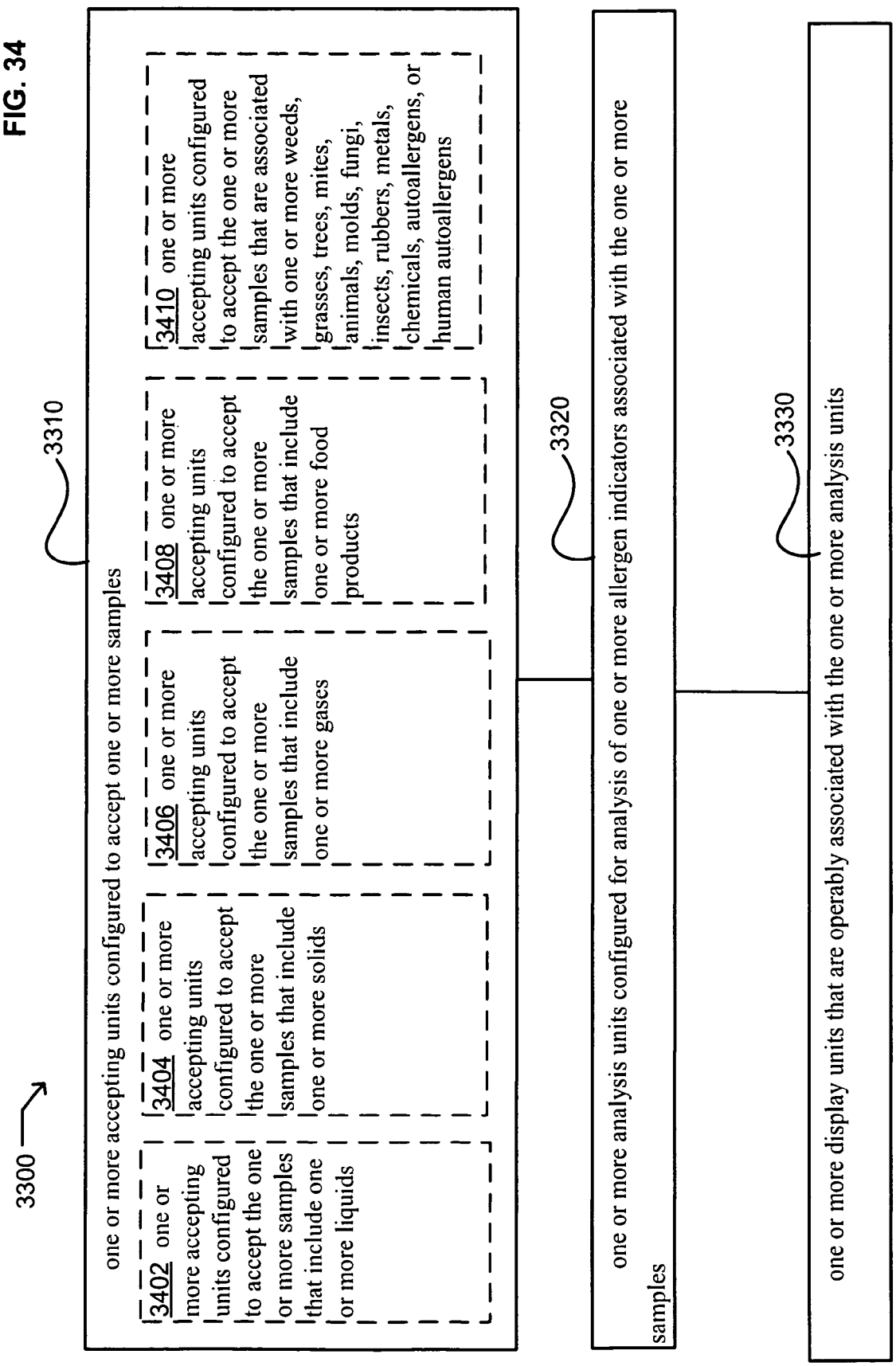
FIG. 34 illustrates alternate embodiments of the microfluidic chip of FIG. 33.

FIG. 34 illustrates alternative embodiments of microfluidic chips 3300 of FIG. 33. FIG. 34 illustrates example embodiments of module 3310. Additional embodiments may include an embodiment 3402, an embodiment 3404, an embodiment 3406, an embodiment 3408, and/or an embodiment 3410.

At embodiment 3402, module 3310 may include one or more accepting units configured to accept the one or more samples that include one or more liquids. In some embodiments, one or more microfluidic chips 108 may include one or more accepting units 110 configured to accept the one or more samples 102 that include one or more liquids. In some embodiments, one or more microfluidic chips 108 may include one or more lancets. Such lancets may be configured to provide for collection of one or more samples 102 that include a fluid. In some embodiments, a microfluidic chip 108 may include one or more septa through which a needle may be passed to deliver a fluid sample 102 to the microfluidic chip 108. In some embodiments, a microfluidic chip 108 may include one or more leur lock connectors to which one or more syringes may be coupled to deliver one or more fluid samples 102 to the microfluidic chip 108. In some embodiments, a microfluidic chip 108 may be configured to operably associate with one or more detection units 122 that are configured to deliver one or more liquid samples 102 to the microfluidic chip 108. In some embodiments, an accepting unit 110 may be configured to extract liquids from one or more samples 102. For example, in some embodiments, an accepting unit 110 may include a space into which a sample 102 may be crushed such that the liquid portion of the sample 102 is available for processing by the microfluidic chip 108. In some embodiments, an accepting unit 110 may include one or more sonicators that facilitate release of the liquid portion from a sample 102 to make it available to a microfluidic chip 108. Microfluidic chips 108 may be configured to accept numerous types of liquids. Examples of such liquids include, but are not limited to, beverages, water, food products, solvents, and the like. In some embodiments, a microfluidic chip 108 may be configured to accept one or more solvents that include one or more dissolved metal samples 102. For example, metal may be contacted with a solvent to obtain a sample 102 of the metal. The solvent may then be delivered to a microfluidic chip 108 for processing and/or analysis. Accordingly, microfluidic chips 108 may be configured in numerous ways such that they may accept one or more samples 102 that include a liquid.

At embodiment 3404, module 3310 may include one or more accepting units configured to accept the one or more samples that include one or more solids. In some embodiments, one or more microfluidic chips 108 may include one or more accepting units 110 configured to accept the one or more samples 102 that include one or more solids. In some embodiments, such accepting units 110 may be configured to suspend a solid sample 102 in a fluid. In some embodiments, such accepting units 110 may be configured to crush a sample 102 into smaller particles. For example, in some embodiments, an accepting unit 110 may accept a solid sample 102. The sample 102 may be ground into smaller particles to facilitate detection of one or more allergen indicators 106 that may be present within the sample 102. In some embodiments, an accepting unit 110 may include one or more sonicators that break the sample 102 into smaller particles to facilitate detection of one or more allergen indicators 106 that may be present within the sample 102. For example, in some embodiments, solid spores may be broken into smaller particles to provide for detection of one or more polynucleotides that are associated with the spores. In some embodiments, an accepting unit 110 may be configured to accept one or more samples 102 that include metal. For example, in some embodiments, an accepting unit 110 may be configured to accept a metal sample 102 (e.g., from a piece of jewelry). In such embodiments, a microfluidic chip 108 may be configured to dissolve the metal sample 102 in a suitable solvent. For example, the metal sample 102 may be dissolved in hydrochloric acid media and then tin may be extracted from the hydrochloric acid with 2-ethylhexyl phosphonic acid mono-2-ethylhexyl ester in toluene. The extracted tin may then be detected through use of an ion-specific electrode. Accordingly, microfluidic chips 108 may be configured in numerous ways such that they may accept one or more samples 102 that include a liquid.

At embodiment 3406, module 3310 may include one or more accepting units configured to accept the one or more samples that include one or more gases. In some embodiments, one or more microfluidic chips 108 may include one or more accepting units 110 configured to accept the one or more samples 102 that include one or more gases. For example, in some embodiments, a microfluidic chip 108 may include one or more fans that blow and/or draw gas into the microfluidic chip 108. In some embodiments, a microfluidic chip 108 may include one or more bubble chambers through which one or more gases pass. In some embodiments, such bubble chambers may be configured to include one or more fluids (e.g., solvents) that may be used to selectively retain (e.g., extract) one or more allergen indicators 106 from one or more gas samples 102. For example, in some embodiments, diesel exhaust particles may be extracted from one or more gas samples 102 by bubbling the gas samples 102 through a solvent (e.g., methylene chloride, aqueous HCl, and the like). In some embodiments, a microfluidic chip 108 may include one or more electrostatic filters through which one or more gases pass. Such electrostatic filters may be configured to capture numerous types of allergen indicators 106. Examples of such allergen indicators 106 include, but are not limited to, dust, lint, dander, pollen, spores, and the like. In some embodiments, a microfluidic chip 108 may include one or more filters through which one or more gases pass. Such filters may be configured to capture allergen indicators 106 according to numerous properties, such as size, hydrophobicity, charge, and the like.

At embodiment 3408, module 3310 may include one or more accepting units configured to accept the one or more samples that include one or more food products. In some embodiments, one or more microfluidic chips 108 may include one or more accepting units 110 configured to accept the one or more samples 102 that include one or more food products. In some embodiments, one or more accepting units 110 may be configured to accept one or more food samples 102 that are liquid, such as beverages, soups, sauces, and the like. For example, in some embodiments, one or more accepting units 110 may include one or more lancets that may be inserted into the food product to withdraw one or more samples 102. In some embodiments, one or more accepting units 110 may include one or more septa that may be configured to operably associate with a syringe or the like. In some embodiments, one or more accepting units 110 may be configured to accept one or more food samples 102 that are solids, such as meats, cheeses, nuts, vegetables, fruits, and the like. In some embodiments, one or more accepting units 110 may include one or more mechanisms that can facilitate processing of the one or more samples 102. Examples of such mechanisms include, but are not limited to, grinders, sonicators, treatment of the one or more samples 102 with degradative enzymes (e.g., protease, nuclease, lipase, collagenase, and the like), strainers, filters, centrifugation chambers, and the like.

At embodiment 3410, module 3310 may include one or more accepting units configured to accept the one or more samples that are associated with one or more weeds, grasses, trees, mites, animals, molds, fungi, insects, rubbers, metals, chemicals, autoallergens, or human autoallergens. In some embodiments, one or more microfluidic chips 108 may include one or more accepting units 110 configured to accept the one or more samples 102 that are associated with one or more weeds, grasses, trees, mites, animals, molds, fungi, insects, rubbers, metals, chemicals, autoallergens, human autoallergens, or substantially any combination thereof. In some embodiments, one or more accepting units 110 may include one or more mechanisms that can facilitate processing of the one or more samples 102. Examples of such mechanisms include, but are not limited to, grinders, sonicators, treatment of the one or more samples 102 with degregative enzymes (e.g., protease, nuclease, lipase, collagenase, and the like), strainers, filters, centrifugation chambers, and the like.

Figure 35:
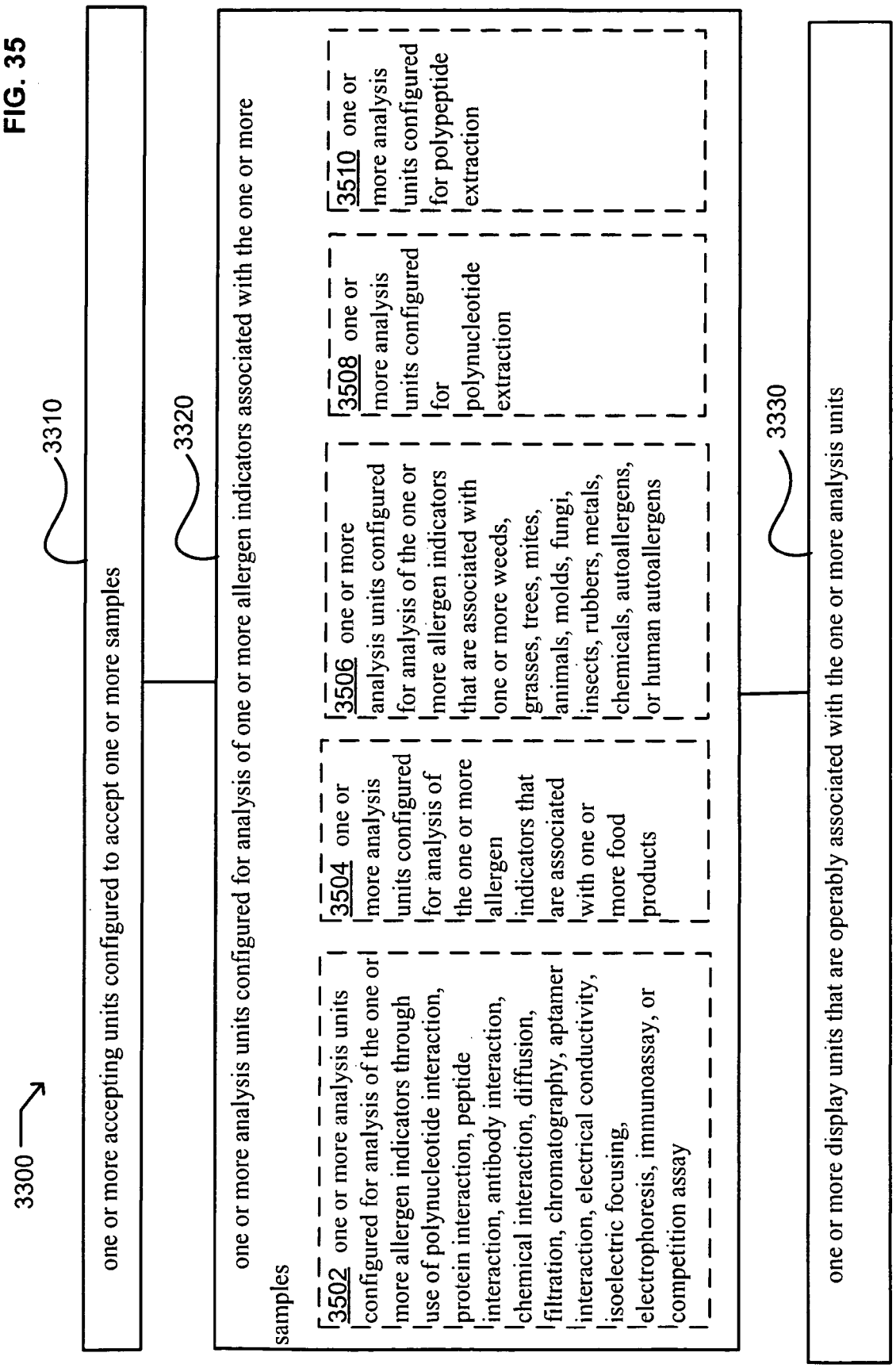
FIG. 35 illustrates alternate embodiments of the microfluidic chip of FIG. 33.

FIG. 35 illustrates alternative embodiments of microfluidic chips 3300 of FIG. 33. FIG. 35 illustrates example embodiments of module 3320. Additional embodiments may include an embodiment 3502, an embodiment 3504, an embodiment 3506, an embodiment 3508, and/or an embodiment 3510.

At embodiment 3502, module 3320 may include one or more analysis units configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay. In some embodiments, one or more microfluidic chips 108 may include one or more analysis units 120 configured for analysis of the one or more allergen indicators 106 through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof.

In some embodiments, one or more microfluidic chips 108 may be configured to process one or more samples 102 through use of polynucleotide interaction. Numerous methods based on polynucleotide interaction may be used. Examples of such methods include, but are not limited to, those based on polynucleotide hybridization, polynucleotide ligation, polynucleotide amplification, polynucleotide degradation, and the like. Methods that utilize intercalation dyes, FRET analysis, capacitive DNA detection, and nucleic acid amplification have been described (e.g., U.S. Pat. Nos. 7,118,910 and 6,960,437; herein incorporated by reference). In some embodiments, fluorescence resonance energy transfer, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube are combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Methods to utilize carbon nanotubes as probes for nucleic acid interaction have been described (e.g., U.S. Pat. No. 6,821,730; herein incorporated by reference).

In some embodiments, one or more microfluidic chips 108 may be configured to process one or more samples 102 through use of protein interaction. Numerous methods based on protein interaction may be used. In some embodiments, protein interaction may be used to immobilize one or more allergen indicators 106. In some embodiments, protein interaction may be used to separate one or more allergen indicators 106 from one or more samples 102. Examples of such methods include, but are not limited to, those based on ligand binding, protein-protein binding, protein cross-linking, use of green fluorescent protein, phage display, the two-hybrid system, protein arrays, fiber optic evanescent wave sensors, chromatographic techniques, fluorescence resonance energy transfer, regulation of pH to control protein assembly and/or oligomerization, and the like. For example, tropomyosin is a major muscle protein in crustaceans that is thought to be a major shrimp allergen 104. Tropomyosin is associated with the well known actin-troponin-myosin complex. Calcium ion binding to troponin enables troponin to bind tropomyosin and shift it from the binding sites of myosin on the actin proteins. Without the presence of Calcium ion, troponin is no longer able to bind to tropomyosin, and tropomyosin again blocks the binding sites of myosin on the actin proteins. Tropomyosin also binds to the calcium-binding protein calcyclin (Nelson et al., Molecular & Cellular Proteomics 1:253-259 (2002) and Liou and Chen, European Journal of Biochemistry, 270: 3092-3100 (2003)). Accordingly, protein interactions may be used to separate tropomyosin (allergen indicator 106) from one or more samples 102. Similar methods may be used with numerous proteins. Methods that may be used to construct protein arrays have been described (e.g., Warren et al., Anal. Chem., 76:4082-4092 (2004) and Walter et al., Trends Mol. Med., 8:250-253 (2002), U.S. Pat. No. 6,780,582; herein incorporated by reference).

In some embodiments, one or more microfluidic chips 108 may be configured to process one or more samples 102 through use of peptide interaction. Peptides are generally described as being polypeptides that include less than one hundred amino acids. For example, peptides include dipeptides, tripeptides, and the like. In some embodiments, peptides may include from two to one hundred amino acids. In some embodiments, peptides may include from two to fifty amino acids. In some embodiments, peptides may include from two to one twenty amino acids. In some embodiments, peptides may include from ten to one hundred amino acids. In some embodiments, peptides may include from ten to fifty amino acids. Accordingly, peptides can include numerous numbers of amino acids. Numerous methods based on peptide interaction may be used. In some embodiments, peptide interaction may be used to immobilize one or more allergen indicators 106. In some embodiments, peptide interaction may be used to separate one or more allergen indicators 106 from one or more samples 102. Examples of such methods include, but are not limited to, those based on ligand binding, peptide-protein binding, peptide-peptide binding, peptide-polynucleotide binding, peptide cross-linking, use of green fluorescent protein, phage display, the two-hybrid system, protein arrays, peptide arrays, fiber optic evanescent wave sensors, chromatographic techniques, fluorescence resonance energy transfer, regulation of pH to control peptide and/or protein assembly and/or oligomerization, and the like. Accordingly, virtually any technique that may be used to analyze proteins may be utilized for the analysis of peptides. In some embodiments, high-speed capillary electrophoresis may be used to detect binding through use of fluorescently labeled phosphopeptides as affinity probes (Yang et al., Anal. Chem., 10.1021/ac061936e (2006)). Methods to immobilize proteins and peptides have been reported (Taylor, Protein Immobilization: Fundamentals and Applications, Marcel Dekker, Inc., New York (1991)).

In some embodiments, one or more microfluidic chips 108 may be configured to process one or more samples 102 through use of antibody interaction. Antibodies may be raised that will bind to numerous allergen indicators 106 through use of known methods (e.g., Harlow and Lane, Antibodies: A Laboratory Manual, Cold Spring Harbor Laboratory Press, Cold Spring Harbor, N.Y. (1988)). Antibodies may be configured in numerous ways within one or more microfluidic chips 108 to process one or more allergen indicators 106. For example, in some embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. A labeled detector antibody that binds to the allergen indicator 106 (or the antibody-allergen indicator 106 complex) may then be passed over the one or more antibody-allergen indicator 106 complexes such that the labeled detector antibody will label the allergen indicator 106 (or the antibody-allergen indicator 106 complex). Numerous labels may be used that include, but are not limited to, enzymes, fluorescent molecules, radioactive labels, spin labels, redox labels, and the like. In other embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. Such binding provides for detection of the antibody-allergen indicator 106 complex through use of methods that include, but are not limited to, surface plasmon resonance, conductivity, and the like (e.g., U.S. Pat. No. 7,030,989; herein incorporated by reference). In some embodiments, antibodies may be coupled to a substrate within a microfluidic chip 108 to provide for a competition assay. One or more samples 102 may be mixed with one or more reagent mixtures that include one or more labeled allergen indicators 106. The mixture may then be passed over the antibodies to facilitate binding of allergen indicators 106 in the sample 102 and labeled allergen indicators 106 in the reagent mixture to the antibodies. The unlabeled allergen indicators 106 in the sample 102 will compete with the labeled allergen indicators 106 in the reagent mixture for binding to the antibodies. Accordingly, the amount of label bound to the antibodies will vary in accordance with the concentration of unlabeled allergen indicators 106 in the sample 102. In some embodiments, antibody interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more antibodies may be used in conjunction with one or more aptamers to process one or more samples 102. Accordingly, in some embodiments, aptamers and antibodies may be used interchangeably to process one or more samples 102.

In some embodiments, one or more microfluidic chips 108 may be configured to process one or more samples 102 through use of chemical interaction. In some embodiments, one or more microfluidic chips 108 may be configured to utilize chemical extraction to process one or more samples 102. For example, in some embodiments, one or more samples 102 may be mixed with a reagent mixture that includes one or more solvents in which the one or more allergen indicators 106 are soluble. Accordingly, the solvent phase containing the one or more allergen indicators 106 may be separated from the sample phase to provide for detection of the one or more allergen indicators 106. In some embodiments, one or more samples 102 may be mixed with a reagent mixture that includes one or more chemicals that cause precipitation of one or more allergen indicators 106. Accordingly, the sample phase may be washed away from the one or more precipitated allergen indicators 106 to provide for detection of the one or more allergen indicators 106. Accordingly, reagent mixtures that include numerous types of chemicals that interact with one or more allergen indicators 106 may be used.

In some embodiments, one or more microfluidic chips 108 may be configured to process one or more samples 102 through use of diffusion. In some embodiments, one or more microfluidic chips 108 may be configured to process one or more fluid samples 102 through use of an H-filter. For example, a microfluidic chip 108 may be configured to include a channel through which a fluid sample 102 and a second fluid flow such that the fluid sample 102 and the second fluid undergo parallel flow through the channel without significant mixing of the sample fluid and the second fluid. As the fluid sample 102 and the second fluid flow through the channel, one or more allergen indicators 106 in the fluid sample 102 may diffuse through the fluid sample 102 into the second fluid. Accordingly, such diffusion provides for the separation of the one or more allergen indicators 106 from the sample 102. Methods to construct H-filters have been described (e.g., U.S. Pat. Nos. 6,742,661; 6,409,832; 6,007,775; 5,974,867; 5,971,158; 5,948,684; 5,932,100; 5,716,852; herein incorporated by reference). In some embodiments, diffusion based methods may be combined with immunoassay based methods to process and detect one or more allergen indicators 106. Methods to conduct microscale diffusion immunoassays have been described (e.g., U.S. Pat. No. 6,541,213; herein incorporated by reference). Accordingly, microfluidic chips 108 may be configured in numerous ways to process one or more allergen indicators 106 through use of diffusion.

In some embodiments, one or more microfluidic chips 108 may be configured to process one or more samples 102 through use of filtration. In some embodiments, one or more microfluidic chips 108 may be configured to include one or more filters that have a molecular weight cut-off. For example, a filter may allow molecules of low molecular weight to pass through the filter while disallowing molecules of high molecular weight to pass through the filter. Accordingly, one or more allergen indicators 106 that are contained within a sample 102 may be allowed to pass through a filter while larger molecules contained within the sample 102 are disallowed from passing through the filter. Accordingly, in some embodiments, a microfluidic chip 108 may include two or more filters that selectively retain, or allow passage, of one or more allergen indicators 106 through the filters. Such configurations provide for selective separation of one or more allergen indicators 106 from one or more samples 102. Membranes and filters having numerous molecular weight cut-offs are commercially available (e.g., Millipore, Billerica, Mass.). In some embodiments, one or more microfluidic chips 108 may be configured to provide for dialysis of one or more samples 102. For example, in some embodiments, a microfluidic chip 108 may be configured to contain one or more samples 102 in one or more sample chambers that are separated from one or more dialysis chambers by a semi-permeable membrane. Accordingly, in some embodiments, one or more allergen indicators 106 that are able to pass through the semi-permeable membrane may be collected in the dialysis chamber. In other embodiments, one or more allergen indicators 106 may be retained in the one or more sample chambers while other sample 102 components may be separated from the one or more allergen indicators 106 by their passage through the semi-permeable membrane into the dialysis chamber. Accordingly, one or more microfluidic chips 108 may be configured to include two or more dialysis chambers for selective separation of one or more allergen indicators 106 from one or more samples 102. Semi-permeable membranes and dialysis tubing is available from numerous commercial sources (e.g., Millipore, Billerica, Mass.; Pierce, Rockford, Ill.; Sigma-Aldrich, St. Louis, Mo.). Methods that may be used for microfiltration have been described (e.g., U.S. Pat. No. 5,922,210; herein incorporated by reference).

In some embodiments, one or more microfluidic chips 108 may be configured to process one or more samples 102 through use of chromatography. Numerous chromatographic methods may be used to process one or more samples 102. Examples of such chromatographic methods include, but are not limited to, ion-exchange chromatography, affinity chromatography, gel filtration chromatography, hydroxyapatite chromatography, gas chromatography, reverse phase chromatography, thin layer chromatography, capillary chromatography, size exclusion chromatography, hydrophobic interaction media, and the like. In some embodiments, a microfluidic chip 108 may be configured to process one or more samples 102 through use of one or more chromatographic methods. In some embodiments, chromatographic methods may be used to process one or more samples 102 for one or more allergen indicators 106 that include one or more polynucleotides. For example, in some embodiments, one or more samples 102 may be applied to a chromatographic media to which the one or more polynucleotides bind. The remaining components of the sample 102 may be washed from the chromatographic media. The one or more polynucleotides may then be eluted from chromatographic media in a more purified state. Similar methods may be used to process one or more samples 102 for one or more allergen indicators 106 that include one or more proteins or polypeptides (e.g., Mondal and Gupta, Biomol. Eng., 23:59-76 (2006)). Chromatography media able to separate numerous types of molecules is commercially available (e.g., Bio-Rad, Hercules, Calif.; Qiagen, Valencia, Calif.; Pfizer, New York, N.Y.; Millipore, Billerica, Mass.; GE Healthcare Bio-Sciences Corp., Piscataway, N.J.).

In some embodiments, one or more microfluidic chips 108 may be configured to process one or more samples 102 through use of aptamer interaction. In some embodiments, one or more aptamers may include polynucleotides (e.g., deoxyribonucleic acid; ribonucleic acid; and derivatives of polynucleotides that may include polynucleotides that include modified bases, polynucleotides in which the phosphodiester bond is replaced by a different type of bond, or many other types of modified polynucleotides). In some embodiments, one or more aptamers may include peptide aptamers. Methods to prepare and use aptamers have been described (e.g., Collett et al., Methods, 37:4-15 (2005); Collet et al., Anal. Biochem., 338:113-123 (2005); Cox et al., Nucleic Acids Res., 30:20 e108 (2002); Kirby et al., Anal. Chem., 76:4066-4075 (2004); Ulrich, Handb. Exp. Pharmacol., 173:305-326 (2006); Baines and Colas, Drug Discovery Today, 11:334-341 (2006); Guthrie et al., Methods, 38:324-330 (2006); Geyer et al., Chapter 13: Selection of Genetic Agents from Random Peptide Aptamer Expression Libraries, Methods in Enzymology, Academic Press, pg. 171-208 (2000); U.S. Pat. No. 6,569,630; herein incorporated by reference). Aptamers may be configured in numerous ways within one or more microfluidic chips 108 to process one or more allergen indicators 106. For example, in some embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Labeled detector antibodies and/or aptamers that bind to the allergen indicator 106 (or the aptamer-allergen indicator 106 complex) may then be passed over the one or more aptamer-allergen indicator 106 complexes such that the labeled detector antibodies and/or aptamers will label the allergen indicator 106 (or the aptamer-allergen indicator 106 complex). Numerous labels may be used that include, but are not limited to, enzymes, fluorescent molecules, radioactive labels, spin labels, redox labels, and the like. In other embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Such binding provides for detection of the aptamer-allergen indicator 106 complex through use of methods that include, but are not limited to, surface plasmon resonance, conductivity, and the like (e.g., U.S. Pat. No. 7,030,989; herein incorporated by reference). In some embodiments, aptamers may be coupled to a substrate within a microfluidic chip 108 to provide for a competition assay. One or more samples 102 may be mixed with one or more reagent mixtures that include one or more labeled allergen indicators 106. The mixture may then be passed over the aptamers to facilitate binding of allergen indicators 106 in the sample 102 and labeled allergen indicators 106 in the reagent mixture to the aptamers. The unlabeled allergen indicators 106 in the sample 102 will compete with the labeled allergen indicators 106 in the reagent mixture for binding to the aptamers. Accordingly, the amount of label bound to the aptamers will vary in accordance with the concentration of unlabeled allergen indicators 106 in the sample 102. In some embodiments, aptamer interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more aptamers may be used in conjunction with one or more antibodies to process one or more samples 102. In some embodiments, aptamers and antibodies may be used interchangeably to process one or more samples 102. Accordingly, in some embodiments, methods and/or systems for processing and/or detecting allergen indicators 106 may utilize antibodies and aptamers interchangeably and/or in combination.

In some embodiments, one or more microfluidic chips 108 may be configured to process one or more samples 102 through use of electrical conductivity. In some embodiments, one or more samples 102 may be processed though use of magnetism. For example, in some embodiments, one or more samples 102 may be combined with one or more tagged polynucleotides that are tagged with a ferrous material, such as a ferrous bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed over an electromagnet to immobilize the hybridized complexes. Other components in the sample 102 may then be washed away from the hybridized complexes. In some embodiments, a chamber containing the magnetically immobilized hybridized complexes may be heated to release the sample polynucleotides from the magnetically immobilized tagged polynucleotides. The sample polynucleotides may then be collected in a more purified state. In other embodiments, similar methods may be used in conjunction with antibodies, aptamers, peptides, ligands, and the like. Accordingly, one or more microfluidic chips 108 may be configured in numerous ways to utilize magnetism to process one or more samples 102. In some embodiments, one or more samples 102 may be processed though use of eddy currents. Eddy current separation uses the principles of electromagnetic induction in conducting materials to separate non-ferrous metals by their different electric conductivities. An electrical charge is induced into a conductor by changes in magnetic flux cutting through it. Moving permanent magnets passing a conductor generates the change in magnetic flux. Accordingly, in some embodiments, one or more microfluidic chips 108 may be configured to include a magnetic rotor such that when conducting particles move through the changing flux of the magnetic rotor, a spiraling current and resulting magnetic field are induced. The magnetic field of the conducting particles may interact with the magnetic field of the magnetic rotor to impart kinetic energy to the conducting particles. The kinetic energy imparted to the conducting particles may then be used to direct movement of the conducting particles. Accordingly, non-ferrous particles, such as metallic beads, may be utilized to process one or more samples 102. For example, in some embodiments, one or more samples 102 may be combined with one or more tagged polynucleotides that are tagged with a non-ferrous material, such as an aluminum bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed through a magnetic field to impart kinetic energy to the non-ferrous bead. This kinetic energy may then be used to separate the hybridized complex. In other embodiments, similar methods may be used in conjunction with antibodies, aptamers, peptides, ligands, and the like. Accordingly, one or more microfluidic chips 108 may be configured in numerous ways to utilize eddy currents to process one or more samples 102. One or more microfluidic chips 108 may be configured in numerous ways to utilize electrical conductivity to process one or more samples 102.

In some embodiments, one or more microfluidic chips 108 may be configured to process one or more samples 102 through use of isoelectric focusing. Methods have been described that may be used to construct capillary isoelectric focusing systems (e.g., Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). Such systems may be modified to provide for the processing of one or more samples 102.

In some embodiments, one or more microfluidic chips 108 may be configured to process one or more samples 102 through use of electrophoresis. In some embodiments, one or more microfluidic chips 108 may be configured to process one or more samples 102 through use of one-dimensional electrophoresis. In some embodiments, one or more microfluidic chips 108 may be configured to process one or more samples 102 through use of two-dimensional electrophoresis. In some embodiments, one or more microfluidic chips 108 may be configured to process one or more samples 102 through use of gradient gel electrophoresis. In some embodiments, one or more microfluidic chips 108 may be configured to process one or more samples 102 through use electrophoresis under denaturing conditions. In some embodiments, one or more microfluidic chips 108 may be configured to process one or more samples 102 through use electrophoresis under native conditions. One or more microfluidic chips 108 may be configured to utilize numerous electrophoretic methods.

In some embodiments, one or more microfluidic chips 108 may be configured to process one or more samples 102 through use of immunoassay. In some embodiments, one or more microfluidic chips 108 may be configured to process one or more samples 102 through use of enzyme linked immunosorbant assay (ELISA). In some embodiments, one or more microfluidic chips 108 may be configured to process one or more samples 102 through use of radioimmuno assay (RIA). In some embodiments, one or more microfluidic chips 108 may be configured to process one or more samples 102 through use of enzyme immunoassay (EIA). In some embodiments, such methods may utilize antibodies (e.g., monoclonal antibodies, polyclonal antibodies, antibody fragments, single-chain antibodies, and the like), aptamers, or substantially any combination thereof. In some embodiments, a labeled antibody and/or aptamer may be used within an immunoassay. In some embodiments, a labeled ligand to which the antibody and/or aptamer binds may be used within an immunoassay. Numerous types of labels may be utilized. Examples of such labels include, but are not limited to, radioactive labels, fluorescent labels, enzyme labels, spin labels, magnetic labels, gold labels, colorimetric labels, redox labels, and the like. Numerous immunoassays are known and may be configured for processing one or more samples 102.

In some embodiments, one or more microfluidic chips 108 may be configured to process one or more samples 102 through use of one or more competition assays. In some embodiments, one or more microfluidic chips 108 may be configured to process one or more samples 102 through use of one or more polynucleotide based competition assays. One or more microfluidic chips 108 may be configured to include one or more polynucleotides coupled to a substrate, such as a polynucleotide array. The one or more microfluidic chips 108 may be further configured so that a sample 102 and/or substantially purified polynucleotides obtained from one or more samples 102, may be mixed with one or more reagent mixtures that include one or more labeled polynucleotides to form an analysis mixture. This analysis mixture is then passed over the substrate such that the labeled polynucleotides and the sample polynucleotides are allowed to hybridize to the polynucleotides that are immobilized on the substrate. The sample polynucleotides and the labeled polynucleotides will compete for binding to the polynucleotides that are coupled on the substrate. Accordingly, the presence and/or concentration of the polynucleotides in the sample 102 can be determined through detection of the label (e.g., the concentration of the polynucleotides in the sample 102 will be inversely related to the amount of label that is bound to the substrate). Numerous labels may be used that include, but are not limited to, enzymes, fluorescent molecules, radioactive labels, spin labels, redox labels, and the like. In some embodiments, one or more microfluidic chips 108 may be configured to include one or more antibodies, proteins, peptides, and/or aptamers that are coupled to a substrate. The one or more microfluidic chips 108 may be further configured so that a sample 102 and/or substantially purified sample polypeptides and/or sample peptides obtained from one or more samples 102, may be mixed with one or more reagent mixtures that include one or more labeled polypeptides and/or labeled peptides to form an analysis mixture. This analysis mixture can then be passed over the substrate such that the labeled polypeptides and/or labeled peptides and the sample polypeptides and/or sample peptides are allowed to bind to the antibodies, proteins, peptides, and/or aptamers that are immobilized on the substrate. The sample polypeptides and/or sample peptides and the labeled polypeptides and/or sample peptides will compete for binding to the antibodies, proteins, peptides, and/or aptamers that are coupled on the substrate. Accordingly, the presence and/or concentration of the sample polypeptides and/or sample peptides in the sample 102 can be determined through detection of the label (e.g., the concentration of the sample polypeptides and/or sample peptides in the sample 102 will be inversely related to the amount of label that is bound to the substrate). Numerous labels may be used that include, but are not limited to, enzymes, fluorescent molecules, radioactive labels, spin labels, redox labels, and the like. Microfluidic chips 108 may be configured to utilize numerous types of competition assays.

In some embodiments, one or more microfluidic chips 108 may be configured to utilize numerous processing methods. For example, in some embodiments, one or more allergen indicators 106 may be precipitated with salt, dialyzed, and then applied to a chromatographic column.

At embodiment 3504, module 3320 may include one or more analysis units configured for analysis of the one or more allergen indicators that are associated with one or more food products. In some embodiments, one or more microfluidic chips 108 may include one or more analysis units 120 configured for analysis of one or more allergen indicators 106 that are associated with one or more food products. Numerous food associated allergen indicators 106 have been referenced herein and have been described (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Examples of such food associated allergen indicators 106 include, but are not limited to, polynucleotides, polypeptides, carbohydrates, lipids, polysaccharides (e.g., chitin), oils, shell components, glycoproteins, and the like.

At embodiment 3506, module 3320 may include one or more analysis units configured for analysis of the one or more allergen indicators that are associated with one or more weeds, grasses, trees, mites, animals, molds, fungi, insects, rubbers, metals, chemicals, autoallergens, or human autoallergens. In some embodiments, one or more microfluidic chips 108 may include one or more analysis units 120 configured for analysis of the one or more allergen indicators 106 that are associated with one or more weeds, grasses, trees, mites, animals, molds, fungi, insects, rubbers, metals, chemicals, autoallergens, human autoallergens, or substantially any combination thereof.

At embodiment 3508, module 3320 may include one or more analysis units configured for polynucleotide extraction. In some embodiments, one or more microfluidic chips 108 may include one or more analysis units 120 configured for polynucleotide extraction. Microfluidic chips 108 may be configured to provide for utilization of numerous methods to extract one or more polynucleotides from one or more samples 102.

In some embodiments, one or more microfluidic chips 108 may be configured to provide for utilization of chemical methods to extract one or more polynucleotides from one or more samples 102. For example, a microfluidic chip 108 may be configured to utilize alkaline lysis (e.g., miniprep procedure) to extract polynucleotides from one or more samples 102. In such examples, a microfluidic chip 108 may include a chamber where one or more samples 102 may be combined with a lysis buffer (e.g., sodium hydroxide/sodium dodecyl sulfate) to solubilize the one or more samples 102. The solubilized samples 102 may then be combined with an agent that precipitates the sodium dodecyl sulfate (e.g., potassium acetate) and the microfluidic chip 108 may be centrifuged through use of a centrifugation unit 118. The supernatant may then be transferred to another chamber where it may be chemically extracted (e.g., phenol/chloroform). The supernatant may then be transferred to another chamber and combined with an agent to precipitate polynucleotides present within the supernatant (e.g., alcohol). The microfluidic chip 108 may then be centrifuged to pellet any polynucleotides and then the supernatant may be drawn off and the pellet resuspended to facilitate analysis of the polynucleotides.

In some embodiments, one or more microfluidic chips 108 may be configured to provide for extraction of one or more polynucleotides from one or more samples 102 through use of magnetic extraction. For example, in some embodiments, one or more microfluidic chips 108 may include one or more chambers where one or more samples 102 that may include one or more sample polynucleotides may be mixed with extraction polynucleotides that are associated with one or more ferrous tags. Hybridization of the extraction polynucleotides with the sample polynucleotides will associate the one or more ferrous tags with the one or more sample polynucleotides. The hybridized polynucleotides may then be subjected to a magnetic field to separate the one or more sample polynucleotides from the one or more samples 102.

In some embodiments, one or more microfluidic chips 108 may be configured to provide for the use of magnetism for extraction of one or more polynucleotides from one or more samples 102. In some embodiments, magnetic and/or ferrous tags may be used in combination with ferrous fluid and/or magnetic fluid to extract one or more polynucleotides from one or more samples 102. In some embodiments, ferrous fluids and/or magnetic fluids may be used in combination with one or more H-filters to extract polynucleotides from one or more samples 102. For example, in some embodiments, a microfluidic chip 108 may be configured to include an H-filter where a sample fluid that includes one or more ferrous tagged polynucleotides may flow next to a magnetic fluid such that the one or more ferrous tagged polynucleotides migrate into the ferrous fluid to facilitate extraction of the one or more polynucleotides. In some embodiments, eddy currents may be used to extract one or more polynucleotides from one or more samples 102. For example, in some embodiments, one or more polynucleotides that are associated with a non-ferrous metallic tag (e.g., an aluminum bead) may be passed through a magnetic field such that kinetic energy is imparted to the non-ferrous metallic tagged polynucleotides to facilitate their extraction from the one or more samples 102. In some embodiments, a microfluidic chip 108 may be configured to include an H-filter where a sample fluid that includes one or more polynucleotides that are associated with one or more non-ferrous metallic tags may flow next to an extraction fluid such that passage of the one or more non-ferrous metallic tagged polynucleotides through a magnetic field will facilitate migration of the tagged polynucleotides into the adjoining extraction fluid.

In some embodiments, one or more microfluidic chips 108 may be configured to utilize immobilized polynucleotides for extraction of one or more polynucleotides that correspond to one or more allergen indicators 106 from one or more samples 102. For example, in some embodiments, one or more samples 102 may be incubated with one or more immobilized polynucleotides (e.g., a polynucleotide array) that include nucleotide sequences that correspond to one or more allergen indicators 106. The one or more samples 102 may then be incubated under conditions that allow hybridization of one or more polynucleotides within the one or more samples 102 with the one or more immobilized polynucleotides. The immobilized polynucleotides may then be washed to extract polynucleotides that correspond to allergen indicators 106 from the one or more samples 102. Microfluidic chips 108 may be configured in numerous ways to utilize polynucleotide hybridization to extract allergen indicators 106 from one or more samples 102.

In some embodiments, one or more microfluidic chips 108 may be configured for extraction of polynucleotides that correspond to one or more allergen indicators 106 from one or more samples 102 through use of numerous polynucleotide conjugates. Such polynucleotide conjugates include, but are not limited to, polynucleotides that include one or more nucleotide sequences that correspond to one or more allergen indicators 106 that are associated with an immobilization tag. Examples of such immobilization tags include, but are not limited to, avidin, biotin, streptavidin, antibodies, aptamers, and the like. Accordingly, in some embodiments, one or more samples 102 may be mixed with one or more polynucleotide conjugates such that the polynucleotide conjugates may hybridize with one or more allergen indicators 106 that are included within the one or more samples 102. The mixture may then be contacted with one or more immobilization tag binders that are linked to a substrate such that the one or more allergen indicators 106 become immobilized. The immobilized polynucleotides may then be washed to extract polynucleotides that correspond to allergen indicators 106 from the one or more samples 102. Microfluidic chips 108 may be configured in numerous ways to utilize polynucleotide conjugates to extract allergen indicators 106 from one or more samples 102.

In some embodiments, one or more microfluidic chips 108 may be configured to utilize chromatographic methods for extraction of polynucleotides that correspond to one or more allergen indicators 106 from one or more samples 102. Numerous methods are known and have been described that may be used to extract one or more polynucleotides from one or more samples 102.

In some embodiments, one or more microfluidic chips 108 may be configured to utilize two or more methods to extract one or more polynucleotides from one or more samples 102.

At embodiment 3510, module 3320 may include one or more analysis units configured for polypeptide extraction. In some embodiments, one or more microfluidic chips 108 may include one or more analysis units 120 configured for polypeptide extraction. Microfluidic chips 108 may be configured to provide for utilization of numerous methods to extract one or more polypeptides from one or more samples 102.

In some embodiments, one or more microfluidic chips 108 may be configured to provide for utilization of chemical methods to extract one or more polypeptides from one or more samples 102. For example, a microfluidic chip 108 may be configured to utilize salt precipitation to extract polypeptides from one or more samples 102. In such examples, a microfluidic chip 108 may include a chamber where one or more samples 102 may be combined with one or more salts (e.g., ammonium sulfate). The microfluidic chip 108 may be centrifuged through use of a centrifugation unit 118 to produce a pellet that includes one or more polypeptides. The supernatant may then be removed and the pellet may be resuspended. The resuspended pellet containing the one or more precipitated polynucleotides may be transferred to another chamber of the microfluidic chip 108 where the salt mixture may be dialyzed to reduce the salt concentration.

In some embodiments, one or more microfluidic chips 108 may be configured to provide for extraction of one or more polypeptides from one or more samples 102 through use of magnetic extraction. For example, in some embodiments, one or more microfluidic chips 108 may include one or more chambers where one or more samples 102 that may include one or more sample polypeptides may be mixed with one or more polypeptide binders that are associated with one or more ferrous tags. Binding of the polypeptide binders with the sample polypeptides will associate the one or more ferrous tags with the one or more sample polypeptides. The polypeptides may then be subjected to a magnetic field to separate the one or more sample polypeptides from the one or more samples 102.

In some embodiments, one or more microfluidic chips 108 may be configured to provide for the use of magnetism for extraction of one or more polypeptides from one or more samples 102. In some embodiments, magnetic and/or ferrous tags may be used in combination with ferrous fluid and/or magnetic fluid to extract one or more polypeptides from one or more samples 102. In some embodiments, ferrous fluids and/or magnetic fluids may be used in combination with one or more H-filters to extract polypeptides from one or more samples 102. For example, in some embodiments, a microfluidic chip 108 may be configured to include an H-filter where a sample fluid that includes one or more ferrous tagged polypeptides may flow next to a magnetic fluid such that the one or more ferrous tagged polypeptides migrate into the ferrous fluid to facilitate extraction of the one or more polypeptides. In some embodiments, eddy currents may be used to extract one or more polypeptides from one or more samples 102. For example, in some embodiments, one or more polypeptides that are associated with a non-ferrous metallic tag (e.g., an aluminum bead) may be passed through a magnetic field such that kinetic energy is imparted to the non-ferrous metallic tagged polypeptides to facilitate their extraction from the one or more samples 102. In some embodiments, a microfluidic chip 108 may be configured to include an H-filter where a sample fluid that includes one or more polypeptides that are associated with one or more non-ferrous metallic tags may flow next to an extraction fluid such that passage of the one or more non-ferrous metallic tagged polypeptides through a magnetic field will facilitate migration of the tagged polypeptides into the adjoining extraction fluid.

In some embodiments, one or more microfluidic chips 108 may be configured to utilize immobilized polypeptide binders for extraction of one or more polypeptides that correspond to one or more allergen indicators 106 from one or more samples 102. For example, in some embodiments, one or more samples 102 may be incubated with one or more immobilized polypeptide binders (e.g., antibodies, aptamers, substrates, polypeptides, peptides, polynucleotides, and the like). The one or more samples 102 may then be incubated under conditions that allow binding of one or more polypeptides within the one or more samples 102 with the one or more immobilized polypeptide binders. The immobilized polypeptides may then be washed to extract polypeptides that correspond to allergen indicators 106 from the one or more samples 102. Microfluidic chips 108 may be configured in numerous ways to utilize polypeptide binding to extract allergen indicators 106 from one or more samples 102.

In some embodiments, one or more microfluidic chips 108 may be configured for extraction of polypeptides that correspond to one or more allergen indicators 106 from one or more samples 102 through use of numerous polypeptide conjugates. Such polypeptide conjugates include, but are not limited to, polypeptides that bind to one or more allergen indicators 106 and that are associated with an immobilization tag. Examples of such immobilization tags include, but are not limited to, avidin, biotin, streptavidin, antibodies, aptamers, and the like. Accordingly, in some embodiments, one or more samples 102 may be mixed with one or more polypeptide conjugates such that the polypeptide conjugates may bind with one or more allergen indicators 106 that are included within the one or more samples 102. The mixture may then be contacted with one or more immobilization tag binders that are linked to a substrate such that the one or more allergen indicators 106 become immobilized. The immobilized polypeptides may then be washed to extract polypeptides that correspond to allergen indicators 106 from the one or more samples 102. Microfluidic chips 108 may be configured in numerous ways to utilize polypeptide conjugates to extract allergen indicators 106 from one or more samples 102.

In some embodiments, one or more microfluidic chips 108 may be configured to utilize chromatographic methods for extraction of polypeptides that correspond to one or more allergen indicators 106 from one or more samples 102. Numerous methods are known and have been described that may be used to extract one or more polypeptides from one or more samples 102.

In some embodiments, one or more microfluidic chips 108 may be configured to utilize two or more methods to extract one or more polypeptides from one or more samples 102.

Figure 36:
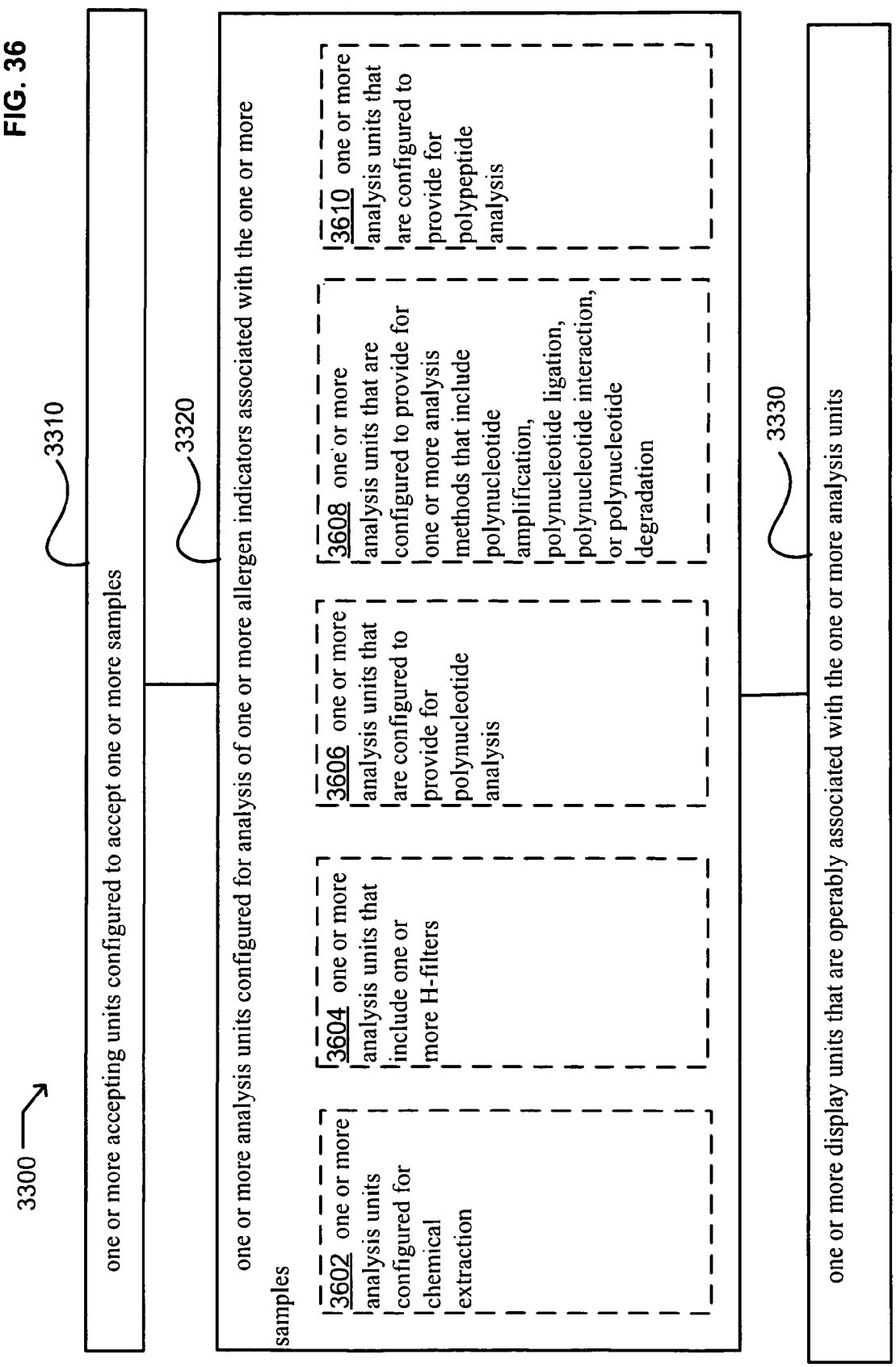
FIG. 36 illustrates alternate embodiments of the microfluidic chip of FIG. 33.

FIG. 36 illustrates alternative embodiments of microfluidic chips 3300 of FIG. 33. FIG. 36 illustrates example embodiments of module 3320. Additional embodiments may include an embodiment 3602, an embodiment 3604, an embodiment 3606, an embodiment 3608, and/or an embodiment 3610.

At embodiment 3602, module 3320 may include one or more analysis units configured for chemical extraction. In some embodiments, one or more microfluidic chips 108 may include one or more analysis units 120 configured for chemical extraction. Such microfluidic chips 108 may be used to extract one or more allergen indicators 106 from one or more samples 102. Microfluidic chips 108 may be configured to provide for use of numerous types of chemical extraction methods. Examples of such extraction methods include, but are not limited to, solvent extraction, acid extraction, base extraction, salt extraction, pH based extraction, and the like. Examples of allergen indicators 106 that may be extracted include, but are not limited to, metals, polynucleotides, polypeptides, carbohydrates, lipids, polysaccharides (e.g., chitin), oils, glycoproteins, and the like.

At embodiment 3604, module 3320 may include one or more analysis units that include one or more H-filters. In some embodiments, one or more microfluidic chips 108 may include one or more analysis units 120 that include one or more H-filters. Methods to construct H-filters have been described (e.g., U.S. Pat. Nos. 6,742,661; 6,409,832; 6,007,775; 5,974,867; 5,971,158; 5,948,684; 5,932,100; 5,716,852; herein incorporated by reference). In some embodiments, H-filters may be configured to provide for immunodiffusion assays. In some embodiments, H-filters may be configured to provide for immunoseparation of one or more allergen indicators 106. In some embodiments, H-filters may be configured to provide for diffusion based separation of one or more allergen indicators 106. In some embodiments, H-filters may be configured for use with one or more ferrofluids and/or magnetic fluids. In some embodiments, two or more H-filters may be coupled to each other in series. In some embodiments, H-filters may be operably coupled with one or more magnets. Accordingly, one or more microfluidic chips 108 may include one or more H-filters that are configured in numerous ways.

At embodiment 3606, module 3320 may include one or more analysis units that are configured to provide for polynucleotide analysis. In some embodiments, one or more microfluidic chips 108 may include one or more analysis units 120 that are configured to provide for polynucleotide analysis. In some embodiments, one or more analysis units 120 may be configured to detect one or more polynucleotides. Microfluidic chips 108 may be configured to provide for the use of numerous methods for detection of one or more polynucleotides. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described (e.g., U.S. Pat. Nos. 7,118,910 and 6,960,437; herein incorporated by reference). Such methods may be adapted to provide for detection of one or more allergen indicators 106. In some embodiments, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more microfluidic chips 108 may be configured to provide for hybridization of one or more polynucleotides that include at least one carbon nanotube with one or more samples 102, and/or one or more partially purified polynucleotides obtained from one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Methods to utilize carbon nanotubes as probes for nucleic acid interaction have been described (e.g., U.S. Pat. No. 6,821,730; herein incorporated by reference). Microfluidic chips 108 may be configured to provide for use of numerous other methods based on polynucleotide detection for detection of one or more allergen indicators 106. In some embodiments, microfluidic chips 108 may be configured to provide for analysis of two or more polynucleotides.

At embodiment 3608, module 3320 may include one or more analysis units that are configured to provide for one or more analysis methods that include polynucleotide amplification, polynucleotide ligation, polynucleotide interaction, or polynucleotide degradation. In some embodiments, one or more microfluidic chips 108 may include one or more analysis units 120 that are configured to provide for one or more analysis methods that include polynucleotide amplification, polynucleotide ligation, polynucleotide interaction, polynucleotide degradation, or substantially any combination thereof.

In some embodiments, one or more microfluidic chips 108 may be configured to provide for analysis of one or more allergen indicators 106 through use of polynucleotide amplification. In some embodiments, one or more microfluidic chips 108 may be configured to provide for polynucleotide amplification by polymerase chain reaction (PCR). In some embodiments, PCR primers may be selected that hybridize to polynucleotides that are allergen indicators 106. Accordingly, such polynucleotides may be amplified. In some embodiments, PCR primers may be selected that include conductive end-groups such that the amplified PCR product may interact with two or more electrodes to bridge the electrodes and complete an electrical circuit. Accordingly, use of such primers provides for detection of the PCR products through use of electrical conductance. In some embodiments, primers that include conductive end-groups may be selected such that the primers themselves are inadequate to complete an electrical circuit and therefore will exhibit minimal background. In some embodiments, a microfluidic chip 108 may be configured to provide for polynucleotide amplification in the presence of altered nucleotides that will be incorporated into the PCR product. Accordingly, incorporation of such altered nucleotides into a PCR product may provide for detection of the PCR product. Examples of such altered nucleotides include, but are not limited to, alexa fluor labeled nucleotides, aminonaphthalenesulfonate labeled nucleotides, biotin labeled nucleotides, biotin labeled AMP, biotin labeled ddNTP, biotin labeled dNTP, BODIPY labeled nucleotides, caged nucleotides, coumarin labeled nucleotides, Cy3 labeled nucleotides, Cy5 labeled nucleotides, digoxigenin labeled nucleotides, digoxigenin labeled dUTP, fluorescein labeled nucleotides, R110 labeled nucleotides, R6G labeled nucleotides, rhodamine green labeled nucleotides, rhodamine labeled nucleotides, ROX labeled nucleotides, Texas red labeled nucleotides, tetramethylrhodamine labeled nucleotides, trinitrophenyl labeled nucleotides, and the like. Methods to conduct PCR amplification are known and have been described (Belgrader et al., Biosensors & Bioelectronics, 14:849-852 (2000); Khandurina et al., Analytical Chemistry, 72:2995-3000 (2000); and Lagally et al., Analytical Chemistry, 73:565-570 (2001)).

In some embodiments, one or more microfluidic chips 108 may be configured to provide for analysis of one or more allergen indicators 106 through use of polynucleotide ligation. In some embodiments, one or more microfluidic chips 108 may be configured to provide for ligase chain reaction (LCR). Reaction conditions that may be used to conduct ligase chain reaction have been described (e.g., O'Connor et al., Thorax, 55:955-957 (2000); Tooley et al., Can. J. Plant Pathol., 24:294-301 (2002) and Ching et al., J. Clin. Microbiol., 33:3111-3114 (1995)). In some embodiments, LCR primers may be selected that include conductive end-groups such that the ligated LCR product may interact with two or more electrodes to bridge the electrodes and complete an electrical circuit. Accordingly, LCR may be used to provide for detection of one or more allergen indicators 106. LCR primers may be selected that include numerous types of end-groups. Examples of such end-groups include, but are not limited to, immobilization tags, detectable labels, and the like. In some embodiments, such end-groups may be used to facilitate detection of one or more allergen indicators 106.

In some embodiments, one or more microfluidic chips 108 may be configured to provide for analysis of one or more samples 102 through use of polynucleotide interaction. Microfluidic chips 108 may be configured to provide for the use of numerous methods based on polynucleotide interaction. Methods that utilize intercalation dyes, FRET analysis, and capacitive DNA detection have been described (e.g., U.S. Pat. Nos. 7,118,910 and 6,960,437; herein incorporated by reference). In some embodiments, microfluidic chips 108 may be configured to provide for fluorescence resonance energy transfer, fluorescence quenching, molecular beacons, electron transfer, electrical conductivity, and the like. In some embodiments, one or more microfluidic chips 108 may be configured to provide for utilization of one or more polynucleotides that include at least one carbon nanotube as has been described (e.g., U.S. Pat. No. 6,821,730; herein incorporated by reference).

In some embodiments, one or more microfluidic chips 108 may be configured to provide for analysis of one or more samples 102 through use of polynucleotide degradation. For example, one or more microfluidic chips 108 may be configured to provide for restriction digestion of one or more polynucleotides. Accordingly, microfluidic chips 108 may be configured to provide for extraction of polynucleotides that are allergen indicators 106 from one or more samples 102, digest the polynucleotides with restriction enzymes, and then subject the polynucleotide fragments to electrophoretic analysis.

At embodiment 3610, module 3320 may include one or more analysis units that are configured to provide for polypeptide analysis. In some embodiments, one or more microfluidic chips 108 may include one or more analysis units 120 that are configured to provide for polypeptide analysis. In some embodiments, microfluidic chips 108 may be configured for utilization of numerous methods for the analysis of polypeptides that are allergen indicators 106.

In some embodiments, a microfluidic chip 108 may be configured to analyze one or more polypeptides through use of one or more electrophoretic methods. Examples of such electrophoretic methods include, but are not limited to, isoelectric focusing, denaturing gel electrophoresis, native gel electrophoresis, agarose gel electrophoresis, gradient gel electrophoresis, and the like.

In some embodiments, a microfluidic chip 108 may be configured to analyze one or more polypeptides through use of one or more chromatographic methods. Examples of such chromatographic methods include, but are not limited to, gel filtration chromatography, ion-exchange chromatography, affinity chromatography, and the like.

In some embodiments, a microfluidic chip 108 may be configured for analysis of one or more polypeptides through use of degradative methods. For example, in some embodiments, one or more polypeptides may be subjected to proteolytic digestion with one or more proteases. The degradative products may then be analyzed through use of numerous methods that may include, but are not limited to, gel electrophoresis, gel chromatography, isoelectric focusing, spectroscopic methods, and the like. Accordingly, in some embodiments, such methods may be used to confirm the presence and/or absence of one or more allergen indicators 106 within one or more samples 102. In some embodiments, degradative methods may be used in combination with immunological based methods. For example, in some embodiments, one or more samples 102 may be proteolytically digested, subjected to electrophoresis, and then probed with antibodies and/or aptamers that are specific for one or more allergen indicators 106 to determine if the one or more allergen indicators 106 are present within the sample 102.

In some embodiments, a microfluidic chip 108 may be configured for analysis of one or more polypeptides through use of microcantilevers. For example, in some embodiments, one or more polypeptide binders may be coupled to a cantilever such that one or more polypeptides that bind, or are bound, by the polypeptide binder will become associated with the microcantilever. Such configurations provide for detection of one or more allergen indicators 106 within one or more samples 102.

In some embodiments, a microfluidic chip 108 may be configured for analysis of one or more polypeptides through use of polypeptide interaction. For example, in some embodiments, a microfluidic chip 108 may include an array of polypeptide binders (e.g., antibodies, aptamers, enzymatic substrates, enzymatic products, or the like) that are immobilized on one or more conductive substrates. Binding of one or more polypeptides to the polypeptide binders will complete an electrical circuit such that interaction may be detected through measurement of electrical current. In some embodiments, one or more microfluidic chips 108 may be configured for utilization of immunological methods for polypeptide analysis. Examples of such immunological methods include, but are not limited to, sandwich assays, use of antibody arrays, immunoprecipitation, immunoseparation, immunodiffusion, and the like. In some embodiments, aptamers may be utilized in place of antibodies or in combination with antibodies with regard to immunological methods.

Accordingly, one or more microfluidic chips 108 may be configured in numerous ways to provide for analysis of one or more allergen indicators 106 that may include one or more polypeptides.

Figure 37:
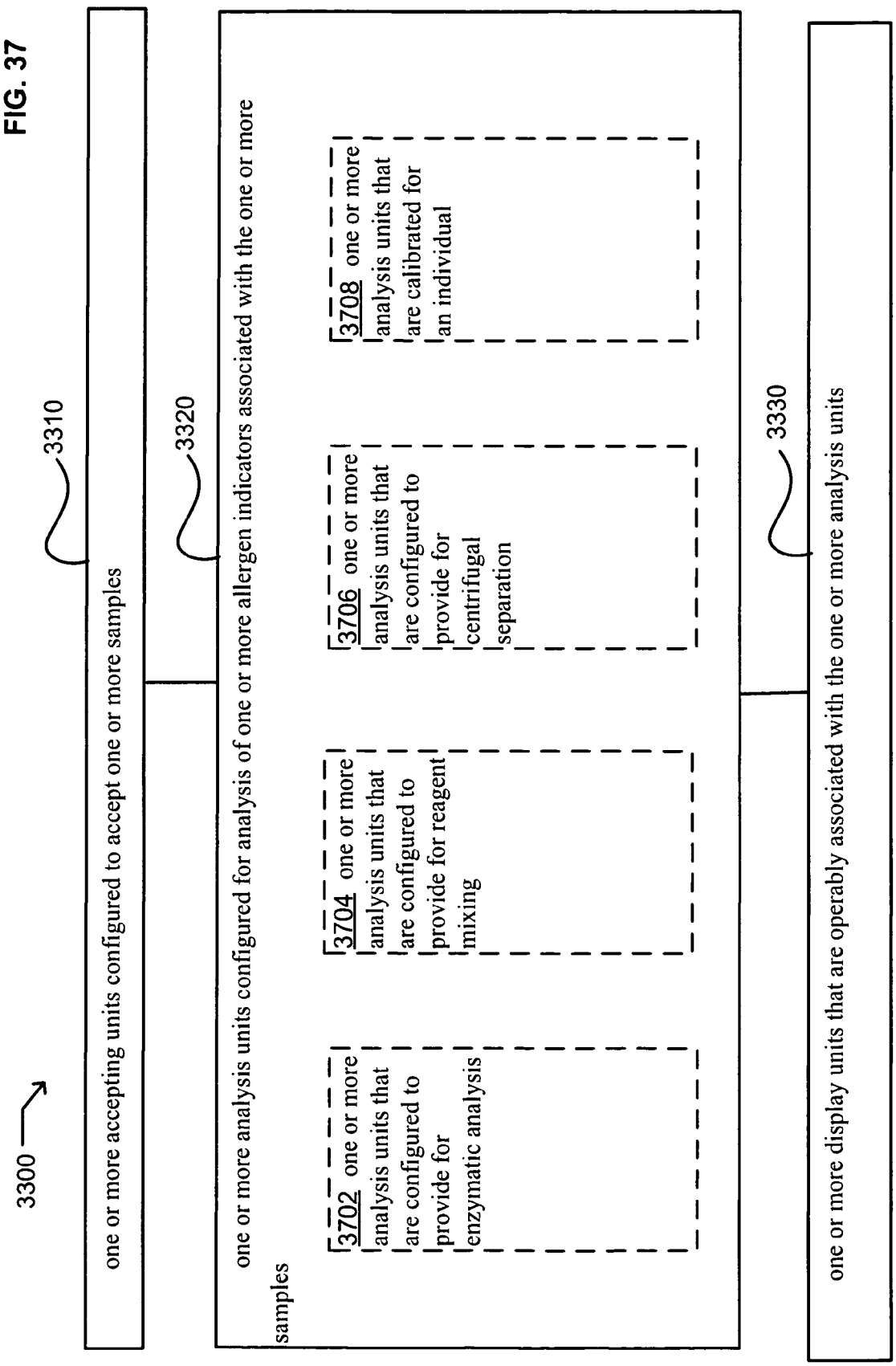
FIG. 37 illustrates alternate embodiments of the microfluidic chip of FIG. 33.

FIG. 37 illustrates alternative embodiments of microfluidic chips 3300 of FIG. 33. FIG. 37 illustrates example embodiments of module 3320. Additional embodiments may include an embodiment 3702, an embodiment 3704, and/or an embodiment 3706.

At embodiment 3702, module 3320 may include one or more analysis units that are configured to provide for enzymatic analysis. In some embodiments, one or more microfluidic chips 108 may include one or more analysis units 120 that are configured to provide for enzymatic analysis. In some embodiments, microfluidic chips 108 may be configured for utilization of numerous methods for the analysis of enzyme activity that is associated with one or more allergen indicators 106.

In some embodiments, enzyme activity may include activity that is directly associated with one or more allergen indicators 106. For example, in some embodiments, allergen indicators 106 exhibit enzyme activity (e.g., Derf1: dust mite cysteine protease; Derf18w: dust mite 60k chitinase; Horv17: barley beta-amylase; Fraa3: strawberry lipid transfer protein; Kiwi: Actc1 cysteine protease; and the like). Accordingly, microfluidic chips 108 may be configured to analyze one or more samples 102 for enzyme activity associated with one or more allergen indicators 106. For example, in some embodiments, one or more microfluidic chips 108 may be configured to present one or more substrates to one or more samples 102 such that enzyme activity within the one or more samples 102 may be detected through analysis of products resulting from enzyme activity. In some embodiments, enzyme substrates may be selected that produce a detectable signal when they are acted upon by one or more allergen indicator 106 associated enzymes. For example, protease substrates may be used that increase in fluorescence upon being cleaved by an allergen indicator 106 associated protease. Numerous types of substrates may be used to analyze enzyme activity.

In some embodiments, enzyme activity may include activity that is indirectly associated with one or more allergen indicators 106. For example, in some embodiments, one or more microfluidic chips 108 may be configured to analyze the activity of one or more enzymes that become associated with one or more allergen indicators 106. For example, in some embodiments, one or more microfluidic chips 108 may be configured to analyze the activity of one or more enzymes that become associated with one or more allergen indicators 106 through binding (e.g., enzyme activity coupled to an antibody that binds to an allergen indicator 106).

In some embodiments, one or more microfluidic chips 108 may be configured to utilize enzymatic analysis in combination with other analysis methods. For example, in some embodiments, enzymatic analysis may be combined with the use of an H-filter. In some embodiments, one or more samples 102 may be incubated with one or more substrates in a reaction mixture such that one or more products of enzymatic activity may be separated from the reaction mixture through use of an H-filter. An example of such a product may be a detectable label having a higher diffusion constant than the substrate to which it was originally coupled. Accordingly, cleavage of the detectable label from the substrate by the enzymatic activity of an allergen indicator 106 may increase diffusion of the detectable label and thereby provide for separation of the detectable label through use of an H-filter.

Microfluidic chips 108 may be configured to utilize numerous methods to analyze enzymatic activity.

At embodiment 3704, module 3320 may include one or more analysis units that are configured to provide for reagent mixing. In some embodiments, one or more microfluidic chips 108 may include one or more analysis units 120 that are configured to provide for reagent mixing. In some embodiments, a microfluidic chip 108 may include one or more mixing chambers. In some embodiments, a microfluidic chip 108 may include one or more mixing chambers that are configured to mix one or more reagents. In some embodiments, a microfluidic chip 108 may include one or more mixing chambers that are configured to mix one or more samples 102. In some embodiments, a microfluidic chip 108 may include one or more mixing chambers that are configured to mix one or more samples 102 with one or more reagents. In some embodiments, one or more mixing chambers may be configured for use of sonication. In some embodiments, one or more mixing chambers may be configured for use of magnetic mixing. For example, in some embodiments, a microfluidic chip 108 may include a mixing chamber which includes one or more ferrous mixing members and electromagnetics which are configured such that motion may be imparted to the one or more ferrous mixing members. In some embodiments, a microfluidic chip 108 may include one or more mixing chambers that include two or more electromagnets positioned around the one or more mixing chambers and one or more ferrous members positioned within the one or more mixing chambers and between the electromagnetics. Accordingly, mixing of one or more materials within the one or more mixing chambers may be facilitated by alternating current between the electromagnets positioned around the mixing chamber. In some embodiments, a mixing chamber may include an elastomeric material that includes a ferrous material (e.g., an elastomeric-ferrous material) such that movement of the elastomeric-ferrous material may be facilitated through use of one or more magnets, such as electromagnets. Microfluidic chips 108 may include mixing chambers that are configured in numerous ways.

At embodiment 3706, module 3320 may include one or more analysis units that are configured to provide for centrifugal separation. In some embodiments, one or more microfluidic chips 108 may include one or more analysis units 120 that are configured to provide for centrifugal separation. A microfluidic chip 108 may be configured to utilize numerous types of centrifugal separation.

In some embodiments, a microfluidic chip 108 may be configured to operably associate with a centrifuge. For example, in some embodiments, a microfluidic chip 108 may be configured for centrifugation within a centrifuge (e.g., such as those made by Sorvall, Beckman, Drucker, and the like). In some embodiments, a microfluidic chip 108 may be configured to fit within a centrifuge rotor (e.g., such as those made by Sorvall, IEC, and the like). In some embodiments, a microfluidic chip 108 may be configured to include one or more centrifugation units 118. In some embodiments, such a centrifugation unit 118 may include a rotor chamber that may be detachably associated with a centrifuge drive that is external to the microfluidic chip 108. In some embodiments, such a centrifugation unit 118 may include a rotor that is operably associated with a centrifuge drive that is included within the microfluidic chip 108. For example, in some embodiments, a microfluidic chip 108 may include a centrifugation unit 118 that includes one or more electromagnets that are configured to be in magnetic association with a rotor chamber that includes ferrous material that is configured to magnetically couple with the one or more electromagnets. Accordingly, in such embodiments, the rotor chamber may be rotated by application of electrical current to the one or more electromagnets. In some embodiments, a microfluidic chip 108 may include one or more rotor chambers that are physically coupled to one or more centrifuge drives (e.g., physically coupled through a drive shaft and/or belt).

Such centrifugation units 118 may be configured in numerous ways. For example, in some embodiments, centrifugation units 118 may be configured to provide for gradients, such as density gradients and/or velocity gradients. In some embodiments, centrifugation units 118 may be configured to spin one or more samples 102 through a chromatographic column (e.g., a spin column). Accordingly, centrifugation units 118 may be configured in numerous ways.

At embodiment 3708, module 3320 may include one or more analysis units that are calibrated for an individual. In some embodiments, one or more microfluidic chips 108 may include one or more analysis units 120 that are calibrated for an individual. In some embodiments, one or more analysis units 120 may be constructed for a specific individual. For example, in some embodiments, an individual may be allergic to shellfish and walnuts. Accordingly, in some embodiments, a microfluidic chip 108 may include one or more analysis units 120 that are configured to analyze one or more samples 102 for shellfish and walnut associated allergen indicators 106. Analysis units 120 may be configured to analyze numerous types of samples 102 and allergen indicators 106.

Figure 38:
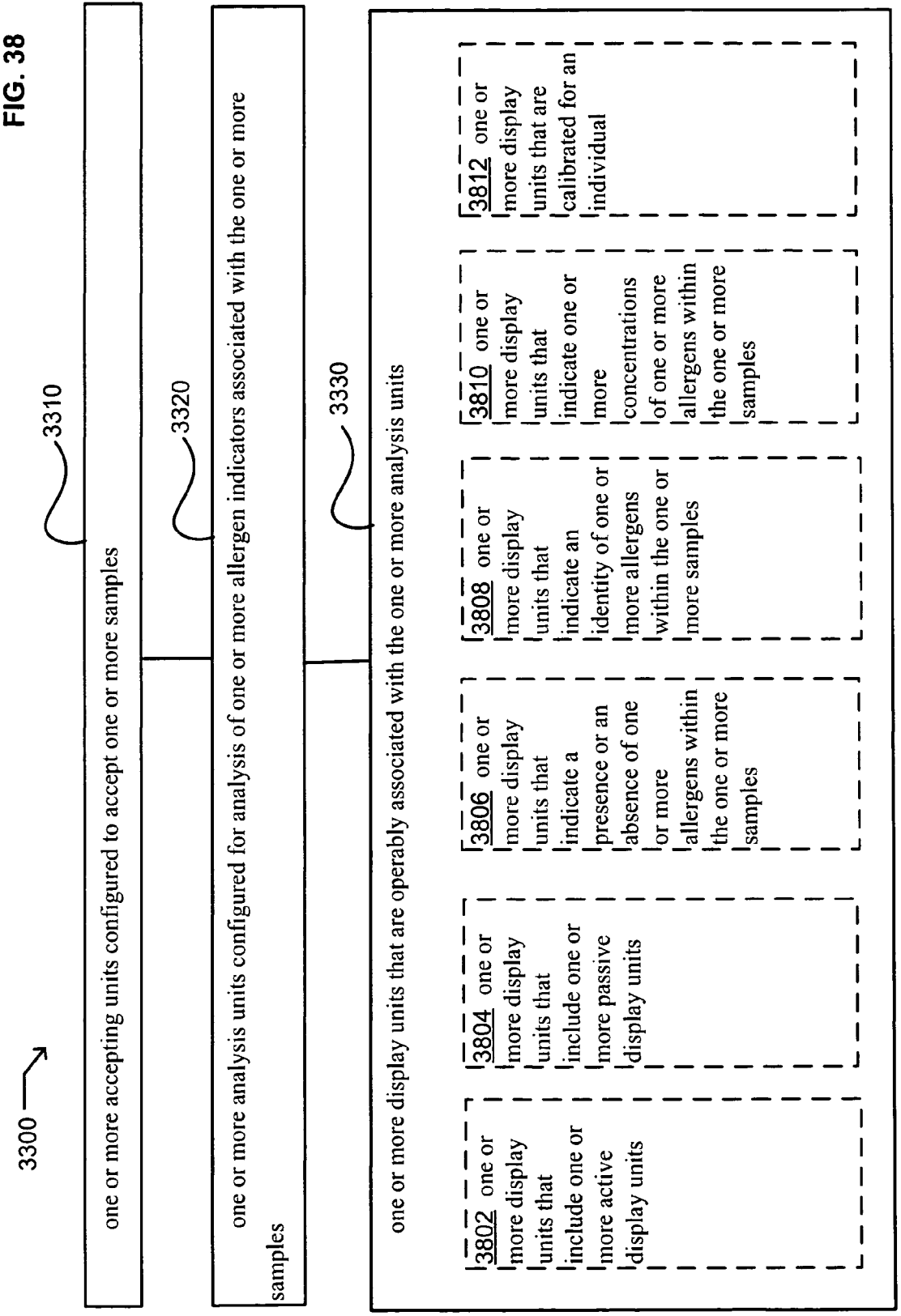
FIG. 38 illustrates alternate embodiments of the microfluidic chip of FIG. 33.

FIG. 38 illustrates alternative embodiments of microfluidic chips 3300 of FIG. 33. FIG. 38 illustrates example embodiments of module 3330. Additional embodiments may include an embodiment 3802, an embodiment 3804, an embodiment 3806, an embodiment 3808, and/or an embodiment 3810.

At embodiment 3802, module 3330 may include one or more display units that include one or more active display units. In some embodiments, one or more microfluidic chips 108 may include one or more display units 124 that include one or more active display units 124. Numerous active display units 124 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), wide ultra extended graphics array (WUXGA).

At embodiment 3804, module 3330 may include one or more display units that include one or more passive display units. In some embodiments, one or more microfluidic chips 108 may include one or more display units 124 that include one or more passive display units 124. In some embodiments, one or more display units 124 may include one or more liquid crystal displays (LCD). Methods to construct passive displays have been described (e.g., U.S. Pat. Nos. 4,807,967; 4,729,636: 4,436,378; 4,257,041; herein incorporated by reference).

At embodiment 3806, module 3330 may include one or more display units that indicate a presence or an absence of one or more allergens within the one or more samples. In some embodiments, one or more microfluidic chips 108 may include one or more display units 124 that may indicate a presence or an absence of one or more allergen indicators 106 within the one or more samples 102. In some embodiments, one or more display units 124 may use a colorimetric message to indicate a presence or an absence of one or more allergen indicators 106 within one or more samples 102. For example, in some embodiments, one or more display units 124 may display a green light if one or more allergen indicators 106 are not found within one or more samples 102 and a red light if one or more allergen indicators 106 are found within one or more samples 102. In some embodiments, one or more display units 124 may use a pictographic message to indicate a presence or an absence of one or more allergen indicators 106 within one or more samples 102. For example, in some embodiments, one or more display units 124 may display a smiley face if one or more allergen indicators 106 are not found within one or more samples 102 and a frowny face if one or more allergen indicators 106 are found within one or more samples 102. In some embodiments, one or more display units 124 may use a typographical message to indicate a presence or an absence of one or more allergen indicators 106 within one or more samples 102. For example, in some embodiments, one or more display units 124 may display an "Allergen Not Present" message if one or more allergen indicators 106 are not found within one or more samples 102 and an "Allergen Present" message if one or more allergen indicators 106 are found within one or more samples 102. Such messages may be displayed in numerous languages. In some embodiments, one or more display units 124 may display one or more messages in multiple formats. For example, in some embodiments, one or more messages may be displayed in colored text.

At embodiment 3808, module 3330 may include one or more display units that indicate an identity of one or more allergens within the one or more samples. In some embodiments, one or more microfluidic chips 108 may include one or more display units 124 that indicate an identity of one or more allergens 104 within the one or more samples 102. In some embodiments, one or more display units 124 may be operably associated with one or more microfluidic chips 108 that are configured to identify one or more allergen indicators 106. Accordingly, in some embodiments, one or more display units 124 may be configured to display the identity of one or more allergens 104 that are present and/or absent from one or more samples 102. For example, in some embodiments, a display unit 124 may be configured to indicate a presence or an absence of beta-lactoglobulin in a food product.

At embodiment 3810, module 3330 may include one or more display units that indicate one or more concentrations of one or more allergens within the one or more samples. In some embodiments, one or more microfluidic chips 108 may include one or more display units 124 that may indicate one or more concentrations of one or more allergens 104 within the one or more samples 102. Concentration may be displayed in numerous formats. For example, in some embodiments, concentration may be expressed numerically (e.g., mass allergen indicator 106 per volume sample 102 (e.g., milligrams per milliliter), mass allergen indicator 106 per mass sample 102 (e.g., milligrams per milligram of sample), parts per million, and the like). In some embodiments, concentration may be expressed graphically. For example, in some embodiments, one or more display units 124 may include a display having a gray scale on which the concentration of one or more allergen indicators 106 that are present within one or more samples 102 may be indicated (e.g., higher concentrations of one or more allergens 104 may be displayed as dark gray while lower concentrations of one or more allergens 104 may be displayed as light gray). In some embodiments, one or more display units 124 may include a display having a color scale on which the concentration of one or more allergen indicators 106 that are present within one or more samples 102 may be indicated (e.g., low concentrations of one or more allergen indicators 106 may be indicated by a green light, intermediate concentrations of one or more allergen indicators 106 may be indicated by a yellow light, high concentrations of one or more allergen indicators 106 may be indicated by a red light). In some embodiments, one or more display units 124 may be calibrated to an individual. For example, in such embodiments, an individual may use the display to obtain an immediate reading that will indicate if a food product contains a dangerous level of one or more allergens 104.

At embodiment 3812, module 3330 may include one or more display units that are calibrated for an individual. In some embodiments, one or more microfluidic chips 108 may include one or more display units 124 that are calibrated for an individual. In some embodiments, one or more display units 124 may be calibrated to display whether one or more allergens 104, and/or allergen indicators 106, that are specific to an individual are present or absent within one or more samples 102. For example, in some embodiments, one or more display units 124 may be configured to display whether one or more samples 102 contain shellfish associated allergens 104 for an individual known to be allergic to shellfish. In some embodiments, one or more display units 124 may be calibrated to indicate safe and/or unsafe concentrations of one or more allergens 104 within one or more samples 102 for an individual.

Figure 39:
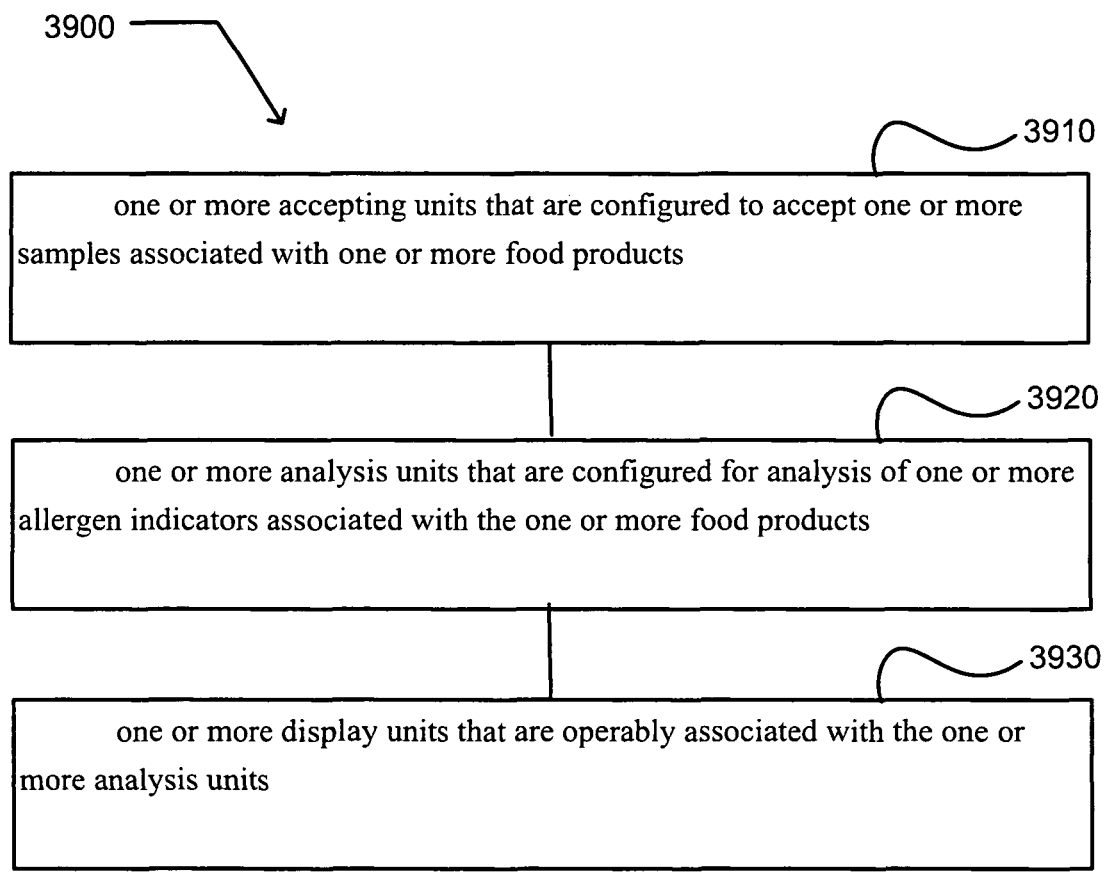
FIG. 39 illustrates an example microfluidic chip 3900 in which embodiments may be implemented.

FIG. 39 illustrates microfluidic chip 3900 that may be configured for analysis of one or more allergen indicators 106. In FIG. 39, discussion and explanation may be provided with respect to use of one or more microfluidic chips 108 within the above-described example of FIG. 1, and/or with respect to other examples and contexts. However, it should be understood that the microfluidic chip 108 may be configured in a number of other environments and contexts, and/or utilized within modified versions of FIG. 1. Also, although the microfluidic chip 108 is presented in the configuration(s) illustrated, it should be understood that the microfluidic chip 108 may be configured in numerous orientations.

The microfluidic chip 3900 includes module 3910 that includes one or more accepting units that are configured to accept one or more samples associated with one or more food products. In some embodiments, one or more microfluidic chips 108 may include one or more accepting units 110 that are configured to accept the one or more samples 102 associated with one or more food products. In some embodiments, module 3910 may include one or more accepting units 110 that are configured to accept one or more samples 102 associated with cod, Atlantic salmon, domestic cattle milk, chicken, shrimp, squid, snail, abalone, frog, oriental mustard, rapeseed, cabbage, turnip, barley, rye, wheat, corn, rice, celery, carrot, hazelnut, strawberry, apple, pear, avocado, apricot, sweet cherry, European plum, almond, peach, asparagus, saffron crocus, lettuce, grape, banana, pineapple, lemon, sweet orange, litchi, yellow mustard, soybean, mung bean, peanut, lentil, pea, kiwi, bell pepper, tomato, potato, Brazil nut, black walnut, English walnut, cashew, castor bean, sesame, muskmelon, Chinese-date, *anacardium occidentale, apium graveolens, daucus carota, citrus sinensis, glycine max, lens culinaris, pisum sativum, lycopersicon sativum, fragaria ananassa, malus domestica, prunus avium, prunus persica*, or substantially any combination thereof.

The microfluidic chip 3900 includes module 3920 that includes one or more analysis units that are configured for analysis of one or more allergen indicators associated with the one or more food products. In some embodiments, one or more microfluidic chips 108 may include one or more analysis units 120 that are configured for analysis of one or more allergen indicators 106 associated with the one or more food products. In some embodiments, module 3920 may include one or more analysis units 120 configured for analysis of one or more allergens 104 that may include Gadc1; Sals1; Bosd4, Bosd5, Bosd6, Bosd7, Bosd8; Gald1, Gald2, Gald3, Gald4, Gald5; Mete1; Pena1, Peni1; Penm1, Penm2; Todp1; Helas1; Halm1; Rane1, Rane2; Braj1; Bran1; Brao3; Brar1, Brar2; Horv15, Horv16, Horv17, Horv21; Secc20; Tria18, Tria19, Tria25, Tria26; Zeam14, Zeam25; Orys1; Apig1, Apig4, Apig5; Dauc1, Dauc4; Cora1.04, Cora2, Cora8; Fraa1, Fraa3, Fraa4; Mald1, Mald2, Mald3, Mald4; Pyrc1, Pyrc4, Pyrc5; Persa1; Pruar1, Pruar3; Pruav1, Pruav2, Pruav3, Pruav4; Prud3; Prudu4; Prup3, Prup4; Aspao1; Cros1, Cros2; Lacs1; Vitv1; Musxp1; Anac1, Anac2; Cit13; Cits1, Cits2, Cits3; Litc1; Sina1; Glym1, Glym2, Glym3, Glym4; Vigr1; Arah1, Arah2, Arah3, Arah4, Arah5, Arah6, Arah7, Arah8; Lenc1, Lenc2; Piss1, Piss2; Actc1, Actc2; Capa1w, Capa2; Lyce1, Lyce2, Lyce3; Solat1, Solat2, Solat3, Solat4; Bere1, Bere2; Jugn1, Jugn2; Jugr1, Jugr2, Jugr3; Anao1, Anao2, Anao3; Ricc1; Sesi1, Sesi2, Sesi3, Sesi4, Sesi5, Sesi6; Cucm1, Cucm2, Cucm3; Zizm1; Anao1.0101, Anao1.0102; Apig1.0101, Apig1.0201; Dauc1.0101, Dauc1.0102, Dauc1.0103, Dauc1.0104, Dauc1.0105, Dauc1.0201; Cits3.0101, Cits3.0102; Glym1.0101, Glym1.0102, Glym3.0101, Glym3.0102; Lenc1.0101, Lenc1.0102, Lenc1.0103; Piss1.0101, Piss1.0102; Lyce2.0101, Lyce2.0102; Fraa3.0101, Fraa3.0102, Fraa3.0201, Fraa3.0202, Fraa3.0203, Fraa3.0204, Fraa3.0301; Mald1.0101, Mald1.0102, Mald1.0103, Mald1.0104, Mald1.0105, Mald1.0106, Mald1.0107, Mald1.0108, Mald1.0109, Mald1.0201, Mald1.0202, Mald1.0203, Mald1.0204, Mald1.0205, Mald1.0206, Mald1.0207, Mald1.0208, Mald1.0301, Mald1.0302, Maid 1.0303, Mald1.0304, Mald1.0401, Mald1.0402, Mald1.0403, Mald3.0101w, Mald3.0102w, Mald3.0201w, Mald3.0202w, Mald3.0203w, Mald4.0101, Mald4.0102, Mald4.0201, Mald4.0202, Mald4.0301, Mald4.0302; Pruav1.0101, Pruav1.0201, Pruav1.0202, Pruav1.0203; Prup4.0101, Prup4.0201, or substantially any combination thereof. In some embodiments, module 3920 may include one or more analysis units that are configured to analyze one or more food allergen associated polynucleotides. In some embodiments, module 3920 may include one or more analysis units that are configured to analyze one or more food allergen associated polypeptides. In some embodiments, module 3920 may include one or more analysis units that are calibrated for an individual.

The microfluidic chip 3900 may optionally include module 3930 that includes one or more display units that are operably associated with the one or more analysis units. In some embodiments, module 3930 may include one or more display units that include one or more active display units. In some embodiments, module 3930 may include one or more display units that include one or more passive display units. In some embodiments, module 3930 may include one or more display units that indicate a presence or an absence of one or more allergens within the one or more samples. In some embodiments, module 3930 may include one or more display units that indicate an identity of one or more allergens within the one or more samples. In some embodiments, module 3930 may include one or more display units that indicate one or more concentrations of one or more allergens within the one or more samples. In some embodiments, module 3930 may include one or more display units that are calibrated for an individual.

FIG. 40 illustrates alternative embodiments of microfluidic chips 3900 of FIG. 39. FIG. 40 illustrates example embodiments of module 3910. Additional embodiments may include an embodiment 4002.

At embodiment 4002, module 3910 may include one or more accepting units that are configured to accept the one or more samples associated with cod, Atlantic salmon, domestic cattle milk, chicken, shrimp, squid, snail, abalone, frog, oriental mustard, rapeseed, cabbage, turnip, barley, rye, wheat, corn, rice, celery, carrot, hazelnut, strawberry, apple, pear, avocado, apricot, sweet cherry, European plum, almond, peach, asparagus, saffron crocus, lettuce, grape, banana, pineapple, lemon, sweet orange, litchi, yellow mustard, soybean, mung bean, peanut, lentil, pea, kiwi, bell pepper, tomato, potato, Brazil nut, black walnut, English walnut, cashew, castor bean, sesame, muskmelon, Chinese-date, *anacardium occidentale, apium graveolens, daucus carota, citrus sinensis, glycine max, lens culinaris, pisum sativum, lycopersicon sativum, fragaria ananassa, malus domestica, prunus avium,* or *prunus persica*. In some embodiments, one or more microfluidic chips 108 may include one or more accepting units 110 that are configured to accept one or more samples 102 associated with cod, Atlantic salmon, domestic cattle milk, chicken, shrimp, squid, snail, abalone, frog, oriental mustard, rapeseed, cabbage, turnip, barley, rye, wheat, corn, rice, celery, carrot, hazelnut, strawberry, apple, pear, avocado, apricot, sweet cherry, European plum, almond, peach, asparagus, saffron crocus, lettuce, grape, banana, pineapple, lemon, sweet orange, litchi, yellow mustard, soybean, mung bean, peanut, lentil, pea, kiwi, bell pepper, tomato, potato, Brazil nut, black walnut, English walnut, cashew, castor bean, sesame, muskmelon, Chinese-date, *anacardium occidentale, apium graveolens, daucus carota, citrus sinensis, glycine max, lens culinaris, pisum sativum, lycopersicon sativum, fragaria ananassa, malus domestica, prunus avium, prunus persica*, or substantially any combination thereof.

Figure 41:
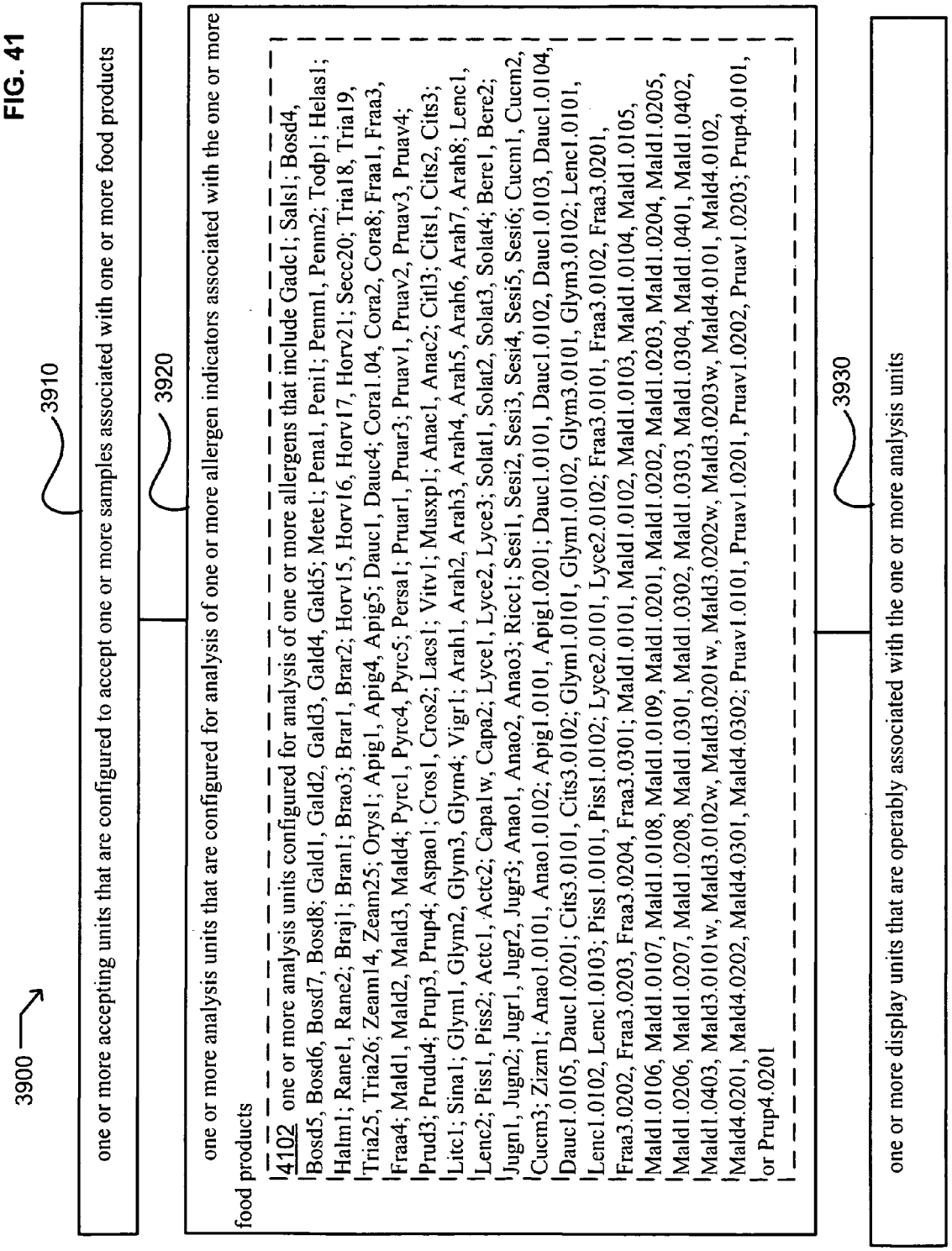
FIG. 41 illustrates alternate embodiments of the microfluidic chip of FIG. 39.

FIG. 41 illustrates alternative embodiments of microfluidic chips 3900 of FIG. 39. FIG. 41 illustrates example embodiments of module 3920. Additional embodiments may include an embodiment 4102.

At embodiment 4102, module 3920 may include one or more analysis units configured for analysis of one or more allergens that include Gadc1; Sals1; Bosd4, Bosd5, Bosd6, Bosd7, Bosd8; Gald1, Gald2, Gald3, Gald4, Gald5; Mete1; Pena1, Peni1; Penm1, Penm2; Todp1; Helas1; Halm1; Rane1, Rane2; Braj1; Bran1; Brao3; Brar1, Brar2; Horv15, Horv16, Horv17, Horv21; Secc20; Tria18, Tria19, Tria25, Tria26; Zeam14, Zeam25; Orys1; Apig1, Apig4, Apig5; Dauc1, Dauc4; Cora1.04, Cora2, Cora8; Fraa1, Fraa3, Fraa4; Mald1, Mald2, Mald3, Mald4; Pyrc1, Pyrc4, Pyrc5; Persa1; Pruar1, Pruar3; Pruav1, Pruav2, Pruav3, Pruav4; Prud3; Prudu4; Prup3, Prup4; Aspao1; Cros1, Cros2; Lacs1; Vitv1; Musxp1; Anac1, Anac2; Cit13; Cits1, Cits2, Cits3; Litc1; Sina1; Glym1, Glym2, Glym3, Glym4; Vigr1; Arah1, Arah2, Arah3, Arah4, Arah5, Arah6, Arah7, Arah8; Lenc1, Lenc2; Piss1, Piss2; Actc1, Actc2; Capa1w, Capa2; Lyce1, Lyce2, Lyce3; Solat1, Solat2, Solat3, Solat4; Bere1, Bere2; Jugn1, Jugn2; Jugr1, Jugr2, Jugr3; Anao1, Anao2, Anao3; Ricc1; Sesi1, Sesi2, Sesi3, Sesi4, Sesi5, Sesi6; Cucm1, Cucm2, Cucm3; Zizm1; Anao1.0101, Anao1.0102; Apig1.0101, Apig1.0201; Dauc1.0101, Dauc1.0102, Dauc1.0103, Dauc1.0104, Dauc1.0105, Dauc1.0201; Cits3.0101, Cits3.0102; Glym1.0101, Glym1.0102, Glym3.0101, Glym3.0102; Lenc1.0101, Lenc1.0102, Lenc1.0103; Piss1.0101, Piss1.0102; Lyce2.0101, Lyce2.0102; Fraa3.0101, Fraa3.0102, Fraa3.0201, Fraa3.0202, Fraa3.0203, Fraa3.0204, Fraa3.0301; Mald1.0101, Mald1.0102, Mald1.0103, Mald1.0104, Mald1.0105, Mald1.0106, Mald1.0107, Mald1.0108, Mald1.0109, Mald1.0201, Mald1.0202, Mald1.0203, Mald1.0204, Mald1.0205, Mald1.0206, Mald1.0207, Mald1.0208, Mald1.0301, Mald1.0302, Mald1.0303, Mald1.0304, Mald1.0401, Mald1.0402, Mald1.0403, Mald3.0101w, Mald3.0102w, Mald3.0201w, Mald3.0202w, Mald3.0203w, Mald4.0101, Mald4.0102, Mald4.0201, Mald4.0202, Mald4.0301, Mald4.0302; Pruav1.0101, Pruav1.0201, Pruav1.0202, Pruav1.0203; Prup4.0101, or Prup4.0201. In some embodiments, one or more microfluidic chips 108 may include one or more analysis units 120 that are configured to analyze one or more allergen indicators 106 that may include Gadc1; Sals1; Bosd4, Bosd5, Bosd6, Bosd7, Bosd8; Gald1, Gald2, Gald3, Gald4, Gald5; Mete1; Pena1, Peni1; Penm1, Penm2; Todp1; Helas1; Halm1; Rane1, Rane2; Braj1; Bran1; Brao3; Brar1, Brar2; Horv15, Horv16, Horv17, Horv21; Secc20; Tria18, Tria19, Tria25, Tria26; Zeam14, Zeam25; Orys1; Apig1, Apig4, Apig5; Dauc1, Dauc4; Cora1.04, Cora2, Cora8; Fraa1, Fraa3, Fraa4; Mald1, Mald2, Mald3, Mald4; Pyrc1, Pyrc4, Pyrc5; Persa1; Pruar1, Pruar3; Pruav1, Pruav2, Pruav3, Pruav4; Prud3; Prudu4; Prup3, Prup4; Aspao1; Cros1, Cros2; Lacs1; Vitv1; Musxp1; Anac1, Anac2; Cit13; Cits1, Cits2, Cits3; Litc1; Sina1; Glym1, Glym2, Glym3, Glym4; Vigr1; Arah1, Arah2, Arah3, Arah4, Arah5, Arah6, Arah7, Arah8; Lenc1, Lenc2; Piss1, Piss2; Actc1, Actc2; Capa1w, Capa2; Lyce1, Lyce2, Lyce3; Solat1, Solat2, Solat3, Solat4; Bere1, Bere2; Jugn1, Jugn2; Jugr1, Jugr2, Jugr3; Anao1, Anao2, Anao3; Ricc1; Sesi1, Sesi2, Sesi3, Sesi4, Sesi5, Sesi6; Cucm1, Cucm2, Cucm3; Zizm1; Anao1.0101, Anao1.0102; Apig1.0101, Apig1.0201; Dauc1.0101, Dauc1.0102, Dauc1.0103, Dauc1.0104, Dauc1.0105, Dauc1.0201; Cits3.0101, Cits3.0102;

Glym1.0101, Glym1.0102, Glym3.0101, Glym3.0102; Lenc1.0101, Lenc1.0102, Lenc1.0103; Piss1.0101, Piss1.0102; Lyce2.0101, Lyce2.0102; Fraa3.0101, Fraa3.0102, Fraa3.0201, Fraa3.0202, Fraa3.0203, Fraa3.0204, Fraa3.0301; Mald1.0101, Mald1.0102, Mald1.0103, Mald1.0104, Mald1.0105, Mald1.0106, Mald1.0107, Mald1.0108, Mald1.0109, Mald1.0201, Mald1.0202, Mald1.0203, Mald1.0204, Mald1.0205, Mald1.0206, Mald1.0207, Mald1.0208, Mald1.0301, Mald1.0302, Mald1.0303, Mald1.0304, Mald1.0401, Mald1.0402, Mald1.0403, Mald3.0101w, Mald3.0102w, Mald3.0201w, Mald3.0202w, Mald3.0203w, Mald4.0101, Mald4.0102, Mald4.0201, Mald4.0202, Mald4.0301, Mald4.0302; Pruav1.0101, Pruav1.0201, Pruav1.0202, Pruav1.0203; Prup4.0101, Prup4.0201, or substantially any combination thereof.

FIG. 42 illustrates alternative embodiments of microfluidic chips 3900 of FIG. 39. FIG. 42 illustrates example embodiments of module 3920. Additional embodiments may include an embodiment 4202 and/or an embodiment 4204.

At embodiment 4202, module 3920 may include one or more analysis units that are configured to analyze one or more food allergen associated polynucleotides. In some embodiments, one or more microfluidic chips 108 may include one or more analysis units 120 that are configured to analyze one or more food allergen 104 associated polynucleotides. Examples of such food allergen 104 associated polynucleotides include, but are not limited to, polynucleotides and/or portions of one or more polynucleotides that have a nucleic acid sequence and/or that encode an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, AY839230, or substantially any combination thereof.

At embodiment 4204, module 3920 may include one or more analysis units that are configured to analyze one or more food allergen associated polypeptides. In some embodiments, one or more microfluidic chips 108 may include one or more analysis units 120 that are configured to analyze one or more food allergen 104 associated polypeptides. Examples of such food allergen 104 associated polypeptides include, but are not limited to, polypeptides and/or portions of one or more polypeptides that have an amino acid sequence that corresponds to, but is not limited to, and/or a polypeptide that is encoded by a nucleic acid sequence corresponding to one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, AY839230, or substantially any combination thereof.

At embodiment 4206, module 3920 may include one or more analysis units that are calibrated for an individual. In some embodiments, one or more microfluidic chips 108 may include one or more analysis units 120 that are calibrated for an individual. In some embodiments, one or more analysis units 120 may be constructed for a specific individual. For example, in some embodiments, an individual may be allergic to shellfish and walnuts. Accordingly, in some embodiments, a microfluidic chip 108 may include one or more analysis units 120 that are configured to analyze one or more samples 102 for shellfish and walnut associated allergen indicators 106. Analysis units 120 may be configured to analyze numerous types of samples 102 and allergen indicators 106.

FIG. 43 illustrates alternative embodiments of microfluidic chips 3900 of FIG. 39. FIG. 43 illustrates example embodiments of module 3930. Additional embodiments may include an embodiment 4302, an embodiment 4304, an embodiment 4306, an embodiment 4308, and/or an embodiment 4310.

At embodiment 4302, module 3930 may include one or more display units that include one or more active display units. In some embodiments, one or more microfluidic chips 108 may include one or more display units 124 that include one or more active display units 124. Numerous active display units 124 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), wide ultra extended graphics array (WUXGA).

At embodiment 4304, module 3930 may include one or more display units that include one or more passive display units. In some embodiments, one or more microfluidic chips 108 may include one or more display units 124 that include one or more passive display units 124. In some embodiments, one or more display units 124 may include one or more liquid crystal displays (LCD). Methods to construct passive displays have been described (e.g., U.S. Pat. Nos. 4,807,967; 4,729,636: 4,436,378; 4,257,041; herein incorporated by reference).

At embodiment 4306, module 3930 may include one or more display units that indicate a presence or an absence of one or more allergens within the one or more samples. In some embodiments, one or more microfluidic chips 108 may include one or more display units 124 that may indicate a presence or an absence of one or more allergens 104 within the one or more samples 102. In some embodiments, one or more display units 124 may use a colorimetric message to indicate a presence or an absence of one or more allergen indicators 106 within one or more samples 102. For example, in some embodiments, one or more display units 124 may display a green light if one or more allergen indicators 106 are not found within one or more samples 102 and a red light if one or more allergen indicators 106 are found within one or more samples 102. In some embodiments, one or more display units 124 may use a pictographic message to indicate a presence or an absence of one or more allergen indicators 106 within one or more samples 102. For example, in some embodiments, one or more display units 124 may display a smiley face if one or more allergen indicators 106 are not found within one or more samples 102 and a frowny face if one or more allergen indicators 106 are found within one or more samples 102. In some embodiments, one or more display units 124 may use a typographical message to indicate a presence or an absence of one or more allergen indicators 106 within one or more samples 102. For example, in some embodiments, one or more display units 124 may display an "Allergen Not Present" message if one or more allergen indicators 106 are not found within one or more samples 102 and an "Allergen Present" message if one or more allergen indicators 106 are found within one or more samples 102. Such messages may be displayed in numerous languages. In some embodiments, one or more display units 124 may display one or more messages in multiple formats. For example, in some embodiments, one or more messages may be displayed in colored text.

At embodiment 4308, module 3930 may include one or more display units that indicate an identity of one or more allergens within the one or more samples. In some embodiments, one or more microfluidic chips 108 may include one or more display units 124 that indicate an identity of one or more allergens 104 within the one or more samples 102. In some embodiments, one or more display units 124 may be operably associated with one or more microfluidic chips 108 that are configured to identify one or more allergen indicators 106. Accordingly, in some embodiments, one or more display units 124 may be configured to display the identity of one or more allergens 104 that are present and/or absent from one or more samples 102. For example, in some embodiments, a display unit 124 may be configured to indicate a presence or an absence of beta-lactoglobulin in a food product.

At embodiment 4310, module 3930 may include one or more display units that indicate one or more concentrations of one or more allergens within the one or more samples. In some embodiments, one or more microfluidic chips 108 may include one or more display units 124 that may indicate one or more concentrations of one or more allergens 104 within the one or more samples 102. Concentration may be displayed in numerous formats. For example, in some embodiments, concentration may be expressed numerically (e.g., mass allergen indicator 106 per volume sample 102 (e.g., milligrams per milliliter), mass allergen indicator 106 per mass sample 102 (e.g., milligrams per milligram of sample), parts per million, and the like). In some embodiments, concentration may be expressed graphically. For example, in some embodiments, one or more display units 124 may include a display having a gray scale on which the concentration of one or more allergen indicators 106 that are present within one or more samples 102 may be indicated (e.g., higher concentrations of one or more allergens 104 may be displayed as dark gray while lower concentrations of one or more allergens 104 may be displayed as light gray). In some embodiments, one or more display units 124 may include a display having a color scale on which the concentration of one or more allergen indicators 106 that are present within one or more samples 102 may be indicated (e.g., low concentrations of one or more allergen indicators 106 may be indicated by a green light, intermediate concentrations of one or more allergen indicators 106 may be indicated by a yellow light, high concentrations of one or more allergen indicators 106 may be indicated by a red light). In some embodiments, one or more display units 124 may be calibrated to an individual. For example, in such embodiments, an individual may use the display to obtain an immediate reading that will indicate if a food product contains a dangerous level of one or more allergens 104.

At embodiment 4312, module 3930 may include one or more display units that are calibrated for an individual. In some embodiments, one or more microfluidic chips 108 may include one or more display units 124 that are calibrated for an individual. In some embodiments, one or more display units 124 may be calibrated to display whether one or more allergens 104, and/or allergen indicators 106, that are specific to an individual are present or absent within one or more samples 102. For example, in some embodiments, one or more display units 124 may be configured to display whether one or more samples 102 contain shellfish associated allergens 104 for an individual known to be allergic to shellfish. In some embodiments, one or more display units 124 may be calibrated to indicate safe and/or unsafe concentrations of one or more allergens 104 within one or more samples 102 for an individual.

Figure 44:
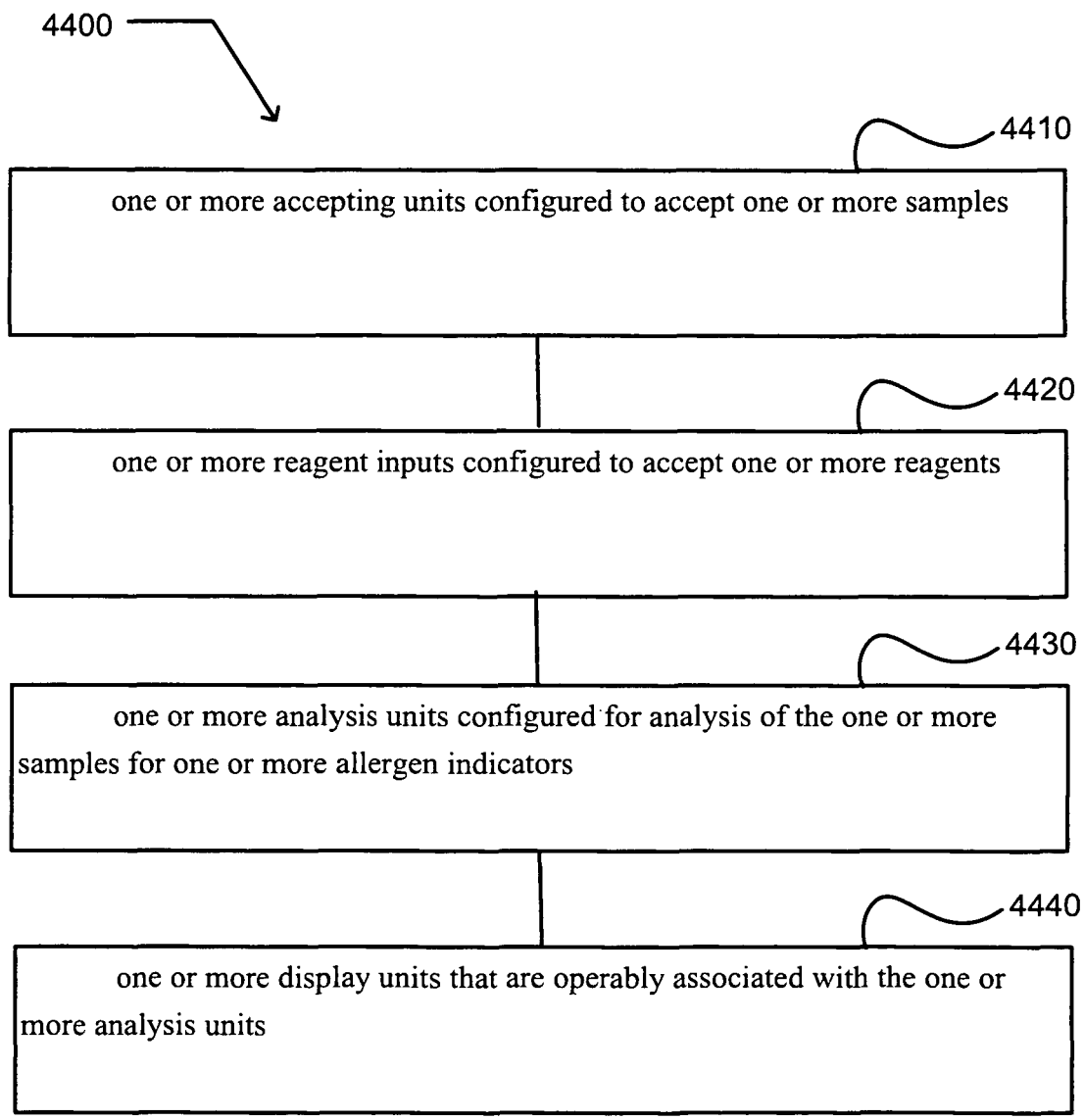
FIG. 44 illustrates an example microfluidic chip 4400 in which embodiments may be implemented.

FIG. 44 illustrates microfluidic chips 4400 that may be configured for analysis of one or more allergens 104. In FIG. 44, discussion and explanation may be provided with respect to use of one or more microfluidic chips 108 within the above-described example of FIG. 1, and/or with respect to other examples and contexts. However, it should be understood that the microfluidic chips 108 may be configured in a number of other environments and contexts, and/or utilized within modified versions of FIG. 1. Also, although the microfluidic chips 108 are presented in the configuration(s) illustrated, it should be understood that the microfluidic chips 108 may be configured in numerous orientations.

The microfluidic chip 4400 includes module 4410 that includes one or more accepting units configured to accept one or more samples. In some embodiments, module 4410 may include one or more accepting units configured to accept the one or more samples that include one or more liquids. In some embodiments, module 4410 may include one or more accepting units configured to accept the one or more samples that include one or more solids. In some embodiments, module 4410 may include one or more accepting units configured to accept the one or more samples that include one or more gases. In some embodiments, module 4410 may include one or more accepting units configured to accept the one or more samples that include one or more food products. In some embodiments, module 4410 may include one or more accepting units configured to accept the one or more samples that are associated with one or more weeds, grasses, trees, mites, animals, molds, fungi, insects, rubbers, metals, chemicals, autoallergens, or human autoallergens.

The microfluidic chip 4400 includes module 4420 that includes one or more reagent inputs configured to accept one or more reagents. In some embodiments, module 4420 may include one or more connectors configured to operably associate with one or more reagent delivery units. In some embodiments, module 4420 may include one or more connectors configured to operably associate with one or more leur lock connectors. In some embodiments, module 4420 may include one or more connectors configured to operably associate with one or more threaded connectors. In some embodiments, module 4420 may include one or more septa configured to accept one or more needles.

The microfluidic chip 4400 includes module 4430 that includes one or more analysis units configured for analysis of the one or more samples for one or more allergen indicators. In some embodiments, module 4430 may include one or more analysis units configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay. In some embodiments, module 4430 may include one or more analysis units configured for analysis of the one or more allergen indicators that are associated with one or more food products. In some embodiments, module 4430 may include one or more analysis units configured for analysis of the one or more allergen indicators that are associated with one or more weeds, grasses, trees, mites, animals, molds, fungi, insects, rubbers, metals, chemicals, autoallergens, or human autoallergens. In some embodiments, module 4430 may include one or more analysis units configured for polynucleotide extraction. In some embodiments, module 4430 may include one or more analysis units configured for polypeptide extraction. In some embodiments, module 4430 may include one or more analysis units configured for chemical extraction. In some embodiments, module 4430 may include one or more analysis units that include one or more H-filters. In some embodiments, module 4430 may include one or more analysis units that are configured to provide for polynucleotide analysis. In some embodiments, module 4430 may include one or more analysis units that are configured to provide for one or more analysis methods that include polynucleotide amplification, polynucleotide ligation, polynucleotide interaction, or polynucleotide degradation. In some embodiments, module 4430 may include one or more analysis units that are configured to provide for polypeptide analysis. In some embodiments, module 4430 may include one or more analysis units that are configured to provide for enzymatic analysis. In some embodiments, module 4430 may include one or more analysis units that are configured to provide for reagent mixing. In some embodiments, module 4430 may include one or more analysis units that are configured to provide for centrifugal separation. In some embodiments, module 4430 may include one or more analysis units that are calibrated for an individual.

The microfluidic chip 4400 may optionally include module 4440 that includes one or more display units that are operably associated with the one or more analysis units. In some embodiments, module 4440 may include one or more display units that are passive display units. In some embodiments, module 4440 may include one or more display units that are active display units. In some embodiments, module 4440 may include one or more display units that indicate a presence or an absence of one or more allergens within the one or more samples. In some embodiments, module 4440 may include one or more display units that indicate an identity of one or more allergens present within the one or more samples. In some embodiments, module 4440 may include one or more display units that indicate one or more concentrations of one or more allergens within the one or more samples. In some embodiments, module 4440 may include one or more display units that are calibrated for an individual.

FIG. 45 illustrates alternative embodiments of microfluidic chip 4400 of FIG. 44. FIG. 45 illustrates example embodiments of module 4410. Additional embodiments may include an embodiment 4502, an embodiment 4504, an embodiment 4506, an embodiment 4508, and/or an embodiment 4510.

At embodiment 4502, module 4410 may include one or more accepting units configured to accept the one or more samples that include one or more liquids. In some embodiments, one or more microfluidic chips 108 may include one or more accepting units 110 configured to accept the one or more samples 105 that include one or more liquids. In some embodiments, one or more microfluidic chips 108 may include one or more lancets. Such lancets may be configured to provide for collection of one or more samples 102 that include a fluid. In some embodiments, a microfluidic chip 108 may include one or more septa through which a needle may be passed to deliver a fluid sample 102 to the microfluidic chip 108. In some embodiments, a microfluidic chip 108 may include one or more leur lock connectors to which one or more syringes may be coupled to deliver one or more fluid samples 102 to the microfluidic chip 108. In some embodiments, a microfluidic chip 108 may be configured to operably associate with one or more detection units 122 that are configured to deliver one or more liquid samples 102 to the microfluidic chip 108. In some embodiments, an accepting unit 110 may be configured to extract liquids from one or more samples 102. For example, in some embodiments, an accepting unit 110 may include a space into which a sample 102 may be crushed such that the liquid portion of the sample 102 is available for processing by the microfluidic chip 108. In some embodiments, an accepting unit 110 may include one or more sonicators that facilitate release of the liquid portion from a sample 102 to make it available to a microfluidic chip 108. Microfluidic chips 108 may be configured to accept numerous types of liquids. Examples of such liquids include, but are not limited to, beverages, water, food products, solvents, and the like. In some embodiments, a microfluidic chip 108 may be configured to accept one or more solvents that include one or more dissolved metal samples 102. For example, metal may be contacted with a solvent to obtain a sample 102 of the metal. The solvent may then be delivered to a microfluidic chip 108 for processing and/or analysis. Accordingly, microfluidic chips 108 may be configured in numerous ways such that they may accept one or more samples 102 that include a liquid.

At embodiment 4504, module 4410 may include one or more accepting units configured to accept the one or more samples that include one or more solids. In some embodiments, one or more microfluidic chips 108 may include one or more accepting units 110 configured to accept the one or more samples that include one or more solids. In some embodiments, such accepting units 110 may be configured to suspend a solid sample 102 in a fluid. In some embodiments, such accepting units 110 may be configured to crush a sample 102 into smaller particles. For example, in some embodiments, an accepting unit 110 may accept a solid sample 102. The sample 102 may be ground into smaller particles to facilitate detection of one or more allergen indicators 106 that may be present within the sample 102. In some embodiments, an accepting unit 110 may include one or more sonicators that break the sample 102 into smaller particles to facilitate detection of one or more allergen indicators 106 that may be present within the sample 102. For example, in some embodiments, solid spores may be broken into smaller-particles to provide for detection of one or more polynucleotides that are associated with the spores. In some embodiments, an accepting unit 110 may be configured to accept one or more samples 102 that include metal. For example, in some embodiments, an accepting unit 110 may be configured to accept a metal sample 102 (e.g., from a piece of jewelry). In such embodiments, a microfluidic chip 108 may be configured to dissolve the metal sample 102 in a suitable solvent. For example, the metal sample 102 may be dissolved in hydrochloric acid media and then tin may be extracted from the hydrochloric acid with 2-ethylhexyl phosphonic acid mono-2-ethylhexyl ester in toluene. The extracted tin may then be detected through use of an ion-specific electrode. Accordingly, microfluidic chips 108 may be configured in numerous ways such that they may accept one or more samples 102 that include a liquid.

At embodiment 4506, module 4410 may include one or more accepting units configured to accept the one or more samples that include one or more gases. In some embodiments, one or more microfluidic chips 108 may include one or more accepting units 110 configured to accept the one or more samples that include one or more gases. For example, in some embodiments, a microfluidic chip 108 may include one or more fans that blow and/or draw gas into the microfluidic chip 108. In some embodiments, a microfluidic chip 108 may include one or more bubble chambers through which one or more gases pass. In some embodiments, such bubble chambers may be configured to include one or more fluids (e.g., solvents) that may be used to selectively retain (e.g., extract) one or more allergen indicators 106 from one or more gas samples 102. For example, in some embodiments, diesel exhaust particles may be extracted from one or more gas samples 102 by bubbling the gas samples 102 through a solvent (e.g., methylene chloride, aqueous HCl, and the like). In some embodiments, a microfluidic chip 108 may include one or more electrostatic filters through which one or more gases pass. Such electrostatic filters may be configured to capture numerous types of allergen indicators 106. Examples of such allergen indicators 106 include, but are not limited to, dust, lint, dander, pollen, spores, and the like. In some embodiments, a microfluidic chip 108 may include one or more filters through which one or more gases pass. Such filters may be configured to capture allergen indicators 106 according to numerous properties, such as size, hydrophobicity, charge, and the like.

At embodiment 4508, module 4410 may include one or more accepting units configured to accept the one or more samples that include one or more food products. In some embodiments, one or more microfluidic chips 108 may include one or more accepting units 110 configured to accept the one or more samples 102 that include one or more food products. In some embodiments, one or more accepting units 110 may be configured to accept one or more food samples 102 that are liquid, such as beverages, soups, sauces, and the like. For example, in some embodiments, one or more accepting units 110 may include one or more lancets that may be inserted into the food product to withdraw one or more samples 102. In some embodiments, one or more accepting units 110 may include one or more septa that may be configured to operably associate with a syringe or the like. In some embodiments, one or more accepting units 110 may be configured to accept one or more food samples 102 that are solids, such as meats, cheeses, nuts, vegetables, fruits, and the like. In some embodiments, one or more accepting units 110 may include one or more mechanisms that can facilitate processing of the one or more samples 102. Examples of such mechanisms include, but are not limited to, grinders, sonicators, treatment of the one or more samples 102 with degreative enzymes (e.g., protease, nuclease, lipase, collagenase, and the like), strainers, filters, centrifugation chambers, and the like.

At embodiment 4510, module 4410 may include one or more accepting units configured to accept the one or more samples that are associated with one or more weeds, grasses, trees, mites, animals, molds, fungi, insects, rubbers, metals, chemicals, autoallergens, or human autoallergens. In some embodiments, one or more microfluidic chips 108 may include one or more accepting units 110 configured to accept the one or more samples 102 that are associated with one or more weeds, grasses, trees, mites, animals, molds, fungi, insects, rubbers, metals, chemicals, autoallergens, human autoallergens, or substantially any combination thereof. In some embodiments, one or more accepting units 110 may include one or more mechanisms that can facilitate processing of the one or more samples 102. Examples of such mechanisms include, but are not limited to, grinders, sonicators, treatment of the one or more samples 102 with degreative enzymes (e.g., protease, nuclease, lipase, collagenase, and the like), strainers, filters, centrifugation chambers, and the like.

FIG. 46 illustrates alternative embodiments of microfluidic chips 4400 of FIG. 44. FIG. 46 illustrates example embodiments of module 4420. Additional embodiments may include an embodiment 4602, an embodiment 4604, an embodiment 4606, and/or an embodiment 4608.

At embodiment 4602, module 4420 may include one or more connectors configured to operably associate with one or more reagent delivery units. In some embodiments, one or more microfluidic chips 108 may include one or more connectors configured to operably associate with one or more reagent delivery units 116. In some embodiments, the one or more connectors are configured to permanently connect with one or more reagent delivery units 116. In some embodiments, the one or more connectors are configured to detachably connect with one or more reagent delivery units 116. A microfluidics chip 108 may include numerous types of connectors that may operably associate with one or more reagent delivery units 116, one or more reservoirs, one or more accepting units 110, or substantially any combination thereof.

At embodiment 4604, module 4420 may include one or more connectors configured to operably associate with one or more leur lock connectors. In some embodiments, one or more microfluidic chips 108 may include one or more connectors configured to operably associate with one or more leur lock connectors. In some embodiments, the one or more leur lock connectors may be configured to connect with one or more syringes. In some embodiments, the one or more leur lock connectors may be configured to connect with tubing. In some embodiments, the one or more leur lock connectors may be configured to connect with one or more needles. In some embodiments, such leur lock connectors may be configured to accept one or more samples 102. In some embodiments, such leur lock connectors may be configured to connect with one or more reagent delivery units 116. In some embodiments, such leur lock connectors may be configured to connect with one or more reservoirs.

At embodiment 4606, module 4420 may include one or more connectors configured to operably associate with one or more threaded connectors. In some embodiments, one or more microfluidic chips 108 may include one or more connectors configured to operably associate with one or more threaded connectors. In some embodiments, the one or more threaded connectors may be configured to connect with one or more syringes. In some embodiments, the one or more threaded connectors may be configured to connect with tubing. In some embodiments, the one or more threaded connectors may be configured to connect with one or more needles. In some embodiments, such threaded connectors may be configured to accept one or more samples 102. In some embodiments, such threaded connectors may be configured to connect with one or more reagent delivery units 116. In some embodiments, such threaded connectors may be configured to connect with one or more reservoirs.

At embodiment 4608, module 4420 may include one or more septa configured to accept one or more needles. In some embodiments, one or more microfluidic chips 108 may include one or more septa configured to accept one or more needles. In some embodiments, such septa may be configured to accept one or more samples 102. In some embodiments, such septa may be configured to connect with one or more reagent delivery units 116. In some embodiments, such septa may be configured to connect with one or more reservoirs.

Figure 47:
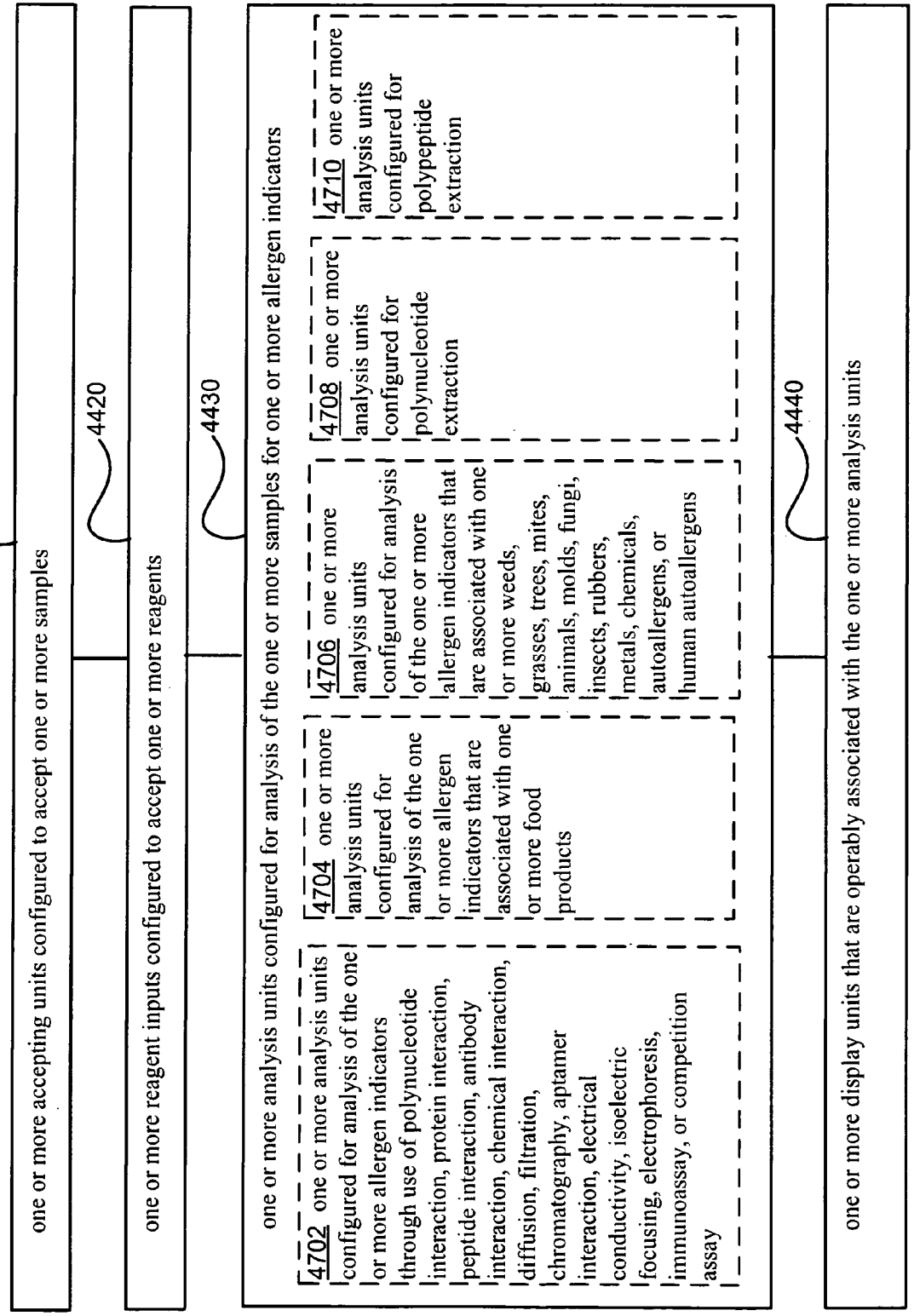
FIG. 47 illustrates alternate embodiments of the microfluidic chip of FIG. 44.

FIG. 47 illustrates alternative embodiments of microfluidic chips 4400 of FIG. 44. FIG. 47 illustrates example embodiments of module 4430. Additional embodiments may include an embodiment 4702, an embodiment 4704, an embodiment 4706, an embodiment 4708, and/or an embodiment 4710.

At embodiment 4702, module 4430 may include one or more analysis units configured for analysis of the one or more allergen indicators through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay. In some embodiments, one or more microfluidic chips 108 may include one or more analysis units 120 configured for analysis of the one or more allergen indicators 106 through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof.

In some embodiments, one or more microfluidic chips 108 may be configured to process one or more samples 102 through use of polynucleotide interaction. Numerous methods based on polynucleotide interaction may be used. Examples of such methods include, but are not limited to, those based on polynucleotide hybridization, polynucleotide ligation, polynucleotide amplification, polynucleotide degradation, and the like. Methods that utilize intercalation dyes, FRET analysis, capacitive DNA detection, and nucleic acid amplification have been described (e.g., U.S. Pat. Nos. 7,118, 910 and 6,960,437; herein incorporated by reference). In some embodiments, fluorescence resonance energy transfer, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube are combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Methods to utilize carbon nanotubes as probes for nucleic acid interaction have been described (e.g., U.S. Pat. No. 6,821,730; herein incorporated by reference).

In some embodiments, one or more microfluidic chips 108 may be configured to process one or more samples 102 through use of protein interaction. Numerous methods based on protein interaction may be used. In some embodiments, protein interaction may be used to immobilize one or more allergen indicators 106. In some embodiments, protein interaction may be used to separate one or more allergen indicators 106 from one or more samples 102. Examples of such methods include, but are not limited to, those based on ligand binding, protein-protein binding, protein cross-linking, use of green fluorescent protein, phage display, the two-hybrid system, protein arrays, fiber optic evanescent wave sensors, chromatographic techniques, fluorescence resonance energy transfer, regulation of pH to control protein assembly and/or oligomerization, and the like. For example, tropomyosin is a major muscle protein in crustaceans that is thought to be a major shrimp allergen 104: Tropomyosin is associated with the well known actin-troponin-myosin complex. Calcium ion binding to troponin enables troponin to bind tropomyosin and shift it from the binding sites of myosin on the actin proteins. Without the presence of Calcium ion, troponin is no longer able to bind to tropomyosin, and tropomyosin again blocks the binding sites of myosin on the actin proteins. Tropomyosin also binds to the calcium-binding protein calcyclin (Nelson et al., Molecular & Cellular Proteomics 1:253-259 (2002) and Liou and Chen, European Journal of Biochemistry, 270: 3092-3100 (2003)). Accordingly, protein interactions may be used to separate tropomyosin (allergen indicator 106) from one or more samples 102. Similar methods may be used with numerous proteins. Methods that may be used to construct protein arrays have been described (e.g., Warren et al., Anal. Chem., 76:4082-4092 (2004) and Walter et al., Trends Mol. Med., 8:250-253 (2002), U.S. Pat. No. 6,780,582; herein incorporated by reference).

In some embodiments, one or more microfluidic chips 108 may be configured to process one or more samples 102 through use of peptide interaction. Peptides are generally described as being polypeptides that include less than one hundred amino acids. For example, peptides include dipeptides, tripeptides, and the like. In some embodiments, peptides may include from two to one hundred amino acids. In some embodiments, peptides may include from two to fifty amino acids. In some embodiments, peptides may include from two to one twenty amino acids. In some embodiments, peptides may include from ten to one hundred amino acids. In some embodiments, peptides may include from ten to fifty amino acids. Accordingly, peptides can include numerous numbers of amino acids. Numerous methods based on peptide interaction may be used. In some embodiments, peptide interaction may be used to immobilize one or more allergen indicators 106. In some embodiments, peptide interaction may be used to separate one or more allergen indicators 106 from one or more samples 102. Examples of such methods include, but are not limited to, those based on ligand binding, peptide-protein binding, peptide-peptide binding, peptide-polynucleotide binding, peptide cross-linking, use of green fluorescent protein, phage display, the two-hybrid system, protein arrays, peptide arrays, fiber optic evanescent wave sensors, chromatographic techniques, fluorescence resonance energy transfer, regulation of pH to control peptide and/or protein assembly and/or oligomerization, and the like. Accordingly, virtually any technique that may be used to analyze proteins may be utilized for the analysis of peptides. In some embodiments, high-speed capillary electrophoresis may be used to detect binding through use of fluorescently labeled phosphopeptides as affinity probes (Yang et al., Anal. Chem., 10.1021/ac061936e (2006)). Methods to immobilize proteins and peptides have been reported (Taylor, Protein Immobilization: Fundamentals and Applications, Marcel Dekker, Inc., New York (1991)).

In some embodiments, one or more microfluidic chips 108 may be configured to process one or more samples 102 through use of antibody interaction. Antibodies may be raised that will bind to numerous allergen indicators 106 through use of known methods (e.g., Harlow and Lane, Antibodies: A Laboratory Manual, Cold Spring Harbor Laboratory Press, Cold Spring Harbor, N.Y. (1988)). Antibodies may be configured in numerous ways within one or more microfluidic chips 108 to process one or more allergen indicators 106. For example, in some embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. A labeled detector antibody that binds to the allergen indicator 106 (or the antibody-allergen indicator 106 complex) may then be passed over the one or more antibody-allergen indicator 106 complexes such that the labeled detector antibody will label the allergen indicator 106 (or the antibody-allergen indicator 106 complex). Numerous labels may be used that include, but are not limited to, enzymes, fluorescent molecules, radioactive labels, spin labels, redox labels, and the like. In other embodiments, antibodies may be coupled to a substrate within a microfluidic chip 108. One or more samples 102 may be passed over the antibodies to facilitate binding of one or more allergen indicators 106 to the one or more antibodies to form one or more antibody-allergen indicator 106 complexes. Such binding provides for detection of the antibody-allergen indicator 106 complex through use of methods that include, but are not limited to, surface plasmon resonance, conductivity, and the like (e.g., U.S. Pat. No. 7,030,989; herein incorporated by reference). In some embodiments, antibodies may be coupled to a substrate within a microfluidic chip 108 to provide for a competition assay. One or more samples 102 may be mixed with one or more reagent mixtures that include one or more labeled allergen indicators 106. The mixture may then be passed over the antibodies to facilitate binding of allergen indicators 106 in the sample 102 and labeled allergen indicators 106 in the reagent mixture to the antibodies; The unlabeled allergen indicators 106 in the sample 102 will compete with the labeled allergen indicators 106 in the reagent mixture for binding to the antibodies. Accordingly, the amount of label bound to the antibodies will vary in accordance with the concentration of unlabeled allergen indicators 106 in the sample 102. In some embodiments, antibody interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more antibodies may be used in conjunction with one or more aptamers to process one or more samples 102. Accordingly, in some embodiments, aptamers and antibodies may be used interchangeably to process one or more samples 102.

In some embodiments, one or more microfluidic chips 108 may be configured to process one or more samples 102 through use of chemical interaction. In some embodiments, one or more microfluidic chips 108 may be configured to utilize chemical extraction to process one or more samples 102. For example, in some embodiments, one or more samples 102 may be mixed with a reagent mixture that includes one or more solvents in which the one or more allergen indicators 106 are soluble. Accordingly, the solvent phase containing the one or more allergen indicators 106 may be separated from the sample phase to provide for detection of the one or more allergen indicators 106. In some embodiments, one or more samples 102 may be mixed with a reagent mixture that includes one or more chemicals that cause precipitation of one or more allergen indicators 106. Accordingly, the sample phase may be washed away from the one or more precipitated allergen indicators 106 to provide for detection of the one or more allergen indicators 106. Accordingly, reagent mixtures that include numerous types of chemicals that interact with one or more allergen indicators 106 may be used.

In some embodiments, one or more microfluidic chips 108 may be configured to process one or more samples 102 through use of diffusion. In some embodiments, one or more microfluidic chips 108 may be configured to process one or more fluid samples 102 through use of an H-filter. For example, a microfluidic chip 108 may be configured to include a channel through which a fluid sample 102 and a second fluid flow such that the fluid sample 102 and the second fluid undergo parallel flow through the channel without significant mixing of the sample fluid and the second fluid. As the fluid sample 102 and the second fluid flow through the channel, one or more allergen indicators 106 in the fluid sample 102 may diffuse through the fluid sample 102 into the second fluid. Accordingly, such diffusion provides for the separation of the one or more allergen indicators 106 from the sample 102. Methods to construct H-filters have been described (e.g., U.S. Pat. Nos. 6,742,661; 6,409,832; 6,007,775; 5,974,867; 5,971,158; 5,948,684; 5,932,100; 5,716,852; herein incorporated by reference). In some embodiments, diffusion based methods may be combined with immunoassay based methods to process and detect one or more allergen indicators 106. Methods to conduct microscale diffusion immunoassays have been described (e.g., U.S. Pat. No. 6,541,213; herein incorporated by reference). Accordingly, microfluidic chips 108 may be configured in numerous ways to process one or more allergen indicators 106 through use of diffusion.

In some embodiments, one or more microfluidic chips 108 may be configured to process one or more samples 102 through use of filtration. In some embodiments, one or more microfluidic chips 108 may be configured to include one or more filters that have a molecular weight cut-off. For example, a filter may allow molecules of low molecular weight to pass through the filter while disallowing molecules of high molecular weight to pass through the filter. Accordingly, one or more allergen indicators 106 that are contained within a sample 102 may be allowed to pass through a filter while larger molecules contained within the sample 102 are disallowed from passing through the filter. Accordingly, in some embodiments, a microfluidic chip 108 may include two or more filters that selectively retain, or allow passage, of one or more allergen indicators 106 through the filters. Such configurations provide for selective separation of one or more allergen indicators 106 from one or more samples 102. Membranes and filters having numerous molecular weight cut-offs are commercially available (e.g., Millipore, Billerica, Mass.). In some embodiments, one or more microfluidic chips 108 may be configured to provide for dialysis of one or more samples 102. For example, in some embodiments, a microfluidic chip 108 may be configured to contain one or more samples 102 in one or more sample chambers that are separated from one or more dialysis chambers by a semi-permeable membrane. Accordingly, in some embodiments, one or more allergen indicators 106 that are able to pass through the semi-permeable membrane may be collected in the dialysis chamber. In other embodiments, one or more allergen indicators 106 may be retained in the one or more sample chambers while other sample 102 components may be separated from the one or more allergen indicators 106 by their passage through the semi-permeable membrane into the dialysis chamber. Accordingly, one or more microfluidic chips 108 may be configured to include two or more dialysis chambers for selective separation of one or more allergen indicators 106 from one or more samples 102. Semi-permeable membranes and dialysis tubing is available from numerous commercial sources (e.g., Millipore, Billerica, Mass.; Pierce, Rockford, Ill.; Sigma-Aldrich, St. Louis, Mo.). Methods that may be used for microfiltration have been described (e.g., U.S. Pat. No. 5,922,210; herein incorporated by reference).

In some embodiments, one or more microfluidic chips 108 may be configured to process one or more samples 102 through use of chromatography. Numerous chromatographic methods may be used to process one or more samples 102. Examples of such chromatographic methods include, but are not limited to, ion-exchange chromatography, affinity chromatography, gel filtration chromatography, hydroxyapatite chromatography, gas chromatography, reverse phase chromatography, thin layer chromatography, capillary chromatography, size exclusion chromatography, hydrophobic interaction media, and the like. In some embodiments, a microfluidic chip 108 may be configured to process one or more samples 102 through use of one or more chromatographic methods. In some embodiments, chromatographic methods may be used to process one or more samples 102 for one or more allergen indicators 106 that include one or more polynucleotides. For example, in some embodiments, one or more samples 102 may be applied to a chromatographic media to which the one or more polynucleotides bind. The remaining components of the sample 102 may be washed from the chromatographic media. The one or more polynucleotides may then be eluted from chromatographic media in a more purified state. Similar methods may be used to process one or more samples 102 for one or more allergen indicators 106 that include one or more proteins or polypeptides (e.g., Mondal and Gupta, Biomol. Eng., 23:59-76 (2006)). Chromatography media able to separate numerous types of molecules is commercially available (e.g., Bio-Rad, Hercules, Calif.; Qiagen, Valencia, Calif.; Pfizer, New York, N.Y.; Millipore, Billerica, Mass.; GE Healthcare Bio-Sciences Corp., Piscataway, N.J.).

In some embodiments, one or more microfluidic chips 108 may be configured to process one or more samples 102 through use of aptamer interaction. In some embodiments, one or more aptamers may include polynucleotides (e.g., deoxyribonucleic acid; ribonucleic acid; and derivatives of polynucleotides that may include polynucleotides that include modified bases, polynucleotides in which the phosphodiester bond is replaced by a different type of bond, or many other types of modified polynucleotides). In some embodiments, one or more aptamers may include peptide aptamers. Methods to prepare and use aptamers have been described (e.g., Collett et al., Methods, 37:4-15 (2005); Collet et al., Anal. Biochem., 338:113-123 (2005); Cox et al., Nucleic Acids Res., 30:20 e108 (2002); Kirby et al., Anal. Chem., 76:4066-4075 (2004); Ulrich, Handb. Exp. Pharmacol., 173:305-326 (2006); Baines and Colas, Drug Discovery Today, 11:334-341 (2006); Guthrie et al., Methods, 38:324-330 (2006); Geyer et al., Chapter 13: Selection of Genetic Agents from Random Peptide Aptamer Expression Libraries, Methods in Enzymology, Academic Press, pg. 171-208 (2000); U.S. Pat. No. 6,569,630; herein incorporated by reference). Aptamers may be configured in numerous ways within one or more microfluidic chips 108 to process one or more allergen indicators 106. For example, in some embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Labeled detector antibodies and/or aptamers that bind to the allergen indicator 106 (or the aptamer-allergen indicator 106 complex) may then be passed over the one or more aptamer-allergen indicator 106 complexes such that the labeled detector antibodies and/or aptamers will label the allergen indicator 106 (or the aptamer-allergen indicator 106 complex). Numerous labels may be used that include, but are not limited to, enzymes, fluorescent molecules, radioactive labels, spin labels, redox labels, and the like. In other embodiments, aptamers may be coupled to a substrate within a microfluidic chip 108. One or more samples 102 may be passed over the aptamers to facilitate binding of one or more allergen indicators 106 to the one or more aptamers to form one or more aptamer-allergen indicator 106 complexes. Such binding provides for detection of the aptamer-allergen indicator 106 complex through use of methods that include, but are not limited to, surface plasmon resonance, conductivity, and the like (e.g., U.S. Pat. No. 7,030,989; herein incorporated by reference). In some embodiments, aptamers may be coupled to a substrate within a microfluidic chip 108 to provide for a competition assay. One or more samples 102 may be mixed with one or more reagent mixtures that include one or more labeled allergen indicators 106. The mixture may then be passed over the aptamers to facilitate binding of allergen indicators 106 in the sample 102 and labeled allergen indicators 106 in the reagent mixture to the aptamers. The unlabeled allergen indicators 106 in the sample 102 will compete with the labeled allergen indicators 106 in the reagent mixture for binding to the aptamers. Accordingly, the amount of label bound to the aptamers will vary in accordance with the concentration of unlabeled allergen indicators 106 in the sample 102. In some embodiments, aptamer interaction may be used in association with microcantilevers to process one or more allergen indicators 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more aptamers may be used in conjunction with one or more antibodies to process one or more samples 102. In some embodiments, aptamers and antibodies may be used interchangeably to process one or more samples 102. Accordingly, in some embodiments, methods and/or systems for processing and/or detecting allergen indicators 106 may utilize antibodies and aptamers interchangeably and/or in combination.

In some embodiments, one or more microfluidic chips 108 may be configured to process one or more samples 102 through use of electrical conductivity. In some embodiments, one or more samples 102 may be processed though use of magnetism. For example, in some embodiments, one or more samples 102 may be combined with one or more tagged polynucleotides that are tagged with a ferrous material, such as a ferrous bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed over an electromagnet to immobilize the hybridized complexes. Other components in the sample 102 may then be washed away from the hybridized complexes. In some embodiments, a chamber containing the magnetically immobilized hybridized complexes may be heated to release the sample polynucleotides from the magnetically immobilized tagged polynucleotides. The sample polynucleotides may then be collected in a more purified state. In other embodiments, similar methods may be used in conjunction with antibodies, aptamers, peptides, ligands, and the like. Accordingly, one or more microfluidic chips 108 may be configured in numerous ways to utilize magnetism to process one or more samples 102. In some embodiments, one or more samples 102 may be processed though use of eddy currents. Eddy current separation uses the principles of electromagnetic induction in conducting materials to separate non-ferrous metals by their different electric conductivities. An electrical charge is induced into a conductor by changes in magnetic flux cutting through it. Moving permanent magnets passing a conductor generates the change in magnetic flux. Accordingly, in some embodiments, one or more microfluidic chips 108 may be configured to include a magnetic rotor such that when conducting particles move through the changing flux of the magnetic rotor, a spiraling current and resulting magnetic field are induced. The magnetic field of the conducting particles may interact with the magnetic field of the magnetic rotor to impart kinetic energy to the conducting particles. The kinetic energy imparted to the conducting particles may then be used to direct movement of the conducting particles. Accordingly, non-ferrous particles, such as metallic beads, may be utilized to process one or more samples 102. For example, in some embodiments, one or more samples 102 may be combined with one or more tagged polynucleotides that are tagged with a non-ferrous material, such as an aluminum bead. The tagged polynucleotides and the polynucleotides in the one or more samples 102 may be incubated to provide hybridized complexes of the tagged polynucleotides and the sample polynucleotides. Hybridization will serve to couple one or more ferrous beads to the polynucleotides in the sample 102 that hybridize with the tagged polynucleotides. Accordingly, the mixture may be passed through a magnetic field to impart kinetic energy to the non-ferrous bead. This kinetic energy may then be used to separate the hybridized complex. In other embodiments, similar methods may be used in conjunction with antibodies, aptamers, peptides, ligands, and the like. Accordingly, one or more microfluidic chips 108 may be configured in numerous ways to utilize eddy currents to process one or more samples 102. One or more microfluidic chips 108 may be configured in numerous ways to utilize electrical conductivity to process one or more samples 102.

In some embodiments, one or more microfluidic chips 108 may be configured to process one or more samples 102 through use of isoelectric focusing. Methods have been described that may be used to construct capillary isoelectric focusing systems (e.g., Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). Such systems may be modified to provide for the processing of one or more samples 102.

In some embodiments, one or more microfluidic chips 108 may be configured to process one or more samples 102 through use of electrophoresis. In some embodiments, one or more microfluidic chips 108 may be configured to process one or more samples 102 through use of one-dimensional electrophoresis. In some embodiments, one or more microfluidic chips 108 may be configured to process one or more samples 102 through use of two-dimensional electrophoresis. In some embodiments, one or more microfluidic chips 108 may be configured to process one or more samples 102 through use of gradient gel electrophoresis. In some embodiments, one or more microfluidic chips 108 may be configured to process one or more samples 102 through use electrophoresis under denaturing conditions. In some embodiments, one or more microfluidic chips 108 may be configured to process one or more samples 102 through use electrophoresis under native conditions. One or more microfluidic chips 108 may be configured to utilize numerous electrophoretic methods.

In some embodiments, one or more microfluidic chips 108 may be configured to process one or more samples 102 through use of immunoassay. In some embodiments, one or more microfluidic chips 108 may be configured to process one or more samples 102 through use of enzyme linked immunosorbant assay (ELISA). In some embodiments, one or more microfluidic chips 108 may be configured to process one or more samples 102 through use of radioimmuno assay (RIA). In some embodiments, one or more microfluidic chips 108 may be configured to process one or more samples 102 through use of enzyme immunoassay (EIA). In some embodiments, such methods may utilize antibodies (e.g., monoclonal antibodies, polyclonal antibodies, antibody fragments, single-chain antibodies, and the like), aptamers, or substantially any combination thereof. In some embodiments, a labeled antibody and/or aptamer may be used within an immunoassay. In some embodiments, a labeled ligand to which the antibody and/or aptamer binds may be used within an immunoassay. Numerous types of labels may be utilized. Examples of such labels include, but are not limited to, radioactive labels, fluorescent labels, enzyme labels, spin labels, magnetic labels, gold labels, colorimetric labels, redox labels, and the like. Numerous immunoassays are known and may be configured for processing one or more samples 102.

In some embodiments, one or more microfluidic chips 108 may be configured to process one or more samples 102 through use of one or more competition assays. In some embodiments, one or more microfluidic chips 108 may be configured to process one or more samples 102 through use of one or more polynucleotide based competition assays. One or more microfluidic chips 108 may be configured to include one or more polynucleotides coupled to a substrate, such as a polynucleotide array. The one or more microfluidic chips 108 may be further configured so that a sample 102 and/or substantially purified polynucleotides obtained from one or more samples 102, may be mixed with one or more reagent mixtures that include one or more labeled polynucleotides to form an analysis mixture. This analysis mixture is then passed over the substrate such that the labeled polynucleotides and the sample polynucleotides are allowed to hybridize to the polynucleotides that are immobilized on the substrate. The sample polynucleotides and the labeled polynucleotides will compete for binding to the polynucleotides that are coupled on the substrate. Accordingly, the presence and/or concentration of the polynucleotides in the sample 102 can be determined through detection of the label (e.g., the concentration of the polynucleotides in the sample 102 will be inversely related to the amount of label that is bound to the substrate). Numerous labels may be used that include, but are not limited to, enzymes, fluorescent molecules, radioactive labels, spin labels, redox labels, and the like. In some embodiments, one or more microfluidic chips 108 may be configured to include one or more antibodies, proteins, peptides, and/or aptamers that are coupled to a substrate. The one or more microfluidic chips 108 may be further configured so that a sample 102 and/or substantially purified sample polypeptides and/or sample peptides obtained from one or more samples 102, may be mixed with one or more reagent mixtures that include one or more labeled polypeptides and/or labeled peptides to form an analysis mixture. This analysis mixture can then be passed over the substrate such that the labeled polypeptides and/or labeled peptides and the sample polypeptides and/or sample peptides are allowed to bind to the antibodies, proteins, peptides, and/or aptamers that are immobilized on the substrate. The sample polypeptides and/or sample peptides and the labeled polypeptides and/or sample peptides will compete for binding to the antibodies, proteins, peptides, and/or aptamers that are coupled on the substrate. Accordingly, the presence and/or concentration of the sample polypeptides and/or sample peptides in the sample 102 can be determined through detection of the label (e.g., the concentration of the sample polypeptides and/or sample peptides in the sample 102 will be inversely related to the amount of label that is bound to the substrate). Numerous labels may be used that include, but are not limited to, enzymes, fluorescent molecules, radioactive labels, spin labels, redox labels, and the like. Microfluidic chips 108 may be configured to utilize numerous types of competition assays.

In some embodiments, one or more microfluidic chips 108 may be configured to utilize numerous processing methods. For example, in some embodiments, one or more allergen indicators 106 may be precipitated with salt, dialyzed, and then applied to a chromatographic column.

At embodiment 4704, module 4430 may include one or more analysis units configured for analysis of the one or more allergen indicators that are associated with one or more food products. In some embodiments, one or more microfluidic chips 108 may include one or more analysis units 120 configured for analysis of the one or more allergen indicators 106 that are associated with one or more food products. Numerous food associated allergen indicators 106 have been referenced herein and have been described (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Examples of such food associated allergen indicators 106 include, but are not limited to, polynucleotides, polypeptides, carbohydrates, lipids, polysaccharides (e.g., chitin), oils, shell components, glycoproteins, and the like.

At embodiment 4706, module 4430 may include one or more analysis units configured for analysis of the one or more allergen indicators that are associated with one or more weeds, grasses, trees, mites, animals, molds, fungi, insects, rubbers, metals, chemicals, autoallergens, or human autoallergens. In some embodiments, one or more microfluidic chips 108 may include one or more analysis units 120 configured for analysis of the one or more allergen indicators 106 that are associated with one or more weeds, grasses, trees, mites, animals, molds, fungi, insects, rubbers, metals, chemicals, autoallergens, human autoallergens, or substantially any combination thereof.

At embodiment 4708, module 4430 may include one or more analysis units configured for polynucleotide extraction. In some embodiments, one or more microfluidic chips 108 may include one or more analysis units 120 configured for polynucleotide extraction. Microfluidic chips 108 may be configured to provide for utilization of numerous methods to extract one or more polynucleotides from one or more samples 102.

In some embodiments, one or more microfluidic chips 108 may be configured to provide for utilization of chemical methods to extract one or more polynucleotides from one or more samples 102. For example, a microfluidic chip 108 may be configured to utilize alkaline lysis (e.g., miniprep procedure) to extract polynucleotides from one or more samples 102. In such examples, a microfluidic chip 108 may include a chamber where one or more samples 102 may be combined with a lysis buffer (e.g., sodium hydroxide/sodium dodecyl sulfate) to solubilize the one or more samples 102. The solubilized samples 102 may then be combined with an agent that precipitates the sodium dodecyl sulfate (e.g., potassium acetate) and the microfluidic chip 108 may be centrifuged through use of a centrifugation unit 118. The supernatant may then be transferred to another chamber where it may be chemically extracted (e.g., phenol/chloroform). The supernatant may then be transferred to another chamber and combined with an agent to precipitate polynucleotides present within the supernatant (e.g., alcohol). The microfluidic chip 108 may then be centrifuged to pellet any polynucleotides and then the supernatant may be drawn off and the pellet resuspended to facilitate analysis of the polynucleotides.

In some embodiments, one or more microfluidic chips 108 may be configured to provide for extraction of one or more polynucleotides from one or more samples 102 through use of magnetic extraction. For example, in some embodiments, one or more microfluidic chips 108 may include one or more chambers where one or more samples 102 that may include one or more sample polynucleotides may be mixed with extraction polynucleotides that are associated with one or more ferrous tags. Hybridization of the extraction polynucleotides with the sample polynucleotides will associate the one or more ferrous tags with the one or more sample polynucleotides. The hybridized polynucleotides may then be subjected to a magnetic field to separate the one or more sample polynucleotides from the one or more samples 102.

In some embodiments, one or more microfluidic chips 108 may be configured to provide for the use of magnetism for extraction of one or more polynucleotides from one or more samples 102. In some embodiments, magnetic and/or ferrous tags may be used in combination with ferrous fluid and/or magnetic fluid to extract one or more polynucleotides from one or more samples 102. In some embodiments, ferrous fluids and/or magnetic fluids may be used in combination with one or more H-filters to extract polynucleotides from one or more samples 102. For example, in some embodiments, a microfluidic chip 108 may be configured to include an H-filter where a sample fluid that includes one or more ferrous tagged polynucleotides may flow next to a magnetic fluid such that the one or more ferrous tagged polynucleotides migrate into the ferrous fluid to facilitate extraction of the one or more polynucleotides. In some embodiments, eddy currents may be used to extract one or more polynucleotides from one or more samples 102. For example, in some embodiments, one or more polynucleotides that are associated with a non-ferrous metallic tag (e.g., an aluminum bead) may be passed through a magnetic field such that kinetic energy is imparted to the non-ferrous metallic tagged polynucleotides to facilitate their extraction from the one or more samples 102. In some embodiments, a microfluidic chip 108 may be configured to include an H-filter where a sample fluid that includes one or more polynucleotides that are associated with one or more non-ferrous metallic tags may flow next to an extraction fluid such that passage of the one or more non-ferrous metallic tagged polynucleotides through a magnetic field will facilitate migration of the tagged polynucleotides into the adjoining extraction fluid.

In some embodiments, one or more microfluidic chips 108 may be configured to utilize immobilized polynucleotides for extraction of one or more polynucleotides that correspond to one or more allergen indicators 106 from one or more samples 102. For example, in some embodiments, one or more samples 102 may be incubated with one or more immobilized polynucleotides (e.g., a polynucleotide array) that include nucleotide sequences that correspond to one or more allergen indicators 106. The one or more samples 102 may then be incubated under conditions that allow hybridization of one or more polynucleotides within the one or more samples 102 with the one or more immobilized polynucleotides. The immobilized polynucleotides may then be washed to extract polynucleotides that correspond to allergen indicators 106 from the one or more samples 102. Microfluidic chips 108 may be configured in numerous ways to utilize polynucleotide hybridization to extract allergen indicators 106 from one or more samples 102.

In some embodiments, one or more microfluidic chips 108 may be configured for extraction of polynucleotides that correspond to one or more allergen indicators 106 from one or more samples 102 through use of numerous polynucleotide conjugates. Such polynucleotide conjugates include, but are not limited to, polynucleotides that include one or more nucleotide sequences that correspond to one or more allergen indicators 106 that are associated with an immobilization tag. Examples of such immobilization tags include, but are not limited to, avidin, biotin, streptavidin, antibodies, aptamers, and the like. Accordingly, in some embodiments, one or more samples 102 may be mixed with one or more polynucleotide conjugates such that the polynucleotide conjugates may hybridize with one or more allergen indicators 106 that are included within the one or more samples 102. The mixture may then be contacted with one or more immobilization tag binders that are linked to a substrate such that the one or more allergen indicators 106 become immobilized. The immobilized polynucleotides may then be washed to extract polynucleotides that correspond to allergen indicators 106 from the one or more samples 102. Microfluidic chips 108 may be configured in numerous ways to utilize polynucleotide conjugates to extract allergen indicators 106 from one or more samples 102.

In some embodiments, one or more microfluidic chips 108 may be configured to utilize chromatographic methods for extraction of polynucleotides that correspond to one or more allergen indicators 106 from one or more samples 102. Numerous methods are known and have been described that may be used to extract one or more polynucleotides from one or more samples 102.

In some embodiments, one or more microfluidic chips 108 may be configured to utilize two or more methods to extract one or more polynucleotides from one or more samples 102.

At embodiment 4710, module 4430 may include one or more analysis units configured for polypeptide extraction. In some embodiments, one or more microfluidic chips 108 may include one or more analysis units 120 configured for polypeptide extraction. Microfluidic chips 108 may be configured to provide for utilization of numerous methods to extract one or more polypeptides from one or more samples 102.

In some embodiments, one or more microfluidic chips 108 may be configured to provide for utilization of chemical methods to extract one or more polypeptides from one or more samples 102. For example, a microfluidic chip 108 may be configured to utilize salt precipitation to extract polypeptides from one or more samples 102. In such examples, a microfluidic chip 108 may include a chamber where one or more samples 102 may be combined with one or more salts (e.g., ammonium sulfate). The microfluidic chip 108 may be centrifuged through use of a centrifugation unit 118 to produce a pellet that includes one or more polypeptides. The supernatant may then be removed and the pellet may be resuspended. The resuspended pellet containing the one or more precipitated polynucleotides may be transferred to another chamber of the microfluidic chip 108 where the salt mixture may be dialyzed to reduce the salt concentration.

In some embodiments, one or more microfluidic chips 108 may be configured to provide for extraction of one or more polypeptides from one or more samples 102 through use of magnetic extraction. For example, in some embodiments, one or more microfluidic chips 108 may include one or more chambers where one or more samples 102 that may include one or more sample polypeptides may be mixed with one or more polypeptide binders that are associated with one or more ferrous tags. Binding of the polypeptide binders with the sample polypeptides will associate the one or more ferrous tags with the one or more sample polypeptides. The polypeptides may then be subjected to a magnetic field to separate the one or more sample polypeptides from the one or more samples 102.

In some embodiments, one or more microfluidic chips 108 may be configured to provide for the use of magnetism for extraction of one or more polypeptides from one or more samples 102. In some embodiments, magnetic and/or ferrous tags may be used in combination with ferrous fluid and/or magnetic fluid to extract one or more polypeptides from one or more samples 102. In some embodiments, ferrous fluids and/or magnetic fluids may be used in combination with one or more H-filters to extract polypeptides from one or more samples 102. For example, in some embodiments, a microfluidic chip 108 may be configured to include an H-filter where a sample fluid that includes one or more ferrous tagged polypeptides may flow next to a magnetic fluid such that the one or more ferrous tagged polypeptides migrate into the ferrous fluid to facilitate extraction of the one or more polypeptides. In some embodiments, eddy currents may be used to extract one or more polypeptides from one or more samples 102. For example, in some embodiments, one or more polypeptides that are associated with a non-ferrous metallic tag (e.g., an aluminum bead) may be passed through a magnetic field such that kinetic energy is imparted to the non-ferrous metallic tagged polypeptides to facilitate their extraction from the one or more samples 102. In some embodiments, a microfluidic chip 108 may be configured to include an H-filter where a sample fluid that includes one or more polypeptides that are associated with one or more non-ferrous metallic tags may flow next to an extraction fluid such that passage of the one or more non-ferrous metallic tagged polypeptides through a magnetic field will facilitate migration of the tagged polypeptides into the adjoining extraction fluid.

In some embodiments, one or more microfluidic chips 108 may be configured to utilize immobilized polypeptide binders for extraction of one or more polypeptides that correspond to one or more allergen indicators 106 from one or more samples 102. For example, in some embodiments, one or more samples 102 may be incubated with one or more immobilized polypeptide binders (e.g., antibodies, aptamers, substrates, polypeptides, peptides, polynucleotides, and the like). The one or more samples 102 may then be incubated under conditions that allow binding of one or more polypeptides within the one or more samples 102 with the one or more immobilized polypeptide binders. The immobilized polypeptides may then be washed to extract polypeptides that correspond to allergen indicators 106 from the one or more samples 102. Microfluidic chips 108 may be configured in numerous ways to utilize polypeptide binding to extract allergen indicators 106 from one or more samples 102.

In some embodiments, one or more microfluidic chips 108 may be configured for extraction of polypeptides that correspond to one or more allergen indicators 106 from one or more samples 102 through use of numerous polypeptide conjugates. Such polypeptide conjugates include, but are not limited to, polypeptides that bind to one or more allergen indicators 106 and that are associated with an immobilization tag. Examples of such immobilization tags include, but are not limited to, avidin, biotin, streptavidin, antibodies, aptamers, and the like. Accordingly, in some embodiments, one or more samples 102 may be mixed with one or more polypeptide conjugates such that the polypeptide conjugates may bind with one or more allergen indicators 106 that are included within the one or more samples 102. The mixture may then be contacted with one or more immobilization tag binders that are linked to a substrate such that the one or more allergen indicators 106 become immobilized. The immobilized polypeptides may then be washed to extract polypeptides that correspond to allergen indicators 106 from the one or more samples 102. Microfluidic chips 108 may be configured in numerous ways to utilize polypeptide conjugates to extract allergen indicators 106 from one or more samples 102.

In some embodiments, one or more microfluidic chips 108 may be configured to utilize chromatographic methods for extraction of polypeptides that correspond to one or more allergen indicators 106 from one or more samples 102. Numerous methods are known and have been described that may be used to extract one or more polypeptides from one or more samples 102.

In some embodiments, one or more microfluidic chips 108 may be configured to utilize two or more methods to extract one or more polypeptides from one or more samples 102.

Figure 48:
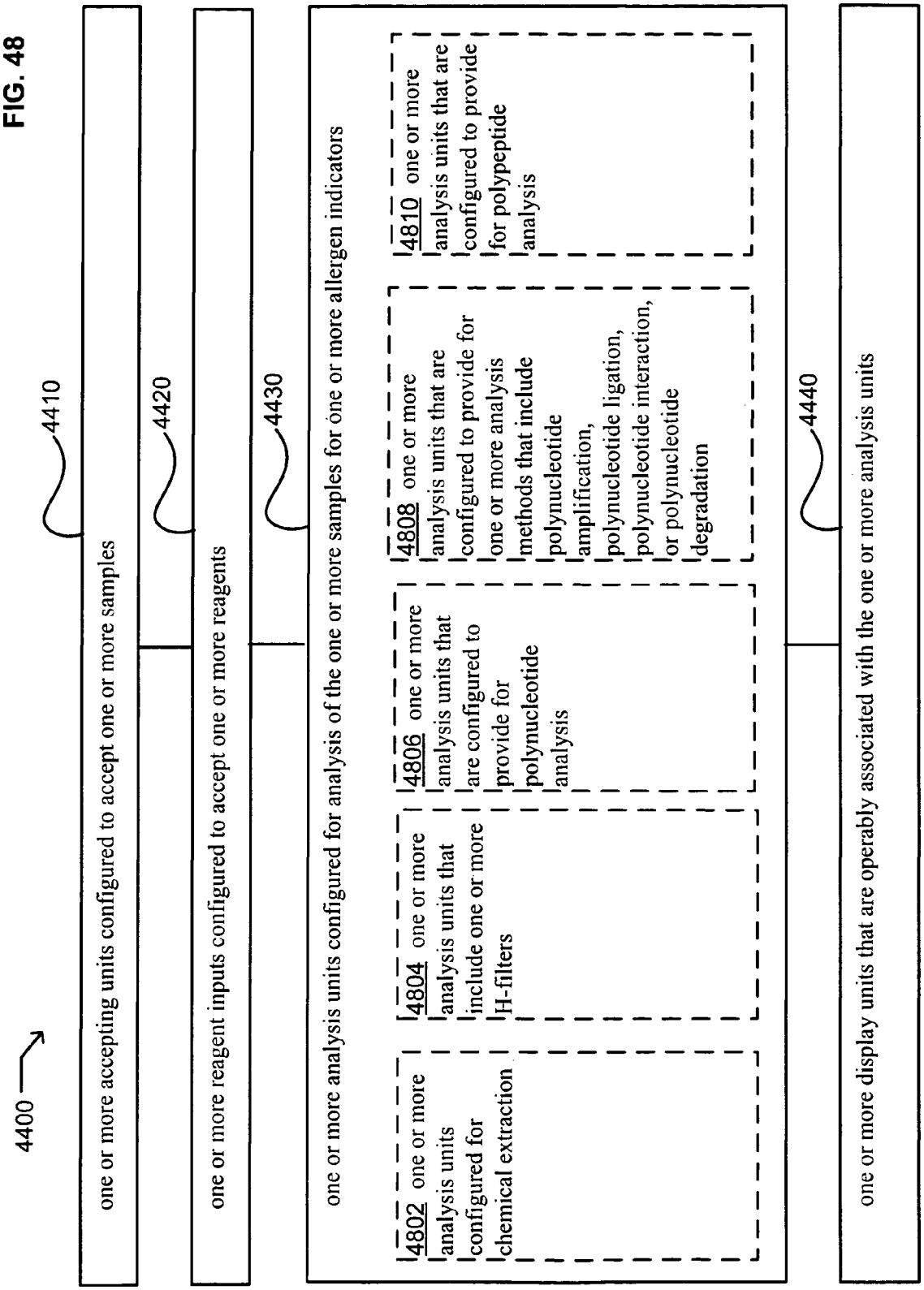
FIG. 48 illustrates alternate embodiments of the microfluidic chip of FIG. 44.

FIG. 48 illustrates alternative embodiments of microfluidic chips 4400 of FIG. 44. FIG. 48 illustrates example embodiments of module 4430. Additional embodiments may include an embodiment 4802, an embodiment 4804, an embodiment 4806, an embodiment 4808, and/or an embodiment 4810.

At embodiment 4802, module 4430 may include one or more analysis units configured for chemical extraction. In some embodiments, one or more microfluidic chips 108 may include one or more analysis units 120 configured for chemical extraction. Such microfluidic chips 108 may be used to extract one or more allergen indicators 106 from one or more samples 102. Microfluidic chips 108 may be configured to provide for use of numerous types of chemical extraction methods. Examples of such extraction methods include, but are not limited to, solvent extraction, acid extraction, base extraction, salt extraction, pH based extraction, and the like. Examples of allergen indicators 106 that may be extracted include, but are not limited to, metals, polynucleotides, polypeptides, carbohydrates, lipids, polysaccharides (e.g., chitin), oils, glycoproteins, and the like.

At embodiment 4804, module 4430 may include one or more analysis units that include one or more H-filters. In some embodiments, one or more microfluidic chips 108 may include one or more analysis units that include one or more H-filters. Methods to construct H-filters have been described (e.g., U.S. Pat. Nos. 6,742,661; 6,409,832; 6,007,775; 5,974,867; 5,971,158; 5,948,684; 5,932,100; 5,716,852; herein incorporated by reference). In some embodiments, H-filters may be configured to provide for immunodiffusion assays. In some embodiments, H-filters may be configured to provide for immunoseparation of one or more allergen indicators 106. In some embodiments, H-filters may be configured to provide for diffusion based separation of one or more allergen indicators 106. In some embodiments, H-filters may be configured for use with one or more ferrofluids and/or magnetic fluids. In some embodiments, two or more H-filters may be coupled to each other in series. In some embodiments, H-filters may be operably coupled with one or more magnets. Accordingly, one or more microfluidic chips 108 may include one or more H-filters that are configured in numerous ways.

At embodiment 4806, module 4430 may include one or more analysis units that are configured to provide for polynucleotide analysis. In some embodiments, one or more microfluidic chips 108 may include one or more analysis units 120 that are configured to provide for polynucleotide analysis. In some embodiments, one or more analysis units 120 may be configured to detect one or more polynucleotides. Microfluidic chips 108 may be configured to provide for the use of numerous methods for detection of one or more polynucleotides. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described (e.g., U.S. Pat. Nos. 7,118,910 and 6,960,437; herein incorporated by reference). Such methods may be adapted to provide for detection of one or more allergen indicators 106. In some embodiments, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more microfluidic chips 108 may be configured to provide for hybridization of one or more polynucleotides that include at least one carbon nanotube with one or more samples 102, and/or one or more partially purified polynucleotides obtained from one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Methods to utilize carbon nanotubes as probes for nucleic acid interaction have been described (e.g., U.S. Pat. No. 6,821,730; herein incorporated by reference). Microfluidic chips 108 may be configured to provide for use of numerous other methods based on polynucleotide detection for detection of one or more allergen indicators 106. In some embodiments, microfluidic chips 108 may be configured to provide for analysis of two or more polynucleotides.

At embodiment 4808, module 4430 may include one or more analysis units that are configured to provide for one or more analysis methods that include polynucleotide amplification, polynucleotide ligation, polynucleotide interaction, or polynucleotide degradation. In some embodiments, one or more microfluidic chips 108 may include one or more analysis units 120 that are configured to provide for one or more analysis methods that include polynucleotide amplification, polynucleotide ligation, polynucleotide interaction, polynucleotide degradation, or substantially any combination thereof.

In some embodiments, one or more microfluidic chips 108 may be configured to provide for analysis of one or more allergen indicators 106 through use of polynucleotide amplification. In some embodiments, one or more microfluidic chips 108 may be configured to provide for polynucleotide amplification by polymerase chain reaction (PCR). In some embodiments, PCR primers may be selected that hybridize to polynucleotides that are allergen indicators 106. Accordingly, such polynucleotides may be amplified. In some embodiments, PCR primers may be selected that include conductive end-groups such that the amplified PCR product may interact with two or more electrodes to bridge the electrodes and complete an electrical circuit. Accordingly, use of such primers provides for detection of the pcr products through use of electrical conductance. In some embodiments, primers that include conductive end-groups may be selected such that the primers themselves are inadequate to complete an electrical circuit and therefore will exhibit minimal background. In some embodiments, a microfluidic chip 108 may be configured to provide for polynucleotide amplification in the presence of altered nucleotides that will be incorporated into the PCR product. Accordingly, incorporation of such altered nucleotides into a PCR product may provide for detection of the PCR product. Examples of such altered nucleotides include, but are not limited to, alexa fluor labeled nucleotides, aminonaphthalenesulfonate labeled nucleotides, biotin labeled nucleotides, biotin labeled AMP, biotin labeled ddNTP, biotin labeled dNTP, BODIPY labeled nucleotides, caged nucleotides, coumarin labeled nucleotides, Cy3 labeled nucleotides, Cy5 labeled nucleotides, digoxigenin labeled nucleotides, digoxigenin labeled dUTP, fluorescein labeled nucleotides, R110 labeled nucleotides, R6G labeled nucleotides, rhodamine green labeled nucleotides, rhodamine labeled nucleotides, ROX labeled nucleotides, Texas red labeled nucleotides, tetramethylrhodamine labeled nucleotides, trinitrophenyl labeled nucleotides, and the like. Methods to conduct PCR amplification are known and have been described (Belgrader et al., Biosensors & Bioelectronics, 14:849-852 (2000); Khandurina et al., Analytical Chemistry, 72:2995-3000 (2000); and Lagally et al., Analytical Chemistry, 73:565-570 (2001)).

In some embodiments, one or more microfluidic chips 108 may be configured to provide for analysis of one or more allergen indicators 106 through use of polynucleotide ligation. In some embodiments, one or more microfluidic chips 108 may be configured to provide for ligase chain reaction (LCR). Reaction conditions that may be used to conduct ligase chain reaction have been described (e.g., O'Connor et al., Thorax, 55:955-957 (2000); Tooley et al., Can. J. Plant Pathol., 24:294-301 (2002) and Ching et al., J. Clin. Microbiol., 33:3111-3114 (1995)). In some embodiments, LCR primers may be selected that include conductive end-groups such that the ligated LCR product may interact with two or more electrodes to bridge the electrodes and complete an electrical circuit. Accordingly, LCR may be used to provide for detection of one or more allergen indicators 106. LCR primers may be selected that include numerous types of end-groups. Examples of such end-groups include, but are not limited to, immobilization tags, detectable labels, and the like. In some embodiments, such end-groups may be used to facilitate detection of one or more allergen indicators 106.

In some embodiments, one or more microfluidic chips 108 may be configured to provide for analysis of one or more samples 102 through use of polynucleotide interaction. Microfluidic chips 108 may be configured to provide for the use of numerous methods based on polynucleotide interaction. Methods that utilize intercalation dyes, FRET analysis, and capacitive DNA detection have been described (e.g., U.S. Pat. Nos. 7,118,910 and 6,960,437; herein incorporated by reference). In some embodiments, microfluidic chips 108 may be configured to provide for fluorescence resonance energy transfer, fluorescence quenching, molecular beacons, electron transfer, electrical conductivity, and the like. In some embodiments, one or more microfluidic chips 108 may be configured to provide for utilization of one or more polynucleotides that include at least one carbon nanotube as has been described (e.g., U.S. Pat. No. 6,821,730; herein incorporated by reference).

In some embodiments, one or more microfluidic chips 108 may be configured to provide for analysis of one or more samples 102 through use of polynucleotide degradation. For example, one or more microfluidic chips 108 may be configured to provide for restriction digestion of one or more polynucleotides. Accordingly, microfluidic chips 108 may be configured to provide for extraction of polynucleotides that are allergen indicators 106 from one or more samples 102, digest the polynucleotides with restriction enzymes, and then subject the polynucleotide fragments to electrophoretic analysis.

At embodiment 4810, module 4430 may include one or more analysis units that are configured to provide for polypeptide analysis. In some embodiments, one or more microfluidic chips 108 may include one or more analysis units 120 that are configured to provide for polypeptide analysis. In some embodiments, microfluidic chips 108 may be configured for utilization of numerous methods for the analysis of polypeptides that are allergen indicators 106.

In some embodiments, a microfluidic chip 108 may be configured to analyze one or more polypeptides through use of one or more electrophoretic methods. Examples of such electrophoretic methods include, but are not limited to, isoelectric focusing, denaturing gel electrophoresis, native gel electrophoresis, agarose gel electrophoresis, gradient gel electrophoresis, and the like.

In some embodiments, a microfluidic chip 108 may be configured to analyze one or more polypeptides through use of one or more chromatographic methods. Examples of such chromatographic methods include, but are not limited to, gel filtration chromatography, ion-exchange chromatography, affinity chromatography, and the like.

In some embodiments, a microfluidic chip 108 may be configured for analysis of one or more polypeptides through use of degradative methods. For example, in some embodiments, one or more polypeptides may be subjected to proteolytic digestion with one or more proteases. The degradative products may then be analyzed through use of numerous methods that may include, but are not limited to, gel electrophoresis, gel chromatography, isoelectric focusing, spectroscopic methods, and the like. Accordingly, in some embodiments, such methods may be used to confirm the presence and/or absence of one or more allergen indicators 106 within one or more samples 102. In some embodiments, degradative methods may be used in combination with immunological based methods. For example, in some embodiments, one or more samples 102 may be proteolytically digested, subjected to electrophoresis, and then probed with antibodies and/or aptamers that are specific for one or more allergen indicators 106 to determine if the one or more allergen indicators 106 are present within the sample 102.

In some embodiments, a microfluidic chip 108 may be configured for analysis of one or more polypeptides through use of microcantilevers. For example, in some embodiments, one or more polypeptide binders may be coupled to a cantilever such that one or more polypeptides that bind, or are bound, by the polypeptide binder will become associated with the microcantilever. Such configurations provide for detection of one or more allergen indicators 106 within one or more samples 102.

In some embodiments, a microfluidic chip 108 may be configured for analysis of one or more polypeptides through use of polypeptide interaction. For example, in some embodiments, a microfluidic chip 108 may include an array of polypeptide binders (e.g., antibodies, aptamers, enzymatic substrates, enzymatic products, or the like) that are immobilized on one or more conductive substrates. Binding of one or more polypeptides to the polypeptide binders will complete an electrical circuit such that interaction may be detected through measurement of electrical current. In some embodiments, one or more microfluidic chips 108 may be configured for utilization of immunological methods for polypeptide analysis. Examples of such immunological methods include, but are not limited to, sandwich assays, use of antibody arrays, immunoprecipitation, immunoseparation, immunodiffusion, and the like. In some embodiments, aptamers may be utilized in place of antibodies or in combination with antibodies with regard to immunological methods.

Accordingly, one or more microfluidic chips 108 may be configured in numerous ways to provide for analysis of one or more allergen indicators 106 that may include one or more polypeptides.

Figure 49:
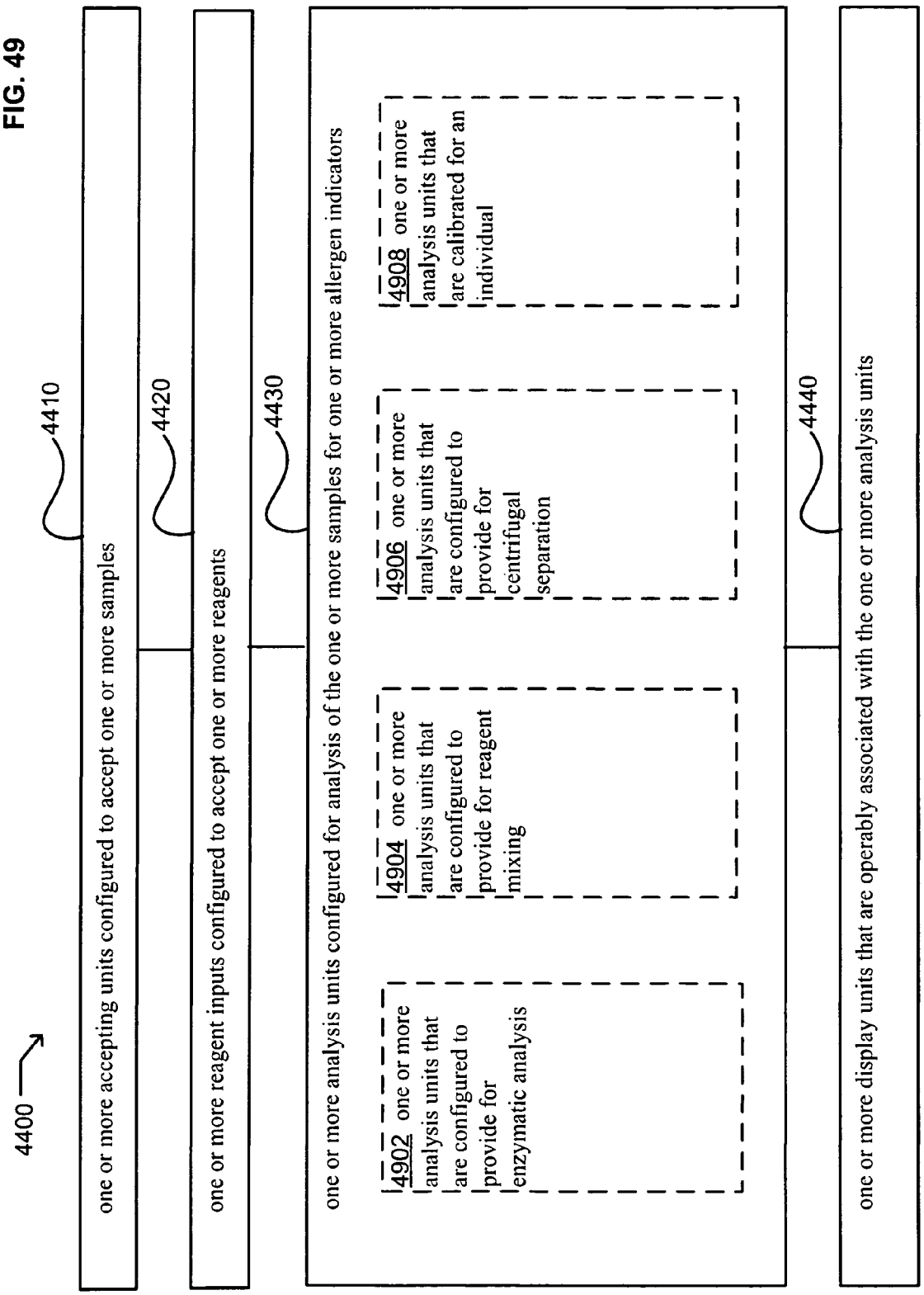
FIG. 49 illustrates alternate embodiments of the microfluidic chip of FIG. 44.

FIG. 49 illustrates alternative embodiments of microfluidic chips 4400 of FIG. 44. FIG. 49 illustrates example embodiments of module 4430. Additional embodiments may include an embodiment 4902, an embodiment 4904, and/or an embodiment 4906.

At embodiment 4902, module 4430 may include one or more analysis units that are configured to provide for enzymatic analysis. In some embodiments, one or more microfluidic chips 108 may include one or more analysis units 120 that are configured to provide for enzymatic analysis. In some embodiments, microfluidic chips 108 may be configured for utilization of numerous methods for the analysis of enzyme activity that is associated with one or more allergen indicators 106.

In some embodiments, enzyme activity may include activity that is directly associated with one or more allergen indicators 106. For example, in some embodiments, allergen indicators 106 exhibit enzyme activity (e.g., Derf1: dust mite cysteine protease; Derf18w: dust mite 60k chitinase; Horv17: barley beta-amylase; Fraa3: strawberry lipid transfer protein; Kiwi: Actc1 cysteine protease; and the like). Accordingly, microfluidic chips 108 may be configured to analyze one or more samples 102 for enzyme activity associated with one or more allergen indicators 106. For example, in some embodiments, one or more microfluidic chips 108 may be configured to present one or more substrates to one or more samples 102 such that enzyme activity within the one or more samples 102 may be detected through analysis of products resulting from enzyme activity. In some embodiments, enzyme substrates may be selected that produce a detectable signal when they are acted upon by one or more allergen indicator 106 associated enzymes. For example, protease substrates may be used that increase in fluorescence upon being cleaved by an allergen indicator 106 associated protease. Numerous types of substrates may be used to analyze enzyme activity.

In some embodiments, enzyme activity may include activity that is indirectly associated with one or more allergen indicators 106. For example, in some embodiments, one or more microfluidic chips 108 may be configured to analyze the activity of one or more enzymes that become associated with one or more allergen indicators 106. For example, in some embodiments, one or more microfluidic chips 108 may be configured to analyze the activity of one or more enzymes that become associated with one or more allergen indicators 106 through binding (e.g., enzyme activity coupled to an antibody that binds to an allergen indicator 106).

In some embodiments, one or more microfluidic chips 108 may be configured to utilize enzymatic analysis in combination with other analysis methods. For example, in some embodiments, enzymatic analysis may be combined with the use of an H-filter. In some embodiments, one or more samples 102 may be incubated with one or more substrates in a reaction mixture such that one or more products of enzymatic activity may be separated from the reaction mixture through use of an H-filter. An example of such a product may be a detectable label having a higher diffusion constant than the substrate to which it was originally coupled. Accordingly, cleavage of the detectable label from the substrate by the enzymatic activity of an allergen indicator 106 may increase diffusion of the detectable label and thereby provide for separation of the detectable label through use of an H-filter.

Microfluidic chips 108 may be configured to utilize numerous methods to analyze enzymatic activity.

At embodiment 4904, module 4430 may include one or more analysis units that are configured to provide for reagent mixing. In some embodiments, one or more microfluidic chips 108 may include one or more analysis units 120 that are configured to provide for reagent mixing. In some embodiments, a microfluidic chip 108 may include one or more mixing chambers. In some embodiments, a microfluidic chip 108 may include one or more mixing chambers that are configured to mix one or more reagents. In some embodiments, a microfluidic chip 108 may include one or more mixing chambers that are configured to mix one or more samples 102. In some embodiments, a microfluidic chip 108 may include one or more mixing chambers that are configured to mix one or more samples 102 with one or more reagents. In some embodiments, one or more mixing chambers may be configured for use of sonication. In some embodiments, one or more mixing chambers may be configured for use of magnetic mixing. For example, in some embodiments, a microfluidic chip 108 may include a mixing chamber which includes one or more ferrous mixing members and electromagnetics which are configured such that motion may be imparted to the one or more ferrous mixing members. In some embodiments, a microfluidic chip 108 may include one or more mixing chambers that include two or more electromagnets positioned around the one or more mixing chambers and one or more ferrous members positioned within the one or more mixing chambers and between the electromagnetics. Accordingly, mixing of one or more materials within the one or more mixing chambers may be facilitated by alternating current between the electromagnets positioned around the mixing chamber. In some embodiments, a mixing chamber may include an elastomeric material that includes a ferrous material (e.g., an elastomeric-ferrous material) such that movement of the elastomeric-ferrous material may be facilitated through use of one or more magnets, such as electromagnets. Microfluidic chips 108 may include mixing chambers that are configured in numerous ways.

At embodiment 4906, module 4430 may include one or more analysis units that are configured to provide for centrifugal separation. In some embodiments, one or more microfluidic chips 108 may include one or more analysis units 120 that are configured to provide for centrifugal separation. A microfluidic chip 108 may be configured to utilize numerous types of centrifugal separation.

In some embodiments, a microfluidic chip 108 may be configured to operably associate with a centrifuge. For example, in some embodiments, a microfluidic chip 108 may be configured for centrifugation within a centrifuge (e.g., such as those made by Sorvall, Beckman, Drucker, and the like). In some embodiments, a microfluidic chip 108 may be configured to fit within a centrifuge rotor (e.g., such as those made by Sorvall, IEC, and the like). In some embodiments, a microfluidic chip 108 may be configured to include one or more centrifugation units 118. In some embodiments, such a centrifugation unit 118 may include a rotor chamber that may be detachably associated with a centrifuge drive that is external to the microfluidic chip 108. In some embodiments, such a centrifugation unit 118 may include a rotor that is operably associated with a centrifuge drive that is included within the microfluidic chip 108. For example, in some embodiments, a microfluidic chip 108 may include a centrifugation unit 118 that includes one or more electromagnets that are configured to be in magnetic association with a rotor chamber that includes ferrous material that is configured to magnetically couple with the one or more electromagnets. Accordingly, in such embodiments, the rotor chamber may be rotated by application of electrical current to the one or more electromagnets. In some embodiments, a microfluidic chip 108 may include one or more rotor chambers that are physically coupled to one or more centrifuge drives (e.g., physically coupled through a drive shaft and/or belt).

Such centrifugation units 118 may be configured in numerous ways. For example, in some embodiments, centrifugation units 118 may be configured to provide for gradients, such as density gradients and/or velocity gradients. In some embodiments, centrifugation units 118 may be configured to spin one or more samples 102 through a chromatographic column (e.g., a spin column). Accordingly, centrifugation units 118 may be configured in numerous ways.

At embodiment 4908, module 4430 may include one or more analysis units that are calibrated for an individual. In some embodiments, one or more microfluidic chips 108 may include one or more analysis units 120 that are calibrated for an individual. In some embodiments, one or more analysis units 120 may be constructed for a specific individual. For example, in some embodiments, an individual may be allergic to shellfish and walnuts. Accordingly, in some embodiments, a microfluidic chip 108 may include one or more analysis units 120 that are configured to analyze one or more samples 102 for shellfish and walnut associated allergen indicators 106. Analysis units 120 may be configured to analyze numerous types of samples 102 and allergen indicators 106.

Figure 50:
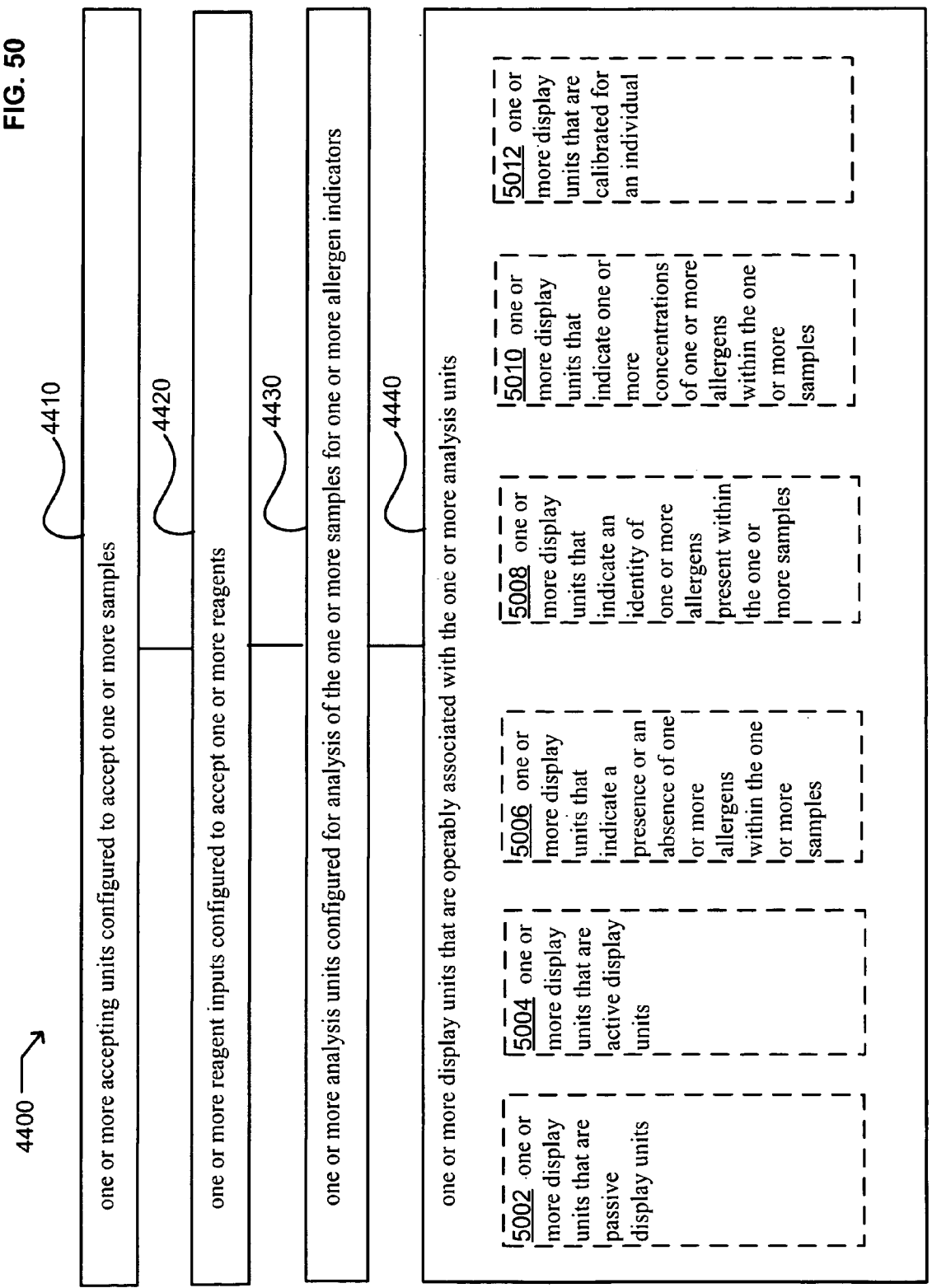
FIG. 50 illustrates alternate embodiments of the microfluidic chip of FIG. 44.

FIG. 50 illustrates alternative embodiments of microfluidic chips 4400 of FIG. 44. FIG. 50 illustrates example embodiments of module 4440. Additional embodiments may include an embodiment 5002, an embodiment 5004, an embodiment 5006, an embodiment 5008, and/or an embodiment 5010.

At embodiment 5002, module 4440 may include one or more display units that are passive display units. In some embodiments, one or more microfluidic chips 108 may include one or more display units 124 that are passive display units 124. In some embodiments, one or more display units 124 may include one or more liquid crystal displays (LCD). Methods to construct passive displays have been described (e.g., U.S. Pat. Nos. 4,807,967; 4,729,636: 4,436,378; 4,257,041; herein incorporated by reference).

At embodiment 5004, module 4440 may include one or more display units that are active display units. In some embodiments, one or more microfluidic chips 108 may include one or more display units 124 that are active display units 124. Numerous active display units 124 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), wide ultra extended graphics array (WUXGA).

At embodiment 5006, module 4440 may include one or more display units that indicate a presence or an absence of one or more allergens within the one or more samples. In some embodiments, one or more microfluidic chips 108 may include one or more display units 124 that indicate a presence or an absence of one or more allergens 104 within the one or more samples 102. In some embodiments, one or more display units 124 may use a colorimetric message to indicate a presence or an absence of one or more allergen indicators 106 within one or more samples 102. For example, in some embodiments, one or more display units 124 may display a green light if one or more allergen indicators 106 are not found within one or more samples 102 and a red light if one or more allergen indicators 106 are found within one or more samples 102. In some embodiments, one or more display units 124 may use a pictographic message to indicate a presence or an absence of one or more allergen indicators 106 within one or more samples 102. For example, in some embodiments, one or more display units 124 may display a smiley face if one or more allergen indicators 106 are not found within one or more samples 102 and a frowny face if one or more allergen indicators 106 are found within one or more samples 102. In some embodiments, one or more display units 124 may use a typographical message to indicate a presence or an absence of one or more allergen indicators 106 within one or more samples 102. For example, in some embodiments, one or more display units 124 may display an "Allergen Not Present" message if one or more allergen indicators 106 are not found within one or more samples 102 and an "Allergen Present" message if one or more allergen indicators 106 are found within one or more samples 102. Such messages may be displayed in numerous languages. In some embodiments, one or more display units 124 may display one or more messages in multiple formats. For example, in some embodiments, one or more messages may be displayed in colored text.

At embodiment 5008, module 4440 may include one or more display units that indicate an identity of one or more allergens present within the one or more samples. In some embodiments, one or more microfluidic chips 108 may include one or more display units 124 that indicate an identity of one or more allergens 104 present within the one or more samples 102. In some embodiments, one or more display units 124 may be operably associated with one or more microfluidic chips 108 that are configured to identify one or more allergen indicators 106. Accordingly, in some embodiments, one or more display units 124 may be configured to display the identity of one or more allergens 104 that are present and/or absent from one or more samples 102. For example, in some embodiments, a display unit 124 may be configured to indicate a presence or an absence of beta-lactoglobulin in a food product.

At embodiment 5010, module 4440 may include one or more display units that indicate one or more concentrations of one or more allergens within the one or more samples. In some embodiments, one or more microfluidic chips 108 may include one or more display units 124 that may indicate one or more concentrations of one or more allergens 104 within the one or more samples 102. Concentration may be displayed in numerous formats. For example, in some embodiments, concentration may be expressed numerically (e.g., mass allergen indicator 106 per volume sample 102 (e.g., milligrams per milliliter), mass allergen indicator 106 per mass sample 102 (e.g., milligrams per milligram of sample), parts per million, and the like). In some embodiments, concentration may be expressed graphically. For example, in some embodiments, one or more display units 124 may include a display having a gray scale on which the concentration of one or more allergen indicators 106 that are present within one or more samples 102 may be indicated (e.g., higher concentrations of one or more allergens 104 may be displayed as dark gray while lower concentrations of one or more allergens 104 may be displayed as light gray). In some embodiments, one or more display units 124 may include a display having a color scale on which the concentration of one or more allergen indicators 106 that are present within one or more samples 102 may be indicated (e.g., low concentrations of one or more allergen indicators 106 may be indicated by a green light, intermediate concentrations of one or more allergen indicators 106 may be indicated by a yellow light, high concentrations of one or more allergen indicators 106 may be indicated by a red light). In some embodiments, one or more display units 124 may be calibrated to an individual. For example, in such embodiments, an individual may use the display to obtain an immediate reading that will indicate if a food product contains a dangerous level of one or more allergens 104.

At embodiment 5012, module 4440 may include one or more display units that are calibrated for an individual. In some embodiments, one or more microfluidic chips 108 may include one or more display units 124 that are calibrated for an individual. In some embodiments, one or more display units 124 may be calibrated to display whether one or more allergens 104, and/or allergen indicators 106, that are specific to an individual are present or absent within one or more samples 102. For example, in some embodiments, one or more display units 124 may be configured to display whether one or more samples 102 contain shellfish associated allergens 104 for an individual known to be allergic to shellfish. In some embodiments, one or more display units 124 may be calibrated to indicate safe and/or unsafe concentrations of one or more allergens 104 within one or more samples 102 for an individual.

IV. Devices for Analysis of One or More Allergens

Figure 51:
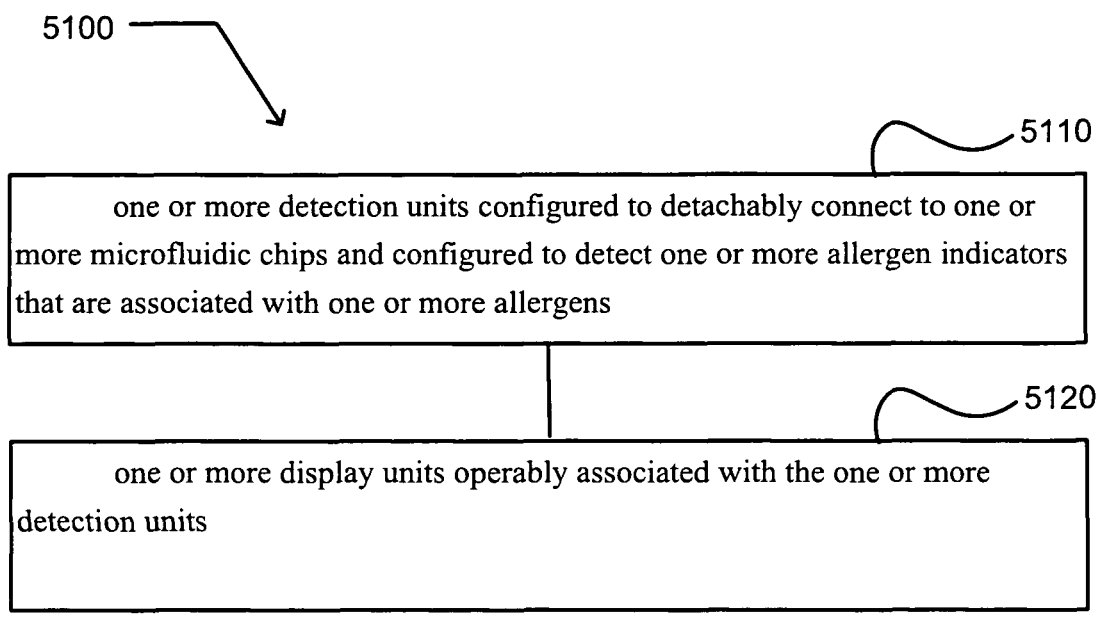
FIG. 51 illustrates an example device 5100 in which embodiments may be implemented.

FIG. 51 illustrates devices 5100 that may be configured for analysis of one or more allergens 104. In FIG. 51, discussion and explanation may be provided with respect to use of one or more devices within the above-described example of FIG. 1, and/or with respect to other examples and contexts. However, it should be understood that the devices may be configured in a number of other environments and contexts, and/or utilized within modified versions of FIG. 1. Also, although the devices are presented in the configuration(s) illustrated, it should be understood that the devices may be configured in numerous orientations.

The device 5100 includes module 5110 that includes one or more detection units configured to detachably connect to one or more microfluidic chips and configured to detect one or more allergen indicators that are associated with one or more allergens. In some embodiments, module 5110 may include one or more detection units configured to detect the one or more allergen indicators that are associated with the one or more allergens that are airborne. In some embodiments, module 5110 may include one or more detection units configured to detect the one or more allergen indicators that are associated with one or more food products. In some embodiments, module 5110 may include one or more detection units configured to detect the one or more allergen indicators that are associated with one or more weeds, grasses, trees, mites, animals, molds, fungi, insects, rubbers, metals, chemicals, autoallergens, or human autoallergens. In some embodiments, module 5110 may include one or more detection units that are calibrated for an individual.

The device 5100 may optionally include module 5120 that includes one or more display units operably associated with the one or more detection units. In some embodiments, module 5120 may include one or more display units that are passive display units. In some embodiments, module 5120 may include one or more display units that are active display units. In some embodiments, module 5120 may include one or more display units that indicate a presence or an absence of the one or more allergens within one or more samples. In some embodiments, module 5120 may include one or more display units that indicate an identity of the one or more allergens present within one or more samples. In some embodiments, module 5120 may include one or more display units that indicate one or more concentrations of the one or more allergens within one or more samples. In some embodiments, module 5120 may include one or more display units that are calibrated for an individual.

FIG. 52 illustrates alternative embodiments of devices 5100 of FIG. 51. FIG. 52 illustrates example embodiments of module 5110. Additional embodiments may include an embodiment 5202, an embodiment 5204, an embodiment 5206, and/or an embodiment 5208.

At embodiment 5202, module 5110 may include one or more detection units configured to detect the one or more allergen indicators that are associated with the one or more allergens that are airborne. In some embodiments, one or more devices may include one or more detection units 122 configured to detect one or more allergen indicators 106 that are associated with the one or more allergens 104 that are airborne. Accordingly, in some embodiments, one or more detection units 122 may be configured to operably associate with the one or more microfluidic chips 108 and to detect one or more airborne allergens 104. For example, in some embodiments, one or more microfluidic chips 108 may be configured to allow one or more air samples 102 to contact the one or more microfluidic chips 108 such that one or more allergen indicators 106 included within the one or more air samples 102 are retained by the one or more microfluidic chips 108. In some embodiments, the one or more air samples 102 may be passed through a filter on which one or more airborne allergen indicators 106 are collected. The collected airborne allergen indicators 106 may then be washed from the filter and caused to pass over an antibody array to which the one or more airborne allergen indicators 106 become immobilized. The immobilized airborne allergen indicators 106 may then be detected through numerous methods that include, but are not limited to, electrical conductivity, immunoassay based methods, and the like. Accordingly, one or more detection units 122 may be configured to detect the one or more airborne allergen indicators 106. In some embodiments, one or more detection units 122 may be configured to operably associate with one or more microfluidic chips 108 such that the one or more detection units 122 facilitate air flow through the one or more microfluidic chips 108 to provide for air sampling. For example, in some embodiments, one or more detection units 122 may include one or more fans to push and/or pull air through one or more operably associated microfluidic chips 108. In some embodiments, one or more detection units 122 may include one or more bellows to push and/or pull air through one or more operably associated microfluidic chips 108. Detection units 122 may be configured in numerous ways to provide for detection of one or more airborne allergen indicators 106.

At embodiment 5204, module 5110 may include one or more detection units configured to detect the one or more allergen indicators that are associated with one or more food products. In some embodiments, one or more devices may include one or more detection units 122 configured to detect one or more allergen indicators 106 that are associated with one or more food products. In some embodiments, one or more microfluidic chips 108 may be configured to provide for detection of one or more allergens 104 that are associated with one or more food products. Accordingly, in some embodiments, one or more detection units 122 may be configured to operably associate with the one or more microfluidic chips 108 and to detect one or more allergen indicators 106 that are associated with one or more food products. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Numerous methods may be used to detect one or more allergen indicators 106 that are associated with one or more food products. Such methods have been described herein. In addition, other detection methods that have been described may be modified to provide for detection of one or more allergen indicators 106 that are associated with one or more food products. In some embodiments, one or more detection units 122 may be configured to detect one or more polynucleotides, one or more polypeptides, one or more portions of one or more polynucleotides, and/or one or more portions of one or more polypeptides that have a nucleic acid sequence and/or an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, AY839230, or substantially any combination thereof.

At embodiment 5206, module 5110 may include one or more detection units configured to detect the one or more allergen indicators that are associated with one or more weeds, grasses, trees, mites, animals, molds, fungi, insects, rubbers, metals, chemicals, autoallergens, or human autoallergens. In some embodiments, one or more devices may include one or more detection units 122 configured to detect one or more allergen indicators 106 that are associated with one or more weeds, grasses, trees, mites, animals, molds, fungi, insects, rubbers, metals, chemicals, autoallergens, human autoallergens, or substantially any combination thereof. Numerous allergen indicators 106 are known to be associated with weeds, grasses, trees, mites, animals, molds, fungi, insects, rubbers, metals, chemicals, autoallergens, or human autoallergens. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Accordingly, in some embodiments, one or more microfluidic chips 108 may be configured to process one or more samples 102 and provide for detection of one or more allergen indicators 106. In some embodiments, an allergen indicator 106 may be an allergenic particle. For example, in some embodiments, an allergen indicator 106 may include a complete pollen particle, such as a pollen particle, a spore, a flake of dander, and the like. In some embodiments, an allergen indicator 106 may be a portion of an allergenic particle. For example, in some embodiments, an allergen indicator 106 may include a portion of a pollen particle (e.g., polynucleotides, sporoderm, and the like). In some embodiments, allergen indicators 106 may include polynucleotides that are associated with one or more allergens 104. In some embodiments, allergen indicators 106 may include fragments of polynucleotides that are associated with one or more allergens 104. In some embodiments, allergen indicators 106 may include polypeptides, peptides, and/or proteins that are associated with one or more allergens 104. In some embodiments, allergen indicators 106 may include polysaccharides that are associated with one or more allergens 104. Accordingly, in some embodiments, one or more microfluidic chips 108 may be configured to provide for detection of one or more allergen indicators 106. In some embodiments, one or more detection units 122 may be configured to operably associate with one or more such microfluidic chips 108 and configured to detect one or more allergen indicators 106. Numerous detection methods may be used to detect one or more allergen indicators 106. Such methods have been described herein. In addition, detection methods that have been described may be modified to provide for detection of one or more allergen indicators 106. In some embodiments, one or more detection units 122 may be configured to detect and determine a concentration of one or more allergen indicators 106 that are included within a sample 102. For example, in some embodiments, one or more microfluidic chips 108 may be configured to provide for detection of one or more polynucleotides that are allergen indicators 106 through detection of electrical current produced upon hybridization of the one or more polynucleotides. Accordingly, in such embodiments, the one or more microfluidic chips 108 may be configured to produce an electrical current that is relative to polynucleotide concentration to provide for determination of polynucleotide concentration within one or more samples 102. Numerous configurations may be used in association with one or more allergen indicators 106 to provide for determination of allergen 104 concentration. In some embodiments, one or more microfluidic chips 108 may be configured to provide for identification of one or more allergens 104. For example, in some embodiments, one or more microfluidic chips 108 may include immobilized polynucleotides that selectively hybridize to one or more polynucleotides that are associated with a known allergen indicator 106. Accordingly, hybridization of one or more polynucleotides with the one or more immobilized polynucleotides indicates that a sample 102 includes one or more allergen indicators 106 that correspond to one or more known allergens 104. Accordingly, one or more detection units 122 may be configured to operably associate with such microfluidic chips 108 to provide for specific detection of one or more allergen indicators 106. In some embodiments, microfluidic chips 108 and/or detection units 122 may be configured to determine the identity and concentration of one or more allergen indicators 106 that are included within one or more samples 102.

At embodiment 5208, module 5110 may include one or more detection units that are calibrated for an individual. In some embodiments, one or more devices may include one or more detection units 122 that are calibrated for an individual. In some embodiments, one or more detection units 122 may be calibrated to detect one or more specific allergens 104 and/or allergen indicators 106 that produce an allergic response by an individual. For example, in some embodiments, one or more detection units 122 may be calibrated to detect peanuts and/or peanut associated products for an individual who is allergic to peanuts. In some embodiments, one or more detection units 122 may be calibrated to detect different concentrations of allergen indicators 106. For example, in some embodiments, an individual may produce an allergic response if exposed to an allergen 104 at a concentration that is above a certain level. Accordingly, in some embodiments, a detection unit 122 may be calibrated to detect one or more concentrations of one or more allergen indicators 106 that produce an allergic response within an individual.

FIG. 53 illustrates alternative embodiments of devices 5100 of FIG. 51. FIG. 53 illustrates example embodiments of module 5120. Additional embodiments may include an embodiment 5302, an embodiment 5304, an embodiment 5306, an embodiment 5308, an embodiment 5310, and/or an embodiment 5312.

At embodiment 5302, module 5120 may include one or more display units that are passive display units. In some embodiments, one or more devices may include one or more display units 124 that are passive display units 124. In some embodiments, one or more display units 124 may include one or more liquid crystal displays (LCD). Methods to construct passive displays have been described (e.g., U.S. Pat. Nos. 4,807,967; 4,729,636: 4,436,378; 4,257,041; herein incorporated by reference).

At embodiment 5304, module 5120 may include one or more display units that are active display units. In some embodiments, one or more devices may include one or more display units 124 that are active display units 124. Numerous active display units 124 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), wide ultra extended graphics array (WUXGA).

At embodiment 5306, module 5120 may include one or more display units that indicate a presence or an absence of the one or more allergens within one or more samples. In some embodiments, one or more devices may include one or more display units 124 that indicate a presence or an absence of one or more allergens 104 within one or more samples 102. In some embodiments, one or more display units 124 may use a colorimetric message to indicate a presence or an absence of one or more allergen indicators 106 within one or more samples 102. For example, in some embodiments, one or more display units 124 may display a green light if one or more allergen indicators 106 are not found within one or more samples 102 and a red light if one or more allergen indicators 106 are found within one or more samples 102. In some embodiments, one or more display units 124 may use a pictographic message to indicate a presence or an absence of one or more allergen indicators 106 within one or more samples 102. For example, in some embodiments, one or more display units 124 may display a smiley face if one or more allergen indicators 106 are not found within one or more samples 102 and a frowny face if one or more allergen indicators 106 are found within one or more samples 102. In some embodiments, one or more display units 124 may use a typographical message to indicate a presence or an absence of one or more allergen indicators 106 within one or more samples 102. For example, in some embodiments, one or more display units 124 may display an "Allergen Not Present" message if one or more allergen indicators 106 are not found within one or more samples 102 and an "Allergen Present" message if one or more allergen indicators 106 are found within one or more samples 102. Such messages may be displayed in numerous languages. In some embodiments, one or more display units 124 may display one or more messages in multiple formats. For example, in some embodiments, one or more messages may be displayed in colored text.

At embodiment 5308, module 5120 may include one or more display units that indicate an identity of the one or more allergens present within one or more samples. In some embodiments, one or more devices may include one or more display units 124 that indicate an identity of one or more allergens 104 present within the one or more samples 102. In some embodiments, one or more display units 124 may be operably associated with one or more microfluidic chips 108 that are configured to identify one or more allergen indicators 106. Accordingly, in some embodiments, one or more display units 124 may be configured to display the identity of one or more allergens 104 that are present and/or absent from one or more samples 102. For example, in some embodiments, a display unit 124 may be configured to indicate a presence or an absence of beta-lactoglobulin in a food product.

At embodiment 5310, module 5120 may include one or more display units that indicate one or more concentrations of the one or more allergens within one or more samples. In some embodiments, one or more devices may include one or more display units 124 that indicate one or more concentrations of one or more allergens 104 within the one or more samples 102. Concentration may be displayed in numerous formats. For example, in some embodiments, concentration may be expressed numerically (e.g., mass allergen indicator 106 per volume sample 102 (e.g., milligrams per milliliter), mass allergen indicator 106 per mass sample 102 (e.g., milligrams per milligram of sample), parts per million, and the like). In some embodiments, concentration may be expressed graphically. For example, in some embodiments, one or more display units 124 may include a display having a gray scale on which the concentration of one or more allergen indicators 106 that are present within one or more samples 102 may be indicated (e.g., higher concentrations of one or more allergens 104 may be displayed as dark gray while lower concentrations of one or more allergens 104 may be displayed as light gray). In some embodiments, one or more display units 124 may include a display having a color scale on which the concentration of one or more allergen indicators 106 that are present within one or more samples 102 may be indicated (e.g., low concentrations of one or more allergen indicators 106 may be indicated by a green light, intermediate concentrations of one or more allergen indicators 106 may be indicated by a yellow light, high concentrations of one or more allergen indicators 106 may be indicated by a red light). In some embodiments, one or more display units 124 may be calibrated to an individual. For example, in such embodiments, an individual may use the display to obtain an immediate reading that will indicate if a food product contains a dangerous level of one or more allergens 104.

At embodiment 5312, module 5120 may include one or more display units that are calibrated for an individual. In some embodiments, one or more devices may include one or more display units 124 that are calibrated for an individual. In some embodiments, one or more display units 124 may be calibrated to display whether one or more allergens 104, and/or allergen indicators 106, that are specific to an individual are present or absent within one or more samples 102. For example, in some embodiments, one or more display units 124 may be configured to display whether one or more samples 102 contain shellfish associated allergens 104 for an individual known to be allergic to shellfish. In some embodiments, one or more display units 124 may be calibrated to indicate safe and/or unsafe concentrations of one or more allergens 104 within one or more samples 102 for an individual.

Figure 54:
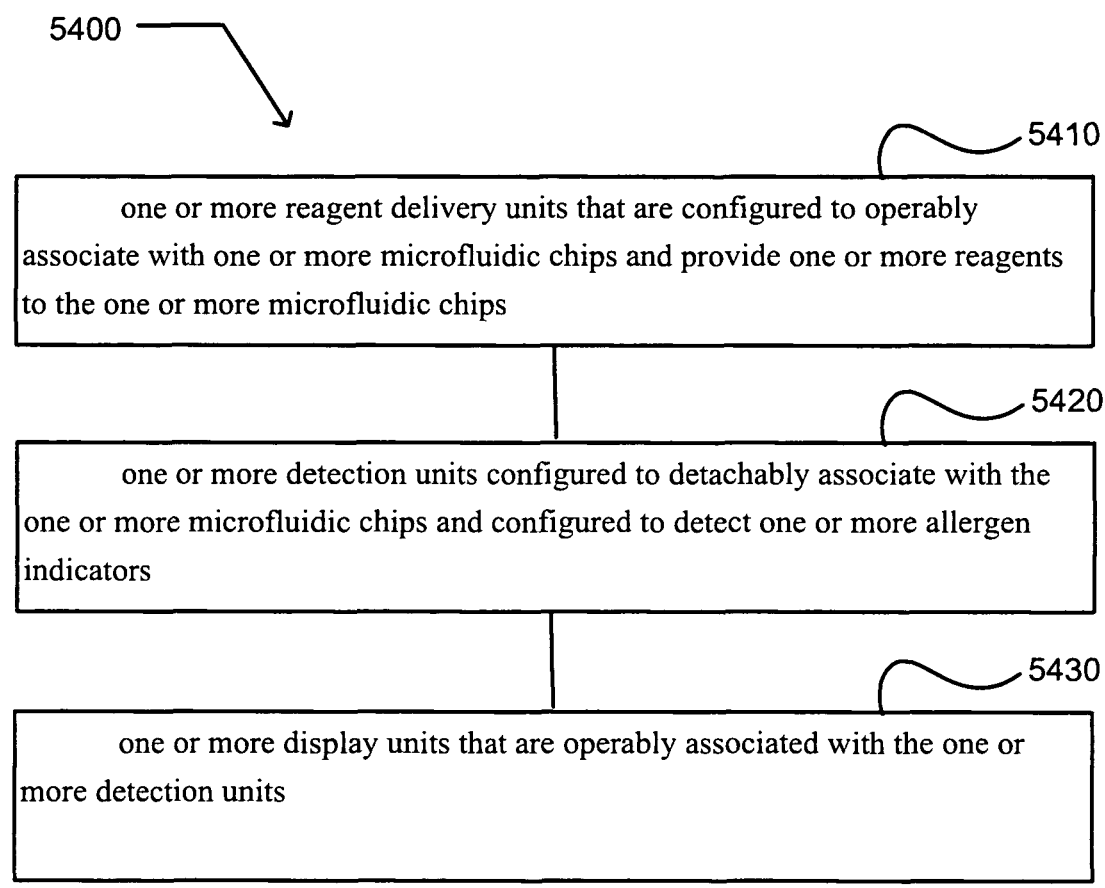
FIG. 54 illustrates an example device 5400 in which embodiments may be implemented.

FIG. 54 illustrates devices 5400 that may be configured for analysis of one or more allergens 104. In FIG. 54, discussion and explanation may be provided with respect to use of one or more devices within the above-described example of FIG. 1, and/or with respect to other examples and contexts. However, it should be understood that the devices may be configured in a number of other environments and contexts, and/or utilized within modified versions of FIG. 1. Also, although the devices are presented in the configuration(s) illustrated, it should be understood that the devices may be configured in numerous orientations.

The device 5400 includes module 5410 that includes one or more reagent delivery units that are configured to operably associate with one or more microfluidic chips and provide one or more reagents to the one or more microfluidic chips. In some embodiments, module 5410 may include one or more reagent delivery units configured for detachable connection to the one or more microfluidic chips. In some embodiments, module 5410 may include one or more reagent reservoirs. In some embodiments, module 5410 may include one or more waste reservoirs. In some embodiments, module 5410 may include one or more reagent delivery units physically coupled to the one or more detection units. In some embodiments, module 5410 may include one or more reagent delivery units that include one or more pumps.

The device 5400 includes module 5420 that includes one or more detection units configured to detachably associate with the one or more microfluidic chips and configured to detect one or more allergen indicators. In some embodiments, module 5420 may include one or more detection units configured to detect the one or more allergen indicators that are associated with one or more allergens that are airborne. In some embodiments, module 5420 may include one or more detection units configured to detect the one or more allergen indicators that are associated with one or more food products. In some embodiments, module 5420 may include one or more detection units configured to detect the one or more allergen indicators that are associated with one or more weeds, grasses, trees, mites, animals, molds, fungi, insects, rubbers, metals, chemicals, autoallergens, or human autoallergens. In some embodiments, module 5420 may include one or more detection units configured to detect the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, module 5420 may include one or more detection units that are calibrated for an individual.

The device 5400 includes module 5430 that includes one or more display units that are operably associated with the one or more detection units. In some embodiments, module 5430 may include one or more display units that are passive display units. In some embodiments, module 5430 may include one or more display units that are active display units. In some embodiments, module 5430 may include one or more display units that indicate a presence or an absence of one or more allergens within one or more samples. In some embodiments, module 5430 may include one or more display units that indicate an identity of one or more allergens present within one or more samples. In some embodiments, module 5430 may include one or more display units that indicate one or more concentrations of one or more allergens within one or more samples. In some embodiments, module 5430 may include one or more display units that are calibrated for an individual.

FIG. 55 illustrates alternative embodiments of devices 5400 of FIG. 54. FIG. 55 illustrates example embodiments of module 5410. Additional embodiments may include an embodiment 5502, an embodiment 5504, an embodiment 5506, an embodiment 5508, and/or an embodiment 5510.

At embodiment 5502, module 5410 may include one or more reagent delivery units configured for detachable connection to the one or more microfluidic chips. In some embodiments, one or more devices may include one or more reagent delivery units 116 configured for detachable connection to the one or more microfluidic chips. In some embodiments, one or more devices may be configured for detachable connection to one or more microfluidic chips 108 that are configured to process and/or provide for detection of the same type of allergen indicator 106. In some embodiments, one or more devices may be configured for detachable connection to one or more microfluidic chips 108 that are configured to process and/or provide for detection of numerous different types of allergen indicators 106. Reagent delivery units 116 may be configured to deliver one or more types of reagents to one or more microfluidic chips 108. In some embodiments, such reagents may be utilized to process one or more samples 102. In some embodiments, such reagents may be utilized to detect one or more allergen indicators 106. Examples of such reagents include, but are not limited to, solvents, water, tags, labels, antibodies, aptamers, polynucleotides, and the like. In some embodiments, one or more reagent delivery units 116 may include connectors that may be coupled to one or more microfluidic chips 108 to provide for delivery of one or more reagents to the one or more microfluidic chips 108. Examples of such connectors include, but are not limited to, leur lock fittings, needles, fluid connectors, and the like. In some embodiments, a reagent delivery unit 116 may include one or more pumps. In some embodiments, a reagent delivery unit 116 may include numerous reservoirs that may include numerous types of reagents. Accordingly, in some embodiments, a reagent delivery unit 116 may be configured to detachably connect with numerous types of microfluidic chips 108 that are configured to process and/or provide for detection of numerous types of allergen indicators 106.

At embodiment 5504, module 5410 may include one or more reagent reservoirs. In some embodiments, one or more devices may be configured to include one or more reagent reservoirs. In some embodiments, the one or more reagent reservoirs may be configured to contain reagents that may be used to process and/or detect a single type of allergen indicator 106. In some embodiments, the one or more reagent reservoirs may be configured to contain reagents that may be used to process and/or detect numerous types of allergen indicators 106.

At embodiment 5506, module 5410 may include one or more waste reservoirs. In some embodiments, one or more devices may be configured to include one or more waste reservoirs.

At embodiment 5508, module 5410 may include one or more reagent delivery units physically coupled to the one or more detection units. In some embodiments, one or more devices may be configured to include one or more reagent delivery units 116 physically coupled to the one or more detection units 122. In some embodiments, one or more reagent delivery units 116 may be coupled to one or more detection units 122 such that the one or more detection units 122 act to control the one or more reagent delivery units 116. For example, in some embodiments, one or more detection units 122 may control delivery of one or more reagents during processing and/or detection of one or more allergen indicators 106.

At embodiment 5510, module 5410 may include one or more reagent delivery units that include one or more pumps. In some embodiments, one or more devices may be configured to include one or more reagent delivery units 116 that include one or more pumps. Numerous types of pumps may be associated with a delivery unit.

FIG. 56 illustrates alternative embodiments of devices 5400 of FIG. 54. FIG. 56 illustrates example embodiments of module 5420. Additional embodiments may include an embodiment 5602, an embodiment 5604, an embodiment 5606, an embodiment 5608, and/or an embodiment 5610.

At embodiment 5602, module 5420 may include one or more detection units configured to detect the one or more allergen indicators that are associated with one or more allergens that are airborne. In some embodiments, one or more devices may include one or more detection units 122 configured to detect the one or more allergen indicators 106 that are associated with one or more allergens 104 that are airborne. Accordingly, in some embodiments, one or more detection units 122 may be configured to operably associate with the one or more microfluidic chips 108 and to detect one or more airborne allergens 104. For example, in some embodiments, one or more microfluidic chips 108 may be configured to allow one or more air samples 102 to contact the one or more microfluidic chips 108 such that one or more allergen indicators 106 included within the one or more air samples 102 are retained by the one or more microfluidic chips 108. In some embodiments, the one or more air samples 102 may be passed through a filter on which one or more airborne allergen indicators 106 are collected. The collected airborne allergen indicators 106 may then be washed from the filter and caused to pass over an antibody array to which the one or more airborne allergen indicators 106 become immobilized. The immobilized airborne allergen indicators 106 may then be detected through numerous methods that include, but are not limited to, electrical conductivity, immunoassay based methods, and the like. Accordingly, one or more detection units 122 may be configured to detect the one or more airborne allergen indicators 106. In some embodiments, one or more detection units 122 may be configured to operably associate with one or more microfluidic chips 108 such that the one or more detection units 122 facilitate air flow through the one or more microfluidic chips 108 to provide for air sampling. For example, in some embodiments, one or more detection units 122 may include one or more fans to push and/or pull air through one or more operably associated microfluidic chips 108. In some embodiments, one or more detection units 122 may include one or more bellows to push and/or pull air through one or more operably associated microfluidic chips 108. Detection units 122 may be configured in numerous ways to provide for detection of one or more airborne allergen indicators 106.

At embodiment 5604, module 5420 may include one or more detection units configured to detect the one or more allergen indicators that are associated with one or more food products. In some embodiments, one or more devices may include one or more detection units 122 configured to detect the one or more allergen indicators 106 that are associated with one or more food products. In some embodiments, one or more microfluidic chips 108 may be configured to provide for detection of one or more allergens 104 that are associated with one or more food products. Accordingly, in some embodiments, one or more detection units 122 may be configured to operably associate with the one or more microfluidic chips 108 and to detect one or more allergen indicators 106 that are associated with one or more food products. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Numerous methods may be used to detect one or more allergen indicators 106 that are associated with one or more food products. Such methods have been described herein. In addition, other detection methods that have been described may be modified to provide for detection of one or more allergen indicators 106 that are associated with one or more food products. In some embodiments, one or more detection units 122 may be configured to detect one or more polynucleotides, one or more polypeptides, one or more portions of one or more polynucleotides, and/or one or more portions of one or more polypeptides that have a nucleic acid sequence and/or an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, AY839230, or substantially any combination thereof.

At embodiment 5606, module 5420 may include one or more detection units configured to detect the one or more allergen indicators that are associated with one or more weeds, grasses, trees, mites, animals, molds, fungi, insects, rubbers, metals, chemicals, autoallergens, or human autoallergens. In some embodiments, one or more devices may include one or more detection units 122 configured to detect the one or more allergen indicators 106 that are associated with one or more weeds, grasses, trees, mites, animals, molds, fungi, insects, rubbers, metals, chemicals, autoallergens, human autoallergens, or substantially any combination thereof. Numerous allergen indicators 106 are known to be associated with weeds, grasses, trees, mites, animals, molds, fungi, insects, rubbers, metals, chemicals, autoallergens, or human autoallergens. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Accordingly, in some embodiments, one or more microfluidic chips 108 may be configured to process one or more samples 102 and provide for detection of one or more allergen indicators 106. In some embodiments, an allergen indicator 106 may be an allergenic particle. For example, in some embodiments, an allergen indicator 106 may include a complete pollen particle, such as a pollen particle, a spore, a flake of dander, and the like. In some embodiments, an allergen indicator 106 may be a portion of an allergenic particle. For example, in some embodiments, an allergen indicator 106 may include a portion of a pollen particle (e.g., polynucleotides, sporoderm, and the like). In some embodiments, allergen indicators 106 may include polynucleotides that are associated with one or more allergens 104. In some embodiments, allergen indicators 106 may include fragments of polynucleotides that are associated with one or more allergens 104. In some embodiments, allergen indicators 106 may include polypeptides, peptides, and/or proteins that are associated with one or more allergens 104. In some embodiments, allergen indicators 106 may include polysaccharides that are associated with one or more allergens 104. Accordingly, in some embodiments, one or more microfluidic chips 108 may be configured to provide for detection of one or more allergen indicators 106. In some embodiments, one or more detection units 122 may be configured to operably associate with one or more such microfluidic chips 108 and configured to detect one or more allergen indicators 106. Numerous detection methods may be used to detect one or more allergen indicators 106. Such methods have been described herein. In addition, detection methods that have been described may be modified to provide for detection of one or more allergen indicators 106. In some embodiments, one or more detection units 122 may be configured to detect and determine a concentration of one or more allergen indicators 106 that are included within a sample 102. For example, in some embodiments, one or more microfluidic chips 108 may be configured to provide for detection of one or more polynucleotides that are allergen indicators 106 through detection of electrical current produced upon hybridization of the one or more polynucleotides. Accordingly, in such embodiments, the one or more microfluidic chips 108 may be configured to produce an electrical current that is relative to polynucleotide concentration to provide for determination of polynucleotide concentration within one or more samples 102. Numerous configurations may be used in association with one or more allergen indicators 106 to provide for determination of allergen 104 concentration. In some embodiments, one or more microfluidic chips 108 may be configured to provide for identification of one or more allergens 104. For example, in some embodiments, one or more microfluidic chips 108 may include immobilized polynucleotides that selectively hybridize to one or more polynucleotides that are associated with a known allergen indicator 106. Accordingly, hybridization of one or more polynucleotides with the one or more immobilized polynucleotides indicates that a sample 102 includes one or more allergen indicators 106 that correspond to one or more known allergens 104. Accordingly, one or more detection units 122 may be configured to operably associate with such microfluidic chips 108 to provide for specific detection of one or more allergen indicators 106. In some embodiments, microfluidic chips 108 and/or detection units 122 may be configured to determine the identity and concentration of one or more allergen indicators 106 that are included within one or more samples 102.

At embodiment 5608, module 5420 may include one or more detection units configured to detect the one or more allergen indicators with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, one or more devices may include one or more detection units 122 configured to detect one or more allergen indicators 106 with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, filtration, electrophoresis, use of a CCD camera, immunoassay, or substantially any combination thereof. In some embodiments, one or more detection units 122 may be configured to detect one or more allergen indicators 106 that have been processed by one or more microfluidic chips 108. For example, in some embodiments, one or more microfluidic chips 108 may include a window (e.g., a quartz window, a cuvette analog, and/or the like) through which one or more detection units 122 may determine if one or more allergen indicators 106 are present or determine the concentration of one or more allergen indicators 106. In such embodiments, numerous techniques may be used to detect the one or more allergen indicators 106, such as visible light spectroscopy, ultraviolet light spectroscopy, infrared spectroscopy, fluorescence spectroscopy, and the like. Accordingly, in some embodiments, one or more detection units 122 may include circuitry and/or electro-mechanical mechanisms to detect one or more allergen indicators 106 present within one or more microfluidic chips 108 through a window in the one or more microfluidic chips 108. In some embodiments, one or more microfluidic chips 108 may be configured to process one or more samples 102 through use of surface plasmon resonance. In some embodiments, the one or more microfluidic chips 108 may include one or more antibodies, aptamers, proteins, peptides, polynucleotides, and the like, that are bound to a substrate (e.g., a metal film) within the one or more microfluidic chips 108. In some embodiments, such microfluidic chips 108 may include a prism through which one or more detection units 122 may shine light to detect one or more allergen indicators 106 that interact with the one or more antibodies, aptamers, proteins, peptides, polynucleotides, and the like, that are bound to a substrate. In some embodiments, one or more microfluidic chips 108 may include an exposed substrate surface that is configured to operably associate with one or more prisms that are included within one or more detection units 122. In some embodiments, one or more microfluidic chips 108 may include a nuclear magnetic resonance (NMR) probe. In such embodiments, the microfluidic chips 108 may be configured to associate with one or more detection units 122 that accept the NMR probe and are configured to detect one or more allergen indicators 106 through use of NMR spectroscopy. Accordingly, microfluidic chips 108 and detection units 122 may be configured in numerous ways to associate with each other to provide for detection of one or more allergen indicators 106.

In some embodiments, one or more allergen indicators 106 may be detected through use of spectroscopy. Numerous types of spectroscopic methods may be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., Clinical Chemistry, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, one or more allergen indicators 106 may be detected through use of electrochemical detection. In some embodiments, one or more polynucleotides may be detected through electrochemical detection. For example, in some embodiments, a polynucleotide that includes a redox label, such as ferrocene is coupled to a gold electrode. The labeled polynucleotide forms a stem-loop structure that can self-assemble onto a gold electrode by means of facile gold-thiol chemistry. Hybridization of a sample 102 polynucleotide induces a large conformational change in the surface-confined polynucleotide structure, which in turn alters the electron-transfer tunneling distance between the electrode and the redoxable label. The resulting change in electron transfer efficiency may be measured by cyclic voltammetry (Fan et al., Proc. Natl. Acad. Sci., 100:9134-9137 (2003); Wang et al., Anal. Chem., 75:3941-3945 (2003); Singh-Zocchi et al., Proc. Natl. Acad. Sci., 100:7605-7610 (2003)). Such methods may be used to detect messenger ribonucleic acid, genomic deoxyribonucleic acid, and fragments thereof.

In some embodiments, one or more allergen indicators 106 may be detected through use of polynucleotide detection. In some embodiments, one or more detection units 122 may be configured to detect one or more allergen indicators 106 through use of polynucleotide detection. Numerous methods may be used to detect one or more polynucleotides. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described (e.g., U.S. Pat. Nos. 7,118,910 and 6,960,437; herein incorporated by reference). Such methods may be adapted to provide for detection of one or more allergen indicators 106. In some embodiments, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube may be combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Accordingly, polynucleotides that hybridize to one or more allergen indicators 106 may include one or more carbon nanotubes. Methods to utilize carbon nanotubes as probes for nucleic acid interaction have been described (e.g., U.S. Pat. No. 6,821,730; herein incorporated by reference). Numerous other methods based on polynucleotide detection may be used to detect one or more allergen indicators 106.

In some embodiments, one or more allergen indicators 106 may be detected through use of fluorescence anisotropy. Fluorescence anisotropy is based on measuring the steady state polarization of sample 102 fluorescence imaged in a confocal arrangement. A linearly polarized laser excitation source preferentially excites fluorescent target molecules with transition moments aligned parallel to the incident polarization vector. The resultant fluorescence is collected and directed into two channels that measure the intensity of the fluorescence polarized both parallel and perpendicular to that of the excitation beam. With these two measurements, the fluorescence anisotropy, r, can be determined from the equation: r=(Intensity parallel−Intensity perpendicular)/(Intensity parallel+2(Intensity perpendicular)) where the I terms indicate intensity measurements parallel and perpendicular to the incident polarization. Fluorescence anisotropy detection of fluorescent molecules has been described. Accordingly, fluorescence anisotropy may be coupled to numerous fluorescent labels as have been described herein and as have been described.

In some embodiments, one or more allergen indicators 106 may be detected through use of fluorescence resonance energy transfer (FRET). Fluorescence resonance energy transfer refers to an energy transfer mechanism between two fluorescent molecules. A fluorescent donor is excited at its fluorescence excitation wavelength. This excited state is then nonradiatively transferred to a second molecule, the fluorescent acceptor. Fluorescence resonance energy transfer may be used within numerous configurations to detect one or more allergen indicators 106. For example, in some embodiments, an antibody may be labeled with a fluorescent donor and one or more allergen indicators 106 may be labeled with a fluorescent acceptor. Accordingly, such labeled antibodies and allergen indicators 106 may be used within competition assays to detect the presence and/or concentration of one or more allergen indicators 106 in one or more samples 102. Numerous combinations of fluorescent donors and fluorescent acceptors may be used to detect one or more allergen indicators 106. Accordingly, one or more detection units 122 may be configured to emit one or more wavelength of light to excite a fluorescent donor and may be configured to detect one or more wavelength of light emitted by the fluorescent acceptor. Accordingly, in some embodiments, one or more detection units 122 may be configured to accept one or more microfluidic chips 108 that include a quartz window through which fluorescent light may pass to provide for detection of one or more allergen indicators 106 through use of fluorescence resonance energy transfer. Accordingly, fluorescence resonance energy transfer may be used in conjunction with competition assays and/or numerous other types of assays to detect one or more allergen indicators 106.

In some embodiments, one or more allergen indicators 106 may be detected through use of electron transfer. Electron transfer is the process by which an electron moves from an electron donor to an electron acceptor causing the oxidation states of the electron donor and the electron acceptor to change. In some embodiments, electron transfer may occur when an electron is transferred from one or more electron donors to an electrode. In some embodiments, electron transfer may be utilized within competition assays to detect one or more allergen indicators 106. For example, in some embodiments, one or more microfluidic chips 108 may include one or more polynucleotides that may be immobilized on one or more electrodes. The immobilized polynucleotides may be incubated with a reagent mixture that includes sample polynucleotides and polynucleotides that are tagged with an electron donor. Hybridization of the tagged polynucleotides to the immobilized polynucleotides allows the electron donor to transfer an electron to the electrode to produce a detectable signal. Accordingly, a decrease in signal due to the presence of one or more polynucleotides that are allergen indicators 106 in the reagent mixture indicates the presence of an allergen indicator 106 in the sample 102. Such methods may be used in conjunction with polynucleotides, polypeptides, peptides, antibodies, aptamers, and the like. One or more microfluidic chips 108 may be configured to utilize numerous electron transfer based assays to provide for detection of one or more allergen indicators 106 by a detection unit 122.

In some embodiments, one or more allergen indicators 106 may be detected through use of one or more enzyme assays. Numerous enzyme assays may be used to provide for detection of one or more allergen indicators 106. Examples of such enzyme assays include, but are not limited to, beta-galactosidase assays, peroxidase assays, catalase assays, alkaline phosphatase assays, and the like. In some embodiments, enzyme assays may be configured such that an enzyme will catalyze a reaction involving an enzyme substrate that produces a fluorescent product. Accordingly, one or more detection units 122 may be configured to detect fluorescence resulting from the fluorescent product. Enzymes and florescent enzyme substrates are known and are commercially available (e.g., Sigma-Aldrich, St. Louis, Mo.). In some embodiments, enzyme assays may be configured as binding assays that provide for detection of one or more allergen indicators 106. For example, in some embodiments, one or more microfluidic chips 108 may be configured to include-a substrate to which is coupled to one or more antibodies, aptamers, peptides, proteins, polynucleotides, ligands, and the like, that will interact with one or more allergen indicators 106. One or more samples 102 may be passed across the substrate such that one or more allergen indicators 106 present within the one or more samples 102 will interact with the one or more antibodies, aptamers, peptides, proteins, polynucleotides, ligands, and the like, and be immobilized on the substrate. One or more antibodies, aptamers, peptides, proteins, polynucleotides, ligands, and the like, that are labeled with an enzyme may then be passed across the substrate such that the one or more labeled antibodies, aptamers, peptides, proteins, polynucleotides, ligands, and the like, will bind to the one or more immobilized allergen indicators 106. An enzyme substrate may then be introduced to the one or more immobilized enzymes such that the enzymes are able to catalyze a reaction involving the enzyme substrate to produce a fluorescent product. Such assays are often referred to as sandwich assays. Accordingly, one or more detection units 122 may be configured to detect one or more products of enzyme catalysis to provide for detection of one or more allergen indicators 106.

In some embodiments, one or more allergen indicators 106 may be detected through use of electrical conductivity. In some embodiments, one or more microfluidic chips 108 may be configured to process one or more samples 102 and provide for detection of one or more allergen indicators 106 through use of electrical conductivity. In some embodiments, such microfluidic chips 108 may be configured to operably associate with one or more detection units 122 such that the one or more detection units 122 can detect one or more allergen indicators 106 through use of electrical conductivity. In some embodiments, one or more microfluidic chips 108 may be configured to include two or more electrodes that are each coupled to one or more detector polynucleotides. Interaction of an allergen associated polynucleotide, such as hybridization, with two detector polynucleotides that are coupled to two different electrodes will complete an electrical circuit. This completed circuit will provide for the flow of a detectable electrical current between the two electrodes and thereby provide for detection of one or more allergen associated polynucleotides that are allergen indicators 106. In some embodiments, the electrodes may be carbon nanotubes (e.g., U.S. Pat. No. 6,958,216; herein incorporated by reference). In some embodiments, electrodes may include, but are not limited to, one or more conductive metals, such as gold, copper, iron, silver, platinum, and the like; one or more conductive alloys; one or more conductive ceramics; and the like. In some embodiments, electrodes may be selected and configured according to protocols typically used in the computer industry that include, but are not limited to, photolithography, masking, printing, stamping, and the like. In some embodiments, other molecules and complexes that interact with one or more allergen indicators 106 may be used to detect the one or more allergen indicators 106 through use of electrical conductivity. Examples of such molecules and complexes include, but are not limited to, proteins, peptides, antibodies, aptamers, and the like. For example, in some embodiments, two or more antibodies may be immobilized on one or more electrodes such that contact of the two or more antibodies with an allergen indicator 106, such as a spore, a pollen particle, a dander particle, and the like, will complete an electrical circuit and facilitate the production of a detectable electrical current. Accordingly, in some embodiments, one or more microfluidic chips 108 may be configured to include electrical connectors that are able to operably associate with one or more detection units 122 such that the detection units 122 may detect an electrical current that is due to interaction of one or more allergen indicators 106 with two or more electrodes. In some embodiments, one or more detection units 122 may include electrical connectors that provide for operable association of one or more microfluidic chips 108 with the one or more detection units 122. In some embodiments, the one or more detectors are configured for detachable connection to one or more microfluidic chips 108. Microfluidic chips 108 and detection units 122 may be configured in numerous ways to process one or more samples 102 and detect one or more allergen indicators 106.

In some embodiments, one or more allergen indicators 106 may be detected through use of isoelectric focusing. In some embodiments, one or more microfluidic chips 108 may be configured to process one or more samples 102 and provide for detection of one or more allergen indicators 106 through use of isoelectric focusing. In some embodiments, native isoelectric focusing may be utilized to process and/or detect one or more allergen indicators 106. In some embodiments, denaturing isoelectric focusing may be utilized to process and/or detect one or more allergen indicators 106. Methods to construct microfluidic channels that may be used for isoelectric focusing have been reported (e.g., Macounova et al., Anal Chem., 73:1627-1633 (2001); Macounova et al., Anal Chem., 72:3745-3751 (2000); Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). In some embodiments, one or more microfluidic chips 108 may be configured to process one or more samples 102 through use of methods that include isoelectric focusing. In some embodiments, one or more detection units 122 may be configured to operably associate with one or more such microfluidic chips 108 such that the one or more detection units 122 can be used to detect one or more allergen indicators 106 that have been focused within one or more microfluidic channels of the one or more microfluidic chips 108. In some embodiments, one or more detection units 122 may be configured to include one or more CCD cameras that can be used to detect one or more allergen indicators 106. In some embodiments, one or more detection units 122 may be configured to include one or more spectrometers that can be used to detect one or more allergen indicators 106. Numerous types of spectrometers may be utilized to detect one or more allergen indicators 106 following isoelectric focusing. In some embodiments, one or more detection units 122 may be configured to utilize refractive index to detect one or more allergen indicators 106. In some embodiments, one or more microfluidic chips 108 may be configured to combine one or more samples 102 with one or more reagent mixtures that include one or more binding molecules and/or binding complexes that bind to one or more allergen indicators 106 that may be present within the one or more samples 102 to form an allergen indicator-binding molecule/binding complex. Examples of such binding molecules and/or binding complexes that bind to one or more allergen indicators 106 include, but are not limited to, antibodies, aptamers, peptides, proteins, polynucleotides, and the like. In some embodiments, an allergen indicator-binding molecule/binding complex may be processed through use of isoelectric focusing and then detected with one or more detection units 122. In some embodiments, one or more binding molecules and/or one or more binding complexes may include a label. Numerous labels may be used and include, but are not limited to, radioactive labels, fluorescent labels, colorimetric labels, spin labels, fluorescent labels, and the like. Accordingly, in some embodiments, an allergen indicator-binding molecule (labeled)/binding complex (labeled) may be processed through use of isoelectric focusing and then detected with one or more detection units 122 that are configured to detect the one or more labels. Microfluidic chips 108 and detection units 122 may be configured in numerous ways to process one or more samples 102 and detect one or more allergen indicators 106 though use of isoelectric focusing.

In some embodiments, one or more allergen indicators 106 may be detected through use of chromatographic methodology alone or in combination with additional processing and/or detection methods. In some embodiments, one or more microfluidic chips 108 may be configured to process one or more samples 102 and provide for detection of one or more allergen indicators 106 through use of chromatographic methods. Accordingly, in some embodiments, one or more detection units 122 may be configured to operably associate with the one or more microfluidic chips 108 and detect one or more allergen indicators 106 that were processed through use of chromatographic methods. In some embodiments, the one or more detection units 122 may be configured to operably associate with one or more microfluidic chips 108 and supply solvents and other reagents to the one or more microfluidic chips 108. For example, in some embodiments, one or more detection units 122 may include pumps and solvent/buffer reservoirs that are configured to supply solvent/buffer flow through chromatographic media (e.g., a chromatographic column) that is operably associated with one or more microfluidic chips 108. In some embodiments, one or more detection units 122 may be configured to operably associate with one or more microfluidic chips 108 and be configured to utilize one or more methods to detect one or more allergen indicators 106. Numerous types of chromatographic methods and media may be used to process one or more samples 102 and provide for detection of one or more allergen indicators 106. Chromatographic methods include, but are not limited to, low pressure liquid chromatography, high pressure liquid chromatography (HPLC), microcapillary low pressure liquid chromatography, microcapillary high pressure liquid chromatography, ion exchange chromatography, affinity chromatography, gel filtration chromatography, size exclusion chromatography, thin layer chromatography, paper chromatography, gas chromatography, and the like. In some embodiments, one or more microfluidic chips 108 may be configured to include one or more high pressure microcapillary columns. Methods that may be used to prepare microcapillary HPLC columns (e.g., columns with a 100 micrometer-500 micrometer inside diameter) have been described (e.g., Davis et al., Methods, A Companion to Methods in Enzymology, 6: Micromethods for Protein Structure Analysis, ed. by John E. Shively, Academic Press, Inc., San Diego, 304-314 (1994); Swiderek et al., Trace Structural Analysis of Proteins. Methods of Enzymology, ed. by Barry L. Karger & William S. Hancock, Spectrum, Publisher Services, 271, Chap. 3, 68-86 (1996); Moritz and Simpson, J. Chromatogr., 599:119-130 (1992)). In some embodiments, one or more microfluidic chips 108 may be configured to include one or more affinity columns. Methods to prepare affinity columns have been described. Briefly, a biotinylated site may be engineered into a polypeptide, peptide, aptamer, antibody, or the like. The biotinylated protein may then be incubated with avidin coated polystyrene beads and slurried in Tris buffer. The slurry may then be packed into a capillary affinity column through use of high pressure packing. Affinity columns may be prepared that may include one or more molecules and/or complexes that interact with one or more allergen indicators 106. For example, in some embodiments, one or more aptamers that bind to one or more allergen indicators 106 may be used to construct an affinity column. Accordingly, numerous chromatographic methods may be used alone, or in combination with additional methods, to process and detect one or more allergen indicators 106. Numerous detection methods may be used in combination with numerous types of chromatographic methods. Accordingly, one or more detection units 122 may be configured to utilize numerous detection methods to detect one or more allergen indicators 106 that are processed through use of one or more chromatographic methods. Examples of such detection methods include, but are not limited to, conductivity detection, use of ion-specific electrodes, refractive index detection, colorimetric detection, radiological detection, detection by retention time, detection through use of elution conditions, spectroscopy, and the like. For example, in some embodiments, one or more chromatographic markers may be added to one or more samples 102 prior to the samples 102 being applied to a chromatographic column. One or more detection units 122 that are operably associated with the chromatographic column may be configured to detect the one or more chromatographic markers and use the elution time and/or position of the chromatographic markers as a calibration tool for use in detecting one or more allergen indicators 106 if those allergen indicators 106 are eluted from the chromatographic column. In some embodiments, one or more detection units 122 may be configured to utilize one or more ion-specific electrodes to detect one or more allergen indicators 106. For example, such electrodes may be used to detect allergen indicators 106 that include, but are not limited to, metals (e.g., tin, silver, nickel, cobalt, chromate), nitrates, nitrites, sulfites, and the like. Such allergen indicators 106 are often associated with food, beverages, clothing, jewelry, and the like. Accordingly, chromatographic methods may be used in combination with additional methods and in combination with numerous types of detection methods.

In some embodiments, one or more allergen indicators 106 may be detected through use of immunoprecipitation. In some embodiments, one or more detection units 122 may be configured to detect one or more allergen indicators 106 through use of immunoprecipitation. In some embodiments, immunoprecipitation may be utilized in combination with additional processing and/or detection methods to detect one or more allergen indicators 106. In some embodiments, one or more microfluidic chips 108 may be configured to process one or more samples 102 through use of immunoprecipitation. For example, in some embodiments, one or more samples 102 may be combined with one or more antibodies that bind to one or more allergen indicators 106 to form one or more antibody-allergen indicator 106 complexes. An insoluble form of an antibody binding constituent, such as protein A (e.g., protein A-sepharose bead, protein A-magnetic bead, protein A-ferrous bead, protein A-non-ferrous bead, and the like), Protein G, a second antibody, an aptamer, and the like, may then be mixed with the antibody-allergen indicator 106 complex such that the insoluble antibody binding constituent binds to the antibody-allergen indicator 106 complex and provides for precipitation of the antibody-allergen indicator 106 complex. Such complexes may be separated from other sample 102 components to provide for detection of one or more allergen indicators 106. For example, in some embodiments, sample 102 components may be washed away from the precipitated antibody-allergen indicator 106 complexes. In some embodiments, one or more microfluidic chips 108 that are configured for immunoprecipitation may be operably associated with one or more centrifugation units 118 to assist in precipitating one or more antibody-allergen indicator 106 complexes. In some embodiments, aptamers (polypeptide and/or polynucleotide) may be used in combination with antibodies or in place of antibodies. Accordingly, one or more detection units 122 may be configured to detect one or more allergen indicators 106 through use of numerous detection methods in combination with immunoprecipitation based methods.

In some embodiments, one or more allergen indicators 106 may be detected through use of immunoseparation. In some embodiments, one or more detection units 122 may be configured to detect one or more allergen indicators 106 through use of immunoseparation. In some embodiments, immunoseparation may be utilized in combination with additional processing and/or detection methods to detect one or more allergen indicators 106. In some embodiments, one or more microfluidic chips 108 may be configured to process one or more samples 102 through use of immunoseparation. For example, in some embodiments, one or more samples 102 may be combined with one or more antibodies that bind to one or more allergen indicators 106 to form one or more antibody-allergen indicator 106 complexes. An antibody binding constituent may be added that binds to the antibody-allergen complex.

Examples of such antibody binding constituents that may be used alone or in combination include, but are not limited to, protein A (e.g., protein A-sepharose bead, protein A-magnetic bead, protein A-ferrous bead, protein A-non-ferrous bead, and the like), Protein G, a second antibody, an aptamer, and the like. Such antibody binding constituents may be mixed with an antibody-allergen indicator 106 complex such that the antibody binding constituent binds to the antibody-allergen indicator 106 complex and provides for separation of the antibody-allergen indicator 106 complex. In some embodiments, the antibody binding constituent may include a tag that allows the antibody binding constituent and complexes that include the antibody binding constituent to be separated from other components in one or more samples 102. In some embodiments, the antibody binding constituent may include a ferrous material. Accordingly, antibody-allergen indicator 106 complexes may be separated from other sample 102 components through use of a magnet, such as an electromagnet. In some embodiments, an antibody binding constituent may include a non-ferrous metal. Accordingly, antibody-allergen indicator 106 complexes may be separated from other sample 102 components through use of an eddy current to direct movement of one or more antibody-allergen indicator 106 complexes. In some embodiments, two or more forms of an antibody binding constituents may be used to detect one or more allergen indicators 106. For example, in some embodiments, a first antibody binding constituent may be coupled to a ferrous material and a second antibody binding constituent may be coupled to a non-ferrous material. Accordingly, the first antibody binding constituent and the second antibody binding constituent may be mixed with antibody-allergen indicator 106 complexes such that the first antibody binding constituent and the second antibody binding constituent bind to antibody-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more antibodies that bind to one or more allergen indicators 106 to form one or more antibody-allergen indicator 106 complexes. In some embodiments, the one or more antibodies may include one or more tags that provide for separation of the antibody-allergen indicator 106 complexes. For example, in some embodiments, an antibody may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with immunoseparation based methods. In some embodiments, aptamers (polypeptide and/or polynucleotide) may be used in combination with antibodies or in place of antibodies.

In some embodiments, one or more allergen indicators 106 may be detected through use of aptamer binding. In some embodiments, one or more detection units 122 may be configured to detect one or more allergen indicators 106 through use of aptamer binding. In some embodiments, aptamer binding may be utilized in combination with additional processing and/or detection methods to detect one or more allergen indicators 106. In some embodiments, one or more microfluidic chips 108 may be configured to process one or more samples 102 through use of aptamer binding. For example, in some embodiments, one or more samples 102 may be combined with one or more aptamers that bind to one or more allergen indicators 106 to form one or more aptamer-allergen indicator 106 complexes. In some embodiments, aptamer binding constituents may be added that bind to the aptamer-allergen complex. Numerous aptamer binding constituents may be utilized. For example, in some embodiments, one or more aptamers may include one or more tags to which one or more aptamer binding constituents may bind. Examples of such tags include, but are not limited to, biotin, avidin, streptavidin, histidine tags, nickel tags, ferrous tags, non-ferrous tags, and the like. In some embodiments, one or more tags may be conjugated with a label to provide for detection of one or more complexes. Examples of such tag-label conjugates include, but are not limited to, Texas red conjugated avidin, alkaline phosphatase conjugated avidin, CY2 conjugated-avidin, CY3 conjugated avidin, CY3.5 conjugated avidin, CY5 conjugated avidin, CY5.5 conjugated avidin, fluorescein conjugated avidin, glucose oxidase conjugated avidin, peroxidase conjugated avidin, rhodamine conjugated avidin, agarose conjugated anti-protein A, alkaline phosphatase conjugated protein A, anti-protein A, fluorescein conjugated protein A, IRDye® 800 conjugated protein A, peroxidase conjugated protein A, sepharose protein A, alkaline phosphatase conjugated streptavidin, AMCA conjugated streptavidin, anti-streptavidin (*Streptomyces avidinii*) (rabbit) IgG Fraction, beta-galactosidase conjugated streptavidin, CY2 conjugated streptavidin, CY3 conjugated streptavidin, CY3.5 conjugated streptavidin, CY5 conjugated streptavidin, CY5.5 conjugated streptavidin, fluorescein conjugated streptavidin, IRDye® 700DX conjugated streptavidin, IRDye® 800 conjugated streptavidin, IRDye® 800CW conjugated streptavidin, peroxidase conjugated streptavidin, phycoerythrin conjugated streptavidin, rhodamine conjugated streptavidin, Texas red conjugated streptavidin, alkaline phosphatase conjugated biotin, anti-biotin (rabbit) IgG fraction, beta-galactosidase conjugated biotin, glucose oxidase conjugated biotin, peroxidase conjugated biotin, alkaline phosphatase conjugated protein G, anti-protein G (rabbit) Agarose conjugated, anti-protein G (Rabbit) IgG fraction, fluorescein conjugated protein G, IRDye® 800 conjugated protein G, peroxidase conjugated protein G, and the like. Many such labeled tags are commercially available (e.g., Rockland Immunochemicals, Inc., Gilbertsville, Pa.). Such labels may also be used in association with other methods to process and detect one or more allergen indicators 106. Aptamer binding constituents may be mixed with an aptamer-allergen indicator 106 complex such that the aptamer binding constituent binds to the aptamer-allergen indicator 106 complex and provides for separation of the aptamer-allergen indicator 106 complex. In some embodiments, the aptamer binding constituent may include a tag that allows the aptamer binding constituent and complexes that include the aptamer binding constituent to be separated from other components in one or more samples 102. In some embodiments, the aptamer binding constituent may include a ferrous material. Accordingly, aptamer-allergen indicator 106 complexes may be separated from other sample 102 components through use of a magnet, such as an electromagnet. In some embodiments, an aptamer binding constituent may include a non-ferrous metal. Accordingly, aptamer-allergen indicator 106 complexes may be separated from other sample 102 components through use of an eddy current to direct movement of one or more aptamer-allergen indicator 106 complexes. In some embodiments, two or more forms of aptamer binding constituents may be used to detect one or more allergen indicators 106. For example, in some embodiments, a first aptamer binding constituent may be coupled to a ferrous material and a second aptamer binding constituent may be coupled to a non-ferrous material. Accordingly, the first aptamer binding constituent and the second aptamer binding constituent may be mixed with aptamer-allergen indicator 106 complexes such that the first aptamer binding constituent and the second aptamer binding constituent bind to aptamer-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more aptamers that bind to one or more allergen indicators 106 to form one or more aptamer-allergen indicator 106 complexes. In some embodiments, the one or more aptamer may include one or more tags that provide for separation of the aptamer-allergen indicator 106 complexes. For example, in some embodiments, an aptamer may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with aptamer binding based methods. In some embodiments, antibodies may be used in combination with aptamers or in place of aptamers.

In some embodiments, one or more allergen indicators 106 may be detected through use of electrophoresis. In some embodiments, one or more microfluidic chips 108 may be configured to process one or more samples 102 through use of electrophoresis. In some embodiments, such microfluidic chips 108 may be configured to operably associate with one or more detection units 122. Accordingly, in some embodiments, one or more detection units 122 may be configured to operably associate with one or more microfluidic chips 108 and detect one or more allergen indicators 106 that were processed through use of electrophoresis. Numerous electrophoretic methods may be utilized to provide for detection of one or more allergen indicators 106. Examples of such electrophoretic methods include, but are not limited to, capillary electrophoresis, one-dimensional electrophoresis, two-dimensional electrophoresis, native electrophoresis, denaturing electrophoresis, polyacrylamide gel electrophoresis, agarose gel electrophoresis, and the like. Numerous detection methods may be used in combination with one or more electrophoretic methods to detect one or more allergen indicators 106. In some embodiments, one or more allergen indicators 106 may be detected according to the position to which the one or more allergen indicators 106 migrate within an electrophoretic field (e.g., a capillary and/or a gel). In some embodiments, the position of one or more allergen indicators 106 may be compared to one or more standards. For example, in some embodiments, one or more samples 102 may be mixed with one or more molecular weight markers prior to gel electrophoresis. The one or more samples 102, that include the one or more molecular weight markers, may be subjected to electrophoresis and then the gel may be stained. In such embodiments, the molecular weight markers may be used as a reference to detect one or more allergen indicators 106 present within the one or more samples 102. In some embodiments, one or more components that are known to be present within one or more samples 102 may be used as a reference to detect one or more allergen indicators 106 present within the one or more samples 102. In some embodiments, gel shift assays may be used to detect one or more allergen indicators 106. For example, in some embodiments, a sample 102 (e.g., a single sample 102 or combination of multiple samples 102) may be split into a first sample 102 and a second sample 102. The first sample 102 may be mixed with an antibody, aptamer, ligand, or other molecule and/or complex that binds to the one or more allergen indicators 106. The first and second samples 102 may then be subjected to electrophoresis. The gels corresponding to the first sample 102 and the second sample 102 may then be analyzed to determine if one or more allergen indicators 106 are present within the one or more samples 102. Microfluidic chips 108 and detection units 122 may be configured in numerous ways to process and detect one or more allergen indicators 106 through use of electrophoresis.

In some embodiments, one or more allergen indicators 106 may be detected through use of one or more charge-coupled device (CCD) cameras. In some embodiments, one or more detection units 122 that include one or more CCD cameras may be configured to operably associate with one or more microfluidic chips 108. Such detection units 122 may be utilized in combination with numerous processing methods. Examples of such methods include, but are not limited to, electrophoresis; competition assays; methods based on polynucleotide interaction, protein interaction, peptide interaction, antibody interaction, aptamer interaction, immunoprecipitation, immunoseparation, and the like. For example, in some embodiments, one or more microfluidic chips 108 may be configured to process one or more samples 102 through use of immunoprecipitation. In some embodiments, one or more antibodies may be conjugated to a fluorescent label such that binding of one or more labeled antibodies to one or more allergen indicators 106 included within one or more samples 102 will form a fluorescently labeled antibody-allergen indicator 106 complex. One or more insoluble allergen indicator 106 binding constituents, such as a sepharose bead that includes an antibody or aptamer that binds to the one or more allergen indicators 106, may be bound to the fluorescently labeled antibody-allergen indicator 106 complex and used to precipitate the complex. One or more detection units 122 that include a CCD camera that is configured to detect fluorescent emission from the one or more fluorescent labels may be used to detect the one or more allergen indicators 106. In some embodiments, one or more CCD cameras may be configured to utilize dark frame subtraction to cancel background and increase sensitivity of the camera. In some embodiments, one or more detection units 122 may include one or more filters to select and/or filter wavelengths of energy that can be detected by one or more CCD cameras (e.g., U.S. Pat. No. 3,971,065; herein incorporated by reference). In some embodiments, one or more detection units 122 may include polarized lenses. One or more detection units 122 may be configured in numerous ways to utilize one or more CCD cameras to detect one or more allergen indicators 106.

In some embodiments, one or more allergen indicators 106 may be detected through use of immunoassay. In some embodiments, one or more microfluidic chips 108 may be configured to process one or more samples 102 through use of immunoassay. In some embodiments, one or more detection units 122 may be configured to operably associate with one or more such microfluidic chips 108 and to detect one or more allergen indicators 106 associated with the use of immunoassay. Numerous types of detection methods may be used in combination with immunoassay based methods. In some embodiments, a label may be used within one or more immunoassays that may be detected by one or more detection units 122. Examples of such labels include, but are not limited to, fluorescent labels, spin labels, fluorescence resonance energy transfer labels, radiolabels, electrochemiluminescent labels (e.g., U.S. Pat. Nos. 5,093,268; 6,090,545; herein incorporated by reference), and the like. In some embodiments, electrical conductivity may be used in combination with immunoassay based methods.

At embodiment 5610, module 5420 may include one or more detection units that are calibrated for an individual. In some embodiments, one or more devices may include one or more detection units 122 that are calibrated for an individual. In some embodiments, one or more detection units 122 may be calibrated to detect one or more specific allergens 104 and/or allergen indicators 106 that produce an allergic response by an individual. For example, in some embodiments, one or more detection units 122 may be calibrated to detect peanuts and/or peanut associated products for an individual who is allergic to peanuts. In some embodiments, one or more detection units 122 may be calibrated to detect different concentrations of allergen indicators 106. For example, in some embodiments, an individual may produce an allergic response if exposed to an allergen 104 at a concentration that is above a certain level. Accordingly, in some embodiments, a detection unit 122 may be calibrated to detect one or more concentrations of one or more allergen indicators 106 that produce an allergic response within an individual.

FIG. 57 illustrates alternative embodiments of devices 5400 of FIG. 54. FIG. 57 illustrates example embodiments of module 5430. Additional embodiments may include an embodiment 5702, an embodiment 5704, an embodiment 5706, an embodiment 5708, an embodiment 5710, and/or an embodiment 5712.

At embodiment 5702, module 5430 may include one or more display units that are passive display units. In some embodiments, one or more devices may include one or more display units 124 that are passive display units 124. In some embodiments, one or more display units 124 may include one or more liquid crystal displays (LCD). Methods to construct passive displays have been described (e.g., U.S. Pat. Nos. 4,807,967; 4,729,636: 4,436,378; 4,257,041; herein incorporated by reference).

At embodiment 5704, module 5430 may include one or more display units that are active display units. In some embodiments, one or more devices may include one or more display units 124 that are active display units 124. Numerous active display units 124 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), wide ultra extended graphics array (WUXGA).

At embodiment 5706, module 5430 may include one or more display units that indicate a presence or an absence of one or more allergens within one or more samples. In some embodiments, one or more devices may include one or more display units 124 that indicate a presence or an absence of one or more allergens 104 within one or more samples 102. In some embodiments, one or more display units 124 may use a colorimetric message to indicate a presence or an absence of one or more allergen indicators 106 within one or more samples 102. For example, in some embodiments, one or more display units 124 may display a green light if one or more allergen indicators 106 are not found within one or more samples 102 and a red light if one or more allergen indicators 106 are found within one or more samples 102. In some embodiments, one or more display units 124 may use a pictographic message to indicate a presence or an absence of one or more allergen indicators 106 within one or more samples 102. For example, in some embodiments, one or more display units 124 may display a smiley face if one or more allergen indicators 106 are not found within one or more samples 102 and a frowny face if one or more allergen indicators 106 are found within one or more samples 102. In some embodiments, one or more display units 124 may use a typographical message to indicate a presence or an absence of one or more allergen indicators 106 within one or more samples 102. For example, in some embodiments, one or more display units 124 may display an "Allergen Not Present" message if one or more allergen indicators 106 are not found within one or more samples 102 and an "Allergen Present" message if one or more allergen indicators 106 are found within one or more samples 102. Such messages may be displayed in numerous languages. In some embodiments, one or more display units 124 may display one or more messages in multiple formats. For example, in some embodiments, one or more messages may be displayed in colored text.

At embodiment 5708, module 5430 may include one or more display units that indicate an identity of one or more allergens present within one or more samples. In some embodiments, one or more devices may include one or more display units 124 that indicate an identity of one or more allergens 104 present within one or more samples 102. In some embodiments, one or more display units 124 may be operably associated with one or more microfluidic chips 108 that are configured to identify one or more allergen indicators 106. Accordingly, in some embodiments, one or more display units 124 may be configured to display the identity of one or more allergens 104 that are present and/or absent from one or more samples 102. For example, in some embodiments, a display unit 124 may be configured to indicate a presence or an absence of beta-lactoglobulin in a food product.

At embodiment 5710, module 5430 may include one or more display units that indicate one or more concentrations of one or more allergens within one or more samples. In some embodiments, one or more devices may include one or more display units 124 that indicate one or more concentrations of one or more allergens 104 within one or more samples 102. Concentration may be displayed in numerous formats. For example, in some embodiments, concentration may be expressed numerically (e.g., mass allergen indicator 106 per volume sample 102 (e.g., milligrams per milliliter), mass allergen indicator 106 per mass sample 102 (e.g., milligrams per milligram of sample), parts per million, and the like). In some embodiments, concentration may be expressed graphically. For example, in some embodiments, one or more display units 124 may include a display having a gray scale on which the concentration of one or more allergen indicators 106 that are present within one or more samples 102 may be indicated (e.g., higher concentrations of one or more allergens 104 may be displayed as dark gray while lower concentrations of one or more allergens 104 may be displayed as light gray). In some embodiments, one or more display units 124 may include a display having a color scale on which the concentration of one or more allergen indicators 106 that are present within one or more samples 102 may be indicated (e.g., low concentrations of one or more allergen indicators 106 may be indicated by a green light, intermediate concentrations of one or more allergen indicators 106 may be indicated by a yellow light, high concentrations of one or more allergen indicators 106 may be indicated by a red light). In some embodiments, one or more display units 124 may be calibrated to an individual. For example, in such embodiments, an individual may use the display to obtain an immediate reading that will indicate if a food product contains a dangerous level of one or more allergens 104.

At embodiment 5712, module 5430 may include one or more display units that are calibrated for an individual. In some embodiments, one or more devices may include one or more display units 124 that are calibrated for an individual. In some embodiments, one or more display units 124 may be calibrated to display whether one or more allergens 104, and/or allergen indicators 106, that are specific to an individual are present or absent within one or more samples 102. For example, in some embodiments, one or more display units 124 may be configured to display whether one or more samples 102 contain shellfish associated allergens 104 for an individual known to be allergic to shellfish. In some embodiments, one or more display units 124 may be calibrated to indicate safe and/or unsafe concentrations of one or more allergens 104 within one or more samples 102 for an individual.

Figure 58:
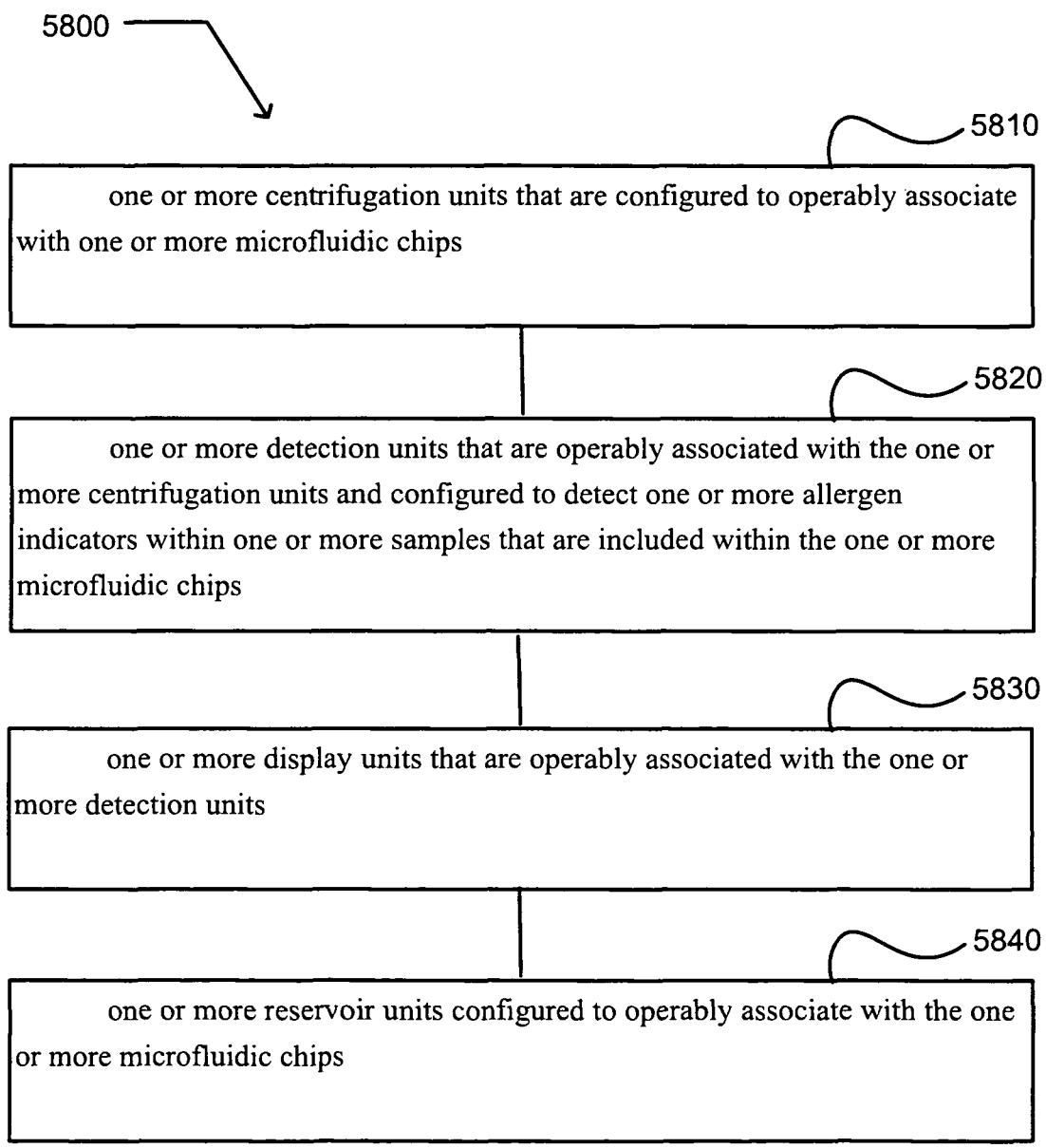
FIG. 58 illustrates an example device 5800 in which embodiments may be implemented.

FIG. 58 illustrates devices 5800 that may be configured for analysis of one or more allergens 104. In FIG. 58, discussion and explanation may be provided with respect to use of one or more devices within the above-described example of FIG. 1, and/or with respect to other examples and contexts. However, it should be understood that the devices may be configured in a number of other environments and contexts, and/or utilized within modified versions of FIG. 1. Also, although the devices are presented in the configuration(s) illustrated, it should be understood that the devices may be configured in numerous orientations.

The device 5800 includes module 5810 that includes one or more centrifugation units that are configured to operably associate with one or more microfluidic chips. In some embodiments, module 5810 may include one or more centrifugation units configured to centrifuge the one or more microfluidic chips that are operably associated with the one or more centrifugation units. In some embodiments, module 5810 may include one or more centrifugation units configured to provide for chromatographic separation of the one or more samples. In some embodiments, module 5810 may include one or more centrifugation units configured for polynucleotide extraction from the one or more samples. In some embodiments, module 5810 may include one or more centrifugation units configured to provide for gradient centrifugation of the one or more samples.

The device 5800 includes module 5820 that includes one or more detection units that are operably associated with the one or more centrifugation units and configured to detect one or more allergen indicators within one or more samples that are included within the one or more microfluidic chips. In some embodiments, module 5820 may include one or more detection units configured to detect the one or more allergen indicators that are associated with one or more allergens that are airborne. In some embodiments, module 5820 may include one or more detection units configured to detect the one or more allergen indicators that are associated with one or more food products. In some embodiments, module 5820 may include one or more detection units configured to detect the one or more allergen indicators that are associated with one or more weeds, grasses, trees, mites, animals, molds, fungi, insects, rubbers, metals, chemicals, autoallergens, or human autoallergens. In some embodiments, module 5820 may include one or more detection units configured to detect one or more allergens with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, module 5820 may include one or more detection units that are calibrated for an individual.

The device 5800 may optionally include module 5830 that includes one or more display units that are operably associated with the one or more detection units. In some embodiments, module 5830 may include one or more display units that are passive display units. In some embodiments, module 5830 may include one or more display units that are active display units. In some embodiments, module 5830 may include one or more display units that indicate a presence or an absence of one or more allergens within the one or more samples. In some embodiments, module 5830 may include one or more display units that indicate an identity of one or more allergens present within the one or more samples. In some embodiments, module 5830 may include one or more display units that indicate one or more concentrations of one or more allergens within the one or more samples. In some embodiments, module 5830 may include one or more display units that are calibrated for an individual.

The device 5800 may optionally include module 5840 that includes one or more reservoir units configured to operably associate with the one or more microfluidic chips. In some embodiments, module 5840 may include one or more reservoir units that are configured for containing one or more reagents. In some embodiments, module 5840 may include one or more reservoir units that are configured as one or more waste reservoirs.

FIG. 59 illustrates alternative embodiments of devices 5800 of FIG. 58. FIG. 59 illustrates example embodiments of module 5810. Additional embodiments may include an embodiment 5902, an embodiment 5904, an embodiment 5906, and/or an embodiment 5908.

At embodiment 5902, module 5810 may include one or more centrifugation units configured to centrifuge the one or more microfluidic chips that are operably associated with the one or more centrifugation units. In some embodiments, one or more devices may include one or more centrifugation units 118 configured to centrifuge the one or more microfluidic chips 108 that are operably associated with the one or more centrifugation units 118. In some embodiments, one or more centrifugation units 118 may be configured to detachably associate with one or more microfluidic chips 108. For example, in some embodiments, a centrifugation unit 118 may include one or more centrifuge drives that are configured to detachably associate with one or more centrifuge rotors that are included within one or more microfluidic chips 108. In some embodiments, such centrifuge drives may magnetically couple with the one or more centrifuge rotors. In some embodiments, such centrifuge drives may physically couple with the one or more centrifuge rotors. In some embodiments, one or more centrifugation units 118 may be configured to centrifuge an entire microfluidic chip 108. For example, in some embodiments, a microfluidic chip 108 may be configured to associate with one or more centrifugation units 118 such that the microfluidic chip 108 is subjected to centrifugal force. In some embodiments, such a microfluidic chip 108 may be configured in a manner that resembles a compact disc. Accordingly, in some embodiments, a centrifugation unit 118 may be configured in a manner that resembles a compact disc player.

At embodiment 5904, module 5810 may include one or more centrifugation units configured to provide for chromatographic separation of the one or more samples. In some embodiments, one or more devices may include one or more centrifugation units 118 configured to provide for chromatographic separation of the one or more samples 102. For example, in some embodiments, one or more centrifugation units 118 may be configured to centrifuge one or more samples 102 through one or more chromatographic columns that are associated with one or more microfluidic chips 108. In some embodiments, such microfluidic chips 108 may be coupled to one or more reagent reservoirs such that one or more fluids may be passed through one or more chromatographic columns through use of centrifugation. For example, in some embodiments, chromatographic separation may be used to separate one or more polynucleotides from one or more samples 102 through use of chromatographic media that is configured as a spin column.

At embodiment 5906, module 5810 may include one or more centrifugation units configured for polynucleotide extraction from the one or more samples. In some embodiments, one or more devices may include one or more centrifugation units 118 configured to provide for polynucleotide extraction from the one or more samples 102. For example, a microfluidic chip 108 may be configured to utilize alkaline lysis (e.g., miniprep procedure) to extract polynucleotides from one or more samples 102. In such examples, a microfluidic chip 108 may include a chamber where one or more samples 102 may be combined with a lysis buffer (e.g., sodium hydroxide/sodium dodecyl sulfate) to solubilize the one or more samples 102. The solubilized samples 102 may then be combined with an agent that precipitates the sodium dodecyl sulfate (e.g., potassium acetate) and the microfluidic chip 108 may be centrifuged through use of a centrifugation unit 118. The supernatant may then be transferred to another chamber where it may be chemically extracted (e.g., phenol/chloroform). The supernatant may then be transferred to another chamber and combined with an agent to precipitate polynucleotides present within the supernatant (e.g., alcohol). The microfluidic chip 108 may then be centrifuged to pellet any polynucleotides and then the supernatant may be drawn off and the pellet resuspended to facilitate analysis of the polynucleotides. In some embodiments, one or more samples 102 may be combined with a lysis buffer (e.g., sodium hydroxide/sodium dodecyl sulfate) to solubilize the one or more samples 102. The solubilized samples 102 may then be combined with an agent that precipitates the sodium dodecyl sulfate (e.g., potassium acetate) and the microfluidic chip 108 may be centrifuged through use of a centrifugation unit 118. The supernatant may then be applied to a chromatographic column. One or more wash buffers may then be centrifuged through the column to further separate the one or more polynucleotides. An elution buffer may then be centrifuged through the column to elute the one or more polynucleotides from the column. The elution buffer that includes the one or more polynucleotides may be combined with an agent (e.g., alcohol) to precipitate any polynucleotides present within the elution buffer. The microfluidic chip 108 may then be centrifuged to pellet any polynucleotides.

At embodiment 5908, module 5810 may include one or more centrifugation units configured to provide for gradient centrifugation of the one or more samples. In some embodiments, one or more devices may include one or more centrifugation units 118 configured to provide for gradient centrifugation of the one or more samples 102. In some embodiments, one or more centrifugation units 118 may be configured to provide for density gradient centrifugation. In some embodiments, one or more centrifugation units 118 may be configured to provide for velocity gradient centrifugation.

FIG. 60 illustrates alternative embodiments of devices 5800 of FIG. 58. FIG. 60 illustrates example embodiments of module 5820. Additional embodiments may include an embodiment 6002, an embodiment 6004, an embodiment 6006, an embodiment 6008, and/or an embodiment 6010.

At embodiment 6002, module 5820 may include one or more detection units configured to detect the one or more allergen indicators that are associated with one or more allergens that are airborne. In some embodiments, one or more devices may include one or more detection units 122 configured to detect the one or more allergen indicators 106 that are associated with one or more allergens 104 that are airborne. Accordingly, in some embodiments, one or more detection units 122 may be configured to operably associate with the one or more microfluidic chips 108 and to detect one or more airborne allergens 104. For example, in some embodiments, one or more microfluidic chips 108 may be configured to allow one or more air samples 102 to contact the one or more microfluidic chips 108 such that one or more allergen indicators 106 included within the one or more air samples 102 are retained by the one or more microfluidic chips 108. In some embodiments, the one or more air samples 102 may be passed through a filter on which one or more airborne allergen indicators 106 are collected. The collected airborne allergen indicators 106 may then be washed from the filter and caused to pass over an antibody array to which the one or more airborne allergen indicators 106 become immobilized. The immobilized airborne allergen indicators 106 may then be detected through numerous methods that include, but are not limited to, electrical conductivity, immunoassay based methods, and the like. Accordingly, one or more detection units 122 may be configured to detect the one or more airborne allergen indicators 106. In some embodiments, one or more detection units 122 may be configured to operably associate with one or more microfluidic chips 108 such that the one or more detection units 122 facilitate air flow through the one or more microfluidic chips 108 to provide for air sampling. For example, in some embodiments, one or more detection units 122 may include one or more fans to push and/or pull air through one or more operably associated microfluidic chips 108. In some embodiments, one or more detection units 122 may include one or more bellows to push and/or pull air through-one or more operably associated microfluidic chips 108. Detection units 122 may be configured in numerous ways to provide for detection of one or more airborne allergen indicators 106.

At embodiment 6004, module 5820 may include one or more detection units configured to detect the one or more allergen indicators that are associated with one or more food products. In some embodiments, one or more devices may include one or more detection units 122 configured to detect the one or more allergen indicators 106 that are associated with one or more food products. In some embodiments, one or more microfluidic chips 108 may be configured to provide for detection of one or more allergens 104 that are associated with one or more food products. Accordingly, in some embodiments, one or more detection units 122 may be configured to operably associate with the one or more microfluidic chips 108 and to detect one or more allergen indicators 106 that are associated with one or more food products. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Numerous methods may be used to detect one or more allergen indicators 106 that are associated with one or more food products. Such methods have been described herein. In addition, other detection methods that have been described may be modified to provide for detection of one or more allergen indicators 106 that are associated with one or more food products. In some embodiments, one or more detection units 122 may be configured to detect one or more polynucleotides, one or more polypeptides, one or more portions of one or more polynucleotides, and/or one or more portions of one or more polypeptides that have a nucleic acid sequence and/or an amino acid sequence that corresponds to, but is not limited to, one or more of the following accession numbers: X97824, M18780, X14712, M73993, X60688, U08008, AF479772, Y14855, AJ315959, AJ414730, P80208, CAA46782, P81729, AJ404845, X12928, P19656, AJ890020, U31771, Z48967, AF129423, P81943, AF456482, AF327622, AF329829, DR027057, AJ243427, AF05730, AF129424, AF071477, Z78202, U93165, U66076, U32440, AF221501, AF129425, AY081850, AY081852, P81402, AY898658, P80274, AF377948, AF377949, D14059, AY049013, A57106, AY792956, X60043, L34402, L77197, AF093541, AF086821, AF059616, AF092846, AF091737, AY328088, P00785, AJ297410, AJ417552, AJ417553, U81996, P15476, P16348, P20347, P30941, P04403, M17146, AY221641, AY102930, AY102931, U66866, AF066055, AF453947, AY081853, P01089, AF240005, AF091841, AF240006, AAG23840, AAD42942, AF091842, D32206, AY271295, P83834, AY839230, or substantially any combination thererof.

At embodiment 6006, module 5820 may include one or more detection units configured to detect the one or more allergen indicators that are associated with one or more weeds, grasses, trees, mites, animals, molds, fungi, insects, rubbers, metals, chemicals, autoallergens, or human autoallergens. In some embodiments, one or more devices may include one or more detection units 122 configured to detect one or more allergen indicators 106 that are associated with one or more weeds, grasses, trees, mites, animals, molds, fungi, insects, rubbers, metals, chemicals, autoallergens, human autoallergens, or substantially any combination thereof. Numerous allergen indicators 106 are known to be associated with weeds, grasses, trees, mites, animals, molds, fungi, insects, rubbers, metals, chemicals, autoallergens, or human autoallergens. Such allergen indicators 106 have been described herein and within additional sources (e.g., Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants). Accordingly, in some embodiments, one or more microfluidic chips 108 may be configured to process one or more samples 102 and provide for detection of one or more allergen indicators 106. In some embodiments, an allergen indicator 106 may be an allergenic particle. For example, in some embodiments, an allergen indicator 106 may include a complete pollen particle, such as a pollen particle, a spore, a flake of dander, and the like. In some embodiments, an allergen indicator 106 may be a portion of an allergenic particle. For example, in some embodiments, an allergen indicator 106 may include a portion of a pollen particle (e.g., polynucleotides, sporoderm, and the like). In some embodiments, allergen indicators 106 may include polynucleotides that are associated with one or more allergens 104. In some embodiments, allergen indicators 106 may include fragments of polynucleotides that are associated with one or more allergens 104. In some embodiments, allergen indicators 106 may include polypeptides, peptides, and/or proteins that are associated with one or more allergens 104. In some embodiments, allergen indicators 106 may include polysaccharides that are associated with one or more allergens 104. Accordingly, in some embodiments, one or more microfluidic chips 108 may be configured to provide for detection of one or more allergen indicators 106. In some embodiments, one or more detection units 122 may be configured to operably associate with one or more such microfluidic chips 108 and configured to detect one or more allergen indicators 106. Numerous detection methods may be used to detect one or more allergen indicators 106. Such methods have been described herein. In addition, detection methods that have been described may be modified to provide for detection of one or more allergen indicators 106. In some embodiments, one or more detection units 122 may be configured to detect and determine a concentration of one or more allergen indicators 106 that are included within a sample 102. For example, in some embodiments, one or more microfluidic chips 108 may be configured to provide for detection of one or more polynucleotides that are allergen indicators 106 through detection of electrical current produced upon hybridization of the one or more polynucleotides. Accordingly, in such embodiments, the one or more microfluidic chips 108 may be configured to produce an electrical current that is relative to polynucleotide concentration to provide for determination of polynucleotide concentration within one or more samples 102. Numerous configurations may be used in association with one or more allergen indicators 106 to provide for determination of allergen 104 concentration. In some embodiments, one or more microfluidic chips 108 may be configured to provide for identification of one or more allergens 104. For example, in some embodiments, one or more microfluidic chips 108 may include immobilized polynucleotides that selectively hybridize to one or more polynucleotides that are associated with a known allergen indicator 106. Accordingly, hybridization of one or more polynucleotides with the one or more immobilized polynucleotides indicates that a sample 102 includes one or more allergen indicators 106 that correspond to one or more known allergens 104. Accordingly, one or more detection units 122 may be configured to operably associate with such microfluidic chips 108 to provide for specific detection of one or more allergen indicators 106. In some embodiments, microfluidic chips 108 and/or detection units 122 may be configured to determine the identity and concentration of one or more allergen indicators 106 that are included within one or more samples 102.

At embodiment 6008, module 5820 may include one or more detection units configured to detect one or more allergens with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, or immunoassay. In some embodiments, one or more devices may include one or more detection units 122 configured to detect one or more allergens with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, filtration, electrophoresis, use of a CCD camera, immunoassay, or substantially any combination thereof. In some embodiments, one or more detection units 122 may be configured to detect one or more allergen indicators 106 that have been processed by one or more microfluidic chips 108. For example, in some embodiments, one or more microfluidic chips 108 may include a window (e.g., a quartz window, a cuvette analog, and/or the like) through which one or more detection units 122 may determine if one or more allergen indicators 106 are present or determine the concentration of one or more allergen indicators 106. In such embodiments, numerous techniques may be used to detect the one or more allergen indicators 106, such as visible light spectroscopy, ultraviolet light spectroscopy, infrared spectroscopy, fluorescence spectroscopy, and the like. Accordingly, in some embodiments, one or more detection units 122 may include circuitry and/or electro-mechanical mechanisms to detect one or more allergen indicators 106 present within one or more microfluidic chips 108 through a window in the one or more microfluidic chips 108. In some embodiments, one or more microfluidic chips 108 may be configured to process one or more samples 102 through use of surface plasmon resonance. In some embodiments, the one or more microfluidic chips 108 may include one or more antibodies, aptamers, proteins, peptides, polynucleotides, and the like, that are bound to a substrate (e.g., a metal film) within the one or more microfluidic chips 108. In some embodiments, such microfluidic chips 108 may include a prism through which one or more detection units 122 may shine light to detect one or more allergen indicators 106 that interact with the one or more antibodies, aptamers, proteins, peptides, polynucleotides, and the like, that are bound to a substrate. In some embodiments, one or more microfluidic chips 108 may include an exposed substrate surface that is configured to operably associate with one or more prisms that are included within one or more detection units 122. In some embodiments, one or more microfluidic chips 108 may include a nuclear magnetic resonance (NMR) probe. In such embodiments, the microfluidic chips 108 may be configured to associate with one or more detection units 122 that accept the NMR probe and are configured to detect one or more allergen indicators 106 through use of NMR spectroscopy. Accordingly, microfluidic chips 108 and detection units 122 may be configured in numerous ways to associate with each other to provide for detection of one or more allergen indicators 106.

In some embodiments, one or more allergen indicators 106 may be detected through use of spectroscopy. Numerous types of spectroscopic methods may be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., Clinical Chemistry, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, one or more allergen indicators 106 may be detected through use of electrochemical detection. In some embodiments, one or more polynucleotides may be detected through electrochemical detection. For example, in some embodiments, a polynucleotide that includes a redox label, such as ferrocene is coupled to a gold electrode. The labeled polynucleotide forms a stem-loop structure that can self-assemble onto a gold electrode by means of facile gold-thiol chemistry. Hybridization of a sample 102 polynucleotide induces a large conformational change in the surface-confined polynucleotide structure, which in turn alters the electron-transfer tunneling distance between the electrode and the redoxable label. The resulting change in electron transfer efficiency may be measured by cyclic voltammetry (Fan et al., Proc. Natl. Acad. Sci., 100:9134-9137 (2003); Wang et al., Anal. Chem., 75:3941-3945 (2003); Singh-Zocchi et al., Proc. Natl. Acad. Sci., 100:7605-7610 (2003)).

Such methods may be used to detect messenger ribonucleic acid, genomic deoxyribonucleic acid, and fragments thereof.

In some embodiments, one or more allergen indicators 106 may be detected through use of polynucleotide detection. In some embodiments, one or more detection units 122 may be configured to detect one or more allergen indicators 106 through use of polynucleotide detection. Numerous methods may be used to detect one or more polynucleotides. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described (e.g., U.S. Pat. Nos. 7,118,910 and 6,960,437; herein incorporated by reference). Such methods may be adapted to provide for detection of one or more allergen indicators 106. In some embodiments, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube may be combined with one or more samples 102, and/or one or more partially purified polynucleotides obtained from one or more samples 102. The one or more polynucleotides that include one or more carbon nanotubes are allowed to hybridize with one or more polynucleotides that may be present within the one or more samples 102. The one or more carbon nanotubes may be excited (e.g., with an electron beam and/or a ultraviolet laser) and the emission spectra of the excited nanotubes may be correlated with hybridization of the one or more polynucleotides that include at least one carbon nanotube with one or more polynucleotides that are included within the one or more samples 102. Accordingly, polynucleotides that hybridize to one or more allergen indicators 106 may include one or more carbon nanotubes. Methods to utilize carbon nanotubes as probes for nucleic acid interaction have been described (e.g., U.S. Pat. No. 6,821,730; herein incorporated by reference). Numerous other methods based on polynucleotide detection may be used to detect one or more allergen indicators 106.

In some embodiments, one or more allergen indicators 106 may be detected through use of fluorescence anisotropy. Fluorescence anisotropy is based on measuring the steady state polarization of sample 102 fluorescence imaged in a confocal arrangement. A linearly polarized laser excitation source preferentially excites fluorescent target molecules with transition moments aligned parallel to the incident polarization vector. The resultant fluorescence is collected and directed into two channels that measure the intensity of the fluorescence polarized both parallel and perpendicular to that of the excitation beam. With these two measurements, the fluorescence anisotropy, r, can be determined from the equation: r=(Intensity parallel−Intensity perpendicular)/(Intensity parallel+2(Intensity perpendicular)) where the I terms indicate intensity measurements parallel and perpendicular to the incident polarization. Fluorescence anisotropy detection of fluorescent molecules has been described. Accordingly, fluorescence anisotropy may be coupled to numerous fluorescent labels as have been described herein and as have been described.

In some embodiments, one or more allergen indicators 106 may be detected through use of fluorescence resonance energy transfer (FRET). Fluorescence resonance energy transfer refers to an energy transfer mechanism between two fluorescent molecules. A fluorescent donor is excited at its fluorescence excitation wavelength. This excited state is then nonradiatively transferred to a second molecule, the fluorescent acceptor. Fluorescence resonance energy transfer may be used within numerous configurations to detect one or more allergen indicators 106. For example, in some embodiments, an antibody may be labeled with a fluorescent donor and one or more allergen indicators 106 may be labeled with a fluorescent acceptor. Accordingly, such labeled antibodies and allergen indicators 106 may be used within competition assays to detect the presence and/or concentration of one or more allergen indicators 106 in one or more samples 102. Numerous combinations of fluorescent donors and fluorescent acceptors may be used to detect one or more allergen indicators 106. Accordingly, one or more detection units 122 may be configured to emit one or more wavelength of light to excite a fluorescent donor and may be configured to detect one or more wavelength of light emitted by the fluorescent acceptor. Accordingly, in some embodiments, one or more detection units 122 may be configured to accept one or more microfluidic chips 108 that include a quartz window through which fluorescent light may pass to provide for detection of one or more allergen indicators 106 through use of fluorescence resonance energy transfer. Accordingly, fluorescence resonance energy transfer may be used in conjunction with competition assays and/or numerous other types of assays to detect one or more allergen indicators 106.

In some embodiments, one or more allergen indicators 106 may be detected through use of electron transfer. Electron transfer is the process by which an electron moves from an electron donor to an electron acceptor causing the oxidation states of the electron donor and the electron acceptor to change. In some embodiments, electron transfer may occur when an electron is transferred from one or more electron donors to an electrode. In some embodiments, electron transfer may be utilized within competition assays to detect one or more allergen indicators 106. For example, in some embodiments, one or more microfluidic chips 108 may include one or more polynucleotides that may be immobilized on one or more electrodes. The immobilized polynucleotides may be incubated with a reagent mixture that includes sample polynucleotides and polynucleotides that are tagged with an electron donor. Hybridization of the tagged polynucleotides to the immobilized polynucleotides allows the electron donor to transfer an electron to the electrode to produce a detectable signal. Accordingly, a decrease in signal due to the presence of one or more polynucleotides that are allergen indicators 106 in the reagent mixture indicates the presence of an allergen indicator 106 in the sample 102. Such methods may be used in conjunction with polynucleotides, polypeptides, peptides, antibodies, aptamers, and the like. One or more microfluidic chips 108 may be configured to utilize numerous electron transfer based assays to provide for detection of one or more allergen indicators 106 by a detection unit 122.

In some embodiments, one or more allergen indicators 106 may be detected through use of one or more enzyme assays. Numerous enzyme assays may be used to provide for detection of one or more allergen indicators 106. Examples of such enzyme assays include, but are not limited to, beta-galactosidase assays, peroxidase assays, catalase assays, alkaline phosphatase assays, and the like. In some embodiments, enzyme assays may be configured such that an enzyme will catalyze a reaction involving an enzyme substrate that produces a fluorescent product. Accordingly, one or more detection units 122 may be configured to detect fluorescence resulting from the fluorescent product. Enzymes and florescent enzyme substrates are known and are commercially available (e.g., Sigma-Aldrich, St. Louis, Mo.). In some embodiments, enzyme assays may be configured as binding assays that provide for detection of one or more allergen indicators 106. For example, in some embodiments, one or more microfluidic chips 108 may be configured to include a substrate to which is coupled to one or more antibodies, aptamers, peptides, proteins, polynucleotides, ligands, and the like, that will interact with one or more allergen indicators 106. One or more samples 102 may be passed across the substrate such that one or more allergen indicators 106 present within the one or more samples 102 will interact with the one or more antibodies, aptamers, peptides, proteins, polynucleotides, ligands, and the like, and be immobilized on the substrate. One or more antibodies, aptamers, peptides, proteins, polynucleotides, ligands, and the like, that are labeled with an enzyme may then be passed across the substrate such that the one or more labeled antibodies, aptamers, peptides, proteins, polynucleotides, ligands, and the like, will bind to the one or more immobilized allergen indicators 106. An enzyme substrate may then be introduced to the one or more immobilized enzymes such that the enzymes are able to catalyze a reaction involving the enzyme substrate to produce a fluorescent product. Such assays are often referred to as sandwich assays. Accordingly, one or more detection units 122 may be configured to detect one or more products of enzyme catalysis to provide for detection of one or more allergen indicators 106.

In some embodiments, one or more allergen indicators 106 may be detected through use of electrical conductivity. In some embodiments, one or more microfluidic chips 108 may be configured to process one or more samples 102 and provide for detection of one or more allergen indicators 106 through use of electrical conductivity. In some embodiments, such microfluidic chips 108 may be configured to operably associate with one or more detection units 122 such that the one or more detection units 122 can detect one or more allergen indicators 106 through use of electrical conductivity. In some embodiments, one or more microfluidic chips 108 may be configured to include two or more electrodes that are each coupled to one or more detector polynucleotides. Interaction of an allergen associated polynucleotide, such as hybridization, with two detector polynucleotides that are coupled to two different electrodes will complete an electrical circuit. This completed circuit will provide for the flow of a detectable electrical current between the two electrodes and thereby provide for detection of one or more allergen associated polynucleotides that are allergen indicators 106. In some embodiments, the electrodes may be carbon nanotubes (e.g., U.S. Pat. No. 6,958,216; herein incorporated by reference). In some embodiments, electrodes may include, but are not limited to, one or more conductive metals, such as gold, copper, iron, silver, platinum, and the like; one or more conductive alloys; one or more conductive ceramics; and the like. In some embodiments, electrodes may be selected and configured according to protocols typically used in the computer industry that include, but are not limited to, photolithography, masking, printing, stamping, and the like. In some embodiments, other molecules and complexes that interact with one or more allergen indicators 106 may be used to detect the one or more allergen indicators 106 through use of electrical conductivity. Examples of such molecules and complexes include, but are not limited to, proteins, peptides, antibodies, aptamers, and the like. For example, in some embodiments, two or more antibodies may be immobilized on one or more electrodes such that contact of the two or more antibodies with an allergen indicator 106, such as a spore, a pollen particle, a dander particle, and the like, will complete an electrical circuit and facilitate the production of a detectable electrical current. Accordingly, in some embodiments, one or more microfluidic chips 108 may be configured to include electrical connectors that are able to operably associate with one or more detection units 122 such that the detection units 122 may detect an electrical current that is due to interaction of one or more allergen indicators 106 with two or more electrodes. In some embodiments, one or more detection units 122 may include electrical connectors that provide for operable association of one or more microfluidic chips 108 with the one or more detection units 122. In some embodiments, the one or more detectors are configured for detachable connection to one or more microfluidic chips 108. Microfluidic chips 108 and detection units 122 may be configured in numerous ways to process one or more samples 102 and detect one or more allergen indicators 106.

In some embodiments, one or more allergen indicators 106 may be detected through use of isoelectric focusing. In some embodiments, one or more microfluidic chips 108 may be configured to process one or more samples 102 and provide for detection of one or more allergen indicators 106 through use of isoelectric focusing. In some embodiments, native isoelectric focusing may be utilized to process and/or detect one or more allergen indicators 106. In some embodiments, denaturing isoelectric focusing may be utilized to process and/or detect one or more allergen indicators 106. Methods to construct microfluidic channels that may be used for isoelectric focusing have been reported (e.g., Macounova et al., Anal Chem., 73:1627-1633 (2001); Macounova et al., Anal Chem., 72:3745-3751 (2000); Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). In some embodiments, one or more microfluidic chips 108 may be configured to process one or more samples 102 through use of methods that include isoelectric focusing. In some embodiments, one or more detection units 122 may be configured to operably associate with one or more such microfluidic chips 108 such that the one or more detection units 122 can be used to detect one or more allergen indicators 106 that have been focused within one or more microfluidic channels of the one or more microfluidic chips 108. In some embodiments, one or more detection units 122 may be configured to include one or more CCD cameras that can be used to detect one or more allergen indicators 106. In some embodiments, one or more detection units 122 may be configured to include one or more spectrometers that can be used to detect one or more allergen indicators 106. Numerous types of spectrometers may be utilized to detect one or more allergen indicators 106 following isoelectric focusing. In some embodiments, one or more detection units 122 may be configured to utilize refractive index to detect one or more allergen indicators 106. In some embodiments, one or more microfluidic chips 108 may be configured to combine one or more samples 102 with one or more reagent mixtures that include one or more binding molecules and/or binding complexes that bind to one or more allergen indicators 106 that may be present within the one or more samples 102 to form an allergen indicator-binding molecule/binding complex. Examples of such binding molecules and/or binding complexes that bind to one or more allergen indicators 106 include, but are not limited to, antibodies, aptamers, peptides, proteins, polynucleotides, and the like. In some embodiments, an allergen indicator-binding molecule/binding complex may be processed through use of isoelectric focusing and then detected with one or more detection units 122. In some embodiments, one or more binding molecules and/or one or more binding complexes may include a label. Numerous labels may be used and include, but are not limited to, radioactive labels, fluorescent labels, colorimetric labels, spin labels, fluorescent labels, and the like. Accordingly, in some embodiments, an allergen indicator-binding molecule (labeled)/binding complex (labeled) may be processed through use of isoelectric focusing and then detected with one or more detection units 122 that are configured to detect the one or more labels. Microfluidic chips 108 and detection units 122 may be configured in numerous ways to process one or more samples 102 and detect one or more allergen indicators 106 though use of isoelectric focusing.

In some embodiments, one or more allergen indicators 106 may be detected through use of chromatographic methodology alone or in combination with additional processing and/or detection methods. In some embodiments, one or more microfluidic chips 108 may be configured to process one or more samples 102 and provide for detection of one or more allergen indicators 106 through use of chromatographic methods. Accordingly, in some embodiments, one or more detection units 122 may be configured to operably associate with the one or more microfluidic chips 108 and detect one or more allergen indicators 106 that were processed through use of chromatographic methods. In some embodiments, the one or more detection units 122 may be configured to operably associate with one or more microfluidic chips 108 and supply solvents and other reagents to the one or more microfluidic chips 108. For example, in some embodiments, one or more detection units 122 may include pumps and solvent/buffer reservoirs that are configured to supply solvent/buffer flow through chromatographic media (e.g., a chromatographic column) that is operably associated with one or more microfluidic chips 108. In some embodiments, one or more detection units 122 may be configured to operably associate with one or more microfluidic chips 108 and be configured to utilize one or more methods to detect one or more allergen indicators 106. Numerous types of chromatographic methods and media may be used to process one or more samples 102 and provide for detection of one or more allergen indicators 106. Chromatographic methods include, but are not limited to, low pressure liquid chromatography, high pressure liquid chromatography (HPLC), microcapillary low pressure liquid chromatography, microcapillary high pressure liquid chromatography, ion exchange chromatography, affinity chromatography, gel filtration chromatography, size exclusion chromatography, thin layer chromatography, paper chromatography, gas chromatography, and the like. In some embodiments, one or more microfluidic chips 108 may be configured to include one or more high pressure microcapillary columns. Methods that may be used to prepare microcapillary HPLC columns (e.g., columns with a 100 micrometer-500 micrometer inside diameter) have been described (e.g., Davis et al., Methods, A Companion to Methods in Enzymology, 6: Micromethods for Protein Structure Analysis, ed. by John E. Shively, Academic Press, Inc., San Diego, 304-314 (1994); Swiderek et al., Trace Structural Analysis of Proteins. Methods of Enzymology, ed. by Barry L. Karger & William S. Hancock, Spectrum, Publisher Services, 271, Chap. 3, 68-86 (1996); Moritz and Simpson, J. Chromatogr., 599:119-130 (1992)). In some embodiments, one or more microfluidic chips 108 may be configured to include one or more affinity columns. Methods to prepare affinity columns have been described. Briefly, a biotinylated site may be engineered into a polypeptide, peptide, aptamer, antibody, or the like. The biotinylated protein may then be incubated with avidin coated polystyrene beads and slurried in Tris buffer. The slurry may then be packed into a capillary affinity column through use of high pressure packing. Affinity columns may be prepared that may include one or more molecules and/or complexes that interact with one or more allergen indicators 106. For example, in some embodiments, one or more aptamers that bind to one or more allergen indicators 106 may be used to construct an affinity column. Accordingly, numerous chromatographic methods may be used alone, or in combination with additional methods, to process and detect one or more allergen indicators 106. Numerous detection methods may be used in combination with numerous types of chromatographic methods. Accordingly, one or more detection units 122 may be configured to utilize numerous detection methods to detect one or more allergen indicators 106 that are processed through use of one or more chromatographic methods. Examples of such detection methods include, but are not limited to, conductivity detection, use of ion-specific electrodes, refractive index detection, colorimetric detection, radiological detection, detection by retention time, detection through use of elution conditions, spectroscopy, and the like. For example, in some embodiments, one or more chromatographic markers may be added to one or more samples 102 prior to the samples 102 being applied to a chromatographic column. One or more detection units 122 that are operably associated with the chromatographic column may be configured to detect the one or more chromatographic markers and use the elution time and/or position of the chromatographic markers as a calibration tool for use in detecting one or more allergen indicators 106 if those allergen indicators 106 are eluted from the chromatographic column. In some embodiments, one or more detection units 122 may be configured to utilize one or more ion-specific electrodes to detect one or more allergen indicators 106. For example, such electrodes may be used to detect allergen indicators 106 that include, but are not limited to, metals (e.g., tin, silver, nickel, cobalt, chromate), nitrates, nitrites, sulfites, and the like. Such allergen indicators 106 are often associated with food, beverages, clothing, jewelry, and the like. Accordingly, chromatographic methods may be used in combination with additional methods and in combination with numerous types of detection methods.

In some embodiments, one or more allergen indicators 106 may be detected through use of immunoprecipitation. In some embodiments, one or more detection units 122 may be configured to detect one or more allergen indicators 106 through use of immunoprecipitation. In some embodiments, immunoprecipitation may be utilized in combination with additional processing and/or detection methods to detect one or more allergen indicators 106. In some embodiments, one or more microfluidic chips 108 may be configured to process one or more samples 102 through use of immunoprecipitation. For example, in some embodiments, one or more samples 102 may be combined with one or more antibodies that bind to one or more allergen indicators 106 to form one or more antibody-allergen indicator 106 complexes. An insoluble form of an antibody binding constituent, such as protein A (e.g., protein A-sepharose bead, protein A-magnetic bead, protein A-ferrous bead, protein A-non-ferrous bead, and the like), Protein G, a second antibody, an aptamer, and the like, may then be mixed with the antibody-allergen indicator 106 complex such that the insoluble antibody binding constituent binds to the antibody-allergen indicator 106 complex and provides for precipitation of the antibody-allergen indicator 106 complex. Such complexes may be separated from other sample 102 components to provide for detection of one or more allergen indicators 106. For example, in some embodiments, sample 102 components may be washed away from the precipitated antibody-allergen indicator 106 complexes. In some embodiments, one or more microfluidic chips 108 that are configured for immunoprecipitation may be operably associated with one or more centrifugation units 118 to assist in precipitating one or more antibody-allergen indicator 106 complexes. In some embodiments, aptamers (polypeptide and/or polynucleotide) may be used in combination with antibodies or in place of antibodies. Accordingly, one or more detection units 122 may be configured to detect one or more allergen indicators 106 through use of numerous detection methods in combination with immunoprecipitation based methods.

In some embodiments, one or more allergen indicators 106 may be detected through use of immunoseparation. In some embodiments, one or more detection units 122 may be configured to detect one or more allergen indicators 106 through use of immunoseparation. In some embodiments, immunoseparation may be utilized in combination with additional processing and/or detection methods to detect one or more allergen indicators 106. In some embodiments, one or more microfluidic chips 108 may be configured to process one or more samples 102 through use of immunoseparation. For example, in some embodiments, one or more samples 102 may be combined with one or more antibodies that bind to one or more allergen indicators 106 to form one or more antibody-allergen indicator 106 complexes. An antibody binding constituent may be added that binds to the antibody-allergen complex.

Examples of such antibody binding constituents that may be used alone or in combination include, but are not limited to, protein A (e.g., protein A-sepharose bead, protein A-magnetic bead, protein A-ferrous bead, protein A-non-ferrous bead, and the like), Protein G, a second antibody, an aptamer, and the like. Such antibody binding constituents may be mixed with an antibody-allergen indicator 106 complex such that the antibody binding constituent binds to the antibody-allergen indicator 106 complex and provides for separation of the antibody-allergen indicator 106 complex. In some embodiments, the antibody binding constituent may include a tag that allows the antibody binding constituent and complexes that include the antibody binding constituent to be separated from other components in one or more samples 102. In some embodiments, the antibody binding constituent may include a ferrous material. Accordingly, antibody-allergen indicator 106 complexes may be separated from other sample 102 components through use of a magnet, such as an electromagnet. In some embodiments, an antibody binding constituent may include a non-ferrous metal. Accordingly, antibody-allergen indicator 106 complexes may be separated from other sample 102 components through use of an eddy current to direct movement of one or more antibody-allergen indicator 106 complexes. In some embodiments, two or more forms of an antibody binding constituents may be used to detect one or more allergen indicators 106. For example, in some embodiments, a first antibody binding constituent may be coupled to a ferrous material and a second antibody binding constituent may be coupled to a non-ferrous material. Accordingly, the first antibody binding constituent and the second antibody binding constituent may be mixed with antibody-allergen indicator 106 complexes such that the first antibody binding constituent and the second antibody binding constituent bind to antibody-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more antibodies that bind to one or more allergen indicators 106 to form one or more antibody-allergen indicator 106 complexes. In some embodiments, the one or more antibodies may include one or more tags that provide for separation of the antibody-allergen indicator 106 complexes. For example, in some embodiments, an antibody may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with immunoseparation based methods. In some embodiments, aptamers (polypeptide and/or polynucleotide) may be used in combination with antibodies or in place of antibodies.

In some embodiments, one or more allergen indicators 106 may be detected through use of aptamer binding. In some embodiments, one or more detection units 122 may be configured to detect one or more allergen indicators 106 through use of aptamer binding. In some embodiments, aptamer binding may be utilized in combination with additional processing and/or detection methods to detect one or more allergen indicators 106. In some embodiments, one or more microfluidic chips 108 may be configured to process one or more samples 102 through use of aptamer binding. For example, in some embodiments, one or more samples 102 may be combined with one or more aptamers that bind to one or more allergen indicators 106 to form one or more aptamer-allergen indicator 106 complexes. In some embodiments, aptamer binding constituents may be added that bind to the aptamer-allergen complex. Numerous aptamer binding constituents may be utilized. For example, in some embodiments, one or more aptamers may include one or more tags to which one or more aptamer binding constituents may bind. Examples of such tags include, but are not limited to, biotin, avidin, streptavidin, histidine tags, nickel tags, ferrous tags, non-ferrous tags, and the like. In some embodiments, one or more tags may be conjugated with a label to provide for detection of one or more complexes. Examples of such tag-label conjugates include, but are not limited to, Texas red conjugated avidin, alkaline phosphatase conjugated avidin, CY2 conjugated avidin, CY3 conjugated avidin, CY3.5 conjugated avidin, CY5 conjugated avidin, CY5.5 conjugated avidin, fluorescein conjugated avidin, glucose oxidase conjugated avidin, peroxidase conjugated avidin, rhodamine conjugated avidin, agarose conjugated anti-protein A, alkaline phosphatase conjugated protein A, anti-protein A, fluorescein conjugated protein A, IRDye® 800 conjugated protein A, peroxidase conjugated protein A, sepharose protein A, alkaline phosphatase conjugated streptavidin, AMCA conjugated streptavidin, anti-streptavidin (*Streptomyces avidinii*) (rabbit) IgG Fraction, beta-galactosidase conjugated streptavidin, CY2 conjugated streptavidin, CY3 conjugated streptavidin, CY3.5 conjugated streptavidin, CY5 conjugated streptavidin, CY5.5 conjugated streptavidin, fluorescein conjugated streptavidin, IRDye® 700DX conjugated streptavidin, IRDye® 800 conjugated streptavidin, IRDye® 800CW conjugated streptavidin, peroxidase conjugated streptavidin, phycoerythrin conjugated streptavidin, rhodamine conjugated streptavidin, Texas red conjugated streptavidin, alkaline phosphatase conjugated biotin, anti-biotin (rabbit) IgG fraction, beta-galactosidase conjugated biotin, glucose oxidase conjugated biotin, peroxidase conjugated biotin, alkaline phosphatase conjugated protein G, anti-protein G (rabbit) Agarose conjugated, anti-protein G (Rabbit) IgG fraction, fluorescein conjugated protein G, IRDye® 800 conjugated protein G, peroxidase conjugated protein G, and the like. Many such labeled tags are commercially available (e.g., Rockland Immunochemicals, Inc., Gilbertsville, Pa.). Such labels may also be used in association with other methods to process and detect one or more allergen indicators 106. Aptamer binding constituents may be mixed with an aptamer-allergen indicator 106 complex such that the aptamer binding constituent binds to the aptamer-allergen indicator 106 complex and provides for separation of the aptamer-allergen indicator 106 complex. In some embodiments, the aptamer binding constituent may include a tag that allows the aptamer binding constituent and complexes that include the aptamer binding constituent to be separated from other components in one or more samples 102. In some embodiments, the aptamer binding constituent may include a ferrous material. Accordingly, aptamer-allergen indicator 106 complexes may be separated from other sample 102 components through use of a magnet, such as an electromagnet. In some embodiments, an aptamer binding constituent may include a non-ferrous metal. Accordingly, aptamer-allergen indicator 106 complexes may be separated from other sample 102 components through use of an eddy current to direct movement of one or more aptamer-allergen indicator 106 complexes. In some embodiments, two or more forms of aptamer binding constituents may be used to detect one or more allergen indicators 106. For example, in some embodiments, a first aptamer binding constituent may be coupled to a ferrous material and a second aptamer binding constituent may be coupled to a non-ferrous material. Accordingly, the first aptamer binding constituent and the second aptamer binding constituent may be mixed with aptamer-allergen indicator 106 complexes such that the first aptamer binding constituent and the second aptamer binding constituent bind to aptamer-allergen indicator 106 complexes that include different allergen indicators 106. Accordingly, in such embodiments, different allergen indicators 106 from a single sample 102 and/or a combination of samples 102 may be separated through use of direct magnetic separation in combination with eddy current based separation. In some embodiments, one or more samples 102 may be combined with one or more aptamers that bind to one or more allergen indicators 106 to form one or more aptamer-allergen indicator 106 complexes. In some embodiments, the one or more aptamer may include one or more tags that provide for separation of the aptamer-allergen indicator 106 complexes. For example, in some embodiments, an aptamer may include a tag that includes one or more magnetic beads, a ferrous material, a non-ferrous metal, an affinity tag, a size exclusion tag (e.g., a large bead that is excluded from entry into chromatographic media such that antibody-allergen indicator 106 complexes pass through a chromatographic column in the void volume), and the like. Accordingly, one or more detection units 122 may be configured to detect one or more allergen indicators 106 through use of numerous detection methods in combination with aptamer binding based methods. In some embodiments, antibodies may be used in combination with aptamers or in place of aptamers.

In some embodiments, one or more allergen indicators 106 may be detected through use of electrophoresis. In some embodiments, one or more microfluidic chips 108 may be configured to process one or more samples 102 through use of electrophoresis. In some embodiments, such microfluidic chips 108 may be configured to operably associate with one or more detection units 122. Accordingly, in some embodiments, one or more detection units 122 may be configured to operably associate with one or more microfluidic chips 108 and detect one or more allergen indicators 106 that were processed through use of electrophoresis. Numerous electrophoretic methods may be utilized to provide for detection of one or more allergen indicators 106. Examples of such electrophoretic methods include, but are not limited to, capillary electrophoresis, one-dimensional electrophoresis, two-dimensional electrophoresis, native electrophoresis, denaturing electrophoresis, polyacrylamide gel electrophoresis, agarose gel electrophoresis, and the like. Numerous detection methods may be used in combination with one or more electrophoretic methods to detect one or more allergen indicators 106. In some embodiments, one or more allergen indicators 106 may be detected according to the position to which the one or more allergen indicators 106 migrate within an electrophoretic field (e.g., a capillary and/or a gel). In some embodiments, the position of one or more allergen indicators 106 may be compared to one or more standards. For example, in some embodiments, one or more samples 102 may be mixed with one or more molecular weight markers prior to gel electrophoresis. The one or more samples 102, that include the one or more molecular weight markers, may be subjected to electrophoresis and then the gel may be stained. In such embodiments, the molecular weight markers may be used as a reference to detect one or more allergen indicators 106 present within the one or more samples 102. In some embodiments, one or more components that are known to be present within one or more samples 102 may be used as a reference to detect one or more allergen indicators 106 present within the one or more samples 102. In some embodiments, gel shift assays may be used to detect one or more allergen indicators 106. For example, in some embodiments, a sample 102 (e.g., a single sample 102 or combination of multiple samples 102) may be split into a first sample 102 and a second sample 102. The first sample 102 may be mixed with an antibody, aptamer, ligand, or other molecule and/or complex that binds to the one or more allergen indicators 106. The first and second samples 102 may then be subjected to electrophoresis. The gels corresponding to the first sample 102 and the second sample 102 may then be analyzed to determine if one or more allergen indicators 106 are present within the one or more samples 102. Microfluidic chips 108 and detection units 122 may be configured in numerous ways to process and detect one or more allergen indicators 106 through use of electrophoresis.

In some embodiments, one or more allergen indicators 106 may be detected through use of one or more charge-coupled device (CCD) cameras. In some embodiments, one or more detection units 122 that include one or more CCD cameras may be configured to operably associate with one or more microfluidic chips 108. Such detection units 122 may be utilized in combination with numerous processing methods. Examples of such methods include, but are not limited to, electrophoresis; competition assays; methods based on polynucleotide interaction, protein interaction, peptide interaction, antibody interaction, aptamer interaction, immunoprecipitation, immunoseparation, and the like. For example, in some embodiments, one or more microfluidic chips 108 may be configured to process one or more samples 102 through use of immunoprecipitation. In some embodiments, one or more antibodies may be conjugated to a fluorescent label such that binding of one or more labeled antibodies to one or more allergen indicators 106 included within one or more samples 102 will form a fluorescently labeled antibody-allergen indicator 106 complex. One or more insoluble allergen indicator 106 binding constituents, such as a sepharose bead that includes an antibody or aptamer that binds to the one or more allergen indicators 106, may be bound to the fluorescently labeled antibody-allergen indicator 106 complex and used to precipitate the complex. One or more detection units 122 that include a CCD camera that is configured to detect fluorescent emission from the one or more fluorescent labels may be used to detect the one or more allergen indicators 106. In some embodiments, one or more CCD cameras may be configured to utilize dark frame subtraction to cancel background and increase sensitivity of the camera. In some embodiments, one or more detection units 122 may include one or more filters to select and/or filter wavelengths of energy that can be detected by one or more CCD cameras (e.g., U.S. Pat. No. 3,971,065; herein incorporated by reference). In some embodiments, one or more detection units 122 may include polarized lenses. One or more detection units 122 may be configured in numerous ways to utilize one or more CCD cameras to detect one or more allergen indicators 106.

In some embodiments, one or more allergen indicators 106 may be detected through use of immunoassay. In some embodiments, one or more microfluidic chips 108 may be configured to process one or more samples 102 through use of immunoassay. In some embodiments, one or more detection units 122 may be configured to operably associate with one or more such microfluidic chips 108 and to detect one or more allergen indicators 106 associated with the use of immunoassay. Numerous types of detection methods may be used in combination with immunoassay based methods. In some embodiments, a label may be used within one or more immunoassays that may be detected by one or more detection units 122. Examples of such labels include, but are not limited to, fluorescent labels, spin labels, fluorescence resonance energy transfer labels, radiolabels, electrochemiluminescent labels (e.g., U.S. Pat. Nos. 5,093,268; 6,090,545; herein incorporated by reference), and the like. In some embodiments, electrical conductivity may be used in combination with immunoassay based methods.

At embodiment 6010, module 5820 may include one or more detection units that are calibrated for an individual. In some embodiments, one or more devices may include one or more detection units 122 that are calibrated for an individual. In some embodiments, one or more detection units 122 may be calibrated to detect one or more specific allergens 104 and/or allergen indicators 106 that produce an allergic response by an individual. For example, in some embodiments, one or more detection units 122 may be calibrated to detect peanuts and/or peanut associated products for an individual who is allergic to peanuts. In some embodiments, one or more detection units 122 may be calibrated to detect different concentrations of allergen indicators 106. For example, in some embodiments, an individual may produce an allergic response if exposed to an allergen 104 at a concentration that is above a certain level. Accordingly, in some embodiments, a detection unit 122 may be calibrated to detect one or more concentrations of one or more allergen indicators 106 that produce an allergic response within an individual.

FIG. 61 illustrates alternative embodiments of devices 5800 of FIG. 58. FIG. 61 illustrates example embodiments of module 5830. Additional embodiments may include an embodiment 6102, an embodiment 6104, an embodiment 6106, an embodiment 6108, an embodiment 6110, and/or an embodiment 6112.

At embodiment 6102, module 5830 may include one or more display units that are passive display units. In some embodiments, one or more devices may include one or more display units 124 that are passive display units 124. In some embodiments, one or more display units 124 may include one or more liquid crystal displays (LCD). Methods to construct passive displays have been described (e.g., U.S. Pat. Nos. 4,807,967; 4,729,636: 4,436,378; 4,257,041; herein incorporated by reference).

At embodiment 6104, module 5830 may include one or more display units that are active display units. In some embodiments, one or more devices may include one or more display units 124 that are active display units 124. Numerous active display units 124 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), wide ultra extended graphics array (WUXGA).

At embodiment 6106, module 5830 may include one or more display units that indicate a presence or an absence of one or more allergens within the one or more samples. In some embodiments, one or more devices may include one or more display units 124 that indicate a presence or an absence of one or more allergens 104 within the one or more samples 102. In some embodiments, one or more display units 124 may use a colorimetric message to indicate a presence or an absence of one or more allergen indicators 106 within one or more samples 102. For example, in some embodiments, one or more display units 124 may display a green light if one or more allergen indicators 106 are not found within one or more samples 102 and a red light if one or more allergen indicators 106 are found within one or more samples 102. In some embodiments, one or more display units 124 may use a pictographic message to indicate a presence or an absence of one or more allergen indicators 106 within one or more samples 102. For example, in some embodiments, one or more display units 124 may display a smiley face if one or more allergen indicators 106 are not found within one or more samples 102 and a frowny face if one or more allergen indicators 106 are found within one or more samples 102. In some embodiments, one or more display units 124 may use a typographical message to indicate a presence or an absence of one or more allergen indicators 106 within one or more samples 102. For example, in some embodiments, one or more display units 124 may display an "Allergen Not Present" message if one or more allergen indicators 106 are not found within one or more samples 102 and an "Allergen Present" message if one or more allergen indicators 106 are found within one or more samples 102. Such messages may be displayed in numerous languages. In some embodiments, one or more display units 124 may display one or more messages in multiple formats. For example, in some embodiments, one or more messages may be displayed in colored text.

At embodiment 6108, module 5830 may include one or more display units that indicate an identity of one or more allergens present within the one or more samples. In some embodiments, one or more devices may include one or more display units 124 that indicate an identity of one or more allergens 104 present within the one or more samples 102. In some embodiments, one or more display units 124 may be operably associated with one or more microfluidic chips 108 that are configured to identify one or more allergen indicators 106. Accordingly, in some embodiments, one or more display units 124 may be configured to display the identity of one or more allergens 104 that are present and/or absent from one or more samples 102. For example, in some embodiments, a display unit 124 may be configured to indicate a presence or an absence of beta-lactoglobulin in a food product.

At embodiment 6110, module 5830 may include one or more display units that indicate one or more concentrations of one or more allergens within the one or more samples. In some embodiments, one or more devices may include one or more display units 124 that indicate one or more concentrations of one or more allergens 104 within the one or more samples 102. Concentration may be displayed in numerous formats. For example, in some embodiments, concentration may be expressed numerically (e.g., mass allergen indicator 106 per volume sample 102 (e.g., milligrams per milliliter), mass allergen indicator 106 per mass sample 102 (e.g., milligrams per milligram of sample), parts per million, and the like). In some embodiments, concentration may be expressed graphically. For example, in some embodiments, one or more display units 124 may include a display having a gray scale on which the concentration of one or more allergen indicators 106 that are present within one or more samples 102 may be indicated (e.g., higher concentrations of one or more allergens 104 may be displayed as dark gray while lower concentrations of one or more allergens 104 may be displayed as light gray). In some embodiments, one or more display units 124 may include a display having a color scale on which the concentration of one or more allergen indicators 106 that are present within one or more samples 102 may be indicated (e.g., low concentrations of one or more allergen indicators 106 may be indicated by a green light, intermediate concentrations of one or more allergen indicators 106 may be indicated by a yellow light, high concentrations of one or more allergen indicators 106 may be indicated by a red light). In some embodiments, one or more display units 124 may be calibrated to an individual. For example, in such embodiments, an individual may use the display to obtain an immediate reading that will indicate if a food product contains a dangerous level of one or more allergens 104.

At embodiment 6112, module 5830 may include one or more display units that are calibrated for an individual. In some embodiments, one or more devices may include one or more display units 124 that are calibrated for an individual. In some embodiments, one or more display units 124 may be calibrated to display whether one or more allergens 104, and/or allergen indicators 106, that are specific to an individual are present or absent within one or more samples 102. For example, in some embodiments, one or more display units 124 may be configured to display whether one or more samples 102 contain shellfish associated allergens 104 for an individual known to be allergic to shellfish. In some embodiments, one or more display units 124 may be calibrated to indicate safe and/or unsafe concentrations of one or more allergens 104 within one or more samples 102 for an individual.

FIG. 62 illustrates alternative embodiments of devices 5800 of FIG. 58. FIG. 62 illustrates example embodiments of module 5840. Additional embodiments may include an embodiment 6202 and/or an embodiment 6204.

At embodiment 6202, module 5840 may include one or more reservoir units that are configured for containing one or more reagents. In some embodiments, one or more devices may include one or more reservoir units 112 that are configured for containing one or more reagents. Reservoir unit 112 may be configured to contain and/or deliver numerous types of reagents. Examples of such reagents include, but are not limited to, phenol, chloroform, alcohol, salt solutions, detergent solutions, solvents, reagents used for polynucleotide precipitation, reagents used for polypeptide precipitation, reagents used for polynucleotide extraction, reagents used for polypeptide extraction, reagents used for chemical extractions, and the like. Accordingly, reservoir unit 112 may be configured to contain and/or deliver virtually any reagent that may be used for the analysis of one or more allergens 104 and/or allergen indicators 106. In some embodiments, one or more reservoir units 112 may include one or more pumps configured to deliver one or more reagents to one or more microfluidic chips 108. In some embodiments, one or more reservoir units 112 may include one or more connectors configured to couple the one or more reservoir units 112 to one or more microfluidic chips 108.

At embodiment 6204, module 5840 may include one or more reservoir units that are configured as one or more waste reservoirs. In some embodiments, one or more devices may include one or more reservoir units 112 that are configured as one or more waste reservoirs. Such waste reservoirs may be configured in numerous ways. For example such waste reservoirs may be configured for containing reagents, samples 102, and the like. In some embodiments, waste reservoirs may be configured to contain liquids, solids, gels, or substantially any combination thereof.

In some embodiments, one or more waste reservoirs may include one or more pumps configured to withdraw one or more reagents from one or more microfluidic chips 108. In some embodiments, one or more waste reservoirs may include one or more connectors configured to couple the one or more waste reservoirs to one or more microfluidic chips 108.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the an absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electromechanical systems include, but are not limited to, a variety of consumer electronics systems, as well as other systems such as motorized transport systems, factory automation systems, security systems, and communication/computing systems. Those skilled in the art will recognize that electromechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity such as Sprint, Cingular, Nextel, etc.), etc.

Although a user 130 is shown/described herein as a single illustrated figure, those skilled in the art will appreciate that a user 130 may be representative of a human user 130, a robotic user 130 (e.g., computational entity), and/or substantially any combination thereof (e.g., a user 130 may be assisted by one or more robotic agents). In addition, a user 130 as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to, physically mateable and/or physically interacting components and/or wirelessly interactable and/or wirelessly interacting components and/or logically interacting and/or logically interactable components.

All of the above U.S. patents, U.S. patent application publications, U.S. patent applications, foreign patents, foreign patent applications and non-patent publications referred to in this specification and/or listed in any Application Data Sheet, are incorporated herein by reference, in their entireties.

What is claimed is:

1. A method at least partially implemented using one or more computer processors, the method comprising:
   receiving information identifying at least one allergen indicator affecting an individual and at least one concentration level of the at least one allergen indicator that produces at least one allergic response in the individual;
   determining at least partly in response to processing of one or more samples with one or more microfluidic chips at least one concentration amount of the at least one allergen indicator in at least some of the one or more samples; and
   outputting at least one unsafe-type indicator for display if the at least one concentration amount of the at least one allergen indicator in at least some of the one or more samples meets or exceeds the at least one concentration level of the at least one allergen indicator that produces at least one allergic response in the individual.

2. The method of claim 1, wherein the receiving information identifying at least one allergen indicator affecting an individual and at least one concentration level of the at least one allergen indicator that produces at least one allergic response in the individual comprises:
   receiving information identifying at least one airborne allergen indicator affecting an individual and at least one concentration level of the at least one airborne allergen indicator that produces at least one allergic response in the individual.

3. The method of claim 1, wherein the receiving information identifying at least one allergen indicator affecting an individual and at least one concentration level of the at least one allergen indicator that produces at least one allergic response in the individual comprises:

receiving information identifying at least one peanut-type allergen indicator affecting an individual and at least one concentration level of the at least one peanut-type allergen indicator that produces at least one allergic response in the individual.

4. The method of claim 1, wherein the determining at least partly in response to processing of one or more samples with one or more microfluidic chips at least one concentration amount of the at least one allergen indicator in at least some of the one or more samples comprises:

determining at least partly in response to processing of one or more air samples with one or more microfluidic chips at least one concentration amount of the at least one allergen indicator in at least some of the one or more air samples.

5. The method of claim 1, wherein the determining at least partly in response to processing of one or more samples with one or more microfluidic chips at least one concentration amount of the at least one allergen indicator in at least some of the one or more samples comprises:

determining at least partly in response to processing of one or more food samples with one or more microfluidic chips at least one concentration amount of the at least one allergen indicator in at least some of the one or more food samples.

6. The method of claim 1, wherein the outputting at least one unsafe-type indicator for display if the at least one concentration amount of the at least one allergen indicator in at least some of the one or more samples meets or exceeds the at least one concentration level of the at least one allergen indicator that produces at least one allergic response in the individual comprises:

displayably outputting (i) the at least one concentration amount of the at least one allergen indicator in at least some of the one or more samples and (ii) at least one unsafe-type indicator if the at least one concentration amount of the at least one allergen indicator in at least some of the one or more samples meets or exceeds the at least one concentration level of the at least one allergen indicator that produces at least one allergic response in the individual.

7. The method of claim 1, wherein the outputting at least one unsafe-type indicator for display if the at least one concentration amount of the at least one allergen indicator in at least some of the one or more samples meets or exceeds the at least one concentration level of the at least one allergen indicator that produces at least one allergic response in the individual comprises:

displayably outputting (i) identification information associated with the at least one allergen indicator and (ii) at least one unsafe-type indicator if the at least one concentration amount of the at least one allergen indicator in at least some of the one or more samples meets or exceeds the at least one concentration level of the at least one allergen indicator that produces at least one allergic response in the individual.

8. The method of claim 1, further comprising:
transmitting one or more signals to one or more recording units.

9. The method of claim 1, wherein the determining at least partly in response to processing of one or more samples with one or more microfluidic chips at least one concentration amount of the at least one allergen indicator in at least some of the one or more samples comprises:

determining at least partly using one or more detection units and at least partly in response to processing of one or more samples with one or more microfluidic chips at least one concentration amount of the at least one allergen indicator in at least some of the one or more samples.

10. The method of claim 1, wherein the determining at least partly in response to processing of one or more samples with one or more microfluidic chips at least one concentration amount of the at least one allergen indicator in at least some of the one or more samples comprises:

detecting at least partly in response to processing of one or more samples with one or more microfluidic chips at least one concentration amount of the at least one allergen indicator in at least some of the one or more samples.

11. The method of claim 1, further comprising:
displaying one or more results with one or more display units.

12. The method of claim 1, wherein the outputting at least one unsafe-type indicator for display if the at least one concentration amount of the at least one allergen indicator in at least some of the one or more samples meets or exceeds the at least one concentration level of the at least one allergen indicator that produces at least one allergic response in the individual comprises:

displayably outputting (i) at least one indication of a presence or an absence of the at least one allergen indicator in at least some of the one or more samples and (ii) at least one unsafe-type indicator if the at least one concentration amount of the at least one allergen indicator in at least some of the one or more samples meets or exceeds the at least one concentration level of the at least one allergen indicator that produces at least one allergic response in the individual.

13. The method of claim 1, wherein the receiving information identifying at least one allergen indicator affecting an individual and at least one concentration level of the at least one allergen indicator that produces at least one allergic response in the individual comprises:

receiving information identifying at least one food allergen indicator affecting an individual and at least one concentration level of the at least one food allergen indicator that produces at least one allergic response in the individual.

14. The method of claim 13, wherein the determining at least partly in response to processing of one or more samples with one or more microfluidic chips at least one concentration amount of the at least one allergen indicator in at least some of the one or more samples comprises:

determining at least partly in response to processing of one or more food samples with one or more microfluidic chips at least one concentration amount of the at least one food allergen indicator in at least some of the one or more food samples.

15. The method of claim 14, wherein the outputting at least one unsafe-type indicator for display if the at least one concentration amount of the at least one allergen indicator in at least some of the one or more samples meets or exceeds the at least one concentration level of the at least one allergen indicator that produces at least one allergic response in the individual comprises:

displayably outputting at least one indicator relative to at least one color of at least one color scale that is associated with one or more unsafe levels if the at least one concentration amount of the at least one food allergen indicator in at least some of the one or more food samples meets or exceeds the at least one concentration level of the at least one food allergen indicator that produces at least one allergic response in the individual.

16. One or more non-transitory media bearing one or more instructions for facilitating operations comprising:
receiving information identifying at least one allergen indicator affecting an individual and at least one concentration level of the at least one allergen indicator that produces at least one allergic response in the individual;
determining at least partly in response to processing of one or more samples with one or more microfluidic chips at least one concentration amount of the at least one allergen indicator in at least some of the one or more samples; and
outputting at least one unsafe-type indicator for display if the at least one concentration amount of the at least one allergen indicator in at least some of the one or more samples meets or exceeds the at least one concentration level of the at least one allergen indicator that produces at least one allergic response in the individual.

17. A system comprising:
at least one article of manufacture bearing one or more instructions for facilitating operations including at least:
receiving information identifying at least one allergen indicator affecting an individual and at least one concentration level of the at least one allergen indicator that produces at least one allergic response in the individual;
determining at least partly in response to processing of one or more samples with one or more microfluidic chips at least one concentration amount of the at least one allergen indicator in at least some of the one or more samples; and
outputting at least one unsafe-type indicator for display if the at least one concentration amount of the at least one allergen indicator in at least some of the one or more samples meets or exceeds the at least one concentration level of the at least one allergen indicator that produces at least one allergic response in the individual.

18. A system comprising:
circuitry configured for receiving information identifying at least one allergen indicator affecting an individual and at least one concentration level of the at least one allergen indicator that produces at least one allergic response in the individual;
circuitry configured for determining at least partly in response to processing of one or more samples with one or more microfluidic chips at least one concentration amount of the at least one allergen indicator in at least some of the one or more samples; and
circuitry configured for outputting at least one unsafe-type indicator for display if the at least one concentration amount of the at least one allergen indicator in at least some of the one or more samples meets or exceeds the at least one concentration level of the at least one allergen indicator that produces at least one allergic response in the individual.

* * * * *